US009617597B2

(12) United States Patent
Helgadottir et al.

(10) Patent No.: US 9,617,597 B2
(45) Date of Patent: Apr. 11, 2017

(54) GENETIC SUSCEPTIBILITY VARIANTS ASSOCIATED WITH CARDIOVASCULAR DISEASE

(75) Inventors: Anna Helgadottir, Reykjavík (IS); Gudmar Thorleifsson, Reykjavík (IS); Andrei Manolescu, Reykjavík (IS)

(73) Assignee: deCode Genetics ehf (IS)

( * ) Notice: Subject to any disclaimer, the term of this patent is extended or adjusted under 35 U.S.C. 154(b) by 434 days.

(21) Appl. No.: 12/302,538

(22) PCT Filed: Feb. 21, 2008

(86) PCT No.: PCT/IS2008/000007
§ 371 (c)(1),
(2), (4) Date: Nov. 26, 2008

(87) PCT Pub. No.: WO2008/102380
PCT Pub. Date: Aug. 28, 2008

(65) Prior Publication Data
US 2010/0068705 A1 Mar. 18, 2010

(30) Foreign Application Priority Data

Feb. 21, 2007 (IS) ............................... 8613
Apr. 30, 2007 (IS) ............................... 8640
Dec. 21, 2007 (IS) ............................... 8701

(51) Int. Cl.
*C12Q 1/68* (2006.01)
*C07H 21/02* (2006.01)
*C07H 21/04* (2006.01)

(52) U.S. Cl.
CPC ..... *C12Q 1/6883* (2013.01); *C12Q 2600/106* (2013.01); *C12Q 2600/136* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 4,376,110 A | 3/1983 | David et al. | |
| 4,683,202 A | 7/1987 | Mullis | |
| 4,851,330 A | 7/1989 | Kohne | |
| 5,143,854 A | 9/1992 | Pirrung et al. | |
| 5,223,409 A | 6/1993 | Ladner et al. | |
| 5,288,611 A | 2/1994 | Kohne | |
| 5,288,644 A | 2/1994 | Beavis et al. | |
| 5,384,261 A | 1/1995 | Winkler et al. | |
| 5,424,186 A | 6/1995 | Fodor et al. | |
| 5,837,832 A | 11/1998 | Chee et al. | |
| 5,858,659 A | 1/1999 | Sapolsky et al. | |
| 7,883,851 B2 | 2/2011 | Cohen et al. | |
| 2004/0267458 A1* | 12/2004 | Judson et al. | 702/20 |
| 2005/0191678 A1* | 9/2005 | Lapointe et al. | 435/6 |
| 2006/0004526 A1* | 1/2006 | Hadd et al. | 702/20 |
| 2008/0274460 A1 | 11/2008 | Cohen et al. | |
| 2008/0274471 A1 | 11/2008 | Cohen et al. | |

FOREIGN PATENT DOCUMENTS

| | | |
|---|---|---|
| WO | WO-90/02809 | 3/1990 |
| WO | WO-90/15070 | 12/1990 |
| WO | WO-91/17271 | 11/1991 |
| WO | WO-92/01047 | 1/1992 |
| WO | WO-92/09690 | 6/1992 |
| WO | WO-92/10092 | 6/1992 |
| WO | WO-92/15679 | 9/1992 |
| WO | WO-92/18619 | 10/1992 |
| WO | WO-92/20791 | 11/1992 |
| WO | WO-93/01288 | 1/1993 |
| WO | WO-2004/035746 | 4/2004 |

OTHER PUBLICATIONS

GenBank rs10757278 added build 120 Mar. 16, 2004.*
Langdahl, Bente et al. Osteoporotic fractures are assoicated with an 86 base pair repeat polymoprhism in the Interleukin 1 receptor antagonist gene but not with polymoprhisms in the Interleukin 1B gene. Journal of Bone and Mineral Research 2000 vol. 15, No. 3, pp. 402-414.*
Wall, Jeffrey et al. Haplotype blocks and linkage disequilibirum in the human genome. Nature Reviews Genetics 2003 vol. 4, pp. 587-597.*
Lemmens, Robin et al. Variant on 9p21 strongly assoicates with coronary heart disease, but lacks associationwith common stroke. 2009 European Journal of Human Genetics. vol. 17 pp. 1287-1293.*
NCBI SNP database. MEthod Detail, Method ID XPLORE, obtained http://www.ncbi.nlm.nih.gov/projects/SNP/snp_view Table.cgi?mid=2929 on Oct. 24, 2010.*
NCBI SNP database, submitted SNP(ss) details ss43784416, obtained from http://www.ncbi.nlm.nih.gov/projects/SNP/snp_cgi?subsnp_id=43784416 on Oct. 24, 2010.*
Andiappan (BMC Genetics. 2010.11" 36).*
Terwilliger and Hiekkalinna European Journal of Human Genetics (2006) 14, 426-437. doi:1 0.1038/sj.ejhg.5201583; published online Feb. 15, 2006.*
Sotos et al. Statistics Education Research Journal Nov. 2009 8(2) 33-55.*
Zill et al. Molecular Psychiatry 2004 vol. 9 pp. 1030-1036.*
Syvanen et al Nature Reviews Genetics 2001 vol. 2 pp. 930-942.*
Adams et al., Classification of subtype of acute ischemic stroke. Definitions for use in a multicenter clinical trial. TOAST. Trial of Org 10172 in Acute Stroke Treatment. *Stroke* 24(1):35-41 (1993).
Altschul et al., A rapid classification protocol for the CATH Domain Database to support structural genomics. *Nucl. Acids Res.*, 25(1):3389-402 (1997).

(Continued)

*Primary Examiner* — Amanda Haney
(74) *Attorney, Agent, or Firm* — Marshall, Gerstein & Borun LLP

(57) ABSTRACT

The invention relates to methods of diagnosing susceptibility to cardiovascular disease, including coronary artery disease. MI, abdominal aorta aneurysm, intracranial aneurysm restenosis and peripheral arterial disease, by assessing the presence or absence of alleles of certain polymorphic markers found to be associated with cardiovascular disease. The invention further relates to kits encompassing reagents for assessing such markers, and methods for assessing the probability of response to therapeutic agents and methods using such markers.

57 Claims, 1 Drawing Sheet

(56) References Cited

OTHER PUBLICATIONS

Amundadottir el al., A common variant associated with prostate cancer in European and African populations. *Nat. Genet.* 38:652-8 (2006).
Bermudez et .al., Interrelationships among circulating interleukin-6, C-reactive protein, and traditional cardiovascular risk factors in women. *Arterioscler. Thromb. Vasc. Biol.*, 22(10):1668-73 (2002).
Brady et al., Abdominal aortic aneurysm expansion: Risk factors and time intervals for surveillance. *Circulation*, 110(1):16-21 (2004).
Brummelkamp et al., A system for stable expression of short interfering RNAs in mammalian cells. *Science*, 296(5567): 550-3 (2002).
Chen et al., Fluorescence polarization in homogeneous nucleic acid analysis. *Genome Res.* 9(5): 492-8 (1999).
Chi et al., Genomewide view of gene silencing by small interfering RNAs. *Proc. Natl. Acad. Sci. USA*, 100(11):6343-6 (2003).
Church et al., Genome sequencing. *Proc. Natl. Acad. Sci. USA*, 81(7):1991-5 (1988).
Cotton et al., Reactivity of cytosine and thymine in single-base-pair mismatches with hydroxylamine and osmium tetroxide and its application to the study of mutations. *Proc. Natl. Acad. Sci. USA*, 85(12):4397-401 (1985).
Dias et al., Antisense oligonucleotides: Basic concepts and mechanisms. *Mol. Cancer Ther.* 1(5):347-55 (2002).
Eckert et al., DNA polymerase fidelity and the polymerase chain reaction. *PCR Methods Appl.* 1(1):17-24 (1991).
Fire et al., Potent specific genetic interference by double-stranded RNA in *Caenorhabditis elegans*. *Nature*, 391 (6669):806-11 (1998).
Fodor et al., Light-directed, spatially addressable parallel chemical synthesis. *Science*, 251(4995):767-73 (1991).
Friedlander et al., Family history of myocardial infarction as an independent risk factor for coronary heart disease. *Br. Heart J.*53(4):382-7 (1985).
Gabriel et al., The structure of haplotype blocks in the human genome. *Science*, 296(5576):2225-9 (2002).
Geever et al., Direct identification of sickle cell anemia by blot hybridization. *Proc. Natl. Acad. Sci. USA*, 78(8):5081-5 (1981).
Grant et al., Variant of transcription factor 7-like 2 (TCF7L2) gene confers risk of type 2 diabetes. *Nat Genet*. 38(3):320-3 (2006).
Gretarsdottir et al., The gene encoding phosphodiesterase 4D confers risk of ischemic stroke. *Nat. Genet.* 35(2):131-8 (2003).
Griffiths et al., Human anti-self antibodies with high specificity from phage display libraries. *EMBO J.* 12(2):725-34 (1993).
Hashimoto et al., Intracranial aneurysms: links among inflammation, hemodynamics and vascular remodeling. *Neurol. Res.* 8(4):372-80 (2006).
Hay et al., Bacteriophage cloning and *Escherichia coli* expression of a human IgM Fab. *Hum. Antibodies Hybridomas* 3(2):81-5 (1992).
Hill et al., The effects of inbreeding at loci with heterozygote advantage. Genetics 60(3): 615-28 (1968).
Huse et al., Generation of a large combinatorial library of the immunoglobulin repertoire in phase lambda. *Science* 246(4935)1275-81 (1989).
Jones et al., Plasma lipoprotein(a) indicates risk for 4 distinct forms of vascular disease. *Clin. Chem.* 53:679-85 (2007).
Karlin et al., Applications and statistics for multiple high-scoring segments in molecular sequences. *Proc. Natl. Acad. Sci. USA*, 90:5873-7 (1993).
Kohler et al., Continuous cultures of fused cells secreting antibody of predefined specificity. *Nature*, 256:495-7 (1975).
Kozbor et al., The production of monoclonal antibodies from human lymphocytes. *Immunol. Today* 4(3): 72-9 (1983).
Kurreck, Antisense technologies. *Eur. J. Biochem.* 270:1628-44 (2003).
Kutyavin et al. A novel endonuclease IV post-PCR genotyping system. *Nucleic Acid Res.* 34(19):e128 (2006).

Lederle et al., The aneurysm detection and management study screening program: validation cohort and final results. Aneurysm Detection and Management Veterans Affairs Cooperative Study Investigators. *Arch. Intern. Med.* 160(10):1425-30 (2000).
Lerner, How to make a hybridoma. *Yale J. Biol. Med.* 54(5):387-402 (1981).
Lewontin, The interaction of selective and linkage, II, optimum models. *Genetics*, 50:757-82 (1964).
Maniatis et al., The first linkage disequilibrium (LD) maps: Delineation of hot and cold blocks by diplotype analysis. *Proc. Natl. Acad. Sci. USA*, 99:2228-33 (2002).
Mattila et al., Fidelity of DNA synthesis by the *Thermococcus litoralis* DNA polymerase—an extremely heat stable enzyme with proofreading activity. *Nucl. Acids Res.* 19(18):4967-73 (1991).
McManus et al., Gene silencing in mammals by small interfering RNAs. *Nat. Rev. Genet.* 3:737-47 (2002).
Minamino et al., Vascular cell senescence: Contribution to atherosclerosis. *Circ. Res.* 100(1):15-26 (2007).
Myers et al., A fine-scale map of recombination rates and hotspots across the human genome. *Science*, 310(5746):321-4 (2005).
Myers et al., Detection of single base substitutions by ribonuclease cleavage at mismatches in RNA:DNA duplexes. *Science*, 230(4731):1242-6 (1985).
Myers et al., The distribution and causes of meiotic recombination in the human genome. *Biochem. Soc. Trans.* 34(Pt 4):526-30 (2006).
Nielsen et al., Sequence-selective recognition of DNA by strand displacement with a thymine-substituted polyamide. *Science*, 254:1497-1500 (1991).
Orita et al., Detection of polymorphisms of human DNA by gel electrophoresis as single-strand conformation polymorphisms. *Proc. Natl. Acad. Sci. USA*, 86(8):2766-70 (1989).
Pasmant et al., Characterization of a germ-line deletion, including the entire INK4/ARF locus, in a melanoma-neural system tumor family: identification of ANRIL, an antisense noncoding RNA whose expression coclusters with ARF. *Cancer Res.* 67(8): 3963-9 (2007).
Patil et al., Blocks of limited haplotype diversity revealed by high-resolution scanning of human chromosome 21. *Science*, 294(5547):1719-23 (2001).
Pearson et al., Improved tools for biological sequence comparison. *Proc. Natl. Acad. Sci. USA*, 85:2444-8 (1988).
Penning et al., Structure-activity relationship studies on 1-[2-(4-phenylphenoxy)ethyl]pyrrolidine (SC-22716), a potent inhibitor of leukotrience A4 (LTA4) hydrolase. *J Med Chem.* 43(4):721-35 (2000).
Penning et al., Synthesis of imidazopyridines and purines as potent inhibitors of leukotriene A4 hydrolase. *Med Chem.* 45(16):3482-90 (2002).
Penning, Inhibitors of leukotrienes A4 (LTA4) hydrolase as potential anti-inflammatory agents. *Curr Pharm Des.* 7(3):163-79 (2001).
Reich et al, Linkage disequilibrium in the human genome. *Nature*, 411:199-204 (2001).
Retterstol et al., C-reactive protein predicts death in patients with previous premature myocardial infarction—A 10 year follow-up study. *Atherosclerosis*, 160:433-40 (2002).
Reynolds, et al., Rational siRNA design for RNA interference. *Nat. Biotechnol.* 22:326-30 (2004).
Ridker et al., Comparison of C-reactive protein and low-density lipoprotein cholesterol levels in the prediction of first cardiovascular events. *N. Engl. J. Med.*, 347(20):1557-65 (2001).
Ridker et al., C-reative protein levels and outcomes after statin therapy. *N. Engl. J. Med.* 352(1): 20-8 (2005).
Risch et al., The future of genetic studies of complex human diseases. *Science*, 273:1516-7 (1996).
Risch et al., The relative power of family-based and case-control designs for linkage disequilibrium studies of complex human diseases I. DNA pooling. *Genome Res.*, 8(12):1273-88 (1998).
Samani et al., A genomewide linkage study of 1,933 families affected by premature coronary artery disease: The British Heart Foundation (BHF) Family Heart Study. *Am. J. Hum. Genet.* 77(6):1011-20 (2005).
Sanger et al., DNA sequencing with chain-terminating inhibitors. *Proc. Natl. Acad. Sci. USA*, 74(12):5463-7 (1977).

(56) References Cited

OTHER PUBLICATIONS

Sheffield et al., Attachment of a 40-base-pair G + C-rich sequence (GC-clamp) to genomic DNA fragments by the polymerase chain reaction results in improved detection of single-base changes. *Proc. Natl. Acad. Sci. USA*, 86(1):232-6 (1989).
Shen et al., Four SNPs on chromosome 9p21 in a South Korean population implicate a genetic locus that confers high cross-race risk for development of coronary artery disease. *Arterioscler. Thromb. Vasc. Biol.* 28(2):360-5 (2008).
Smith et al., A high-density admixture map for disease gene discovery in African Americans. *Am. J. Hum. Genet.* 74:1001-13 (2004).
Stacey et al., Comoon variants on chromosomes 2q35 and 16q12 confer susceptibility to estrogen receptor-positive breast-cancer. *Nat Genet.* 39: 865-9 (2007).
Stein, Laboratory surrogates for anti-atherosclerotic drug development. *Am. J. Cardiol.* 87:(suppl):21A-26A (2001).
Steinthorsdottir et al., A variant in CDKAL1 influences insulin response and risk of type 2 diabetes. *Nat. Genet.* 39:770-5 (2007).
Terwilliger et al., A haplotype-based 'haplotype relative risk' approach to detecting allelic associates. *Hum. Hered.* 42:337-46 (1992).
Thom et al., Heart disease and stroke statistics—2006 update: a report from the American Heart Association Statistics Committee and Stroke Statistics Subcommittee. *Circulation*, 113(6):e85-151 (2006).
Vickers et al., Efficient reduction of target RNAs by small interfering RNA and RNase H-dependent antisense agents. *J. Biol. Chem.* 278:7108-18 (2003).
Wang et al., Distribution of recombination crossovers and the origin of haplotype blocks: the interplay of population history, recombination, and mutation. *Am. J. Hum. Genet.* 71(5):1227-34 (2002).
Wang et al., Premature myocardial infarction novel susceptibility locus on chromosome 1P34-36 identified by genomewide linkage analysis. *Am. J. Hum. Genet.* 74(2):262-71 (2004).
Weinsheimer et al., Association of kallikrein gene polymorphisms with intracranial aneurysms. *Stroke*, 38(10):2670-6 (2007).
Yeager et al, Genome-wide association study of prostate cancer identifies a second risk locus at 8q24. *Nat. Genet.* 39:645-9 (2007).
Zhang et al., A dynamic programming algorithm for haplotype block partitioning. *Proc. Natl. Acad. Sci. USA*, 99:7335-9 (2002).
Zimmerli et al., Urinary proteomic biomarkers in coronary artery disease. *Mol Cell Proteomics* 7(2):290-8 (2008).
NCBI Accession No. SS66599780, Genotyping assay for SNP rs10116277, dated Nov. 11, 2006.
NCBI Accession No. SS66735836, Genotyping assay for SNP rs1333040, dated Nov. 11, 2006.
NCBI Accession No. SS66710789, Genotyping assay for SNP rs2383207, dated Nov. 11, 2006.
NCBI Accession No. SS43784416, Genotyping assay for SNP rs10757278, dated Jul. 18, 2005.
Helgadottir et al., A common variant on chromosome 9p21 affects the risk of myocardial infarction. *Science*, 316(5830): 1491-3 (2007).
McPherson et al., A commone allele on chromosome 9 associated with coronary heart disease. *Science*, 316(5839): 1488-91 (2007).
International HapMap Consortium, A haplotype map of the human genome, *Nature*, 437(7063): 1299-320 (2005).
International Search Reporting, PCT/IS2008/000007, European Patent Office, dated Jun. 12, 2008.
Agami, RNAi and related mechanisms and their potential use for therapy. *Curr. Opin. Chem. Biol.* 6(6):829-34 (2002).
Amarzguioui et al. Approaches for chemically synthesized siRNA and vector-mediated RNAi. *FEBS Lett.* 579(26):5974-81 (2005).
Barani et al., Inflammatory mediators are associated with 1-year mortality in critical limb ischemia. *J. Vasc. Surg.* 42(1):75-80 (2005).
Bennett, Efficiency of antisense oligonucleotide drug delivery. *Antisense Nucleic Acid Drug.Dev.* 12(3):215-24 (2002).
Bosher et al., RNA interference: genetic wand and genetic watchdog. *Nat. Cell Biol.* 2(2):E31-6 (2000).
Brisman et al., Cerebral aneurysms. *N. Engl. J. Med.* 355(9):928-39 (2006).
Chatzizisis et al., Role of endothelial shear stress in the natural history of coronary atherosclerosis and vascular remodeling: molecular, cellular, and vascular behavior. *J. Am. Coll. Cardiol.* 49(25):2379-93 (2007).
Chen et al., The evolution of gene regulation by transcription factors and microRNAs. *Nat. Rev. Genet.* 8(2): 93-103 (2007).
Chen, Clinical development of antisense oligonucleotides as anticancer therapeutics. *Methods Mol. Med.* 75:621-636 (2003).
Daly et al., High-resolution haplotype structure in the human genome. *Nature Genet.* 29(2):229-32 (2001).
Dawson et al., A first-generation linkage disequilibrium map of human chromosome 22. *Nature*, 418(6897):544-8 (2002).
Devlin et al., Genomic control for association studies. *Biometrics*, 55(4): 997-1004 (1999).
Doggen et al., C-reactive protein, cardiovascular risk factors and the association with myocardial infarction in men. *J Internal Med.*, 248(5):406-14 (2000).
Dormandy et al., Management of peripheral arterial disease (PAD). TASC Working Group. TransAtlantic Inter-Society Consensus (TASC). *J Vasc Surg* 31(1 Pt 2):S1-S296 (2000).
Falk et al., Haplotype relative risks: an easy reliable way to construct a proper control sample for risk calculations. *Hum. Genet.* 51(Pt 3):227-33 (1987).
Flavell et al., Analysis of the beta-delta-globin gene loci in normal and Hb Lepore DNA: direct determination of gene linkage and intergene distance. *Cell*, 15(1):25-41 (1978).
Flex et al., The -174 G/C polymorphism of the interleukin-6 gene promoter is associated with peripheral artery occlusive disease. *Eur J Vasc Endovasc Surg* 24(3): 264-8 (2002).
Fuchs et al., Targeting recombinant antibodies to the surface of *Escherichia coli*: Fusion to a peptidoglycan associated lipoprotein. Bio/Technology 9: 1370-1372 (1991).
Galfre et al., Antibodies to major histocompatibility antigens produced by hybrid cell lines. *Nature*, 266(5602):550-2 (1977).
Genome-wide association study of 14,000 cases of seven common diseases and 3,000 shared controls. *Nature*, 447(7145):661-78 (2007).
Gill, An assessment of the utility of single nucleotide polymorphisms (SNPs) for forensic purposes. *Int. J. Legal Med.* 114(4-5):204-10 (2001).
Gudmundsson et al., Two variants on chromosome 17 confer prostate cancer risk, and the one in TCF2 protects against type 2 diabetes. *Nat. Genet.* 39:977-83 (2007).
Haiman et al., Multiple regions within 8q24 independently affect risk for prostate cancer. *Nat. Genet.* 39(5):638-44 (2007).
Hopkins et al., Family history as an independent risk factor for incident coronary artery disease in a high-risk cohort in Utah. *Am. J. Cardiol.* 62(10 Pt 1):703-7 (1988).
Hunter, Genetics: A touch of elegance with RNAi. *Curr. Biol.* 9(12):R440-2 (1999).
Jeffreys et al., Intensely punctate meiotic recombination in the class II region of the major histocompatibility complex. *Nat. Genet.* 29(2):217-22 (2001).
Kim et al., Strategies for silencing human disease using RNA interference. *Nature Rev. Genet.* 8(3):173-204 (2007).
Kim et al., Synthetic dsRNA Dicer substrates enhance RNAi potency and efficacy. *Nat. Biotechnol.* 23(2):222-6 (2005).
Kim et al., The regulation of INK4/ARF in cancer and aging. *Cell*, 127(2):265-75 (2006).
Lavery et al., Antisense and RNAi: powerful tools in drug target discovery and validation. *Curr. Opin. Drug Discov. Devel.* 6(4):561-9 (2003).
Lederle et al, Abdominal aortic aneurysm in women. *J. Vasc. Surg.* 34(1):122-6 (2001).
Lusis, Atherosclerosis. *Nature*, 407(6801):233-41 (2000).
Mantel et al., Statistical aspects of the analysis of data from retrospective studies of disease. *J. Natl. Cancer Inst.* 22(4):719-48 (1959).

(56) References Cited

OTHER PUBLICATIONS

Marques et al., A structural basis for discriminating between self and nonself double-stranded RNAs in mammalian cells. *Nat. Biotechnol.* 24(5):559-65 (2006).

May et al., Crossover clustering and rapid decay of linkage disequilibrium in the Xp/Yp pseudoautosomal gene SHOX. *Nat. Genet.* 31(3):272-5 (2002).

Moore et al, Fluid wall shear stress measurements in a model of the human abdominal aorta: oscillatory behavior and relationship to atherosclerosis. *Atherosclerosis* 110(2):225-40 (2006).

Nicolae et al., Measuring the relative information in allele-sharing linkage studies. *Biometrics*, 60(2):368-75 (2004).

Nielsen et al., Peptide nucleic acid (PNA). A DNA mimic with a peptide backbone. *Bioconjug. Chem.* 5(1):3-7 (1994).

Ogata et al., Genetic analysis of polymorphisms in biologically relevant candidate genes in patients with abdominal aortic aneurysms. *J. Vasc. Surg.* 41(6):1036-42 (2005).

Phillips et al., Chromosome-wide distribution of haplotype blocks and the role of recombination hot spots. *Nat. Genet.* 33(3):382-7 (2003).

Schievink, Intracranial aneurysms. *N. Engl. J. Med.* 336(1):28-40 (1997).

Shea et al., Family history as an independent risk factor for coronary artery disease. *J. Am. Coll. Cardiol.* 4:793-801 (1984).

Shen et al., Association between four SNPs on chromosome 9p21 and myocardial infarction is replicated in an Italian population. *J. Hum. Genet.* 53(2):144-50 (2008).

Shi, Mammalian RNAi for the masses. *Trends Genet.* 19:9-12 (2003).

Shuey et al., RNAi: gene-silencing in therapeutic intervention. *Drug Discov. Today*, 7(20):1040-6 (2002).

Siolas et al., Synthetic shRNAs as potent RNAi triggers. *Nat. Biotechnol.* 23(2):227-31 (2005).

St Jean et al., Characterization of a dinucleotide repeat in the 92 kDa type IV collagenase gene (CLG4B), localization of CLG4B to chromosome 20 and the role of CLG4B in aortic aneurysmal disease. *Ann. Hum. Genet.* 59(Pt 1):17-24 (1995).

Stefansson et al., A common inversion under selection in Europeans. *Nat. Genet.* 37:129-37 (2005).

Stephens et al., Antisense oligonucleotide therapy and cancer. *Curr. Opin. Mol. Ther.* 5(2):118-22 (2003).

Stumpf et al., A Y chromosome census of the British Isles *Curr. Biol.* 13:1-8 (2003).

Suggested standards for reports dealing with lower extremity ischemia. Prepared by the Ad Hoc Committee on Reporting Standards, Society for Vascular Surgery/North America Chapter, International Society for Cardiovascular Surgery. *J. Vasc. Surg.* 4:80-94 (1986).

The World Health Organization MONICA Project (monitoring trends and determinants in cardiovascular disease): A major international collaboration. WHO MONICA Project Principal Investigation. *J Clin Epidemiol* 41(2): 105-14 (1988).

Thompson, Applications of antisense and siRNAs during preclinical drug development. *Drug Discovery Today*, 7(17):912-7 (2002).

Thompson, Reflections on the pathogenesis of abdominal aortic aneurysms. *Cardiovasc. Surg.* 10: 389-94 (2002).

Torellis et al., ADVANCE and ADAM: two algorithms for the analysis of global similarity between homologous informational sequences. *Comput. Appl. Biosci.* 10(1):3-5 (1994).

Wall et al., Haplotype blocks and linkage disequilibrium in the human genome. *Nat. Rev. Genet.* 4(8):587-97 (2003).

Wang et al., Antisense anticancer oligonucleotide therapeutics. *Curr. Cancer Drug Targets* 1(3):177-96 (2001).

Xia et al., siRNA-mediated gene silencing in vitro and in vivo. *Nat. Biotechnol.* 20(10):1006-10 (2002).

Zintzaras et al., Identification of chromosomal regions linked to premature myocardial infarction: a meta-analysis of whole-genome searches. *J. Hum. Genet.* 51(11):1015-21 (2006).

Adams, et al., "Markers in Cardiology: A Case-orientated Approach," Blackwell Publishing, Contents, Contributors, Preface, and pp. 207-261 (2007).

Cho, et al., The Cardiology Intensive Board Review Question Book, 2nd Ed. Lippincott Williams, pp. vii-xiv, Chapters 3, 4, and 10, and pp. 369-385 (2009).

Crawford, MH., Current Diagnosis & Treatment in Cardiology, 2nd Ed. McGraw-Hill Companies, Inc., Contents, Authors, & Preface; Chapters 1, 2, and 5; and pp. 611-627 (2003).

Foody, JM, "Preventive Cardiology: Insights Into the Prevention and Treatment of Cardiovascular Disease," 2nd Ed. Humana Press Inc. NJ, Preface, Contents, Contributors, Chapter 17 and pp. 339-346 (2006).

Griffin, et al., "The Cleveland Clinic Cardiology Board Review," Lippincott Williams & Wilkins Publishing, Contents, Contributors, Preface, Chapter 42, and pp. 791-809 (2007).

Perk, et al., "Cardiovascular Prevention and Rehabilitation," Spring-Verlag, Preface, Table of Contents, Chapter 11, and pp. 503-517 (2007).

Willerson, et al., Cardiovascular Medicine, 3rd Ed., Springer-Verlag, Preface, Table of Contents, Chapters 26, 27, 74, 120, 122-125, 131, and pp. 2839-2906 (2007).

* cited by examiner

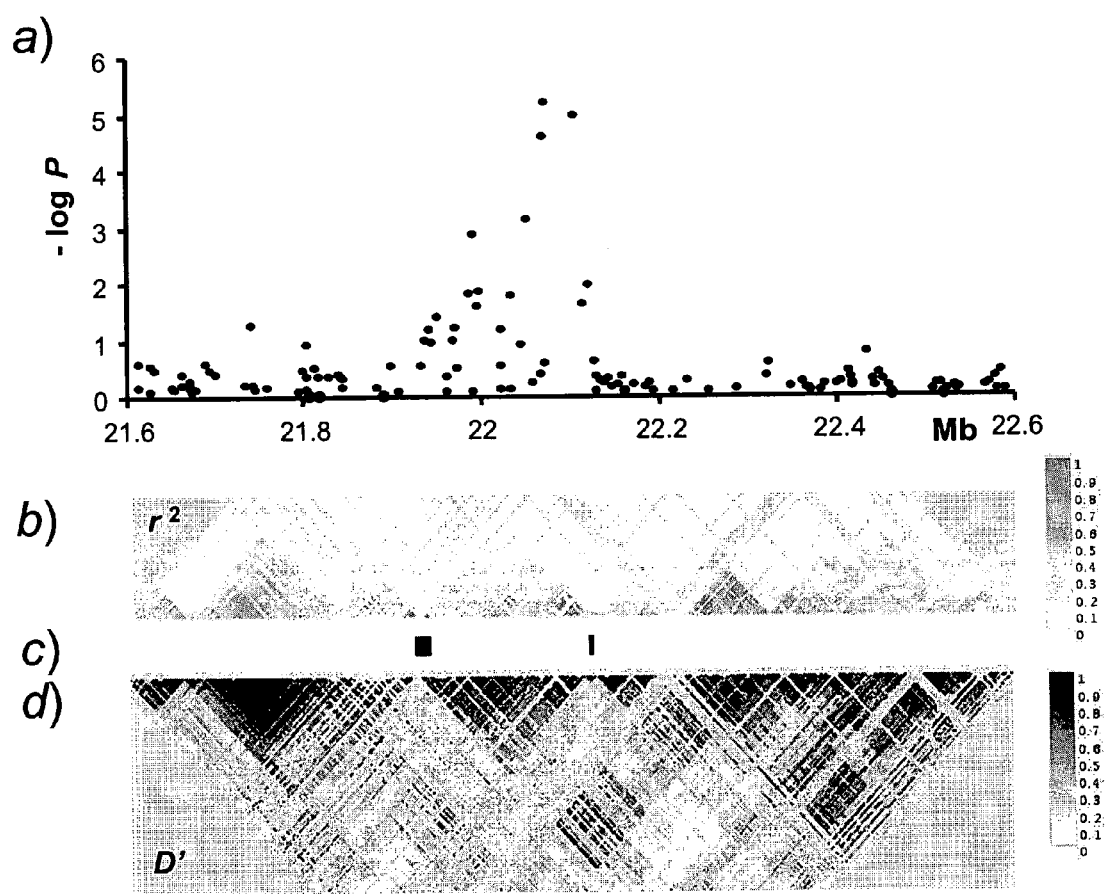

GENETIC SUSCEPTIBILITY VARIANTS ASSOCIATED WITH CARDIOVASCULAR DISEASE

This application is the U.S. national phase of International Application No. PCT/IS2008/000007, filed Feb. 21, 2008, which claims priority benefit of Iceland Application No. 8613 filed Feb. 21, 2007, Iceland Application No. 8640 filed Apr. 30, 2007 and Iceland Application No. 8701 filed Dec. 21, 2007.

BACKGROUND OF THE INVENTION

Coronary Artery Disease and Myocardial Infarction

The major complications of Coronary Artery Disease, i.e. Myocardial infarction (MI) and Acute Coronary Syndrome (ACS), are the leading causes of hospital admissions in industrialized countries. Cardiovascular disease continues to be the principle cause of death in the United States, Europe and Japan. The costs of the disease are high both in terms of morbidity and mortality, as well as in terms of the financial burden on health care systems.

Myocardial infarction generally occurs when there is an abrupt decrease in coronary blood flow following a thrombotic occlusion of a coronary artery previously damaged by atherosclerosis (i.e. in subjects with coronary artery disease). In most cases, infarction occurs when an atherosclerotic plaque fissures, ruptures or ulcerates and when conditions favor thrombogenesis. In rare cases, infarction may be due to coronary artery occlusion caused by coronary emboli, congenital abnormalities, coronary spasm, and a wide variety of systemic, particularly inflammatory diseases. Medical risk factors for MI include cigarette smoking, diabetes, hypertension and serum total cholesterol levels >200 mg/dL, elevated serum LDL cholesterol, and low serum HDL cholesterol. Event rates in individuals without a prior history of cardiovascular disease are about 1%. In individuals who have had a first MI or ACS, the risk of a repeat MI within the next year is 10-14%, despite maximal medical management including angioplasty and stent placement.

Atherosclerosis can affect vascular beds in many large and medium arteries. Myocardial infarction and unstable angina (acute coronary syndrome (ACS)) stem from coronary artery atherosclerosis (Coronary Artery Disease), while ischemic stroke most frequently is a consequence of carotid or cerebral artery atherosclerosis. Limb ischemia caused by peripheral arterial occlusive disease (PAOD) may occur as a consequence of iliac, femoral and popliteal artery atherosclerosis. The atherosclerotic diseases remain common despite the wide-spread use of medications that inhibit thrombosis (aspirin) or treat medical risk factors such as elevated cholesterol levels in blood (statins), diabetes, or hypertension (diuretics and anti-hypertensives).

Atherosclerotic disease is initiated by the accumulation of lipids within the artery wall, and in particular, the accumulation of low-density lipoprotein (LDL) cholesterol. The trapped LDL becomes oxidized and internalized by macrophages. This causes the formation of atherosclerotic lesions containing accumulations of cholesterol-engorged macrophages, referred to as "foam cells". As disease progresses, smooth muscle cells proliferate and grow into the artery wall forming a "fibrous cap" of extracellular matrix enclosing a lipid-rich, necrotic core. Present in the arterial walls of most people throughout their lifetimes, fibrous atherosclerotic plaques are relatively stable. Such fibrous lesions cause extensive remodeling of the arterial wall, outwardly displacing the external, elastic membrane, without reduction in luminal diameter or serious impact on delivery of oxygen to the heart. Accordingly, patients can develop large, fibrous atherosclerotic lesions without luminal narrowing until late in the disease process. However, the coronary arterial lumen can become gradually narrowed over time and in some cases compromise blood flow to the heart, especially under high demand states such as exercise. This can result in reversible ischemia causing chest pain relieved by rest called stable angina.

In contrast to the relative stability of fibrous atherosclerotic lesions, the culprit lesions associated with myocardial infarction and unstable angina (each of which are part of the acute coronary syndrome) are characterized by a thin fibrous cap, a large lipid core, and infiltration of inflammatory cells such as T-lymphocytes and monocyte/macrophages. Non-invasive imaging techniques have shown that most MI's occur at sites with low-or intermediate-grade stenoses, indicating that coronary artery occlusion is due most frequently to rupture of culprit lesions with consequent formation of a thrombus or blood clot and not solely due to luminal narrowing by stenosis. Plaque rupture may be due to erosion or uneven thinning of the fibrous cap, usually at the margins of the lesion where macrophages enter, accumulate, and become activated by a local inflammatory process. Thinning of the fibrous cap may result from degradation of the extracellular matrix by proteases released from activated macrophages. These changes producing plaque instability and risk of MI may be augmented by production of tissue-factor procoagulant and other factors increasing the likelihood of thrombosis.

In acute coronary syndrome, the culprit lesion showing rupture or erosion with local thrombosis typically is treated by angioplasty or by balloon dilation and placement of a stent to maintain luminal patency. Patients experiencing ACS are at high risk for a second coronary event due to the multi-vessel nature of coronary artery disease with event rates approaching 10-14% within 12 months after the first incident.

The emerging view of MI is as an inflammatory disease of the arterial vessel wall on preexisting chronic atherosclerotic lesions, sometimes triggering rupture of culprit lesions and leading to local thrombosis and subsequent myocardial infarction. The process that triggers and sustains arterial wall inflammation leading to plaque instability is unknown, however, it results in the release into the circulation of tumor necrosis factor alpha and interleukin-6. These and other cytokines or biological mediators released from the damaged vessel wall stimulate an inflammatory response in the liver causing elevation in several non-specific general inflammatory markers including C-reactive protein. Although not specific to atherosclerosis, elevated C-reactive protein (CRP) and serum amyloid A appear to predict risk for MI, perhaps as surrogates for vessel wall inflammation. Many general inflammatory markers predict risk of coronary heart disease, although these markers are not specific to atherosclerosis. For example, Stein (Stein, S., *Am J Cardiol*, 87 (suppl):21A-26A (2001)) discusses the use of any one of the following serum inflammatory markers as surrogates for predicting risk of coronary heart disease including C-reactive protein (CRP), serum amyloid A, fibrinogen, interleukin-6, tissue necrosis factor-alpha, soluble vascular cell adhesion molecules (sVCAM), soluble intervascular adhesion molecules (sICAM), E-selectin, matrix metalloprotease type-1, matrix metalloprotease type-2, matrix metalloprotease type-3, and matrix metalloprotease type-9. Elevation in one more of these serum inflammatory markers is not specific to coronary heart disease but also occurs with age or in association with cerebrovascular disease, peripheral vascular disease, non-insulin dependent diabetes, osteoarthritis, bacterial infection, and sepsis.

Elevated CRP or other serum inflammatory markers is also prognostic for increased risk of a second myocardial infarct in patients with a previous myocardial infarct (Retterstol, L. et al., *Atheroscler.*, 160: 433-440 (2002)).

Although classical risk factors such as smoking, hyperlipidemia, hypertension, and diabetes are associated with many cases of coronary heart disease (CHD) and MI, many patients do not have involvement of these risk factors. In fact, many patients who exhibit one or more of these risk factors do not develop MI. Family history has long been recognized as one of the major risk factors. Although some of the familial clustering of MI reflects the genetic contribution to the other conventional risk factors, a large number of studies have suggested that there are significant genetic susceptibility factors, beyond those of the known risk factors (Friedlander Y, et al., *Br. Heart J.* 1985; 53:382-7, Shea S. et al., *J. Am. Coll. Cardiol.* 1984; 4:793-801, and Hopkins P. N., et al., *Am. J. Cardiol.* 1988; 62:703-7). Major genetic susceptibility factors have only been identified for the rare Mendelian forms of hyperlipidemia such as a familial hypercholesterolemia.

Genetic risk is conferred by subtle differences in genes among individuals in a population. Genes differ between individuals most frequently due to single nucleotide polymorphisms (SNP), although other variations are also important. SNP are located on average every 1000 base pairs in the human genome. Accordingly, a typical human gene containing 250,000 base pairs may contain 250 different SNP. Only a minor number of SNPs are located in exons and alter the amino acid sequence of the protein encoded by the gene. Most SNPs may have little or no effect on gene function, while others may alter transcription, splicing, translation, or stability of the mRNA encoded by the gene. Additional genetic polymorphism in the human genome is caused by insertion, deletion, translocation, or inversion of either short or long stretches of DNA. Genetic polymorphisms conferring disease risk may therefore directly alter the amino acid sequence of proteins, may increase the amount of protein produced from the gene, or may decrease the amount of protein produced by the gene.

As genetic polymorphisms conferring risk of disease are uncovered, genetic testing for such risk factors is becoming important for clinical medicine. Examples are apolipoprotein E testing to identify genetic carriers of the apoE4 polymorphism in dementia patients for the differential diagnosis of Alzheimer's disease, and of Factor V Leiden testing for predisposition to deep venous thrombosis. More importantly, in the treatment of cancer, diagnosis of genetic variants in tumor cells is used for the selection of the most appropriate treatment regime for the individual patient. In breast cancer, genetic variation in estrogen receptor expression or heregulin type 2 (Her2) receptor tyrosine kinase expression determine if anti-estrogenic drugs (tamoxifen) or anti-Her2 antibody (Herceptin) will be incorporated into the treatment plan. In chronic myeloid leukemia (CML) diagnosis of the Philadelphia chromosome genetic translocation fusing the genes encoding the Bcr and Abl receptor tyrosine kinases indicates that Gleevec (STI571), a specific inhibitor of the Bcr-Abl kinase should be used for treatment of the cancer. For CML patients with such a genetic alteration, inhibition of the Bcr-Abl kinase leads to rapid elimination of the tumor cells and remission from leukemia.

Restenosis

Coronary balloon angioplasty was introduced in the late 1970s as a less invasive method for revascularization of coronary artery disease patients than the coronary artery bypass graft (CABG) surgeries. Since then there has been a quick progress in the development of new percutaneous devices to revascularize areas with limited blood flow. However, the expanded use of angioplasty has shown that the arteries react to angioplasty by a proliferative process that limits the success of this treatment. This process is known as restenosis.

Restenosis is defined as a re-narrowing of the treated segment, which equals or exceeds 50% of the lumen in the adjacent normal segment of the artery. Depending on the patient population studied, the restenosis rates range from 30% to 44% of lesions treated by balloon dilation. This problem prompted a search for interventional techniques that minimizes the risk of restenosis. Several clinical trials have shown a significant reduction in the restenosis rates with endovascular stenting. The purpose of stenting is to maintain the arterial lumen by a scaffolding process that provides radial support. Stents, usually made of stainless steel, are placed in the artery either by a self-expanding mechanism or, using balloon expansion. However, in-stent restenosis still remains a major problem in the field of percutaneous, transluminal coronary angioplasty (PTCA), requiring patients to undergo repeated procedures and surgery. Restenosis is the result of the formation of neointima, a composition of smooth muscle-like cells in a collagen matrix. The current treatment modalities for in-stent restenosis include repeat balloon angioplasty, repeat stenting, cutting balloon angioplasty, directional coronary atherectomy, rotational coronary atherectomy, brachytherapy, and drug-eluting stents (DES). The restenosis problem can be minimised by local intravascular irradiation (intracoronary brachytherapy) and by the introduction of DES and these treatments have been shown to successfully preventing cell proliferation after stent implantation or angioplasty.

Intracoronary brachytherapy is a treatment in which sealed sources of radioactive material are used to deliver radiation at a very short distance by placing them in the artery lumen at the site of the atherosclerotic lesion. The physical benefit of brachytherapy is that doses of radiation can be delivered almost directly to the target with a very rapid falloff of dose to the surrounding normal tissue. The rationale underlining this modality is based on the ability of ionizing radiation to inhibit cell proliferation, in this case, the proliferation of smooth muscle cells that tend to form a neointima. In the near future, it would be important to be able to classify patients with respect to the risk of having in-stent restenosis. This classification can potentially be made on the basis of genetic risk factors. The outcome of the classification may determine which therapy is most appropriate and also where coronary bypass surgery has to be considered.

Aneurysms

Degenerative changes of the arterial wall may cause localized dilatation, or aneurysm, of the artery, including abdominal aorta aneurysm (AAA) and intracranial aneurysm (IA). Atherosclerotic changes of the vessel wall are found in the majority of AAA that are characterized histopathologically by chronic inflammation, destructive remodelling of elastic media and depletion of medial smooth muscle cells resulting in marked weakening of the aortic wall. In contrast, berry aneurysms of intracranial arteries are not associated with atherosclerosis. Furthermore, the histopathological features of IA are different. The typical berry aneurysms of intracranial arteries, located at arterial bifurcations, have a thin, or no, media and the internal elastic lamina is either absent or severely fragmented.

Both AAA and IA represent a degenerative process of the arteries leading to their enlargement that is usually asymptomatic with natural history culminating in either a therapeutic intervention or rupture. Rupture of IA leads to subarachnoid haemorrhage, and rupture of both IA and AAA have high morbidity and mortality. In the case of AAA the rupture risk increases with the growth rate as well as the size of the aneurysm.

Intracranial aneurysm (IA), also called cerebral aneurysm or brain aneurysm is a cerebrovascular disorder in which weakness in the wall of a cerebral artery or vein causes a localized dilation or ballooning of the blood vessel.

A common location of cerebral aneurysms is on the arteries at the base of the brain, known as the Circle of Willis. Approximately 85% of cerebral aneurysms develop in the anterior part of the Circle of Willis, and involve the internal carotid arteries and their major branches that supply the anterior and middle sections of the brain. It is believed that aneurysms may result from congenital defects, preexisting conditions such as high blood pressure and atherosclerosis, or head trauma. Cerebral aneurysms occur more commonly in adults than in children but they may occur at any age.

Cerebral aneurysms are classified both by size and shape. Small aneurysms have a diameter of less than 15 mm. Larger aneurysms include those classified as large (15 to 25 mm), giant (25 to 50 mm), and super giant (over 50 mm). Saccular aneurysms are those with a saccular outpouching and are the most common form of cerebral aneurysm. Berry aneurysms are saccular aneurysms with necks or stems resembling a berry. Fusiform aneurysms are aneurysms without stems.

A small, unchanging aneurysm will produce no symptoms. Before a larger aneurysm ruptures, the individual may experience such symptoms as a sudden and unusually severe headache, nausea, vision impairment, vomiting, and loss of consciousness, or the individual may be asymptomatic, experiencing no symptoms at all. Onset is usually sudden and without warning. Rupture of a cerebral aneurysm is dangerous and usually results in bleeding into the meninges or the brain itself, leading to a subarachnoid hemorrhage (SAH) or intracranial hematoma (ICH), either of which constitutes a stroke. Rebleeding, hydrocephalus (the excessive accumulation of cerebrospinal fluid), vasospasm (spasm, or narrowing, of the blood vessels), or multiple aneurysms may also occur. The risk of rupture from an unruptured cerebral aneurysm varies according to the size of an aneurysm, with the risk rising as the aneurysm size increases. The overall rate of aneurysm rupture is estimated at 1.3% per year. The risk of short term re-rupture increases dramatically after an aneurysm has bled, though after approximately 6 weeks the risk returns to baseline.

Emergency treatment for individuals with a ruptured cerebral aneurysm generally includes restoring deteriorating respiration and reducing intracranial pressure. Currently there are two treatment options for brain aneurysms: surgical clipping or endovascular coiling. Either surgical clipping or endovascular coiling is usually performed within the first three days to occlude the ruptured aneurysm and reduce the risk of rebleeding.

The prognosis for a patient with a ruptured cerebral aneurysm depends on the extent and location of the aneurysm, the person's age, general health, and neurological condition. Some individuals with a ruptured cerebral aneurysm die from the initial bleeding. Other individuals with cerebral aneurysm recover with little or no neurological deficit. The most significant factors in determining outcome are severity of the aneurysm and age.

Abdominal aortic aneurysm (AAA) is a localized dilatation of the abdominal aorta, that exceeds the normal diameter by more than 50%. The normal diameter of the infrarenal aorta is 2 cm. It is caused by a degenerative process of the aortic wall. The aneurysm is most commonly located infrarenally (90%), other possible locations are suprarenal and pararenal. The aneurysm can extend to include one or both of the iliac arteries. An aortic aneurysm may also occur in the thorax.

AAA is uncommon in individuals of African, African American, Asian, and Hispanic heritage. The frequency varies strongly between males and females. The peak incidence is among males around 70 years of age, the prevalence among males over 60 years totals 2-6%. The frequency is much higher in smokers than in non-smokers (8:1). Other risk factors include hypertension and male sex. In the US, the incidence of AAA is 2-4% in the adult population. Rupture of the AAA occurs in 1-3% of men aged 65 or more, the mortality being 70-95%.

The exact causes of the degenerative process remain unclear. Known risk factors include genetic factors, hemodynamic influences, atherosclerosis, and various other factors such as infection, trauma, connective tissue disorders, arterities, etc. AAAs are commonly divided according to their size and symptomatology. An aneurysm is usually considered to be present if the measured outer aortic diameter is over 3 cm (normal diameter of aorta is around 2 cm). The natural history is of increasing diameter over time, followed eventually by the development of symptoms (usually rupture). If the outer diameter exceeds 5 cm, the aneurysm is considered to be large. For aneurysms under 5 cm, the risk of rupture is low, so that the risks of surgery usually outweigh the risk of rupture. Aneurysms less than 5 cm are therefore usually kept under surveillance until such time as they become large enough to warrant repair, or develop symptoms. The vast majority of aneurysms are asymptomatic. The risk of rupture is high in a symptomatic aneurysm, which is therefore considered an indication for surgery. Possible symptoms include low back pain, flank pain, abdominal pain, groin pain or pulsating abdominal mass. The complications include rupture, peripheral embolisation, acute aortic occlusion, aortocaval or aortoduodenal fistulae. On physical examination, a palpable abdominal mass can be noted. Bruits can be present in case of renal or visceral arterial stenosis.

The main treatment options for asymptomatic AAA are immediate repair and surveillance with a view to eventual repair. Surveillance is indicated in small aneurysms, where the risk of repair exceeds the risk of rupture. As an AAA grows in diameter the risk of rupture increases. Although some controversy exists around the world, most vascular surgeons would not consider repair until the aneurysm reached a diameter of 5 cm. The threshold for repair varies slightly from individual to individual, depending on the balance of risks and benefits when considering repair versus ongoing surveillance. The size of an individual's native aorta may influence this, along with the presence of comorbities that increase operative risk or decrease life expectancy. Currently, the main modes of repair available for an AAA are open aneurysm repair (OR), and endovascular aneurysm repair (EVAR). Open repair is indicated in young patients as an elective procedure, or in growing or large, symptomatic or ruptured aneurysms. Open repair has been the mainstay of intervention from the 1950's until recently.

Endovascular repair first became practical in the 1990's and although it is now an established alternative to open repair, its role is yet to be clearly defined. It is generally indicated in older, high-risk patients or patients unfit for open repair. However, endovascular repair is feasible for only a proportion of AAA's, depending on the morphology of the aneurysm. The main advantage over open repair is that the peri-operative period has less impact on the patient.

Stroke

Stroke is a group of diverse disorders encompassing several pathophysiological mechanisms. The clinical phenotype of stroke is complex but is broadly divided into: ischemic and hemorrhagic stroke. The majority of stroke events, appr 80%, is due to ischemia (cerebral infarction), that occurs when a cerebral artery becomes completely occluded and the blood supply to a part of the brain is totally or partially blocked (due to thrombosis or an embolism). Ischemic stroke is further subdivided into large artery disease (LAA) (also called large vessel disease, LVD), cardioembolic stroke and small vessel disease. Approximately 25% of ischemic stroke events are due to large-artery disease of the carotid and vertebral arteries, the two pairs of large arteries that supply the brain with blood. The most common cause of large-artery disease is atherosclerosis. Cardioembolic strokes are caused by an embolism that originates inside the heart. Embolism of cardiac origin accounts for about ¼ of ischemic strokes. Strokes due to cardioembolism are in general severe and prone to early and long-term recurrence. Ischemic heart disease, rheumatic mitral stenosis, and prosthetic cardiac valves are major sources of cardioembolic stroke but atrial fibrillation remains the commonest cause.

There is a continued and great need to understand the genetic variants conferring risk (increased and decreased) of the cardiovascular diseases. The present invention provides genetic variants that have been shown to be associated with susceptibility to cardiovascular disease, including MI, Coronary Artery Disease (CAD), Intracranial aneurysm (IA), Abdominal Aorta Aneurysm (AAA), Peripheral Arterial Disease (PAD) and Restenosis. These variants are useful in risk management and methods for therapeutic intervention of cardiovascular diseases.

SUMMARY OF THE INVENTION

The present invention relates to methods of determining a susceptibility to cardiovascular diseases, including Coronary Artery Disease, Myocardial Infarction, Peripheral Artery Disease, Stroke, Restenosis, Intracranial Aneurysm and Abdominal Aorta Aneurysm. The invention also relates to various uses, kits, procedures and apparati useful in the determination of a susceptibility to cardiovascular disease based on evaluation of certain polymorphic markers and/or haplotypes that have been found to be associated with susceptibility to cardiovascular disease.

In one aspect, the invention relates to a method for determining a susceptibility to cardiovascular disease in a human individual, comprising determining the presence or absence of at least one allele of at least one polymorphic marker in a nucleic acid sample obtained from the individual or in a genotype dataset derived from the individual, wherein the at least one polymorphic marker is selected from the polymorphic markers set forth in Table 10, and markers in linkage disequilibrium therewith, and wherein the presence of the at least one allele is indicative of a susceptibility to cardiovascular disease. The method may in one embodiment relate to determination of the presence or absence of at least one allele of at least one polymorphic marker in a nucleic acid sample obtained from the individual. In another embodiment, the method relates to determination of the presence or absence of at least one allele of at least one polymorhpic marker in a genotype dataset derived from the individual. The genotype dataset is derived from the individual in the sense that the information that is relates to a particular nucleic acid sample as a template relates to a single individual, for whom genetic information is derived.

In another aspect, the present invention relates to a method of determining a susceptibility to cardiovascular disease in a human individual, comprising determining the presence or absence of at least one allele of at least one polymorphic marker in a nucleic acid sample obtained from the individual, wherein the at least one polymorphic marker is selected from markers associated with LD Block C09 (SEQ ID NO:94), wherein determination of the presence or absence of the at least one allele is indicative of a susceptibility to cardiovascular disease. In one embodiment, the at least one polymorphic marker is selected from the markers set forth in Table 3, and markers in linkage disequilibrium therewith.

In an alternative aspect, the invention relates to a method of diagnosing a susceptibility to Cardiovascular Disease in a human individual, the method comprising determining the presence or absence of at least one allele of at least one polymorphic marker in a nucleic acid sample obtained from the individual, or in a genotype dataset derived from the individual, wherein the at least one polymorphic marker is selected from the group of markers associated with LD block C09, wherein the presence of the at least one allele is indicative of a susceptibility to Cardiovascular Disease. In one embodiment, linkage disequilibrium is used as a quantitative measure of the degree to which specific markers are associated with LD Block C09.

In another aspect, the invention relates to a method of determining a susceptibility to cardiovascular disease in a human individual, comprising determining whether at least one at-risk allele in at least one polymorphic marker is present in a genotype dataset derived from the individual, wherein the at least one polymorphic marker is selected from the markers within the LD Block C09 (SEQ ID NO:94), and markers in linkage disequilibrium therewith, and wherein determination of the presence of the at least one at-risk allele is indicative of increased susceptibility to cardiovascular disease in the individual.

The genotype dataset comprises in one embodiment information about marker identity, and the allelic status of the individual, i.e. information about the identity of the two alleles carried by the individual for the marker. The genotype dataset may comprise allelic information about one or more marker, including two or more markers, three or more markers, five or more markers, one hundred or more markers, etc. In some embodiments, the genotype dataset comprises genotype information from a whole-genome assessment of the individual including hundreds of thousands of markers, or even one million or more markers.

In one embodiment, the at least one polymorphic marker is present within the genomic segment LD Block C09, with the nucleotide sequence as set forth in SEQ ID NO:94. In another embodiment, the at least one polymorphic marker comprises at least one marker selected from rs7041637, rs2811712, rs3218018, rs3217992, rs2069426, rs2069422, rs1333034, rs1011970, rs10116277, rs1333040, rs2383207, rs1333050, D9S1814, rs10757278, rs10757274, rs1333049, D9S1870, and markers in linkage disequilibrium therewith. In another embodiment, the at least one polymorphic marker is selected from rs10757278, rs10757274, and rs10333049, and markers in linkage disequilibrium therewith. In another embodiment, the at least one polymorphic marker comprises at least one marker in strong linkage disequilibrium, as defined by numeric values for |D'| of greater than 0.8 and/or r$^2$ of greater than 0.2, with one or more markers selected from the group consisting of the markers set forth in Table 3.

In one embodiment, the method of determining a susceptibility, or diagnosing a susceptibility of, cardiovascular disease, further comprises assessing the frequency of at least one haplotype in the individual. In one such embodiment, the at least one haplotype is selected from the haplotypes that comprise at least one polymorphic marker within the genomic segment LD Block C09 (SEQ ID NO:94). In another embodiment, the at least one haplotype is selected from haplotypes that are in linkage disequilibrium with at least one marker as set forth in Table 3. In another embodiment, the at least one haplotype is selected from the haplotypes that comprise at least one polymorphic marker selected from at least one marker selected from rs7041637, rs2811712, rs3218018, rs3217992, rs2069426, rs2069422, rs1333034, rs1011970, rs10116277, rs1333040, rs2383207, rs1333050, D9S1814, rs10757278, rs10757274, rs10333049, rs1333049, D9S1870, and markers in linkage disequilibrium therewith.

In another aspect, the invention relates to a method of determining a susceptibility to Cardiovascular disease in a human individual, comprising determining whether at least one at-risk allele in at least one polymorphic marker is present in a genotype dataset derived from the individual, wherein the at least one polymorphic marker is selected from the markers set forth in Table 3, and markers in linkage disequilibrium therewith, and wherein determination of the presence of the at least one at-risk allele is indicative of increased susceptibility to Cardiovascular disease in the individual. The genotype dataset comprises in one embodiment information about marker identity, and the allelic status of the individual, i.e. information about the identity of the two alleles carried by the individual for the marker. The genotype dataset may comprise allelic information about one or more marker, including two or more markers, three or more markers, five or more markers, one hundred or more markers, etc. In some embodiments, the genotype dataset comprises genotype information from a whole-genome assessment of the individual including hundreds of thousands of markers, or even one million or more markers.

In one embodiment, the at least one polymorphic marker is present within SEQ ID NO:94, as set forth herein. In another embodiment, the at least one polymorphic marker comprises at least one marker selected from rs7041637, rs2811712, rs3218018, rs3217992, rs2069426, rs2069422, rs1333034, rs1011970, rs10116277, rs1333040, rs2383207, rs1333050, D9S1814, rs10757278, rs10757274, rs1333049, D9S1870, and markers in linkage disequilibrium therewith. In another embodiment, the at least one polymorphic marker comprises at least one marker in strong linkage disequilibrium, as defined by numeric values for |D'| of greater than 0.8 and/or r$^2$ of greater than 0.2, with one or more markers selected from the group consisting of the markers set forth in Table 3. In one preferred embodiment, the at least one polymorphic marker is selected from markers rs10757278, rs10757274, and rs1333049, and markers in linkage disequilibrium therewith. In another preferred embodiment, the at least one polymorphic marker is selected from markers rs10757278, rs10757274, and rs1333049. In yet another embodiment, the at least one polymorphic marker is selected from markers associated with LD Block C09 (SEQ ID NO:94). In one such embodiment, the at least one polymorphic marker is in linkage disequilibrium with at least one polymorphic marker within LD Block C09 (SEQ ID NO:94).

In one embodiment, the method of determining a susceptibility, or diagnosing a susceptibility of, Cardiovascular disease, further comprises assessing the frequency of at least one haplotype in the individual. In one such embodiment, the at least one haplotype is selected from the haplotypes that comprise at least one polymorphic marker as set forth in Table 10, and polymorphic markers in linkage disequilibrium therewith. In another embodiment, the at least one haplotype is selected from the haplotypes that comprise at least one polymorphic marker as set forth in Table 3, and polymorphic markers in linkage disequilibrium therewith. In another embodiment, the at least one haplotype is selected from the haplotypes that comprise at least one polymorphic marker selected from rs7041637, rs2811712, rs3218018, rs3217992, rs2069426, rs2069422, rs1333034, rs1011970, rs10116277, rs1333040, rs2383207, rs1333050, D9S1814, rs10757278, rs10757274, rs10333049, D9S1870, and markers in linkage disequilibrium therewith.

In certain embodiments of the invention, determination of the presence of at least one at-risk allele of at least one polymorphic marker in a nucleic acid sample from the individual is indicative of an increased susceptibility to the Cardiovascular disease. In one embodiment, the increased susceptibility is characterized by a relative risk (RR) or odds ratio (OR) of at least 1.15. In another embodiment, the increased susceptibility is characterized by a relative risk (RR) or odds ratio (OR) of at least 1.20. In another embodiment, the increased susceptibility is characterized by a relative risk (RR) or odds ratio (OR) of at least 1.30.

In some embodiments, the presence of rs7041637 allele A, rs2811712 allele A, rs3218018 allele A, rs3217992 allele A, rs2069426 allele C, rs2069422 allele A, rs1333034 allele A, rs1011970 allele G, rs10116277 allele T, rs1333040 allele T, rs2383207 allele G, rs1333050 allele T, D9S1814 allele 0, rs10757278 allele G, rs1333049 allele C, rs10757274 allele G, and/or D9S1870 allele X (composite allele of all alleles smaller than 2) is indicative of increased susceptibility of the Cardiovascular disease.

In particular embodiments, the presence of at least one protective allele in a nucleic acid sample from the individual is indicative of a decreased susceptibility of Cardiovascular disease. In another embodiment, the absence of at least one at-risk allele in a nucleic acid sample from the individual is indicative of a decreased susceptibility of Cardiovascular disease.

Another aspect of the invention relates to a method of assessing a susceptibility to Cardiovascular disease in a human individual, comprising screening a nucleic acid from the individual for at least one polymorphic marker or haplotype in the genomic segment with the sequence as set forth in SEQ ID NO:94, that correlates with increased occurrence of Cardiovascular disease in a human population, wherein the presence of an at-risk marker allele in the at least one polymorphism or an at-risk haplotype in the nucleic acid identifies the individual as having elevated susceptibility to the Cardiovascular disease, and wherein the absence of the at least one at-risk marker allele or at-risk haplotype in the nucleic acid identifies the individual as not having the elevated susceptibility.

In one such embodiment, the at least one polymorphic marker or haplotype comprises at least one polymorphic marker selected from the markers set forth in Table 10, and polymorphic markers in linkage disequilibrium therewith. In another embodiment, the at least one marker or haplotype comprises at least one polymorphic marker selected from the markers set forth in Table 3, and polymorphic markers in linkage disequilibrium therewith. In another embodiment, the at least one polymorphic marker or haplotype comprises at least one polymorphic marker selected from the markers rs7041637, rs2811712, rs3218018, rs3217992, rs2069426, rs2069422, rs1333034, rs1011970, rs10116277, rs1333040, rs2383207, rs1333050, D9S1814, rs10757278, rs10757274, rs10333049, D9S1870, and markers in linkage disequilibrium therewith. In certain embodiments, linkage disequilibrium is characterized by numeric values for |D'| of greater than 0.8 and/or $r^2$ of greater than 0.2.

Certain embodiments of the invention further comprise a step of screening the nucleic acid for the presence of at least one at-risk genetic variant for a Cardiovascular disease not associated with LD Block C09 (SEQ ID NO:94). Such additional genetic variants can in specific embodiments include any variant that has been identified as a susceptibility or risk variant for Cardiovascular disease.

In another aspect of the present invention, the presence of the marker or haplotype found to be associated with Cardiovascular disease, and as such useful for determining a susceptibility to Cardiovascular disease, is indicative of a different response rate of the subject to a particular treatment modality for Cardiovascular disease.

In another aspect, the invention relates to a method of identification of a marker for use in assessing susceptibility to a Cardiovascular disease in human individuals, the method comprising:
  identifying at least one polymorphic marker in linkage disequilibrium with at least one of the markers within LD Block C09 (SEQ ID NO:94);
  determining the genotype status of a sample of individuals diagnosed with, or having a susceptibility to, Cardiovascular disease; and
  determining the genotype status of a sample of control individuals;
wherein a significant difference in frequency of at least one allele in at least one polymorphism in individuals diagnosed with, or having a susceptibility to, the Cardiovascular disease, as compared with the frequency of the at least one allele in the control sample is indicative of the at least one polymorphism being useful for assessing susceptibility to the Cardiovascular disease.

In one embodiment, "significant" is determined by statistical means, e.g. the difference is statistically significant. In one such embodiment, statistical significance is characterized by a P-value of less than 0.05. In other embodiments, the statistical significance is characterized a P-value of less than 0.01, less than 0.001, less than 0.0001, less than 0.00001, less than 0.000001, less than 0.0000001, less than 0.0000000001, or less than 0.00000001.

In one embodiment, the at least one polymorphic marker is in linkage disequilibrium, as characterized by numerical values of $r^2$ of greater than 0.2 and/or |D'| of greater than 0.8 with at least one marker selected from markers set forth in Table 21. In another embodiment, the at least one polymorphic marker is in linkage disequilibrium, as characterized by numerical values of $r^2$ of greater than 0.2 and/or |D'| of greater than 0.8 with at least one marker selected from markers rs10757278, rs10757274, and rs1333049.

In one embodiment, an increase in frequency of the at least one allele in the at least one polymorphism in individuals diagnosed with, or having a susceptibility to, a Cardiovascular disease, as compared with the frequency of the at least one allele in the control sample, is indicative of the at least one polymorphism being useful for assessing increased susceptibility to the Cardiovascular disease. In another embodiment, a decrease in frequency of the at least one allele in the at least one polymorphism in individuals diagnosed with, or having a susceptibility to, a Cardiovascular disease, as compared with the frequency of the at least one allele in the control sample is indicative of the at least one polymorphism being useful for assessing decreased susceptibility to, or protection against, the Cardiovascular disease.

Another aspect of the invention relates to a method of genotyping a nucleic acid sample obtained from a human individual, comprising determining the presence or absence of at least one allele of at least one polymorphic marker in the sample, wherein the at least one marker is selected from the markers set forth in Table 3 and Table 21, and markers in linkage disequilibrium therewith, and wherein determination of the presence or absence of the at least one allele of the at least one polymorphic marker is predictive of a susceptibility of a Cardiovascular disease.

In one embodiment, genotyping comprises amplifying a segment of a nucleic acid that comprises the at least one polymorphic marker by Polymerase Chain Reaction (PCR), using a nucleotide primer pair flanking the at least one polymorphic marker. In another embodiment, genotyping is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, and single-stranded conformation analysis. In one particular embodiment, the process comprises allele-specific probe hybridization. In another embodiment, the process comprises DNA sequencing. In a preferred embodiment, the method comprises:
  1) contacting copies of the nucleic acid with a detection oligonucleotide probe and an enhancer oligonucleotide probe under conditions for specific hybridization of the oligonucleotide probe with the nucleic acid;
    wherein
    a) the detection oligonucleotide probe is from 5-100 nucleotides in length and specifically hybridizes to a first segment of the nucleic acid whose nucleotide sequence is given by SEQ ID NO:94 that comprises at least one polymorphic site;
    b) the detection oligonucleotide probe comprises a detectable label at its 3' terminus and a quenching moiety at its 5' terminus;
    c) the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; and
    d) a single base gap exists between the first segment and the second segment, such that when the oligonucleotide probe and the enhancer oligonucleotide probe are both hybridized to the nucleic acid, a single base gap exists between the oligonucleotides;
  2) treating the nucleic acid with an endonuclease that will cleave the detectable label from the 3' terminus of the detection probe to release free detectable label when the detection probe is hybridized to the nucleic acid; and
  3) measuring free detectable label, wherein the presence of the free detectable label indicates that the detection probe specifically hybridizes to the first segment of the nucleic acid, and indicates the sequence of the polymorphic site as the complement of the detection probe.

In a particular embodiment, the copies of the nucleic acid are provided by amplification by Polymerase Chain Reaction (PCR). In another embodiment, the susceptibility determined is increased susceptibility. In another embodiment, the susceptibility determined is decreased susceptibility.

Another aspect of the invention relates to a method of assessing an individual for probability of response to a therapeutic agent for preventing and/or ameliorating symptoms associated with a Cardiovascular disease, comprising: determining the presence or absence of at least one allele of at least one polymorphic marker in a nucleic acid sample obtained from the individual, wherein the at least one polymorphic marker is selected from the markers set forth in Table 21, and markers in linkage disequilibrium therewith, wherein determination of the presence of the at least one allele of the at least one marker is indicative of a probability of a positive response to the Cardiovascular disease therapeutic agent. In one embodiment, the at least one polymorphic marker is selected from marker rs1333040, rs10116277, rs2383207 and rs10757278, and markers in linkage disequilibrium therewith. In one embodiment, the therapeutic agent is selected from beta blockers, anticoagulation agents, including heparin and/or low molecular weight heparin, antiplatelet agents, such as clopidogrel, aspirin, beta blockers, including metoprolol and carvedilol, ACE inhibitors, Statins, Aldosterone antagonists, including eplerenone, leukotriene synthesis inhibitors, the agents set forth in Agent Table I, Agent Table II, (R)-(+)-alpha-cyclopentyl-4-(2-quinolinylmethoxy)-Benzeneacetic acid, atreleuton, and 4-{(S)-2-[4-(4-Chloro-phenoxy)-phenoxymethyl]-pyrrolidin-1-yl}-butyramide, also known as DG-051. Other embodiments may include any one or a combination of the therapeutic agents described herein to be useful for therapeutic intervention of Cardiovascular disease.

Yet another aspect of the invention relates to a method of predicting prognosis of an individual diagnosed with, a Cardiovascular disease, the method comprising determining the presence or absence of at least one allele of at least one polymorphic marker in a nucleic acid sample obtained from the individual, wherein the at least one polymorphic marker is selected from the group consisting of rs1333040, rs10116277, rs2383207 and rs10757278, and markers in linkage disequilibrium therewith, wherein determination of the presence of the at least one allele is indicative of a worse prognosis of the Cardiovascular disease in the individual. The prognosis may in certain embodiment relate to susceptibility of recurrent MI events, recurrent stroke events, or susceptibility to other complications relating to a Cardiovascular disease.

A further aspect of the invention relates to a method of monitoring progress of a treatment of an individual undergoing treatment for a Cardiovascular disease, the method comprising determining the presence or absence of at least one allele of at least one polymorphic marker in a nucleic acid sample obtained from the individual, wherein the at least one polymorphic marker is selected from the group consisting of rs1333040, rs10116277, rs2383207 and rs10757278, and markers in linkage disequilibrium therewith, wherein determination of the presence of the at least one allele is indicative of the treatment outcome of the individual. The treatment may in certain embodiments be surgical treatment. In other embodiments, the treatment is by administration of a therapeutic agent, optionally including lifestyle changes or alterations in environmental exposure to risk factors for cardiovascular disease, as described further herein.

In one embodiment, the method further comprises assessing at least one biomarker in a sample from the individual. The biomarker is in certain embodiments a cardiac marker or an inflammatory marker. In one embodiment, the at least one biomarker is selected from creatin kinase, troponin, glycogen phosphorylase, C-reactive protein (CRP), serum amyloid A, fibrinogen, interleukin-6, tissue necrosis factor-alpha, soluble vascular cell adhesion molecules (sVCAM), soluble intervascular adhesion molecules (sICAM), E-selectin, matrix metalloprotease type-1, matrix metalloprotease type-2, matrix metalloprotease type-3, matrix metalloprotease type-9, serum sCD40L, leukotrienes, leukotriene metabolites, interleukin-6, tissue necrosis factor-alpha, myeloperoxidase (MPO), and N-tyrosine. In one embodiment, the leukotriene is selected from LTB4, LTC4, LTD4 and LTE4. In another embodiment, the method further comprises analyzing non-genetic information to make risk assessment, diagnosis, or prognosis of the individual. The non-genetic information is in one embodiment selected from age, gender, ethnicity, socioeconomic status, previous disease diagnosis, medical history of subject, family history of Cardiovascular disease, biochemical measurements, and clinical measurements. In a particular preferred embodiment, a further step comprising calculating overall risk is employed.

Another aspect of the invention relates to analyzing a sample comprising genomic DNA from a human individual or a genotype dataset derived from a human individual for the presence or absence of at least one at-risk allele of at least one at-risk variant for cardiovascular disease not in linkage disequilibrium with any one of the markers set forth in Table 10. Thus, the variants described herein to be associated with Cardiovascular disease may be combined with other genetic variants for Cardiovascular disease, that are not genetically related (i.e., not in linkage disequilibrium with) the markers described herein Such analysis may be undertaken in combination with any of the methods described herein. Furthermore any two markers herein, or any other combination of markers and/or haplotypes described herein to be associated with cardiovascular disease may be combined to assess an increased susceptibility to cardiovascular disease.

In some embodiments of the methods of the invention, non-genetic information is analyzed, to make risk assessment, diagnosis, or prognosis of the individual. The non-genetic information is in certain embodiments selected from age, gender, ethnicity, socioeconomic status, previous disease diagnosis, medical history of subject, family history of cardiovascular disease, biochemical measurements, and clinical measurements. Combined genetic factors and/or combinations of genetic and non-genetic factors may be analyzed by known methods, to generate a combined risk.

The invention also relates to a kit for assessing susceptibility to a Cardiovascular disease in a human individual, the kit comprising reagents for selectively detecting the presence or absence of at least one allele of at least one polymorphic marker in the genome of the individual, wherein the polymorphic marker is selected from the markers set forth in Tables 10, and markers in linkage disequilibrium therewith, and wherein the presence of the at least one allele is indicative of a susceptibility to a Cardiovascular diseases.

In one embodiment, the at least one polymorphic marker is present within the genomic segment with the sequence as set forth in SEQ ID NO:94. In another embodiment, the at least one polymorphic marker is selected from the group of markers set forth in Table 21, and markers in linkage disequilibrium therewith. In another embodiment, the at least one polymorphic markers is selected from rs1333040, rs10116277, rs2383207 and rs10757278, and markers in linkage disequilibrium therewith.

In one embodiment, the reagents comprise at least one contiguous oligonucleotide that hybridizes to a fragment of the genome of the individual comprising the at least one polymorphic marker, a buffer and a detectable label. In one embodiment, the reagents comprise at least one pair of oligonucleotides that hybridize to opposite strands of a genomic nucleic acid segment obtained from the subject, wherein each oligonucleotide primer pair is designed to selectively amplify a fragment of the genome of the individual that includes one polymorphic marker, and wherein the fragment is at least 30 base pairs in size. In a particular embodiment the at least one oligonucleotide is completely complementary to the genome of the individual. In another embodiment, the at least one oligonucleotide can comprise at least one mismatch to the genome of the individual. In one embodiment, the oligonucleotide is about 18 to about 50 nucleotides in length. In another embodiment, the oligonucleotide is 20-30 nucleotides in length.

In one preferred embodiment, the kit comprises:
a detection oligonucleotide probe that is from 5-100 nucleotides in length; an enhancer oligonucleotide probe that is from 5-100 nucleotides in length; and an endonuclease enzyme;
wherein the detection oligonucleotide probe specifically hybridizes to a first segment of the nucleic acid whose nucleotide sequence is given by SEQ ID NO:94 that comprises at least one polymorphic site; and wherein the detection oligonucleotide probe comprises a detectable label at its 3' terminus and a quenching moiety at its 5' terminus; wherein the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; wherein a single base gap exists between the first segment and the second segment, such that when the oligonucleotide probe and the enhancer oligonucleotide probe are both hybridized to the nucleic acid, a single base gap exists between the oligonucleotides; and wherein treating the nucleic acid with the endonuclease will cleave the detectable label from the 3' terminus of the detection probe to release free detectable label when the detection probe is hybridized to the nucleic acid.

A further aspect of the invention relates to the use of an oligonucleotide probe in the manufacture of a diagnostic reagent for diagnosing and/or assessing susceptibility to Cardiovascular disease in a human individual, wherein the probe hybridizes to a segment of a nucleic acid whose nucleotide sequence is given by SEQ ID NO: 94 that comprises at least one polymorphic site, wherein the fragment is 15-500 nucleotides in length. In one embodiment, the polymorphic site is selected from the polymorphic markers rs1333040, rs10116277, rs2383207 and rs10757278, and markers in linkage disequilibrium therewith Yet another aspect of the invention relates to a computer-readable medium on which is stored: an identifier for at least one polymorphic marker; an indicator of the frequency of at least one allele of said at least one polymorphic marker in a plurality of individuals diagnosed with a Cardiovascular disease; and an indicator of the frequency of the least one allele of said at least one polymorphic markers in a plurality of reference individuals; wherein the at least one polymorphic marker is selected from the polymorphic markers set forth in Table 10, and markers in linkage disequilibrium therewith. In one embodiment, the at least one polymorphic marker is selected from rs1333040, rs10116277, rs2383207 and rs10757278, and markers in linkage disequilibrium therewith.

Another aspect relates to an apparatus for determining a genetic indicator for Type 2 diabetes in a human individual, comprising: a computer readable memory; and a routine stored on the computer readable memory; wherein the routine is adapted to be executed on a processor to analyze marker and/or haplotype information for at least one human individual with respect to at least one polymorphic marker selected from the markers set forth in Table 10, and markers in linkage disequilibrium therewith, and generate an output based on the marker or haplotype information, wherein the output comprises a risk measure of the at least one marker or haplotype as a genetic indicator of a Cardiovascular disease for the human individual.

In one embodiment, the routine further comprises an indicator of the frequency of at least one allele of at least one polymorphic marker or at least one haplotype in a plurality of individuals diagnosed with a Cardiovascular disease, and an indicator of the frequency of at the least one allele of at least one polymorphic marker or at least one haplotype in a plurality of reference individuals, and wherein a risk measure is based on a comparison of the at least one marker and/or haplotype status for the human individual to the indicator of the frequency of the at least one marker and/or haplotype information for the plurality of individuals diagnosed with the Cardiovascular disease.

The present invention, as described herein, may be reduced to practice using any one, or a combination of, the polymorphic markers described herein as being useful for the determination of a susceptibility to cardiovascular disease. This includes markers that are shown herein to be associated with cardiovascular disease, but also includes markers that are in linkage disequilibrium with such variants. In one embodiment, the at least one marker is selected from the markers set forth in any of the Tables 3, 10, 21 and 26. In another embodiment, the at least one marker is selected from the markers set forth in Table 10. In another embodiment, the at least one marker is selected from the markers set forth in Table 3 and Table 21. In another embodiment, the at least one marker is selected from the markers set forth in Table 3. In another embodiment, the at least one marker is selected from the markers set forth in Table 21. In another embodiment, the at least one marker is selected from markers in linkage disequilibrium with the CDKN2A and/or CDKN2B genes. In another embodiment, the at least one marker is selected from the markers rs10811650, rs10116277, rs1333040, rs10738607, rs4977574, rs6475608, D9S1870, rs2383207, rs1333045, rs1333046, rs10757278 and rs1333048. In another embodiment, the at least one marker is selected from the markers rs1333040, rs10116277, rs2383207 and rs10757278. In another embodiment the at least one marker is rs1333040 (SEQ ID NO:59). In another embodiment, the at least one marker is rs10116277 (SEQ ID NO:56). In another embodiment, the at least one marker is rs2383207 (SEQ ID NO:82). In another embodiment, the at least one marker is rs10757278 (SEQ ID NO:88). In some embodiments, the at least one marker is further optionally selected from markers in linkage disequilibrium with any on or a combination of more than one of the above mentioned markers.

The Cardiovascular disease in the various aspects of the invention relating to methods, uses, apparatus or kits is in some embodiments an arterial disease. In one such embodiment, the arterial disease phenotype is selected from Myocardial Infarction, Acute Coronary Syndrome (ACS), Coronary Artery Disease, Stroke, Peripheral Artery Disease, Restenosis, Intracranial Aneurysm and Aorta Abdominal Aneurysm, transluminal coronary angioplasty (PTCA), and coronary artery bypass surgery (CABG). In one embodiment, the Cardiovascular disease is Myocardial Infarction. In another embodiment, the Cardiovascular disease is Myocardial Infarction or Coronary Artery Disease. In yet another embodiment, the Cardiovascular disease is Myocardial Infarction, Coronary Artery Disease, Aorta Abdominal Aneurysm or Intracranial Aneurysm. In another embodiment, the Cardiovascular Disease is Myocardial Infarction, Coronary Artery Disease, Restenosis, Aorta Abdominal Aneurysm or Intracranial Aneurysm. In one embodiment, the Stroke phenotype is Large Artery Atherosclerotic Stroke and/or Cardiogenic Stroke. The Restenosis phenotype is in one embodiment Coronary In-stent Restenosis. In certain embodiments, the In-stent Restenosis is either Restenosis following Bare Metal Stent (BMS) placement, or it is Restenosis following placement of a Drug Eluting Stent (DES).

Variants (markers and/or haplotypes comprising polymorphic markers) in linkage disequilibrium with the markers and haplotypes of the present invention are also useful for the methods and kits of the invention. The invention therefore also pertains to markers in linkage disequilibrium with the markers and haplotypes of the invention. In certain embodiments of the methods, uses, apparatus or kits of the invention, linkage disequilibrium is characterized by specific cutoff values for a quantitative measure of linkage disequilibrium. In one such embodiment, linkage disequilibrium is characterized by specific cutoff values for $r^2$. In another such embodiment, linkage disequilibrium is characterized by specific cutoff values for $|D'|$. In yet another embodiment, linkage disequilibrium is characterized by specific cutoff values for $r^2$ and $|D'|$. In one preferred embodiment, linkage disequilibrium is characterized by values for $r^2$ of greater than 0.1. In another preferred embodiment, linkage disequilibrium is characterized by values for $r^2$ of greater than 0.2. Other cutoff values for $r^2$ are also possible, including, but not limited to, 0.3, 0.4, 0.5, 0.6, 0.7, 0.8, 0.9, 0.95, 0.96, 0.97, 0.98, 0.99. In another preferred embodiment, linkage disequilibrium is characterized by values for $|D'|$ of greater than 0.5. In another preferred embodiment, linkage disequilibrium is characterized by values for $|D'|$ of greater than 0.8. Other cutoff values for $|D'|$ are also possible, including, but not limited to, 0.2, 0.3, 0.4, 0.6, 0.7, 0.8, 0.9, 0.95, 0.96, 0.97, 0.98 and 0.99. In certain embodiments, linkage disequilibrium is characterized by numeric cutoff values for either $|D'|$ and $r^2$. In one such embodiment linkage disequilibrium is characterized by numeric cutoff values for either $|D'|$ of greater than 0.8 and $r^2$ of greater than 0.2, or both.

In certain other embodiments of the methods, uses, apparatus or kits of the invention, the individual is of a specific human ancestry. In one embodiment, the ancestry is selected from black African ancestry, Caucasian ancestry and Chinese ancestry. In another embodiment, the ancestry is black African ancestry. In another embodiment, the ancestry is African American ancestry. In another embodiment, the ancestry is European ancestry. In another embodiment, the ancestry is Caucasian ancestry. The ancestry is in certain embodiment self-reported by the individual who undergoes genetic analysis or genotyping. In other embodiments, the ancestry is determined by genetic determination comprising detecting at least one allele of at least one polymorphic marker in a nucleic acid sample from the individual, wherein the presence or absence of the allele is indicative of the ancestry of the individual.

In other particular other embodiments of the methods, uses, apparatus or kits of the invention, the presence of at least one at-risk variant, i.e. an at-risk allele in at least one polymorphic marker or an at-risk haplotype, is indicative of an early onset of the Cardiovascular disease. Early onset is in some embodiments categorized as onset before age 75. In other embodiments, early onset is categorized as onset before age 70, before age 65, before age 60, before age 55, before age 50, before age 45, or before age 40. Other values for categorization of age at onset are also contemplated, including, but not limited to, all integer values of age, and such age categories are also within scope of the invention. In certain embodiments, the Cardiovascular disease is Myocardial Infarction, and the age at onset is below 50 for males and/or below 60 for females.

BRIEF DESCRIPTION OF THE DRAWINGS

The foregoing and other objects, features and advantages of the invention will be apparent from the following more particular description of preferred embodiments of the invention.

FIG. 1 shows a) Association results for 127 SNPs located in a 1 Mb interval (21.6-22.6 Mb, Build 34) on chromosome 9. Plotted is —log P, where P is the P-value adjusted for relatedness of the individual against the chromosomal location of the SNPs. b) The corresponding pair-wise correlation $r^2$ between 1004 common SNPs in the same region from the HapMap release 19 for the CEU population. c) Location of two recombination hot-spots based on the HapMap dataset (*Nature* 437, 1299-1320 (27 Oct. 2005)) that define the LD-block (position 21,920,147 to 21,149,982 in NCBI Build 36; SEQ ID NO:94 that includes the strongest association results. d) The pair-wise correlation structure in the region measured by D' for the same set of SNPs as used in panel b. All four panel use the same horizontal Mb scale indicated in panel a.

DETAILED DESCRIPTION OF THE INVENTION

A description of preferred embodiments of the invention follows.

Definitions

Unless otherwise indicated, nucleic acid sequences are written left to right in a 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by the ordinary person skilled in the art to which the invention pertains.

The following terms shall, in the present context, have the meaning as indicated:

A "polymorphic marker", sometime referred to as a "marker", as described herein, refers to a genomic polymorphic site. Each polymorphic marker has at least two sequence variations characteristic of particular alleles at the polymorphic site. Thus, genetic association to a polymorphic marker implies that there is association to at least one specific allele of that particular polymorphic marker. The marker can comprise any allele of any variant type found in the genome, including SNPs, microsatellites, insertions, deletions, duplications and translocations.

An "allele" refers to the nucleotide sequence of a given locus (position) on a chromosome. A polymorphic marker allele thus refers to the composition (i.e., sequence) of the marker on a chromosome. Genomic DNA from an individual contains two alleles (e.g., allele-specific sequences) for any given polymorphic marker, representative of each copy of the marker on each chromosome. Sequence codes for nucleotides used herein are: A=1, C=2, G=3, T=4. For microsatellite alleles, the CEPH sample (Centre d'Etudes du Polymorphisme Humain, genomics repository, CEPH sample 1347-02) is used as a reference, the shorter allele of each microsatellite in this sample is set as 0 and all other alleles in other samples are numbered in relation to this reference. Thus, e.g., allele 1 is 1 bp longer than the shorter allele in the CEPH sample, allele 2 is 2 bp longer than the shorter allele in the CEPH sample, allele 3 is 3 bp longer than the lower allele in the CEPH sample, etc., and allele −1 is 1 bp shorter than the shorter allele in the CEPH sample, allele −2 is 2 bp shorter than the shorter allele in the CEPH sample, etc.

Sequence conucleotide ambiguity as described herein is as proposed by IUPAC-IUB. These codes are compatible with the codes used by the EMBL, GenBank, and PIR databases.

| IUB code | Meaning |
| --- | --- |
| A | Adenosine |
| C | Cytidine |
| G | Guanine |
| T | Thymidine |
| R | G or A |
| Y | T or C |
| K | G or T |
| M | A or C |
| S | G or C |
| W | A or T |
| B | C G or T |
| D | A G or T |
| H | A C or T |
| V | A C or G |
| N | A C G or T (Any base) |

A nucleotide position at which more than one sequence is possible in a population (either a natural population or a synthetic population, e.g., a library of synthetic molecules) is referred to herein as a "polymorphic site".

A "Single Nucleotide Polymorphism" or "SNP" is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI).

A "variant", as described herein, refers to a segment of DNA that differs from the reference DNA. A "marker" or a "polymorphic marker", as defined herein, is a variant. Alleles that differ from the reference are referred to as "variant" alleles.

A "microsatellite" is a polymorphic marker that has multiple small repeats of bases that are 2-8 nucleotides in length (such as CA repeats) at a particular site, in which the number of repeat lengths varies in the general population. An "indel" is a common form of polymorphism comprising a small insertion or deletion that is typically only a few nucleotides long.

A "haplotype," as described herein, refers to a segment of genomic DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles. Haplotypes are described herein in the context of the marker name and the allele of the marker in that haplotype, e.g., "G rs10757278" refers to the 3 allele of marker rs10757278 being in the haplotype, and is equivalent to "rs10757278 allele G". Furthermore, allelic codes in haplotypes are as for individual markers, i.e. 1=A, 2=C, 3=G and 4=T.

The term "susceptibility", as described herein, refers to an individual (or group of individuals) being prone to developing a certain state (e.g., a certain trait, phenotype or disease), or being less able to resist a particular state than the average individual. The term encompasses both increased susceptibility and decreased susceptibility. Thus, particular alleles at polymorphic markers and/or haplotypes of the invention as described herein may be characteristic of increased susceptibility (i.e., increased risk) of cardiovascular disease, as characterized by a relative risk (RR) or odds ratio (OR) of greater than one for the particular allele or haplotype. Alternatively, the markers and/or haplotypes of the invention are characteristic of decreased susceptibility (i.e., decreased risk) of cardiovascular disease, as characterized by a relative risk of less than one.

The term "and/or" shall in the present context be understood to indicate that either or both of the items connected by it are involved. In other words, the term herein shall be taken to mean "one or the other or both".

The term "look-up table", as described herein, is a table that correlates one form of data to another form, or one or more forms of data to a predicted outcome to which the data is relevant, such as phenotype or trait. For example, a look-up table can comprise a correlation between allelic data for at least one polymorphic marker and a particular trait or phenotype, such as a particular disease diagnosis, that an individual who comprises the particular allelic data is likely to display, or is more likely to display than individuals who do not comprise the particular allelic data. Look-up tables can be multidimensional, i.e. they can contain information about multiple alleles for single markers simultaneously, or they can contain information about multiple markers, and they may also comprise other factors, such as particulars about diseases diagnoses, racial information, biomarkers, biochemical measurements, therapeutic methods or drugs, etc.

A "computer-readable medium", is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

A "nucleic acid sample" is a sample obtained from an individuals that contains nucleic acid. In certain embodiments, i.e. the detection of specific polymorphic markers and/or haplotypes, the nucleic acid sample comprises genomic DNA. Such a nucleic acid sample can be obtained from any source that contains genomic DNA, including as a blood sample, sample of amniotic fluid, sample of cerebrospinal fluid, or tissue sample from skin, muscle, buccal or conjunctival mucosa, placenta, gastrointestinal tract or other organs.

The term "cardiovascular disease therapeutic agent", as described herein, refers to an agent that can be used to ameliorate or prevent symptoms associated with a cardiovascular disease.

The term "coronary artery disease therapeutic agent", as described herein, refers to an agent that can be used to ameliorate or prevent symptoms associated with coronary artery disease. Such agents can for example be statins, beta blockers, calcium channel blockers, cardiac glycosides, antihypertensive agents, diuretics, agents acting on the renin-angiotensin system, and aspirin.

The term "coronary stenosis" or "coronary stenosis therapeutic method", as described herein, refers to methods that can be used to ameliorate or prevent symptoms associated with coronary artery disease. Such methods can be balloon angioplasty, stenting, cutting balloon angioplasty, percutaneous transluminal coronary angioplasty (PTCA), directional coronary atherectomy, rotational coronary atherectomy, brachytherapy, drug-eluting stent (DES) insertion, metal stent insertion, or coronary artery surgeries, such as Coronary Artery Bypass Surgery (CABG).

The term "cardiovascular disease-associated nucleic acid", as described herein, refers to a nucleic acid that has been found to be associated to cardiovascular disease. This includes, but is not limited to, the markers and haplotypes described herein and markers and haplotypes in strong linkage disequilibrium (LD) therewith.

The term "LD Block C09", as described herein, refers to the Linkage Disequilibrium (LD) block on Chromosome 9 between positions 21,920,147 and 22,149,982 base pairs on Chromosome 9 of NCBI (National Center for Biotechnology Information) Build 34, Build 35 and Build 36. The nucleotide sequence of the LD Block region from these Builds is set forth in SEQ ID NO:94.

The term "cardiovascular disease", as described herein, refers to the class of diseases that involve the heart or blood vessels (arteries and veins). In one embodiment, the invention pertains to arterial disease, which relate to atherosclerotic events, which are believed to have similar causes and mechanisms. Cardiovascular diseases have certain common risk factors (age, smoking, Diabetes mellitus, hypercholesterolemia, obesity, high blood pressure, stress, depression, elevated heart rate, sleep deprivation, environmental exposure).

The abbreviations "PCTA", "CABG", "MI", "PAD", "CAD", "LAA", "IA", and "AAA", as described herein, refer to the following: "PCTA" refers to Transluminal Coronary Angiopathy, "CABG" refers to Coronary Artery Bypass Surgery, "MI" refers to Myocardial Infarction, "PAD" refers to Peripheral Artery Disease, "CAD" refers to Coronary Artery Disease, "LAA Stroke" refers to Large Artery Atherosclerotic Stroke, "IA" refers to Intracranial Aneurysm and "AAA" refers to Abdominal Aortic Aneurysm.

The term "early onset", as described herein, refers to onset of a disease that is lower than is typically observed. In the present exemplary context, the term, as applied to the MI phenotype, is defined as a MI event before the age of 50 for males and before the age of 60 for females. The term can, in alternative embodiments of the invention, be defined in alternative manner as known to the skilled person and described in further detail herein.

Association of Genetic Variants to Coronary Artery Disease

Through an association study between SNP markers on a chip containing approximately 317,000 such SNPs, the present invention has identified association of certain markers on chromosome 9 with cardiovascular diseases. The original discovery was made when an analysis of SNP data from patients diagnosed with Myocardial Infarction was made, as illustrated in Table 1 and Table 12. Several markers in a region described herein as LD block C09 were found to be strongly associated with MI, with RR values as high as 1.2. Two microsatellites within the region, D9S1814 and D9S1870, were found also to be correlated with the MI phenotype. The composite allele X of D9S1870 (a composite of all alleles shorter than 2 (alleles, −6, −4, −2 and 0, respectively), was found to associate strongly with MI (Table 1). Further investigations identified close to 90 additional markers that are strongly correlated with the five markers giving strongest association to MI (rs10116277, rs1333040, rs2383207, D9S1814 and D9S1870; see Table 3). These markers could thus serve as surrogate markers for any of these five markers and therefore be used in the methods of the present invention.

The D9S1870 marker was subsequently genotyped in a very large sample of individuals (over 70,000), including additional MI cases as well as other cardiovascular diseases, plus tenths of thousands of additional population controls. A replication study in three cohorts from the US was also performed, all containing individuals of Caucasian origin. Results of these studies for the phenotype MI revealed replication of the original finding (Table 4 and 12-14), with a combined p-value of approximately $10^{-12}$. The corresponding population attributable risk is about 17% for this variant.

Further studies of this variant revealed a significant correlation to age at onset of MI. Arbitrarily defining early-onset MI as MI before age 50 for males and below age 60 for females revealed an increase in this early-onset group of 1.33, compared to 1.21 for all MI cases. Multiple regression of the number of copies of the composite X allele of D9S1870 and the age of onset of MI revealed a very significant decrease in age at onset for each copy of X carried by the MI individuals (Table 8). This shows that other definitions of age at onset of MI than the cutoff of 50 for males and 60 for females could also be used for detecting this trend in age at onset with carrier status for the X allele.

The present invention has also identified association between other cardiovascular diseases and variants within the LD block C09, using the X allele of D9S1870 as surrogate marker. Thus significant association was found to Peripheral Artery Disease (PAD), even after removing individuals diagnosed with MI from the PAD cohort. We also observed increased risk of Stroke as broad phenotype, as well as the Stroke subphenotype Large Vessel disease (LVD) (Table 5 and Table 29). We have also investigated association of the at-risk variants to the related disorders peripheral artery disease (PAD) and abdominal aorta aneurysm (AAA) As can be seen in Table 29, these markers are associated with these related disorders. The association is particularly compelling for AAA, wherein significant association is observed for a large number of markers in addition to these three, as shown in Table 30. These results illustrate that the markers and haplotypes of the invention are indeed reflective of disorders related to coronary artery disease, MI and in-stent restenosis, such as abdominal aorta aneurysm.

A further analysis of individuals with diagnosis of in-stent restenosis was performed (Table 9). Significant association was detected for both mild restenosis (<50%) and severe restenosis (>50%). This indicates that the present invention can be used to indicate which individuals are at increased risk of in-stent restenosis after undergoing transluminal coronary angioplasty (PTCA).

The known genes located within the LD block C09, are called CDKN2A and CDKN2B. These genes encode three proteins that are known as ARF (also known as $p19^{ARF}$ and $p14^{ARF}$), $p15^{INK4b}$ and $p16^{INK4a}$, all of which encode tumor suppressor proteins. $p15^{INK4b}$ has its own open reading frame, but $p16^{INK4a}$ and ARF have different first exons that are spliced to a common second and third exons. Despite the sharing of exons between $p16^{INK4a}$ and ARF the proteins are encoded in different reading frames. Therefore, $p16^{INK4a}$ and ARF are proteins that do not share homology. The products of these genes have been extensively studied and are known to play a widespread role in tumor suppression. Recent data has suggested that the ARF, $p15^{INK4b}$ and $p16^{INK4a}$ locus also has a role in aging of cells, i.e. the decline of replicative potential of self-renewing cells. Several groups have shown that the expression of $p16^{INK4a}$ increases with aging in many tissues of rodents and humans. It has even been proposed that the expression of $p16^{INK4a}$ could be used as a biomarker of physiologic, as opposed to chronologic age.

Human cancers frequently have homozygous deletions of the ARF, $p15^{INK4b}$ and $p16^{INK4a}$ locus with reduced expression of all three proteins, and decreased tumor suppressor activity. Knock-out studies of mice deficient for ARF, $p15^{INK4b}$ or $p16^{INK4a}$ have revealed that these strains are more prone to cancers than wild-type mice. Furthermore, mice with overexpression of the ARF, $p15^{INK4b}$ or $p16^{INK4a}$ locus show reduction in incidence of spontaneous cancers. Since cancer is the principal cause of death in mice on this background one may argue that the tumor resistance of the mice overexpressing the ARF, $p15^{INK4b}$ or $p16^{INK4a}$ locus would also lead to longer lifespan of these mice. However, this is not the case since these mice demonstrate a normal lifespan. This may suggest that the increased ARF, $p15^{INK4b}$ or $p16^{INK4a}$ locus function and diminished tumor incidence may come at the expense of excess mortality from non-malignant causes related to aging (Cell, 127, Oct. 20, 2006), such as atherosclerotic disease.

Sequencing of the exons of CDKN2A and CDKN2B regions, including exons, exon-intron junctions and potential regulatory regions was performed using the primers as indicated in Table 12, resulting in the identification of a number of SNPs, as shown in Table 13. Three of those SNPs were not found in public databases, and the flanking sequences of those SNPs are indicated in Table 14. As it is possible that SNP markers or other polymorphisms in LD with the markers found to be associating to MI in this region of chromosome 9 show association with a higher risk, we genotyped these additional markers by sequencing, as indicated in Table 13. Several of the markers show association to MI with RR values as high as 1.7-1.8, in particular markers SG09S291 and rs2069416. These markers, and/or other markers within the CDKN2A and CDKN2B genes that are in LD with the markers of the present invention as described herein, are thus also within the scope of the invention, as those markers may represent either true disease-causing variants, or variants in strong LD with an underlying causative variant(s).

Investigation of association of the rs10757278 variant to Intracranial Aneurysm shows significant association to this phenotype in the original Icelandic cohort, as well as replication in independent cohorts from the Netherlands and Finland (e.g., Table 32). Furthermore, the original finding of association to AAA was replicated in several cohorts from Belgium, Canada, USA, Netherlands, UK and New Zealand (Table 32). These results show that the rs10757278 marker, and markers in LD therewith, are indeed significantly associated with cardiovascular disorders, including the arterial diseases than myocardial infarction, peripheral artery disease, stroke, intracranial aneurysm and abdominal aortic aneurysm.

The original discovery of the association between variants on chromosome 9p21 and cardiovascular diseases described herein (see also Helgadottir, A., et. al., *Science* 316:1491-3 2007) has been replicated in several independent studies, including studies of subjects with CAD and controls. The association with CAD/MI in Caucasians has been replicated in 4,251 cases and 4,443 controls of the PROCARDIS Consortium (*Hum Mol Genet*. Epub 2007 Nov. 29), in an Italian population including 416 MI cases and 308 controls (*J Hum Genet*. 2008; 53(2):144-50. Epub 2007 Dec. 8), in participants of the Framingham Heart Study (*BMC Med Genet*. 2007 Sep. 19; 8 Suppl 1:55), and in the Northwick Park Heart Study II (*Clin Chem*. Epub 2008 Feb. 4). The association of rs10757278, as well as other correlated SNPs, with CAD has also been confirmed in Asian populations from Japan and Korea with comparable odds ratios as published for Caucasians (see *Arterioscler Thromb Vasc Biol*. 2008 February; 28(2):360-5. Epub 2007 Nov. 29, and *J Hum Genet*. Epub 2008 Feb. 9). These studies, together with the data shown herein, clearly indicate that variants within the LD Block C09 region on Chromosome 9p21 are associated with cardiovascular disease in all populations.

Assessment for Markers and Haplotypes

The genomic sequence within populations is not identical when individuals are compared. Rather, the genome exhibits sequence variability between individuals at many locations in the genome. Such variations in sequence are commonly referred to as polymorphisms, and there are many such sites within each genome For example, the human genome exhibits sequence variations which occur on average every 500 base pairs. The most common sequence variant consists of base variations at a single base position in the genome, and such sequence variants, or polymorphisms, are commonly called Single Nucleotide Polymorphisms ("SNPs"). These SNPs are believed to have occurred in a single mutational event, and therefore there are usually two possible alleles possible at each SNPsite; the original allele and the mutated allele. Due to natural genetic drift and possibly also selective pressure, the original mutation has resulted in a polymorphism characterized by a particular frequency of its alleles in any given population. Many other types of sequence variants are found in the human genome, including microsatellites, insertions, deletions, inversions and copy number variations. A polymorphic microsatellite has multiple small repeats of bases (such as CA repeats, TG on the complimentary strand) at a particular site in which the number of repeat lengths varies in the general population. In general terms, each version of the sequence with respect to the polymorphic site represents a specific allele of the polymorphic site. These sequence variants can all be referred to as polymorphisms, occurring at specific polymorphic sites characteristic of the sequence variant in question. In general terms, polymorphisms can comprise any number of specific alleles. Thus in one embodiment of the invention, the polymorphism is characterized by the presence of two or more alleles in any given population. In another embodiment, the polymorphism is characterized by the presence of three or more alleles. In other embodiments, the polymorphism is characterized by four or more alleles, five or more alleles, six or more alleles, seven or more alleles, nine or more alleles, or ten or more alleles. All such polymorphisms can be utilized in the methods and kits of the present invention, and are thus within the scope of the invention.

In some instances, reference is made to different alleles at a polymorphic site without choosing a reference allele. Alternatively, a reference sequence can be referred to for a particular polymorphic site. The reference allele is sometimes referred to as the "wild-type" allele and it usually is chosen as either the first sequenced allele or as the allele from a "non-affected" individual (e.g., an individual that does not display a trait or disease phenotype).

Alleles for SNP markers as referred to herein refer to the bases A, C, G or T as they occur at the polymorphic site in the SNP assay employed. The allele codes for SNPs used herein are as follows: 1=A, 2=C, 3=G, 4=T. The person skilled in the art will however realise that by assaying or reading the opposite DNA strand, the complementary allele can in each case be measured. Thus, for a polymorphic site (polymorphic marker) containing an A/G polymorphism, the assay employed may either measure the percentage or ratio of the two bases possible, i.e. A and G. Alternatively, by designing an assay that determines the opposite strand on the DNA template, the percentage or ratio of the complementary bases T/C can be measured. Quantitatively (for example, in terms of relative risk), identical results would be obtained from measurement of either DNA strand (+ strand or − strand). Polymorphic sites (polymorphic markers) can allow for differences in sequences based on substitutions, insertions or deletions. For example, a polymorphic microsatellite has multiple small repeats of bases (such as CA repeats) at a particular site in which the number of repeat lengths varies in the general population. Each version of the sequence with respect to the polymorphic site represents a specific allele of the polymorphic site.

Typically, a reference sequence is referred to for a particular sequence. Alleles that differ from the reference are referred to as "variant" alleles. For example, the genomic DNA sequence from position 21,920,147 to position 22,149,982 base pairs on Chromosome 9 of NCBI Build 34 ("LD black C09"; SEQ ID NO:94) represents a reference sequence. A variant sequence, as used herein, refers to a sequence that differs from the reference sequence but is otherwise substantially similar. Alleles at the polymorphic genetic markers that make up the haplotypes described herein are variants. Additional variants can include changes that affect a polypeptide. Sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence, as described in detail herein. Such sequence changes alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with coronary artery disease and in-stent restenosis or a susceptibility to coronary artery disease and in-stent restenosis can be a synonymous change in one or more nucleotides (i.e., a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level. The polypeptide encoded by the reference nucleotide sequence is the "reference" polypeptide with a particular reference amino acid sequence, and polypeptides encoded by variant alleles are referred to as "variant" polypeptides with variant amino acid sequences.

A haplotype refers to a segment of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles, each allele corresponding to a specific polymorphic marker along the segment. Haplotypes can comprise a combination of various polymorphic markers, e.g., SNPs and microsatellites, having particular alleles at the polymorphic sites. The haplotypes thus comprise a combination of alleles at various genetic markers.

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (e.g., Chen, X. et al., *Genome Res.* 9(5): 492-98 (1999); Kutyavin et al., *Nucleic Acid Res.* 34:e128 (2006)), utilizing PCR, LCR, Nested PCR and other techniques for nucleic acid amplification. Specific methodologies available for SNP genotyping include, but are not limited to, TaqMan genotyping assays and SNPlex platforms (Applied Biosystems), mass spectrometry (e.g., MassARRAY system from Sequenom), minisequencing methods, real-time PCR, Bio-Plex system (BioRad), CEQ and SNPstream systems (Beckman), Molecular Inversion Probe array technology (e.g., Affymetrix GeneChip), and BeadArray Technologies (e.g., Illumina GoldenGate and Infinium assays). By these or other methods available to the person skilled in the art, one or more alleles at polymorphic markers, including microsatellites, SNPs or other types of polymorphic markers, can be identified.

In certain methods described herein, an individual who is at an increased susceptibility (i.e., at risk) for cardiovascular disease is an individual in whom at least one specific allele at one or more polymorphic marker or haplotype conferring increased susceptibility for cardiovascular disease is identified (i.e., at-risk marker alleles or haplotypes). In one aspect, the at-risk marker or haplotype is one that confers a significant increased risk (or susceptibility) of cardiovascular disease. In one embodiment, significance associated with a marker or haplotype is measured by a relative risk. In one embodiment, significance associated with a marker or haplotype is measured by a relative risk (RR). In another embodiment, significance associated with a marker or haplotype is measured by an odds ratio (OR). In a further embodiment, the significance is measured by a percentage. In one embodiment, a significant increased risk is measured as a risk (relative risk and/or odds ratio) of at least 1.2, including but not limited to: at least 1.2, at least 1.3, at least 1.4, at least 1.5, at least 1.6, at least 1.7, 1.8, at least 1.9, at least 2.0, at least 2.5, at least 3.0, at least 4.0, and at least 5.0. In a particular embodiment, a risk (relative risk and/or odds ratio) of at least 1.2 is significant. In another particular embodiment, a risk of at least 1.3 is significant. In yet another embodiment, a risk of at least 1.4 is significant. In a further embodiment, a relative risk of at least 1.5 is significant. In another further embodiment, a significant increase in risk is at least 1.7 is significant. However, other cutoffs are also contemplated, e.g., at least 1.15, 1.25, 1.35, and so on, and such cutoffs are also within scope of the present invention. In other embodiments, a significant increase in risk is at least about 20%, including but not limited to about 25%, 30%, 35%, 40%, 45%, 50%, 55%, 60%, 65%, 70%, 75%, 80%, 85%, 90%, 95%, 100%, 150%, 200%, 300%, and 500%. In one particular embodiment, a significant increase in risk is at least 20%. In other embodiments, a significant increase in risk is at least 30%, at least 40%, at least 50%, at least 60%, at least 70%, at least 80%, at least 90% and at least 100%. Other cutoffs or ranges as deemed suitable by the person skilled in the art to characterize the invention are however also contemplated, and those are also within scope of the present invention. In certain embodiments, a significant increase in risk is characterized by a p-value, such as a p-value of less than 0.05, less than 0.01, less than 0.001, less than 0.0001, less than 0.00001, less than 0.000001, less than 0.0000001, less than 0.00000001, or less than 0.000000001.

An at-risk polymorphic marker or haplotype of the present invention is one where at least one allele of at least one marker or haplotype is more frequently present in an individual at risk for cardiovascular disease (affected), compared to the frequency of its presence in a healthy individual (control), and wherein the presence of the marker or haplotype is indicative of susceptibility to cardiovascular disease. The control group may in one embodiment be a population sample, i.e. a random sample from the general population. In another embodiment, the control group is represented by a group of individuals who are disease-free. Such disease-free control may in one embodiment be characterized by the absence of one or more specific disease-associated symptoms. In another embodiment, the disease-free control group is characterized by the absence of one or more disease-specific risk factors. Such risk factors are in one embodiment at least one environmental risk factor. Representative environmental factors are natural products, minerals or other chemicals which are known to affect, or contemplated to affect, the risk of developing the specific disease or trait. Other environmental risk factors are risk factors related to lifestyle, including but not limited to food and drink habits, geographical location of main habitat, and occupational risk factors. In another embodiment, the risk factors comprise at least one additional genetic risk factor.

As an example of a simple test for correlation would be a Fisher-exact test on a two by two table. Given a cohort of chromosomes, the two by two table is constructed out of the number of chromosomes that include both of the markers or haplotypes, one of the markers or haplotypes but not the other and neither of the markers or haplotypes. Other statistical tests of association known to the skilled person are also contemplated and are also within scope of the invention.

In other embodiments of the invention, an individual who is at a decreased susceptibility (i.e., at a decreased risk) for a disease or trait is an individual in whom at least one specific allele at one or more polymorphic marker or haplotype conferring decreased susceptibility for the disease or trait is identified. The marker alleles and/or haplotypes conferring decreased risk are also said to be protective. In one aspect, the protective marker or haplotype is one that confers a significant decreased risk (or susceptibility) of the disease or trait. In one embodiment, significant decreased risk is measured as a relative risk (or odds ratio) of less than 0.9, including but not limited to less than 0.9, less than 0.8, less than 0.7, less than 0.6, less than 0.5, less than 0.4, less than 0.3, less than 0.2 and less than 0.1. In one particular embodiment, significant decreased risk is less than 0.7. In another embodiment, significant decreased risk is less than 0.5. In yet another embodiment, significant decreased risk is less than 0.3. In another embodiment, the decrease in risk (or susceptibility) is at least 20%, including but not limited to at least 25%, at least 30%, at least 35%, at least 40%, at least 45%, at least 50%, at least 55%, at least 60%, at least 65%, at least 70%, at least 75%, at least 80%, at least 85%, at least 90%, at least 95% and at least 98%. In one particular embodiment, a significant decrease in risk is at least about 30%. In another embodiment, a significant decrease in risk is at least about 50%. In another embodiment, the decrease in risk is at least about 70%. Other cutoffs or ranges as deemed suitable by the person skilled in the art to characterize the invention are however also contemplated, and those are also within scope of the present invention.

The person skilled in the art will appreciate that for markers with two alleles present in the population being studied (such as SNPs), and wherein one allele is found in increased frequency in a group of individuals with a trait or disease in the population, compared with controls, the other allele of the marker will be found in decreased frequency in the group of individuals with the trait or disease, compared with controls. In such a case, one allele of the marker (the one found in increased frequency in individuals with the trait or disease) will be the at-risk allele, while the other allele will be a protective allele.

A genetic variant associated with a disease or a trait (e.g. cardiovascular disease) can be used alone to predict the risk of the disease for a given genotype. For a biallelic marker, such as a SNP, there are 3 possible genotypes: homozygote for the at risk variant, heterozygote, and non carrier of the at risk variant. Risk associated with variants at multiple loci can be used to estimate overall risk. For multiple SNP variants, there are k possible genotypes $k=3^n \times 2^p$; where n is the number autosomal loci and p the number of gonosomal (sex chromosomal) loci. Overall risk assessment calculations usually assume that the relative risks of different genetic variants multiply, i.e. the overall risk (e.g., RR or OR) associated with a particular genotype combination is the product of the risk values for the genotype at each locus. If the risk presented is the relative risk for a person, or a specific genotype for a person, compared to a reference population with matched gender and ethnicity, then the combined risk—is the product of the locus specific risk values—and which also corresponds to an overall risk estimate compared with the population. If the risk for a person is based on a comparison to non-carriers of the at risk allele, then the combined risk corresponds to an estimate that compares the person with a given combination of genotypes at all loci to a group of individuals who do not carry risk variants at any of those loci. The group of non-carriers of any at risk variant has the lowest estimated risk and has a combined risk, compared with itself (i.e., non-carriers) of 1.0, but has an overall risk, compare with the population, of less than 1.0. It should be noted that the group of non-carriers can potentially be very small, especially for large number of loci, and in that case, its relevance is correspondingly small.

The multiplicative model is a parsimonious model that usually fits the data of complex traits reasonably well. Deviations from multiplicity have been rarely described in the context of common variants for common diseases, and if reported are usually only suggestive since very large sample sizes are usually required to be able to demonstrate statistical interactions between loci.

By way of an example, let us consider a total of eight variants that have been described to associate with prostate cancer (Gudmundsson, J., et al., *Nat Genet* 39:631-7 (2007), Gudmundsson, 3., et al., *Nat Genet* 39:977-83 (2007); Yeager, M., et al, *Nat Genet* 39:645-49 (2007), Amundadottir, L., et al., *Nat Genet* 38:652-8 (2006); Haiman, C. A., et al., *Nat Genet* 39:638-44 (2007)). Seven of these loci are on autosomes, and the remaining locus is on chromosome X. The total number of theoretical genotypic combinations is then $3^7 \times 2^1 = 4374$. Some of those genotypic classes are very rare, but are still possible, and should be considered for overall risk assessment. It is likely that the multiplicative model applied in the case of multiple genetic variant will also be valid in conjugation with non-genetic risk variants assuming that the genetic variant does not clearly correlate with the "environmental" factor. In other words, genetic and non-genetic at-risk variants can be assessed under the multiplicative model to estimate combined risk, assuming that the non-genetic and genetic risk factors do not interact.

Using the same quantitative approach, the combined or overall risk associated with a plurality of variants associated with any cardiovascular disease, as described herein, may be assessed.

Linkage Disequilibrium

The natural phenomenon of recombination, which occurs on average once for each chromosomal pair during each meiotic event, represents one way in which nature provides variations in sequence (and biological function by consequence). It has been discovered that recombination does not occur randomly in the genome; rather, there are large variations in the frequency of recombination rates, resulting in small regions of high recombination frequency (also called recombination hotspots) and larger regions of low recombination frequency, which are commonly referred to as Linkage Disequilibrium (LD) blocks (Myers, S. et al., *Biochem Soc Trans* 34:526-530 (2006); Jeffreys, A. J., et al., *Nature Genet* 29:217-222 (2001); May, C. A., et al., *Nature Genet* 31:272-275 (2002)).

Linkage Disequilibrium (LD) refers to a non-random assortment of two genetic elements. For example, if a particular genetic element (e.g., "alleles" of a polymorphic marker) occurs in a population at a frequency of 0.50 (50%) and another occurs at a frequency of 0.50 (50%), then the predicted occurrence of a person's having both elements is 0.25 (25%), assuming a random distribution of the elements. However, if it is discovered that the two elements occur together at a frequency higher than 0.25, then the elements are said to be in linkage disequilibrium, since they tend to be inherited together at a higher rate than what their independent allele frequencies would predict. Roughly speaking, LD is generally correlated with the frequency of recombination events between the two elements. Allele or haplotype frequencies can be determined in a population by genotyping individuals in a population and determining the frequency of the occurrence of each allele or haplotype in the population. For populations of diploids, e.g., human populations, individuals will typically have two alleles or allelic combinations for each genetic element (e.g., a marker, haplotype or gene).

Many different measures have been proposed for assessing the strength of linkage disequilibrium (LD). Most capture the strength of association between pairs of biallelic sites. Two important pairwise measures of LD are $r^2$ (sometimes denoted $\Delta^2$) and $|D'|$. Both measures range from 0 (no disequilibrium) to 1 ('complete' disequilibrium), but their interpretation is slightly different. $|D'|$ is defined in such a way that it is equal to 1 if just two or three of the possible haplotypes are present, and it is <1 if all four possible haplotypes are present. Therefore, a value of $|D'|$ that is <1 indicates that historical recombination may have occurred between two sites (recurrent mutation can also cause $|D'|$ to be <1, but for single nucleotide polymorphisms (SNPs) this is usually regarded as being less likely than recombination). The measure $r^2$ represents the statistical correlation between two sites, and takes the value of 1 if only two haplotypes are present.

The $r^2$ measure is arguably the most relevant measure for association mapping, because there is a simple inverse relationship between $r^2$ and the sample size required to detect association between susceptibility loci and SNPs. These measures are defined for pairs of sites, but for some applications a determination of how strong LD is across an entire region that contains many polymorphic sites might be desirable (e.g., testing whether the strength of LD differs significantly among loci or across populations, or whether there is more or less LD in a region than predicted under a particular model). Measuring LD across a region is not straightforward, but one approach is to use the measure r, which was developed in population genetics. Roughly speaking, r measures how much recombination would be required under a particular population model to generate the LD that is seen in the data. This type of method can potentially also provide a statistically rigorous approach to the problem of determining whether LD data provide evidence for the presence of recombination hotspots. For the methods described herein, a significant $r^2$ value can be at least 0.1 such as at least 0.1, 0.15, 0.2, 0.25, 0.3, 0.35, 0.4, 0.45, 0.5, 0.55, 0.6, 0.65, 0.7, 0.75, 0.8, 0.85, 0.9, 0.91, 0.92, 0.93, 0.94, 0.95, 0.96, 0.97, 0.98, or at least 0.99. In one preferred embodiment, the significant $r^2$ value can be at least 0.2. Alternatively, linkage disequilibrium as described herein, refers to linkage disequilibrium characterized by values of $|D'|$ of at least 0.2, such as 0.3, 0.4, 0.5, 0.6, 0.7, 0.8, 0.85, 0.9, 0.95, 0.96, 0.97, 0.98, or at least 0.99. Thus, linkage disequilibrium represents a correlation between alleles of distinct markers. It is measured by correlation coefficient or $|D'|$ ($r^2$ up to 1.0 and $|D'|$ up to 1.0). In certain embodiments, linkage disequilibrium is defined in terms of values for both the $r^2$ and $|D'|$ measures. In one such embodiment, a significant linkage disequilibrium is defined as $r^2 > 0.1$ and $|D'| > 0.8$. In another embodiment, a significant linkage disequilibrium is defined as $r^2 > 0.2$ and $|D'| > 0.9$. Other combinations and permutations of values of $r^2$ and $|D'|$ for determining linkage disequilibrium are also contemplated, and are also within the scope of the invention. Linkage disequilibrium can be determined in a single human population, as defined herein, or it can be determined in a collection of samples comprising individuals from more than one human population. In one embodiment of the invention, LD is determined in a sample from one or more of the HapMap populations (caucasian, african, japanese, chinese), as defined (http://www.hapmap.org). In one such embodiment, LD is determined in the CEU population of the HapMap samples. In another embodiment, LD is determined in the YRI population. In yet another embodiment, LD is determined in samples from the Icelandic population.

If all polymorphisms in the genome were independent at the population level (i.e., no LD), then every single one of them would need to be investigated in association studies, to assess all the different polymorphic states. However, due to linkage disequilibrium between polymorphisms, tightly linked polymorphisms are strongly correlated, which reduces the number of polymorphisms that need to be investigated in an association study to observe a significant association. Another consequence of LD is that many polymorphisms may give an association signal due to the fact that these polymorphisms are strongly correlated.

Genomic LD maps have been generated across the genome, and such LD maps have been proposed to serve as framework for mapping disease-genes (Risch, N. & Merkiangas, K, *Science* 273:1516-1517 (1996); Maniatis, N., et al., *Proc Natl Acad Sci USA* 99:2228-2233 (2002); Reich, D E et al, *Nature* 411:199-204 (2001)). It is also now established that many portions of the human genome can be broken into series of discrete haplotype blocks containing a few common haplotypes; for these blocks, linkage disequilibrium data provides little evidence indicating recombination (see, e.g., Wall., J. D. and Pritchard, J. K., *Nature Reviews Genetics* 4:587-597 (2003); Daly, M. et al., *Nature Genet.* 29:229-232 (2001); Gabriel, S. B. et al., *Science* 296:2225-2229 (2002); Patil, N. et al., *Science* 294:1719-1723 (2001); Dawson, E. et al., *Nature* 418:544-548 (2002); Phillips, M. S. et al., *Nature Genet.* 33:382-387 (2003)). There are two main methods for defining these haplotype blocks: blocks can be defined as regions of DNA that have limited haplotype diversity (see, e.g., Daly, M. et al., *Nature Genet.* 29:229-232 (2001); Patil, N. et al., *Science* 294:1719-1723 (2001); Dawson, E. et al., *Nature* 418:544-548 (2002); Zhang, K. et al., *Proc. Natl. Acad. Sci. USA* 99:7335-7339 (2002)), or as regions between transition zones having extensive historical recombination, identified using linkage disequilibrium (see, e.g., Gabriel, S. B. et al., *Science* 296:2225-2229 (2002); Phillips, M. S. et al., *Nature Genet.* 33:382-387 (2003); Wang, N. et al., *Am. J. Hum. Genet.* 71:1227-1234 (2002); Stumpf, M. P., and Goldstein, D. B., *Curr. Biol.* 13:1-8 (2003)). More recently, a fine-scale map of recombination rates and corresponding hotspots across the human genome has been generated (Myers, S., et al., *Science* 310:321-32324 (2005); Myers, S. et al., *Biochem Soc Trans* 34:526530 (2006)). The map reveals the enormous variation in recombination across the genome, with recombination rates as high as 10-60 cM/Mb in hotspots, while closer to 0 in intervening regions, which thus represent regions of limited haplotype diversity and high LD. The map can therefore be used to define haplotype blocks/LD blocks as regions flanked by recombination hotspots. As used herein, the terms "haplotype block" or "LD block" includes blocks defined by any of the above described characteristics, or other alternative methods used by the person skilled in the art to define such regions. Haplotype blocks (LD blocks) can be used to map associations between phenotype and haplotype status, using single markers or haplotypes comprising a plurality of markers. The main haplotypes can be identified in each haplotype block, and then a set of "tagging" SNPs or markers (the smallest set of SNPs or markers needed to distinguish among the haplotypes) can then be identified. These tagging SNPs or markers can then be used in assessment of samples from groups of individuals, in order to identify association between phenotype and haplotype. If desired, neighboring haplotype blocks can be assessed concurrently, as there may also exist linkage disequilibrium among the haplotype blocks.

It has thus become apparent that for any given observed association to a polymorphic marker in the genome, it is likely that additional markers in the genome also show association. This is a natural consequence of the uneven distribution of LD across the genome, as observed by the large variation in recombination rates. The markers used to detect association thus in a sense represent "tags" for a genomic region (i.e., a haplotype block or LD block; e.g., the C09 LD block) that is associating with a given disease or trait, and as such are useful for use in the methods and kits of the present invention. One or more causative (functional) variants or mutations may reside within the region found to be associating to the disease or trait. Such variants may confer a higher relative risk (RR) or odds ratio (OR) than observed for the tagging markers used to detect the association. The present invention thus refers to the markers used for detecting association to the disease, as described herein, as well as markers in linkage disequilibrium with the markers. Thus, in certain embodiments of the invention, markers that are in LD with the markers and/or haplotypes of the invention, as described herein, may be used as surrogate markers. The surrogate markers have in one embodiment relative risk (RR) and/or odds ratio (OR) values smaller than for the markers or haplotypes initially found to be associating with the disease, as described herein. In other embodiments, the surrogate markers have RR or OR values greater than those initially determined for the markers initially found to be associating with the disease, as described herein. An example of such an embodiment would be a rare, or relatively rare (such as <10% allelic population frequency) variant in LD with a more common variant (>10% population frequency) initially found to be associating with the disease, such as the variants described herein. Identifying and using such markers for detecting the association discovered by the inventors as described herein can be performed by routine methods well known to the person skilled in the art, and are therefore within the scope of the present invention.

Determination of Haplotype Frequency

The frequencies of haplotypes in patient and control groups can be estimated using an expectation-maximization algorithm (Dempster A. et al., *J. R. Stat. Soc. B,* 39:1-38 (1977)). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk-haplotype, which can include the markers described herein, is allowed to have a higher frequency in patients than controls, while the ratios of the frequencies of other haplotypes are assumed to be the same in both groups. Likelihoods are maximized separately under both hypotheses and a corresponding 1-df likelihood ratio statistic is used to evaluate the statistical significance.

To look for at-risk and protective markers and haplotypes within a linkage region, for example, association of all possible combinations of genotyped markers is studied, provided those markers span a practical region. The combined patient and control groups can be randomly divided into two sets, equal in size to the original group of patients and controls. The marker and haplotype analysis is then repeated and the most significant p-value registered is determined. This randomization scheme can be repeated, for example, over 100 times to construct an empirical distribution of p-values. In a preferred embodiment, a p-value of <0.05 is indicative of an significant marker and/or haplotype association.

Haplotype Analysis

One general approach to haplotype analysis involves using likelihood-based inference applied to NEsted MOdels (Gretarsdottir S., et al., *Nat. Genet.* 35:131-38 (2003)). The method is implemented in the program NEMO, which allows for many polymorphic markers, SNPs and microsatellites. The method and software are specifically designed for case-control studies where the purpose is to identify haplotype groups that confer different risks. It is also a tool for studying LD structures. In NEMO, maximum likelihood estimates, likelihood ratios and p-values are calculated directly, with the aid of the EM algorithm, for the observed data treating it as a missing-data problem.

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. The information measure for haplotype analysis is described in Nicolae and Kong (Technical Report 537, Department of Statistics, University of Statistics, University of Chicago; *Biometrics,* 60(2):368-75 (2004)) as a natural extension of information measures defined for linkage analysis, and is implemented in NEMO.

For single marker association to a disease, the Fisher exact test can be used to calculate two-sided p-values for each individual allele. Usually, all p-values are presented unadjusted for multiple comparisons unless specifically indicated. The presented frequencies (for microsatellites, SNPs and haplotypes) are allelic frequencies as opposed to carrier frequencies. To minimize any bias due the relatedness of the patients who were recruited as families for the linkage analysis, first and second-degree relatives can be eliminated from the patient list. Furthermore, the test can be repeated for association correcting for any remaining relatedness among the patients, by extending a variance adjustment procedure described in Risch, N. & Teng, J. (*Genome Res.,* 8:1273-1288 (1998)), DNA pooling (ibid) for sibships so that it can be applied to general familial relationships, and present both adjusted and unadjusted p-values for comparison. The differences are in general very small as expected. To assess the significance of single-marker association corrected for multiple testing we can carry out a randomization test using the same genotype data. Cohorts of patients and controls can be randomized and the association analysis redone multiple times (e.g., up to 500,000 times) and the p-value is the fraction of replications that produced a p-value for some marker allele that is lower than or equal to the p-value we observed using the original patient and control cohorts.

For both single-marker and haplotype analyses, relative risk (RR) and the population attributable risk (PAR) can be calculated assuming a multiplicative model (haplotype relative risk model) (Terwilliger, J. D. & Ott, 3., *Hum. Hered.* 42:337-46 (1992) and Falk, C. T. & Rubinstein, P, *Ann. Hum. Genet.* 51 (Pt 3):227-33 (1987)), i.e., that the risks of the two alleles/haplotypes a person carries multiply. For example, if RR is the risk of A relative to a, then the risk of a person homozygote AA will be RR times that of a heterozygote Aa and $RR^2$ times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes, $h_i$ and $h_j$, $risk(h_i)/risk(h_j)=(f_i/p_i)/(f_j/p_j)$, where f and p denote, respectively, frequencies in the affected population and in the control population. While there is some power loss if the true model is not multiplicative, the loss tends to be mild except for extreme cases. Most importantly, p-values are always valid since they are computed with respect to null hypothesis.

Linkage Disequilibrium Using NEMO

LD between pairs of markers can be calculated using the standard definition of D' and $r^2$ (Lewontin, R., *Genetics* 49:49-67 (1964); Hill, W. G. & Robertson, A. *Theor. Appl. Genet.* 22:226-231 (1968)). Using NEMO, frequencies of the two marker allele combinations are estimated by maximum likelihood and deviation from linkage equilibrium is evaluated by a likelihood ratio test. The definitions of D' and $r^2$ are extended to include microsatellites by averaging over the values for all possible allele combination of the two markers weighted by the marginal allele probabilities.

Risk Assessment and Diagnostics

Within any given population, there is an absolute risk of developing a disease or trait, defined as the chance of a person developing the specific disease or trait over a specified time-period. For example, a woman's lifetime absolute risk of breast cancer is one in nine. That is to say, one woman in every nine will develop breast cancer at some point in their lives. Risk is typically measured by looking at very large numbers of people, rather than at a particular individual. Risk is often presented in terms of Absolute Risk (AR) and Relative Risk (RR). Relative Risk is used to compare risks associating with two variants or the risks of two different groups of people. For example, it can be used to compare a group of people with a certain genotype with another group having a different genotype. For a disease, a relative risk of 2 means that one group has twice the chance of developing a disease as the other group. The Risk presented is usually the relative risk for a person, or a specific genotype of a person, compared to the population with matched gender and ethnicity. Risks of two individuals of the same gender and ethnicity could be compared in a simple manner. For example, if, compared to the population, the first individual has relative risk 1.5 and the second has relative risk 0.5, then the risk of the first individual compared to the second individual is 1.5/0.5=3.

As described herein, certain polymorphic markers and haplotypes comprising such markers are found to be useful for risk assessment of cardiovascular disease, e.g., arterial diseases, e.g. myocardial infarction, coronary artery disease, restenosis, peripheral artery disease, stroke, intracranial aneurysm and abdominal aortic aneurysm. Risk assessment can involve the use of the markers for diagnosing a susceptibility to the cardiovascular disease. Particular alleles of polymorphic markers are found more frequently in individuals with cardiovascular disease, than in individuals without diagnosis of cardiovascular disease. Therefore, these marker alleles have predictive value for detecting cardiovascular disease, or a susceptibility to cardiovascular disease, in an individual. Tagging markers within haplotype blocks or LD blocks comprising at-risk markers, such as the markers of the present invention, can be used as surrogates for other markers and/or haplotypes within the haplotype block or LD block. Markers with values of $r^2$ equal to 1 are perfect surrogates for the at-risk variants, i.e. genotypes for one marker perfectly predicts genotypes for the other. Markers with smaller values of $r^2$ than 1 can also be surrogates for the at-risk variant, or alternatively represent variants with relative risk values as high as or possibly even higher than the at-risk variant. The at-risk variant identified may not be the functional variant itself, but is in this instance in linkage disequilibrium with the true functional variant. The present invention encompasses the assessment of such surrogate markers for the markers as disclosed herein. Such markers are annotated, mapped and listed in public databases, as well known to the skilled person, or can alternatively be readily identified by sequencing the region or a part of the region identified by the markers of the present invention in a group of individuals, and identify polymorphisms in the resulting group of sequences. As a consequence, the person skilled in the art can readily and without undue experimentation genotype surrogate markers in linkage disequilibrium with the markers and/or haplotypes as described herein. The tagging or surrogate markers in LD with the at-risk variants detected, also have predictive value for detecting association to the cardiovascular disease, or a susceptibility to the cardiovascular disease, in an individual. These tagging or surrogate markers that are in LD with the markers of the present invention can also include other markers that distinguish among haplotypes, as these similarly have predictive value for detecting susceptibility to cardiovascular disease.

The present invention can in certain embodiments be practiced by assessing a sample comprising genomic DNA from an individual for the presence of variants described herein to be associated with cardiovascular disease. Such assessment includes steps of detecting the presence or absence of at least one allele of at least one polymorphic marker, using methods well known to the skilled person and further described herein, and based on the outcome of such assessment, determine whether the individual from whom the sample is derived is at increased or decreased risk (increased or decreased susceptibility) of cardiovascular disease. Alternatively, the invention can be practiced utilizing a dataset comprising information about the genotype status of at least one polymorphic marker described herein to be associated with cardiovascular disease (or markers in linkage disequilibrium with at least one marker shown herein to be associated with cardiovascular disease). In other words, a dataset containing information about such genetic status, for example in the form of genotype counts at a certain polymorphic marker, or a plurality of markers (e.g., an indication of the presence or absence of certain at-risk alleles), or actual genotypes for one or more markers, can be queried for the presence or absence of certain at-risk alleles at certain polymorphic markers shown by the present inventors to be associated with cardiovascular disease. A positive result for a variant (e.g., marker allele) associated with cardiovascular disease, as shown herein, is indicative of the individual from which the dataset is derived is at increased susceptibility (increased risk) of at least one cardiovascular disease (e.g., arterial diseases, e.g. myocardial infarction, coronary artery disease, restenosis, peripheral artery disease, stroke, intracranial aneurysm and abdominal aortic aneurysm).

In certain embodiments of the invention, a polymorphic marker is correlated to a cardiovascular disease by referencing genotype data for the polymorphic marker to a look-up table that comprises correlations between at least one allele of the polymorphism and the disease. In some embodiments, the table comprises a correlation for one polymorphism. In other embodiments, the table comprises a correlation for a plurality of polymorphisms. In both scenarios, by referencing to a look-up table that gives an indication of a correlation between a marker and cardiovascular disease, a risk for cardiovascular disease, or a susceptibility to cardiovascular disease, can be identified in the individual from whom the sample is derived. In some embodiments, the correlation is reported as a statistical measure. The statistical measure may be reported as a risk measure, such as a relative risk (RR), an absolute risk (AR) or an odds ratio (OR).

The markers and haplotypes of the invention, e.g., the markers presented in Tables 1-36 herein, e.g. the markers in Table 3, 10 and 21, may be useful for risk assessment and diagnostic purposes for cardiovascular disease (e.g., arterial diseases, e.g. myocardial infarction, coronary artery disease, restenosis, peripheral artery disease, stroke, intracranial aneurysm and abdominal aortic aneurysm), either alone or in combination. Thus, even in the cases where the increase in risk by individual markers is relatively modest, i.e. on the order of 10-30%, the association may have significant implications. Thus, relatively common variants may have significant contribution to the overall risk (Population Attributable Risk is high), or combination of markers can be used to define groups of individual who, based on the combined risk of the markers, is at significant combined risk of developing a cardiovascular disease.

Biomarkers

The cardiovascular diseases are known to have several common biomarkers, which are believed to relate to increased risk of developing cardiovascular disease. These include elevated fibrinogen, PAI-1, homocysteine, asymmetric dimethylarginine, C-reactive protein and B-type naturietic peptide (BNP). These common biomarkers underscore the common etiology for the cardiovascular diseases. Recently, urinary peptides have been shown to be promising biomarkers for Cardiovascular disease, in particular Coronary Artery Disease (CAD) (Zimmerli, L. U., et al., *Mol Cell Proteomics* 7:290-8 (2008)). These have the advantage of being non-invasive, only requiring a urine sample from the individual to be assessed. In one application, a pattern of polypeptides in the urine sample is characteristic of increased risk of CAD.

Many general inflammatory markers are predictive of risk of coronary heart disease, including CAD and MI, although these markers are not specific to atherosclerosis. For example, Stein (Stein, S., *Am J Cardiol*, 87 (suppl):21A-26A (2001)) discusses the use of any one of the following serum inflammatory markers as surrogates for predicting risk of coronary heart disease including C-reactive protein (CRP), serum amyloid A, fibrinogen, interleukin-6, tissue necrosis factor-alpha, soluble vascular cell adhesion molecules (sVCAM), soluble intervascular adhesion molecules (sICAM), E-selectin, matrix metalloprotease type-1, matrix metalloprotease type-2, matrix metalloprotease type-3, and matrix metalloprotease type-9.

A significant association between CRP levels in serum and increased risk for coronary heart disease was found in the Women's Health Study, with the highest relative risk of 4.5 seen for those women in the highest quintile of serum CRP (Ridker, P. M. et al., *New England. J. Med.*, 347: 1557-1565 (2001)). A similar correlation between increased serum CRP and increased risk for coronary heart disease in women has been reported (Ridker, P. M et al., *New Engld. J. Med.*, 342:836-843 (2000); Bermudez, E. A. et. al., *Arterioscler. Thromb. Vasc. Biol.*, 22: 1668-1673 (2002)). A similar correlation between increased serum inflammatory markers such as CRP and increased risk for coronary heart disease has been reported for men (Doggen, C. J. M. et al., *J. Internal Med.*, 248:406-414 (2000) and Ridker, P. M. et al., *New England. J. Med.*, 336: 973-979 (1997)). Elevated CRP or other serum inflammatory markers is also prognostic for increased risk of a second myocardial infarct in patients with a previous myocardial infarct (Retterstol, L. et al., *Atheroscler.*, 160: 433-440 (2002)). Emerging evidence also suggests that elevated CRP is an independent risk factor for adverse clinical outcomes. See, e.g., Ridker et al., N. Engl. J. Med. 352: 1 (Jan. 6, 2005).

The end products of the leukotriene pathway are potent inflammatory lipid mediators derived from arachidonic acid. They can potentially contribute to development of atherosclerosis and destabilization of atherosclerotic plaques through lipid oxidation and/or proinflammatory effects, and LTC4, LTD4, and LTE4, are known to induce vasoconstriction. On the other hand, LTB4 is a strong proinflammatory agent. Increased production of these end products of the leukotriene pathway, could therefore serve as a risk factor for MI and atherosclerosis, whereas both inflammation and vasoconstriction/vasospasm have a well established role in the pathogenesis of MI and atherosclerosis.

In certain embodiments of the invention, the genetic risk variants for cardiovascular disease, such as MI, CAD, AAA, IA, stroke and/or PAD are assessed in combination with at least one biomarker. For example, levels of an inflammatory marker in an appropriate test sample (e.g., serum, plasma or urine) can be measured and the determination of the biomarker level in the sample, relative to a control (either a normal, disease-free control, or a random sample from the population) is made. The result of the analysis can be analyzed in combination with genetic risk conferred by the variants described herein, to determine overall risk. Representative inflammatory markers include: C-reactive protein (CRP), serum amyloid A, fibrinogen, serum sCD40L, a leukotriene (e.g., LTB4, LTC4, LTD4, LTE4), a leukotriene metabolite, interleukin-6, tissue necrosis factor-alpha, soluble vascular cell adhesion molecules (sVCAM), soluble intervascular adhesion molecules (sICAM), E-selectin, matrix metalloprotease type-1, matrix metalloprotease type-2, matrix metalloprotease type-3, matrix metalloprotease type-9, myeloperoxidase (MPO), and N-tyrosine. In a preferred embodiment, the marker is CRP, sCD40L or MPO. The determination of biomarkers can be made by standard methods known to the skilled person. For example, in one embodiment, production of a leukotriene metabolite is stimulated in a first test sample from the individual, using a calcium ionophore. The level of production is compared with a control level. The control level is a level that is typically found in control individual(s), such as individual who are not at risk for MI, CAD, AAA, IA, stroke or PAD; alternatively, a control level is the level that is found by comparison of disease risk in a population associated with the lowest band of measurement (e.g., below the mean or median, the lowest quartile or the lowest quintile) compared to higher bands of measurement (e.g., above the mean or median, the second, third or fourth quartile; the second, third, fourth or fifth quintile).

As described in the above, the haplotype block structure of the human genome has the effect that a large number of variants (markers and/or haplotypes) in linkage disequilibrium with the variant originally associated with a disease or trait may be used as surrogate markers for assessing association to the disease or trait. The number of such surrogate markers will depend on factors such as the historical recombination rate in the region, the mutational frequency in the region (i.e., the number of polymorphic sites or markers in the region), and the extent of LD (size of the LD block) in the region. These markers are usually located within the physical boundaries of the LD block or haplotype block in question as defined using the methods described herein, or by other methods known to the person skilled in the art. However, sometimes marker and haplotype association is found to extend beyond the physical boundaries of the haplotype block as defined. Such markers and/or haplotypes may in those cases be also used as surrogate markers and/or haplotypes for the markers and/or haplotypes physically residing within the haplotype block as defined. As a consequence, markers and haplotypes in LD (typically characterized by $r^2$ greater than 0.1, such as $r^2$ greater than 0.2, including $r^2$ greater than 0.3, also including $r^2$ greater than 0.4) with the markers and haplotypes of the present invention are also within the scope of the invention, even if they are physically located beyond the boundaries of the haplotype block as defined. This includes markers that are described herein (e.g., Tables 1-36; e.g., Tables 3, 10, and 21), but may also include other markers that are in strong LD (e.g., characterized by $r^2$ greater than 0.1 or 0.2 and/or |D'|>0.8) with one or more of the markers listed in Tables 1-35, including the markers set forth in Tables 3, 10 and 21.

For the SNP markers described herein, the opposite allele to the allele found to be in excess in patients (at-risk allele) is found in decreased frequency in cardiovascular disease. These markers and haplotypes are thus protective for cardiovascular disease, i.e. they confer a decreased risk or susceptibility of individuals carrying these markers and/or haplotypes developing cardiovascular disease.

Certain variants of the present invention, including certain haplotypes comprise, in some cases, a combination of various genetic markers, e.g., SNPs and microsatellites. Detecting haplotypes can be accomplished by methods known in the art and/or described herein for detecting sequences at polymorphic sites. Furthermore, correlation between certain haplotypes or sets of markers and disease phenotype can be verified using standard techniques. A representative example of a simple test for correlation would be a Fisher-exact test on a two by two table.

In specific embodiments, a marker allele or haplotype associated with cardiovascular disease (e.g., marker alleles as listed in Tables 3, 10 and 21) is one in which the marker allele or haplotype is more frequently present in an individual at risk for cardiovascular disease, (affected), compared to the frequency of its presence in a healthy individual (control), wherein the presence of the marker allele or haplotype is indicative of cardiovascular disease or a susceptibility to cardiovascular disease. In other embodiments, at-risk markers in linkage disequilibrium with one or more markers found to be associated with cardiovascular disease, including coronary artery disease and in-stent restenosis (e.g., markers as listed in Tables 3, 10 and 21) are tagging markers that are more frequently present in an individual at risk for cardiovascular disease (affected), compared to the frequency of their presence in a healthy individual (control), wherein the presence of the tagging markers is indicative of increased susceptibility to cardiovascular disease. In a further embodiment, at-risk markers alleles (i.e. conferring increased susceptibility) in linkage disequilibrium with one or more markers found to be associated with cardiovascular disease (e.g., marker alleles as listed in Tables 3, 10 and 21, and markers in linkage disequilibrium therewith), are markers comprising one or more allele that is more frequently present in an individual at risk for cardiovascular disease, compared to the frequency of their presence in a healthy individual (control), wherein the presence of the markers is indicative of increased susceptibility to the cardiovascular disease.

Study Population

In a general sense, the methods and kits of the invention can be utilized from samples containing nucleic acid material (DNA or RNA) from any source and from any individual. In preferred embodiments, the individual is a human individual. The individual can be an adult, child, or fetus. The nucleic acid source may be any sample comprising nucleic acid material, including biological samples, or a sample comprising nucleic acid material derived therefrom. The present invention also provides for assessing markers and/or haplotypes in individuals who are members of a target population. Such a target population is in one embodiment a population or group of individuals at risk of developing the disease, based on other genetic factors, biomarkers, biophysical parameters (e.g., weight, BMD, blood pressure), or general health and/or lifestyle parameters (e.g., history of disease or related diseases, previous diagnosis of disease, family history of disease).

The invention provides for embodiments that include individuals from specific age subgroups, such as those over the age of 40, over age of 45, or over age of 50, 55, 60, 65, 70, 75, 80, or 85. Other embodiments of the invention pertain to other age groups, such as individuals aged less than 85, such as less than age 80, less than age 75, or less than age 70, 65, 60, 55, 50, 45, 40, 35, or age 30. Other embodiments relate to individuals with age at onset of the disease in any of the age ranges described in the above. It is also contemplated that a range of ages may be relevant in certain embodiments, such as age at onset at more than age 45 but less than age 60. Other age ranges are however also contemplated, including all age ranges bracketed by the age values listed in the above. The invention furthermore relates to individuals of either gender, males or females.

The Icelandic population is a Caucasian population of Northern European ancestry. A large number of studies reporting results of genetic linkage and association in the Icelandic population have been published in the last few years. Many of those studies show replication of variants, originally identified in the Icelandic population as being associating with a particular disease, in other populations (Stacey, S. N., et al., *Nat Genet*. May 27, 2007 (Epub ahead of print; Helgadottir, A., et al., *Science* 316:1491-93 (2007); Steinthorsdottir, V., et al., *Nat Genet*. 39:770-75 (2007); Gudmundsson, J., et al., *Nat Genet*. 39:631-37 (2007); Amundadottir, L. T., et al., *Nat Genet*. 38:652-58 (2006); Grant, S. F., et al., *Nat Genet*. 38:320-23 (2006)). Thus, genetic findings in the Icelandic population have in general been replicated in other populations, including populations from Africa and Asia.

The markers of the present invention found to be associated with cardiovascular disease are believed to show similar association in other human populations. Particular embodiments comprising individual human populations are thus also contemplated and within the scope of the invention. Such embodiments relate to human subjects that are from one or more human population including, but not limited to, Caucasian populations, European populations, American populations, Eurasian populations, Asian populations, Central/South Asian populations, East Asian populations, Middle Eastern populations, African populations, Hispanic populations, and Oceanian populations. European populations include, but are not limited to, Swedish, Norwegian, Finnish, Russian, Danish, Icelandic, Irish, Kelt, English, Scottish, Dutch, Belgian, French, German, Spanish, Portuguese, Italian, Polish, Bulgarian, Slavic, Serbian, Bosnian, Chech, Greek and Turkish populations. The invention furthermore in other embodiments can be practiced in specific human populations that include Bantu, Mandenk, Yoruba, San, Mbuti Pygmy, Orcadian, Adygel, Russian, Sardinian, Tuscan, Mozabite, Bedouin, Druze, Palestinian, Balochi, Brahui, Makrani, Sindhi, Pathan, Burusho, Hazara, Uygur, Kalash, Han, Dai, Daur, Hezhen, Lahu, Miao, Orogen, She, Tujia, Tu, Xibo, Yi, Mongolan, Naxi, Cambodian, Japanese, Yakut, Melanesian, Papuan, Karitianan, Surui, Colmbian, Maya and Pima.

In one preferred embodiment, the invention relates to populations that include black African ancestry such as populations comprising persons of African descent or lineage. Black African ancestry may be determined by self reporting as African-Americans, Afro-Americans, Black Americans, being a member of the black race or being a member of the negro race. For example, African Americans or Black Americans are those persons living in North America and having origins in any of the black racial groups of Africa. In another example, self-reported persons of black African ancestry may have at least one parent of black African ancestry or at least one grandparent of black African ancestry. In another embodiment, the invention relates to individuals of Caucasian origin.

The racial contribution in individual subjects may also be determined by genetic analysis. Genetic analysis of ancestry may be carried out using unlinked microsatellite markers such as those set out in Smith et al. (*Am J Hum Genet* 74, 1001-13 (2004)).

In certain embodiments, the invention relates to markers and/or haplotypes identified in specific populations, as described in the above. The person skilled in the art will appreciate that measures of linkage disequilibrium (LD) may give different results when applied to different populations. This is due to different population history of different human populations as well as differential selective pressures that may have led to differences in LD in specific genomic regions. It is also well known to the person skilled in the art that certain markers, e.g. SNP markers, have different population frequency in different populations, or are polymorphic in one population but not in another. The person skilled in the art will however apply the methods available and as thought herein to practice the present invention in any given human population. This may include assessment of polymorphic markers in the LD region of the present invention, so as to identify those markers that give strongest association within the specific population. Thus, the at-risk variants of the present invention may reside on different haplotype background and in different frequencies in various human populations. However, utilizing methods known in the art and the markers of the present invention, the invention can be practiced in any given human population.

Utility of Genetic Testing

The person skilled in the art will appreciate and understand that the variants described herein in general do not, by themselves, provide an absolute identification of individuals who will develop a particular cardiovascular disease. The variants described herein do however indicate increased and/or decreased likelihood that individuals carrying the at-risk or protective variants of the invention will develop symptoms associated with at least one cardiovascular disease (e.g., MI, CAD, IA, AAA, restenosis, stroke PAD). This information is however extremely valuable in itself, as outlined in more detail in the below, as it can be used to, for example, initiate preventive measures at an early stage, perform regular physical and/or mental exams to monitor the progress and/or appearance of symptoms, or to schedule exams at a regular interval to identify early symptoms, so as to be able to apply treatment at an early stage.

The knowledge about a genetic variant that confers a risk of developing cardiovascular disease offers the opportunity to apply a genetic test to distinguish between individuals with increased risk of developing the disease (i.e. carriers of the at-risk variant) and those with decreased risk of developing the disease (i.e. carriers of the protective variant). The core values of genetic testing, for individuals belonging to both of the above mentioned groups, are the possibilities of being able to diagnose disease, or a predisposition to disease, at an early stage and provide information to the clinician about prognosis/aggressiveness of disease in order to be able to apply the most appropriate treatment.

Individuals with a family history of cardiovascular diseases and carriers of at-risk variants may benefit from genetic testing since the knowledge of the presence of a genetic risk factor, or evidence for increased risk of being a carrier of one or more risk factors, may provide increased incentive for implementing a healthier lifestyle (e.g., lose weight, increase exercise, give up smoking, reduce stress, etc.), by avoiding or minimizing known environmental risk factors for cardiovascular diseases. Genetic testing of patients may furthermore give valuable information about the primary cause of the cardiovascular disease and can aid the clinician in selecting the best treatment options and medication for each individual.

The present invention can be thus be used for risk assessment for cardiovascular disease, including diagnosing whether an individual is at risk for developing a cardiovascular disease, such as Myocardial Infarction, Coronary Artery Disease, PAD, AAA, IA, stroke or restenosis. The polymorphic markers of the present invention can be used alone or in combination, as well as in combination with other factors, including known biomarkers, for risk assessment of an individual for cardiovascular disease. Many factors known to affect the predisposition of individual towards developing risk of developing Cardiovascular disease are known to the person skilled in the art and can be utilized in such assessment. These include, but are not limited to, age, gender, smoking status, physical activity, waist-to-hip circumference ratio, family history of Cardiovascular Disease, previously diagnosed cardiovascular disease, obesity, diagnosis of Diabetes mellitus, stress, depression, elevated heart rate, hypertriglyceridemia, low HDL cholesterol, hypertension, elevated blood pressure, cholesterol levels, HDL cholesterol, LDL cholesterol, triglycerides, apolipoprotein AI and B levels, fibrinogen, ferritin, C-reactive protein and leukotriene levels. Methods known in the art can be used for such assessment, including multivariate analyses or logistic regression, as described further herein.

Methods

Methods for risk assessment cardiovascular disease are described herein and are encompassed by the invention. The invention also encompasses methods of assessing an individual for probability of response to a therapeutic agent for a cardiovascular disease, methods for predicting the effectiveness of a therapeutic agent for cardiovascular disease, nucleic acids, polypeptides and antibodies and computer-implemented functions. Kits for assaying a sample from a subject to detect susceptibility to cardiovascular disease are also encompassed by the invention.

Diagnostic Methods

In certain embodiments, the present invention pertains to methods of diagnosing, or aiding in the diagnosis of, cardiovascular disease (e.g., MI, CAD, IA, AAA, stroke, PAD, restenosis) or a susceptibility to cardiovascular disease, by detecting particular alleles at genetic markers that appear more frequently in subjects with at least one cardiovascular disease or subjects who are susceptible to cardiovascular disease. In a particular embodiment, the invention is a method of diagnosing a susceptibility to cardiovascular disease by detecting at least one allele of at least one polymorphic marker (e.g., the markers described herein). The present invention describes methods whereby detection of particular alleles of particular markers or haplotypes is indicative of a susceptibility to cardiovascular disease. Such prognostic or predictive assays can also be used to determine prophylactic treatment of a subject prior to the onset of symptoms of the cardiovascular disease. The present invention pertains in some embodiments to methods of clinical applications of diagnosis, e.g., diagnosis performed by a medical professional. In other embodiments, the invention pertains to methods of diagnosis or determination of a susceptibility performed by a layman. Recent technological advances in genotyping technologies, including high-throughput genotyping of SNP markers, such as Molecular Inversion Probe array technology (e.g., Affymetrix GeneChip), and BeadArray Technologies (e.g., Illumina GoldenGate and Infinium assays) have made it possible for individuals to have their own genome assessed for up to one million SNPs simultaneously, at relatively little cost. The resulting genotype information, made available to the individual can be compared to information from the public literature about disease or trait risk associated with various SNPs. The diagnostic application of disease-associated alleles as described herein, can thus be performed either by the individual, through analysis of his/her genotype data, or by a health professional based on results of a clinical test. In other words, the diagnosis or assessment of a susceptibility based on genetic risk can be made by health professionals, genetic counselors or by the layman, based on information about his/her genotype and publications on various risk factors. In the present context, the term "diagnosing", "diagnose a susceptibility" and "determine a susceptibility" is meant to refer to any available diagnostic method, including those mentioned above.

In addition, in certain other embodiments, the present invention pertains to methods of diagnosing, or aiding in the diagnosis of, a decreased susceptibility to cardiovascular disease, by detecting particular genetic marker alleles or haplotypes that appear less frequently in patients diagnosed with cardiovascular disease than in individual not diagnosed with cardiovascular disease or in the general population.

As described and exemplified herein, particular marker alleles or haplotypes (e.g. the markers and haplotypes as listed in Tables 3, 10 and 21, and markers in linkage disequilibrium therewith) are associated with cardiovascular disease. In one embodiment, the marker allele or haplotype is one that confers a significant risk or susceptibility to cardiovascular disease. In another embodiment, the invention relates to a method of diagnosing a susceptibility to cardiovascular disease in a human individual, the method comprising determining the presence or absence of at least one allele of at least one polymorphic marker in a nucleic acid sample obtained from the individual, or in a genotype dataset derived from the individual, wherein the at least one polymorphic marker is selected from the group consisting of the polymorphic markers listed in Table 3, 10 or 21, and markers in linkage disequilibrium therewith. In another embodiment, the invention pertains to methods of diagnosing a susceptibility to cardiovascular disease in a human individual, by screening for at least one marker allele or haplotype as listed in Table 21 or markers in linkage disequilibrium therewith. In another embodiment, the marker allele or haplotype is more frequently present in a subject having, or who is susceptible to, cardiovascular disease (affected), as compared to the frequency of its presence in a healthy subject (control, such as population controls). In certain embodiments, the significance of association of the at least one marker allele or haplotype is characterized by a p value <0.05. In other embodiments, the significance of association is characterized by smaller p-values, such as <0.01, <0.001, <0.0001, <0.00001, <0.000001, <0.0000001, <0.00000001 or <0.000000001.

In these embodiments, the presence of the at least one marker allele or haplotype is indicative of a susceptibility to cardiovascular disease (e.g., MI, CAD, IA, Stroke, AAA, restenosis, PAD). These diagnostic methods involve detecting the presence or absence of at least one marker allele or haplotype that is associated with cardiovascular disease. The haplotypes described herein include combinations of alleles at various genetic markers (e.g., SNPs, microsatellites). The detection of the particular genetic marker alleles that make up the particular haplotypes can be performed by a variety of methods described herein and/or known in the art. For example, genetic markers can be detected at the nucleic acid level (e.g., by direct nucleotide sequencing or by other means known to the skilled in the art) or at the amino acid level if the genetic marker affects the coding sequence of a protein encoded by a cardiovascular disease, including coronary artery disease and in-stent restenosis-associated nucleic acid (e.g., by protein sequencing or by immunoassays using antibodies that recognize such a protein). The marker alleles or haplotypes of the present invention correspond to fragments of a genomic DNA sequence associated with cardiovascular disease. Such fragments encompass the DNA sequence of the polymorphic marker or haplotype in question, but may also include DNA segments in strong LD (linkage disequilibrium) with the marker or haplotype (e.g., as determined by particular values of $r^2$ and/or |D'|).

In one embodiment, diagnosis of a susceptibility to cardiovascular disease can be accomplished using hybridization methods, including, but not limited to, Southern analysis, Northern analysis, and/or in situ hybridizations (see Current Protocols in Molecular Biology, Ausubel, F. et al., eds., John Wiley & Sons, including all supplements). The presence of a specific marker allele can be indicated by sequence-specific hybridization of a nucleic acid probe specific for the particular allele. The presence of more than one specific marker allele or a specific haplotype can be indicated by using several sequence-specific nucleic acid probes, each being specific for a particular allele. In one embodiment, a haplotype can be indicated by a single nucleic acid probe that is specific for the specific haplotype (i.e., hybridizes specifically to a DNA strand comprising the specific marker alleles characteristic of the haplotype). A sequence-specific probe can be directed to hybridize to genomic DNA, RNA, or cDNA. A "nucleic acid probe", as used herein, can be a DNA probe or an RNA probe that hybridizes to a complementary sequence. One of skill in the art would know how to design such a probe so that sequence specific hybridization will occur only if a particular allele is present in a genomic sequence from a test sample.

To determine or diagnose a susceptibility to cardiovascular disease, a hybridization sample is formed by contacting the test sample containing an cardiovascular disease-associated nucleic acid, such as a genomic DNA sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length that is sufficient to specifically hybridize under stringent conditions to appropriate mRNA or genomic DNA. For example, the nucleic acid probe can comprise all or a portion of the nucleotide sequence of LD Block C09 (SEQ ID NO:94), as described herein, optionally comprising at least one allele of a marker described herein, or at least one haplotype described herein, or the probe can be the complementary sequence of such a sequence. In a particular embodiment, the nucleic acid probe is a portion of the nucleotide sequence of LD Block C09 (SEQ ID NO:94), as described herein, optionally comprising at least one allele of a marker described herein, or at least one allele of one polymorphic marker or haplotype comprising at least one polymorphic marker described herein, or the probe can be the complementary sequence of such a sequence. Other suitable probes for use in the diagnostic assays of the invention are described herein. Hybridization can be performed by methods well known to the person skilled in the art (see, e.g., Current Protocols in Molecular Biology, Ausubel, F. et al., eds., John Wiley & Sons, including all supplements). In one embodiment, hybridization refers to specific hybridization, i.e., hybridization with no mismatches (exact hybridization). In one embodiment, the hybridization conditions for specific hybridization are high stringency.

Specific hybridization, if present, is then detected using standard methods. If specific hybridization occurs between the nucleic acid probe and the coronary artery disease and in-stent restenosis-associated nucleic acid in the test sample, then the sample contains the allele that is complementary to the nucleotide that is present in the nucleic acid probe. The process can be repeated for other markers of the present invention, or markers that make up a haplotype of the present invention, or multiple probes can be used concurrently to detect more than one marker alleles at a time. It is also possible to design a single probe containing more than one marker alleles of a particular haplotype (e.g., a probe containing alleles complementary to 2, 3, 4, 5 or all of the markers that make up a particular haplotype). Detection of the particular markers of the haplotype in the sample is indicative that the source of the sample has the particular haplotype (e.g., a haplotype) and therefore is susceptible to cardiovascular disease (e.g., MI, CAD, IA, Stroke, AAA, restenosis, PAD).

In one preferred embodiment, a method utilizing a detection oligonucleotide probe comprising a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In another hybridization method, Northern analysis (see Current Protocols in Molecular Biology, Ausubel, F. et al., eds., John Wiley & Sons, supra) is used to identify the presence of a polymorphism associated with cardiovascular disease. For Northern analysis, a test sample of RNA is obtained from the subject by appropriate means. As described herein, specific hybridization of a nucleic acid probe to RNA from the subject is indicative of a particular allele complementary to the probe. For representative examples of use of nucleic acid probes, see, for example, U.S. Pat. Nos. 5,288,611 and 4,851,330.

Additionally, or alternatively, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, Nielsen, P., et al., *Bioconjug. Chem.* 5:3-7 (1994)). The PNA probe can be designed to specifically hybridize to a molecule in a sample suspected of containing one or more of the marker alleles or haplotypes that are associated with cardiovascular disease. Hybridization of the PNA probe is thus diagnostic for cardiovascular disease.

In one embodiment of the invention, a test sample containing genomic DNA obtained from the subject is collected and the polymerase chain reaction (PCR) is used to amplify a fragment comprising one or more markers or haplotypes of the present invention. As described herein, identification of a particular marker allele or haplotype associated with cardiovascular disease, can be accomplished using a variety of methods (e.g., sequence analysis, analysis by restriction digestion, specific hybridization, single stranded conformation polymorphism assays (SSCP), electrophoretic analysis, etc.). In another embodiment, diagnosis is accomplished by expression analysis using quantitative PCR (kinetic thermal cycling). This technique can, for example, utilize commercially available technologies, such as TaqMan® (Applied Biosystems, Foster City, Calif.). The technique can assess the presence of an alteration in the expression or composition of a polypeptide or splicing variant(s) that is encoded by a nucleic acid associated with a cardiovascular disease. Further, the expression of the variant(s) can be quantified as physically or functionally different.

In another embodiment of the methods of the invention, analysis by restriction digestion can be used to detect a particular allele if the allele results in the creation or elimination of a restriction site relative to a reference sequence. A test sample containing genomic DNA is obtained from the subject. PCR can be used to amplify particular regions that are associated with cardiovascular disease (e.g. the polymorphic markers and haplotypes of Table 3, 10 or 21, and markers in linkage disequilibrium therewith) nucleic acid in the test sample from the test subject. Restriction fragment length polymorphism (RFLP) analysis can be conducted, e.g., as described in Current Protocols in Molecular Biology, supra. The digestion pattern of the relevant DNA fragment indicates the presence or absence of the particular allele in the sample.

Sequence analysis can also be used to detect specific alleles at polymorphic sites associated with cardiovascular disease, including coronary artery disease and in-stent restenosis (e.g. the polymorphic markers and haplotypes of Table 3, 10 or 21, and markers in linkage disequilibrium therewith). Therefore, in one embodiment, determination of the presence or absence of a particular marker alleles or haplotypes comprises sequence analysis. For example, a test sample of DNA or RNA can be obtained from the test subject. PCR or other appropriate methods can be used to amplify a portion of a nucleic acid associated with cardiovascular disease, and the presence of a specific allele can then be detected directly by sequencing the polymorphic site (or multiple polymorphic sites) of the genomic DNA in the sample.

In another embodiment, arrays of oligonucleotide probes that are complementary to target nucleic acid sequence segments from a subject, can be used to identify polymorphisms in a nucleic acid associated with cardiovascular disease (e.g. the polymorphic markers of Table 3, 10, and 21, and markers in linkage disequilibrium therewith). For example, an oligonucleotide array can be used. Oligonucleotide arrays typically comprise a plurality of different oligonucleotide probes that are coupled to a surface of a substrate in different known locations. These arrays can generally be produced using mechanical synthesis methods or light directed synthesis methods that incorporate a combination of photolithographic methods and solid phase oligonucleotide synthesis methods, or by other methods known to the person skilled in the art (see, e.g., Fodor, S. et al., *Science,* 251:767-773 (1991); Pirrung et al., U.S. Pat. No. 5,143,854 (see also published PCT Application No. WO 90/15070); and Fodor. S. et al., published PCT Application No. WO 92/10092 and U.S. Pat. No. 5,424,186, the entire teachings of each of which are incorporated by reference herein). Techniques for the synthesis of these arrays using mechanical synthesis methods are described in, e.g., U.S. Pat. No. 5,384,261; the entire teachings of which are incorporated by reference herein. In another example, linear arrays can be utilized. Additional descriptions of use of oligonucleotide arrays for detection of polymorphisms can be found, for example, in U.S. Pat. Nos. 5,858,659 and 5,837,832, the entire teachings of both of which are incorporated by reference herein.

Other methods of nucleic acid analysis that are available to those skilled in the art can be used to detect a particular allele at a polymorphic site associated with cardiovascular disease. Representative methods include, for example, direct manual sequencing (Church and Gilbert, *Proc. Natl. Acad. Sci. USA*, 81: 1991-1995 (1988); Sanger, F., et al., *Proc. Natl. Acad. Sci. USA*, 74:5463-5467 (1977); Beavis, et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V., et al., *Proc. Natl. Acad. Sci. USA*, 86:232-236 (1989)), mobility shift analysis (Orita, M., et al., *Proc. Natl. Acad. Sci. USA*, 86:2766-2770 (1989)), restriction enzyme analysis (Flavell, R., et al., *Cell*, 15:25-41 (1978); Geever, R., et al., *Proc. Natl. Acad. Sci. USA*, 78:5081-5085 (1981)); heteroduplex analysis; chemical mismatch cleavage (CMC) (Cotton, R., et al., *Proc. Natl. Acad. Sci. USA*, 85:4397-4401 (1985)); RNase protection assays (Myers, R., et al., *Science*, 230: 1242-1246 (1985); use of polypeptides that recognize nucleotide mismatches, such as *E. coli* mutS protein; and allele-specific PCR.

In another embodiment of the invention, diagnosis of cardiovascular disease or a susceptibility to cardiovascular disease can be made by examining expression and/or composition of a polypeptide encoded by a nucleic acid associated with cardiovascular disease in those instances where the genetic marker(s) or haplotype(s) of the present invention result in a change in the composition or expression of the polypeptide. Thus, diagnosis of a susceptibility to cardiovascular disease can be made by examining expression and/or composition of one of these polypeptides, or another polypeptide encoded by a nucleic acid associated with cardiovascular disease, in those instances where the genetic marker or haplotype of the present invention results in a change in the composition or expression of the polypeptide. The haplotypes and markers of the present invention that show association to cardiovascular disease may play a role through their effect on one or more of these nearby genes (e.g, the CDKN2A and CDKN2B genes). Possible mechanisms affecting these genes include, e.g., effects on transcription, effects on RNA splicing, alterations in relative amounts of alternative splice forms of mRNA, effects on RNA stability, effects on transport from the nucleus to cytoplasm, and effects on the efficiency and accuracy of translation.

Thus, in another embodiment, the variants (markers or haplotypes) of the invention showing association to cardiovascular disease affect the expression of a nearby gene (e.g., CDKN2A and/or CDKN2B). It is well known that regulatory element affecting gene expression may be located far away, even as far as tenths or hundreds of kilobases away, from the promoter region of a gene. By assaying for the presence or absence of at least one allele of at least one polymorphic marker of the present invention, it is thus possible to assess the expression level of such nearby genes. It is thus contemplated that the detection of the markers or haplotypes of the present invention can be used for assessing expression for one or more of the CDKN2A and/or CDKN2B genes.

A variety of methods can be used for detecting protein expression levels, including enzyme linked immunosorbent assays (ELISA), Western blots, immunoprecipitations and immunofluorescence. A test sample from a subject is assessed for the presence of an alteration in the expression and/or an alteration in composition of the polypeptide encoded by a nucleic acid associated with cardiovascular disease. An alteration in expression of a polypeptide encoded by a nucleic acid associated with cardiovascular disease can be, for example, an alteration in the quantitative polypeptide expression (i.e., the amount of polypeptide produced). An alteration in the composition of a polypeptide encoded by a nucleic acid associated with a cardiovascular disease is an alteration in the qualitative polypeptide expression (e.g., expression of a mutant polypeptide or of a different splicing variant). In one embodiment, diagnosis of a susceptibility to cardiovascular disease is made by detecting a particular splicing variant encoded by a nucleic acid associated with cardiovascular disease, or a particular pattern of splicing variants.

Both such alterations (quantitative and qualitative) can also be present. An "alteration" in the polypeptide expression or composition (e.g., the CDKN2A and/or CDKN2B polypeptides), as used herein, refers to an alteration in expression or composition in a test sample, as compared to the expression or composition of the polypeptide in a control sample. A control sample is a sample that corresponds to the test sample (e.g., is from the same type of cells), and is from a subject who is not affected by, and/or who does not have a susceptibility to, cardiovascular disease. In one embodiment, the control sample is from a subject that does not possess a marker allele or haplotype associated with cardiovascular disease, as described herein. Similarly, the presence of one or more different splicing variants in the test sample, or the presence of significantly different amounts of different splicing variants in the test sample, as compared with the control sample, can be indicative of a susceptibility to cardiovascular disease. An alteration in the expression or composition of the polypeptide in the test sample, as compared with the control sample, can be indicative of a specific allele in the instance where the allele alters a splice site relative to the reference in the control sample. Various means of examining expression or composition of a polypeptide encoded by a nucleic acid are known to the person skilled in the art and can be used, including spectroscopy, colorimetry, electrophoresis, isoelectric focusing, and immunoassays (e.g., David et al., U.S. Pat. No. 4,376,110) such as immunoblotting (see, e.g., Current Protocols in Molecular Biology, particularly chapter 10, supra).

For example, in one embodiment, an antibody (e.g., an antibody with a detectable label) that is capable of binding to a polypeptide encoded by a nucleic acid associated with cardiovascular disease (e.g., CDKN2A and/or CDKN2B polypeptides) can be used. Antibodies can be polyclonal or monoclonal. An intact antibody, or a fragment thereof (e.g., Fv, Fab, Fab', F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a labeled secondary antibody (e.g., a fluorescently-labeled secondary antibody) and end-labeling of a DNA probe with biotin such that it can be detected with fluorescently-labeled streptavidin.

In one embodiment of this method, the level or amount of polypeptide encoded by a nucleic acid associated with cardiovascular disease in a test sample is compared with the level or amount of the polypeptide in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid, and is diagnostic for a particular allele or haplotype responsible for causing the difference in expression. Alternatively, the composition of the polypeptide in a test sample is compared with the composition of the polypeptide in a control sample. In another embodiment, both the level or amount and the composition of the polypeptide can be assessed in the test sample and in the control sample.

In another embodiment, the diagnosis of a susceptibility to cardiovascular disease is made by detecting at least one marker or haplotypes of the present invention (e.g., associated alleles of the markers listed in Table 3, 10 and/or 21, and markers in linkage disequilibrium therewith), in combination with an additional protein-based, RNA-based or DNA-based assay.

Kits

Kits useful in the methods of the invention comprise components useful in any of the methods described herein, including for example, primers for nucleic acid amplification, hybridization probes, restriction enzymes (e.g., for RFLP analysis), allele-specific oligonucleotides, antibodies that bind to an altered polypeptide encoded by a nucleic acid associated with cardiovascular disease (e.g., MI, CAD, IA, Stroke, AAA, restenosis, PAD) (e.g., antibodies that bind to a polypeptide encoded by LD Block C09 (SEQ ID NO:94), or the CDKN2A and/or CDKN2B genes or fragments thereof, e.g., a genomic segment comprising at least one polymorphic marker and/or haplotype of the present invention) or to a non-altered (native) polypeptide encoded by a nucleic acid associated with a cardiovascular disease, means for amplification of a nucleic acid associated with a cardiovascular disease, means for analyzing the nucleic acid sequence of a nucleic acid associated with a cardiovascular disease, means for analyzing the amino acid sequence of a polypeptide encoded by a nucleic acid associated with a cardiovascular disease, etc. The kits can for example include necessary buffers, nucleic acid primers for amplifying nucleic acids of the invention (e.g., a nucleic acid segment comprising one or more of the polymorphic markers as described herein), and reagents for allele-specific detection of the fragments amplified using such primers and necessary enzymes (e.g., DNA polymerase). Additionally, kits can provide reagents for assays to be used in combination with the methods of the present invention, e.g., reagents for use with other diagnostic assays as described herein.

In one embodiment, the invention pertains to a kit for assaying a sample from a subject to detect cardiovascular disease or a susceptibility to cardiovascular disease, wherein the kit comprises reagents necessary for selectively detecting at least one allele of at least one polymorphism of the present invention in the genome of the individual. In a particular embodiment, the reagents comprise at least one contiguous oligonucleotide that hybridizes to a fragment of the genome of the individual comprising at least one polymorphism of the present invention. In another embodiment, the reagents comprise at least one pair of oligonucleotides that hybridize to opposite strands of a genomic segment obtained from a subject, wherein each oligonucleotide primer pair is designed to selectively amplify a fragment of the genome of the individual that includes one polymorphism, wherein the polymorphism is selected from the group consisting of the polymorphisms as listed in any of the Tables 3, 10 and 21, and polymorphic markers in linkage disequilibrium therewith. In yet another embodiment the fragment is at least 20 base pairs in size. Such oligonucleotides or nucleic acids (e.g., oligonucleotide primers) can be designed using portions of the nucleic acids flanking polymorphisms (e.g., SNPs or microsatellites) that are indicative of a cardiovascular disease. In another embodiment, the kit comprises one or more labeled nucleic acids capable of detecting one or more specific polymorphic markers or haplotypes associated with cardiovascular disease, and reagents for detection of the label. Suitable labels include, e.g., a radioisotope, a fluorescent label, an enzyme label, an enzyme co-factor label, a magnetic label, a spin label, an epitope label.

In particular embodiments, the polymorphic marker or haplotype to be detected by the reagents of the kit comprises one or more markers, two or more markers, three or more markers, four or more markers or five or more markers selected from the group consisting of the markers in Table 3, 10 and 21, and markers in linkage disequilibrium therewith. In another embodiment, the marker or haplotype to be detected comprises the markers listed in Table 3, 10 or 21. In another embodiment, the marker or haplotype to be detected comprises at least one marker from the group of markers in strong linkage disequilibrium, as defined by values of $r^2$ greater than 0.2, to at least one of the group of markers consisting of rs10757278, rs10116277, rs1333040, D9S1814, D9S1870 and rs2383207. In yet another embodiment, the marker or haplotype to be detected comprises at least one marker selected from the group of markers consisting of rs10757278, rs7041637, rs2811712, rs3218018, rs3217992, rs2069426, rs2069422, rs1333034, rs1011970, rs10116277, rs1333040, rs2383207, rs1333050, D9S1814, and D9S1870.

In one preferred embodiment, the kit for detecting the markers of the invention comprises a detection oligonucleotide probe, that hybridizes to a segment of template DNA containing a SNP polymorphisms to be detected, an enhancer oligonucleotide probe and an endonuclease. As explained in the above, the detection oligonucleotide probe comprises a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection, and primers for such amplification are included in the reagent kit. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In one such embodiment, the presence of the marker or haplotype is indicative of a susceptibility (increased susceptibility or decreased susceptibility) to Cardiovascular disease. In another embodiment, the presence of the marker or haplotype is indicative of response to a therapeutic agent for a Cardiovascular disease. In another embodiment, the presence of the marker or haplotype is indicative of prognosis of a Cardiovascular disease. In yet another embodiment, the presence of the marker or haplotype is indicative of progress of treatment of a cardiovascular disease. Such treatment may include intervention by surgery, medication or by other means (e.g., lifestyle changes).

In a further aspect of the present invention, a pharmaceutical pack (kit) is provided, the pack comprising a therapeutic agent and a set of instructions for administration of the therapeutic agent to humans diagnostically tested for one or more variants of the present invention, as disclosed herein. The therapeutic agent can be a small molecule drug, an antibody, a peptide, an antisense or RNAi molecule, or other therapeutic molecules. In one embodiment, an individual identified as a carrier of at least one variant of the present invention is instructed to take a prescribed dose of the therapeutic agent. In one such embodiment, an individual identified as a homozygous carrier of at least one variant of the present invention is instructed to take a prescribed dose of the therapeutic agent. In another embodiment, an individual identified as a non-carrier of at least one variant of the present invention is instructed to take a prescribed dose of the therapeutic agent.

In certain embodiments, the kit further comprises a set of instructions for using the reagents comprising the kit.

Therapeutic Agents

Variants of the present invention (e.g., the markers and/or haplotypes of the invention as described herein, e.g., the markers listed in Table 3, 10 and 21) can be used to identify novel therapeutic targets for cardiovascular disease. For example, genes containing, or in linkage disequilibrium with, variants (markers and/or haplotypes) associated with cardiovascular disease, or their products (e.g., the CDKN2A and CDKN2B genes and their gene products), as well as genes or their products that are directly or indirectly regulated by or interact with these genes or their products, can be targeted for the development of therapeutic agents to treat cardiovascular disease, or prevent or delay onset of symptoms associated with cardiovascular disease. Therapeutic agents may comprise one or more of, for example, small non-protein and non-nucleic acid molecules, proteins, peptides, protein fragments, nucleic acids (DNA, RNA), PNA (peptide nucleic acids), or their derivatives or mimetics which can modulate the function and/or levels of the target genes or their gene products.

The nucleic acids and/or variants of the invention, or nucleic acids comprising their complementary sequence, may be used as antisense constructs to control gene expression in cells, tissues or organs. The methodology associated with antisense techniques is well known to the skilled artisan, and is described and reviewed in *Antisense Drug Technology: Principles, Strategies, and Applications*, Crooke, ed., Marcel Dekker Inc., New York (2001). In general, antisense nucleic acid molecules are designed to be complementary to a region of mRNA expressed by a gene, so that the antisense molecule hybridizes to the mRNA, thus blocking translation of the mRNA into protein. Several classes of antisense oligonucleotide are known to those skilled in the art, including cleavers and blockers. The former bind to target RNA sites, activate intracellular nucleases (e.g., RnaseH or Rnase L), that cleave the target RNA. Blockers bind to target RNA, inhibit protein translation by steric hindrance of the ribosomes. Examples of blockers include nucleic acids, morpholino compounds, locked nucleic acids and methylphosphonates (Thompson, *Drug Discovery Today*, 7:912-917 (2002)). Antisense oligonucleotides are useful directly as therapeutic agents, and are also useful for determining and validating gene function, for example by gene knock-out or gene knock-down experiments. Antisense technology is further described in Lavery et al., *Curr. Opin. Drug Discov. Devel.* 6:561-569 (2003), Stephens et al., *Curr. Opin. Mol. Ther.* 5:118-122 (2003), Kurreck, *Eur. J. Biochem.* 270:1628-44 (2003), Dias et al., *Mol. Cancer Ther.* 1:347-55 (2002), Chen, *Methods Mol. Med.* 75:621-636 (2003), Wang et al., *Curr. Cancer Drug Targets* 1:177-96 (2001), and Bennett, *Antisense Nucleic Acid Drug. Dev.* 12:215-24 (2002)

The variants described herein can be used for the selection and design of antisense reagents that are specific for particular variants. Using information about the variants described herein, antisense oligonucleotides or other antisense molecules that specifically target mRNA molecules that contain one or more variants of the invention can be designed. In this manner, expression of mRNA molecules that contain one or more variant of the present invention (markers and/or haplotypes) can be inhibited or blocked. In one embodiment, the antisense molecules are designed to specifically bind a particular allelic form (i.e., one or several variants (alleles and/or haplotypes)) of the target nucleic acid, thereby inhibiting translation of a product originating from this specific allele or haplotype, but which do not bind other or alternate variants at the specific polymorphic sites of the target nucleic acid molecule.

As antisense molecules can be used to inactivate mRNA so as to inhibit gene expression, and thus protein expression, the molecules can be used to treat a disease or disorder, such as a cardiovascular disease. The methodology can involve cleavage by means of ribozymes containing nucleotide sequences complementary to one or more regions in the mRNA that attenuate the ability of the mRNA to be translated. Such mRNA regions include, for example, protein-coding regions, in particular protein-coding regions corresponding to catalytic activity, substrate and/or ligand binding sites, or other functional domains of a protein.

The phenomenon of RNA interference (RNAi) has been actively studied for the last decade, since its original discovery in *C. elegans* (Fire et al., *Nature* 391:806-11 (1998)), and in recent years its potential use in treatment of human disease has been actively pursued (reviewed in Kim & Rossi, *Nature Rev. Genet.* 8:173-204 (2007)). RNA interference (RNAi), also called gene silencing, is based on using double-stranded RNA molecules (dsRNA) to turn off specific genes. In the cell, cytoplasmic double-stranded RNA molecules (dsRNA) are processed by cellular complexes into small interfering RNA (siRNA). The siRNA guide the targeting of a protein-RNA complex to specific sites on a target mRNA, leading to cleavage of the mRNA (Thompson, *Drug Discovery Today,* 7:912-917 (2002)). The siRNA molecules are typically about 20, 21, 22 or 23 nucleotides in length. Thus, one aspect of the invention relates to isolated nucleic acid molecules, and the use of those molecules for RNA interference, i.e. as small interfering RNA molecules (siRNA). In one embodiment, the isolated nucleic acid molecules are 18-26 nucleotides in length, preferably 19-25 nucleotides in length, more preferably 20-24 nucleotides in length, and more preferably 21, 22 or 23 nucleotides in length.

Another pathway for RNAi-mediated gene silencing originates in endogenously encoded primary microRNA (pri-miRNA) transcripts, which are processed in the cell to generate precursor miRNA (pre-miRNA). These miRNA molecules are exported from the nucleus to the cytoplasm, where they undergo processing to generate mature miRNA molecules (miRNA), which direct translational inhibition by recognizing target sites in the 3' untranslated regions of mRNAs, and subsequent mRNA degradation by processing P-bodies (reviewed in Kim & Rossi, *Nature Rev. Genet.* 8:173-204 (2007)).

Clinical applications of RNAi include the incorporation of synthetic siRNA duplexes, which preferably are approximately 20-23 nucleotides in size, and preferably have 3' overlaps of 2 nucleotides. Knockdown of gene expression is established by sequence-specific design for the target mRNA. Several commercial sites for optimal design and synthesis of such molecules are known to those skilled in the art.

Other applications provide longer siRNA molecules (typically 25-30 nucleotides in length, preferably about 27 nucleotides), as well as small hairpin RNAs (shRNAs; typically about 29 nucleotides in length). The latter are naturally expressed, as described in Amarzguioui et al. (*FEBS Lett.* 579:5974-81 (2005)). Chemically synthetic siRNAs and shRNAs are substrates for in vivo processing, and in some cases provide more potent gene-silencing than shorter designs (Kim et al., *Nature Biotechnol.* 23:222-226 (2005); Siolas et al., *Nature Biotechnol.* 23:227-231 (2005)). In general siRNAs provide for transient silencing of gene expression, because their intracellular concentration is diluted by subsequent cell divisions. By contrast, expressed shRNAs mediate long-term, stable knockdown of target transcripts, for as long as transcription of the shRNA takes place (Marques et al., *Nature Biotechnol.* 23:559-565 (2006); Brummelkamp et al., *Science* 296: 550-553 (2002)).

Since RNAi molecules, including siRNA, miRNA and shRNA, act in a sequence-dependent manner, the variants of the present invention (e.g., the markers and haplotypes set forth in Tables 3, 10 and 21) can be used to design RNAi reagents that recognize specific nucleic acid molecules comprising specific alleles and/or haplotypes (e.g., the alleles and/or haplotypes of the present invention), while not recognizing nucleic acid molecules comprising other alleles or haplotypes. These RNAi reagents can thus recognize and destroy the target nucleic acid molecules. As with antisense reagents, RNAi reagents can be useful as therapeutic agents (i.e., for turning off disease-associated genes or disease-associated gene variants), but may also be useful for characterizing and validating gene function (e.g., by gene knockout or gene knock-down experiments).

Delivery of RNAi may be performed by a range of methodologies known to those skilled in the art. Methods utilizing non-viral delivery include cholesterol, stable nucleic acid-lipid particle (SNALP), heavy-chain antibody fragment (Fab), aptamers and nanoparticles. Viral delivery methods include use of lentivirus, adenovirus and adeno-associated virus. The siRNA molecules are in some embodiments chemically modified to increase their stability. This can include modifications at the 2' position of the ribose, including 2'-O-methylpurines and 2'-fluoropyrimidines, which provide resistance to Rnase activity. Other chemical modifications are possible and known to those skilled in the art.

The following references provide a further summary of RNAi, and possibilities for targeting specific genes using RNAi: Kim & Rossi, *Nat. Rev. Genet.* 8:173-184 (2007), Chen & Rajewsky, *Nat. Rev. Genet.* 8: 93-103 (2007), Reynolds, et al., *Nat. Biotechnol.* 22:326-330 (2004), Chi et al., *Proc. Natl. Acad. Sci. USA* 100:6343-6346 (2003), Vickers et al., *J. Biol. Chem.* 278:7108-7118 (2003), Agami, *Curr. Opin. Chem. Biol.* 6:829-834 (2002), Lavery, et al., *Curr. Opin. Drug Discov. Devel.* 6:561-569 (2003), Shi, *Trends Genet.* 19:9-12 (2003), Shuey et al., *Drug Discov. Today* 7:1040-46 (2002), McManus et al., *Nat. Rev. Genet.* 3:737-747 (2002), Xia et al., *Nat. Biotechnol.* 20:1006-10 (2002), Plasterk et al., *Curr. Opin. Genet. Dev.* 10:562-7 (2000), Bosher et al., *Nat. Cell Biol.* 2:E31-6 (2000), and Hunter, *Curr. Biol.* 9:R440-442 (1999).

A genetic defect leading to increased predisposition or risk for development of a cardiovascular disease, or a defect causing the disease, may be corrected permanently by administering to a subject carrying the defect a nucleic acid fragment that incorporates a repair sequence that supplies the normal/wild-type nucleotide(s) at the site of the genetic defect. Such site-specific repair sequence may concompass an RNA/DNA oligonucleotide that operates to promote endogenous repair of a subject's genomic DNA. The administration of the repair sequence may be performed by an appropriate vehicle, such as a complex with polyethelenimine, encapsulated in anionic liposomes, a viral vector such as an adenovirus vector, or other pharmaceutical compositions suitable for promoting intracellular uptake of the adminstered nucleic acid. The genetic defect may then be overcome, since the chimeric oligonucleotides induce the incorporation of the normal sequence into the genome of the subject, leading to expression of the normal/wild-type gene product. The replacement is propagated, thus rendering a permanent repair and alleviation of the symptoms associated with the disease or condition.

The present invention provides methods for identifying compounds or agents that can be used to treat cardiovascular disease. Thus, the variants of the invention are useful as targets for the identification and/or development of therapeutic agents. In certain embodiments, such methods include assaying the ability of an agent or compound to modulate the activity and/or expression of a nucleic acid that includes at least one of the variants (markers and/or haplotypes) of the present invention, or the encoded product of the nucleic acid (e.g, one or both of the CDKN2A and CDKN2B genes). This in turn can be used to identify agents or compounds that inhibit or alter the undesired activity or expression of the encoded nucleic acid product. Assays for performing such experiments can be performed in cell-based systems or in cell-free systems, as known to the skilled person. Cell-based systems include cells naturally expressing the nucleic acid molecules of interest, or recombinant cells that have been genetically modified so as to express a certain desired nucleic acid molecule.

Variant gene expression in a patient can be assessed by expression of a variant-containing nucleic acid sequence (for example, a gene containing at least one variant of the present invention, which can be transcribed into RNA containing the at least one variant, and in turn translated into protein), or by altered expression of a normal/wild-type nucleic acid sequence due to variants affecting the level or pattern of expression of the normal transcripts, for example variants in the regulatory or control region of the gene. Assays for gene expression include direct nucleic acid assays (mRNA), assays for expressed protein levels, or assays of collateral compounds involved in a pathway, for example a signal pathway. Furthermore, the expression of genes that are up-or down-regulated in response to the signal pathway can also be assayed. One embodiment includes operably linking a reporter gene, such as luciferase, to the regulatory region of the gene(s) of interest.

Modulators of gene expression can in one embodiment be identified when a cell is contacted with a candidate compound or agent, and the expression of mRNA is determined. The expression level of mRNA in the presence of the candidate compound or agent is compared to the expression level in the absence of the compound or agent. Based on this comparison, candidate compounds or agents for treating cardiovascular disease can be identified as those modulating the gene expression of the variant gene. When expression of mRNA or the encoded protein is statistically significantly greater in the presence of the candidate compound or agent than in its absence, then the candidate compound or agent is identified as a stimulator or up-regulator of expression of the nucleic acid. When nucleic acid expression or protein level is statistically significantly less in the presence of the candidate compound or agent than in its absence, then the candidate compound is identified as an inhibitor or down-regulator of the nucleic acid expression.

The invention further provides methods of treatment using a compound identified through drug (compound and/or agent) screening as a gene modulator (i.e. stimulator and/or inhibitor of gene expression).

Methods of Assessing Probability of Response to Therapeutic Agents and Methods, Methods of Monitoring Treatment Progress and Methods for Treating Cardiovascular Disease As is known in the art, individuals can have differential responses to a particular therapy (e.g., a therapeutic agent or therapeutic method). Pharmacogenomics addresses the issue of how genetic variations (e.g., the variants (markers and/or haplotypes) of the present invention) affect drug response, due to altered drug disposition and/or abnormal or altered action of the drug. Thus, the basis of the differential response may be genetically determined in part. Clinical outcomes due to genetic variations affecting drug response may result in toxicity of the drug in certain individuals (e.g., carriers or non-carriers of the genetic variants of the present invention), or therapeutic failure of the drug. Therefore, the variants of the present invention may determine the manner in which a therapeutic agent and/or method acts on the body, or the way in which the body metabolizes the therapeutic agent.

Accordingly, in one embodiment, the presence of a particular allele of a polymorhpic marker, or the presence of a haplotype as described herein is indicative of a different response rate to a particular treatment modality for a cardiovascular disease. This means that a patient diagnosed with cardiovascular disease, or at risk for a cardiovascular disease, and carrying a certain allele at a polymorphic or haplotype of the present invention (e.g., the at-risk alleles and/or haplotypes of the invention) would respond better to, or worse to, a specific therapeutic, drug and/or other therapy used to treat the cardiovascular disease. Therefore, the presence or absence of the marker allele or haplotype could aid in deciding what treatment should be used for a the patient. For example, for a newly diagnosed patient, the presence of a marker or haplotype of the present invention may be assessed (e.g., through testing DNA derived from a blood sample or other sample containing genomic DNA, as described herein). If the patient is positive for a marker allele or haplotype at (that is, at least one specific allele of the marker, or haplotype, is present), then the physician recommends one particular therapy (e.g., one particular therapeutic agent or a combination of therapeutic agents), while if the patient is negative for the at least one allele of a marker, or a haplotype, then a different course of therapy may be recommended (which may include recommending that no immediate therapy, other than serial monitoring for progression of the disease, be performed). Thus, the patient's carrier status could be used to help determine whether a particular treatment modality should be administered. The value lies within the possibilities of being able to diagnose the disease at an early stage and provide information to the clinician about prognosis/aggressiveness of the disease in order to be able to apply the most appropriate treatment.

As one example, the application of a genetic test for restenosis can identify subjects who are at high risk of developing restenosis after coronary stent procedure. While it is know that some treatment methods for coronary artery disease, such as introducing drug-eluting stents and brachytherapy, are associated with decreased risk of in-stent restenosis, the use of these methods are restricted because of number of reasons, including economical reasons. Identification of individuals within the group of those undergoing coronary stent procedure who are carriers of genetic risk variants for in-stent restenosis will allow targeting of those individuals that would benefit most from therapy associated with decreased risk of in-stent restenosis.

The present invention also relates to methods of monitoring effectiveness of a treatment for a cardiovascular disease, including coronary artery disease, MI, stroke, PAD, IA, AAA and restenosis. This can be done based on the genotype and/or haplotype status of the markers and haplotypes of the present invention, or by monitoring expression of genes that are associated with the variants (markers and haplotypes) of the present invention (e.g., CDKN2A and CDKN2B). The risk gene mRNA or the encoded polypeptide can be measured in a tissue sample (e.g., a peripheral blood sample, or a biopsy sample). Expression levels and/or mRNA levels can thus be determined before and during treatment to monitor its effectiveness. Alternatively, or concomitantly, the genotype and/or haplotype status of at least one risk variant for cardiovascular disease as presented herein is determined before and during treatment to monitor its effectiveness.

The treatment modules of a cardiovascular disease to which the invention pertains includes, but is not limited to, methods of treatment for myocardial infarction or susceptibility to myocardial infarction; methods of prophylaxis therapy for myocardial infarction; methods of treatment for transient ischemic attack or stroke, or susceptibility to stroke; methods of treatment for claudication, PAD or susceptibility to PAD; methods of treatment for acute coronary syndrome (e.g., unstable angina, non-ST-elevation myocardial infarction (NSTEMI) or ST-elevation myocardial infarction (STEMI)); methods for reducing risk of MI, stroke or PAD; methods for decreasing risk of a second myocardial infarction or stroke; methods of treatment for atherosclerosis, such as for patients requiring treatment (e.g., angioplasty, stents, revascularization procedure) to restore blood flow in arteries (e.g., coronary, carotid, and/or femoral arteries); methods of treatment for asymptomatic ankle/brachial index of less than 0.9; and/or methods for decreasing leukotriene synthesis (e.g., for treatment of myocardial infarction, stroke or PAD), methods for treatment of abdominal aorta aneurysm, methods for treatment of intracranial aneurysm.

Treatment of coronary artery disease and MI may be categorized as (i) preventive treatment and (ii) disease management. The main goal of the latter is to minimize damage to the heart and prevent further complications. The first line of disease management typically includes one or more of administration of oxygen, aspirin, glyceryl nitrate (nitroglycerin) and analgesia, such as morphine or related drugs. Once diagnosis of MI is made, additional therapy may include beta blockers, anticoagulation agents, including heparin and/or low molecular weigth heparin, and possibly also antiplatelet agents, such as clopidogrel. Secondary prevention, i.e. the management of risk of a recurrent MI, typically includes one or more of the following: Antiplatelet drug therapy, including aspirin and/or clopidogrel, beta blocker therapy, including metoprolol and carvedilol, ACE inhibitor therapy, Statin therapy, Aldosterone antagonist therapy, including eplerenone. Further, non-therapeutic administration of food supplements such as omega-3 fatty acids may be beneficial.

New preventive therapy for cardiovascular disease, including CAD, MI and stroke, includes agents that act on the formation and/or rupture of plaques, and also includes phosphodiesterase inhibitors. Such therapeutic agents are useful in the methods of the invention, as described herein. This includes, but is not limited to, agents that target the leukotriene synthesis pathway. The leukotriene synthesis inhibitor can be any agent that inhibits or antagonizes a member of the leukotriene synthesis pathway (e.g., FLAP, 5-LO, LTC4S, LTA4H, and LTB4DH). For example, the leukotriene synthesis inhibitor can be an agent that inhibits or antagonizes FLAP polypeptide activity (e.g., a FLAP inhibitor) and/or FLAP nucleic acid expression (e.g., a FLAP nucleic acid antagonist). In another embodiment, the leukotriene synthesis inhibitor is an agent that inhibits or antagonizes polypeptide activity and/or nucleic acid expression of another member of the leukotriene biosynthetic pathway (e.g., LTC4S, LTA4H) or that increases breakdown of leukotrienes (e.g., LTB4DH). In preferred embodiments, the agent alters activity and/or nucleic acid expression of FLAP, LTA4H or of 5-LO. Preferred agents include those set forth in the Agent Table I herein. In another embodiment, preferred agents can be: 1-((4-chlorophenyl)methyl)-3-((1,1-dimethylethyl)thio)-alpha,alpha-dimethyl-5-(2-quinolinylmethoxy)-1H-Indole-2-propanoic acid otherwise known as MK-0591, (R)-(+)-alpha-cyclopentyl-4-(2-quinolinylmethoxy)-Benzeneacetic acid, otherwise known as BAY-x-1005, 3-(3-(1,1-dimethylethylthio-5-(quinoline-2-ylmethoxy)-1-(4-chloromethylphenyl)indole-2-yl)-2,2-dimethylpropionaldehyde oxime-O-2-acetic acid otherwise known as A-81834; or can be zileuton, atreleuton, 6-((3-fluoro-5-(tetrahydro-4-methoxy-2H-pyran-4yl)phenoxy) methyl)-1-methyl-2(1H)-quinlolinone otherwise known as ZD-2138, 1-((4-chlorophenyl)methyl)-3-((1,1-dimethylethyl)thio)-alpha,alpha-dimethyl-5-(2-quinolinylmethoxy)-1H-Indole-2-propanoic acid otherwise known as MK-886, 4-(3-(4-(2-Methyl-imidazol-1-yl)-phenylsulfanyl)-phenyl)-tetrahydro-pyran-4-carboxylic acid amide otherwise known as 0-13610. Additional agents include those described in Penning et al., *Med Chem.* 2002 45(16):3482-90, Penning, *Curr Pharm Des.* 2001, 7(3):163-79 and Penning et al., *J Med Chem.* 2000 43(4):721-35. In another embodiment, the agent alters metabolism or activity of a leukotriene (e.g., LTA4, LTB4, LTC4, LTD4, LTE4, Cys LT1, Cys LT2), such as leukotriene antagonists or antibodies to leukotrienes, as well as agents which alter activity of a leukotriene receptor (e.g., BLT1, BLT2, CysLTR1, and CysLTR2).

In other preferred embodiments, the agent alters activity and/or nucleic acid expression of LTA4H. Preferred agents include those set forth in the Agent Table II; but also include the following agents: 1-[2-[4-(phenylmethyl)phenoxy] ethyl]-2-methyl-4-tetrazolylpieridine; 1-[2-[4-(4-oxazolyl) phenoxy)phenoxy]ethyl]pyrrolidine; 3-[methyl[3-[4-(2-thienylmethyl)phenoxy]propyl]amino]propionic acid; methyl 3-[methyl[3-[4-(2-thienylmethyl)phenoxy]propyl] amino]propionate; 3-[methyl[3-[4-(3-thienylmethyl)phenoxy]propyl]amino]propionic acid; methyl-3-[methyl[3-4-(3-thienylmethyl)phenoxy]propyl]amino]propionate; 3-[methyl[3-[4-(4-fluorophenoxy)phenoxy]propyl]amino] propionic acid; 3-[methyl[3-[4-(4-biphenyloxy)phenoxy] propyl]amino]propionic acid; N-[3-[[3-[4-(phenylmethyl) phenoxy]propyl]methylamino]propionyl] benzenesulfonamide; 1-[2-[4-(phenylmethyl)phenoxy] ethyl]-2-methyl-4-(1H-tetrazol-5-yl)piperidine; 1-[2-[4-(phenylmethyl)phenoxy]ethyl]-4-(1H-tetrazol-5-yl) piperidine. In another embodiment, preferred agents can be: ethyl-1-[2-[4-(phenylmethyl)phenoxy]ethyl]-4-piperidine-carboxylate, otherwise known as SC-56938; [4-[5-(3-Phenyl-propyl)thiophen-2-yl]butoxy]acetic acid, otherwise known as RP64966; (R) —S-[[4-(dimethylamino)phenyl] methyl]-N-(3-mercapto-2-methyl-1-oxopropyl-L-cycteine, otherwise known as SA6541. In one preferred embodiment, the therapeutic agent is 4-{(S)-2-[4-(4-Chloro-phenoxy)-phenoxymethyl]-pyrrolidin-1-yl}-butyramide, also known as DG-051.

The agents for treating or preventing a cardiovascular disease can be administered alone, or in combination with a statin. Statins include, but are not limited to, the agents rovuvastatin, fluvastatin, atorvastatin, lovastatin (also known as mevolin), simvastatin, pravastatin, pitavastatin, mevastatin, crevastatin, ML-236A, ML-236B, MBV-530A and MB-530B.

All agents listed in the above and in Agent Table I and Agent Table II also include their optically pure enantiomers, salts, chemical derivatives, and analogues.

AGENT TABLE I

| | Product_Name (Code) | Structure |
|---|---|---|
| Abbott | atreleuton (ABT-761) | |
| Abbott | A-81834 | |
| Abbott | A-86886 | |
| Abbott | A-93178 | |
| AstraZeneca | | 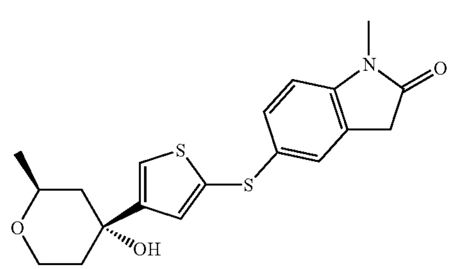 [SMILES: C[C@H]1C[C@@](O)(c2csc(Sc3ccc4c(c3)CC(=O)N4C)c2)CCO1] |

AGENT TABLE I-continued

AstraZeneca ZD-2138

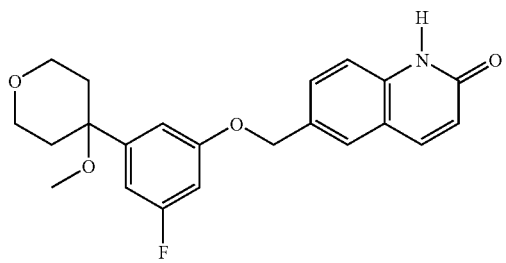 [SMILES: COC1(c2cc(F)cc(OCc3ccc4[nH]c(=O)ccc4c3)c2)CCOCC1]

Bayer BAY-X-1005

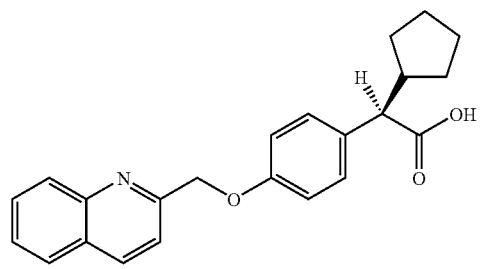 [SMILES: O=C(O)[C@@H](c1ccc(OCc2ccc3ccccc3n2)cc1)C1CCCC1]

Merck MK-0591

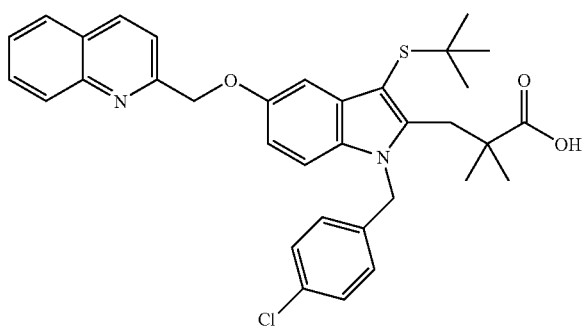 [SMILES: CC(C)(C)Sc1c(CC(C)(C)C(=O)O)n(Cc2ccc(Cl)cc2)c2ccc(OCc3ccc4ccccc4n3)cc12]

Merck MK-866

Merck MK-886

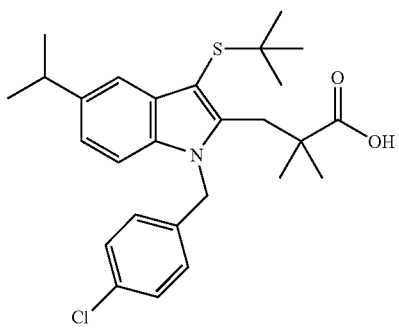 [SMILES: CC(C)c1ccc2c(c1)c(SC(C)(C)C)c(CC(C)(C)C(=O)O)n2Cc1ccc(Cl)cc1]

Pfizer CJ-13610

| | Chemical Name | Patent Ref | Date Patent Issued/ Application Published | MOA |
|---|---|---|---|---|
| Abbott | (R)-(+)-N-[3[5-[(4-fluorophenyl)methyl]-2thienyl]-1methyl-2-propynyl]-N-hydroxurea | U.S. Pat. No. 5288751, U.S. Pat. No. 5288743, U.S. Pat. No. 5616596 | 2/22/94 04/01/97 | 5-LPO inhibitor |
| Abbott | 3-(3-(1,1-dimethylethylthio-5-(quinoline-2-ylmethoxy)-1-(4-chloromethylphenyl)indole-2-yl)-2,2-dimethylpropionaldehyde oxime-0-2-acetic acid | WO9203132, U.S. Pat. No. 5459150 | 3/5/1992, 10/17/95 | FLAP inhibitor |

AGENT TABLE I-continued

| | | | | |
|---|---|---|---|---|
| Abbott | 3-(3-(1,1-dimethylethylthio-5-(pyridin-2-ylmethoxy)-1-(4-chloromethylphenyl)indole-2-yl)-2,2-dimethylpropionaldehyde oxime-0-2-acetic acid | WO9203132, U.S. Pat. No. 5459150 | 3/5/1992, 10/17/95 | 5-LPO inhibitor |
| Abbott | | | | FLAP Inhibitor |
| AstraZeneca | | EP 623614 | 09/11/94 | 5-LPO inhibitor |
| AstraZeneca | 6-((3-fluoro-5-(tetrahydro-4-methoxy-2H-pyran-4yl)phenoxy)methyl) 1-methyl-2(1H)-quinlolinone (alternatively NH can be N-methyl) | EP 466452 | | 5-LPO inhibitor |
| Bayer | (R)-(+) -alpha-cyclopentyl 4-(2-quinolinylmethoxy)-Benzeneacetic acid | U.S. Pat. No. 4970215 EP 344519, DE 19880531 | | FLAP inhibitor |
| Merck | 1-((4-chlorophenyl)methyl)-3-((1,1-dimethylethyl)thio) alpha,alpha-dimethyl-5-(2-quinolinylmethoxy)-1H-Indole-2-propanoic acid | EP 419049, U.S. Pat. No. 19890822 | | FLAP inhibitor |
| Merck | (3[3-)4-chlorobenzyl)-3-t-butyl-thio-5-isopropylindol-2yl]2,2-dimethyl-proanoic acid | | | 5-LPO inhibitor |
| Merck | 1-((4-chlorophenyl)methyl)-3-((1,1dimethylethyl)thio)-alpha,alpha-dimethyl-5-(2-quinolinylmethoxy-1H-Indole-2-propanoic acid | EP 419049, U.S. Pat. No. 19890822 | | 5-LPO inhibitor |
| Pfizer | 4-(3-(4-(2-Methyl-imidazol-1-yl)-phenylsulfanyl)-phenyl)-tetrahydro-pyran-4-carboxylic acid amide | | | 5-LPO inhibitor |

AGENT TABLE II

| Target | Compound ID | Chemical Name | Patent/Reference |
|---|---|---|---|
| LTA4H Inhibitor | SC-57461A | 3-[methyl[3-[4-(phenylmethyl)phenoxy]-propyl]amino]propionic acid | Penning, T. D. et.al. Bioorg Med. Chem. Letters (2003), 13, 1137-1139. ibid, (2002), 12, 3383-3386 |
| LTA4H Inhibitor | SC-56938 | Ethyl-1-[2-[4-(phenylmethyl)phenoxy]ethyl]-4-piperidine-carboxylate | Penning, T. D. et.al. Bioorg Med. Chem. Letters (2003), 13, 1137-1139. ibid, (2002), 12, 3383-3386. US 6,506,87 6A1 |
| LTA4H Inhibitor | RP 64966 | [4-[5-(3-Phenyl-propyl)thiophen-2-yl]butoxy]acetic acid | WO9627585 |
| LTA4H Inhibitor | SA 6541 | (R)—S-[[4-(dimethylamino)phenyl]methyl]-N-(3-mercapto-2methyl-1-oxopropyl-L-cycteine | WO9809943 |
| LTA4H Inhibitor | SA-9499/ SA-6541 | (R)-3-(4-Dimethylamino-benzylsulfanyl)-2-((R)-3-mercapto-2-methyl-propionylamino)-propionic acid | |
| LTB4 Receptor Antagonist | Amelubant/ BIIL-284 | Carbamic acid,((4-(3-((4-(1-(4-hydroxyphenyl)-1-methylethyl)phenoxy)methyl)phenyl)methoxy)phenyl)iminomethyl)-ethyl ester | U.S. Pat. No. 6,576,669 |

AGENT TABLE II-continued

| Target | Compound ID | Chemical Name | Patent/Reference |
|---|---|---|---|
| LTB4 Receptor Antagonist | BIRZ-227 | 5-Chloro-2-[3-(4-methoxy-phenyl)-2-pyridin-2-yl-pyrrolidin-1-yl]-benzooxazole | Journal of Organic Chemistry 1998, 63: 2(326-330). |
| LTB4 Receptor Antagonist | CP 195543 | 2-[(3S,4R)-3,4-dihydro-4-hydroxy-3-(phenylmethyl)-2H-1-benzopyran-7-yl]-4-(trifluoromethyl)benzoic acid | Process: WO 98/11085 1998, priority US 60/26372 1996; J. Pharamacology and Expert. Therapy, 1998, 285: 946-54 |
| LTB4 Receptor Antagonist | Ebselen | 2-Phenyl-benzo[d]isoselenazol-3-one | Journal of Cerebral Blood Flow and Metabolism 1995, July 2-6 (S162); Drugs of the Future 1995, 20: 10 (1057) |
| LTB4 Receptor Antagonist | LTB 019; CGS-25019C | 4-[5-(4-Carbamimidoyl-phenoxy)-pentyloxy]-N,N-diisopropyl-3-methoxy-benzamide maleate | ACS Meeting 1994, 207th: San Diego (MEDI 003); International Congress of the Inflammation Research Association 1994, 7th: White Haven (Abs W23) |
| LTB4 Receptor Antagonist | LY 210073 | 5-(2-Carboxy-ethyl)-6-[6-(4-methoxy-phenyl)-hex-5-enyloxy]-9-oxo-9H-xanthene-2-carboxylic acid | J Med Chem 1993 36 (12) 1726-1734 |
| LTB4 Receptor Antagonist | LY 213024 | 5-(3-carboxybenzoyl)-2-(decyloxy)benzenepropanoic acid | J Med Chem 1993 36 (12) 1726-1734 |
| LTB4 Receptor Antagonist | LY 255283 | 1-[5-ethyl-2-hydroxy-4-[[6-methyl-6-(1H-tetrazol-5-yl)heptyl]oxy]phenyl]ethanone | EP 276064 B 1990, priority US 2479 1987 |
| LTB4 Receptor Antagonist | LY 264086 | 7-carboxy-3-(decyloxy)-9-oxo-9H-xanthene-4-propanoic acid | U.S. Pat. No. 4,996,230 1991, priority US 481413 1990 |
| LTB4 Receptor Antagonist | LY 292728 | 7-carboxy-3-[3-[(5-ethyl-4'-fluoro-2-hydroxy[1,1'-biphenyl]-4-yl)oxy]propoxy]-9-oxo-9H-xanthene-4-propanoic acid disodium salt | EP 743064 A 1996, priority US 443179 1995 |
| LTB4 Receptor Antagonist | LY-293111 (VML-295) | Benzoic acid, 2-(3-(3-((5-ethyl-4'-fluoro-2-hydroxy(1,1'-biphenyl)-4-yl)oxy)propoxy)-2-propylphenoxy)- | Proceedings of the American Society for Clinical Oncology 2002, 21: 1 (Abs 343) [LY-293111 for Cancer] SCRIP World Pharmaceutical News 1997, 2272 (13) [for VML-295] |
| LTB4 Receptor Antagonist | ONO 4057; LB 457 | (E)-2-(4-carboxybutoxy)-6-[[6-(4-methoxyphenyl)-5-hexenyl]oxy]benzenepropanoic acid | EP 405116 A 1991 |
| LTB4 Receptor Antagonist | PF 10042 | 1-[5-hydroxy-5-[8-(1-hydroxy-2-phenylethyl)-2-dibenzofuranyl]-1-oxopentyl]pyrrolidine | EP 422329 B 1995, priority US 409630 1989 |
| LTB4 Receptor Antagonist | RG-14893 | 8-Benzyloxy-4-[(methyl-phenethyl-carbamoyl)-methyl]-naphthalene-2-carboxylic acid | SCRIP World Pharmaceutical News 1996, 2168 (20) |
| LTB4 Receptor Antagonist | SB-201993 | 3-{6-(2-Carboxy-vinyl)-5-[8-(4-methoxy-phenyl)-octyloxy]-pyridin-2-ylmethylsulfanylmethyl}-benzoic acid | WO-09500487 |
| LTB4 Receptor Antagonist | SC-52798 | 7-[3-(2-Cyclopropylmethyl-3-methoxy-4-thiazol-4-yl-phenoxy)-propoxy]-8-propyl-chroman-2-carboxylic acid | Bioorganic and Medicinal Chemistry Letters 1994, 4: 6 (811-816); Journal of Medicinal Chemistry 1995, 38: 6 (858-868) |
| LTB4 Receptor Antagonist | SC-53228 | 3-{7-[3-(2-Cyclopropylmethyl-3-methoxy-4-methylcarbamoyl-phenoxy)-propoxy]-8-propyl-chroman-2-yl}-propionic acid | International Congress of the Inflammation Research Association 1994, 7th: White Haven (Abs W5) |

AGENT TABLE II-continued

| Target | Compound ID | Chemical Name | Patent/Reference |
|---|---|---|---|
| LTB4 Receptor Antagonist | WAY 121006 | 3-fluoro-4'-(2-quinolinylmethoxy)-[1,1'-biphenyl]-4-acetic acid | Drugs under Experimental and Clinical research 1991, 17: 8 (381-387) |
| LTB4 Receptor Antagonist | ZD-2138 | 3-Amino-3-(4-methoxy-tetrahydro-pyran-4-yl)-acrylic acid 1-methyl-2-oxo-1,2-dihydro-quinolin-6-ylmethyl ester | International Symposium on Medicinal Chemistry 1994, 13th: Paris (P 197) |

Alternatively, biological networks or metabolic pathways related to the markers and haplotypes of the present invention can be monitored by determining mRNA and/or polypeptide levels. This can be done for example, by monitoring expression levels or polypeptides for several genes belonging to the network and/or pathway, in samples taken before and during treatment. Alternatively, metabolites belonging to the biological network or metabolic pathway can be determined before and during treatment. Effectiveness of the treatment is determined by comparing observed changes in expression levels/metabolite levels during treatment to corresponding data from healthy subjects.

In a further aspect, the markers of the present invention can be used to increase power and effectiveness of clinical trials. Thus, individuals who are carriers of the at-risk variants of the present invention may be more likely to respond to a particular treatment modality. In one embodiment, individuals who carry at-risk variants for gene(s) in a pathway and/or metabolic network for which a particular treatment (e.g., small molecule drug, e.g. the small molecule drugs as listed in the above, e.g., the drugs listed in Agent Table I and Agent Table II) is targeting, are more likely to be responders to the treatment. In another embodiment, individuals who carry at-risk variants for a gene, which expression and/or function is altered by the at-risk variant, are more likely to be responders to a treatment modality targeting that gene, its expression or its gene product.

In a further aspect, the markers and haplotypes of the present invention can be used for targeting the selection of pharmaceutical agents for specific individuals. Personalized selection of treatment modalities, lifestyle changes (e.g., change in diet, exercise, weight loss program, smoking abstinence, less stressful lifestyle, etc.) or combination of the two, can be realized by the utilization of the at-risk variants of the present invention. Thus, the knowledge of an individual's status for particular markers of the present invention, can be useful for selection of treatment options that target genes or gene products affected by the at-risk variants of the invention. Certain combinations of variants may be suitable for one selection of treatment options, while other gene variant combinations may target other treatment options. Such combination of variant may include one variant, two variants, three variants, or four or more variants, as needed to determine with clinically reliable accuracy the selection of treatment module.

In addition to the diagnostic and therapeutic uses of the variants of the present invention, the variants (markers and haplotypes) can also be useful markers for human identification, and as such be useful in forensics, paternity testing and in biometrics. The specific use of SNPs for forensic purposes is reviewed by Gill (Int. J. Legal Med. 114:204-10 (2001)). Genetic variations in genomic DNA between individuals can be used as genetic markers to identify individuals and to associate a biological sample with an individual.

Genetic markers, including SNPs and microsatellites, can be useful to distinguish individuals. The more markers that are analyzed, the lower the probability that the allelic combination of the markers in any given individual is the same as in an unrelated individual (assuming that the markers are unrelated, i.e. that the markers are in perfect linkage equilibrium). Thus, the variants used for these purposes are preferably unrelated, i.e. they are inherited independently. Thus, preferred markers can be selected from available markers, such as the markers of the present invention, and the selected markers may comprise markers from different regions in the human genome, including markers on different chromosomes.

In certain applications, the SNPs useful for forensic testing are from degenerate codon positions (i.e., the third position in certain codons such that the variation of the SNP does not affect the amino acid encoded by the codon). In other applications, such for applications for predicting phenotypic characteristics including race, ancestry or physical characteristics, it may be more useful and desirable to utilize SNPs that affect the amino acid sequence of the encoded protein. In other such embodiments, the variant (SNP or other polymorphic marker) affects the expression level of a nearby gene, thus leading to altered protein expression.

Computer-Implemented Aspects

The present invention also relates to computer-implemented applications of the polymorphic markers and haplotypes described herein to be associated with cardiovascular disease. Such applications can be useful for storing, manipulating or otherwise analyzing genotype data that is useful in the methods of the invention. One example pertains to storing genotype information derived from an individual on readable media, so as to be able to provide the genotype information to a third party (e.g., the individual), or for deriving information from the genotype data, e.g., by comparing the genotype data to information about genetic risk factors contributing to increased susceptibility to cardiovascular disease, and reporting results based on such comparison.

One such aspect relates to computer-readable media. In general terms, such medium has capabilities of storing (i) identifier information for at least one polymorphic marker or a haplotype; (ii) an indicator of the frequency of at least one allele of said at least one marker, or the frequency of a haplotype, in individuals with cardiovascular disease (e.g., MI; CAD, IA, AAA, stroke, restenosis, PAD); and an indicator of the frequency of at least one allele of said at least one marker, or the frequency of a haplotype, in a reference population. The reference population can be a disease-free population of individuals. Alternatively, the reference population is a random sample from the general population, and is thus representative of the population at large. The frequency indicator may be a calculated frequency, a count of alleles and/or haplotype copies, or normalized or otherwise manipulated values of the actual frequencies that are suitable for the particular medium.

Additional information about the individual can be stored on the medium, such as ancestry information, information about sex, physical attributes or characteristics (including height and weight), biochemical measurements (such as blood pressure, blood lipid levels, lipid levels, such as cholesterol levels), biomarkers relevant for cardiovascular disease, as described further herein, or other useful information that is desirable to store or manipulate in the context of the genotype status of a particular individual.

The invention furthermore relates to an apparatus that is suitable for determination or manipulation of genetic data useful for determining a susceptibility to cardiovascular disease in a human individual. Such an apparatus can include a computer-readable memory, a routine for manipulating data stored on the computer-readable memory, and a routine for generating an output that includes a measure of the genetic data. Such measure can include values such as allelic or haplotype frequencies, genotype counts, sex, age, phenotype information, values for odds ratio (OR) or relative risk (RR), population attributable risk (PAR), or other useful information that is either a direct statistic of the original genotype data or based on calculations based on the genetic data.

The markers and haplotypes shown herein to be associated with increased susceptibility (e.g., increased risk) of cardiovascular disease, are in certain embodiments useful for interpretation and/or analysis of genotype data. Thus in certain embodiments, an identification of an at-risk allele for a cardiovascular disease, as shown herein, or an allele at a polymorphic marker in LD with any one of the markers shown herein to be associated with cardiovascular disease, is indicative of the individual from whom the genotype data originates is at increased risk of cardiovascular disease. In one such embodiment, genotype data is generated for at least one polymorphic marker shown herein to be associated with cardiovascular disease, or a marker in linkage disequilibrium therewith. The genotype data is subsequently made available to the individual from whom the data originates, for example via a user interface accessible over the internet, together with an interpretation of the genotype data, e.g., in the form of a risk measure (such as an absolute risk (AR), risk ratio (RR) or odds ration (OR)) for the cardiovascular disease. In another embodiment, at-risk markers identified in a genotype dataset derived from an individual are assessed and results from the assessment of the risk conferred by the presence of such at-risk variants in the dataset are made available to the individual, for example via a secure web interface, or by other communication means. The results of such risk assessment can be reported in numeric form (e.g., by risk values, such as absolute risk, relative risk, and/or an odds ratio, or by a percentage increase in risk compared with a reference), by graphical means, or by other means suitable to illustrate the risk to the individual from whom the genotype data is derived. In particular embodiments, the results of risk assessment is made available to a third party, e.g., a physician, other healthcare worker or genetic counselor.

Markers Useful in Various Aspects of the Invention

The above-described applications can all be practiced with the markers and haplotypes of the invention that have in more detail been described with respect to methods of assessing susceptibility to cardiovascular disease and described in detail herein. Thus, these applications can in general be reduced to practice using any of the markers listed in Tables 1-35, and markers in linkage disequilibrium therewith. In some embodiments, the marker is selected from the markers set forth in Tables 3, 10 or 21, and markers in linkage disequilibrium therewith. In one embodiment, the markers or haplotypes are present within the genomic segment whose sequence is set forth in SEQ ID NO:94. In another embodiment, the markers and haplotypes comprise at least one marker selected from rs7041637, rs2811712, rs3218018, rs3217992, rs2069426, rs2069422, rs1333034, rs1011970, rs10116277, rs1333040, rs2383207, rs1333050, D9S1814, rs10757278, rs10757274, rs10333049, D9S1870, optionally including markers in linkage disequilibrium therewith. In one specific embodiment, linkage disequilibrium is defined by numerical values for $r^2$ of greater than 0.2. In another embodiment, the marker or haplotype comprises at least one marker selected from rs7041637 allele A, rs2811712 allele A, rs3218018 allele A, rs3217992 allele A, rs2069426 allele C, rs2069422 allele A, rs1333034 allele A, rs1011970 allele G, rs10116277 allele T, rs1333040 allele T, rs2383207 allele G, rs1333050 allele T, D9S1814 allele 0, rs10757278 allele G, rs1333049 allele C, rs10757274 allele G, and/or D9S1870 allele X (composite allele of all alleles smaller than 2), wherein the indicated allele is indicative of increased susceptibility of the Cardiovascular disease.

Nucleic Acids and Polypeptides

The nucleic acids and polypeptides described herein can be used in methods and kits of the present invention. An "isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA library). For example, an isolated nucleic acid of the invention can be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material can be purified to essential homogeneity, for example as determined by polyacrylamide gel electrophoresis (PAGE) or column chromatography (e.g., HPLC). An isolated nucleic acid molecule of the invention can comprise at least about 50%, at least about 80% or at least about 90% (on a molar basis) of all macromolecular species present. With regard to genomic DNA, the term "isolated" also can refer to nucleic acid molecules that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells or heterologous organisms, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Such isolated nucleotide sequences are useful, for example, in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis or other hybridization techniques.

The invention also pertains to nucleic acid molecules that hybridize under high stringency hybridization conditions, such as for selective hybridization, to a nucleotide sequence described herein (e.g., nucleic acid molecules that specifically hybridize to a nucleotide sequence containing a polymorphic site associated with a haplotype described herein). In one embodiment, the invention includes variants that hybridize under high stringency hybridization and wash conditions (e.g., for selective hybridization) to a nucleotide sequence that comprises the nucleotide sequence of LD Block C09 (SEQ ID NO:94) or a fragment thereof (or a nucleotide sequence comprising the complement of the nucleotide sequence of LD Block C09 as set forth in SEQ ID NO:94), wherein the nucleotide sequence comprises at least one at-risk allele of at least one polymorphic marker, or at least one haplotype, as described herein.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions×100). In certain embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S. and Altschul, S., *Proc. Natl. Acad. Sci. USA*, 90:5873-5877 (1993). Such an algorithm is incorporated into the NBLAST and XBLAST programs (version 2.0), as described in Altschul, S. et al., *Nucleic Acids Res.*, 25:3389-3402 (1997). When utilizing BLAST and Gapped BLAST programs, the default parameters of the respective programs (e.g., NBLAST) can be used. See the website on the world wide web at ncbi.nlm.nih.gov. In one embodiment, parameters for sequence comparison can be set at score=100, wordlength=12, or can be varied (e.g., W=5 or W=20). Other examples include the algorithm of Myers and Miller, CABIOS (1989), ADVANCE and ADAM as described in Torellis, A. and Robotti, C., *Comput. Appl. Biosci.* 10:3-5 (1994); and FASTA described in Pearson, W. and Lipman, D., *Proc. Natl. Acad. Sci. USA*, 85:2444-48 (1988). In another embodiment, the percent identity between two amino acid sequences can be accomplished using the GAP program in the GCG software package (Accelrys, Cambridge, UK).

The present invention also provides isolated nucleic acid molecules that contain a fragment or portion that hybridizes under highly stringent conditions to a nucleic acid that comprises, or consists of, the nucleotide sequence of LD Block C09 (SEQ ID NO:94), or a nucleotide sequence comprising, or consisting of, the complement of the nucleotide sequence of LD Block C09 (SEQ ID NO:94), wherein the nucleotide sequence comprises at least one polymorphic allele contained in the markers and haplotypes described herein. The nucleic acid fragments of the invention are at least about 15, at least about 18, 20, 23 or 25 nucleotides, and can be 30, 40, 50, 100, 200, 500, 1000, 10,000 or more nucleotides in length.

The nucleic acid fragments of the invention are used as probes or primers in assays such as those described herein. "Probes" or "primers" are oligonucleotides that hybridize in a base-specific manner to a complementary strand of a nucleic acid molecule. In addition to DNA and RNA, such probes and primers include polypeptide nucleic acids (PNA), as described in Nielsen, P. et al., *Science* 254:1497-1500 (1991). A probe or primer comprises a region of nucleotide sequence that hybridizes to at least about 15, typically about 20-25, and in certain embodiments about 40, 50 or 75, consecutive nucleotides of a nucleic acid molecule comprising a contiguous nucleotide sequence from LD Block C09 and comprising at least one allele of at least one polymorphic marker or at least one haplotype described herein, or the complement thereof. In particular embodiments, a probe or primer can comprise 100 or fewer nucleotides; for example, in certain embodiments from 6 to 50 nucleotides, or, for example, from 12 to 30 nucleotides. In other embodiments, the probe or primer is at least 70% identical, at least 80% identical, at least 85% identical, at least 90% identical, or at least 95% identical, to the contiguous nucleotide sequence or to the complement of the contiguous nucleotide sequence. In another embodiment, the probe or primer is capable of selectively hybridizing to the contiguous nucleotide sequence or to the complement of the contiguous nucleotide sequence. Often, the probe or primer further comprises a label, e.g., a radioisotope, a fluorescent label, an enzyme label, an enzyme co-factor label, a magnetic label, a spin label, an epitope label.

The nucleic acid molecules of the invention, such as those described above, can be identified and isolated using standard molecular biology techniques and the sequence information provided by the nucleotide sequence of LD Block C09 (SEQ ID NO:94). See generally *PCR Technology: Principles and Applications for DNA Amplification* (ed. H.A. Erlich, Freeman Press, NY, N.Y., 1992); *PCR Protocols: A Guide to Methods and Applications* (Eds. Innis, et al., Academic Press, San Diego, Calif., 1990); Mattila, P. et al., *Nucleic Acids Res.*, 19:4967-4973 (1991); Eckert, K. and Kunkel, T., *PCR Methods and Applications*, 1:17-24 (1991); PCR (eds. McPherson et al., IRL Press, Oxford); and U.S. Pat. No. 4,683,202, the entire teachings of each of which are incorporated herein by reference.

In general, the isolated nucleic acid sequences of the invention can be used as molecular weight markers on Southern gels, and as chromosome markers that are labeled to map related gene positions. The nucleic acid sequences can also be used to compare with endogenous DNA sequences in patients to identify a susceptibility to a cardiovascular disease, and as probes, such as to hybridize and discover related DNA sequences or to subtract out known sequences from a sample (e.g., subtractive hybridization). The nucleic acid sequences can further be used to derive primers for genetic fingerprinting, to raise anti-polypeptide antibodies using immunization techniques, and/or as an antigen to raise anti-DNA antibodies or elicit immune responses.

Two polypeptides, as described herein (or a region of the polypeptides) are substantially homologous or identical when the amino acid sequences are at least about 45-55%. In other embodiments, two polypeptides (or a region of the polypeptides) are substantially homologous or identical when they are at least about 70-75%, at least about 80-85%, at least about 90%, at least about 95% homologous or identical, or are identical. A substantially homologous amino acid sequence, according to the present invention, will be encoded by a nucleic acid molecule comprising the nucleotide sequence of LD Block C09 (SEQ ID NO:94) or a portion thereof, and further comprising at least one polymorphism as shown in Table 3, 10 or 21, wherein the encoding nucleic acid will hybridize to the nucleotide sequence of LD Block C09 (SEQ ID NO:94), under stringent conditions as more particularly described herein. In on embodiment, the polypeptide comprises all or a portion of the amino acid sequence of CDKN2A and/or CDKN2B.

Antibodies

Polyclonal antibodies and/or monoclonal antibodies that specifically bind one form of the gene product but not to the other form of the gene product are also provided. Antibodies are also provided which bind a portion of either the variant or the reference gene product that contains the polymorphic site or sites. The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, Nature 256:495-497 (1975), the human B cell hybridoma technique (Kozbor et al., Immunol. Today 4: 72 (1983)), the EBV-hybridoma technique (Cole et al., Monoclonal Antibodies and Cancer Therapy, Alan R. Liss, 1985, Inc., pp. 77-96) or trioma techniques. The technology for producing hybridomas is well known (see generally Current Protocols in Immunology (1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., Current Protocols in Immunology, supra; Galfre et al., Nature 266:55052 (1977); R. H. Kenneth, in Monoclonal Antibodies: A New Dimension In Biological Analyses, Plenum Publishing Corp., New York, N.Y. (1980); and Lerner, Yale J. Biol. Med. 54:387-402 (1981)). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., Bio/Technology 9: 1370-1372 (1991); Hay et al., Hum. Antibod. Hybridomas 3:81-85 (1992); Huse et al., Science 246: 1275-1281 (1989); and Griffiths et al., EMBO J. 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies may also be useful in pharmacogenomic analysis. In such embodiments, antibodies against variant proteins encoded by nucleic acids according to the invention, such as variant proteins that are encoded by nucleic acids that contain at least one polymorphic marker of the invention, can be used to identify individuals that require modified treatment modalities.

Antibodies can furthermore be useful for assessing expression of variant proteins in disease states, such as in active stages of a cardiovascular disease, or in an individual with a predisposition to a disease related to the function of the protein, in particular a cardiovascular disease. Examples are provided by biomarker (e.g., cardiac markers), as described further herein. Antibodies specific for a variant protein of the present invention that is encoded by a nucleic acid that comprises at least one polymorphic marker or haplotype as described herein (e.g., CDKN2A and/or CDKN2B) can be used to screen for the presence of the variant protein, for example to screen for a predisposition to cardiovascular disease as indicated by the presence of the variant protein.

Antibodies can be used in other methods. Thus, antibodies are useful as diagnostic tools for evaluating proteins, such as variant proteins of the invention, in conjunction with analysis by electrophoretic mobility, isoelectric point, tryptic or other protease digest, or for use in other physical assays known to those skilled in the art. Antibodies may also be used in tissue typing. In one such embodiment, a specific variant protein has been correlated with expression in a specific tissue type, and antibodies specific for the variant protein can then be used to identify the specific tissue type.

Subcellular localization of proteins, including variant proteins, can also be determined using antibodies, and can be applied to assess aberrant subcellular localization of the protein in cells in various tissues. Such use can be applied in genetic testing, but also in monitoring a particular treatment modality. In the case where treatment is aimed at correcting the expression level or presence of the variant protein or aberrant tissue distribution or developmental expression of the variant protein, antibodies specific for the variant protein or fragments thereof can be used to monitor therapeutic efficacy.

Antibodies are further useful for inhibiting variant protein function (e.g., CDKN2A and/or CDKN2B), for example by blocking the binding of a variant protein to a binding molecule or partner. Such uses can also be applied in a therapeutic context in which treatment involves inhibiting a variant protein's function. An antibody can be for example be used to block or competitively inhibit binding, thereby modulating (i.e., agonizing or antagonizing) the activity of the protein. Antibodies can be prepared against specific protein fragments containing sites required for specific function or against an intact protein that is associated with a cell or cell membrane. For administration in vivo, an antibody may be linked with an additional therapeutic payload, such as radionuclide, an enzyme, an immunogenic epitope, or a cytotoxic agent, including bacterial toxins (diphtheria or plant toxins, such as ricin). The in vivo half-life of an antibody or a fragment thereof may be increased by pegylation through conjugation to polyethylene glycol.

The present invention further relates to kits for using antibodies in the methods described herein. This includes, but is not limited to, kits for detecting the presence of a variant protein in a test sample. One preferred embodiment comprises antibodies such as a labelled or labelable antibody and a compound or agent for detecting variant proteins in a biological sample, means for determining the amount or the presence and/or absence of variant protein in the sample, and means for comparing the amount of variant protein in the sample with a standard, as well as instructions for use of the kit.

The present invention will now be exemplified by the following non-limiting examples.

Exemplification

The following contains description of the identification of susceptibility factors found to be associated with coronary artery disease and in-stent restenosis through single-point analysis of SNP markers and microsatellite markers.

Methods

The study was approved by the Data Protection Commission of Iceland and the National Bioethics Committee.

Icelandic Coronary Artery Disease and in-Stent Restenosis Cohort

The association between markers in LD block C09 to coronary artery disease was originally discovered as an association between the markers and myocardial infarction, which is the most feared complication of coronary artery disease (subphenotype of coronary artery disease).

Over the last eight years individuals who have suffered an MI we have been recruited through cardiovascular disease (CVD) genetic programs at deCODE. Currently blood samples have been collected from 2525 MI patients. The individuals who had suffered an MI were identified from a registry of over 10,000 individuals who: a) had an MI before the age of 75 in Iceland in the years 1981 to 2002 and satisfy the MONICA criteria (*J Clin Epidemiol* 41, 105-14 (1988)); b) participated in a large prospective epidemiology study (1) done by the Icelandic Heart Association (IHA) over the past 30 years and had MI prior to 1981; c) had MI discharge diagnosis from the major hospitals in Reykjavik in the years 2003 and 2004. MI diagnoses of all individuals in the registry follow strict diagnostic rules based on signs, symptoms, electrocardiograms, cardiac enzymes and necropsy findings (2). The patients were contacted through collaborating physicians in the CVD genetic programs at deCODE. Most of the participants in the study visited the IHA and had their blood drawn, although participants who lived outside the Reykjavik area visited their local health care center.

Additional subjects with coronary artery disease, but are without known history of myocardial infarction, are identified from a list of those who have undergone coronary stent procedure in the major hospitals in Reykjavik in the years 1993 and 2003.

For over 700 subjects on this list, information on in-stent restenosis is available, including subjects with variable degree of restenosis (0-100% in-stent restenosis). A confirmed proband with restenosis is a subject who has 50% in-stent stenosis or more as determined by coronary angiography read by an intervention cardio/radiologist.

The controls used for the study were recruited as a part of various genetic programs at deCODE. The medical history for the controls were unknown unless if the control subjects also had participated in any of the CVD genetic programs (i.e. MI, stroke, peripheral vascular disease, type II diabetes, obesity, familial combined hyperlipidemia, coronary restenosis, and hypertension genetic programs). Individuals with known MI, stroke, peripheral vascular or coronary artery disease were excluded as controls.

Subjects from the United States

Cohort from Philadelphia

The study participants from Philadelphia were enrolled at the University of Pennsylvania Medical Center through the PENN CATH study program which studies the association of biochemical and genetic factors to coronary artery disease (CAD) in subjects undergoing cardiac catheterization. A total of 3850 subjects have participated. For the purpose of the current study we selected from the PENN CATH study individuals diagnosed with one of the following coronary artery disease: MI based on criteria for acute MI in terms of elevations of cardiac enzymes and electrocardiographic changes, or a self-reported history of MI, history of coronary artery bypass surgery (CABG) or percutaneous, transluminal coronary angioplasty (PTCA). To use as controls we selected individuals who were without significant luminal stenosis on coronary angiography (luminal stenosis less than 50%). Ethnicity information was self-reported.

The University of Pennsylvania Institutional Review Board approved the study and all subjects provided written informed consent.

Cohort from Cleveland

The study participants were enrolled at the Cleveland Clinic Heart Center through the Genebank program, which is a registry of data in conjunction with biological samples for individuals undergoing coronary catheterization. The diagnostic criteria for MI were based on at least two of the following: prolonged chest pain, ECG patterns consistent with acute MI or significant elevation of cardiac enzymes. Subjects from the Genebank registry who were without significant luminal stenosis (<50% stenosis), as assessed with coronary angiography, and were without previous history of CAD, were selected as controls for the current study.

This study was approved by the Cleveland Clinic Foundation Institutional Review Board on Human Subjects and all subjects gave written informed consent.

Cohort from Atlanta

The study participants were enrolled at the Emory University Hospital, the Emory Clinic and Grady Memorial Hospitals through its Emory Genebank study and Clinical Registry in Neurology (CRIN). The Emory Genebank studies the association of biochemical and genetic factors with CAD in subjects undergoing cardiac catheterization. For the purpose of the current study those subjects who had a self-reported history of MI, CABG, or PTCA, were selected and used as a patient group. Control subjects were selected from a group of individuals with non-vascular neurological diseases (mainly Parkinson's and Alzheimer's diseases) recruited from CRIN, their spouses, unrelated friends and community volunteers. These subjects were matched for age, and ethnicity to the patient population. Controls were excluded if they had a known history of MI or coronary artery disease. All subjects provided written informed consent. Information on ethnicity was self-reported.

Genotyping

A genome-wide scan of 1570 Icelandic individuals diagnosed with myocardial infarction (MI) and 7088 population controls was performed using Infinium HumanHap300 SNP chips from Illumina for assaying approximately 317,000 single nucleotide polymorphisms (SNPs) on a single chip (Illumina, San Diego, Calif., USA). SNP genotyping for replication in other case-control cohorts was carried using the Centaurus platform (Nanogen).

Statistical Methods for Association Analysis

To test individual markers for association to disease phenotypes such as coronary artery disease or myocardial infarction, we use a likelihood ratio test to calculate a two-sided P-value for each allele of the markers. We calculate relative risk (RR) and population attributable risk (PAR) assuming a multiplicative model (C. T. Falk, P. Rubinstein, *Ann Hum Genet* 51 (Pt 3), 227 (1987); J. D. Terwilliger, J. Ott, *Hum Hered* 42, 337 (1992)). To elucidate the linkage disequilibrium between markers in the region we used the CEPH Caucasian HapMap data. We calculated LD between pairs of SNPs using the standard definition of D' (R. C. Lewontin, *Genetics* 50, 757 (1964)) and for the correlation coefficient $r^2$ (W. G. Hill, A. Robertson, *Genetics* 60, 615 (November, 1968). For the Icelandic cohort, to take into account that some of the individuals are related to each other, we obtained the null statistic of the test statistic either by simulating genotypes through the Icelandic genealogy or from the test statistic for all the 300,000 tested for association in the initial genome-wide association scan (citation). Model-free estimates of the genotype relative risk are generated as follows: RR of genotype $G_1$ compared to genotype $G_0$ was estimated by $[n(G_1)/n(G_0)]/[m(G_1)/m(G_0)]$ where n and m denote genotype counts in patients and controls respectively. Results from different cohorts were combined using a Mantel-Hanezel model (citation) where cohorts are allowed to have different population frequencies for the alleles/genotypes but assume to have common relative risks.

We use multiple regression to test for association between markers and quantitative traits, such as ago of onset of MI in the cases, where the number of copies of the at-risk variant carried by an individual is taken as explanatory variable and the quantitative trait as the response variable. The association is adjusted for age and gender, where appropriate, by including corresponding terms in the regression analysis as explanatory variables.

Correction for Relatedness of the Subjects and Genomic Control

Some of the individuals in both the Icelandic patient and control groups are related to each other, causing the chi-square test statistic to have a mean >1 and median >0.675 (Devlin, B & Roeder, K., *Biometrics* 55, 997 (1999)). We estimated the inflation factor for the genome-wide association by calculating the average of the 305,953 chi-square statistics, which was a method of genomic control (Devlin, B & Roeder, K., *Biometrics* 55, 997 (1999)) to adjust for both relatedness and potential population stratification. The inflation factor was estimated as 1.129 and the results presented from the genome-wide association are based on adjusting the chi-square statistics by dividing each of them by 1.129. For the Icelandic replication cohort and the combined Icelandic replication and discovery cohort, we used a previously described procedure where we simulated genotypes through the genealogy of 708,683 Icelanders to estimate the adjustment factor (S9). The corresponding adjustment factors were 1.092 and 1.029, respectively.

PCR Screening of cDNA Libraries cDNA libraries were constructed from whole blood (pool of 90 individuals), EBV-transformed human lymphoblastoid cells (pool of 90 individuals), human cardiac myocyte cells (Sciencell, Cat. no. 6200), human aortic smooth muscle cells (Sciencell, Cat. no. 6110), human cardiac fibroblast ventricular cells (Sciencell Cat. no. 6310) and human primary umbilical vein endothelial cells (HUVEC) (pool of 4 individuals). Total RNA was isolated using the RNeasy RNA isolation kit (Qiagen, Cat. no. 75144), the RNeasy RNA isolation from whole blood kit (Qiagen, Cat. no. 52304) or the mirVana RNA isolation kit, using the total RNA isolation procedure (Ambion Inc. Cat. no. 1560) according to manufacturer's recommendations. cDNA libraries were prepared at deCODE using the High Capacity cDNA Archive Kit with random primers (Applied Biosystems PN 4322171). In addition to the libraries above, two commercial cDNA libraries from whole heart (Clontech-639304) and aorta (Clontech-639325) were screened.

PCR screening was carried out using the Advantage2® Polymerase mix (Clontech cat. no. 639202) according to manufacturer's instructions with primers from Operon Biotechnologies. The PCR reactions were carried out in 10 µl volume at a final concentration of 3.5 µM of forward and reverse primers, 2 mM dNTP, 1× Advantage 2 PCR buffer, 0.2 µl of Advantage enzyme and 0.5 µl of cDNA library. (See Table 23). Expression was detected for all of the ESTs in several of the libraries tested (Table 24). None of the ESTs have an open reading frame larger than 77 bp. Many of them overlap with a recently reported antisense non-coding RNA whose expression has been shown to cocluster with p14/ARF (Pasmant, E., et al., *Cancer Res* 67, 3963 (2007)).

Sequencing of CDKN2A and CDKN2B

PCR amplifications and sequencing reactions were set up on Zymark SciClone ALH300 robotic workstations and amplified on MJR Tetrads. PCR products were verified for correct length by agarose gel electrophoresis and purified using AMPure (Agencourt Bioscience). Purified products were sequenced using an ABI PRISM Fluorescent Dye Terminator system, repurified using CleanSEQ (Agencourt), and resolved on Applied Biosystems 3730 capillary sequencers. SNP calling from primary sequence data was carried out using deCODE Genetics Sequence Miner software. All CDKN2A and CDKN2B variants identified by the automated systems were confirmed by manual inspection of primary signal traces. Samples from 96 early onset MI patients were sequenced using primers indicated in Table 25 and a list of the SNPs identified is provided in Table 26.

Surveying for Candidate Regulatory Variants in the Candidate Region

The University of California Santa Cruz genome browser (genome.ucsc.edu) was used to extract positions of SNPs and conserved TF binding sites for a 600 kb surrounding the MI region (hg release 17, chromosome 9, bases 21800000 to 22400000). The two tables were cross referenced using Python scripts and SNPs that resided in binding sites were interrogated for LD with rs1333040 in the CEU sample of Hapmap (release 22). The analyses were implemented for release 18 of the human genome, and the results converted to hg 17 coordinates.

This bioinformatic analysis of 600 kb surrounding the MI region yielded 16 SNPs which coincide with conserved binding sites for transcription factors (Table 27). Lack of LD to SNPs tagging the MI haplotype enabled exclusion of a half of the 16 SNPs from this candidate list. The remaining polymorphisms could impact gene function by altering conserved TF binding sites. In parallel we looked for correlation between SNPs located in conserved blocks (based on Multiz alignments available through the UCSC genome browser, release hg 18) and the MI haplotype tagging SNPs. While about half of the 74 SNPs are represented in HapMap, we found none that were highly correlated with the MI haplotype (data not shown). In sum, these analyses do not identify particular SNPs as putative regulatory variants on the MI haplotypes. Note of caution, the analysis will only detect a proportion of the functional candidates in the region because; i) the MI haplotypes have not been sequenced fully, ii) several candidate SNPs are not typed in Hapmap, hence it is unknown whether they sit on the risk conferring haplotypes. In addition, it is a realistic possibility that polymorphisms in less conserved regions are the functional MI variants.

EXAMPLE 1

Genome-Wide Association Study

We successfully genotyped 1570 Icelandic myocardial infarction patients and 7088 population control individuals without known history of coronary artery disease (Cohort A) using the Illumina 330K chip. We performed a genome-wide scan for association to MI, testing individually each of the 309,091 SNPs that was successfully genotyped. Three markers (rs10116277, rs1333040, rs2383207), all located in a single LD block (denoted herein as LD block C09) on chromosome 9p show strong association to MI (see FIG. 1 and Table 1a). All three markers are strongly correlated (Table 2) and the population frequency of the at-risk variants range from 42% to 49%, and the corresponding relative risk is approximately 1.2. The risk alleles of the same three markers also showed a significant correlation to lower age at onset within the MI patient—individuals carrying the at-risk variant are at significant risk of developing MI at a younger age than individuals who are non-carriers of the at-risk allele (Table 8a).

The LD-block LD block C09 containing the three associated marker is flanked and defined by two recombination hot-spots—one at approximately 21,920,000 bp in Build 34, the other approximately 22,150,000 bp on chromosome 9 (*Nature* 437, 1299-1320 (27 Oct. 2005))). Investigating other genetic markers in LD block C09, we identified two micro-satellite markers, D9S1870 and D9S1814, that are strongly correlated with the at-risk alleles of the markers rs10116277, rs1333040, and rs2383207. Table 1b shows the association of each of the alleles of the microsatellite markers to MI in the same cohort of MI patients and controls that was used in the genome-wide association scan. For marker D9S1814 the associated allele was allele 0, however for D9S1870 multiple alleles (alleles −4, −2 and 0) showed increased risk of MI. By investigating the correlation between the different alleles of D9S1870 to the at-risk alleles of the markers rs10116277, rs1333040 and rs2383207, observed that by pooling together all alleles of D9S1870 shorter than 2 (alleles −6, −4, −2 and 0 respectively), the composite allele, denoted X, was strongly correlated to the original at-risk alleles of the SNP (Table 2). Composite allele X of D9S1870 and allele 0 of D9S1814 show similar association to MI as the at-risk alleles of rs10116277, rs1333040 and rs2383207 (Table 1c) and all five at-risk alleles are highly correlated (Table 2).

Further investigation of all SNPs in the HapMap v9 CEU dataset that are located in the chromosomal region defined by LD block C09 identified further 88 markers that are strongly correlated with the at-risk allele of at least one of the five markers rs10116277, rs1333040, rs2383207, D9S1814 and D9S1870 (Table 3) and hence those markers could also be used as surrogate markers to tag the observed association to MI in LD block C09.

We genotyped the micro-satellite marker D9S1870 in a large cohort of over 70,000 Icelanders that included, among others, 668 additional MI cases and 58,643 additional controls without known history of coronary artery disease (Cohort B). In addition we typed the microsatellite D9S1870 in three replication cohorts from US including; 549 MI patients and 606 controls from Cleveland; 580 MI cases and 404 controls from UPenn; and 400 MI cases and 477 controls from Emory. All individuals in the US cohorts are of Caucasian origin. We tested the composite allele X for association to MI in all four cohorts (Table 4a and b), and all but one (Cleveland) showed significant association. Combining the results from the four replication cohorts (Table 4c) yielded a combined P-value=$2.65\times10^{-8}$. Combined with the original Icelandic cohort used in the genome-wide association (Cohort A) the P-value is $1.44\times10^{-12}$ and, assuming a multiplicative model, each allele X confers an estimated relative risk (RR) of 1.214 [95% CI: 1.151-1.281] per copy carried, compare with the risk for non-carriers. The corresponding combined population attributable risk (PAR) is 17.1%.

If we investigate separately the risk conferred for individuals heterozygous for the risk allele X and individuals homozygous for X, relative to individuals that do not carry X (Table 7a), the estimated genotype relative risk (GRR) for heterozygous individuals is 1.204 [CI: 1.094-1.324] and for homozygous individuals GRR is 1.507 [CI: 1.360-1.670]. This is consistent with the multiplicative model, i.e an additive contribution of the allele X to the risk of MI.

We further investigated the correlation of the risk allele X to age of onset of MI in all four cohorts. Restricting the analysis to early-onset MI cases, defined as a MI event before the age of 50 for males and before the age of 60 for females, the relative risk for the cohorts combined increases to 1.331 [CI: 1.223-1.449; P=$3.96\times10^{-11}$; PAR=24.7%] compared to 1.214 for all MI cases (Table 6c). Correspondingly the genotype relative risk increases to 1.314 [CI: 1.105-1.562] and 1.790 [CI: 1.517-2.113] for heterozygous and homozygous carriers of allele X respectively (Table 7b). Alternatively, we tested using multiple regression the correlation between the number of copies of X carried by individuals in the MI case group and the age of onset of MI (Table 8b). Combining results from all four cohorts, we observed that the mean age of onset decreased by 0.95 year [SE=0.25] for each copy of X carried by the MI individuals (P=0.000099).

Among individuals typed for the marker D9S1870 in the Icelandic and the Emory cohort are individuals that have undergone percutaneous transluminal coronary angioplasty (PTCA) or coronary artery bypass graft surgery (CABG), both indicative of severe coronary artery disease (CAD). We tested if those individuals also had an increased frequency of the risk allele X compared to controls, speculating that the variant might predispose individuals to a more general coronary artery disease than just MI (Table 5a and c). In both cohorts we observed similarly increased risk for PTCA and CABG as for MI, if not stronger, that was very significant in the Icelandic cohort, although for the Emory cohort only the association to PTCA was significant. It should be noted, however, that the number of individuals with PTCA and CABG in the Emory cohort is small. This association remained in the Icelandic cohort even after removing known MI cases from the PTCA and CABG groups (Table 5b).

In addition, in the Icelandic cohort we investigated the association to other diseases related to coronary artery disease, such as peripheral artery disease (PAD) and stroke phenotypes such as infarct or transient ischemic attack (TIA). For 1661 PAD cases we observed a very significant association, P=$5.36\times10^{-5}$ and RR=1.154 [CI: 1.074-1.239] (Table 5a)—this association remained significant after removing MI cases from the PAD cohort in the analysis although the effect was somewhat weaker (Table 5b). For 1678 individuals with infarct or TIA we did not observe significant association to X, however, for individuals diagnosed with large vessel diseases (LVD)—the stroke sub-phenotype that is most closely related to coronary artery disease—we observed an increased risk, RR=1.120 or 1.172 if we include or exclude MI cases respectively (Table 5a and b). There are however only 197 individuals in the Icelandic cohort diagnosed with LVD and this association in not statistically significant.

We investigated the frequency of the risk variant X of marker D9S1870 in a group of 454 Icelandic individuals for which we had information on in-stent restenosis and that are genotyped for the variant. The cohort was divided into individuals with severe in-stent restenosis (50% or greater) and individuals with mild in-stent restenosis (less than 50%). As all those individuals have undergone PTCA, and hence have coronary artery disease, both groups have significantly higher frequency of the variant X than is observed in controls (Table 9a). However, the frequency in the group of individuals with severe restenosis is higher than in the group with mild restenosis, RR=1.067 [CI: 0.827-1.376], and although this difference is not significant (Table 9b), this suggests that the variant could be indicative of the severity of in-stent restenosis in coronary artery disease patients that have undergone PT

EXAMPLE 2

A Common Variant on Chromosome 9p21 Affects the Risk of Myocardial Infarction

Coronary artery disease (CAD), including acute myocardial infarction (MI), is the leading cause of death worldwide (Thom, T., et al., *Circulation* 113:e85 (2006)). Identification of the underlying genetic architecture of heart disease may provide improved risk assessment and better measures for prevention and treatment.

To this end we conducted a genome-wide association study on Icelandic patients with MI, using the Illumina Hap300 chip. After quality filtering, 305,953 SNPs were tested for association to MI in a sample of 1607 cases, with age at onset before 70 in males and 75 in females, and 6728 controls without a history of CAD (Helgadottir, A., et al., *Science* 316:1491 (2007)). The results were adjusted for relatedness between individuals and potential population stratification using a method of genomic control (3). Although none of the SNPs were significant after adjusting for the number of tests performed more signals bordering on significance were observed than expected by chance. Hence, we further explored the SNPs that were closest to genome wide significance.

The strongest association to MI was observed with three correlated SNPs, rs1333040, rs2383207 and rs10116277, each with odds ratio (OR) around 1.22 for the risk allele and P of approximately $1\times10^{-6}$ (Table 15). All three SNPs are located within the linkage disequilibrium (LD) block on chromosome 9p21 denoted herein as LD block C09 (FIG. 1). Apart from these three SNPs, eleven other SNPs in the same LD block showed nominally significant association to MI. The associations to these SNPs tended to become weaker after accounting for the association to the three SNPs mentioned above (Table 15). After adjustment, a few remained nominally significant (P<0.05), but none had a P<0.01.

To replicate the observed associations we genotyped the three SNPs, rs1333040, rs2383207 and rs10116277, in an additional 665 Icelandic MI cases and 3533 controls and in three case-control sample sets of European descent from three cities from the United States: Philadelphia, Atlanta, and Durham (2). For consistency we used the same age at onset criteria in the association analysis as for the discovery group. The association to MI was replicated with significance in all four groups (Table 16). When the replication sets were combined using a Mantel-Haenszel model (Mantel, N. & Haenszel, *J. Natl. Cancer Inst.* 22:719 (1959)), all three SNPs showed highly significant association to MI (P<1×10$^{-8}$), with ORs comparable to those observed in the Icelandic discovery samples. When all groups were combined, rs2383207 showed the most significant association (P=2.0× 10$^{-16}$), with an OR of 1.25 (95% CI 1.18-1.31) for the risk allele G. It is noted that rs2383207 and rs10116277 are highly correlated ($r^2$=0.90) and their effects could not be reliably distinguished from each other in these data. The SNP rs1333040 is also substantially correlated with rs2383207 and rs10116277 ($r^2$=0.57 and 0.67 respectively). In an attempt to refine this association signal, we identified the SNPs that are substantially correlated with rs2383207 ($r^2$>0.5) based on the Hapmap CEU data and are not part of the Illumina Hap300 chip. Among the 36 such SNPs, we selected eight to be genotyped. Each of the 36 SNPs was either one of the eight or it had a very good surrogate among them ($r^2$>0.90) (Table 21). With data from all case-control groups combined, allele G of the refinement SNP rs10757278 showed the strongest association to the disease (OR=1.28, P=1.2×10$^{-20}$; Tables 12 and 16). Furthermore, while rs2383207 was no longer significant after adjusting for rs10757278 (P=0.25), rs10757278 remained significant with adjustment for rs2383207 (P=2.0×10$^{-5}$). Among the SNPs in this region that showed very significant association to the disease when tested individually, none was significant after adjustment for rs10757278 with the exception of the refinement SNP rs13330406, which was marginally significant (P=0.044) with adjustment (Table 22). Henceforth, for simplicity of presentation, we focus on the most significant SNP rs10757278 in the main text but additional results for other SNPs in the region are provided Tables 16 to 20.

To investigate the mode of inheritance in more detail, we computed genotype specific ORs for rs10757278. With results from all groups combined, relative to non-carriers, the ORs for heterozygous and homozygous carriers of the risk allele G were 1.26 and 1.64, respectively (Table 13). Assuming a frequency of 45.3% for the allele, the average of the frequencies in Iceland and the US, the corresponding PAR is 21%.

Because the impact of genetic factors on CAD has been shown to be greater at early ages (5) we investigated the correlation of allele G of rs10757278 to age at onset of MI. Note that in this analysis we used all cases with a known age at onset including those who had onset after the age of 70 or 75 for males and females, respectively. This added a total of 973 cases to the study groups compared to what was used in the case-control analyses. Regressing the age at onset on the number of risk alleles showed that, for each copy of the risk allele, the age at onset of MI was on average reduced by approximately one year (P=2.9×10$^{-7}$) (Table 18). Alternatively, restricting the case-control analysis to early onset MI, defined as an MI before the age of 50 for males and before the age of 60 for females, the allelic OR for rs10757278 G in all groups combined increased to 1.42 (95% CI 1.31-1.53) (Table 19). Relative to non-carriers, genotype specific OR for early onset MI is 1.49 and 2.02 for heterozygous and homozygous carriers of the risk allele, respectively (Table 13).

Having established that allele G of rs10757278 is associated to MI, we explored its impact on the broader phenotype of CAD (Table 14). To eliminate bias that could have arisen from the selection of the most significant variants in the initial genome-wide study, the cases and controls from the Icelandic discovery group (Iceland A) were not included here. We do note that if the latter were included, there would be little change to the estimated effects, but the results would become more significant due to the larger sample sizes. Also, the group from Durham did not have CAD cases without MI. As expected, rs10757278 was associated with high significance to CAD (OR=1.29, P=3.6×10$^{-14}$ for the groups combined). After removal of MI cases from the analyses, the associations remained significant for the groups from Iceland and Atlanta, but not in the Philadelphia group. Combining results from the three groups gave an OR of 1.24 (P=0.000011).

The variants on chromosome 9q21 associated to MI are located in an LD block that contains the CDKN2A and CDKN2B genes. The proteins encoded by these genes, called p16$^{INK4a}$, ARF and p15$^{INK4b}$ have a critical role in regulating cell proliferation, cell aging/senescence, and apoptosis in many cell types (Kim, W. Y. & Sharpless, N. E. *Cell* 127:265 (2006)). These are all important features of atherogenesis, the underlying cause of MI and CAD (Lusis, A. J. *Nature* 407:233 (2000); Minamino, T. & Komuro, I. *Circ Res* 100:15 (2007)). Sequencing of 93 early onset MI patients across exons, exon-intron junctions, and regulatory regions of CDKN2A and CDKN2B did not reveal obvious candidates for functional variants or other variants that could account for the observed association to rs10757278 (Tables 25 and 26). In addition to CDKN2A and CDKN2B genes, the LD block contains two exons of the mRNA transcript AF109294, a hypothetical methylthioadenosine phosphorylase fusion protein mRNA and several ESTs that are expressed in various tissues (Helgadottir, A., et al., *Science* 316:1491 (2007)). The functional relevance of the variants of this genomic region to MI/CAD remains to be elucidated.

In summary, we have shown that a common genetic variant located in the vicinity of the tumor suppressor genes CDKN2A and CDKN2B on chromosome 9p21 associate to MI. This is the first common variant discovered to consistently confer substantial risk (OR>1.20) of MI in multiple case-control groups of European descent. Due to its high frequency, the population attributable risk of the variant is approximately 21% for MI in general and approximately 31% for early onset cases, which is substantial from a public health point of view. However, as the relative risks are not extremely high, it explains only a small fraction of the familial clustering of the disease and would not generate large linkage scores. Hence, others susceptibility variants remain to be identified and some could be located in candidate regions identified by genome-wide linkage scans (Zintzaras, E. & Kitsios, G., *J Hum Genet* 51:1015 (2006); Wang Q., et al., *Am J Hum Genet* 74:262 (2004); Samani, N. J., et al., *Am J Hum Genet* 77:1011 (2005)). There is evidence supporting that the variant identified here could increase the risk of CAD in general in addition to their impact on MI, an observation that warrants further investigation. The mechanism whereby the genetic variants exert their effects in the pathogenesis of MI remains to be elucidated.

EXAMPLE 3

Genotyping of Polymorphic Markers Identified Through Sequencing

Sequencing of the exons of CDKN2A and CDKN2B genes, the exon-intron junctions and potential regulatory regions using the primers as indicated in Table 25 resulted in the identification of a number of SNPs, as shown in Table 26. Flanking sequences for three of those SNPs that were not found in public databases are indicated in Table 31. As it is possible that SNP markers or other polymorphisms in LD with the markers found to be associating to MI in this region of chromosome 9 show association with a higher risk, we genotyped these additional markers by sequencing, as indicated in Table 28. Several of the markers show association to MI with RR values as high as 1.7-1.8, in particular markers SG09S291 and rs2069416.

EXAMPLE 4

Association to Related Cardiovascular Disorders

We have investigated association of the at-risk variants of the invention to the related disorders peripheral artery disease (PAD), abdominal aorta aneurysm (AAA) and large vessel disease stroke (LVD) for three of the markers giving signal on Chromosome 9 as presented herein. As can be seen in Table 29, these markers are associated with these related disorders. The association is particularly compelling for AAA, wherein significant association is observed for a large number of markers in addition to these three, as shown in Table 30. These results illustrate that the markers and haplotypes of the invention are indeed reflective of disorders related to coronary artery disease, MI and in-stent restenosis, such as abdominal aorta aneurysm.

EXAMPLE 5

Further Refinement of Association to the Arterial Phenotypes AAA, IA and Stroke

To investigate the effect of rs10757278 on other cardiovascular diseases in more detail, we further explored the association to abdominal aortic aneurysm (AAA) and Stroke, and also investigated the arterial disorder intracranial aneurysm (IA).
Methods
Study Populations
Coronary Artery Disease Groups The coronary artery disease groups from Iceland and the United States were as described above (see also Helgadottir, A., et. al., Science 316:1491-3 (2007))
Icelandic Controls The 14278 Icelandic controls used in the association study were selected among individuals who have participated in various GWA studies and were recruited as part of genetic programs at deCODE. The medical histories of the controls were unknown unless they had also participated in one or more of the CVD genetic programs (i.e. MI, stroke, PAD, T2D, obesity, familial combined hyperlipidemia, coronary restenosis, and hypertension). Individuals with known MI, stroke, PAD or CAD, or with T2D were excluded as controls. Of the 14259 controls 9202 overlap with those used in our previous GWA study in MI (Helgadottir, A., et. al., Science 316:1491-3 (2007)). The controls included 5615 males and 8644 females and their mean age was 55.2 (SD 21.7). The breakdown of the control group into the various genetic programs was approximately (with the frequency of the two variants, rs10757278 allele G and rs10811661 allele T in parenthesis): Schizophrenia 500 (0.428/0.825), Prostate cancer 900 (0.447/0.815), Breast Cancer 1300 (0.433/0.817), Colon Cancer 700 (0.413/0.817), Addiction 2600 (0.444/0.814), Anxiety 900 (0.442/0.824), Infectious diseases 1200 (0.434/0.821), Population Controls 700 (0.427/0.830), Microarray expression studies 400 (0.445/0.817), Longevity 1100 (0.450/0.819), Migraine 1100 (0.446/0.818), Restless Leg Syndrome 400 (0.439/0.812), Alzheimer disease 350 (0.457/0.822), Asthma 1300 (0.419/0.819), Dyslexia 600 (0.438/0.830). No significant differences in frequencies were observed between the disease groups for either of the two variants (P=0.52 and P=0.99 for rs10757278 and rs10811661, respectively).
Stroke Groups Icelandic stroke patients were recruited from a registry of over 4000 individuals which includes individuals diagnosed with ischemic stroke or TIA at the major hospital in Reykjavik, the Landspitali University Hospital, during the years 1993 to 2002. Stroke patients have been enrolled over the past nine years through the cardiovascular disease (CVD) genetics program at deCODE. Swedish patients with ischemic stroke or TIA attending the stroke unit or the stroke outpatient clinic at Karolinska University Hospital, Huddinge unit in Stockholm, Sweden were recruited from 1996 to 2002 as part of an ongoing genetic epidemiology study, the South Stockholm Ischemic Stroke Study (SSISS). All patients from Iceland and Sweden had clinically relevant investigations performed, including brain imaging with computed tomography (CT) or/and magnetic resonance imaging (MRI) as well as ancillary diagnostic investigations including duplex ultrasonography of the carotid and vertebral arteries, echocardiography, Holter monitoring, MR-angiography, CT-angiography and standardized blood tests. Patients were classified into ischemic subtypes according to the Trial of Org 10172 in Acute Stroke Treatment (TOAST) classification by a physician reviewing original imaging and data (Adams, H. P. Jr., et al., Stroke 24:35-41 (1993)). Patients classified with cardioembolic stroke and documented atrial fibrillation were excluded from the analysis. The Swedish controls used in this study are population-based controls recruited from the same region in central Sweden as the patients, representing the general population in this area. The individuals were either blood donors (recruited in 2001) or healthy volunteers (collected in 1990-1994) recruited by the Clinical Chemistry Department at the Karolinska University Hospital to represent a normal reference population. These stroke studies from Iceland and Sweden were approved by relevant Institutional Review Boards or ethics committees and all participants provided written informed consent.
Intracranial Aneurysm Groups Icelandic IA patients were identified through an inpatient database from 1994-2006 at the Landspitali University Hospital, which is the only hospital with a neurosurgical service in the country. All patients in the years 1996-2006 with the ICD10 diagnosis 160.0-7 (aneurysmal subarachnoid hemorrhage), 167.1 (ruptured cerebral aneurysm) and 169.0 (sequele of subarachnoid haemorrhage) were enrolled, as well as patients with the ICD9 diagnosis 430 (subarachnoid hemorrhage from ruptured cerebral aneurysm) in the years 1994-1996. This totaled 367 IA patients. All patients had clinically relevant investigations performed, including CT scan of the head and or conventional cerebral angiogram, CT-angiogram or MRi angiogram. DNA samples were available for 170 of the 367 patients.

Dutch patients with ruptured (91.5%) or unruptured (8.5%) IA admitted to the University Medical Center Utrecht were used for the study. Ruptured intracranial aneurysms were defined by symptoms suggestive of subarachnoidal hemorrhage (SAH) combined with subarachnoid blood on CT and a proven aneurysm at angiography (conventional angiogram, CT-or MR-angiogram) and unruptured intracranial aneurysms were identified by CT or MR angiography or conventional angiography. Multiple intracranial aneurysms were found in 20.5% of cases. Mean age at time of SAH was 49.5 years (range 10-84) and 66.1% of the patients were females. The controls were healthy Dutch blood bank donors of European origin.

Finnish IA patients admitted for treatment of intracranial aneurysm at either the University Hospital of Kuopio, or University Hospital of Helsinki, in Finland, were used for the study. This study group and the Finnish controls used have been described previously (Weinsheimer, S. et al., *Stroke* 38:2670-6 (2007)).

The Icelandic, Dutch and Finnish IA studies were approved by relevant Institutional Review Boards or ethics committees and all participants provided written informed consent.

Peripheral Arterial Disease Groups

Icelandic patients with PAD were recruited from a registry of individuals diagnosed with PAD at the major hospital in Reykjavik, the Landspitali University Hospital, during the years 1983 to 2006. The PAD diagnosis was confirmed by vascular imaging or segmental pressure measurements. PAD patients have been enrolled over the past nine years as part of the CVD genetics program at deCODE.

Italian patients and controls were recruited among subjects consecutively admitted to the Department of Internal Medicine and Angiology of the A. Gemelli University Hospital of Rome, from 2000 to 2001. Inclusion criteria for the PAD group were European descent and presence of PAD. Diagnosis of PAD was performed in accordance with established criteria (*J Vasc Surg* 4:80-94 (1986)). All patients had an ankle/arm pressure index lower than 0.8 and were at Fontaine's stage II, with intermittent claudication and no rest pain or trophic lesions. Inclusion criteria for the control group were European descent, absence of PAD and CAD and no relationship with cases. Additional, exclusion criteria from the study were tumours, chronic inflammatory diseases, and autoimmune diseases (Flex, A., et al., *Eur J Vasc Endovasc Surg* 24: 264-8 (2002)).

Swedish PAD patients and controls were recruited at the Department of Vascular Diseases at Malmö University Hospital, a single referral centre for all patients with critical limb ischemia in the three southernmost health-care districts in Sweden (723,750 inhabitants in 2001). The diagnosis of critical limb ischemia was made in accordance with Trans-Atlantic Inter-Society Consensus scientific criteria of ulceration, gangrene, or rest pain caused by PAD proven by ankle pressure (<50 to 70 mm Hg), reduced toe pressure (<30 to 50 mm Hg), or reduced transcutaneous oxygen tension (Dormandy, J. A. & Rutherford, R. B., *J Vasc Surg* 31:S1-5296 (2000)). Diagnosis was confirmed by an experienced vascular surgery consultant and toe pressure measurements in patients with arteries in the affected leg that were non-compressible and the ankle pressure was >50 to 70 mm Hg. The control group consisted of healthy individuals included in a health screening programme for a preventive medicine project. None of those had symptomatic PAD (Barani, J., et al., *J Vasc Surg* 42:75-80 (2005)).

New Zealand PAD patients were recruited from the Otago-Southland region of the country, the vast majority (>97%) being of Anglo-European ancestry as reported previously (Jones G. T., et al., *Clin Chem* 53:679-85 (2007)). PAD was confirmed by an ankle brachial index <0.7, pulse volume recordings and angiography/ultrasound imaging. The control group consisted of elderly individuals with no previous history of vascular disease from the same geographical region. Controls were asymptomatic for PAD and had ankle brachial indexes >1. An abdominal ultrasound scan excluded concurrent AAA from both the PAD and control groups.

The Icelandic, Italian, Swedish, and New Zealand PAD studies were approved by relevant Institutional Review Boards or ethics committees and all participants provided written informed consent.

Abdominal Aortic Aneurysm Groups

Icelandic patients with AAA were recruited from a registry of individuals who were admitted either for emergency repair of symptomatic or ruptured AAA or for an elective surgery to the Landspitali, University Hospital, in Reykjavik, Iceland in the years 1980-2005. Subjects with AAA were enrolled over the last nine years as part of the CVD genetics program at deCODE. In some of the analyses AAA cases that overlapped with a comprehensive list of CAD patients (Helgadottir, A., et. al., *Science* 316:1491-3 (2007)) diagnosed in Iceland in the years 1981-2006 were excluded. Of the 397 (288 males and 109 females, mean age 75.3 (SD 8.7)) AAA cases, 208 overlapped with the CAD patients. Of the 189 (131 males and 58 females, mean age 75.5 (SD 9.3)) remaining CAD, information was not available for 138 cases and 51 individuals reported in a questionnaire as not having been diagnosed with CAD.

UK patients with AAA referred to vascular surgeons at 93 UK hospitals were entered into UK Small Aneurysm Trial. For the purpose of the current study those randomised to surveillance in the UK Small Aneurysm Trial with AAA diameter 4.0-5.5 cm were selected as a patient group, although some patients had been monitored before their aneurysm reached the 4.0 cm threshold for the trial. Mean AAA diameter at baseline was 4.5 cm (3.2-5.5 cm) (Eriksson, P., et al., *Br J Surg* 92:1372-6 (2005)). Information on the occurrence of CAD was available for 97% (466 out of 479) of AAA cases. History of CAD was regarded as positive if the subject was under treatment for angina, had a previous MI, coronary artery bypass graft surgery or angioplasty or if ECG coding had any indications of ischaemia, as judged by two independent expert observers. Among those with this information, the frequency of CAD amongst the AAA subjects was 52%. Controls were of European descent, recruited from England.

Belgian and Canadian patients with AAA who were admitted either for emergency repair of ruptured AAA or for an elective surgery to the University Hospital of Liège in Belgium and to Dalhousie University Hospital in Halifax Canada, respectively, were used for this study. Details of these case-control sets have been previously reported (Ogata, T., et al., *J Vasc Surg* 41:1036-42 (2005)). All patients were of European descent and had a diameter of infrarenal aorta ≥3 cm. Thirty-five patients were diagnosed with AAA using ultrasonography and did not undergo surgery because of old age or because the aneurysm was relatively small. Approximately 40% of AAA patients had a family history of AAA. For Belgian AAA patients, information on CAD history was ascertained for those who underwent surgery through interviews as well as from medical files. In addition, all patients underwent cardiologic explorations such as transthoracic echography, stress tests and coronary angiography if CAD was suspected. CAD information for this study was available for 45% (79 out of 176) of AAA cases from Belgium. Among those with this information, the frequency of CAD amongst the AAA subjects was 29%. Control samples (51% males) of European descent were obtained from spouses of AAA patients or from individuals admitted to the same hospitals for reasons other than AAA.

Patients admitted to the University Hospital of Pittsburgh for either elective or emergency surgery for AAA were selected for the study (St Jean, P. L., et al., *Ann Hum Genet*

59:17-24 (1995)). History of CAD was self-reported and was available for 86% (87 out of 101). Among those with this information, the frequency of CAD amongst the AAA subjects was 48%. Controls were selected from participants of the PENN CATH study program at the University of Pennsylvania Medical Center Philadelphia. The control group represents individuals who were without significant luminal stenosis on coronary angiography (luminal stenosis less than 50%) and did not have a history of MI. These are the same controls as were used in the association analysis for the CAD samples from Pennsylvania (Helgadottir, A., et. al., *Science* 316:1491-3 (2007)).

New Zealand patients with AAA were recruited from the Otago-Southland region of the country, the vast majority (>97%) being of Anglo-European ancestry as reported previously (Jones, G. T., et al., *Clin Chem* 53:679-85 (2007)). Approximately 80% of patients had undergone surgical AAA repair (typically AAA's >50 mm in diameter). Controls were the same vascular disease free individuals as described for comparison with the New Zealand PAD group. CAD information was available for 98% (575 out of 588) of the AAA patients. Of those with information the frequency of CAD was 40%.

AAA sample set from the Netherlands was recruited from 8 centres in the country, mostly when patients visited their vascular surgeon or in rare cases during hospital admission. The controls were healthy Dutch blood donors of European origin. Information on other CVD was self-reported and available for 69% (330 out of 480). Treatment for angina pectoris, previous MI, coronary bypass surgery or stent insert was considered as CAD. Of the 330 with information, 96 had CAD (29%).

These AAA studies from Iceland, UK, Belgium, Canada, Pennsylvania, The Netherlands and New Zealand were approved by relevant Institutional Review Boards or ethics committees and all participants provided written informed consent.

SNP Genotyping.

SNP genotyping for all samples was carried out at deCODE genetics in Reykjavik, Iceland. Individual SNP genotyping was carried out with the Centaurus (Nanogen) platform (Kutyavin, I. V., et al., *Nucleic Acids Res* 34:e128 (2006)). The quality of each Centaurus SNP assay was evaluated by genotyping each assay in the CEU and/or YRI HapMap samples and comparing the results to the HapMap data. The key markers rs10757278 and rs10811661 were re-genotyped on more than 10% of samples and a mismatch was observed in less than 0.5% of samples. For some of the samples we had previously genotyped the SNPs rs1333040, rs2383207, and rs10116277 either with the Illumina 317K Bead chip or with the Centaurus method. These SNPs are highly correlated with rs10757278 ($r^2$=0.57, 0.87, and 0.90, respectively, in the HapMap CEU dataset) and were used to impute the genotypes for rs10757278 where they were missing. In addition, for a large number of the Icelandic samples the SNP rs2383208, which is present on the Illumina 317K Bead chip, was previously genotyped. This SNP is a perfect surrogate for the SNP rs10811661 ($r^2$=1 in the HapMap CEU dataset) and was used to impute genotypes for rs10811661.

The SNPs did not deviate from Hardy Weinberg Equilibrium in any of study cohorts used for the analyses.

Association Analysis

We used a standard likelihood ratio statistics, implemented in the NEMO software (to calculate two-sided P values and odds ratio (OR) for each individual allele, assuming a multiplicative model for risk, i.e., that the risk of the two alleles a person carries multiply. Allelic frequencies, rather than carrier frequencies are presented for the markers, and, for the Icelandic study groups, P values are given after adjustment for the relatedness of the subjects by simulating genotypes through the genealogy of 708,683 Icelanders as previously described (Stefansson, H., et al., *Nat Genet* 37:129-37 (2005)). When estimating genotype specific OR (Table 34) genotype frequencies in the population were estimated assuming HWE. Heterogeneity tests were performed assuming that the estimates of OR for various groups have log-normal distributions. A likelihood ratio chi-square test was used with associated degrees of freedom equal to the number of groups compared minus one.

In general, allele/haplotype frequencies are estimated by maximum likelihood and tests of differences between cases and controls are performed using a generalized likelihood ratio test. This method is particularly useful in situations where there are some missing genotypes for the marker of interest and genotypes of another marker, which is in strong LD with the marker of interest, are used to provide some partial information. To handle uncertainties with phase and missing genotypes, maximum likelihood estimates, likelihood ratios and P values are computed directly for the observed data, and hence the loss of information due to uncertainty in phase and missing genotypes is automatically captured by the likelihood ratios.

The correlation of rs10757278 allele G and rs10811661 allele IT to both age and sex was tested in the Icelandic control population. Neither of the alleles demonstrated significant association to these covariates. In addition, no significant difference was detected in the frequency of the variants between males and females within the AAA cases (data not shown). Furthermore, including age and sex as covariates in the association analysis of rs10757278 allele G to AAA in the Icelandic samples had negligible impact on the results. Thus, for simplicity, the association analysis is presented without adjustment for age and sex.

The possibility that the association results observed for rs10757278 allele G to AAA was influenced by population stratification was addressed for the UK AAA cases and controls by typing 13 SNPs identified by the WTCCC as showing strong evidence for geographic differentiation in the WTCCC samples (*Nature* 447:661-78 (2007)). Only one of those SNPs showed nominally significant difference between the UK AAA cases and controls (P=0.017), which is not significant if we adjust for having tested 13 SNPs. If we adjust for this SNP in the case-control analysis, the association of rs10757278 allele G to AAA in the UK case-control group is not affected (P=0.0052 and OR=1.36 instead of P=0.0063 and OR=1.35). In the Icelandic case-control analysis we have adjusted for the relatedness of the study individuals. This adjustment has been shown to agree very well with the adjustment based on genomic control, which would include adjustment for any population stratification, in recent publications of genome-wide association studies in the Icelandic population (Steinthorsdottir, V., et al., *Nat Genet* 39:770-5 (2007); Gudmundsson, J. et al., *Nat Genet* 39:631-7 (2007)). Most importantly, the very similar allelic odds ratios obtained from the five AAA data sets makes it highly unlikely that population stratification has any substantial impact on the estimates of the effect.

Results from multiple case-control groups were combined using a Mantel-Haenszel model in which the groups were allowed to have different population frequencies for alleles, haplotypes and genotypes but were assumed to have common relative risks (Mantel, N. & Haenszel, W. *J Natl Cancer Inst* 22: 719-48 (1959)).

Results

The results shown in Table 32 shows results from the Icelandic IA cohort, replication cohorts, and a combined analysis for the cohorts. When data from the multiple case-control groups studied were combined separately for IA, AAA, PAD and LAA/cardiogenic stroke, rs10757278 allele G showed significant association to all of the four phenotypes. However, the estimated effect size differed substantially and was strongest for AAA (combined analysis, OR=1.31, P=1.2×10$^{-12}$) and IA (combined analysis, OR=1.29, P=2.5×10$^{-6}$). In addition to the high overall statistical significance, it is also important to note that the estimated risk conferred by rs10757278 allele G to IA and AAA was very similar across the three IA sample sets from Iceland (OR=1.36), Finland (OR=1.33), and the Netherlands (OR=1.24) ($P_{het}$, the P-value for the test of heterogeneity=0.75), and the seven AAA sample sets from Iceland (OR=1.37), Belgium (OR=1.21), Canada (OR=1.29), Pennsylvania US (OR=1.39), United Kingdom (UK) (OR=1.35), Netherlands (OR=1.31), and New Zealand (OR=1.25), ($P_{het}$=0.98). The effect of rs10757278 allele G on IA and AAA is comparable to that previously reported for CAD (Helgadottir, A., et al. Science 316:1491-3 (2007)) (Table 32).

Because of high co-morbidity between AAA and CAD, we explored the nature of the effect of the variant on the two conditions, by repeating the association analysis for AAA after removing cases with evidence of CAD. As shown in Table 33, the effect of rs10757278 allele G on AAA without evidence of CAD was only slightly smaller than that for the whole sample sets, or OR=1.3 for the Icelandic, 1.31 for UK, 1.19 for Pennsylvania, 1.20 for Belgian, 1.25 for The Netherlands, and 1.18 for the New Zealand sample sets. For the six different groups with available CAD information, after removing known CAD cases the combined OR was 1.25 and P=3.0×10$^{-6}$, indicating that the association to AAA is not simply a consequence of the association between rs10757278 allele G and CAD. To our knowledge there is no evidence in the literature suggesting co-segregation of IA and CAD. Furthermore, the gender ratio in IA is also different from that for the atherosclerotic diseases such as CAD; IA is more frequent in females than in males, and the peak incidence is also at a younger age than for CAD (Schievink, W. I., N Engl J Med 336:28-40 (1997)). The effect of rs10757278 allele G on IA is thus not mediated through CAD.

When genotype-specific effects were studied based on data from all seven AAA and the three IA sample sets the ORs for heterozygous and homozygous carriers of the risk allele G were estimated to be 1.36 and 1.74, respectively for AAA and 1.38 and 1.72, respectively, for IA (Table 34). Assuming a population frequency of 47.5% for the G allele, the corresponding population attributable risk is about 26% for both AAA and IA. It is noted that rs10757278 allele G is the first common sequence variant described that affects the risk of IA or AAA.

The prevalence of AAA (defined as >3 cm aortic diameter) has been reported to be 4.3% and 1.0% in men and women over 50 years of age, respectively (Lederle, F. A., et al, J Vasc Surg 34:122-6 (2001); Lederle, F. A., et al. Arch Intern Med 160:1425-30 (2000)), and 2-5% of the general population have IA (Brisman, J. L, et al., N Engl J Med 355:928-39 (2006)). Both AAA and IA represent a degenerative process of the arteries leading to their enlargement that is usually asymptomatic with natural history culminating in either a therapeutic intervention or rupture. Rupture of IA leads to subarachnoid haemorrhage, and rupture of both IA and AAA have high morbidity and mortality (Brisman, J. L, et al., N Engl J Med 355:928-39 (2006); Thompson, R. w. Cardiovasc Surg 10: 389-94 (2002)). In the case of AAA the rupture risk increases with the growth rate as well as the size of the aneurysm. While patients from the UK study group included only those with small asymptomatic aneurysms (aortas <5.5 cm diameter), the other study groups included mainly patients undergoing aneurysm repair and are therefore likely to be biased towards larger and symptomatic aneurysms (aortas >5.5 cm diameter). Despite recruitment differences the ORs were similar, suggesting that the variant does not confer direct risk of the growth of aortic aneurysms. This concept was further investigated in the sample set from UK, where the subjects with small asymptomatic AAA had been followed with sequential aortic aneurysm size measurements (Eriksson, P. et al., Br J Surg 92:1372-6 (2005)). As shown in Table 35, there is no evidence of an association between rs10757278 allele G and either aneurysm growth or rupture. Rather there is some indication that allele G is correlated with slow growth. The difference in average growth rates between the homozygous GG group and the heterozygous AG group is −0.46 mm/year and is nominally significant (P=0.05), an observation that warrants further investigation. If confirmed, this inverse association would echo previous findings where slower aneurysm growth rates were observed in patients with low ankle/brachial pressure index, a marker of generalised atherosclerosis (Brady A. R., et al., Circulation 110:16-21 (2004)). These data suggest that the sequence variant leads to increased susceptibility of developing aneurysm rather than increasing the risk of rapid aneurysm progression.

The effect of rs10757278 allele G on the risk of PAD and LAA/cardiogenic stroke appeared to be weaker than that for AAA, IA and CAD (Table 32). In the Icelandic samples there was no difference in the frequency of rs10757278 allele G between the AAA and IA cases, however the frequency was lower in both the PAD and LAA/cardiogenic stroke cases than in the combined group of AAA and IA cases (P=0.012 and P=0.052, respectively). Furthermore, after excluding PAD and LAA/cardiogenic stroke subjects with known CAD from the analysis the effect was reduced even further, particularly for PAD (Table 33).

We tested the association of several variants in the LD block C09 region with MI in African American samples. As shown by the results presented in Table 36, the effect in African Americans is comparable in magnitude, as measured by Relative Risk, to the effect in Caucasian samples. The lack of nominal statistical significance of the association (p-value less than 0.05) in the African American samples for many of the markers is due to the relatively small samples size. Most importantly, the association observed in African Americans, together with reported association in Asian samples originating from Japan and Korea with comparable risk to that determined for Caucasians (see Arterioscler Thromb Vasc Biol. 2008 February; 28(2):360-5. Epub 2007 Nov. 29, and J Hum Genet. Epub 2008 Feb. 9) shows that the genetic effects originally discovered in Caucasian samples from Iceland manifests itself in other human populations. The effect therefore has implications for cardiovascular disease in all major human populations.

These data demonstrate that rs10757278 allele G has less effect on the atherosclerotic diseases, PAD and LAA/cardiogenic stroke, than on CAD. In contrast, the effect on the two aneurysmal diseases, AAA with weaker association to atherosclerosis and IA with no such relationship, was comparable to that on CAD, suggesting that the variant plays a role in a pathophysiological component common to these arterial phenotypes. This may involve abnormal vascular remodelling and/or repair which has been identified as a key in the pathogenesis CAD, AAA and IA (Chatzidisis, Y. S. et al., *J Am Coll Cardiol* 49:2379-93 (2007); Hashimoto, T. et al., *Neurol Res* 8:372-80 (2006); Moore, J. E., Jr., et al, *Atherosclerosis* 110:225-40 (2006)). The sequence variant rs10757278 allele G on chromosome 9p21, and/or variants in linkage disequilibrium with rs10757278, may thus function as a genetic determinant of the tissue response to unfavourable conditions that prevail in the lower abdominal aorta, in the circle of Willis where IAs occur, and in those regions of the coronary tree that are prone to develop unstable, rupture prone atherosclerotic plaques.

TABLE 1 a) Results for the 12 SNPs in LD block C09 that showed nominally significant association to myocardial infarction in the Icelandic discovery cohort (Cohort A) of 1570 MI cases and 7088 controls. Shown is the frequency of the risk allele in cases and controls, the corresponding relative risk (RR), the unadjusted P-value and the P-value after adjusting for the relatedness of cases and controls. Also included are results for a test of association to MI for the same SNPs conditioned on the association of the SNP rs1333040. b) Association to MI for the different alleles of the micro-satellites D9S1814 and D9S1870 in Cohort A. c) Association to MI of the at-risk allele 0 for D9S1814 and of the composite at-risk allele X of D9S1870 in Cohort A. The composite allele X includes alleles −6, −4, −2 and 0 of D9S1870.

| | SNP | Allele | Position | Frequency Cases | Frequency Controls | RR | P | P* | Conditioned on rs1333040 RR | P | r2*** |
|---|---|---|---|---|---|---|---|---|---|---|---|
| a) | rs7041637 | A | 21951866 | 0.251 | 0.232 | 1.104 | 0.031 | 0.044 | 1.003 | 0.96 | 0.12 |
| | rs2811712 | A | 21988035 | 0.890 | 0.874 | 1.171 | 0.010 | 0.016 | 1.146 | 0.040 | 0.05 |
| | rs3218018 | A | 21988139 | 0.894 | 0.878 | 1.174 | 0.010 | 0.016 | 1.149 | 0.038 | 0.03 |
| | rs3217992 | A | 21993223 | 0.376 | 0.344 | 1.149 | 0.00071 | 0.0015 | 1.015 | 0.80 | 0.28 |
| | rs2069426 | C | 21996273 | 0.895 | 0.880 | 1.159 | 0.019 | 0.028 | 1.134 | 0.063 | 0.02 |
| | rs2069422 | A | 21998026 | 0.891 | 0.874 | 1.174 | 0.0092 | 0.015 | 1.149 | 0.037 | 0.05 |
| | rs1333034 | A | 22034122 | 0.890 | 0.874 | 1.168 | 0.012 | 0.018 | 1.143 | 0.043 | 0.05 |
| | rs1011970 | G | 22052134 | 0.801 | 0.772 | 1.189 | 0.00034 | 0.00081 | 1.114 | 0.050 | 0.13 |
| | rs10116277 | T | 22071397 | 0.463 | 0.419 | 1.195 | $7.05 \times 10^{-6}$ | $2.63 \times 10^{-5}$ | 1.054 | 0.52 | 0.67 |
| | rs1333040 | T | 22073404 | 0.538 | 0.491 | 1.209 | $1.56 \times 10^{-6}$ | $6.98 \times 10^{-6}$ | NA | NA | NA |
| | rs2383207 | G | 22105959 | 0.502 | 0.456 | 1.204 | $2.64 \times 10^{-6}$ | $1.11 \times 10^{-5}$ | 1.102 | 0.15 | 0.57 |
| | rs1333050 | T | 22115913 | 0.694 | 0.672 | 1.107 | 0.017 | 0.025 | 1.005 | 0.92 | 0.27 |
| b) | D9S1814 | −2 | 22078225 | 0.019 | 0.019 | 1.049 | 0.79 | 0.81 | — | — | — |
| | D9S1814 | 0 | 22078225 | 0.500 | 0.451 | 1.217 | $1.35 \times 10^{-6}$ | $6.17 \times 10^{-6}$ | — | — | — |
| | D9S1814 | 2 | 22078225 | 0.359 | 0.385 | 0.895 | 0.015 | 0.023 | — | — | — |
| | D9S1814 | 4 | 22078225 | 0.112 | 0.149 | 0.720 | $4.00 \times 10^{-6}$ | $1.60 \times 10^{-5}$ | — | — | — |
| | D9S1870 | −6 | 22093010 | 0.019 | 0.020 | 0.961 | 0.79 | 0.81 | — | — | — |
| | D9S1870 | −4 | 22093010 | 0.039 | 0.029 | 1.352 | 0.0090 | 0.015 | — | — | — |
| | D9S1870 | −2 | 22093010 | 0.376 | 0.339 | 1.177 | 0.00011 | 0.00031 | — | — | — |
| | D9S1870 | 0 | 22093010 | 0.044 | 0.043 | 1.038 | 0.72 | 0.74 | — | — | — |
| | D9S1870 | 2 | 22093010 | 0.072 | 0.074 | 0.974 | 0.74 | 0.76 | — | — | — |
| | D9S1870 | 4 | 22093010 | 0.166 | 0.200 | 0.797 | $2.96 \times 10^{-5}$ | $9.31 \times 10^{-5}$ | — | — | — |
| | D9S1870 | 6 | 22093010 | 0.104 | 0.114 | 0.905 | 0.14 | 0.17 | — | — | — |
| | D9S1870 | 8 | 22093010 | 0.079 | 0.080 | 0.989 | 0.89 | 0.89 | — | — | — |
| | D9S1870 | 10 | 22093010 | 0.072 | 0.077 | 0.931 | 0.37 | 0.40 | — | — | — |
| | D9S1870 | 12 | 22093010 | 0.021 | 0.018 | 1.152 | 0.34 | 0.37 | — | — | — |
| c) | D9S1814 | 0 | 22078225 | 0.500 | 0.451 | 1.217 | $1.35 \times 10^{-6}$ | $6.17 \times 10^{-6}$ | 1.118 | 0.099 | 0.53 |
| | D9S1870 | X | 22093010 | 0.486 | 0.438 | 1.211 | $2.52 \times 10^{-6}$ | $1.07 \times 10^{-5}$ | 1.113 | 0.081 | 0.55 |

*P-value adjuste for relatedness of cases and controls.
**P-value adjusted for relatedness and conditioned on the association to rs133304, and the corresponding relative risk.
***Pair-wise correlation r2 between the SNP and the at-risk variant rs1333040

TABLE 2

Pair-wise correlation among the 5 markers, 3 SNPs and 2 micro-satellites, that show strongest association to myocardial infarction in LD block C09, based on the HapMap v19 CEU dataset. In the upper right corner are shown values for the correlation coefficient $r^2$, while in the lower left corner are values for D'.

| | Marker | rs10116277 | rs1333040 | D9S1814 | D9S1870 | rs2383207 |
|---|---|---|---|---|---|---|
| D' | rs10116277 | — | 0.667 | 0.806 | 0.839 | 0.905 |
| | rs1333040 | 1.000 | — | 0.528 | 0.550 | 0.569 |
| | D9S1814 | 0.964 | 0.829 | — | 0.651 | 0.743 |
| | D9S1870 | 1.000 | 1.000 | 0.954 | — | 0.779 |
| | rs2383207 | 1.000 | 0.879 | 0.893 | 1.000 | — |

TABLE 3

List of all SNPs (from HapMap v19 CEU dataset) in LD block C09 that are correlated, with correlation coefficient $r^2 \geq 0.2$, with at least one of the five markers (rs10116277, rs1333040, D9S1814, D9S1870 or rs2383207). For each SNP shown the table includes the position (in Build 34 and in SEQ ID NO: 94) and the correlation coefficient $r^2$ to each of the five at-risk markers.

| SNP | Position[a] | Position[b] | D9S1814 | D9S1870 | rs1333040 | rs2383207 | rs10116277 |
|---|---|---|---|---|---|---|---|
| rs7041637 | 21951866 | 31720 | 0.18 | 0.12 | 0.20 | 0.21 | 0.15 |
| rs3218020 | 21987872 | 67726 | 0.46 | 0.33 | 0.37 | 0.55 | 0.41 |
| rs3217992 | 21993223 | 73077 | 0.43 | 0.28 | 0.34 | 0.53 | 0.38 |
| rs1063192 | 21993367 | 73221 | 0.22 | 0.09 | 0.27 | 0.28 | 0.16 |
| rs2069418 | 21999698 | 79552 | 0.19 | 0.06 | 0.25 | 0.25 | 0.14 |
| rs2069416 | 22000004 | 79858 | 0.41 | 0.24 | 0.32 | 0.50 | 0.36 |
| rs573687 | 22001642 | 81496 | 0.23 | 0.07 | 0.28 | 0.20 | 0.17 |
| rs545226 | 22002422 | 82276 | 0.31 | 0.18 | 0.24 | 0.40 | 0.27 |
| rs10811640 | 22003411 | 83265 | 0.21 | 0.09 | 0.29 | 0.29 | 0.19 |
| rs10811641 | 22004137 | 83991 | 0.41 | 0.27 | 0.33 | 0.50 | 0.36 |
| rs2106120 | 22007101 | 86955 | 0.23 | 0.10 | 0.31 | 0.32 | 0.21 |
| rs2106119 | 22007550 | 87404 | 0.23 | 0.10 | 0.31 | 0.32 | 0.21 |
| rs643319 | 22007836 | 87690 | 0.22 | 0.09 | 0.29 | 0.32 | 0.20 |
| rs7044859 | 22008781 | 88635 | 0.23 | 0.10 | 0.31 | 0.32 | 0.21 |
| rs523096 | 22009129 | 88983 | 0.17 | 0.05 | 0.22 | 0.23 | 0.12 |
| rs10757264 | 22009732 | 89586 | 0.21 | 0.09 | 0.29 | 0.30 | 0.19 |
| rs10965212 | 22013795 | 93649 | 0.29 | 0.14 | 0.38 | 0.40 | 0.27 |
| rs1292137 | 22014023 | 93877 | 0.24 | 0.09 | 0.31 | 0.34 | 0.21 |
| rs1292136 | 22014351 | 94205 | 0.30 | 0.16 | 0.37 | 0.41 | 0.28 |
| rs10811644 | 22015067 | 94921 | 0.25 | 0.11 | 0.33 | 0.34 | 0.22 |
| rs7035484 | 22015240 | 95094 | 0.24 | 0.10 | 0.32 | 0.33 | 0.22 |
| rs10738604 | 22015493 | 95347 | 0.49 | 0.35 | 0.41 | 0.60 | 0.44 |
| rs615552 | 22016077 | 95931 | 0.17 | 0.06 | 0.21 | 0.20 | 0.10 |
| rs543830 | 22016639 | 96493 | 0.23 | 0.08 | 0.28 | 0.31 | 0.17 |
| rs1591136 | 22016834 | 96688 | 0.29 | 0.14 | 0.38 | 0.40 | 0.27 |
| rs7049105 | 22018801 | 98655 | 0.29 | 0.14 | 0.38 | 0.40 | 0.27 |
| rs679038 | 22019080 | 98934 | 0.23 | 0.08 | 0.28 | 0.31 | 0.17 |
| rs10965215 | 22019445 | 99299 | 0.27 | 0.13 | 0.35 | 0.38 | 0.25 |
| rs564398 | 22019547 | 99401 | 0.21 | 0.07 | 0.26 | 0.29 | 0.15 |
| rs7865618 | 22021005 | 100859 | 0.24 | 0.10 | 0.29 | 0.31 | 0.18 |
| rs10115049 | 22022119 | 101973 | 0.29 | 0.14 | 0.38 | 0.40 | 0.27 |
| rs634537 | 22022152 | 102006 | 0.24 | 0.08 | 0.29 | 0.33 | 0.20 |
| rs2157719 | 22023366 | 103220 | 0.26 | 0.11 | 0.32 | 0.33 | 0.19 |
| rs2151280 | 22024719 | 104573 | 0.27 | 0.15 | 0.36 | 0.38 | 0.25 |
| rs1008878 | 22026112 | 105966 | 0.24 | 0.12 | 0.30 | 0.32 | 0.18 |
| rs1556515 | 22026367 | 106221 | 0.26 | 0.13 | 0.32 | 0.35 | 0.20 |
| rs1333037 | 22030765 | 110619 | 0.28 | 0.12 | 0.34 | 0.36 | 0.21 |
| rs1360590 | 22031443 | 111297 | 0.31 | 0.15 | 0.40 | 0.43 | 0.29 |
| rs1412829 | 22033926 | 113780 | 0.23 | 0.08 | 0.28 | 0.31 | 0.17 |
| rs1360589 | 22035317 | 115171 | 0.30 | 0.12 | 0.36 | 0.40 | 0.23 |
| rs7028570 | 22038683 | 118537 | 0.31 | 0.14 | 0.40 | 0.43 | 0.29 |
| rs944801 | 22041670 | 121524 | 0.30 | 0.12 | 0.36 | 0.40 | 0.23 |
| rs10965219 | 22043687 | 123541 | 0.30 | 0.13 | 0.40 | 0.48 | 0.27 |
| rs7030641 | 22044040 | 123894 | 0.30 | 0.12 | 0.36 | 0.40 | 0.23 |
| rs10120688 | 22046499 | 126353 | 0.38 | 0.18 | 0.47 | 0.51 | 0.35 |
| rs2184061 | 22051562 | 131416 | 0.50 | 0.24 | 0.59 | 0.44 | 0.40 |
| rs1537378 | 22051614 | 131468 | 0.50 | 0.24 | 0.59 | 0.44 | 0.40 |
| rs8181050 | 22054391 | 134245 | 0.47 | 0.22 | 0.55 | 0.40 | 0.38 |
| rs8181047 | 22054465 | 134319 | 0.33 | 0.49 | 0.38 | 0.28 | 0.21 |
| rs10811647 | 22055002 | 134856 | 0.70 | 0.49 | 0.59 | 0.83 | 0.62 |
| rs1333039 | 22055657 | 135511 | 0.47 | 0.22 | 0.55 | 0.40 | 0.38 |
| rs10965224 | 22057276 | 137130 | 0.45 | 0.21 | 0.53 | 0.40 | 0.35 |
| rs10811650 | 22057593 | 137447 | 0.70 | 0.49 | 0.59 | 0.83 | 0.63 |
| rs10811651 | 22057830 | 137684 | 0.48 | 0.23 | 0.56 | 0.41 | 0.39 |
| rs4977756 | 22058652 | 138506 | 0.47 | 0.22 | 0.55 | 0.40 | 0.38 |
| rs10757269 | 22062264 | 142118 | 0.94 | 0.66 | 0.80 | 0.78 | 0.84 |
| rs9632884 | 22062301 | 142155 | 0.93 | 0.65 | 0.80 | 0.78 | 0.84 |
| rs1412832 | 22067543 | 147397 | 0.32 | 0.48 | 0.37 | 0.28 | 0.22 |
| rs10116277 | 22071397 | 151251 | — | 0.67 | 0.81 | 0.84 | 0.90 |
| rs10965227 | 22071796 | 151650 | 0.28 | 0.02 | 0.13 | 0.18 | 0.31 |
| rs6475606 | 22071850 | 151704 | 1.00 | 0.67 | 0.81 | 0.84 | 0.90 |
| rs1333040 | 22073404 | 153258 | 0.67 | — | 0.53 | 0.55 | 0.57 |
| rs1537370 | 22074310 | 154164 | 1.00 | 0.67 | 0.81 | 0.84 | 0.90 |
| rs7857345 | 22077473 | 157327 | 0.36 | 0.55 | 0.43 | 0.32 | 0.26 |
| rs10738607 | 22078094 | 157948 | 1.00 | 0.69 | 0.81 | 0.84 | 0.90 |
| rs10757272 | 22078260 | 158114 | 1.00 | 0.67 | 0.81 | 0.84 | 0.90 |
| rs4977574 | 22088574 | 168428 | 1.00 | 0.67 | 0.81 | 0.84 | 0.90 |
| rs2891168 | 22088619 | 168473 | 1.00 | 0.67 | 0.81 | 0.84 | 0.90 |
| rs1537371 | 22089568 | 169422 | 1.00 | 0.67 | 0.81 | 0.84 | 0.90 |
| rs1556516 | 22090176 | 170030 | 1.00 | 0.67 | 0.81 | 0.84 | 0.90 |
| rs6475608 | 22091702 | 171556 | 0.36 | 0.54 | 0.42 | 0.31 | 0.25 |
| rs7859727 | 22092165 | 172019 | 1.00 | 0.66 | 0.80 | 0.84 | 0.90 |

TABLE 3-continued

List of all SNPs (from HapMap v19 CEU dataset) in LD block C09 that are correlated, with correlation coefficient $r^2 \geq 0.2$, with at least one of the five markers (rs10116277, rs1333040, D9S1814, D9S1870 or rs2383207). For each SNP shown the table includes the position (in Build 34 and in SEQ ID NO: 94) and the correlation coefficient $r^2$ to each of the five at-risk markers.

| SNP | Position[a] | Position[b] | D9S1814 | D9S1870 | rs1333040 | rs2383207 | rs10116277 |
|---|---|---|---|---|---|---|---|
| rs1537373 | 22093341 | 173195 | 1.00 | 0.67 | 0.81 | 0.84 | 0.90 |
| rs1333042 | 22093813 | 173667 | 0.97 | 0.63 | 0.81 | 0.81 | 0.94 |
| rs7859362 | 22095927 | 175781 | 0.90 | 0.57 | 0.74 | 0.78 | 1.00 |
| rs1333043 | 22096731 | 176585 | 0.94 | 0.60 | 0.74 | 0.81 | 0.97 |
| rs1412834 | 22100131 | 179985 | 0.90 | 0.57 | 0.74 | 0.78 | 1.00 |
| rs7341786 | 22102241 | 182095 | 0.88 | 0.54 | 0.71 | 0.75 | 0.97 |
| rs10511701 | 22102599 | 182453 | 0.88 | 0.54 | 0.71 | 0.75 | 0.97 |
| rs10733376 | 22104469 | 184323 | 0.90 | 0.57 | 0.74 | 0.78 | 1.00 |
| rs10738609 | 22104495 | 184349 | 0.90 | 0.57 | 0.74 | 0.78 | 1.00 |
| rs2383206 | 22105026 | 184880 | 0.90 | 0.57 | 0.74 | 0.78 | 1.00 |
| rs944797 | 22105286 | 185140 | 0.90 | 0.57 | 0.74 | 0.78 | 1.00 |
| rs1004638 | 22105589 | 185443 | 0.90 | 0.57 | 0.74 | 0.78 | 1.00 |
| rs2383207 | 22105959 | 185813 | 0.90 | 0.57 | 0.74 | 0.78 | — |
| rs1537374 | 22106046 | 185900 | 0.90 | 0.57 | 0.74 | 0.78 | 1.00 |
| rs1537375 | 22106071 | 185925 | 0.90 | 0.57 | 0.74 | 0.78 | 1.00 |
| rs1333045 | 22109195 | 189049 | 0.69 | 0.37 | 0.52 | 0.60 | 0.65 |
| rs10738610 | 22113766 | 193620 | 0.94 | 0.60 | 0.77 | 0.78 | 0.97 |
| rs1333046 | 22114123 | 193977 | 0.94 | 0.60 | 0.77 | 0.78 | 0.97 |
| rs10757278 | 22114477 | 194331 | 0.90 | 0.57 | 0.74 | 0.75 | 0.87 |
| rs1333047 | 22114504 | 194358 | 0.90 | 0.59 | 0.72 | 0.74 | 0.88 |
| rs4977575 | 22114744 | 194598 | 0.90 | 0.59 | 0.72 | 0.74 | 0.88 |
| rs1333048 | 22115347 | 195201 | 0.97 | 0.63 | 0.77 | 0.81 | 0.94 |
| rs1333049 | 22115503 | 195357 | 0.90 | 0.59 | 0.72 | 0.74 | 0.88 |
| rs1333050 | 22115913 | 195767 | 0.17 | 0.27 | 0.06 | 0.15 | 0.20 |

[a]Position with respect to NCBI Build 34, Build 35 or Build 36
[b]Position with respect to SEQ ID NO: 94 (LD Block C09)

TABLE 4 a) Association of the composite at-risk allele X of the micro-satellite D9S1870 to myocardial infarction (MI) in a replication cohort (Cohort B) of 668 Icelandic MI cases and 58,543 controls and in the combined Icelandic cohort (Cohort A + B). Included in the table is the number of cases n and controls m, the allele frequency in cases and controls, the corresponding P value adjusted for relatedness of the study individuals, the relative risk (RR) with 95% confidence interval (CI), and the population attributed risk (PAR). Known CAD or CVD cases have been excluded from the control cohort. b) Association of allele X to MI in three distinct US replication cohorts. All cases and controls in those three cohorts are of Caucasian origin. c) Combined association results, using a Mantel-Haenzel model, for the composite at-risk allele X in all replication cohorts combined, and in all cohorts combined, respectively.

| Cohort (n/m) | Frequency | | P* | RR | CI | PAR |
|---|---|---|---|---|---|---|
| | Cases | Controls | | | | |
| a) Iceland | | | | | | |
| Cohort B (668/58643) | 0.501 | 0.441 | $1.39 \times 10^{-5}$ | 1.274 | [1.142, 1.420] | 0.203 |
| Cohort A + B (2238/65731) | 0.491 | 0.441 | $8.91 \times 10^{-10}$ | 1.221 | [1.145, 1.301] | 0.169 |
| b) US replication cohorts | | | | | | |
| Cleveland (549/606) | 0.501 | 0.478 | 0.27 | 1.097 | [0.932, 1.292] | 0.087 |
| UPenn (580/404) | 0.539 | 0.483 | 0.014 | 1.252 | [1.046, 1.499] | 0.205 |
| Emory (400/477) | 0.548 | 0.482 | 0.0064 | 1.299 | [1.076, 1.569] | 0.236 |
| c) Combined** | | | | | | |
| Replication cohorts (2197/60130) | | | $2.65 \times 10^{-8}$ | 1.231 | [1.144, 1.324] | 0.183 |
| All cohorts (3767/67218) | | | $1.44 \times 10^{-12}$ | 1.214 | [1.151, 1.281] | 0.171 |

*P-values for the Icelandic cohorts are adjusted for relatedness using simulations (see methods)
**Mantel-Haenzel model was used to combine the results from the different cohorts.

TABLE 5 a) Association of the composite at-risk allele X of D9S1870 in Icelandic cases with various cardiovascular disease phenotypes. Included in the table are association results for individuals who have undergone PTCA or CABG, for the combined MI and CAD (PTCA and CABG) cohort, individuals with PAD or that have had infarct or TIA, and stroke patients diagnosed with LVD. In all tests the same set of 65,731 Icelandic controls without known CAD complications is used. b) Association of allele X in Iceland to the same coronary artery disease phenotypes as in a) after excluding all known cases of MI from the list of cases. C) Association of allele X to PTCA, CABG and a combined phenotype MI and other CAD, in the Emory cohort.

| Phenotype (n) | Frequency Cases | Frequency Controls | RR | CI | P | P* | PAR |
|---|---|---|---|---|---|---|---|
| a) Iceland | | | | | | | |
| PTCA (1791) | 0.489 | 0.441 | 1.211 | [1.129, 1.298] | 2.69E−08 | 8.60E−08 | 0.163 |
| CABG (642) | 0.514 | 0.441 | 1.338 | [1.189, 1.506] | 3.38E−07 | 1.31E−06 | 0.243 |
| MI + other CAD (3513) | 0.488 | 0.441 | 1.209 | [1.148, 1.273] | 2.57E−14 | 6.24E−13 | 0.162 |
| PAD (1661) | 0.477 | 0.441 | 1.154 | [1.074, 1.239] | 5.36E−05 | 8.58E−05 | 0.123 |
| Stroke, Infarct + TIA (1678) | 0.448 | 0.441 | 1.027 | [0.958, 1.102] | 0.45 | 0.45 | 0.023 |
| Stroke, LVD (197) | 0.469 | 0.441 | 1.120 | [0.915, 1.370] | 0.27 | 0.27 | 0.098 |
| b) Iceland, excl. MI cases | | | | | | | |
| PTCA (941) | 0.483 | 0.441 | 1.183 | [1.077, 1.300] | 0.00033 | 0.00045 | 0.144 |
| CABG (221) | 0.501 | 0.441 | 1.270 | [1.044, 1.545] | 0.013 | 0.017 | 0.202 |
| PAD (1322) | 0.464 | 0.441 | 1.096 | [1.012, 1.186] | 0.021 | 0.025 | 0.079 |
| Stroke, Infarct + TIA (1390) | 0.450 | 0.441 | 1.037 | [0.960, 1.119] | 0.35 | 0.36 | 0.032 |
| Stroke, LVD (153) | 0.480 | 0.441 | 1.172 | [0.934, 1.470] | 0.17 | 0.17 | 0.136 |
| c) Emory | | | | | | | |
| PTCA (141) | 0.567 | 0.482 | 1.408 | [1.079, 1.839] | 0.012 | NA | 0.302 |
| CABG (112) | 0.549 | 0.482 | 1.308 | [0.977, 1.751] | 0.071 | NA | 0.242 |
| MI + other CAD (476) | 0.551 | 0.482 | 1.320 | [1.103, 1.581] | 0.0025 | NA | 0.250 |

*P-value adjusted for relatedness using simulations.

TABLE 6

Association of the composite at-risk allele X of D9S1870 to early-onset MI or CAD a) in Iceland, b) in the three US replication cohorts, c) in all early-onset MI cohorts combined. Early-onset MI is defined as a MI event before the age 50 for males and before the age 60 for females.

| Phenotype (n) | Frequency Cases | Frequency Controls | RR | CI | P | P* | PAR |
|---|---|---|---|---|---|---|---|
| a) Iceland | | | | | | | |
| Early onset MI (646/65731) | 0.514 | 0.441 | 1.339 | [1.193, 1.503] | 3.63E−07 | 7.51E−07 | 0.243 |
| Early onset CAD (320/65731) | 0.532 | 0.441 | 1.439 | [1.227, 1.687] | 6.12E−06 | 7.40E−06 | 0.298 |
| Early onset MI + CAD (877/65731) | 0.511 | 0.441 | 1.325 | [1.200, 1.464] | 9.87E−09 | 2.70E−08 | 0.235 |
| b) US cohorts | | | | | | | |
| Emory EO MI (222/477) | 0.559 | 0.482 | 1.359 | [1.084, 1.703] | 0.0078 | NA | 0.273 |
| Cleveland EO MI (183/606) | 0.514 | 0.478 | 1.155 | [0.914, 1.459] | 0.2281 | NA | 0.133 |
| Upenn EO MI (275/490) | 0.569 | 0.473 | 1.469 | [1.191, 1.811] | 0.00033 | NA | 0.330 |
| c) All cohorts combined | | | | | | | |
| Early onset MI (1326/67304) | — | — | 1.331 | [1.223, 1.449] | 3.96E−11 | NA | 0.247 |

*P-value adjusted for relatedness using simulations.

TABLE 7

Model-free estimates of the genotype relative risks (GRR) of the composite allele X of D9S1870. Included is the risk for heterozygous carriers (OX) and homozygous carriers (XX) compared with risk for non-carriers (OO) and the corresponding 95% confidence intervals (CI). Results are shown for a) all MI cases versus controls and b) for early-onset MI cases versus controls for the whole Icelandic cohort, the three US replication cohorts and for all the cohorts combined using a Mantel-Haenzel model.

| | Genotype relative risk (GRR) | | | |
|---|---|---|---|---|
| Phenotype (n/m) | OX | CI | XX | CI |
| a) All MI cases | | | | |
| Iceland (2238/65731) | 1.173 | [1.060, 1.298] | 1.507 | [1.338, 1.697] |
| Cleveland (549/606) | 1.077 | [0.804, 1.443] | 1.204 | [0.860, 1.686] |
| UPenn (679/490) | 1.443 | [1.074, 1.938] | 1.728 | [1.228, 2.431] |
| Emory (400/477) | 1.213 | [0.836, 1.760] | 1.669 | [1.144, 2.435] |
| Combined (3866/67304) | 1.204 | [1.094, 1.324] | 1.507 | [1.360, 1.670] |
| b) Early onset MI cases | | | | |
| Iceland (641/65731) | 1.191 | [0.982, 1.444] | 1.803 | [1.453, 2.237] |
| Cleveland (183/606) | 1.432 | [0.932, 2.201] | 1.867 | [1.176, 2.964] |
| UPenn (275/490) | 1.692 | [1.134, 2.524] | 2.237 | [1.440, 3.476] |
| Emory (222/477) | 1.069 | [0.567, 2.017] | 1.328 | [0.827, 2.133] |
| Combined (1321/67304) | 1.314 | [1.105, 1.562] | 1.790 | [1.517, 2.113] |

TABLE 8 a) Association of the risk alleles of the markers rs10116277, rs1333040 and rs2383207 to age of onset of MI in the Icelandic Cohort A. The analysis is done using multiple regression where age of onset of MI is taken as the response variable and the number of copies of X is used as explanatory variable. The analysis is adjusted for gender by include sex of the individuals as an explanatory variable. Included in the table is the effect size, the standard error of the mean (SE) and the corresponding P-value. b) Association of the composite at-risk allele X of D9S1870 to age-of-onset of MI in the combined Icelandic MI patient cohort, and for the three US replication cohorts. Results for the four cohorts are combined weighting the contribution from each cohort proportional to the inverse of the standard error. In all tests only cases with known age-of-onset are included.

| Cohort/Marker (n) | Effect | SE | P |
|---|---|---|---|
| a) SNPs in Iceland A | | | |
| rs10116277 (1293) | −0.94 | 0.32 | 0.0039 |
| rs1333040 (1293) | −1.01 | 0.32 | 0.0018 |
| rs2383207 (1293) | −0.79 | 0.32 | 0.015 |
| b) D9S1870 allele X | | | |
| Iceland (2127) | −0.93 | 0.29 | 0.0016 |
| Cleveland (424) | −0.47 | 0.79 | 0.55 |
| UPenn (646) | −1.19 | 0.69 | 0.083 |
| Emory (403) | −1.38 | 0.87 | 0.11 |
| Combined (3600) | −0.95 | 0.25 | 0.000099 |

TABLE 9 a) Association of the composite risk allele X of D9S1870 to either mild (<50%) or severe (≥50%) in-stent restenosis in coronary artery disease patients that have undergone PTCA compared to controls without known history of CAD. b) Comparison of the frequency of the risk variant X in patients with severe in-stent restenosis to patients with mild in-stent restenosis.

| | Frequency | | | | |
|---|---|---|---|---|---|
| Phenotype (n, m) | Cases | Controls | RR | CI | P |
| a) Restenosis patients vs controls | | | | | |
| Mild restenosis, <50% (323/65731) | 0.492 | 0.441 | 1.228 | [1.050, 1.436] | 0.010 |
| Severe restenosis (≥50% (193/65731) | 0.509 | 0.441 | 1.313 | [1.071, 1.608] | 0.0086 |
| b) Severe vs mild restenosis (193/323) | 0.509 | 0.492 | 1.067 | [0.827, 1.376] | 0.62 |

TABLE 10

A. SNP markers within LD Block C09 (Between 21,920,147 and 22,149,982 on C09; NCBI Build 34, Build 35 and Build 36 (SEQ ID NO: 94)).

| Marker | Type of polymorphism | Location (NCBI Build 34/35/36) | Orientation | Location (SEQ ID NO: 1) |
|---|---|---|---|---|
| rs7864029 | C/G | 21920147 | + | 1 |
| rs2518714 | A/C | 21920303 | + | 157 |
| rs10965187 | A/G | 21920505 | + | 359 |
| rs2811715 | G/T | 21920571 | + | 425 |
| rs2518715 | C/T | 21920700 | + | 554 |
| rs12002708 | A/C | 21920762 | + | 616 |
| rs10811639 | A/G | 21920803 | + | 657 |
| rs11998828 | C/T | 21920812 | + | 666 |
| rs7868374 | A/G | 21921609 | + | 1463 |

TABLE 10-continued

| rs4977570 | G/T | 21921642 | + | 1496 |
|---|---|---|---|---|
| rs7390564 | G/T | 21921642 | + | 1496 |
| rs7869004 | G/T | 21921896 | + | 1750 |
| rs974679 | A/G | 21922245 | + | 2099 |
| rs2891010 | A/G | 21922261 | + | 2115 |
| rs12003714 | A/G | 21922366 | + | 2220 |
| rs28756321 | C/G | 21923029 | + | 2883 |
| rs12000395 | A/G | 21923096 | + | 2950 |
| rs2188126 | C/G | 21923125 | + | 2979 |
| rs12003027 | C/T | 21924442 | + | 4296 |
| rs7023582 | A/C | 21924684 | + | 4538 |
| rs28613732 | A/G | 21925807 | + | 5661 |
| rs10965188 | C/G | 21925874 | + | 5728 |
| rs12552975 | C/T | 21926059 | + | 5913 |
| rs7875199 | C/T | 21926381 | + | 6235 |
| rs12236992 | A/C | 21927299 | + | 7153 |
| rs7021848 | C/T | 21927351 | + | 7205 |
| rs7036999 | A/G | 21927875 | + | 7729 |
| rs12345808 | A/G | 21928367 | + | 8221 |
| rs35148759 | C/T | 21929306 | + | 9160 |
| rs7872310 | A/G | 21929387 | + | 9241 |
| rs2811716 | C/T | 21930017 | + | 9871 |
| rs10965189 | A/C | 21930588 | + | 10442 |
| rs4308829 | C/T | 21931196 | + | 11050 |
| rs10965190 | A/G | 21931385 | + | 11239 |
| rs10965191 | A/G | 21932535 | + | 12389 |
| rs12345373 | A/G | 21933199 | + | 13053 |
| rs4977750 | A/C | 21934317 | + | 14171 |
| rs10965193 | A/G | 21934544 | + | 14398 |
| rs4246843 | C/T | 21934627 | + | 14481 |
| rs4382559 | A/G | 21934818 | + | 14672 |
| rs4360371 | A/C | 21935562 | + | 15416 |
| rs16938595 | A/T | 21935605 | + | 15459 |
| rs10965194 | A/G | 21936214 | + | 16068 |
| rs2811717 | C/T | 21936322 | + | 16176 |
| rs6475598 | C/T | 21936322 | + | 16176 |
| rs2811718 | A/T | 21936891 | + | 16745 |
| rs10965196 | C/G | 21937472 | + | 17326 |
| rs2811719 | C/G | 21937472 | + | 17326 |
| rs2811720 | C/G | 21937957 | + | 17811 |

TABLE 10-continued

| rs6475599 | C/G | 21937957 | + | 17811 |
| rs11521166 | C/T | 21938376 | + | 18230 |
| rs2518718 | A/T | 21938489 | + | 18343 |
| rs10965197 | C/T | 21938666 | + | 18520 |
| rs2106117 | G/T | 21939527 | + | 19381 |
| rs2106118 | A/T | 21939528 | + | 19382 |
| rs2427852 | A/T | 21940432 | + | 20286 |
| rs2157716 | C/T | 2194043146 | + | 20300 |
| rs2263145 | C/T | 21940452 | + | 20306 |
| rs2427853 | C/T | 21940472 | + | 20326 |
| rs2382894 | C/G | 21940523 | + | 20377 |
| rs2427854 | A/T | 21940721 | + | 20575 |
| rs7047211 | A/T | 21940722 | + | 20576 |
| rs11532909 | A/T | 21940723 | + | 20577 |
| rs13297154 | A/T | 21940725 | + | 20579 |
| rs13298455 | A/T | 21940741 | + | 20595 |
| rs2891092 | A/G | 21940782 | + | 20636 |
| rs6415737 | A/G | 21940782 | + | 20636 |
| rs4503179 | A/G | 21940879 | + | 20733 |
| rs12349081 | A/C | 21941902 | + | 21756 |
| rs2518722 | C/T | 21942926 | + | 22780 |
| rs10757260 | A/G | 21943137 | + | 22991 |
| rs28369665 | C/T | 21944487 | + | 24341 |
| rs10965199 | C/T | 21944653 | + | 24507 |
| rs10757261 | A/G | 21944953 | + | 24807 |
| rs12335859 | A/G | 21945460 | + | 25314 |
| rs12335941 | A/G | 21945669 | + | 25523 |
| rs2027938 | A/G | 21946078 | + | 25932 |
| rs9657608 | C/T | 21946230 | + | 26084 |
| rs2518716 | A/G | 21946470 | + | 26324 |
| rs2027939 | A/G | 21946492 | + | 26346 |
| rs7869996 | C/T | 21946914 | + | 26768 |
| rs10965200 | C/G | 21948142 | + | 27996 |
| rs717326 | A/G | 21948524 | - | 28378 |
| rs35116241 | A/C | 21949093 | + | 28947 |
| rs2518717 | C/T | 21949751 | + | 29605 |
| rs3948753 | A/G | 21949860 | + | 29714 |
| rs2106115 | C/T | 21949900 | + | 29754 |
| rs10965201 | C/G | 21949950 | + | 29804 |
| rs2106116 | C/T | 21949966 | + | 29820 |

TABLE 10-continued

| | | | | |
|---|---|---|---|---|
| rs10965202 | A/G | 21951180 | + | 31034 |
| rs1985742 | A/T | 21951227 | + | 31081 |
| rs7041637 | A/C | 21951866 | + | 31720 |
| rs2263146 | C/T | 21953048 | + | 32902 |
| rs35732310 | A/C | 21953841 | + | 33695 |
| rs4518744 | A/C | 21954015 | + | 33869 |
| rs2188127 | C/G | 21955232 | + | 35086 |
| rs3731257 | C/T | 21956221 | − | 36075 |
| rs3731256 | C/T | 21956617 | − | 36471 |
| rs11793581 | G/T | 21957446 | + | 37300 |
| rs28695347 | A/C | 21957706 | + | 37560 |
| rs3731255 | C/G | 21957855 | − | 37709 |
| rs3731253 | C/G | 21957952 | − | 37806 |
| rs3088440 | A/G | 21958159 | + | 38013 |
| rs11515 | C/G | 21958199 | − | 38053 |
| rs34011899 | A/C | 21958712 | + | 38566 |
| rs2255962 | A/G | 21959827 | + | 39681 |
| rs2518719 | A/G | 21960427 | + | 40281 |
| rs3731249 | A/G | 21960916 | − | 40770 |
| rs6413464 | G/T | 21960979 | − | 40833 |
| rs34170727 | C/T | 21960988 | − | 40842 |
| rs6413463 | A/T | 21960989 | − | 40843 |
| rs35741010 | A/G | 21961054 | − | 40908 |
| rs34886500 | C/T | 21961063 | − | 40917 |
| rs4987127 | A/G | 21961085 | − | 40939 |
| rs11552822 | G/T | 21961108 | − | 40962 |
| rs34968276 | A/C | 21961109 | − | 40963 |
| rs11552823 | C/T | 21961116 | − | 40970 |
| rs3731247 | C/T | 21961352 | − | 41206 |
| rs12377672 | C/T | 21961418 | + | 41272 |
| rs3731246 | C/G | 21961989 | − | 41843 |
| rs3731245 | A/G | 21962445 | − | 42299 |
| rs3731244 | A/G | 21962813 | − | 42667 |
| rs3731243 | A/G | 21963050 | − | 42904 |
| rs2811708 | G/T | 21963422 | + | 43276 |
| rs3731241 | A/G | 21963767 | − | 43621 |
| rs13288666 | C/T | 21963857 | + | 43711 |
| rs3731240 | A/G | 21964131 | − | 43985 |
| rs3731239 | C/T | 21964218 | − | 44072 |
| rs3814960 | A/C/G/T | 21965017 | + | 44871 |

TABLE 10-continued

| rs3731238 | A/G | 21965561 | − | 45415 |
|---|---|---|---|---|
| rs3731237 | A/G | 21965728 | − | 45582 |
| rs3731236 | C/T | 21966976 | − | 46830 |
| rs3731235 | G/T | 21967450 | − | 47304 |
| rs12350633 | C/G | 21967553 | + | 47407 |
| rs3731234 | A/C | 21967579 | − | 47433 |
| rs3731233 | A/T | 21968358 | − | 48212 |
| rs3731232 | C/G | 21968443 | − | 48297 |
| rs2518720 | C/T | 21968979 | + | 48833 |
| rs3731230 | C/T | 21969163 | − | 49017 |
| rs2518721 | A/G | 21969204 | + | 49058 |
| rs3731229 | A/C | 21969497 | − | 49351 |
| rs3731228 | A/G | 21969602 | − | 49456 |
| rs2811709 | A/G | 21970151 | + | 50005 |
| rs3731227 | C/T | 21970744 | − | 50598 |
| rs3731226 | C/T | 21970792 | − | 50646 |
| rs13297747 | C/G | 21970941 | + | 50795 |
| rs36170221 | C/G | 21970941 | + | 50795 |
| rs36153543 | C/T | 21970944 | + | 50798 |
| rs7874405 | C/T | 21970944 | + | 50798 |
| rs13302595 | C/T | 21971034 | + | 50888 |
| rs13301751 | A/G | 21971039 | + | 50893 |
| rs13302611 | C/T | 21971068 | + | 50922 |
| rs13302761 | C/T | 21971100 | + | 50954 |
| rs13302792 | C/T | 21971168 | + | 51022 |
| rs3731225 | A/G | 21971351 | − | 51205 |
| rs3731224 | C/T | 21971411 | − | 51265 |
| rs4074785 | A/G | 21971583 | + | 51437 |
| rs3731223 | A/G | 21973834 | − | 53688 |
| rs3731222 | A/G | 21973914 | − | 53768 |
| rs3731221 | A/G | 21974010 | − | 53864 |
| rs3731220 | A/G | 21974019 | − | 53873 |
| rs3731219 | A/G | 21974086 | − | 53940 |
| rs3731218 | C/T | 21974331 | − | 54185 |
| rs3731217 | G/T | 21974661 | − | 54515 |
| rs3731216 | G/T | 21975576 | − | 55430 |
| rs3731215 | C/T | 21975771 | − | 55625 |
| rs3731214 | A/G | 21975968 | − | 55822 |
| rs3731213 | A/G | 21976218 | − | 56072 |
| rs3731212 | C/T | 21976271 | − | 56125 |

TABLE 10-continued

| | | | | |
|---|---|---|---|---|
| rs3731211 | A/T | 21976847 | − | 56701 |
| rs3731210 | A/G | 21976859 | − | 56713 |
| rs3731208 | C/T | 21977155 | − | 57009 |
| rs3731207 | C/T | 21977353 | − | 57207 |
| rs12376353 | C/G | 21977433 | + | 57287 |
| rs3731206 | A/G | 21977472 | − | 57326 |
| rs3731205 | A/G | 21977522 | − | 57376 |
| rs3731204 | A/G | 21977584 | − | 57438 |
| rs10757262 | A/T | 21977874 | + | 57728 |
| rs3731202 | A/G | 21978800 | − | 58654 |
| rs3731201 | A/G | 21978896 | − | 58750 |
| rs3731199 | A/G | 21979330 | − | 59184 |
| rs3731198 | A/G | 21979477 | − | 59331 |
| rs7036656 | C/T | 21980457 | + | 60311 |
| rs7867492 | C/T | 21981016 | + | 60870 |
| rs3731197 | A/G | 21981371 | − | 61225 |
| rs3731196 | A/G | 21981652 | − | 61506 |
| rs3731195 | C/T | 21981695 | − | 61549 |
| rs3731194 | C/G | 21981752 | − | 61606 |
| rs2811710 | C/T | 21981923 | + | 61777 |
| rs3731192 | G/T | 21982274 | − | 62128 |
| rs3731191 | C/T | 21983048 | − | 62902 |
| rs2811711 | C/T | 21983964 | + | 63818 |
| rs3731190 | C/T | 21984282 | − | 64136 |
| rs2518723 | A/G | 21985882 | − | 65736 |
| rs7860185 | C/T | 21986986 | + | 66840 |
| rs3218024 | A/G | 21987437 | − | 67291 |
| rs3218023 | C/T | 21987597 | − | 67451 |
| rs3218022 | A/G | 21987723 | − | 67577 |
| rs3218021 | G/T | 21987752 | − | 67606 |
| rs3218020 | C/T | 21987872 | − | 67726 |
| rs3218019 | A/G | 21987904 | − | 67758 |
| rs2811712 | A/G | 21988035 | + | 67889 |
| rs3218018 | A/C | 21988139 | − | 67993 |
| rs3218016 | A/G | 21988273 | − | 68127 |
| rs3218015 | C/G | 21988392 | − | 68246 |
| rs3218013 | C/T | 21988556 | − | 68410 |
| rs3218012 | C/T | 21988660 | − | 68514 |
| rs3218011 | A/G | 21988676 | − | 68530 |
| rs3218010 | A/G | 21988733 | − | 68587 |

TABLE 10-continued

| | | | | |
|---|---|---|---|---|
| rs3218009 | C/G | 21988757 | − | 68611 |
| rs10965208 | A/G | 21988965 | + | 68819 |
| rs2811713 | A/G | 21989328 | + | 69182 |
| rs2811714 | C/T | 21989334 | + | 69188 |
| rs3218007 | A/G | 21989800 | − | 69654 |
| rs3218006 | G/T | 21989980 | − | 69834 |
| rs3218005 | A/G | 21990247 | − | 70101 |
| rs3218004 | C/G | 21990687 | − | 70541 |
| rs3218003 | C/G | 21990770 | − | 70624 |
| rs3218002 | C/T | 21990841 | − | 70695 |
| rs3218001 | C/G | 21990959 | − | 70813 |
| rs3218000 | C/T | 21991078 | − | 70932 |
| rs3217999 | C/T | 21991572 | − | 71426 |
| rs3217998 | A/C | 21991667 | − | 71521 |
| rs3217997 | A/G | 21992316 | − | 72170 |
| rs3217996 | C/T | 21992322 | − | 72176 |
| rs3217994 | A/G | 21992864 | − | 72718 |
| rs3217993 | C/T | 21993169 | − | 73023 |
| rs3217992 | A/G | 21993223 | − | 73077 |
| rs1063192 | C/T | 21993367 | − | 73221 |
| rs3217990 | A/C | 21993521 | − | 73375 |
| rs3217989 | A/G | 21993790 | − | 73644 |
| rs3217988 | A/G | 21994082 | − | 73936 |
| rs2285329 | C/T | 21994153 | − | 74007 |
| rs10965209 | A/G | 21994669 | + | 74523 |
| rs3217987 | C/T | 21995061 | − | 74915 |
| rs11792943 | A/G | 21995123 | + | 74977 |
| rs11792944 | G/T | 21995127 | + | 74981 |
| rs3217986 | A/C | 21995330 | − | 75184 |
| rs3217985 | C/T | 21995453 | − | 75307 |
| rs3217984 | C/G | 21995493 | − | 75347 |
| rs3217983 | C/T | 21995623 | − | 75477 |
| rs3217982 | C/T | 21995647 | − | 75501 |
| rs3217981 | A/G | 21996269 | − | 76123 |
| rs2069426 | A/C | 21996273 | − | 76127 |
| rs974336 | A/G | 21996348 | − | 76202 |
| rs3217980 | C/T | 21996607 | − | 76461 |
| rs2069425 | C/T | 21996793 | − | 76647 |
| rs2285328 | C/T | 21996966 | − | 76820 |
| rs2285327 | A/G | 21997048 | − | 76902 |

TABLE 10-continued

| | | | | |
|---|---|---|---|---|
| rs3217979 | A/G | 21997187 | − | 77041 |
| rs3217978 | G/T | 21997330 | − | 77184 |
| rs2069423 | C/T | 21997771 | − | 77625 |
| rs2069422 | A/C | 21998026 | − | 77880 |
| rs2069421 | A/G | 21998313 | − | 78167 |
| rs3217976 | A/C | 21998439 | − | 78293 |
| rs2069420 | A/T | 21998504 | − | 78358 |
| rs2069419 | A/C/T | 21999337 | − | 79191 |
| rs2069418 | C/G | 21999698 | − | 79552 |
| rs3217974 | A/C | 21999908 | − | 79762 |
| rs3217973 | C/T | 21999960 | − | 79814 |
| rs2069416 | A/C/T | 22000004 | − | 79858 |
| rs495490 | C/T | 22000412 | − | 80266 |
| rs3808845 | A/G | 22000575 | + | 80429 |
| rs3808846 | A/G | 22000946 | + | 80800 |
| rs575427 | C/T | 22001477 | − | 81331 |
| rs573687 | C/T | 22001642 | − | 81496 |
| rs13298881 | C/T | 22002051 | + | 81905 |
| rs16935753 | A/G | 22002229 | + | 82083 |
| rs16935754 | C/T | 22002236 | + | 82090 |
| rs545226 | C/T | 22002422 | − | 82276 |
| rs7032979 | C/T | 22002457 | + | 82311 |
| rs10811640 | G/T | 22003411 | + | 83265 |
| rs10757263 | C/T | 22003805 | + | 83659 |
| rs10811641 | C/G | 22004137 | + | 83991 |
| rs7042051 | C/T | 22004758 | + | 84612 |
| rs7027610 | C/T | 22004872 | + | 84726 |
| rs7045307 | C/T | 22005057 | + | 84911 |
| rs1101330 | G/T | 22005465 | − | 85319 |
| rs13295358 | A/C | 22005465 | + | 85319 |
| rs1101329 | A/G | 22005997 | − | 85851 |
| rs1633381 | A/G | 22005997 | − | 85851 |
| rs10217269 | C/T | 22006173 | + | 86027 |
| rs10217281 | A/G | 22006617 | + | 86471 |
| rs10965211 | C/T | 22006891 | + | 86745 |
| rs28451206 | C/G | 22006921 | + | 86775 |
| rs2157718 | G/T | 22007025 | − | 86879 |
| rs2106120 | A/C | 22007101 | − | 86955 |
| rs16905562 | A/T | 22007425 | + | 87279 |
| rs2106119 | C/T | 22007550 | − | 87404 |

TABLE 10-continued

| | | | | |
|---|---|---|---|---|
| rs643319 | G/T | 22007836 | − | 87690 |
| rs575237 | C/T | 22008108 | − | 87962 |
| rs642323 | C/T | 22008121 | − | 87975 |
| rs7044859 | A/T | 22008781 | + | 88635 |
| rs523096 | C/T | 22009129 | − | 88983 |
| rs518394 | C/G | 22009673 | − | 89527 |
| rs10757264 | A/G | 22009732 | + | 89586 |
| rs490005 | C/T | 22010493 | − | 90347 |
| rs7858261 | C/T | 22010757 | + | 90611 |
| rs34623146 | A/G | 22010822 | + | 90676 |
| rs597816 | A/G | 22011172 | − | 91026 |
| rs7048912 | A/G | 22011425 | + | 91279 |
| rs568447 | C/T | 22011615 | − | 91469 |
| rs567453 | C/G | 22011737 | − | 91591 |
| rs7018665 | A/G | 22011819 | + | 91673 |
| rs11515247 | C/T | 22012269 | + | 92123 |
| rs581876 | A/G | 22012376 | − | 92230 |
| rs7039304 | A/T | 22012786 | + | 92640 |
| rs11789770 | C/G | 22012982 | + | 92836 |
| rs10965212 | A/T | 22013795 | + | 93649 |
| rs1292137 | A/T | 22014023 | − | 93877 |
| rs504318 | A/T | 22014023 | − | 93877 |
| rs1292136 | A/G | 22014351 | − | 94205 |
| rs496892 | A/G | 22014351 | − | 94205 |
| rs647188 | A/C | 22014965 | − | 94819 |
| rs10811643 | A/G | 22014966 | + | 94820 |
| rs10811644 | A/T | 22015067 | + | 94921 |
| rs7035484 | C/G | 22015240 | + | 95094 |
| rs10738604 | A/G | 22015493 | + | 95347 |
| rs11791383 | C/G | 22015814 | + | 95668 |
| rs615552 | A/G | 22016077 | − | 95931 |
| rs1591137 | C/T | 22016483 | − | 96337 |
| rs613312 | C/T | 22016594 | − | 96448 |
| rs543830 | A/T | 22016639 | − | 96493 |
| rs1591136 | C/G | 22016834 | − | 96688 |
| rs10965214 | A/T | 22017274 | + | 97128 |
| rs599452 | C/T | 22017402 | − | 97256 |
| rs598664 | A/G | 22017551 | − | 97405 |
| rs7049105 | A/G | 22018801 | + | 98655 |
| rs679038 | C/T | 22019080 | − | 98934 |

TABLE 10-continued

| | | | | |
|---|---|---|---|---|
| rs10965215 | A/G | 22019445 | + | 99299 |
| rs564398 | A/G | 22019547 | − | 99401 |
| rs4977753 | C/T | 22020027 | + | 99881 |
| rs662463 | C/T | 22020438 | − | 100292 |
| rs7865618 | A/G | 22021005 | + | 100859 |
| rs649436 | C/T | 22021085 | − | 100939 |
| rs10115049 | A/G | 22022119 | + | 101973 |
| rs634537 | A/C | 22022152 | − | 102006 |
| rs2157719 | A/G | 22023366 | − | 103220 |
| rs1759417 | A/G | 22023389 | − | 103243 |
| rs1633383 | A/G | 22023532 | − | 103386 |
| rs2151280 | C/T | 22024719 | − | 104573 |
| rs1008878 | G/T | 22026112 | + | 105966 |
| rs7029531 | C/G | 22026170 | + | 106024 |
| rs1556515 | A/G | 22026367 | − | 106221 |
| rs35975148 | A/T | 22027071 | + | 106925 |
| rs17694478 | C/G | 22027171 | + | 107025 |
| rs12376000 | C/T | 22029426 | + | 109280 |
| rs1333037 | A/G | 22030765 | − | 110619 |
| rs7028469 | G/T | 22031342 | + | 111196 |
| rs1360590 | A/G | 22031443 | − | 111297 |
| rs17694493 | C/G | 22031998 | + | 111852 |
| rs12352425 | A/G | 22032086 | + | 111940 |
| rs12686542 | A/C | 22032227 | + | 112081 |
| rs10965216 | C/T | 22032879 | + | 112733 |
| rs1412830 | A/G | 22033612 | − | 113466 |
| rs1333036 | A/G | 22033819 | − | 113673 |
| rs1412829 | C/T | 22033926 | − | 113780 |
| rs1333035 | C/T | 22034059 | − | 113913 |
| rs1333034 | A/G | 22034122 | − | 113976 |
| rs10965217 | A/T | 22034317 | + | 114171 |
| rs13290048 | C/T | 22034804 | + | 114658 |
| rs28419335 | A/G | 22035035 | + | 114889 |
| rs28621545 | G/T | 22035037 | + | 114891 |
| rs1360589 | A/G | 22035317 | − | 115171 |
| rs12338105 | C/G | 22035344 | + | 115198 |
| rs1333033 | A/G | 22035653 | − | 115507 |
| rs17834131 | A/G | 22036168 | + | 116022 |
| rs12340618 | A/G | 22037050 | + | 116904 |
| rs7851706 | C/T | 22037437 | + | 117291 |

TABLE 10-continued

| | | | | |
|---|---|---|---|---|
| rs12683931 | A/G | 22037916 | + | 117770 |
| rs10120806 | C/T | 22037945 | + | 117799 |
| rs7027950 | C/T | 22038391 | + | 118245 |
| rs7028268 | A/G | 22038414 | + | 118268 |
| rs7028570 | A/G | 22038683 | + | 118537 |
| rs10757265 | C/T | 22038859 | + | 118713 |
| rs10738605 | C/G | 22039130 | + | 118984 |
| rs10757266 | C/T | 22039555 | + | 119409 |
| rs10811645 | A/G | 22039656 | + | 119510 |
| rs2151279 | C/T | 22039845 | − | 119699 |
| rs6475603 | A/G | 22040612 | + | 120466 |
| rs944799 | A/G | 22040613 | + | 120467 |
| rs944800 | A/G | 22040898 | + | 120752 |
| rs17694555 | A/G | 22041295 | + | 121149 |
| rs944801 | C/G | 22041670 | + | 121524 |
| rs6475604 | C/T | 22042734 | + | 122588 |
| rs10757267 | C/G | 22042810 | + | 122664 |
| rs4433231 | G/T | 22043244 | + | 123098 |
| rs11790231 | A/G | 22043591 | + | 123445 |
| rs7854869 | A/C | 22043651 | + | 123505 |
| rs10965219 | A/G | 22043687 | + | 123541 |
| rs7027048 | A/G | 22043709 | + | 123563 |
| rs17756311 | A/G | 22043895 | + | 123749 |
| rs7030641 | C/T | 22044040 | + | 123894 |
| rs17694572 | A/G | 22044356 | + | 124210 |
| rs7874604 | C/T | 22044690 | + | 124544 |
| rs2383204 | A/G | 22045048 | + | 124902 |
| rs7036489 | A/G | 22045992 | + | 125846 |
| rs7039467 | A/G | 22046213 | + | 126067 |
| rs7866660 | A/T | 22046233 | + | 126087 |
| rs10965220 | A/G | 22046279 | + | 126133 |
| rs7853090 | C/T | 22046295 | + | 126149 |
| rs7866783 | A/G | 22046359 | + | 126213 |
| rs10120688 | A/G | 22046499 | + | 126353 |
| rs13292618 | A/G | 22047339 | + | 127193 |
| rs10121501 | C/G | 22047390 | + | 127244 |
| rs13299593 | C/T | 22048918 | + | 128772 |
| rs7021816 | A/C | 22049277 | + | 129131 |
| rs10757268 | C/T | 22049905 | + | 129759 |
| rs2095144 | C/T | 22050136 | − | 129990 |

TABLE 10-continued

| rs2383205 | A/G | 22050935 | + | 130789 |
|---|---|---|---|---|
| rs2184061 | G/T | 22051562 | − | 131416 |
| rs1537378 | C/T | 22051614 | − | 131468 |
| rs4977754 | A/C | 22052012 | + | 131866 |
| rs1011970 | G/T | 22052134 | + | 131988 |
| rs10965221 | G/T | 22052999 | + | 132853 |
| rs8181050 | A/G | 22054391 | + | 134245 |
| rs8181047 | A/G | 22054465 | + | 134319 |
| rs10811647 | C/G | 22055002 | + | 134856 |
| rs1333038 | A/G | 22055572 | + | 135426 |
| rs4144664 | C/T | 22055656 | + | 135510 |
| rs1333039 | C/G | 22055657 | + | 135511 |
| rs4977755 | A/T | 22056363 | + | 136217 |
| rs28557075 | A/G | 22056572 | + | 136426 |
| rs10965223 | A/G | 22057004 | + | 136858 |
| rs10965224 | A/T | 22057276 | + | 137130 |
| rs10811648 | C/T | 22057542 | + | 137396 |
| rs10811649 | C/T | 22057554 | + | 137408 |
| rs10811650 | A/G | 22057593 | + | 137447 |
| rs10811651 | A/G | 22057830 | + | 137684 |
| rs16905597 | A/G | 22058074 | + | 137928 |
| rs1412831 | A/G | 22058646 | + | 138500 |
| rs4977756 | A/G | 22058652 | + | 138506 |
| rs16905599 | A/G | 22059144 | + | 138998 |
| rs34871414 | A/C | 22059537 | + | 139391 |
| rs7042970 | A/G | 22059580 | + | 139434 |
| rs4451405 | C/T | 22061750 | + | 141604 |
| rs4645630 | A/G | 22061751 | + | 141605 |
| rs12555547 | C/G | 22062040 | + | 141894 |
| rs10757269 | A/G | 22062264 | + | 142118 |
| rs9632884 | C/G | 22062301 | + | 142155 |
| rs9632885 | A/G | 22062638 | + | 142492 |
| rs10757270 | A/G | 22062719 | + | 142573 |
| rs17761197 | C/T | 22062730 | + | 142584 |
| rs10965226 | G/T | 22063170 | + | 143024 |
| rs16923583 | A/T | 22063334 | + | 143188 |
| rs1855185 | G/T | 22063996 | + | 143850 |
| rs7855162 | C/T | 22064793 | + | 144647 |
| rs1831733 | C/T | 22066071 | + | 145925 |
| rs1831734 | C/T | 22066208 | + | 146062 |

TABLE 10-continued

| | | | | |
|---|---|---|---|---|
| rs10757271 | A/G | 22066795 | + | 146649 |
| rs10811652 | A/C | 22067085 | + | 146939 |
| rs1412832 | C/T | 22067543 | + | 147397 |
| rs7855660 | C/T | 22068305 | + | 148159 |
| rs6475605 | C/G | 22069020 | + | 148874 |
| rs16905613 | A/G | 22070363 | + | 150217 |
| rs7858034 | A/T | 22070791 | + | 150645 |
| rs12347950 | A/G | 22071128 | + | 150982 |
| rs1412833 | A/G | 22071346 | + | 151200 |
| rs10116277 | G/T | 22071397 | + | 151251 |
| rs10965227 | A/G | 22071796 | + | 151650 |
| rs6475606 | C/T | 22071850 | + | 151704 |
| rs1547704 | A/G | 22072340 | + | 152194 |
| rs1547705 | A/C | 22072375 | + | 152229 |
| rs10965228 | A/G | 22072380 | + | 152234 |
| rs7853953 | A/C | 22073017 | + | 152871 |
| rs1333040 | C/T | 22073404 | + | 153258 |
| rs1537370 | C/T | 22074310 | + | 154164 |
| rs10122192 | G/T | 22074633 | + | 154487 |
| rs1970112 | C/T | 22075598 | + | 155452 |
| rs10120722 | A/C | 22076840 | + | 156694 |
| rs16905635 | C/T | 22076883 | + | 156737 |
| rs7857345 | C/T | 22077473 | + | 157327 |
| rs10738606 | A/T | 22078090 | + | 157944 |
| rs10738607 | A/G | 22078094 | + | 157948 |
| rs10757272 | C/T | 22078260 | + | 158114 |
| rs16905640 | A/G | 22078556 | + | 158410 |
| rs13300638 | G/T | 22078937 | + | 158791 |
| rs13284693 | A/T | 22079014 | + | 158868 |
| rs12235973 | A/T | 22079193 | + | 159047 |
| rs10757273 | A/C | 22080301 | + | 160155 |
| rs10965230 | C/T | 22080416 | + | 160270 |
| rs9644859 | A/G | 22080521 | + | 160375 |
| rs7019916 | C/T | 22080683 | + | 160537 |
| rs7020031 | C/T | 22080753 | + | 160607 |
| rs7034707 | C/T | 22080811 | + | 160665 |
| rs34597771 | C/T | 22081731 | + | 161585 |
| rs34555767 | G/T | 22081924 | + | 161778 |
| rs7866503 | G/T | 22081924 | + | 161778 |
| rs7869527 | A/G | 22082097 | + | 161951 |

TABLE 10-continued

| | | | | |
|---|---|---|---|---|
| rs2210538 | A/G | 22082257 | + | 162111 |
| rs7870178 | A/G | 22082551 | + | 162405 |
| rs34184423 | A/G | 22082924 | + | 162778 |
| rs34168773 | A/T | 22083299 | + | 163153 |
| rs9722878 | G/T | 22083462 | + | 163316 |
| rs7848875 | A/G | 22084281 | + | 164135 |
| rs35537809 | A/G | 22084330 | + | 164184 |
| rs4977757 | A/G | 22084330 | + | 164184 |
| rs7388840 | A/G | 22084330 | + | 164184 |
| rs10738608 | A/C | 22084796 | + | 164650 |
| rs35869261 | A/T | 22085567 | + | 165421 |
| rs35062160 | G/T | 22085730 | + | 165584 |
| rs2891167 | C/T | 22085851 | + | 165705 |
| rs10757274 | A/G | 22086055 | + | 165909 |
| rs16905644 | C/T | 22087022 | + | 166876 |
| rs6475607 | A/G | 22087693 | + | 167547 |
| rs7037832 | A/G | 22088038 | + | 167892 |
| rs1333041 | C/G | 22088374 | + | 168228 |
| rs4977574 | A/G- | 22088574 | + | 168428 |
| rs2891168 | A/G | 22088619 | + | 168473 |
| rs10965231 | A/G | 22088674 | + | 168528 |
| rs11787814 | A/G | 22088683 | + | 168537 |
| rs1537371 | A/C | 22089568 | + | 169422 |
| rs7856476 | A/T | 22089940 | + | 169794 |
| rs1556516 | C/G | 22090176 | + | 170030 |
| rs12238050 | A/C | 22090726 | + | 170580 |
| rs10965232 | C/T | 22091120 | + | 170974 |
| rs13292938 | G/T | 22091259 | + | 171113 |
| rs7028026 | A/G | 22091435 | + | 171289 |
| rs6475608 | C/T | 22091702 | + | 171556 |
| rs10125231 | A/G | 22092128 | + | 171982 |
| rs7859727 | C/T | 22092165 | + | 172019 |
| rs1537372 | G/T | 22093183 | + | 173037 |
| rs10965233 | A/G | 22093314 | + | 173168 |
| rs1537373 | G/T | 22093341 | + | 173195 |
| rs7022719 | C/T | 22093748 | + | 173602 |
| rs1333042 | A/G | 22093813 | + | 173667 |
| rs4336695 | C/G | 22094450 | + | 174304 |
| rs7872591 | A/C | 22095595 | + | 175449 |
| rs7859362 | C/T | 22095927 | + | 175781 |

TABLE 10-continued

| | | | | |
|---|---|---|---|---|
| rs10757275 | A/G | 22096225 | + | 176079 |
| rs6475609 | A/G | 22096271 | + | 176125 |
| rs1333043 | A/T | 22096731 | + | 176585 |
| rs7855190 | C/T | 22098069 | + | 177923 |
| rs10217720 | A/G | 22098942 | + | 178796 |
| rs10217426 | C/G | 22099387 | + | 179241 |
| rs1412834 | C/T | 22100131 | + | 179985 |
| rs17761319 | G/T | 22100478 | + | 180332 |
| rs16905648 | A/G | 22101973 | + | 181827 |
| rs7341786 | A/C | 22102241 | + | 182095 |
| rs7341791 | A/G | 22102427 | + | 182281 |
| rs10511701 | C/T | 22102599 | + | 182453 |
| rs17834367 | C/T | 22102606 | + | 182460 |
| rs7032115 | A/G | 22102943 | + | 182797 |
| rs13301964 | C/G | 22103324 | + | 183178 |
| rs16905652 | A/T | 22103924 | + | 183778 |
| rs10733376 | C/G | 22104469 | + | 184323 |
| rs10738609 | A/G | 22104495 | + | 184349 |
| rs2383206 | A/G | 22105026 | + | 184880 |
| rs10965234 | G/T | 22105078 | + | 184932 |
| rs10965235 | A/C | 22105105 | + | 184959 |
| rs4990722 | G/T | 22105217 | + | 185071 |
| rs944796 | C/G | 22105285 | + | 185139 |
| rs944797 | C/T | 22105286 | + | 185140 |
| rs1004638 | A/T | 22105589 | − | 185443 |
| rs10965236 | C/G | 22105633 | + | 185487 |
| rs2383207 | A/G | 22105959 | + | 185813 |
| rs1537374 | A/G | 22106046 | + | 185900 |
| rs1537375 | C/T | 22106071 | + | 185925 |
| rs1537376 | C/T | 22106220 | + | 186074 |
| rs7851006 | A/G | 22107669 | + | 187523 |
| rs17834457 | C/T | 22108026 | + | 187880 |
| rs17761446 | G/T | 22108102 | + | 187956 |
| rs7854631 | A/C | 22108378 | + | 188232 |
| rs4977758 | A/T | 22108481 | + | 188335 |
| rs4977759 | C/T | 22108885 | + | 188739 |
| rs1333044 | A/G | 22109128 | + | 188982 |
| rs1333045 | C/T | 22109195 | + | 189049 |
| rs12685422 | A/C | 22111167 | + | 191021 |
| rs10217586 | A/T | 22111349 | + | 191203 |

TABLE 10-continued

| | | | | |
|---|---|---|---|---|
| rs7860589 | C/T | 22111353 | + | 191207 |
| rs7020671 | A/T | 22112193 | + | 192047 |
| rs10965237 | A/C | 22112530 | + | 192384 |
| rs13285121 | A/T | 22112912 | + | 192766 |
| rs7869069 | G/T | 22113590 | + | 193444 |
| rs10738610 | A/C | 22113766 | + | 193620 |
| rs7854016 | A/C | 22113967 | + | 193821 |
| rs1333046 | A/T | 22114123 | + | 193977 |
| rs7857118 | A/T | 22114140 | + | 193994 |
| rs17761458 | A/G | 22114368 | + | 194222 |
| rs10757277 | A/G | 22114450 | + | 194304 |
| rs10811656 | C/T | 22114472 | + | 194326 |
| rs10757278 | A/G | 22114477 | + | 194331 |
| rs1333047 | A/T | 22114504 | + | 194358 |
| rs10757279 | A/G | 22114630 | + | 194484 |
| rs4977575 | C/G | 22114744 | + | 194598 |
| rs1333048 | A/C | 22115347 | + | 195201 |
| rs1333049 | C/G | 22115503 | + | 195357 |
| rs1333050 | C/T | 22115913 | + | 195767 |
| rs12345199 | A/G | 22116454 | + | 196308 |
| rs12336106 | A/G | 22116885 | + | 196739 |
| rs10757281 | C/T | 22117613 | + | 197467 |
| rs10811657 | A/G | 22117641 | + | 197495 |
| rs17834529 | C/G | 22117777 | + | 197631 |
| rs1889086 | C/T | 22117879 | − | 197733 |
| rs10965238 | A/G | 22117883 | + | 197737 |
| rs10965239 | A/G | 22117965 | + | 197819 |
| rs12379111 | C/G | 22118180 | + | 198034 |
| rs10811658 | A/G | 22118600 | + | 198454 |
| rs12347779 | C/G | 22118709 | + | 198563 |
| rs10965240 | C/T | 22119164 | + | 199018 |
| rs7020996 | C/T | 22119579 | + | 199433 |
| rs10965241 | C/G | 22119594 | + | 199448 |
| rs10965243 | A/G | 22120065 | + | 199919 |
| rs10965244 | A/T | 22120389 | + | 200243 |
| rs10965245 | A/G | 22120515 | + | 200369 |
| rs2891169 | A/G | 22121825 | + | 201679 |
| rs4977576 | A/C | 22121861 | + | 201715 |
| rs2383208 | A/G | 22122076 | + | 201930 |
| rs10965246 | C/T | 22122698 | + | 202552 |

TABLE 10-continued

| rs10965247 | A/G | 22122729 | + | 202583 |
|---|---|---|---|---|
| rs10965248 | C/T | 22122878 | + | 202732 |
| rs10965249 | C/T | 22123131 | + | 202985 |
| rs7045889 | A/G | 22123251 | + | 203105 |
| rs10965250 | A/G | 22123284 | + | 203138 |
| rs10217762 | C/T | 22123645 | + | 203499 |
| rs10811659 | C/T | 22123716 | + | 203570 |
| rs12686509 | A/T | 22123767 | + | 203621 |
| rs10757282 | C/T | 22123984 | + | 203838 |
| rs10965251 | A/G | 22124029 | + | 203883 |
| rs10811660 | A/G | 22124068 | + | 203922 |
| rs10811661 | C/T | 22124094 | + | 203948 |
| rs10757283 | C/T | 22124172 | + | 204026 |
| rs10811662 | A/G | 22124253 | + | 204107 |
| rs7019437 | C/G | 22124302 | + | 204156 |
| rs7019472 | C/T | 22124395 | + | 204249 |
| rs7019778 | A/C | 22124651 | + | 204505 |
| rs13287212 | G/T | 22125071 | + | 204925 |
| rs10965252 | A/G | 22125919 | + | 205773 |
| rs12555274 | C/G | 22126440 | + | 206294 |
| rs1333051 | A/T | 22126489 | + | 206343 |
| rs10965253 | G/T | 22126687 | + | 206541 |
| rs7018475 | G/T | 22127685 | + | 207539 |
| rs9969854 | G/T | 22127710 | + | 207564 |
| rs11791416 | A/G | 22128105 | + | 207959 |
| rs10757284 | C/G | 22128458 | + | 208312 |
| rs4977761 | C/T | 22128762 | + | 208616 |
| rs35660019 | A/G | 22128865 | + | 208719 |
| rs10811663 | A/G | 22129220 | + | 209074 |
| rs10965254 | A/G | 22129485 | + | 209339 |
| rs10965255 | C/T | 22130019 | + | 209873 |
| rs2065501 | A/C | 22130224 | + | 210078 |
| rs2065503 | A/T | 22130336 | + | 210190 |
| rs7866021 | C/T | 22130339 | + | 210193 |
| rs7866410 | G/T | 22130627 | + | 210481 |
| rs12340450 | A/T | 22130678 | + | 210532 |
| rs7854629 | A/G | 22131034 | + | 210888 |
| rs7026735 | C/T | 22131269 | + | 211123 |
| rs2065504 | G/T | 22131552 | + | 211406 |
| rs2065505 | A/G | 22131790 | + | 211644 |

TABLE 10-continued

| | | | | |
|---|---|---|---|---|
| rs4977577 | C/T | 22131875 | + | 211729 |
| rs6475610 | C/T | 22131894 | + | 211748 |
| rs12376511 | C/T | 22132756 | + | 212610 |
| rs10811664 | A/G | 22132907 | + | 212761 |
| rs7859532 | A/C | 22132956 | + | 212810 |
| rs7862936 | A/G | 22133133 | + | 212987 |
| rs7849199 | A/T | 22133293 | + | 213147 |
| rs7849302 | C/T | 22133377 | + | 213231 |
| rs10757287 | A/T | 22133570 | + | 213424 |
| rs2151285 | A/T | 22134255 | − | 214109 |
| rs2151284 | C/G | 22134276 | − | 214130 |
| rs2151283 | G/T | 22134305 | − | 214159 |
| rs2151282 | A/G | 22134316 | − | 214170 |
| rs7867100 | A/G | 22134460 | + | 214314 |
| rs7853656 | G/T | 22134530 | + | 214384 |
| rs2065500 | A/G | 22135694 | + | 215548 |
| rs7030345 | A/T | 22135739 | + | 215593 |
| rs13298423 | A/C | 22136196 | + | 216050 |
| rs13298664 | C/T | 22136202 | + | 216056 |
| rs10811665 | C/T | 22136604 | + | 216458 |
| rs7022662 | C/G | 22137715 | + | 217569 |
| rs13286296 | A/T | 22137761 | + | 217615 |
| rs13285137 | A/C | 22137863 | + | 217717 |
| rs28752115 | A/G | 22137944 | + | 217798 |
| rs12341394 | C/T | 22138055 | + | 217909 |
| rs28539212 | A/G | 22138269 | + | 218123 |
| rs4614078 | C/G | 22140034 | + | 219888 |
| rs7856219 | C/T | 22140261 | + | 220115 |
| rs7043398 | A/C | 22140707 | + | 220561 |
| rs12337417 | C/T | 22140792 | + | 220646 |
| rs12115577 | A/T | 22140863 | + | 220717 |
| rs10811666 | A/T | 22140867 | + | 220721 |
| rs13293520 | C/T | 22140897 | + | 220751 |
| rs7873930 | C/T | 22141050 | + | 220904 |
| rs6475611 | A/G | 22141139 | + | 220993 |
| rs7047414 | A/C | 22141412 | + | 221266 |
| rs10965256 | A/G | 22141465 | + | 221319 |
| rs10965257 | C/T | 22141528 | + | 221382 |
| rs7849231 | C/T | 22142401 | + | 222255 |
| rs4097833 | C/G | 22142520 | − | 222374 |

TABLE 10-continued

| | | | | |
|---|---|---|---|---|
| rs6475612 | A/G | 22142580 | + | 222434 |
| rs6475613 | G/T | 22142643 | + | 222497 |
| rs7021554 | C/T | 22142884 | + | 222738 |
| rs6475614 | C/T | 22143265 | + | 223119 |
| rs7853123 | A/G | 22143360 | + | 223214 |
| rs10965258 | A/G | 22143663 | + | 223517 |
| rs7853621 | A/T | 22143714 | + | 223568 |
| rs7045424 | C/T | 22144009 | + | 223863 |
| rs6475615 | A/G | 22144408 | + | 224262 |
| rs12001831 | G/T | 22144411 | + | 224265 |
| rs13295528 | A/T | 22144432 | + | 224286 |
| rs7046009 | C/T | 22144458 | + | 224312 |
| rs10965259 | C/T | 22144489 | + | 224343 |
| rs10965260 | A/T | 22144539 | + | 224393 |
| rs10965261 | C/T | 22144585 | + | 224439 |
| rs10965262 | C/T | 22144592 | + | 224446 |
| rs7030057 | C/T | 22144628 | + | 224482 |
| rs10965263 | C/G | 22144648 | + | 224502 |
| rs10965264 | C/G | 22144655 | + | 224509 |
| rs7046289 | C/T | 22144664 | + | 224518 |
| rs7029976 | A/T | 22144682 | + | 224536 |
| rs10965265 | G/T | 22144683 | + | 224537 |
| rs7046298 | C/T | 22144684 | + | 224538 |
| rs7030278 | C/G | 22144691 | + | 224545 |
| rs12343752 | A/G | 22145075 | + | 224929 |
| rs7033903 | A/G | 22145090 | + | 224944 |
| rs944802 | A/G | 22145709 | − | 225563 |
| rs1930590 | C/T | 22146785 | − | 226639 |
| rs7028213 | G/T | 22147360 | + | 227214 |
| rs7856172 | C/T | 22147489 | + | 227343 |
| rs7042842 | A/G | 22147512 | + | 227366 |
| rs7856274 | G/T | 22147532 | + | 227386 |
| rs7869966 | C/G | 22147546 | + | 227400 |
| rs7869852 | A/T | 22147555 | + | 227409 |
| rs7870203 | C/G | 22147567 | + | 227421 |
| rs7870099 | C/T | 22147624 | + | 227478 |
| rs7856433 | C/T | 22147671 | + | 227525 |
| rs7856749 | G/T | 22147902 | + | 227756 |
| rs1333052 | A/C | 22147908 | + | 227762 |
| rs12238587 | A/T | 22148168 | + | 228022 |

TABLE 10-continued

| rs10738611 | A/G | 22148598 | + | 228452 |
| rs10122243 | C/T | 22148924 | + | 228778 |
| rs10757288 | C/T | 22149416 | + | 229270 |
| rs10811667 | A/C | 22149982 | + | 229836 |

B. Microsatellite markers within LD Block on C09 (between 21,920,147 and 22,149,982; NCBI Build 34/35/36) (Forward primers: SEQ ID NOs: 187-192, respectively; Reverse primers: SEQ ID NOs: 193-198, respectively).

| Marker | Start position | End position | strand | Forward primer | Reverse Primer |
|---|---|---|---|---|---|
| DG9S762 | 21977346 | 21977478 | + | TTATTACGAGCCTGGTCTGGA | CTGTTCGTGCAGGATGAATG |
| DG9S761 | 21980412 | 21980677 | + | CCCATCTAAGGGTAGAGAAGC | AAGCAAGATTCCAAACAGTAAACA |
| DG9S760 | 21994905 | 21995264 | + | AGCAATCTAGGCGTTTGCAC | TGCTGGCCTTTGCTCTTACT |
| DG9S746 | 22034929 | 22035109 | + | TGCTAAATGATCTATTTCCACCAT | CCTTTGCATAGGGAGACCAC |
| D9S1814 | 22078225 | 22078501 | + | CTTCGATTGCTGGGATTATG | GGGCCTGTGAACCTACTGAC |
| D9S1870 | 22093010 | 22093220 | − | TGGGTATGGTTTTCTGG | TTGAGGCAGGTCAAATAA |

TABLE 11

Amplimers for surrogate SNPs for rs10116277, rs1333040, and/or rs2383207 in the CEU population, as listed in Table 3.

rs7041637 (SEQ ID NO: 1)
TTTCGCAATGCTTATTTTCAATTTCTTCAGAAATGCCTTAAAGATATTAATGGAGGTAACAACTTAA
TCTCAAATAGTAATCCATAGACAGAATATGTAA[A/C]AGCAATGTTCTCTGATCTGTTCTTTGGCTTCTATT
CCCTAGAGAAATAGTTCTCTAAGACCAAACAGTCTATAGATAGAATTGTAGCAACAGTCAATTAT rs3218020 (SEQ ID NO: 2)
GTGGAGAGAAAATGATTATACTTTGAGCTATATGGCTCCAATAAACAAAGATAGATCCCTCAATTT
AAATTTGATCCTCAGAAAACTGAGGGTCAGAGAA[C/T]CCCTCAGGCATGACGGGATAATGTGACAGTTA
ATTTGGTATGTCAACTTGGCTAGGCGTGTGGTACCCAGTGTTTGAGTCAAACACCAGTCTAAATATTGC rs3217992 (SEQ ID NO: 3)
AGTACTATATTACACTGTTTTTTTTGTTTGTTTTGTTAGTTTTTTTATTTAAAGCAAACCTCAAACA
TTATTGGGTATCAATTACCACCTGGTTGTATT[A/G]AAATAGTAACTTATCAATGCCATGTAAAAATTAATTC
CATTTTCGAAGCCACCTGGCAGACAGGTTTAGCTGTTTCATCAGCAGCCTAATATATACTGTT rs1063192 (SEQ ID NO: 4)
CATTATACTGGGTCATGAAAAATTATCCCTTGAAATAGATATGAAACATGTTACTTCATTTCTGGTT
TAAATAACTTGTGGAATCTTTCCTAATGACAAC[C/T]TGATATTAAGGGAAACTAAAGAAAATGTTATTGTG
GATCCCACAGTACTATATTACACTGTTTTTTTTGTTTGTTTTGTTAGTTTTTTTATTTAAAGCA rs2069418 (SEQ ID NO: 5)
TGATACAAGTTATGAAACTTGTGAAGCCCAAGTACTGCCTGGGGATGAATTTAACTTGTATGACA
GGTGCAGAGCTGTCGCTTTCAGACATCTTAAGAAA[C/G]ACGGAGTTATTTGAATGACTTTCTCTCGGTC
ACAAGGGAGCCACCAACGTCTCCACAGTGAAACCAACTGGCTGGCTGAAGGAACAGAAATCCTCTGCT rs2069416 (SEQ ID NO: 6)
AAATAAAAATAAGATACCTGACAAAGTGGGTTTAAATAGGTAAGAGTGCAAACAAAGATTTACTGT
ACAAATATGATGAAACTGGGATCTCAGATTCTTA[A/C/T]AGTATAATTTTTTTTGTCTTATGTGTGCCAGG
TTGCCACTCTCAATCTCGAACTAGTTTTTTTCTCTTTTAAGGGTTGTATCCATAATGCAAAAATGGA rs573687 (SEQ ID NO: 7)
GTCCAAGACAAATGTGCTATTGTATTACATGTGAAATGTCATCTTTGAAGTCTGGTAAGGGTGTGC
TGTGAGGTGAGCCATCTGGAAAACACAGTGTAGA[C/T]TGAAAATAATTATAAGCCAGTTTATTACTTTTT
TCCAGTTAAGCCTACCATGACAGCTGCTAAAAAAAACACTATGTAGTATAAAGGGTAAAAGACTC rs545226 (SEQ ID NO: 8)
GGGGTGCAGGTTGTTGGTGTGCCACACTTCTTCTTGCGGCAATTGACAGCATAGGGGTGCAGG
AGAGCATAGCGCTTATGGCAGATCATCTTGTTTCAG[C/T]TGTATTTCTAGGTGAGCTGGAAGAGTGAAGG
CTCAATAATGCCACCTCGCAGGTGCAGCACCAGGTGCGGGGTGGGCTGTTTCTGGACGTTGTAGTCTGA rs10811640 (SEQ ID NO: 9)
TCTTAATTTTTACACATTTTACTTTTCATTTCTTTTTAAACTGTTATTAATAATTTATTCATTTGAATA
AGGATTAAAATAAGGCTAGGATATTGAAATT[G/T]GTTGAAATTGCTACAGTCTCTTGTATCTCTCTCTC
TCTTTTTTTTCTTATAAGGGACAGGTTTCATTCACCTTGTCGACCAGGCTGGAGTGCAATACT

TABLE 11-continued

Amplimers for surrogate SNPs for rs10116277, rs1333040, and/or rs2383207 in the CEU population, as listed in Table 3.

rs10811641 (SEQ ID NO: 10)
TGTGATTCTAGCAGCCATGGATAATTATTTCATAGATTATTATTTTCTTGGGGATGGCAAAATGGT
GATATTCTAATTTTACTATTCCTTCATTTACTAG[C/G]TGGAATGTCTTTTTAAATTATTTATTTATTTATTTA
TTATTTGAGACAGAGTCTTGCACTGTCACCCAGGCTGGAGTGCAGTGGTGTGATCATAGCTCAC rs2106120 (SEQ ID NO: 11)
TGCGCGCCTCGGCCTCCCAAAGTGCTGGGATTACAGGCGTGAGCCACTGCGCCTCGCCAACTTC
CTTATTTTAAATGCCATTTCCCACTAAAAATAAAAC[A/C]AGTAATTCTTTGAAAAAAAGTTAATATTATGTA
TAGGACTGGAAGTATATAAGATAAACTGGAATATATTGTCATACCAGAAATCAAAGATTTTGTCAA rs2106119 (SEQ ID NO: 12)
ATTACTGATGTGACAAGGTACACAAGCCAATGTTGACATAATGTTTTCAAAATGGGGTGTCTGCTG
TAACTGAACTAAATATAATAACTTTATTCAAGAA[C/T]GAGTTTCAATGATAGGACAAAACTTGATAAAATG
AATAAATAAATAATTATATGCCAGAGTTCAGTAAACCCTGTGTGTACACCTGAAAAAGCTCAAACT rs643319 (SEQ ID NO: 13)
GAACAGAGCAGAAGAGAGTCTGGATACACAAATTTCACAATTATTGGCTCCCATCAACATATCTAA
CTCAAGCATAAAGTTGTTTCAGCAGTAGTTTAAG[G/T]TTGGTTACTAATGCAACACCTCTTTGCATGCAAT
GGCCCATTAAATTATCTTCAACTTTAAAAGGTTCCTTTGTTTTTAAATGCTTATAATGAACAAATA rs7044859 (SEQ ID NO: 14)
TATGTGATGTAAAGAGCGCCAACATGTTTATATCCTCCTATTTCAATCTACTTTTACTTCATCTACA
TTTTTAGCAATAATGTGAACATGAAATCTTGAA[A/T]AATTAGCTATCTGTAATATATTTACTCATCCACTCA
AAATATTGAGCCCCCCCAATAAATATCATACACTATATTCTAGGTACAGGTGATAAACAATTCA rs10757264 (SEQ ID NO: 15)
CCAGTGAAAGTTAGAGAGAGGGGTCTAGAGCTCAGGGAGGAGTGTGTATCCCTAATTTAGACTA
ATTTGCATTAACAGCTGTAGTAATGCAATTTTCTCT[A/G]TACTGAAATGCAGACATTTGAGTATAGAAAAT
TAGCAGACATTTGAATATAGAAGAAAGATTTACTTTCCTTCAGAAAAAGAATAGTAGAGTATAAGAA rs10965212 (SEQ ID NO: 16)
TCGTGCCACTGCACTCCAGCCTGGGTGAGTTGAGAGTCCGTATCAAAAGCAAACCTACACATTTT
TGTGGCCTGTTTTTAGCTCTATCAAGTCAGTTACA[A/T]TCTTCTGTATTCTAGCTTTTTTATCTGTAAGCTC
CTGCAATGCTTTATTAGAATTTTTAGTTCCTTTGCATTTTGTTACAACATACTCCTATAACTCTGC rs1292137 (SEQ ID NO: 17)
TAAAAGAAAAAATAATCCAAATGTCAGCAACCTCAAAGATTGAAGGTAGATGAGCCCACAAAGAT
AAGAAATAATCAGCACAAGAACACTGAAAACTCAA[A/T]AATCAAGAGTACCTTCTTTCCTCCAAAGGACC
ACATCACCTCTCTGGCAAGCGTTCAGTACCAGGCTGAGGCTGAGATGGCTGAAATGATAGAAGCAGAA rs10811644 (SEQ ID NO: 18)
CAAGACCACTCTGCAGATATCAAGTCTGAAAATTCCCCTAGGGCCAAAGTCTATTATGGGAGCAA
GTTGAGCCTAGAGGGATCGCCATCCCTGTCCATGC[A/T]CTGCTGTAGACACTCCTGCACTAAACCCTCTG
GGCTCCACATCAGCTGGCTTGCTGCTCTACCACTTTGCTTGTCTCTTGGGGGCTCCACCCCAGAGAGA rs7035484 (SEQ ID NO: 19)
GTCTCTTGGGGGCTCCACCCCAGAGAGATGTGGGTCAGCAATCATTCAGTTCAATCAGCCCAGGA
TGGAGAGTCTGTGCTATGGGCCCAAGCCAGGGGCT[C/G]TCTGTCTGGTGACGAGCAGCTGGGGGGTGG
GGTGGGACCTGTGGGAGATGGACTGGCCTCCTCTCCTTGAGTCAACTGCTGCTTATTGGAGGTGTGGATG rs10738604 (SEQ ID NO: 20)
CCATTGCAGAGGTAGTGGCAGAGAGGCTTTCAGTTGTCCGTGGCGGCTCTGTCCAGGGAGTTGC
TGAGTTGCTATTGGCTTGATATCTCTGGTGGGGTGT[A/G]GCTAGAGGTCCAGGCCTGGAGGACCTGCTC
GTTGAAGAGATGTGGGAATGGGCACCCACATAACAGTCTGTTCACTTTTCCATAGGGCTGCTGTAGTATG rs615552 (SEQ ID NO: 21)
GGGGAGCTTAAGCAGGGGTGGAAGGGGAACCCCAGCACAGAACAGCTGCCCGACAAAAATGTG
GCCACACTGCTTTTTTTTTTTTTTTAGCAGGTCCCCA[A/G]TCCCGTTCCTCATCACTGGGTAGAGTCTCCC
ATCTGGGGTCCCCGGCTACCCCAACTGGTGT1TCTCTGACTGAGAGAGGTTTCAGACTTCCATGGGACCT rs543830 (SEQ ID NO: 22)
TGGGCAAAAGTAGCTGCGACTTTGGCAAAGCTGGAGGTTAGACCCCCAAACATACCCCAGGAGG
TTAGACTCCCATACATACCCCAGAAAAGAGGCTGAA[A/T]CCAGCGAGATCAGCAGAGAAGGTCTACAGG
CCCCACTTCCACAGCGCCTCACAGGATAAGACCCACTGGCTTGGAATTCCAGCTAGCCACCAGTAGCAAC rs1591136 (SEQ ID NO: 23)
AAGTGGTAAGTGAATGCGCAACTCTGGGAATCCACACTGCTCTCACAGATCTTTGCAAACCTCAG
ATCAGGAGATCCCCTTGTGAACTCACTCCATTAGG[C/G]CCTTCACACACAGCCACGTGGAGTCTCAGCA
GAGCAGCCACTCAGGCATGCATGGAGACCCAAGAGCTTTAGCTACTCCAGCTTTCTGGGTGTCTGGGCA rs7049105 (SEQ ID NO: 24)
CTTAACAGCAAAGTATCAGATTCATTTATAAAACAATGTGACTGATCTTTATGTATGGTTTGTGAAA
CATTTATGCAGTGTCACTTCAGAAAACTCTGCC[A/G]TTATAGATTTGAATTGATTAAGGATATCCACTCCT
TTCCTTGGCATGATACAAATAAATTACTAAAGTATAATTGTAACAATGATAAATATAAGTGACAA

TABLE 11-continued

Amplimers for surrogate SNPs for rs10116277, rs1333040, and/or rs2383207 in the CEU population, as listed in Table 3.

rs679038 (SEQ ID NO: 25)
CACCCTTTGGGGAAGGGGATCAAAATATAGTGATTTTCTAATTCTAAGATTCGTTCTGTGTATATT
AGCTGCTATTCTTCTAGAAAGAAGACTTTCACCA[C/T]CGTCCCTTGGATTTTTTTTTTAATTTTTGTATGG
TTTAAATTGCATCATCATTCTTTTTGATGTCCAAATTGTCCCAAATTAAGCCAGTTAGAGAAACA rs10965215 (SEQ ID NO: 26)
TAATGGGATTCCTGATGGAATGTTTAGTCTGAATCTAATCACATAGAGACTTGTCTGACAAATCCA
GATTTTTTGGATGTTTTGCAGGACTATTTGCCAC[A/G]ACATTTCAAAGGATTCCAAGAGAGAATATTGGT
GTCCATGCTGTGATGATTCCTCAGCTCCTCTCATCTGATCTCCGTCCTGGCCCCCATGACTTTCTTT rs564398 (SEQ ID NO: 27)
CTCTTCTTTTATCACACAGACCTGAAAGATGATGGTTTCCCAAACAGCACTTACAGCAATAGGTGT
GGGCCTCAGTGGCACATACCACACCCTAACTACC[A/G]CAAAGAAAGTCATGGGGGCCAGGACGGAGAT
CAGATGAGAGGAGCTGAGGAATCATCACAGCATGGACACCAATATTCTCTCTTGGAATCCTTTGAAATG rs10115049 (SEQ ID NO: 28)
CAAATCTTTCCCTAAGGGAGATTTCAGATGAGGCCCCCAGCCTTGGTAGACACCTTGATTGCAGT
CTTGTGAGAGATTGTGAAGCAGAGCTATTCTCAGA[A/G]TTCATGGGTGTTTTAAGCTATGAGGTTTTTTT
GGGGGGAGAATGGTCATTTGTGATTCAGCTATACATAAGTCTACAAAAGTCATTCCAGAAGTGATTC rs634537 (SEQ ID NO: 29)
TGGGGCTCACAACCACATGATTCTACCTCCACTGAATCACTTCTGGAATGACTTTTGTAGACTTAT
GTATAGCTGAATCACAAATGACCATTCTCCCCCC[A/C]AAAAAACCTCATAGCTTAAAACACCCATGAATT
CTGAGAATAGCTCTGCTTCACAATCTCTCACAAGACTGCAATCAAGGTGTCTACCAAGGCTGGGGG rs2157719 (SEQ ID NO: 30)
TTTTTATAGTGTGACTCATTTACATATGCATGTGTATGTTTAGGTGCTATTATTAAATTTTGCTGGC
ATATAGTGAGGAAATTGTGATTCAAATTCGTCC[A/G]TATGTACTCCTCCCCCACCATCTGCTCTGCCCCTC
CATTTACCAGAAGGCTAGCTTTAGCTACTTGTGCATGTAAAACAGAAGCAAGCAACACTGTGAAA rs2151280 (SEQ ID NO: 31)
GAACATAGATACTCCTTCATTCATGTATTGTCTATGGGTGAGTCTTTATTACAACAGCAGAGATGA
GTAGTTGTGACAGAAACTCGATGGCCCTCAAAAG[C/T]GAAACAAGCTACTATCAGGACCTCTATAGAAAA
AGTTTGCCAACCTCTACACTGTAGTATGCCTTAAGGATTTTTAGAAGATTGAGTATGATAAACACTT rs1008878 (SEQ ID NO: 32)
GAAGGGATGATCAGTCCTTCCCTCCTCTATTTTCTTGAGCCCCGTTTTTCACCTTTCTTTTTCTCTC
TCCTTTCTTATCATGAAGAATAAAGACAAATGA[G/T]AACAGATCTACCTTAGGCTGATACAGGGCAGGGA
ATCCATTTAATAATAAAACGTGGGTCAAAATTCACTTTTCTCCTTTTGAATTGAAATTATATTGTG rs1556515 (SEQ ID NO: 33)
ATTTGATGCAACTTACACACTGTTGTTATACCTCTAGAATTAAAATGACAATTTTTTAAATAATTTTG
GGGGGCCTAGATTTGCTATTTAACCTATCAAA[A/G]AATTGTGTCTTACAGTATTATTCAAATGTAGTGTGT
AAAGACTTATACTATTGGTCCTAAGCACTACTGGTTGTTTTAGGCTTTTTCTCTTTCTCTGTAG rs1333037 (SEQ ID NO: 34)
ACATTTATATATAATTAAGATGCTAACACTGACTGACAGAAATGTCAGTAAGATGAAATCAGACTGCA
TGGGAGTTTTATGTTACATTAATTTGTAAATTGT[A/G]TATCTCTGTATTCATGTGAGTGTGGCTATCATGA
TGTTAGACATCCAGCTACAAAGGAGGCATTCGTGCACACACAGTCTCCAATCTTCTGTTTACCT rs1360590 (SEQ ID NO: 35)
TAGACAAAGTTTAATGTTCCCTTTTATATGTTTTCCTGGTAAACAAAAATTGTCTCAGGGTTATTAT
GCATATATGATATTGTCAAGAAACTTTCTGGGT[A/G]CTGTGGGGCAAAGTCTTCTCCATAAATAAGCTAG
GGTTGATTGGAGTTTTCACTTTGAAAAATATCGCACAGGAGGATCTCAACAGCTAGACAATTTCCA rs1412829 (SEQ ID NO: 36)
AAATTAAATGACATACGTAAAGTCCTCAATAAATAATAGCTCTTATTACCATTGCTATGGTTACTAT
CACTATTTCTGTATTTTCTTTTGCCATTCCTCA[C/T]GCTTGAATATGAATCTCATGGGTAGAGTTTCCCAAA
GCATGATATGTGTAGTACTACTAAAGGCAAGATTTTGGGTGCATACAGACAAAAAAATAATTTA rs1360589 (SEQ ID NO: 37)
AAACCAGAGGAGTAAAATTCTACTTTCACCAGTAATTAGCAGTGTGGAGTTGAGTAAATAAACCTC
TCTAAGTCTCAGTTTCTACATCTACTAAATCTAA[A/G]CAAATTCAAACAGTGATTATTTCATTAGATTAGA
TATTTTGATTAGTCTTAAATGTCTAATATATAATAAACACTCAACAGGTAGTAGCTATTCTATGT rs7028570 (SEQ ID NO: 38)
TCATTTCTTCTTTTAAGGTCTTAATTTCTTGTTTTTCGAGTTTCATGGGAGATATCCAGTCACCAAT
CCAATCCATATCGGGGAAAAGTACAACAAATGA[A/G]TGAAATTTGTAACCAACCTTGGATGATGGAATAA
GACATTTGGGAGAACACAGGAGAAGTGGGGAGGTTAAGGAGGGATAGCTCTGTGAAAATTTTGCAT rs944801 (SEQ ID NO: 39)
AACTAATTCTCCAAATTTGCAATTTGGCAGCATCCTACTGGGACTCTAGAAGGCTGATAAATCATG
GAGAGTAGGTATTCATATAGGAACTATGAAAGCT[C/G]TATGTAGTAAACACTACTTAAGAAGGCCTTACA
TTTCATAAAAAGTTGGAGATTTTTGTGGAGACTCATAAAATGCATCCTTTATATCAGTGAAGTTTTT

TABLE 11-continued

Amplimers for surrogate SNPs for rs10116277, rs1333040, and/or
rs2383207 in the CEU population, as listed in Table 3.

rs10965219 (SEQ ID NO: 40)
ACTCGTAGCCAGAGCTACCTTCCAGATGACTTCTTTCTACCACTTTCTTTCTTCCCAGTGTAAGAG
AATGCAAGTATATGCTGATGTTTGGAGCAAGAAC[A/G]TTCAAAAATTTTCTTATTAACATAACTTCTAATG
GAAATACAGTATACTACTATGGTGCATACAAAGAAGAAATAGCAACATATATTTGTTTTAGACCTG rs7030641 (SEQ ID NO: 41)
ATAAGCAGCCTTAAATTAAAAAAAAAAAAGTTAACTCATAACTAACTGTGTGACCTGGGATAAGTT
ACTGACCCTCTTTAGGGCTTAGGGTCCTAATCTG[C/T]AAAACGGAAATTATAATAATAACCTTAGCTAGCA
TTTCTTGTGCACATACTATAAGCTGGTGATAAACAATTTATACACACTATCTCATTTAATCCTCAC rs10120688 (SEQ ID NO: 42)
TCCAATGCAAAAGAATAATAGGAGCAAAAGCACAGTGGTGAGAAATTGGAGGGGAACTGTGAAA
ATTGCCACATAGATTAGAGGCAGGAAAATAAAGGAC[A/G]GCTAAGTTTATATAGTGAACAGTGAGCCGC
ATGGACACAGGTGACTGTTTTCTCCTTTTTGAACCCCTGCTTACTCCAGAGTCACCACCTCTCCTGGCTT rs2184061 (SEQ ID NO: 43)
TATTCTGAGTATTAATTCCTGTTTCCAAATAGATTACTCTTTTAAACATAGCACTACTACTTACCTAA
TGAAATTTAGTTGCTATTAATGGATGAATTTT[G/T]TATCTAACAGGCTTGATTTTGATTATGCATTTTAAAT
GTCAGTCAGACACATATTAATAATGATCCATGTTTGTAGCTAATAGGCCCAATATATACTTTT rs1537378 (SEQ ID NO: 44)
GTAAGGGCTGGGACAAATAAACACAAGTAATTTTCAAATATATTAATAATAATATTCTGAGTATTAA
TTCCTGTTTCCAAATAGATTACTCTTTTAAACA[C/T]AGCACTACTACTTACCTAATGAAATTTAGTTGCTAT
TAATGGATGAATTTTGTATCTAACAGGCTTGATTTTGATTATGCATTTTAAATGTCAGTCAGAC rs8181050 (SEQ ID NO: 45)
TGGTGGTCCTAAAGTGGCATTAAGGAGCCAATAAATTGTCATTCCTACCTTAGCTCTGTGTCAGAT
GAAATACACAGCATAGTGTGGGGAGAAAATGTTG[A/G]GCTTATTGGGGATGGGGTCTTTCACATAAAGG
AAGAAGGTTTCAGAAGGCATAGTGGTATGAAAAGAGGAGAAACCAAAGGGAGGAAGGTCAATAAAGGG rs8181047 (SEQ ID NO: 46)
CAGCATAGTGTGGGGAGAAAATGTTGGGCTTATTGGGGATGGGGTCTTTCACATAAAGGAAGAA
GGTTTCAGAAGGCATAGTGGTATGAAAAGAGGAGAA[A/G]CCAAAGGGAGGAAGGTCAATAAAGGGTTA
AGAACGAGGGGAGGCAAATTGACTTTCTTTCAGCATATGAGGATTATAGGAATGGAAACCTTAATTGGAAT rs10811647 (SEQ ID NO: 47)
GAGGATTTAATGCAATTGTTTGTGGGAAAGCACTTTAACAACTCTAAATTACGATATATATGCTAG
GTTTTATTGTTACCCACACCTTTGATGTATTTCT[C/G]TTTGTACTCTTCACTGTATCTGTAACACATTCCCT
AGGATAATTAGGGCTACCCTTTAACAAAGCCAAGATTCTATTTATAGTGGTAAGCTGGCACCTGG rs1333039 (SEQ ID NO: 48)
CTTCTGCTATTGAACGAACTTTTTGTTAAGGTAGCTCCCAAGCAGGTTCAGTAGCTTTGTTCTATTA
TCACTTTTCTACTGACAGTGATTTTTTTCCTTT[C/G]AAGGCCTGGGACATGGAGACTGCTTTTCTGCAGAA
ACCACATCCCTTGGAGTAATGAGCTACACCTACCTCAATTATTCAGTGCAGTACAACACTCCAGG rs10965224 (SEQ ID NO: 49)
ACATTGTGCACATGTACCCTAGAACTTAAAGTATAATAATAAACAAAAAAAACCACTGCACAATCT
CTAGTATTCAGATGGAGACTAAGCATGATTTTTC[A/T]TATAAAAGAGCAGATCAGAATGTTGTATCTTTTA
TTCAGAAGACTGGAGTTAATCACTGTTATCTTTAGTACTTAGTGCTGCCAAGGCTGTGTGTTCACA rs10811650 (SEQ ID NO: 50)
ACAGAGTGCTTATTTAAAGAAAAATAAAAAGAACACACACACACACGCACGCACACACACACGCA
CGCACACACACACATGTAGCTACATGTCTAGGA[A/G]GGATGTGGAGAGCTGAAATATGAAGGCAAAA
TAAAACATCTTTTTCAAAGTATACAGCCTACAGTGGTTAGCACAGAGCTGGCCACATAGCAGGGGTTTC rs10811651 (SEQ ID NO: 51)
CAATAATGTAGAAGCAAAGAGCCTAAAGTGTTTTCATAAATCTTAAGTGGTAGCTTTATGTTCCAG
TTCAGCAAAACACAAATTTGAAGGCAATCTGTAC[A/G]TTAGGGTTCAGGTGAAGAAGGCAAAGGAATCA
ATGAAATTGTAAAAGCTTTCCAAATTTGCCTTTTCTCTTAAGATTGTCTTTCTCTCATTCTCTTCTCC rs4977756 (SEQ ID NO: 52)
TTTCTGTAGCAGAAGTGTAAGGGTGTTACTCGTAGGAGGCCTCTATTGAACTCTTTTCCAGTGAC
GTAGTGTGTGGTCTTTAAGTGGCTTTGCAATGATA[A/G]TAAGATCAGCATTGCATTACTGAATGAGCTCC
TTTAGTAAACGTGGATATGTGCTTTCTGAATCTATTTGTTTGTTTTTCCCAAGTCATAAACAGTGAAT rs10757269 (SEQ ID NO: 53)
CCATTTAGAGTACTTGCCTCTGAGGGAAATAAAAATTTGCTAGCAATTTTCTCTAAATGACATTATC
ATAGGCACTTAATTCCTTGATAGGTCTTTTAG[A/G]TAATTTTTTTATAATGAAGCAATTAATTTGATTCAC
GAAAGTAAGTTTCTAGTTTATATAAAGACCAGATCTGGCCTATTTCTTAGCTTGTCTACATTTG rs9632884 (SEQ ID NO: 54)
TGCTAGCAATTTTCTCTAAATGACATTATCATAGGCACTTAATTCCTTGATAGGTCTTTTAGATAA
TTTTTTTATAATGAAGCAATTAATTTGATTCAC[C/G]AAAGTAAGTTTCTAGTTTATATAAAGACCAGATCTG
GCCTATTTCTTAGCTTGTCTACATTTGAGTAGTTCCATTGCTGGAAAATGACCCTGGAGCTTTT

TABLE 11-continued

Amplimers for surrogate SNPs for rs10116277, rs1333040, and/or rs2383207 in the CEU population, as listed in Table 3.

rs1412832 (SEQ ID NO: 55)
AAGTTGCTCTCAACATACTTAAAGTTTTCCAATAACTGAATTAAATATCAGTTTATCAGTTTAATATA
AACAATTAGGGTAAATGAAAATAAAATTTCAG[C/T]TCTTTGGTTCCATTAGCCATGGTTCAGGAGCAGAAT
AGTCACCTGAGGCTAGTGACAACGCTTTTGGATCACAGGAAAGAAGAAAAAAAATCAAAATAAT rs10116277 (SEQ ID NO: 56)
TTATAACTAATGAGGCAATGTGTCTTGAGTATTTTGAATTAACTCTCTAGAATCGATTCTTGGGGA
GGTTATTTACTTTGAAGTGATGGACAGAGTGTAG[G/T]AGATTTATGAGTGAACTCTTGTCTGATTTGGAA
ATATAGAGTTGTTTAGGCTAGGTATTACCAACCCAAAGTTGACACTTGAGTCACCTAAGTTCTTCTC rs10965227 (SEQ ID NO: 57)
TATTAGTTGTGTAATCTTGAAAAAATCTCTGACACTTTTCCCTCTGACTCAGTTTCCCCATCTGGCA
CCCAATCTTTTACAGTGTTATGAAAAATAGGGA[A/G]AATGTAGAAAGGAAGAACATGGCACCCAATCCTT
AATGGACACTCAGTGAAAGCTGGCTATCATCATCATTTTTGGGGTTGTTGTGTTCTACAAATGTAT rs6475606 (SEQ ID NO: 58)
TCCCCATCTGGCACCCAATCTTTTACAGTGTTATGAAAAATAGGGAAAATGTAGAAAGGAAGAAC
ATGGCACCCAATCCTTAATGGACACTCAGTGAAAG[C/T]TGGCTATCATCATCATTTTTGGGGTTGTTGTG
TTCTACAAATGTATTTTCCCAGGAGTTTTTTTTACTCTGTCTCCTCTTTCCTTCATATACCCCCAGCC rs1333040 (SEQ ID NO: 59)
TGGGAAGGATGAATTAATGGGATGGAGTGCAGGGGATGCAGAGTGCCCACTTATGGAATGATTT
CATTCAAGAGAGACAGGAGGGTCAGAGGTAAGAATG[C/T]TACCGCTGGGACAGAGAGGAAGGTACAGA
TATGAGATATGGTAAGAAGGTATACTACAACAGTGGCTCCCAAATCTCAATGAGTAGCCAGTTCTCATGGA rs1537370 (SEQ ID NO: 60)
TTTGAGCCCAAGTCTCTTTCTGACTCTAGGCTTAGAGCTTTAGGGCTATTTCACAAAAGGGCTGTT
CCTAGGTCAGGCATGACAACTTCTATATTACCTT[C/T]GTAAAAGAAGCAATATAATCTACCACTATTAAAT
TTTGCAGGTTAATTTTATATTATGTTTAAATACAGAAAACTTTATTTAAAACTCAGTTGAATTTCT rs7857345 (SEQ ID NO: 61)
GAAACTGGATCCCTGATGACATTGAACCATTGACTGAATCTACCCTGGAACCATCAGGAAATAAT
CCTTAGTTTTTTAAAGATGCTTTTAGTTGTGTTTT[C/T]TATTACAAGTACCTGAAAGCATCCTAACTAATCA
ATGCTAAATGCATCTCTCACAGTTTATGCTTATTTTTCAGAAATGCCTAGTGGAAATTTCTATTGC rs10738607 (SEQ ID NO: 62)
TCCTTCCACTGACTGAGACTATTTCCTTGCCACAATCAGAAGAACTAAAAGAAAGGAGGATATCTG
TTAATATATGAATTTATCTAAATGTCATGCAGTG[A/G]CTTCTAAAATCATCTGGTGTGCTCTGTTTCCCCTT
GGAGGTGACTTAGGCCTGGCATCCCAAACAATACATACTGGAGTGAAGCTCCAGGAAACCCTGAG rs10757272 (SEQ ID NO: 63)
ATACATACTGGAGTGAAGCTCCAGGAAACCCTGAGGAGAAGAGAAGGGCTTTAAAGAGCAATCAG
CCTTCGATTGCTGGGATTATGAAAGGTCGTAAGAAG[C/T]GAATGTTGCAATGTTTTATTATACTTGATATT
GAAGCAAGGACAAGTAATAATTTATTATTCTCTCCATGTCAGTGGTATTTACCTTTTTGGAATCATGT rs4977574 (SEQ ID NO: 64)
ATAAAAATAAAATAAAATAAAAAATGAAAAACAAAGTCCACTTGTAACCACATGTCAGTAGCATGT
TTGCTTTCAGGGTACATCAAATGCATTCTATAGC[A/G]CAGGATGTTCCAGTCACTCTAACAAAAGATGTC
CTGTTTGGAACACCAACTCTGTATCAGTTACTTCAGACACTTTCTCTCATTGAGTCCCTTCAGCAAG rs2891168 (SEQ ID NO: 65)
AACCACATGTCAGTAGCATGTTTGCTTTCAGGGTACATCAAATGCATTCTATAGCACAGGATGTTC
CAGTCACTCTAACAAAAGATGTCCTGTTTGGAAC[A/G]CCAACTCTGTATCAGTTACTTCAGACACTTTCTC
TCATTGAGTCCCTTCAGCAAGCCCTTTTAGGTTTATGTTCTTAGATGAGGAAACCAAGTCTTAGAA rs1537371 (SEQ ID NO: 66)
ATATTTTCTTGTTTTTAGATGCACATATACGTACTTTTTTAGCTGGTCATTTCTTTCTGAAATTGGAA
TGAATCTTACAATCAATGGCATGTTATAATTT[A/C]ATTGGCAGCATTATTTGTCTCTTAAGGGCCCCCAAA
TAATAGTGTGTCACATAACTGATAGCATCTCAAATTAGATGAAATACAGTAGTCCAGGCAAGAA rs1556516 (SEQ ID NO: 67)
GTTATGGGATAAAGGCGATAGTATTTTATTGACTATATTTTATTCTTTTAATTATTCCTCTAATTTCT
TAAAACAACTTTATTGAGGTATAACTTCCACG[C/G]TATAATTTCACCCATTTTAAGTGCATGAATTCAGTG
ATTTTTAGTAGAGTCATTGAGTAGTGTAACCATTCCTACAATGGTTATAGCACATTTTTATCAT rs6475608 (SEQ ID NO: 68)
TGTTTTCTTTTATTTTTCCTTCTAAAATAATCACACGTTTCATTGCAACCCTAACCCTCTTCAACACA
CACACACACACACACACACACACACACACACA[C/T]GGCTTCTAGATTCTACATGTACAAGAGTGCAAATC
AAACTACCATAGAAAAACTAAGAAGAGAGGCCTAGAAGCAAGAGGCTGATACACTATCTCAGGCT rs7859727 (SEQ ID NO: 69)
AACCAACACTTAAAATGCAGGGAATTTAAGATAAAAAATTGATAAAAATGGGAAGATTTGGCCGTA
TTGGGCTCATGGTAACTGAGATGCATCTGAATGA[C/T]AGGCATTCCTTTGAATTGCACATTTGCTCTTGTT
TTTACTATAGGCCACTCTCACTTTCTGTTTTTTTCCCCGGCTTTGAAACGATCAGTTTTAGTACTG

TABLE 11-continued

Amplimers for surrogate SNPs for rs10116277, rs1333040, and/or rs2383207 in the CEU population, as listed in Table 3.

rs1537373 (SEQ ID NO: 70)
ATGACTGGGCAATTATGTCATTATCACCACTGATATATAGCTGGAAGAGTTTAGTGTTGCCCTGCT
AAGATCTGGATTTTCTTTTCTGGAGCTTGGCTAT[G/T]GGGGCATTGAGAAGTCCAGCCAGGAGGTTGGT
CAGAGGCTAACCCAAAAAGCTTTGCTTAACTCTGGGCTACAGCTGGGGGTTGCCAGAGAGAAGTGCCT rs1333042 (SEQ ID NO: 71)
AATTTATTTGAGTAGACAGCCAACCCCCTGTATTGTACTCCTTTAAAAAATATTTTAGGCTTTTTAA
ATGCTGAGGCAAGGGGACATACCAAACACTAAC[A/G]GGCACATTGGGGTTTTCTGGCTATTGAAATAAA
AATGTCCTTACATAACACTGATGTACTGGAATAGCACTGCGTTCCAGTGACGGTTATTGCAACTCAG rs7859362 (SEQ ID NO: 72)
GGAGCATGATGTGCTTTGATTTCAACTATGGGCTTTATTACTTACTAACTGGGTTACTTTGGTTAA
GTTGTTTGACTCTTGTTTTTTGAGATGGAGTCAG[C/T]CTGGGAGACTCCAGCTCTGTCGCCCAGGCCGGA
GTGCAATGGCACGATCTTGGCTCACTGCAACCTCTGCCTCCCGGATACAAGCGATTCTCATGCCTTA rs1333043 (SEQ ID NO: 73)
CTGGCACAAAGTAGGCACTTCATATATAAAAGCTGTGATTATTGATGAACCAGTAGTGAGGTACAT
AACTGGGGAAGGAGAAGGGGCCAGTTTGTGGGAA[A/T]GCTTTTTTAGTTATTAATAGTAAGGTGGTAAA
ATAATAATAGTAATAATAACCAAAAGTTACTGAAAACTAAATACAGTGCTAAACTCTTTAAAAGGAGT rs1412834 (SEQ ID NO: 74)
CTTCTTTAGCTGTAAATAAGTAATTGTATGAGGTGATGGTTAAGGTGATTTACTAATTTTACAATTC
TATTATTTTATGAATAGACCCTAGTTAGGATAG[C/T]TTGAAATAGATACTTAATCCACTATTATTCTCTCTT
CTAAGATATAGTTACTAGTTGATCATACTTTTCCTTAAAGGCTGAACTGAATTCTCTGATATCA rs7341786 (SEQ ID NO: 75)
GAAACATACTGGTTAATGGAATTCCAGAAAGGACTGAACAATCAAACCATTTTGAAGGACAGCAT
AGAGCTGGACTCTAGAACAGCCAAAACAAGGGGTT[A/C]AACCACTGCGAGGGATCTCTCTCCAACTCTT
GCTCAGGCTTTTCTCCCTGGCTTGACTTTCTTCTCTTTCACTGTAGATTGGCTTCTCTCACATGGCAAG rs10511701 (SEQ ID NO: 76)
TATTATGTGTGGCTGACTATATAAAAACATGGATATTTTCTTGGAATCACTTGGTTTGACTGGGAG
AAGACCATTCTCAAACAAAGGAAGTGCAATTTA[C/T]AGAAGGTAGTAGAATAGGCAGATAAAACAATAA
TTCTTCACTATATTGCTCAAATAATCCCCATGACATTTTTAGTATATTATAAAGAGAGTTCTAAAGT rs10733376 (SEQ ID NO: 77)
GAGAAAGATGTTAAGATGAAATTAGATGTGCAAGAGATTCGCCGAGGTAAACCTTGTGGGAGAAA
ATGGAGAGGTACATAGAGGAGCCTGGGCAGACTGT[C/G]TGGCTACTATGTAAGACTCATCCCCATGAAG
GAGAAAGGAGAGGAAGGCAAAGAAGAAAAACCTTAAGATTTCAATTCTAAGAACGTTTTGACAAAGCTG rs10738609 (SEQ ID NO: 78)
TGTGCAAGAGATTCGCCGAGGTAAACCTTGTGGGAGAAAATGGAGAGGTACATAGAGGAGCCTG
GGCAGACTGTGTGGCTACTATGTAAGACTCATCCCC[A/G]TGAAGGAGAAAGGAGAGGAAGGCAAAGAA
GAAAAACCTTAAGATTTCAATTCTAAGAACGTTTTGACAAAGCTGATTAGGAGTATTTAAGGCAAAGCTGC rs2383206 (SEQ ID NO: 79)
AAATACTTTAACTCATGGCCCGATGATTTTCAGTTAACCAAATTCTCCCTTACTATCCTGGTTGCCC
CTTCTGTCTTTTCCTTAGAAATGTTATTGTAGT[A/G]TTTGCAAGATGGCCTGAATCCTGAACCCCCCATCT
TCAATGAGCACCAAATGGTAATTATAGATTCCCAGCTGTAGAGCTATGTCAGACAAAGGAAACTT rs944797 (SEQ ID NO: 80)
CTCTTCCTTGGTGGCTTAAAGTTAGGCTGAAGAAGATTTACATTATGTTGTGCATGACCTCTTTAG
TTTGGTTCTACTTATACTTTCAAGGAGGGAAGAC[C/T]GGGGAAGGTGTCCCTTAGTGAGCATATTTTGTA
CAAATGAAAACAGGGTACTAACACTTATGCCAGGACGCATGCATAAACTAGGATGGTTCTGAGAAAA rs1004638 (SEQ ID NO: 81)
AGAACCTTAATGGGAGCACAGGTCCCACCCACCCCTTGCTACCCCATGTACTTGTTCCCATCTTCA
CCCAAGAGAGGAAACACTCTGGAACTAGGGCAGC[A/T]TAAGTGAAGCAGAGTGAAAAGGAATGTGAAG
TTTTGAGAAGAAAGAAAAGGCTAAAGTGTCTATCTTTCCACATTGCTTTTTTCAGGTTTCTCTTCGGAA rs2383207 (SEQ ID NO: 82)
GATGAAAAATTCATATTCATCTGAATTTTATAAGTGAATCATGAGAACTCAAAGATACTTAGCCCTT
GGGACCATTTTTTACTCCTGTTCGGATCCCTTC[A/G]GCTAAGCATGATTATTTACTATTTTCAGCTATTAG
TTATGTCTTGTTGAAAAAGTATGAAAAGAGCTGCCCAATAAATTAGAGTGTATGCTCAACATTCT rs1537374 (SEQ ID NO: 83)
TTCGGATCCCTTCAGCTAAGCATGATTATTTACTATTTTCAGCTATTAGTTATGTCTTGTTGAAAAA
GTATGAAAAGAGCTGCCCAATAAATTAGAGTGT[A/G]TGCTCAACATTCTCTTAGCTTCTTTATCTCTTTCC
AAAATTGGATCAAATGACATTGGACATGATCAACTTCTTACTGTTTTGACAAACATCTGAGGATA rs1537375 (SEQ ID NO: 84)
TTATTTACTATTTTCAGCTATTAGTTATGTCTTGTTGAAAAAGTATGAAAAGAGCTGCCCAATAAAT
TAGAGTGTATGCTCAACATTCTCTTAGCTTCTT[C/T]ATCTCTTTCCAAAATTGGATCAAATGACATTGGAC
ATGATCAACTTCTTACTGTTTTGACAAACATCTGAGGATACTTTTATAATTGATAATTTGGACTA

TABLE 11-continued

Amplimers for surrogate SNPs for rs10116277, rs1333040, and/or
rs2383207 in the CEU population, as listed in Table 3.

rs1333045 (SEQ ID NO: 85)
TTTTGTGCCTCAGTTTCCTCATTCAATATGGGTGTAATAACTGTGCCTGTCTTGTAGGATTATTGTG
AGGCCCAAGTGCAATAATATATAGTACACTGTG[C/T]CTGGCATCTAGTAAGCATTCATTAAGATGACATG
AAGATAACACAGATATATCTTAACATGTAATTATGATTTTGCTTATTCAAGGCCAAGCATTCCAAT rs10738610 (SEQ ID NO: 86)
GAAGAAGAAGACAGTCAGAGAGAAGTGAGGGCTTACTTTTCATGTTTAAAGTCTGTTATGTGGTA
AAGGGATTAGATTTATCTGTGTTGTTCCAGGGGAC[A/C]GAAATAGGACAAATGGATGCAAATAGAGTGA
GGAAGATTTAAAACAAATGGAGAAGACATTCTAAAATCAACTACAATGAGCGTAAACAATGACAACGGA rs1333046 (SEQ ID NO: 87)
TCATATGCATAGACAAATACACCAAACTGATGAATATTTGCCTTGTATAATCTTTTTGTAGTTTTTTT
ATGAACATATATTACTCAAACAATTTAGAACA[A/T]TTGGCAATATATATATATTTCATTTATAAAAGGTTAG
GAAGATTAATTACACTTTCTGAGGTCGCAACTAAAAGCCAAGATTTTAATCCATTTCTATTTG rs10757278 (SEQ ID NO: 88)
AGTGTCACTGGAAAGTGACAAAGAGGACAGTTAAGTTAGTTGGAACTGAACTGAGGCCAGACAG
GGCTGTGGGACAAGTCAGGGTGTGGTCATTCCGGTA[A/G]GCAGCGATGCAGAATCAAGACAGAGTAGT
TTCTCCTTCTCTCTCTCTTTAATTGTAACGCCTTTTATAACAAACAAATATTATGCTTATTTCTGTCTT rs1333047 (SEQ ID NO: 89)
CAGTTAAGTTAGTTGGAACTGAACTGAGGCCAGACAGGGCTGTGGGACAAGTCAGGGTGTGGTC
ATTCCGGTAAGCAGCGATGCAGAATCAAGACAGAGT[A/T]GTTTCTCCTTCTCTCTCTCTTTAATTGTAA
CGCCTTTTATAACAAACAAATATTATGCTTATTCTGTCTTTAAATTTTTTGTAGTAATTTCTCATCA rs4977575 (SEQ ID NO: 90)
TTTTCTAGTTGAGCTATCATTCATATTTATTATGTGGAACTAGAGGGTAGTCCTGGCTACTTGGGAA
CAGCGTGGAGTCTAGCCATGTCAGGGCCAGAAGT[C/G]GTCTCAGCTAAGTTAGAATGTGATACCATTGT
TTACACAAGTGTGGCCTGCCTTCAAGATAGGGTGAGGTGTTTTATGACCACAGGCTTTATGAGTTATA rs1333048 (SEQ ID NO: 91)
TGACTCTGAAGATCATACCCGAAGTAGAGCTGCAAAGATATTTGGAATATTGGTAATATCCAATAA
AGAATGACCTTCATGCTATTTTGAGGAGATGTTT[A/C]AATGTCGAATTATTGAAATATTTATAAAATACAA
ATAAACTAACTCTGCTTCATATTCCAACTTGTGTATGACACTTCTTAGGCTATCATTTCATTCCAA rs1333049 (SEQ ID NO: 92)
TTCCAACTTGTGTATGACACTTCTTAGGCTATCATTTCATTCCAAATTTATGGTCACTACCCTACTG
TCATTCCTCATACTAACCATATGATCAACAGTT[C/G]AAAAGCAGCCACTCGCAGAGGTAAGCAAGATATA
TGGTAAATACTGTGTTGACAAAAGTATGCAGAAGCAGTCACATTTATACAGTAGTGAAGGAAATGT rs1333050 (SEQ ID NO: 93)
AATTACAGTATATCTAAAAAAAGAATAATATATAACAACTGAAAAAATAAAATAGTTGATATAAGCA
GATATTCCAAGATCTGCCAGACATATTGTTAAA[C/T]GAAAAATCTAGATACAAAATTGTTTATAGTTCTCTT
TCATACTATAGCCAAAGAAAATTCAGAAAAAACTACTTACAGTTGATCCTTGAATAATGCAGCA

TABLE 12

Association results for the MI phenotype for rs2383207 (G) and rs10757278 (G), in
9p21 in Iceland and the US. Results are shown for the initial Icelandic discovery MI
case-control group (Iceland A), an independent Icelandic replication group (Iceland B)
and for the three US replication groups of Caucasian origin. Also included are the
results for the MI case-control groups combined.

| Study population (n/m)[a] | Frequency | | | |
|---|---|---|---|---|
| Variant (allele) | Controls | Cases | OR (95% CI) | P |
| Iceland A (1607/6728) | | | | |
| rs2383207 (G) | 0.455 | 0.506 | 1.22 (1.13-1.33) | $1.4 \times 10^{-6}$ |
| rs10757278 (G) | 0.434 | 0.489 | 1.25 (1.15-1.36) | $1.5 \times 10^{-7}$ |
| Iceland B (665/3533) | | | | |
| rs2383207 (G) | 0.462 | 0.525 | 1.29 (1.15-1.45) | 0.000026 |
| rs10757278 (G) | 0.436 | 0.503 | 1.31 (1.16-1.47) | 0.000014 |
| Atlanta (596/1284) | | | | |
| rs2383207 (G) | 0.541 | 0.593 | 1.23 (1.07-1.42) | 0.0030 |
| rs10757278 (G) | 0.484 | 0.551 | 1.31 (1.14-1.50) | 0.00015 |

TABLE 12-continued

Association results for the MI phenotype for rs2383207 (G) and rs10757278 (G), in 9p21 in Iceland and the US. Results are shown for the initial Icelandic discovery MI case-control group (Iceland A), an independent Icelandic replication group (Iceland B) and for the three US replication groups of Caucasian origin. Also included are the results for the MI case-control groups combined.

| Study population (n/m)[a] Variant (allele) | Frequency Controls | Cases | OR (95% CI) | P |
|---|---|---|---|---|
| Philadelphia (582/504) | | | | |
| rs2383207 (G) | 0.524 | 0.602 | 1.37 (1.16-1.63) | 0.00026 |
| rs10757278 (G) | 0.470 | 0.550 | 1.38 (1.17-1.64) | 0.00019 |
| Durham (1137/718) | | | | |
| rs2383207 (G) | 0.513 | 0.559 | 1.20 (1.05-1.37) | 0.0060 |
| rs10757278 (G) | 0.460 | 0.521 | 1.28 (1.12-1.46) | 0.00027 |
| Combined | | | | |
| Iceland[b] (2274/10260) | | | | |
| rs2383207 (G) | 0.458 | 0.511 | 1.24 (1.16-1.33) | $3.3 \times 10^{-10}$ |
| rs10757278 (G) | 0.435 | 0.493 | 1.26 (1.18-1.35) | $5.3 \times 10^{-12}$ |
| US groups[c] (2315/2508) | | | | |
| rs2383207 (G) | 0.526 | 0.585 | 1.25 (1.15-1.36) | $1.1 \times 10^{-7}$ |
| rs10757278 (G) | 0.471 | 0.541 | 1.31 (1.21-1.43) | $1.5 \times 10^{-10}$ |
| Replication groups[d] (2980/6041) | | | | |
| rs2383207 (G) | 0.494 | 0.555 | 1.27 (1.18-1.36) | $1.4 \times 10^{-11}$ |
| rs10757278 (G) | 0.454 | 0.522 | 1.31 (1.22-1.40) | $1.0 \times 10^{-14}$ |
| All groups[b,d] (4589/12768) | | | | |
| rs2383207 (G) | 0.492 | 0.548 | 1.25 (1.18-1.31) | $2.0 \times 10^{-16}$ |
| rs10757278 (G) | 0.453 | 0.517 | 1.28 (1.22-1.35) | $1.2 \times 10^{-20}$ |

[a]Number of MI cases (n) and controls (m).
[b]When combining the Icelandic cohorts they are analysed together and the results adjusted for relatedness in the combined group.
[c]For the combined groups OR and P value are calculated using a Mantel-Haenszel model and the frequency in cases and controls is a simple average over the frequency in the individual groups.
[d]When combining Icelandic and US groups, the frequency in cases and controls is the average over the two populations.

TABLE 13

Genotype specific odds ratio for the risk allele of rs10757278. Shown is the risk for heterozygous carriers (0X) and homozygous carriers (XX) compared to the risk for non-carriers (00), together with 95% confidence intervals (CI), and the population attributable risk (PAR). The lower part of the table includes the corresponding values when the analysis is restricted to early-onset MI cases.

| Study population (n/m)[a] Variant (allele) | 00 | 0X (95% CI) | XX (95% CI) | PAR[b] |
|---|---|---|---|---|
| Iceland[c] (2272/10261) | | | | |
| rs10757278 (G) | 1 | 1.25 (1.12-1.39) | 1.58 (1.38-1.81) | 0.19 |
| US groups (2315/2508) | | | | |
| rs10757278 (G) | 1 | 1.28 (1.14-1.45) | 1.72 (1.45-2.03) | 0.23 |
| All groups (4587/12769) | | | | |
| rs10757278 (G) | 1 | 1.26 (1.16-1.36) | 1.64 (1.47-1.82) | 0.21 |
| Early onset MI (<50 for males; <60 for females) | | | | |
| Iceland[c] (621/10261) | | | | |
| rs10757278 (G) | 1 | 1.38 (1.13-1.69) | 1.94 (1.53-2.46) | 0.27 |
| US groups (1080/2508) | | | | |
| rs10757278 (G) | 1 | 1.56 (1.32-1.85) | 2.08 (1.69-2.58) | 0.34 |
| All groups (1701/12769) | | | | |
| rs10757278 (G) | 1 | 1.49 (1.31-1.69) | 2.02 (1.72-2.36) | 0.31 |

[a]Number of MI cases (n) and control (m).
[b]Genotype specific odds ratio for heterozygous (0X) and homozygous carrier (XX) compared to non-carriers (00).
[c]Population attributable risk (PAR).
[d]For the Icelandic groups, P values and OR were adjusted for relatedness using simulations.

TABLE 14

Association of the G allele of rs10757278 to coronary artery disease (CAD). The association results are shown for CAD, both including and excluding known MI cases. Results are shown for the Icelandic case-control group (excluding the discovery group), for two of the US groups, and for the groups combined.

| Study population (n1/n2/m)[a]<br>Variant (allele) | Cont. frq | All CAD cases | | | Excluding MI cases | | |
|---|---|---|---|---|---|---|---|
| | | Case. frq | OR (95% CI) | P | Case. frq | OR (95% CI) | P |
| Iceland[b] (1563/773/3533) | | | | | | | |
| rs10757278 (G) | 0.439 | 0.496 | 1.26 (1.15-1.37) | $1.9 \times 10^{-7}$ | 0.490 | 1.22 (1.09-1.37) | 0.00050 |
| Atlanta (724/128/1284) | | | | | | | |
| rs10757278 (G) | 0.484 | 0.552 | 1.31 (1.15-1.50) | 0.000036 | 0.557 | 1.34 (1.04-1.73) | 0.026 |
| Philadelphia (709/126/504) | | | | | | | |
| rs10757278 (G) | 0.470 | 0.547 | 1.36 (1.16-1.60) | 0.00019 | 0.528 | 1.26 (0.96-1.66) | 0.10 |
| Combined US groups[c] (1433/254/1788) | | | | | | | |
| rs10757278 (G) | 0.477 | 0.550 | 1.33 (1.20-1.47) | $2.7 \times 10^{-8}$ | 0.542 | 1.30 (1.08-1.57) | 0.0059 |
| All groups[c] (2996/1027/5321) | | | | | | | |
| rs10757278 (G) | 0.458 | 0.523 | 1.29 (1.21-1.38) | $3.6 \times 10^{-14}$ | 0.525 | 1.24 (1.13-1.37) | 0.000011 |

[a]Number of all cases (n$_1$), cases excluding MI patients (n$_2$), and controls (m).
[b]Individuals used in the initial discovery group have been excluded both from cases and controls.
[c]For the combined groups, the allelic frequency in cases and controls is a simple average over the individual groups or, when combining Icelandic and US groups, the average over the two populations.

TABLE 15

Association to MI on 9p21
Shown are all SNPs in the region 21.92 to 22.12 (NCBI build 34) on 9p21 that show nominally significant association to MI in the genome-wide association study. Results are shown for 1607 MI cases and 6728 controls from the Icelandic discovery cohort. Also included are the corresponding results if the association test is done adjusting for the observed association to the three SNPs, rs1333040, rs10116277 and rs2383207 (indicated in bold).

| SNP | Allele | Position | Frequency | | OR | P[a] | OR[b] | P[b] |
|---|---|---|---|---|---|---|---|---|
| | | | Controls | MI cases | | | | |
| rs10757260 | A | 21943137 | 0.606 | 0.627 | 1.09 | 0.041 | 1.10 | 0.037 |
| rs7041637 | A | 21951866 | 0.233 | 0.253 | 1.12 | 0.021 | 0.99 | 0.91 |
| rs2811712 | A | 21988035 | 0.875 | 0.893 | 1.19 | 0.0076 | 1.16 | 0.022 |
| rs3218018 | A | 21988139 | 0.879 | 0.896 | 1.20 | 0.0074 | 1.17 | 0.021 |
| rs3217992 | A | 21993223 | 0.344 | 0.378 | 1.16 | 0.00055 | 0.98 | 0.75 |
| rs2069426 | C | 21996273 | 0.881 | 0.897 | 1.18 | 0.0146 | 1.15 | 0.038 |
| rs2069422 | A | 21998026 | 0.875 | 0.894 | 1.20 | 0.0059 | 1.17 | 0.018 |
| rs2151280 | T | 22024719 | 0.464 | 0.486 | 1.09 | 0.038 | 0.96 | 0.43 |
| rs1333034 | A | 22034122 | 0.875 | 0.893 | 1.19 | 0.0073 | 1.17 | 0.021 |
| rs1011970 | G | 22052134 | 0.772 | 0.806 | 1.22 | $9.2 \times 10^{-5}$ | 1.14 | 0.020 |
| rs10116277 | T | 22071397 | 0.418 | 0.468 | 1.22 | $1.9 \times 10^{-6}$ | na | na |
| rs1333040 | T | 22073404 | 0.490 | 0.542 | 1.23 | $6.1 \times 10^{-7}$ | na | na |
| rs2383207 | G | 22105959 | 0.455 | 0.506 | 1.22 | $1.4 \times 10^{-6}$ | na | na |
| rs1333050 | T | 22115913 | 0.671 | 0.693 | 1.11 | 0.020 | 0.97 | 0.61 |

[a]P value adjusted using genomic controls.
[b]P value and OR adjusted for the observed association to rs1333040, rs2383207 and rs10116277.

TABLE 16

Association to MI. Shown is the association for the risk alleles of the three SNPs from the genome-wide study, rs1333040, rs2383207 and rs10116277, and the most significant refinement SNP, rs10757278, to MI in the combined Icelandic case-control group and in the three US case-controls groups.

| Study population (n/m)[a]<br>Variant (allele) | Controls | | Cases | | OR (95% CI) | P |
|---|---|---|---|---|---|---|
| | AA/Aa/aa | Frq. | AA/Aa/aa | Frq | | |
| Iceland A (1607/6728) | | | | | | |
| rs1333040 (T) | 1770/3315/1636 | 0.490 | 342/783/478 | 0.542 | 1.23 (1.14-1.34) | $6.1 \times 10^{-7}$ |
| rs2383207 (G) | 2022/3280/1418 | 0.455 | 389/811/408 | 0.506 | 1.22 (1.13-1.33) | $1.4 \times 10^{-6}$ |

TABLE 16-continued

Association to MI. Shown is the association for the risk alleles of the three SNPs from the genome-wide study, rs1333040, rs2383207 and rs10116277, and the most significant refinement SNP, rs10757278, to MI in the combined Icelandic case-control group and in the three US case-controls groups.

| Study population (n/m)[a] | Controls | | Cases | | | |
|---|---|---|---|---|---|---|
| Variant (allele) | AA/Aa/aa | Frq. | AA/Aa/aa | Frq | OR (95% CI) | P |
| rs10116277 (T) | 2305/3212/1208 | 0.418 | 454/805/350 | 0.468 | 1.22 (1.13-1.33) | $1.9 \times 10^{-6}$ |
| rs10757278 (G) | 592/869/318 | 0.434 | 413/770/376 | 0.489 | 1.25 (1.15-1.36) | $1.5 \times 10^{-7}$ |
| Iceland B (665/3533) | | | | | | |
| rs1333040 (T) | 893/1750/889 | 0.499 | 135/312/188 | 0.541 | 1.18 (1.05-1.33) | 0.0065 |
| rs2383207 (G) | 1016/1770/746 | 0.462 | 146/319/171 | 0.525 | 1.29 (1.15-1.45) | 0.000026 |
| rs10116277 (T) | 1160/1770/602 | 0.421 | 178/317/148 | 0.480 | 1.27 (1.12-1.43) | 0.00010 |
| rs10757278 (G) | 224/366/128 | 0.436 | 160/329/161 | 0.503 | 1.31 (1.16-1.47) | 0.000014 |
| Atlanta (596/1284) | | | | | | |
| rs1333040 (T) | 190/588/369 | 0.573 | 63/253/230 | 0.648 | 1.37 (1.19-1.58) | 0.000016 |
| rs2383207 (G) | 273/603/381 | 0.541 | 100/270/206 | 0.593 | 1.23 (1.07-1.42) | 0.0030 |
| rs10116277 (T) | 296/571/310 | 0.503 | 114/273/190 | 0.565 | 1.28 (1.12-1.47) | 0.00041 |
| rs10757278 (G) | 341/618/287 | 0.484 | 119/291/175 | 0.551 | 1.31 (1.14-1.50) | 0.00015 |
| Philadelphia (582/504) | | | | | | |
| rs1333040 (T) | 80/225/172 | 0.585 | 55/263/232 | 0.661 | 1.38 (1.16-1.65) | 0.00031 |
| rs2383207 (G) | 105/250/127 | 0.524 | 86/274/197 | 0.602 | 1.37 (1.16-1.63) | 0.00026 |
| rs10116277 (T) | 120/222/125 | 0.505 | 86/262/178 | 0.587 | 1.39 (1.18-1.65) | 0.00013 |
| rs10757278 (G)' | 137/254/103 | 0.470 | 116/281/169 | 0.550 | 1.38 (1.17-1.64) | 0.00019 |
| Durham (1137/718) | | | | | | |
| rs1333040 (T) | 101/364/230 | 0.588 | 159/520/427 | 0.618 | 1.14 (0.99-1.30) | 0.067 |
| rs2383207 (G) | 156/377/176 | 0.513 | 230/535/353 | 0.559 | 1.20 (1.05-1.37) | 0.0060 |
| rs10116277 (T) | 166/366/174 | 0.504 | 256/526/334 | 0.534 | 1.13 (0.99-1.29) | 0.076 |
| rs10757278 (G) | 189/370/134 | 0.460 | 261/545/304 | 0.521 | 1.28 (1.12-1.46) | 0.00027 |
| Combined Iceland[b] (2274/10260) | | | | | | |
| rs1333040 (T) | 2663/5065/2525 | 0.493 | 477/1095/666 | 0.542 | 1.21 (1.14-1.30) | $1.6 \times 10^{-8}$ |
| rs2383207 (G) | 3038/5050/2164 | 0.458 | 535/1130/579 | 0.511 | 1.24 (1.16-1.33) | $3.3 \times 10^{-10}$ |
| rs10116277 (T) | 3465/4982/1810 | 0.419 | 632/1122/498 | 0.471 | 1.23 (1.15-1.32) | $1.1 \times 10^{-9}$ |
| rs10757278 (G) | 816/1235/446 | 0.435 | 573/1099/537 | 0.493 | 1.26 (1.18-1.35) | $5.3 \times 10^{-12}$ |
| US groups[c] (2315/2508) | | | | | | |
| rs1333040 (T) | | 0.582 | | 0.642 | 1.27 (1.17-1.39) | $3.6 \times 10^{-8}$ |
| rs2383207 (G) | | 0.526 | | 0.585 | 1.25 (1.15-1.36) | $1.1 \times 10^{-7}$ |
| rs10116277 (T) | | 0.504 | | 0.562 | 1.24 (1.14-1.35) | $3.1 \times 10^{-7}$ |
| rs10757278 (G) | | 0.471 | | 0.541 | 1.31 (1.21-1.43) | $1.5 \times 10^{-10}$ |
| Replication groups[d] (2980/6041) | | | | | | |
| rs1333040 (T) | | 0.541 | | 0.592 | 1.24 (1.16-1.33) | $1.3 \times 10^{-9}$ |
| rs2383207 (G) | | 0.494 | | 0.555 | 1.27 (1.18-1.36) | $1.4 \times 10^{-11}$ |
| rs10116277 (T) | | 0.463 | | 0.521 | 1.25 (1.17-1.34) | $1.3 \times 10^{-10}$ |
| rs10757278 (G) | | 0.454 | | 0.522 | 1.31 (1.22-1.40) | $1.0 \times 10^{-14}$ |
| All groups[b,d] (4589/12768) | | | | | | |
| rs1333040 (T) | | 0.538 | | 0.592 | 1.24 (1.17-1.30) | $4.1 \times 10^{-15}$ |
| rs2383207 (G) | | 0.492 | | 0.548 | 1.25 (1.18-1.31) | $2.0 \times 10^{-16}$ |
| rs10116277 (T) | | 0.492 | | 0.548 | 1.24 (1.17-1.30) | $1.8 \times 10^{-15}$ |
| rs10757278 (G) | | 0.453 | | 0.517 | 1.28 (1.22-1.35) | $1.2 \times 10^{-20}$ |

[a]Number of MI cases (n) and controls (m).
[b]When combining the Icelandic cohorts they are analysed together and the results adjusted for relatedness in the combined group.
[c]For the combined groups OR and P value are calculated using a Mantel-Haenszel model and the frequency in cases and controls is a simple average over the frequency in the individual groups.
[d]When combining Icelandic and US groups, the frequency in cases and controls is the average over the two populations.

TABLE 17

Genotype specific odds ratio.
The upper part shows the genotype specific odds ratios for the risk alleles of the three SNPs from the genome-wide study, rs1333040, rs2383207 and rs10116277, and the most significant refinement SNP, rs10757278, for all MI cases. Shown is the risk for heterozygous carriers (0X) and homozygous carriers (XX) compared to the risk for non-carriers (00), together with 95% confidence intervals (CI). Also included is the population attributed risk (PAR). The lower part of the table includes the corresponding values when the analysis is restricted to early-onset MI cases.

| Study population (n/m)[a] | Genotype specific Odds Ratio[b] | | | |
|---|---|---|---|---|
| Variant (allele) | 00 | 0X (95% CI) | XX (95% CI) | PAR[c] |
| Iceland[d] (2272/10261) | | | | |
| rs1333040 (T) | 1 | 1.18 (1.05-1.32) | 1.46 (1.28-1.68) | 0.17 |
| rs2383207 (G) | 1 | 1.26 (1.13-1.40) | 1.53 (1.34-1.76) | 0.19 |
| rs10116277 (T) | 1 | 1.23 (1.11-1.37) | 1.52 (1.32-1.74) | 0.17 |
| rs10757278 (G) | 1 | 1.25 (1.12-1.39) | 1.58 (1.38-1.81) | 0.19 |
| US groups (2315/2508) | | | | |
| rs1333040 (T) | 1 | 1.34 (1.16-1.55) | 1.65 (1.38-1.97) | 0.28 |
| rs2383207 (G) | 1 | 1.18 (1.04-1.34) | 1.54 (1.30-1.82) | 0.19 |
| rs10116277 (T) | 1 | 1.16 (1.03-1.31) | 1.52 (1.29-1.79) | 0.17 |
| rs10757278 (G) | 1 | 1.28 (1.14-1.45) | 1.72 (1.45-2.03) | 0.23 |
| All groups (4587/12768) | | | | |
| rs1333040 (T) | 1 | 1.24 (1.14-1.35) | 1.52 (1.37-1.69) | 0.22 |
| rs2383207 (G) | 1 | 1.22 (1.13-1.32) | 1.54 (1.39-1.71) | 0.20 |
| rs10116277 (T) | 1 | 1.20 (1.11-1.30) | 1.53 (1.38-1.69) | 0.18 |
| rs10757278 (G) | 1 | 1.26 (1.16-1.36) | 1.64 (1.47-1.82) | 0.21 |
| Early onset MI (<50 for males; <60 for females) | | | | |
| Iceland[d] (621/10261) | | | | |
| rs1333040 (T) | 1 | 1.28 (1.01-1.63) | 1.94 (1.50-2.50) | 0.27 |
| rs2383207 (G) | 1 | 1.30 (1.04-1.62) | 1.80 (1.40-2.32) | 0.24 |
| rs10116277 (T) | 1 | 1.32 (1.06-1.63) | 1.86 (1.44-2.40) | 0.24 |
| rs10757278 (G) | 1 | 1.38 (1.13-1.69) | 1.94 (1.53-2.46) | 0.27 |
| US groups (1080/2508) | | | | |
| rs1333040 (T) | 1 | 1.58 (1.29-1.94) | 2.00 (1.58-2.53) | 0.38 |
| rs2383207 (G) | 1 | 1.40 (1.16-1.67) | 1.88 (1.52-2.33) | 0.31 |
| rs10116277 (T) | 1 | 1.50 (1.26-1.79) | 1.90 (1.53-2.35) | 0.32 |
| rs10757278 (G) | 1 | 1.56 (1.32-1.85) | 2.08 (1.69-2.58) | 0.34 |
| All groups (1701/12769) | | | | |
| rs1333040 (T) | 1 | 1.46 (1.25-1.70) | 1.95 (1.65-2.32) | 0.34 |
| rs2383207 (G) | 1 | 1.36 (1.18-1.56) | 1.84 (1.56-2.17) | 0.28 |
| rs10116277 (T) | 1 | 1.43 (1.25-1.64) | 1.87 (1.58-2.20) | 0.29 |
| rs10757278 (G) | 1 | 1.49 (1.31-1.69) | 2.02 (1.72-2.36) | 0.31 |

[a]Number of MI cases (n) and control (m).
[b]Genotype specific odds ratio for heterozygous (0X) and homozygous carrierr (XX) compared to non-carriers (00).
[c]Population attibuted risk (PAR).
[d]For the Icelandic groups, P values and OR were adjusted for relatedness using simulations.

TABLE 18

Association to age at onset of MI.
Shown is the association of the risk alleles of the three SNPs from the genome-wide study, rs1333040, rs2383207 and rs10116277, and the most significant refinement SNP, rs10757278, to age at onset of MI. The results are based on regressing the sex adjusted age at onset on the number of risk alleles an individual carries. The combined analysis is done by including a cohort indicator as a explanatory variable in the regression. All MI cases with known age at onset, including late-onset MI, from the four study groups are included in the analysis; this adds 973 MI cases to the study groups compared to the case-controls analysis.

| Study population (n/m)[a] | Effect (s.e.m.) | P |
|---|---|---|
| Iceland (2896/750) | | |
| rs1333040 (T) | −1.20 (0.31) | 0.00012 |
| rs2383207 (G) | −1.04 (0.31) | 0.00080 |
| rs10116277 (T) | −1.05 (0.31) | 0.00069 |
| rs10757278 (G) | −1.08 (0.31) | 0.00042 |
| Atlanta (611/40) | | |
| rs1333040 (T) | −1.36 (0.69) | 0.050 |
| rs2383207 (G) | −1.16 (0.65) | 0.075 |
| rs10116277 (T) | −1.47 (0.64) | 0.023 |
| rs10757278 (G) | −1.35 (0.65) | 0.038 |
| Philadelphia (555/82) | | |
| rs1333040 (T) | −0.85 (0.79) | 0.28 |
| rs2383207 (G) | −1.01 (0.76) | 0.19 |
| rs10116277 (T) | −1.01 (0.76) | 0.18 |
| rs10757278 (G) | −1.25 (0.74) | 0.092 |
| Durham (1213/101) | | |
| rs1333040 (T) | −0.89 (0.48) | 0.19 |
| rs2383207 (G) | −1.11 (0.46) | 0.017 |
| rs10116277 (T) | −1.14 (0.46) | 0.013 |
| rs10757278 (G) | −1.19 (0.46) | 0.0098 |
| Combined | | |
| US groups (2379/223) | | |
| rs1333040 (T) | −0.97 (0.36) | 0.0014 |
| rs2383207 (G) | −1.09 (0.34) | 0.0014 |
| rs10116277 (T) | −1.19 (0.34) | 0.00039 |
| rs10757278 (G) | −1.26 (0.34) | 0.00019 |
| All groups (5275/793) | | |
| rs1333040 (T) | −1.10 (0.23) | $2.7 \times 10^{-6}$ |
| rs2383207 (G) | −1.06 (0.23) | $3.5 \times 10^{-6}$ |
| rs10116277 (T) | −1.12 (0.23) | $9.2 \times 10^{-7}$ |
| rs10757278 (G) | −1.16 (0.23) | $2.9 \times 10^{-7}$ |

[a]n is the number of MI cases used in the regression and m is the number of MI cases used that were not included in the case-control analysis.

TABLE 19

Association to early-onset MI.
Shown is the association of the risk alleles of the three SNPs from the genome-wide study, rs1333040, rs2383207 and rs10116277, and the most significant refinement SNP, rs10757278, to early-onset MI in the combined Icelandic case-control group and in the three US case-controls groups. Early-onset MI is defined as a MI event before the age of 50 for males and before the age of 60 for females.

| Study population (n/m)[a] | Controls | | | Cases | | | |
|---|---|---|---|---|---|---|---|
| Variant (allele) | AA/Aa/aa | Frq. | | AA/Aa/aa | Frq | OR (95% CI) | P |
| Iceland[b] (621/10261) | | | | | | | |
| rs1333040 (T) | 2663/5065/2525 | 0.493 | | 114/293/210 | 0.576 | 1.40 (1.24-1.57) | $1.9 \times 10^{-8}$ |
| rs2383207 (G) | 3038/5050/2164 | 0.458 | | 133/310/176 | 0.533 | 1.35 (1.20-1.52) | $3.4 \times 10^{-7}$ |
| rs10116277 (T) | 3465/4982/1810 | 0.419 | | 156/308/153 | 0.496 | 1.36 (1.21-1.53) | $1.9 \times 10^{-7}$ |
| rs10757278 (G) | 816/1235/446 | 0.435 | | 142/299/166 | 0.518 | 1.40 (1.24-1.57) | $3.5 \times 10^{-8}$ |
| Atlanta (305/1284) | | | | | | | |
| rs1333040 (T) | 190/588/369 | 0.573 | | 27/131/121 | 0.659 | 1.44 (1.20-1.74) | 0.00011 |
| rs2383207 (G) | 273/603/381 | 0.541 | | 45/145/105 | 0.600 | 1.27 (1.06-1.52) | 0.0082 |
| rs10116277 (T) | 296/571/310 | 0.504 | | 47/150/97 | 0.584 | 1.38 (1.16-1.65) | 0.00035 |
| rs10757278 (G) | 341/618/287 | 0.484 | | 53/161/86 | 0.558 | 1.35 (1.13-1.61) | 0.00099 |
| Philadelphia (211/504) | | | | | | | |
| rs1333040 (T) | 80/225/172 | 0.585 | | 17/102/83 | 0.661 | 1.38 (1.09-1.75) | 0.0075 |
| rs2383207 (G) | 105/250/127 | 0.524 | | 30/95/75 | 0.618 | 1.47 (1.17-1.85) | 0.0011 |
| rs10116277 (T) | 120/222/125 | 0.505 | | 27/97/66 | 0.593 | 1.42 (1.13-1.79) | 0.0026 |
| rs10757278 (G) | 137/254/103 | 0.470 | | 39/103/63 | 0.561 | 1.44 (1.15-1.81) | 0.0017 |
| Durham (564/720) | | | | | | | |
| rs1333040 (T) | 101/364/230 | 0.588 | | 64/249/234 | 0.651 | 1.31 (1.11-1.54) | 0.0012 |
| rs2383207 (G) | 156/377/176 | 0.513 | | 91/271/192 | 0.596 | 1.40 (1.20-1.64) | 0.000026 |
| rs10116277 (T) | 166/366/174 | 0.504 | | 97/278/178 | 0.572 | 1.31 (1.12-1.53) | 0.00070 |
| rs10757278 (G) | 189/370/134 | 0.459 | | 105/278/168 | 0.559 | 1.49 (1.28-1.75) | $5.0 \times 10^{-7}$ |
| Combined US groups[c] (1080/2508) | | | | | | | |
| rs1333040 (T) | | 0.582 | | | 0.657 | 1.37 (1.23-1.52) | $1.6 \times 10^{-8}$ |
| rs2383207 (G) | | 0.526 | | | 0.605 | 1.37 (1.23-1.52) | $4.8 \times 10^{-9}$ |
| rs10116277 (T) | | 0.504 | | | 0.583 | 1.36 (1.22-1.51) | $9.5 \times 10^{-9}$ |
| rs10757278 (G) | | 0.471 | | | 0.559 | 1.43 (1.29-1.59) | $1.7 \times 10^{-11}$ |
| All groups[c] (1701/12769) | | | | | | | |
| rs1333040 (T) | | 0.538 | | | 0.617 | 1.38 (1.28-1.50) | $1.6 \times 10^{-15}$ |
| rs2383207 (G) | | 0.492 | | | 0.569 | 1.36 (1.26-1.47) | $8.2 \times 10^{-15}$ |
| rs10116277 (T) | | 0.462 | | | 0.540 | 1.36 (1.26-1.47) | $9.2 \times 10^{-15}$ |
| rs10757278 (G) | | 0.453 | | | 0.539 | 1.42 (1.31-1.53) | $3.3 \times 10^{-18}$ |

[a]Number of MI cases (n) and controls (m).
[b]For the Icelandic group the P value and CI are adjusted for relatedness using simulations.
[c]For the combined groups, the frequency in cases and controls is a simple average over the frequency in the individual group or, when combining Icelandic and US groups, the average over the two populations.

TABLE 20

Association to coronary artery disease.
Association of the risk alleles of the three SNPs from the genome-wide study, rs1333040, rs2383207 and rs10116277, and the most significant refinement SNP, rs10757278, to coronary artery disease (CAD) in an Icelandic group of CAD patients and in groups of CAD patients from two of the US study groups. The study group from Durham does not include any CAD patients in addition to the MI patients and was excluded from this part of the analysis. Also included are the corresponding results if all known MI cases are excluded from the CAD patient group.

| Study population ($n_1/n_2/m$)[a] | Controls | | All CAD cases | | | | Excluding MI cases | | | |
|---|---|---|---|---|---|---|---|---|---|---|
| Variant (allele) | AA/Aa/aa | Frq. | AA/Aa/aa | Frq. | OR (95% CI) | P | AA/Aa/aa | Frq | OR (95% CI) | P |
| Iceland[b] (1563/773/3533) | | | | | | | | | | |
| rs1333040 (T) | 893/1750/889 | 0.499 | 308/697/413 | 0.533 | 1.15 (1.05-1.25) | 0.0020 | 152/328/192 | 0.527 | 1.12 (1.00-1.25) | 0.057 |
| rs2383207 (G) | 1016/1770/746 | 0.462 | 353/732/387 | 0.513 | 1.23 (1.13-1.34) | $2.2 \times 10^{-6}$ | 186/353/185 | 0.500 | 1.17 (1.04-1.31) | 0.0067 |
| rs10116277 (T) | 1160/1770/602 | 0.421 | 409/707/333 | 0.474 | 1.24 (1.14-1.35) | $9.5 \times 10^{-7}$ | 204/333/158 | 0.468 | 1.21 (1.08-1.35) | 0.0010 |
| rs10757278 (G) | 224/366/128 | 0.439 | 393/745/376 | 0.496 | 1.26 (1.15-1.37) | $1.9 \times 10^{-7}$ | 203/365/188 | 0.490 | 1.22 (1.09-1.37) | 0.00050 |
| Atlanta (724/128/1284) | | | | | | | | | | |
| rs1333040 (T) | 190/588/369 | 0.572 | 75/310/281 | 0.649 | 1.38 (1.21-1.58) | $2.4 \times 10^{-6}$ | 12/57/51 | 0.655 | 1.42 (1.09-1.86) | 0.010 |
| rs2383207 (G) | 273/603/381 | 0.541 | 117/335/249 | 0.595 | 1.25 (1.09-1.42) | 0.00093 | 17/65/43 | 0.606 | 1.30 (1.00-1.69) | 0.046 |

TABLE 20-continued

Association to coronary artery disease.
Association of the risk alleles of the three SNPs from the genome-wide study, rs1333040, rs2383207 and rs10116277,
and the most significant refinement SNP, rs10757278, to coronary artery disease (CAD) in an Icelandic
group of CAD patients and in groups of CAD patients from two of the US study groups. The study group
from Durham does not include any CAD patients in addition to the MI patients and was excluded from this
part of the analysis. Also included are the corresponding results if all known MI cases are excluded from the CAD patient group.

| Study population $(n_1/n_2/m)^a$ Variant (allele) | Controls AA/Aa/aa | Frq. | All CAD cases AA/Aa/aa | Frq. | OR (95% CI) | P | Excluding MI cases AA/Aa/aa | Frq | OR (95% CI) | P |
|---|---|---|---|---|---|---|---|---|---|---|
| rs10116277 (T) | 296/571/310 | 0.503 | 130/341/228 | 0.571 | 1.31 (1.15-1.50) | 0.000038 | 16/68/38 | 0.598 | 1.47 (1.13-1.90) | 0.0039 |
| rs10757278 (G) | 341/618/287 | 0.484 | 139/362/207 | 0.552 | 1.31 (1.15-1.50) | 0.000036 | 20/71/32 | 0.557 | 1.34 (1.04-1.73) | 0.026 |
| Philadelphia (709/126/504) | | | | | | | | | | |
| rs1333040 (T) | 80/225/172 | 0.585 | 59/273/235 | 0.648 | 1.31 (1.11-1.55) | 0.00170 | 24/49/47 | 0.588 | 1.02 (0.76-1.35) | 0.92 |
| rs2383207 (G) | 105/250/127 | 0.524 | 89/285/200 | 0.600 | 1.36 (1.15-1.60) | 0.00023 | 25/52/46 | 0.587 | 1.29 (0.98-1.71) | 0.072 |
| rs10116277 (T) | 120/222/125 | 0.504 | 90/274/180 | 0.582 | 1.37 (1.16-1.61) | 0.00017 | 26/52/43 | 0.556 | 1.23 (0.93-1.62) | 0.14 |
| rs10757278 (G) | 137/254/103 | 0.470 | 146/339/208 | 0.547 | 1.36 (1.16-1.60) | 0.00019 | 30/57/38 | 0.528 | 1.26 (0.96-1.66) | 0.10 |
| Combined US groups$^c$ (1433/254/1788) | | | | | | | | | | |
| rs1333040 (T) | | 0.579 | | 0.649 | 1.35 (1.22-1.50) | $19 \times 10^{-8}$ | | 0.621 | 1.23 (1.01-1.51) | 0.044 |
| rs2383207 (G) | | 0.533 | | 0.598 | 1.29 (1.17-1.43) | $9.8 \times 10^{-7}$ | | 0.597 | 1.30 (1.08-1.57) | 0.0068 |
| rs10116277 (T) | | 0.504 | | 0.577 | 1.34 (1.21-1.48) | $2.1 \times 10^{-8}$ | | 0.577 | 1.35 (1.12-1.63) | 0.0018 |
| rs10757278 (G) | | 0.477 | | 0.550 | 1.33 (1.20-1.47) | $2.7 \times 10^{-8}$ | | 0.542 | 1.30 (1.08-1.57) | 0.0059 |
| All groups$^c$ (2996/1027//5321) | | | | | | | | | | |
| rs1333040 (T) | | 0.539 | | 0.591 | 1.22 (1.14-1.31) | $3.2 \times 10^{-9}$ | | 0.590 | 1.14 (1.04-1.26) | 0.0082 |
| rs2383207 (G) | | 0.497 | | 0.555 | 1.25 (1.17-1.34) | $1.3 \times 10^{-11}$ | | 0.565 | 1.20 (1.09-1.32) | 0.00019 |
| rs10116277 (T) | | 0.462 | | 0.525 | 1.28 (1.20-1.37) | $1.7 \times 10^{-13}$ | | 0.541 | 1.25 (1.13-1.37) | $7.8 \times 10^{-6}$ |
| rs10757278 (G) | | 0.458 | | 0.523 | 1.29 (1.21-1.38) | $3.6 \times 10^{-14}$ | | 0.525 | 1.24 (1.13-1.37) | 0.000011 |

$^a$Number of all cases ($n_1$), cases excluding MI patients ($n_2$), and controls (m).
$^b$Individuals used in the initial discovery group have been excluded both from cases and controls.
$^c$For the combined groups, the allelic frequency in cases and controls is a simple average over the individual groups or, when combining Icelandic and US groups, the average over the two populations.

TABLE 21

Markers correlated with the at-risk signal.
All SNPs in the LD-block (based on the HapMap v19 CEU dataset) that are
correlated, with $r^2 \geq 0.5$, to at least one of the three SNPs, rs1333040,
rs10116277 and rs2383207, together with the correlation coefficients D' and
$r^2$. Additional markers selected for typing on both the Icelandic and all
the US case/control groups are indicated in bold italic.

| | | | | rs1333040 | | rs10116277 | | rs2383207 | |
|---|---|---|---|---|---|---|---|---|---|
| SNP | Position$^a$ | Position$^b$ | Frq | D' | $r^2$ | D' | $r^2$ | D' | $r^2$ |
| rs10811647 | 22055002 | 134856 | 0.449 | 0.95 | 0.49 | 0.92 | 0.70 | 0.92 | 0.62 |
| *rs10811650* | 22057593 | 137447 | 0.450 | 0.95 | 0.49 | 0.93 | 0.70 | 0.92 | 0.63 |
| rs9632884 | 22062301 | 142155 | 0.521 | 0.96 | 0.65 | 1 | 0.93 | 0.93 | 0.84 |
| *rs10116277* | 22071397 | 151251 | 0.500 | 1 | 0.67 | 1 | 1 | 1 | 0.90 |
| rs6475606 | 22071850 | 151704 | 0.500 | 1 | 0.67 | 1 | 1 | 1 | 0.90 |
| *rs1333040* | 22073404 | 153258 | 0.600 | 1 | 1 | 1 | 0.67 | 0.88 | 0.57 |
| rs1537370 | 22074310 | 154164 | 0.500 | 1 | 0.67 | 1 | 1 | 1 | 0.90 |
| rs7857345 | 22077473 | 157327 | 0.733 | 1 | 0.55 | 1 | 0.36 | 0.81 | 0.26 |
| *rs10738607* | 22078094 | 157948 | 0.504 | 1 | 0.69 | 1 | 1 | 1 | 0.90 |
| rs10757272 | 22078260 | 158114 | 0.500 | 1 | 0.67 | 1 | 1 | 1 | 0.90 |
| *rs4977574* | 22088574 | 168428 | 0.500 | 1 | 0.67 | 1 | 1 | 1 | 0.90 |
| rs2891168 | 22088619 | 168473 | 0.500 | 1 | 0.67 | 1 | 1 | 1 | 0.90 |
| rs1537371 | 22089568 | 169422 | 0.500 | 1 | 0.67 | 1 | 1 | 1 | 0.90 |
| rs1556516 | 22090176 | 170030 | 0.500 | 1 | 0.67 | 1 | 1 | 1 | 0.90 |
| *rs6475608* | 22091702 | 171556 | 0.737 | 1 | 0.54 | 1 | 0.36 | 0.8 | 0.25 |
| rs7859727 | 22092165 | 172019 | 0.496 | 1 | 0.66 | 1 | 1 | 1 | 0.90 |
| rs1537373 | 22093341 | 173195 | 0.500 | 1 | 0.67 | 1 | 1 | 1 | 0.90 |
| rs1333042 | 22093813 | 173667 | 0.508 | 0.96 | 0.63 | 1 | 0.97 | 1 | 0.94 |
| rs7859362 | 22095927 | 175781 | 0.525 | 0.88 | 0.57 | 1 | 0.90 | 1 | 1 |
| rs1333043 | 22096731 | 176585 | 0.517 | 0.92 | 0.60 | 1 | 0.94 | 1 | 0.97 |
| rs1412834 | 22100131 | 179985 | 0.525 | 0.88 | 0.57 | 1 | 0.90 | 1 | 1 |
| rs7341786 | 22102241 | 182095 | 0.533 | 0.84 | 0.54 | 1 | 0.88 | 1 | 0.97 |
| rs10511701 | 22102599 | 182453 | 0.533 | 0.84 | 0.54 | 1 | 0.88 | 1 | 0.97 |

TABLE 21-continued

Markers correlated with the at-risk signal.
All SNPs in the LD-block (based on the HapMap v19 CEU dataset) that are correlated, with $r^2 \geq 0.5$, to at least one of the three SNPs, rs1333040, rs10116277 and rs2383207, together with the correlation coefficients D' and $r^2$. Additional markers selected for typing on both the Icelandic and all the US case/control groups are indicated in bold italic.

| | | | | rs1333040 | | rs10116277 | | rs2383207 | |
|---|---|---|---|---|---|---|---|---|---|
| SNP | Position[a] | Position[b] | Frq | D' | $r^2$ | D' | $r^2$ | D' | $r^2$ |
| rs10733376 | 22104469 | 184323 | 0.525 | 0.88 | 0.57 | 1 | 0.90 | 1 | 1 |
| rs10738609 | 22104495 | 184349 | 0.525 | 0.88 | 0.57 | 1 | 0.90 | 1 | 1 |
| rs2383206 | 22105026 | 184880 | 0.525 | 0.88 | 0.57 | 1 | 0.90 | 1 | 1 |
| rs944797 | 22105286 | 185140 | 0.525 | 0.88 | 0.57 | 1 | 0.90 | 1 | 1 |
| rs1004638 | 22105589 | 185443 | 0.525 | 0.88 | 0.57 | 1 | 0.90 | 1 | 1 |
| rs2383207 | 22105959 | 185813 | 0.525 | 0.88 | 0.57 | 1 | 0.90 | 1 | 1 |
| rs1537374 | 22106046 | 185900 | 0.525 | 0.88 | 0.57 | 1 | 0.90 | 1 | 1 |
| rs1537375 | 22106071 | 185925 | 0.525 | 0.88 | 0.57 | 1 | 0.90 | 1 | 1 |
| *rs1333045* | 22109195 | 189049 | 0.548 | 0.68 | 0.37 | 0.92 | 0.69 | 0.85 | 0.65 |
| rs10738610 | 22113766 | 193620 | 0.517 | 0.92 | 0.60 | 1 | 0.94 | 1 | 0.97 |
| *rs1333046* | 22114123 | 193977 | 0.517 | 0.92 | 0.60 | 1 | 0.94 | 1 | 0.97 |
| *rs10757278* | 22114477 | 194331 | 0.491 | 0.95 | 0.57 | 0.96 | 0.90 | 1 | 0.87 |
| rs1333047 | 22114504 | 194358 | 0.492 | 0.96 | 0.59 | 0.97 | 0.90 | 1 | 0.88 |
| rs4977575 | 22114744 | 194598 | 0.492 | 0.96 | 0.59 | 0.97 | 0.90 | 1 | 0.88 |
| *rs1333048* | 22115347 | 195201 | 0.508 | 0.96 | 0.63 | 1 | 0.97 | 1 | 0.94 |
| rs1333049 | 22115503 | 195357 | 0.492 | 0.96 | 0.59 | 0.97 | 0.90 | 1 | 0.88 |

[a]Base-pair location in NCBI Build 34, Build 35 and Build 36.
[b]Position in SEQ ID NO: 94 (LD Block C09)

TABLE 22a

Association to MI for additional markers typed in the LD block C09.
Association to MI of the three SNPs from the genome-wide association study and of the 10 highly correlated refinement markers. The association is calculated for the combined Icelandic and US case-control groups with OR and P-values combined using a Mantel-Haenszel model. Also included are the corresponding adjusted P values for each marker when the association is tested conditional on the observed association of each of the other markers.

| | | | Frequency[b] | | Unadjusted | | Adjusted P values | | |
|---|---|---|---|---|---|---|---|---|---|
| SNP | Allele | Position[a] | Controls | Cases | OR | P | rs10811650 | rs10116277 | rs1333040 |
| rs10811650 | G | 22057593 | 0.398 | 0.449 | 1.21 | $3.0 \times 10^{-12}$ | na | 0.79 | 0.10 |
| rs10116277 | T | 22071397 | 0.461 | 0.516 | 1.24 | $1.8 \times 10^{-15}$ | $1.2 \times 10^{-4}$ | na | 0.011 |
| rs1333040 | T | 22073404 | 0.537 | 0.592 | 1.24 | $4.1 \times 10^{-15}$ | $6.6 \times 10^{-5}$ | 0.040 | na |
| rs10738607 | G | 22078094 | 0.463 | 0.525 | 1.27 | $2.1 \times 10^{-19}$ | $6.2 \times 10^{-9}$ | $2.5 \times 10^{-5}$ | $4.2 \times 10^{-6}$ |
| rs4977574 | G | 22088574 | 0.465 | 0.525 | 1.27 | $1.1 \times 10^{-18}$ | $1.6 \times 10^{-6}$ | $1.8 \times 10^{-4}$ | $1.7 \times 10^{-5}$ |
| rs6475608 | C | 22091702 | 0.700 | 0.737 | 1.18 | $6.3 \times 10^{-8}$ | 0.058 | 0.52 | 0.84 |
| rs2383207 | G | 22105959 | 0.492 | 0.548 | 1.25 | $2.0 \times 10^{-16}$ | $9.2 \times 10^{-6}$ | 0.017 | $3.8 \times 10^{-4}$ |
| rs1333045 | C | 22109195 | 0.508 | 0.563 | 1.24 | $6.3 \times 10^{-15}$ | $3.4 \times 10^{-5}$ | 0.024 | $4.1 \times 10^{-4}$ |
| rs1333046 | A | 22114123 | 0.468 | 0.526 | 1.25 | $2.5 \times 10^{-17}$ | $6.2 \times 10^{-7}$ | 0.0036 | $1.5 \times 10^{-4}$ |
| rs10757278 | G | 22114477 | 0.453 | 0.517 | 1.28 | $1.2 \times 10^{-20}$ | $4.8 \times 10^{-10}$ | $2.7 \times 10^{-6}$ | $4.8 \times 10^{-7}$ |
| rs1333048 | C | 22115347 | 0.472 | 0.532 | 1.26 | $6.0 \times 10^{-18}$ | $1.6 \times 10^{-7}$ | $9.5 \times 10^{-4}$ | $4.6 \times 10^{-5}$ |

| | Adjusted P values | | | | | | |
|---|---|---|---|---|---|---|---|
| SNP | rs10738607 | rs4977574 | rs6475608 | rs2383207 | rs1333045 | rs1333046 | rs10757278 | rs1333048 |
| rs10811650 | 0.43 | 0.47 | $1.6 \times 10^{-6}$ | 0.47 | 0.063 | 1.00 | 0.51 | 0.86 |
| rs10116277 | 0.47 | 0.83 | $3.0 \times 10^{-9}$ | 0.20 | 0.0046 | 0.38 | 0.67 | 0.65 |
| rs1333040 | 0.18 | 0.11 | $1.6 \times 10^{-8}$ | 0.011 | $2.3 \times 10^{-4}$ | 0.027 | 0.15 | 0.050 |
| rs10738607 | na | 0.056 | $7.1 \times 10^{-13}$ | $2.8 \times 10^{-4}$ | $8.0 \times 10^{-6}$ | 0.0015 | 0.61 | 0.0079 |
| rs4977574 | 0.43 | na | $2.7 \times 10^{-12}$ | 0.0021 | $7.3 \times 10^{-5}$ | 0.033 | 0.61 | 0.076 |
| rs6475608 | 0.71 | 0.72 | na | 0.70 | 0.83 | 0.93 | 0.73 | 0.93 |
| rs2383207 | 0.42 | 0.73 | $3.2 \times 10^{-10}$ | na | 0.0020 | 0.56 | 0.25 | 0.78 |
| rs1333045 | 0.92 | 0.85 | $1.2 \times 10^{-8}$ | 0.15 | na | 0.50 | 0.17 | 0.62 |
| rs1333046 | 0.20 | 0.68 | $5.0 \times 10^{-11}$ | 0.038 | $5.0 \times 10^{-4}$ | na | 0.044 | 0.74 |
| rs10757278 | 0.039 | 0.0041 | $5.0 \times 10^{-14}$ | $2.0 \times 10^{-5}$ | $2.6 \times 10^{-7}$ | $2.4 \times 10^{-5}$ | na | $1.1 \times 10^{-4}$ |
| rs1333048 | 0.39 | 0.94 | $1.2 \times 10^{-11}$ | 0.017 | $2.4 \times 10^{-4}$ | 0.24 | 0.10 | na |

[a]Base-pair location in NCBI Build 34.
[b]The frequency in cases and controls is a simple average over the frequency in Iceland and in US.

TABLE 22b

Genotype count for additional markers typed in the LD block C09.
Genotype counts in cases and controls for the eight additional refinement SNPs typed in the LD block C09 and for the three SNPs from the genome-wide study, rs1333040, rs2383207 and rs10116277. Genotype counts are shown for the combined Icelandic case-control group (Iceland A + B) and for the three US replication cohorts. For each SNP counts are shown for the risk allele a and the wild type allele A.

| | | | Iceland A + B | | Philadelphia | | Atlanta | | Durham | |
|---|---|---|---|---|---|---|---|---|---|---|
| SNP | Risk Allele | Position[a] | Controls AA/aA/aa | Cases AA/aA/aa | Controls AA/aA/aa | Cases AA/aA/aa | Controls AA/aA/aa | Cases AA/aA/aa | Controls AA/aA/aa | Cases AA/aA/aa |
| rs10811650 | G | 22057593 | 819/1015/279 | 652/878/336 | 143/193/74 | 107/239/119 | 293/394/147 | 165/271/133 | 202/380/112 | 344/527/222 |
| rs10116277 | T | 22071397 | 3465/4982/1810 | 632/1122/498 | 120/222/125 | 86/262/178 | 296/571/310 | 114/273/190 | 166/366/174 | 256/526/334 |
| rs1333040 | T | 22073404 | 2663/5065/2525 | 477/1095/666 | 80/225/172 | 55/263/232 | 190/588/369 | 63/253/230 | 101/364/230 | 159/520/427 |
| rs10738607 | G | 22078094 | 1502/2326/933 | 558/1099/547 | 131/244/116 | 105/278/173 | 332/603/312 | 114/283/186 | 187/373/137 | 261/552/312 |
| rs4977574 | G | 22088574 | 1507/2335/964 | 554/1105/556 | 130/246/119 | 103/286/180 | 332/597/325 | 115/274/188 | 187/383/144 | 267/549/316 |
| rs6475608 | C | 22091702 | 235/980/1135 | 170/870/1059 | 36/200/250 | 26/199/342 | 101/476/616 | 24/210/330 | 58/276/353 | 67/415/588 |
| rs2383207 | G | 22105959 | 3038/5050/2164 | 535/1130/579 | 105/250/127 | 86/274/197 | 273/603/381 | 100/270/206 | 156/377/176 | 230/535/353 |
| rs1333045 | C | 22109195 | 610/1264/638 | 433/1102/655 | 115/262/114 | 95/289/180 | 286/605/347 | 93/290/200 | 159/378/169 | 218/548/345 |
| rs1333046 | A | 22114123 | 1519/2266/959 | 583/1078/554 | 123/244/120 | 102/274/181 | 315/586/330 | 114/273/191 | 182/378/154 | 251/539/323 |
| rs10757278 | G | 22114477 | 816/1235/446 | 573/1099/537 | 137/254/103 | 116/281/169 | 341/618/287 | 119/291/175 | 189/370/134 | 261/545/304 |
| rs1333048 | C | 22115347 | 1372/2202/926 | 473/947/478 | 119/247/120 | 99/274/184 | 210/418/231 | 108/286/188 | 175/379/154 | 247/532/325 |

[a]Base-pair location in NCBI Build 34.

TABLE 23

Primers in the AF109294 gene and ESTs used for PCR screening of cDNA libraries (Forward primers: SEQ ID NO: 95-102, respectively; Reverse primers SEQ ID NOs: 103-110, respectively).

| ESTs* | Forward primer | Reverse primer |
|---|---|---|
| AF109294 | TTGGTGTCCATGCTGTGATGATT | GGTTGGGGACCCCTGGTGTA |
| CN277071 | GGTTCAAGCATCACTGTTAGGTGT | GAGGCGGGCGAATCACGA |
| AW169296 | GCTCAGAGCAATTCCAGTGCAAG | GGTTCCAGTCCTGGTTCTGC |
| BX100299 | TCTCATTGGGGATACGAAGCTCT | TCTGGCCCTAGCCTCCATGT |

| ESTs* | Nested forward primer | Nested reverse primer |
|---|---|---|
| AF109294 | AACTCCAAAGAAACCATCAGAGG | TGGGGACCCCTGGTGTAGTG |
| CN277071 | CTTTCCCGAGTCAGTACTGCTTTCT | CGGGCGAATCACGAGGTC |
| AW169296 | TTCCAGTGCAAGTATGGTCTGTGA | CCAGTCCTGGTTCTGCCACA |
| BX100299 | TCATTGGGGATACGAAGCTCTACA | CAGAAAGCTGCAAAGGCCTCA |

ESTs* names are from NCBI Build 36.

TABLE 24

Expression analysis of ESTs and AF109294 in various cDNA libraries by PCR screening

| | cDNA libraries | | | | | | |
|---|---|---|---|---|---|---|---|
| ESTs | Whole blood | EBV transf. lymphoblasts | Whole heart | Aorta | Cardiac fibro-myocytes | Ventricular fibroblasts | Endothelial cells (HUVEC) |
| AF109294 | positive | nd | nd | positive | positive | nd | nd |
| CN277071 | positive | positive | nd | positive | positive | positive | positive |

TABLE 24-continued

Expression analysis of ESTs and AF109294 in various cDNA libraries by PCR screening

| ESTs | Whole blood | EBV transf. lymphoblasts | Whole heart | Aorta | Cardiac fibro-myocytes | Ventricular fibroblasts | Endothelial cells (HUVEC) |
|---|---|---|---|---|---|---|---|
| AW169296 | positive | positive | positive | positive | positive | positive | positive |
| BX100299 | positive | positive | nd | positive | positive | positive | positive | nd: not detected.
positive: generated PCR products that were confirmed by sequencing

TABLE 25

Primers used for sequencing of CDKN2A and CDKN2B (Forward primers: SEQ ID NO: 111-148, respectively; Reverse primers SEQ ID NOs: 149-186, respectively).

| Primer alias | Forward primer | Primer alias | Reverse primer |
|---|---|---|---|
| CDKA.1e-f.F | AAAGAAGCCAGACACGGAAG | CDKA.1e-f.R | GTAACTGAATCCAGCCAACC |
| CDKA.1f.F | GGATGAGGCAGCGTGGAC | CDKA.1f.R | AAGCCGTGTCTCAAGATCG |
| CDKA.1g.F | TCCGGTTTGGCAGCAGTC | CDKA.1g.R | CTAGCAAATGGCAGAACCA |
| CDKA.1h.F | CAACAGTGTCAGAAACGATGC | CDKA.1h.R | ATCAGTCACCGAAGGTCCTA |
| CDKA.3b.F | CTTGATCTCCCAAAGTGAAGG | CDKA.3b.R | CGACTCTGGAGGACGAAGTT |
| CDKA.4d.F | AGATCTCGGAACGGCTCT | CDKA.4d.R | GAGGCGTGCAGCGGTTTA |
| CDKA.4e.F | GGAAGAAAGGAAAGCGAGGT | CDKA.4e.R | CGGGATCAAGGGGAGTCG |
| CDKA.4f.F | TCCTCGCGTAGAATGGTTGT | CDKA.4f.R | AGCCCGCGAGGTTTAGGAC |
| CDKA.4g.F | CCTGAGCGCGGTCTAAGC | CDKA.4g.R | CGTTTTGTCTTGGGTTTGTACC |
| CKDN2A.1.F | CCCCTTCAGATCTTCTCAGC | CKDN2A.1.R | AGCACCGGAGGAAGAAAGAG |
| CKDN2A.2.F | CCCGCACCTCCTCTACCC | CKDN2A.2.R | AGTGAACGCACTCAAACACG |
| CKDN2A.3.F | TTGGCAAGGAAGGAGGACTG | CKDN2A.3.R | TACCAGGCAATGTACACGTC |
| CKDN2A.4.F | GGTTCACTAAGTCAGAAACCCTAGT | CKDN2A.4.R | AGCTTAGGATGTGTGGCACT |
| CKDN2A.5.F | AGTCTTCATTGCTCCGCAGT | CKDN2A.5.R | GACACGCTGGTGGTGCTG |
| CKDN2A.6.F | ATCTATGCGGGCATGGTTAC | CKDN2A.6.R | ACAGTGCTCTCTGCCTGTGAC |
| CKDN2A.7.F | CAAAATGCTTGTCATGAAGTCG | CKDN2A.7.R | GTGAAGCCATTGCGAGAA |
| CKDN2A.8.F | TTTCAATCGGGGATGTCTGC | CKDN2A.8.R | CCACTGAGACTCATTATATAACACTCGTT |
| p14.1.F | ATTCCCACCCAGGATATTCG | p14.1.R | GGTCCCAGTCTGCAGTTAAG |
| p14.2.F | CTGCGCACCATGTTCTCG | p14.2.R | CGAGCAGCACCAGAATCC |
| CDKB.06.F | CCCTACTGACTATTACATATCAATGC | CDKB.06.R | CAGAAAATTAAATATACCTGTTAAGTTCG |
| CDKB.07.F | TTTTAACCATTTAAGGCATAGGA | CDKB.07.R | GCAAACCTCAAACATTATTGG |
| CDKB.08.F | CTGCTGATGAAACAGCTAAACC | CDKB.08.R | GCACTCAATCATTAGAGGCTACA |
| CDKB.09.F | TCTTGGAATTTAAGATATAGAGGTCAA | CDKB.09.R | TGCACAAAGAAGTGCATCTAGT |
| CDKB.10.F | GTTAGAGAAAGAAAAGCCACCTTAG | CDKB.10.R | ACAAGTCATTTGAGAGTGGAGAC |
| CDKB.11.F | AACATATGCTCTGATTCTCAACTAAC | CDKB.11.R | GGGATTTAATTTCCAGGGTTG |
| CDKB.12.F | CAAACATTGAGAGAAGGGAACC | CDKB.12.R | GGAAGAACTACAGCTCTTAAATGTAGC |
| CDKB.13.F | TCTGCACCCTGAGACACTCTA | CDKB.13.R | GGAGACCCTCGCCCAACT |
| CDKB.14.F | TAAGAGCAAAGGCCAGCATCC | CDKB.14.R | CACTCACCATGAAGCGAAAC |
| CDKB.15.F | TAATCACTGCCTTCTCCCACTC | CDKB.15.R | GGAGGGCTTCCTGGACAC |

TABLE 25-continued

Primers used for sequencing of CDKN2A and CDKN2B (Forward primers: SEQ ID NO: 111-148, respectively; Reverse primers SEQ ID NOs: 149-186, respectively).

| Primer alias | Forward primer | Primer alias | Reverse primer |
|---|---|---|---|
| CDKB.16.F | GGGTGGGAAATTGGGTAA | CDKB.16.R | GGAAAGTGGATTGCATCAGC |
| CDKB.17.F | GGCAGGTATGGGAGATGC | CDKB.17.R | TCTCCCCTAAACCATTACTCC |
| CDKB.23.F | ACAATACAACAGATTTCATATAGTAGCTTAG | CDKB.23.R | TAGTGGAGAAGGTGCGACAG |
| CDKB.24.F | TAGGTTCCAGCCCCGATCC | CDKB.24.R | GGCTGGCTCCCCACTCTG |
| CDKB.25.F | TTCCTGGCGCTCAAGAACC | CDKB.25.R | CACAAGGGAGCCACCAAC |
| COKB.26.F | CACTGCCCTCAGCTCCTA | CDKB.26.R | CCTGACAAAGTGGGTTTAAATAGGT |
| CDKB.27.F | TGCATTATGGATACAACCCTTA | CDKB.27.R | TCTTCCTCAGCACTCCGAAC |
| CDKB.28.F | CGGATGCTACATTGGATAGG | CDKB.28.R | GGCTCAAGAATTGGGTCA |
| CDKB.a29.F | GAAGGGAACCGGGTAGCA | CDKB.a29.R | CCATAATGTCCTTTCTATTTGACG |

TABLE 26

Sequencing variants in CDKN2A and CDKN2B.
Shown are all SNPs identified through sequencing of CDKN2A and CDKN2B for 93 early onset MI cases using primers in Table 25. Many of the SNPs identified in the sequencing effort are rare, and have low correlation with rs10757278. These SNPs cannot account for the correlation of rs10757278 to the disease. Two common SNPs, rs3217992 and rs2069416 have modest correlation with rs10757278 ($r^2 = 0.36$ and 0.37 respectively). rs3217992 is a part of the Illumina Hap300 chip. For Iceland A, rs10757278 gave a P value of $1.5 \times 10^{-7}$, while rs3217992 gave a P value of $5.4 \times 10^{-4}$. Hence rs3217992 cannot account for the association of rs10757278. Neither can rs2069416 since it is highly correlated with rs3217992 ($r^2 > 0.8$ both in HapMap CEU and Iceland). SNP rs1063192, which has $r^2$ of 0.23 with rs10757278 in these sequenced individuals, is also an Illumina SNP and did not even show nominal significance in Iceland A (P > 0.05). Rs2069418 is highly correlated with rs1063192.

| MAF$^a$ | A | a | Position$^b$ | Position$^d$ | rs names | D'$^c$ | $r^2$ $^c$ | Location |
|---|---|---|---|---|---|---|---|---|
| CDKN2A | | | | | | | | |
| 0.069 | A | G | 21958159 | 38013 | rs3088440 | 0.5 | 0.02 | Exon3 |
| 0.176 | C | G | 21958199 | 38053 | rs11515 | 0.44 | 0.03 | Exon3 |
| 0.005 | C | T | 21960674 | 40528 | | 1 | 0 | Intron2 |
| 0.042 | T | C | 21960916 | 40770 | rs3731249 | 1 | 0.04 | Exon2 |
| 0.005 | A | G | 21961188 | 41042 | | 1 | 0 | Exon2 |
| 0.01 | G | C | 21964859 | 44713 | rs1800586 | 1 | 0.01 | Exon1 |
| 0.356 | C | T | 21965017 | 44871 | rs3814960 | 0.18 | 0.02 | 5'UTR |
| 0.042 | A | T | 21965319 | 45173 | SG09S293* | 1 | 0.04 | 5'UTR |
| 0.036 | T | C | 21965561 | 45415 | rs3731238 | 1 | 0.03 | 5'UTR |
| 0.057 | A | C | 21965807 | 45661 | SG09S291* | 0.49 | 0.01 | 5'UTR |
| 0.094 | C | T | 21983964 | 63818 | rs2811711 | 0.42 | 0.02 | 5'UTR |
| CDKN2B | | | | | | | | |
| 0.005 | A | G | 21957014 | 36868 | | 1 | 0.01 | 3'UTR |
| 0.01 | A | G | 21957207 | 37061 | | 1 | 0.01 | 3'UTR |
| 0.01 | G | T | 21957291 | 37145 | | 1 | 0.01 | 3'UTR |
| 0.005 | C | A | 21957479 | 37333 | | 1 | 0.01 | 3'UTR |
| 0.005 | G | C | 21957838 | 37692 | | 1 | 0.01 | 3'UTR |
| 0.071 | A | G | 21958159 | 38013 | | 0.33 | 0.01 | 3'UTR |
| 0.38 | G | A | 21964218 | 44072 | rs3731239 | 0.41 | 0.13 | 3'UTR |
| 0.005 | G | C | 21964355 | 44209 | | 1 | 0.01 | 3'UTR |
| 0.01 | G | T | 21985044 | 64898 | | 1 | 0.01 | 3'UTR |
| 0.005 | T | C | 21985467 | 65321 | | 1 | 0.01 | 3'UTR |
| 0.323 | T | C | 21985882 | 65736 | rs2518723 | 0.29 | 0.07 | 3'UTR |
| 0.422 | T | C | 21993223 | 73077 | rs3217992 | 0.78 | 0.36 | Exon2 |
| 0.398 | G | A | 21993367 | 73221 | rs1063192 | 0.53 | 0.23 | Exon2 |
| 0.005 | C | A | 21993417 | 73271 | | 1 | 0 | Exon2 |
| 0.005 | C | T | 21993591 | 73445 | | 1 | 0.01 | Exon2 |
| 0.078 | G | T | 21995330 | 75184 | rs3217986 | 0.58 | 0.03 | Exon2 |
| 0.005 | C | G | 21995493 | 75347 | rs3217984 | 1 | 0.01 | Exon2 |
| 0.104 | T | G | 21996273 | 76127 | rs2069426 | 0.08 | 0 | Intron1 |
| 0.005 | A | G | 21996303 | 76157 | | 1 | 0.01 | Intron1 |
| 0.104 | T | C | 21996348 | 76202 | rs974336 | 0.08 | 0 | Intron1 |

TABLE 26-continued

Sequencing variants in CDKN2A and CDKN2B.

Shown are all SNPs identified through sequencing of CDKN2A and CDKN2B for 93 early onset MI cases using primers in Table 25. Many of the SNPs identified in the sequencing effort are rare, and have low correlation with rs10757278. These SNPs cannot account for the correlation of rs10757278 to the disease. Two common SNPs, rs3217992 and rs2069416 have modest correlation with rs10757278 ($r^2$ = 0.36 and 0.37 respectively). rs3217992 is a part of the Illumina Hap300 chip. For Iceland A, rs10757278 gave a P value of 1.5 × $10^{-7}$, while rs3217992 gave a P value of 5.4 × $10^{-4}$. Hence rs3217992 cannot account for the association of rs10757278. Neither can rs2069416 since it is highly correlated with rs3217992 ($r^2$ > 0.8 both in HapMap CEU and Iceland). SNP rs1063192, which has $r^2$ of 0.23 with rs10757278 in these sequenced individuals, is also an Illumina SNP and did not even show nominal significance in Iceland A (P > 0.05). Rs2069418 is highly correlated with rs1063192.

| MAF[a] | A | a | Position[b] | Position[d] | rs names | D'[c] | $r^{2\ c}$ | Location |
|---|---|---|---|---|---|---|---|---|
| 0.005 | G | A | 21996536 | 76390 | | 1 | 0.01 | Intron1 |
| 0.382 | G | C | 21999698 | 79552 | rs2069418 | 0.55 | 0.23 | 5'UTR |
| 0.011 | G | A | 21999915 | 79769 | | 1 | 0.01 | 5'UTR |
| 0.005 | T | C | 21999953 | 79807 | | 1 | 0.01 | 5'UTR |
| 0.1 | del | A | 21999996 | 79850 | rs2069417 | 0 | 0 | 5'UTR |
| 0.395 | A | T | 22000004 | 79858 | rs2069416 | 0.8 | 0.37 | 5'UTR |
| 0.089 | G | A | 22000412 | 80266 | rs495490 | 0.03 | 0 | 5'UTR |
| 0.021 | A | G | 22000681 | 80535 | SG09S492* | 1 | 0.02 | 5'UTR |
| 0.005 | C | G | 22001083 | 80937 | | 1 | 0.01 | 5'UTR |
| 0.005 | C | G | 22001158 | 81012 | | 1 | 0.01 | 5'UTR |

[a] MAF: minor allele frequency.
[b] Base-pair location in NCBI Build 34.
[c] Correlation to the refinement SNP rs10757278 based on the 93 sequenced MI cases.
[d] Position in SEQ ID NO: 94 (LD Block C09).
*Alternate names used herein for non-public SNPs

TABLE 27

SNPs in conserved TF bindings sites within the MI region.

| SNP | | | TF binding site | | LD to rs1333040 | | |
|---|---|---|---|---|---|---|---|
| Name | Location | TF Name | Start | End | D' | $r^2$ | P |
| rs16935754 | 22002235 | PAX2 | 22002234 | 22002253 | nd | nd | nd |
| rs35113513 | 22023540 | FOXO4 | 22023540 | 22023551 | nd | nd | nd |
| rs35834365 | 22023550 | FOXO4 | 22023540 | 22023551 | nd | nd | nd |
| rs17694493 | 22031997 | STAT | 22031995 | 22032004 | 0.41 | 0.05 | 0.03 |
| rs1412830 | 22033611 | FOXO4* | 22033601 | 22033615 | nd | nd | nd |
| rs1412830 | 22033611 | FOXO3* | 22033601 | 22033615 | nd | nd | nd |
| rs4977758 | 22108480 | EVI1 | 22108480 | 22108496 | nd | nd | nd |
| rs34974971 | 22126835 | EVI1 | 22126830 | 22126839 | nd | nd | nd |
| rs6475610 | 22131893 | AREB6 | 22131892 | 22131905 | 0.11 | 0.01 | 0.36 |
| rs10757289# | 22150453 | MRF2 | 22150444 | 22150458 | 0.14 | 0.02 | 0.22 |
| rs10757289# | 22150453 | SEF1 | 22150452 | 22150471 | 0.14 | 0.02 | 0.22 |
| rs1679013 | 22196986 | BACH1 | 22196977 | 22196992 | 0.01 | 0 | 0.96 |
| rs1679014 | 22197036 | PAX6 | 22197025 | 22197046 | 0.21 | 0 | 0.57 |
| rs10965296 | 22205659 | GATA6 | 22205657 | 22205667 | 1 | 0.01 | 0.31 |
| rs7043085 | 22323165 | OCT1 | 22323163 | 22323176 | nd | nd | nd |
| rs1969926 | 22347344 | SOX9 | 22347334 | 22347348 | nd | nd | nd |
| rs10113901 | 22364031 | HNF1 | 22364024 | 22364039 | 0.06 | 0 | 0.64 |
| rs7046709 | 22366969 | MEF2 | 22366953 | 22366975 | 0.13 | 0.01 | 0.34 |

All coordinates are for human genome release 17 (build 35).
*Two related TFs recognize the same motif.
A SNP lands in two partially overlapping TF binding sites.
LD between SNPs and the rs1333040 is summarized by D', $r^2$ and a P value determined by Chi-square tests the CEU hapmap sample.
nd: Measures of LD could not be ascertained for SNPs not represented in the CEU hapmap.

TABLE 28

Shown are all SNP association results from sequencing of CDKN2A and CDKN2B using primers in Table 25 and association results for early onset MI cases and controls.

| location[a] | rs names | Allele | RR | #aff | aff. freq | #con | con. freq | p-value | Variation |
|---|---|---|---|---|---|---|---|---|---|
| 21958159 | rs3088440 | A | 0.7264 | 118 | 0.080508 | 674 | 0.107567 | 0.194719 | G/a |
| 21958199 | rs11515 | C | 1.0349 | 118 | 0.161017 | 668 | 0.156437 | 0.858926 | G/c |
| 21960916 | rs3731249 | T | 1.4053 | 119 | 0.037815 | 680 | 0.027206 | 0.384391 | C/t |

TABLE 28-continued

Shown are all SNP association results from sequencing of CDKN2A and CDKN2B using primers in Table 25 and association results for early onset MI cases and controls.

| location[a] | rs names | Allele | RR | #aff | aff. freq | #con | con. freq | p-value | Variation |
|---|---|---|---|---|---|---|---|---|---|
| 21964218 | rs3731239 | A | 1.0712 | 96 | 0.619792 | 87 | 0.603448 | 0.748662 | A/g |
| 21965017 | rs3814960 | C | 0.8697 | 118 | 0.347458 | 686 | 0.379738 | 0.34197 | T/c |
| 21965319 | SG09S293 | A | 1.4498 | 119 | 0.037815 | 682 | 0.026393 | 0.344886 | T/a |
| 21965561 | rs3731238 | T | 1.2498 | 120 | 0.033333 | 689 | 0.026851 | 0.582384 | C/t |
| 21965807 | SG09S291 | A | 1.7884 | 120 | 0.058333 | 687 | 0.033479 | 0.077647 | C/a |
| 21983964 | rs2811711 | C | 0.8364 | 119 | 0.088235 | 675 | 0.103704 | 0.458559 | T/c |
| 21985882 | rs2518723 | T | 1.0818 | 65 | 0.323077 | 49 | 0.306122 | 0.784969 | C/t |
| 21993223 | rs3217992 | T | 1.3279 | 96 | 0.421875 | 86 | 0.354651 | 0.188816 | C/t |
| 21993367 | rs1063192 | A | 1.27 | 93 | 0.602151 | 80 | 0.54375 | 0.273278 | A/g |
| 21995330 | rs3217986 | T | 1.1274 | 96 | 0.921875 | 86 | 0.912791 | 0.753194 | T/g |
| 21996273 | rs2069426 | T | 1.0602 | 96 | 0.104167 | 86 | 0.098837 | 0.866531 | G/t |
| 21996348 | rs974336 | T | 1.0078 | 96 | 0.104167 | 87 | 0.103448 | 0.982048 | G/t |
| 21999698 | rs2069418 | C | 1.4107 | 93 | 0.61828 | 87 | 0.534483 | 0.107569 | C/g |
| 22000004 | rs2069416 | A | 1.6529 | 93 | 0.387097 | 85 | 0.276471 | 0.026641 | T/a/g |
| 22000004 | rs2069416 | T | 0.6509 | 93 | 0.569892 | 85 | 0.670588 | 0.050367 | T/a/g |
| 22000004 | rs2069416 | G | 0.804 | 93 | 0.043011 | 85 | 0.052941 | 0.660944 | T/a/g |
| 22000412 | rs495490 | A | 1.2051 | 95 | 0.910526 | 85 | 0.894118 | 0.600156 | A/g |
| 22000681 | SG09S492 | A | 3.587 | 94 | 0.021277 | 83 | 0.006024 | 0.206723 | G/a |

[a]location applies to NCBI build 34. Allele: the allele shown is the one tested for association to myocardial infarction.
RR is the relative risk.
aff: number of affected individuals.
Aff. freq: frequency of allele in affected individuals.
con: number of controls.
Con. freq.; frequency of allele in controls.
Variation*: Shown are the alleles of the SNPs with major allele shown with capital letters.

TABLE 29

Association to atherosclerosis in other vascular beds. Shown is the association of the SNPs, rs1333040, rs2383207 and rs10116277 to peripheral artery disease (PAD), abdominal aorta aneurysm (AAA), and to large vessel disease stroke (LVD).

| Study population (n/m)[a] | Frequency | | | |
|---|---|---|---|---|
| Variant (allele) | Controls | Cases | RR (95% CI) | P |
| Iceland PAD (1504/3533) | | | | |
| rs1333040 (T) | 0.499 | 0.503 | 1.01 (0.93-1.11) | 0.75 |
| rs2383207 (G) | 0.462 | 0.481 | 1.08 (0.99-1.18) | 0.082 |
| rs10116277 (T) | 0.421 | 0.438 | 1.07 (0.98-1.17) | 0.12 |
| Emory PAD (34/1284) | | | | |
| rs1333040 (T) | 0.573 | 0.721 | 1.92 (1.12-3.30) | 0.017 |
| rs2383207 (G) | 0.541 | 0.692 | 1.91 (1.15-3.17) | 0.012 |
| rs10116277 (T) | 0.504 | 0.676 | 2.06 (1.25-3.39) | 0.0044 |
| Iceland LVD (154/3533) | | | | |
| rs1333040 (T) | 0.499 | 0.527 | 1.12 (0.87-1.44) | 0.39 |
| rs2383207 (G) | 0.462 | 0.488 | 1.11 (0.88-1.41) | 0.38 |
| rs10116277 (T) | 0.421 | 0.457 | 1.16 (0.91-1.48) | 0.24 |
| Iceland AAA (287/3533) | | | | |
| rs1333040 (T) | 0.499 | 0.572 | 1.34 (1.12-1.60) | 0.0012 |
| rs2383207 (G) | 0.462 | 0.536 | 1.35 (1.13-1.61) | 0.00073 |
| rs10116277 (T) | 0.421 | 0.485 | 1.30 (1.09-1.54) | 0.0035 |

[a]Number of cases (n) and controls (m).
[b]Individuals used in the initial discovery group have been excluded both from cases and controls.
[c]For the combined groups, the allelic frequency in cases and controls is the weighted average over the individual groups.

TABLE 30

Association of refinement markers to MI, early-onset MI and AAA in Iceland. Shown is the association to MI, early-onset MI and AAA case-control groups for 10 of the markers included in Table 23b. All tests use the same set of 10260 controls.

| SNP | Allele | Position | MI (2270/10260) | | | | Early onset MI (621/10260) | | | |
|---|---|---|---|---|---|---|---|---|---|---|
| | | | Con. frq | Case. frq | OR | P | Con. frq | Case. frq | RR | P |
| rs10116277 | T | 22071397 | 0.419 | 0.471 | 1.23 | 3.2E−10 | 0.419 | 0.496 | 1.36 | 1.3E−07 |
| rs1333040 | T | 22073404 | 0.493 | 0.541 | 1.21 | 6.7E−09 | 0.493 | 0.576 | 1.40 | 1.3E−08 |
| rs10738607 | G | 22078094 | 0.441 | 0.497 | 1.25 | 8.4E−12 | 0.441 | 0.521 | 1.38 | 4.0E−08 |
| rs4977574 | G | 22088574 | 0.444 | 0.499 | 1.25 | 2.0E−11 | 0.443 | 0.522 | 1.37 | 8.3E−08 |
| rs6475608 | C | 22091702 | 0.683 | 0.709 | 1.13 | 1.7E−03 | 0.689 | 0.737 | 1.26 | 6.3E−04 |
| D9S1870 | X | 22093010 | 0.440 | 0.490 | 1.22 | 2.5E−09 | 0.441 | 0.513 | 1.34 | 1.2E−06 |
| rs2383207 | G | 22105959 | 0.458 | 0.511 | 1.24 | 6.5E−11 | 0.458 | 0.535 | 1.36 | 1.4E−07 |
| rs1333045 | C | 22109195 | 0.503 | 0.551 | 1.21 | 2.0E−08 | 0.506 | 0.575 | 1.32 | 3.5E−06 |

TABLE 30-continued

Association of refinement markers to MI, early-onset MI and AAA in Iceland.
Shown is the association to MI, early-onset MI and AAA case-control groups for 10 of
the markers included in Table 23b. All tests use the same set of 10260 controls.

| rs1333046 | A | 22114123 | 0.439 | 0.494 | 1.24 | 4.6E-11 | 0.440 | 0.518 | 1.37 | 8.3E-08 |
| rs10757278 | G | 22114477 | 0.435 | 0.492 | 1.26 | 2.8E-12 | 0.434 | 0.518 | 1.40 | 1.2E-08 |

| | AAA (323/10260) | | | | CAD[a] (508/10260) | | | |
|---|---|---|---|---|---|---|---|---|
| SNP | Con. frq | Case. frq | RR | P | Con. frq | Case. frq | RR | P |
| rs10116277 | 0.419 | 0.488 | 1.32 | 6.0E-04 | 0.419 | 0.456 | 1.16 | 0.024 |
| rs1333040 | 0.493 | 0.579 | 1.41 | 2.7E-05 | 0.493 | 0.519 | 1.11 | 0.130 |
| rs10738607 | 0.441 | 0.522 | 1.38 | 5.8E-05 | 0.441 | 0.474 | 1.14 | 0.043 |
| rs4977574 | 0.444 | 0.527 | 1.39 | 3.8E-05 | 0.443 | 0.474 | 1.13 | 0.056 |
| rs6475608 | 0.693 | 0.752 | 1.35 | 1.8E-03 | 0.695 | 0.722 | 1.14 | 0.110 |
| D9S1870 | 0.441 | 0.507 | 1.31 | 1.2E-03 | 0.441 | 0.471 | 1.13 | 0.073 |
| rs2383207 | 0.458 | 0.537 | 1.38 | 7.4E-05 | 0.458 | 0.487 | 1.13 | 0.068 |
| rs1333045 | 0.508 | 0.580 | 1.34 | 4.2E-04 | 0.508 | 0.554 | 1.20 | 0.007 |
| rs1333046 | 0.442 | 0.528 | 1.42 | 1.7E-05 | 0.440 | 0.472 | 1.14 | 0.053 |
| rs10757278 | 0.436 | 0.522 | 1.41 | 1.8E-05 | 0.435 | 0.474 | 1.17 | 0.016 |

[a]Known cases of MI are excluded from the CAD cases.
[b]For the microsatellite D9S1870, all alleles smaller than 2 have been combined in to a composite risk allele X.

TABLE 31

Amplimers for non-public SNPs identified in table 26.

SG09S293 (SEQ ID NO: 199)

GGAAGCAGCCCTCGCCAGAGCCAGCGTTGGCAAGGAAGGAGGACTGGGCTCCTCCCCACCTGCC

CCCCACACCGCCCTCCGGCCTCCCTGCTCCCAGCCGCGCTCCCCCGCCTGCCAGCAAAGGCGTG

TTTGAGTGCGTTCACTCTGTTAAAAAGAAATCCGCCCCCGCCCCGTTTCCTTCCTCCGCGATACAA

CCTTCC[T/a]AACTGCCAAATTGAATCGGGGTGTTTGGTGTCATAGGGAAAGTATGGCTTCTTCT

TTTAATCATAAGAAAAAGCAAAACTATTCTTTCCTAGTTGTGAGAGCCCCACCGAGAATCGAAATC

ACCTGTACGACTAGAAAGTGTCCCCCTACCCCCTCAACCCTTGATTTTCAGGAGCGCGGGGTTCA

CTAAGTCAGAAACCCTAGTTCAAAGGA

SG09S291 (SEQ ID NO: 200)

ATTGGAAGGACGGACTCCATTCTCAAAGTCATAATTCCTAGACCAGAAAAAGTGCTCAGTGTTCTA

GAAGCAGAGTTG[C/a]ACAGTGATCCAAAGACCAGCTTCAAATACTGTCCTGTCTCCTTCACACT

TCTCACATTTCTCTTTCCTACTGAAAATACCTTGCATTTTTCGTAATTATAAAGGGGAAGGGAATA

TGAGTGCCCCCTGCTTTATAGGGGTTGTTGTGAGTTTAAATGATGTATTAATACATATAAGCCTTAA

GAACAGTGCCACACATCCTAAGCTAATACCTGTTAGCTCTTGAATTATCCGCTTTGAGGACTGGCT

TGCAATCTTGTTTTGAGGCATAGAAAGAAAATGCTTTGGAGCAGGACGCGGTGGCTCACACCTGT

AATCCCAGCACTTTGGGAAGCCGAGGCGGGCA

SG09S492 (SEQ ID NO: 201)

TGAATCAACATTTATTACTTAAAATATTTAAAACATTTCAGCGGATGCTACATTGGATAGGAAGAGA

ACCGCAAGTTATGGATTTGTTGCCTAAAAACTTTGGTGAGGAACTGCATAAGTGGACCTCTCCTAA

AAGTGAACAaTTTTTGTTTACAGAATCATTTTGGTTCGGAGTGCTGAGGAAGACAAAGTCTTAACA

GGAGGGCAATTGCTTGTGTATTGCAAAATGAGAGTCTTCACATGTTTTTTTAGGATACCTTAGCT

CTGACTCCTCATCCCCCAAATCCCTGTAGAATTAAAAAAAgCTCTTTCTTTTAAAGGCAGTGGAAGT

GCCACCACCATGGAAGTGCTGGTTAGGGCTGAAAATCTACTGACAGAGCCTCAACAGAGCTGAAA

TCCACCTGGACAGG[G/a]AAGGGAACCGGGTAGCATTAATAACAATTTCTTTTTCTTTCCCATCC

AACCCCCATTTCCTAGTCTTCAGTTTCTTAATTTCTCTACCTTTTACTCTTATGCTCTTGTTTTGACC

TABLE 31-continued

Amplimers for non-public SNPs identified in table 26.

TTTGAGTTTCTCTGAAACTTATCAGAAAAGTTAGGACAAGATAGTCTGACCCAATTCTTGAGCCATT

TTCTTAGGTAGTAAATATGTCAGAAAAATGAAAGCTGTTTGGAGTTGATAAGGAAATGGAAGATAA

TGTTTTTCTTTGAGGGgGACATAAAGAATGGTGATAGGGAAAGAACCAATGACTAAGTAAAATGAC

TGAGAATCTTGCACGAGGCAGATGTGTGAGCTTCGCGAAGCAAGTTGACTGAATGAAAAACAACT

TTGGGTAGGGAAAACGTTGCCGGGGGCATTCGC

TABLE 32

Association between rs10757278 allele G and arterial diseases

| Phenotype | Frequency | | | |
|---|---|---|---|---|
| Study population (n/m) | Controls | Cases | OR (95% CI) | P |
| Abdominal Aortic Aneurysm (AAA) | | | | |
| Iceland (14259/398) | 0.437 | 0.515 | 1.37 (1.18-1.58) | $2.6 \times 10^{-5}$ |
| Belgium (267/176) | 0.527 | 0.574 | 1.21 (0.92-1.58) | 0.18 |
| Canada (150/206) | 0.470 | 0.533 | 1.29 (0.96-1.74) | 0.097 |
| Pennsylvania, US (447/101) | 0.468 | 0.549 | 1.39 (1.02-1.89) | 0.037 |
| The Netherlands (915/476) | 0.461 | 0.529 | 1.31 (1.12-1.53) | 0.00078 |
| UK (252/478) | 0.470 | 0.545 | 1.35 (1.09-1.68) | 0.0064 |
| New Zealand (442/588) | 0.474 | 0.530 | 1.25 (1.05-1.50) | 0.012 |
| All groups (16732/2836) | | | 1.31 (1.22-1.42) | $1.2 \times 10^{-12}$ |
| Intracranial Aneurysm (IA) | | | | |
| Iceland (14259/170) | 0.437 | 0.514 | 1.36 (1.10-1.69) | 0.0048 |
| The Netherlands (915/644) | 0.461 | 0.516 | 1.24 (1.08-1.43) | 0.0029 |
| Finland (307/320) | 0.400 | 0.469 | 1.33 (1.06-1.66) | 0.015 |
| All groups (15481/1134) | | | 1.29 (1.16-1.43) | $2.5 \times 10^{-6}$ |
| Peripheral Artery Disease (PAD) | | | | |
| Iceland (14259/1764) | 0.437 | 0.473 | 1.16 (1.07-1.25) | 0.00014 |
| Italy (181/179) | 0.510 | 0.499 | 0.96 (0.71-1.29) | 0.78 |
| Sweden (143/206) | 0.427 | 0.507 | 1.38 (1.02-1.87) | 0.036 |
| New Zealand (463/450) | 0.474 | 0.491 | 1.07 (0.89-1.29) | 0.47 |
| All groups (15025/2599) | | | 1.14 (1.07-1.22) | $6.1 \times 10^{-5}$ |
| LAA/Cardiogenic Stroke | | | | |
| Iceland (14259/415) | 0.437 | 0.473 | 1.16 (1.00-1.34) | 0.046 |
| Sweden (734/290) | 0.433 | 0.468 | 1.15 (0.95-1.39) | 0.16 |
| All groups (15012/705) | | | 1.15 (1.03-1.29) | 0.015 |
| Coronary Artery Disease (CAD)[a] | | | | |
| Iceland (14259/3051) | 0.437 | 0.492 | 1.25 (1.17-1.32) | $1.9 \times 10^{-12}$ |
| Atlanta (1246/840) | 0.479 | 0.544 | 1.30 (1.15-1.48) | 0.000033 |
| Philadelphia (447/724) | 0.467 | 0.547 | 1.38 (1.17-1.63) | 0.00017 |
| Durham (614/1201) | 0.455 | 0.521 | 1.30 (1.13-1.50) | 0.00018 |
| All groups (16566/5539) | | | 1.28 (1.22-1.34) | $1.2 \times 10^{-23}$ |

Association results for rs10757278 allele G for the arterial diseases: AAA, IA, PAD, combined LAA (Large Artery Atherosclerotic)/cardiogenic stroke, and CAD, and for T2D, in several study populations. Also included are the results for each phenotype after combining the study populations using a Mantel-Haenszel model. Number of controls (n) and cases (m) is shown. The results for the Icelandic population are adjusted for relatedness of the individuals.
[a]The results presented for CAD have been published previously[1] (apart from the Icelandic control group that has been increased) and are presented here for comparison of the results with the other arterial phenotypes.

TABLE 33

Association between rs10757278 allele G and arterial diseases after excluding known CAD cases from the sample sets

| Phenotype | Frequency | | | |
|---|---|---|---|---|
| Study population (n/m) | Controls | Cases | OR (95% CI) | P |
| Abdominal Aortic Aneurysm (AAA) | | | | |
| Iceland (14259/190) | 0.437 | 0.503 | 1.30 (1.06-1.60) | 0.013 |
| Belgium (267/156) | 0.527 | 0.573 | 1.20 (0.91-1.60) | 0.200 |

TABLE 33-continued

Association between rs10757278 allele G and arterial diseases after excluding known CAD cases from the sample sets

| Phenotype | Frequency | | | |
|---|---|---|---|---|
| Study population (n/m) | Controls | Cases | OR (95% CI) | P |
| Pennsylvania, US (447/62) | 0.469 | 0.513 | 1.19 (0.82-1.74) | 0.36 |
| The Netherlands (915/380) | 0.461 | 0.517 | 1.25 (1.06-1.48) | 0.0097 |
| UK (252/220) | 0.470 | 0.538 | 1.31 (1.02-1.70) | 0.038 |
| New Zealand (442/360) | 0.474 | 0.516 | 1.18 (0.97-1.44) | 0.097 |
| All groups (16639/2017) | | | 1.25 (1.14-1.37) | $3.0 \times 10^{-6}$ |
| Peripheral Artery Disease (PAD) | | | | |
| Iceland (14259/732) | 0.437 | 0.463 | 1.12 (1.00-1.25) | 0.055 |
| Italy (181/113) | 0.509 | 0.488 | 0.92 (0.66-1.28) | 0.62 |
| New Zealand (463/326) | 0.474 | 0.491 | 1.07 (0.87-1.31) | 0.51 |
| All groups (14882/1171) | | | 1.09 (0.99-1.20) | 0.075 |
| LAA/Cardiogenic Stroke | | | | |
| Iceland (14259/278) | 0.437 | 0.458 | 1.09 (0.92-1.30) | 0.32 |
| Sweden (734/213) | 0.433 | 0.467 | 1.15 (0.92-1.42) | 0.22 |
| All groups (14993/491) | | | 1.11 (0.97-1.27) | 0.12 |

Association results are shown for rs10757278-G for the arterial diseases: AAA, IA, PAD, combined LAA (Large Artery Atherosclerotic)/cardiogenic stroke, after excluding cases with known CAD. Number of controls (n) and cases (m) is shown. The results for the Icelandic population are adjusted for relatedness. No information on CAD was available for the AAA group from Canada and the PAD group from Sweden. Those study groups were excluded from this analysis. Information on the occurrence of CAD among the AAA cases was available for 97% (466 out of 479) of AAA cases from UK, 86% (87 out of 101) of cases from Pennsylvania, 45% (79 out of 176) of cases from Belgium, 69% (330 out of 476) of cases from The Netherlands, and 98% (575 out of 588) of cases from New Zealand. Among those with this information, the frequency of CAD amongst the AAA subjects was 52% in the UK group, 48% in the Pennsylvania group, 29% in the Belgium group, 29% in the Dutch group and 40% in the group from New Zealand.

TABLE 34

Genotype specific odds ratio for rs10757278 for abdominal aortic aneurysm and intracranial aneurysm

| | | Genotype Specific Odds Ratio | |
|---|---|---|---|
| Study population (n/m) | AA | AG (95% CI) | GG (95% CI) |
| Abdominal Aortic Aneurysm (AAA) | | | |
| Iceland (14259/398) | 1 | 1.22 (0.95-1.56) | 1.85 (1.39-2.45) |
| Belgium (267/176) | 1 | 1.42 (0.91-2.20) | 1.52 (0.87-2.66) |
| Canada (150/206) | 1 | 1.04 (0.69-1.57) | 1.62 (0.90-2.91) |
| Pennsylvania, US (447/101) | 1 | 2.00 (1.17-3.44) | 2.06 (1.06-4.03) |
| The Netherlands (915/476) | 1 | 1.43 (1.12-1.84) | 1.76 (1.28-2.43) |
| UK (252/478) | 1 | 1.60 (1.19-2.15) | 1.95 (1.26-3.03) |
| New Zealand (442/588) | 1 | 1.22 (0.94-1.58) | 1.50 (1.04-2.17) |
| Combined (16732/2836) | 1 | 1.36 (1.21-1.52) | 1.74 (1.49-2.02) |
| Intracranial Aneurysm (IA) | | | |
| Iceland (14259/170) | 1 | 1.39 (0.96-2.02) | 1.90 (1.24-2.93) |
| The Netherlands (915/644) | 1 | 1.34 (1.08-1.66) | 1.61 (1.20-2.16) |
| Finland (307/320) | 1 | 1.45 (1.06-1.98) | 1.79 (1.12-2.86) |
| Combined (15481/1134) | 1 | 1.38 (1.18-1.63) | 1.72 (1.39-2.13) |

Genotype specific odds ratios for rs10757278 for AAA and IA cases versus controls. Shown is the risk for heterozygous carriers (AG) and homozygous carriers (GG) compared to the risk for non-carriers (AA), together with 95% confidence intervals (CI). Results are shown for the AAA case-control groups from Iceland, Belgium, Canada, Pennsylvania, US, UK, The Netherlands and New Zealand and for all the groups combined and for the IA case-control groups from Iceland, The Netherlands and Finland. Number of controls (n) and cases (m) is shown. Tests of heterogeneity showed no significant difference in the genotype specific odds ratio between the different study groups For AAA, $P_{het} = 0.38$ and $P_{het} = 0.95$ for the AG and the GG genotype, and for IA, $P_{het} = 0.91$ and $P_{het} = 0.81$.

TABLE 35

Correlation between growth rate of AAA and genotypes for rs10757278 from the UK Small Aneurysm Trial

| Genotype of rs10757278 | n | Mean baseline diameter (mm) | Linear growth rate (mm/year) | Mean difference (95% CI) |
|---|---|---|---|---|
| AA | 79 | 45.3 | 3.20 | 0.03 (−0.38-0.41) |
| AG | 214 | 44.8 | 3.15 | reference |
| GG | 107 | 44.7 | 2.53 | −0.46 (−0.93-0.00) |

Linear growth rates were determined as previously described[16]. At least three AAA diameter measurements and growth rate were available for 400 patients who had been genotyped for rs10757278 and n is the number of individuals with the different genotypes. The largest group (AG) was set as the reference group and then the growth rates in the other genotype groups were compared with the mean of the reference group. This leads to estimation of the mean difference [95% CI] of the growth rates in the homozygous groups. The analysis of the average difference was adjusted for age, sex, smoking status, baseline diameter and curvature in growth pattern. In this cohort there were 24 ruptured AAA; 6 with the AA genotype, 14 with AG, and 4 with GG.

TABLE 36

Association of SNPs in chromosome 9p21 region to MI in African-Americans. We tested 9 SNPs for association with MI in African Americans. These SNPs included 2 SNPs from the genome-wide scan on MI in Icelanders (rs10116277 and rs2383207) and rs10757278, which showed strongest association with MI in Caucasians, as well as six other SNPs that were correlated with rs10757278 in Caucasians. As shown in the Table all, SNPs have greater frequency in cases compared to the control groups and the odds ratios are comparable to that for Caucasians.

| SNP | Allele | Position | Combined[a] RR (95CI) | Pa | Philadelphia (93/139) Con. frq | Case. frq | OR | P | Durham (262/243) Con. frq | Case. frq | RR | P |
|---|---|---|---|---|---|---|---|---|---|---|---|---|
| rs8181050 | A | 22054391 | 1.30 (0.91-1.86) | 0.14 | 0.921 | 0.920 | 0.99 | 0.98 | 0.912 | 0.926 | 1.20 | 0.43 |
| rs10116277 | T | 22071397 | 1.37 (1.05-1.80) | 0.022 | 0.889 | 0.893 | 1.05 | 0.89 | 0.870 | 0.901 | 1.35 | 0.13 |
| rs10738607 | G | 22078094 | 1.12 (0.92-1.35) | 0.27 | 0.238 | 0.290 | 1.31 | 0.22 | 0.233 | 0.254 | 1.12 | 0.43 |
| rs4977574 | G | 22088574 | 1.20 (0.97-1.48) | 0.096 | 0.175 | 0.250 | 1.57 | 0.051 | 0.184 | 0.204 | 1.13 | 0.430 |
| rs2383207 | G | 22105959 | 1.34 (1.03-1.74) | 0.027 | 0.881 | 0.877 | 0.96 | 0.88 | 0.872 | 0.906 | 1.43 | 0.078 |
| rs1333045 | C | 22109195 | 1.22 (1.04-1.43) | 0.014 | 0.455 | 0.497 | 1.18 | 0.38 | 0.472 | 0.525 | 1.24 | 0.093 |
| rs1333046 | A | 22114123 | 1.19 (0.99-1.44) | 0.069 | 0.227 | 0.294 | 1.42 | 0.11 | 0.257 | 0.291 | 1.18 | 0.24 |
| rs10757278 | G | 22114477 | 1.19 (0.98-1.45) | 0.08 | 0.183 | 0.257 | 1.54 | 0.059 | 0.194 | 0.223 | 1.20 | 0.250 |
| rs1333048 | C | 22115347 | 1.16 (0.96-1.40) | 0.12 | 0.277 | 0.301 | 1.13 | 0.57 | 0.288 | 0.321 | 1.17 | 0.25 |

| SNP | Cleveland (46/81) Con. frq | Case. frq | RR | P | Atlanta (91/357) Con. frq | Case. frq | RR | P |
|---|---|---|---|---|---|---|---|---|
| rs8181050 | 0.887 | 0.913 | 1.34 | 0.51 | 0.934 | 0.967 | 2.08 | 0.075 |
| rs10116277 | 0.856 | 0.891 | 1.39 | 0.41 | 0.886 | 0.934 | 1.82 | 0.049 |
| rs10738607 | 0.228 | 0.244 | 1.09 | 0.77 | 0.226 | 0.220 | 0.97 | 0.87 |
| rs4977574 | 0.160 | 0.163 | 1.02 | 0.95 | 0.173 | 0.187 | 1.10 | 0.68 |
| rs2383207 | 0.877 | 0.880 | 1.04 | 0.93 | 0.888 | 0.945 | 2.18 | 0.015 |
| rs1333045 | 0.416 | 0.435 | 1.08 | 0.78 | 0.473 | 0.544 | 1.33 | 0.094 |
| rs1333046 | 0.204 | 0.213 | 1.06 | 0.86 | 0.240 | 0.258 | 1.10 | 0.61 |
| rs10757278 | 0.160 | 0.152 | 0.94 | 0.86 | 0.187 | 0.198 | 1.07 | 0.74 |
| rs1333048 | 0.251 | 0.304 | 1.30 | 0.37 | 0.283 | 0.303 | 1.10 | 0.61 |

[a]Results for the four African-American cohorts are combined using a Mantel-Haenzsel model. Shown is the association to MI in four African-American MI case-control groups for 9 markers in the chromosome 9p21LD-block (LD Block C09). These SNPs are correlated in Caucasians. The markers include 2 SNPs from the genome-wide scan (rs10116277 and rs2383207) and rs10757278 that showed strongest association with MI in Caucasians, and six other correlated SNPs.

TABLE 37

Key to sequence listing.

| Sequence | SEQ ID NO: |
|---|---|
| rs7041637 | 1 |
| rs3218020 | 2 |
| rs3217992 | 3 |
| rs1063192 | 4 |
| rs2069418 | 5 |
| rs2069416 | 6 |
| rs573687 | 7 |
| rs545226 | 8 |
| rs10811640 | 9 |
| rs10811641 | 10 |
| rs2106120 | 11 |
| rs2106119 | 12 |
| rs643319 | 13 |
| rs7044859 | 14 |
| rs10757264 | 15 |
| rs10965212 | 16 |
| rs1292137 | 17 |
| rs10811644 | 18 |
| rs7035484 | 19 |
| rs10738604 | 20 |
| rs615552 | 21 |
| rs543830 | 22 |
| rs1591136 | 23 |
| rs7049105 | 24 |
| rs679038 | 25 |
| rs10965215 | 26 |
| rs564398 | 27 |
| rs10115049 | 28 |
| rs634537 | 29 |
| rs2157719 | 30 |
| rs2151280 | 31 |
| rs1008878 | 32 |
| rs1556515 | 33 |
| rs1333037 | 34 |
| rs1360590 | 35 |

TABLE 37-continued

Key to sequence listing.

| Sequence | SEQ ID NO: |
|---|---|
| rs1412829 | 36 |
| rs1360589 | 37 |
| rs7028570 | 38 |
| rs944801 | 39 |
| rs10965219 | 40 |
| rs7030641 | 41 |
| rs10120688 | 42 |
| rs2184061 | 43 |
| rs1537378 | 44 |
| rs8181050 | 45 |
| rs8181047 | 46 |
| rs10811647 | 47 |
| rs1333039 | 48 |
| rs10965224 | 49 |
| rs10811650 | 50 |
| rs10811651 | 51 |
| rs4977756 | 52 |
| rs10757269 | 53 |
| rs9632884 | 54 |
| rs1412832 | 55 |
| rs10116277 | 56 |
| rs10965227 | 57 |
| rs6475606 | 58 |
| rs1333040 | 59 |
| rs1537370 | 60 |
| rs7857345 | 61 |
| rs10738607 | 62 |
| rs10757272 | 63 |
| rs4977574 | 64 |
| rs2891168 | 65 |
| rs1537371 | 66 |
| rs1556516 | 67 |
| rs6475608 | 68 |
| rs7859727 | 69 |
| rs1537373 | 70 |

TABLE 37-continued

Key to sequence listing.

| Sequence | SEQ ID NO: |
|---|---|
| rs1333042 | 71 |
| rs7859362 | 72 |
| rs1333043 | 73 |
| rs1412834 | 74 |
| rs7341786 | 75 |
| rs10511701 | 76 |
| rs10733376 | 77 |
| rs10738609 | 78 |
| rs2383206 | 79 |
| rs944797 | 80 |
| rs1004638 | 81 |
| rs2383207 | 82 |
| rs1537374 | 83 |
| rs1537375 | 84 |
| rs1333045 | 85 |
| rs10738610 | 86 |
| rs1333046 | 87 |
| rs10757278 | 88 |
| rs1333047 | 89 |
| rs4977575 | 90 |
| rs1333048 | 91 |
| rs1333049 | 92 |
| rs1333050 | 93 |
| LD Block C09 | 94 |

The invention claimed is:

1. A method for determining a susceptibility to arterial disease in a human individual, comprising
analyzing a nucleic acid sample from the human individual for allele G of polymorphic marker rs10757278,
detecting the presence of the allele G of polymorphic marker rs10757278 in the nucleic acid sample,
determining an increased genetic susceptibility to arterial disease for the human individual from the presence of the allele G of polymorphic marker rs10757278 in the nucleic acid sample, and
administering to the human individual determined to have the increased genetic susceptibility to arterial disease at least one agent selected from statins, beta blockers, calcium channel blockers, antihypertensive agents, diuretics, antiplatelet agents, and anticoagulants.

2. The method according to claim 1, that comprises administering to the individual at least one anticoagulant selected from heparin and low molecular weight heparin.

3. The method of claim 1 that comprises administering to the individual at least one antiplatelet agent selected from aspirin and clopidogrel.

4. The method according to claim 1 that comprises administering to the individual at least one beta blocker selected from metoprolol and carvedilol.

5. The method according to claim 1, further comprising assessing the frequency of a haplotype in the individual, wherein the haplotype comprises the polymorphic marker.

6. The method of claim 1, further comprising assessing at least one biomarker in a sample from the individual.

7. The method of claim 6, wherein the at least one biomarker is a cardiac marker or an inflammatory marker.

8. The method of claim 6, wherein the at least one biomarker is selected from creatine kinase, troponin, glycogen phosphorylase, C-reactive protein (CRP), serum amyloid A, fibrinogen, interleukin-6, tissue necrosis factor-alpha, soluble vascular cell adhesion molecules (sVCAM), soluble intervascular adhesion molecules (sICAM), E-selectin, matrix metalloprotease type-1, matrix metalloprotease type-2, matrix metalloprotease type-3, matrix metalloprotease type-9, serum sCD40L, leukotrienes, leukotriene metabolites, interleukin-6, tissue necrosis factor-alpha, myeloperoxidase (MPO), and N-tyrosine.

9. The method of claim 8, wherein the at least one biomarker is a leukotriene selected from LTB4, LTC4, LTD4 and LTE4.

10. The method according to claim 1, wherein the arterial disease is at least one of myocardial infarction, coronary artery disease, restenosis, peripheral arterial disease, stroke, abdominal aorta aneurysm and intracranial aneurysm.

11. The method according to claim 10, wherein the arterial disease is at least one of myocardial infarction, coronary artery disease, restenosis, intracranial aneurysm and abdominal aorta aneurysm.

12. The method according to claim 10, wherein the arterial disease is large artery atherosclerotic stroke or cardiogenic stroke.

13. The method according to claim 10, wherein the arterial disease is an early onset myocardial infarction.

14. The method according to claim 1, wherein the arterial disease is myocardial infarction and/or coronary artery disease with an onset before age 50 for males or age 60 for females.

15. The method according to claim 1, wherein the analyzing comprises contacting nucleic acid from the individual with an oligonucleotide probe, wherein the probe comprises a contiguous segment 5-100 nucleotides in length of the nucleotide sequence set forth in SEQ ID NO: 88 or the complement of SEQ ID NO: 88.

16. The method of claim 1, wherein the step of analyzing the nucleic acid sample comprises at least one technique selected from: polymerase chain reaction, allele-specific hybridization, allele-specific primer extension, allele-specific amplification, nucleic acid sequencing, 5'-exonuclease digestion, molecular beacon assay, oligonucleotide ligation assay, size analysis, and single-stranded conformation analysis.

17. The method of claim 1, comprising calculating a risk score that includes a genetic susceptibility calculation based on the detection of the presence of the allele G of polymorphic marker rs10757278.

18. The method of claim 17, that comprises determining an increased genetic susceptibility to arterial disease for the individual with a relative risk or odds ratio attributed to the presence of the allele G of polymorphic marker rs10757278 of at least 1.2.

19. The method of claim 17, further comprising making a communication that includes the risk score available to the individual, to a physician or healthcare worker, or to a genetic counselor.

20. The method of claim 19, wherein the communication is made available by a secured internet interface.

21. The method according to claim 18, further comprising assessing at least one cardiac or inflammatory biomarker for the individual selected from the group consisting of creatine kinase, troponin, glycogen phosphorylase, C-reactive protein (CRP), serum amyloid A, fibrinogen, interleukin-6, tissue necrosis factor-alpha, soluble vascular cell adhesion molecules (sVCAM), soluble intervascular adhesion molecules (sICAM), E-selectin, matrix metalloprotease type-1, matrix metalloprotease type-2, matrix metalloprotease type-3, matrix metalloprotease type-9, serum sCD40L, leukotrienes, leukotriene metabolites, interleukin-6, tissue necrosis factor-alpha, myeloperoxidase (MPO), and N-tyrosine; and
calculating a combined risk for arterial disease from the genetic susceptibility and the at least one cardiac or inflammatory biomarker, using a multiplicative model.

22. The method according to claim 18, further comprising assessing at least one medical risk factor for the individual selected from the group consisting of smoking, hyperlipidemia, hypertension, diabetes, serum total cholesterol, serum LDL, and serum HDL; and
calculating a combined risk for arterial disease from the genetic susceptibility and the at least one medical risk factor, using a multiplicative model.

23. The method of claim 1, further comprising communicating the susceptibility determination to at least one entity selected from the group consisting of the individual, a genetic counselor, a physician, and a healthcare worker.

24. The method of claim 1, wherein the determining susceptibility is performed using an apparatus for determining a genetic indicator for arterial disease in a human individual, the apparatus comprising:
a computer readable memory, and
a routine stored on the computer readable memory, and
a processor specifically program to execute the routine:
to analyze marker information for a human individual with respect to the polymorphic marker, and
to generate an output based on the marker information, wherein the output comprises a risk measure of the marker as a genetic indicator of arterial disease for the human individual.

25. The method of claim 24, wherein the routine further comprises an indicator of the frequency of the allele G of the polymorphic marker rs10757278 in a plurality of individuals diagnosed with arterial disease, and an indicator of the frequency of the allele G of the polymorphic marker rs10757278 in a plurality of reference individuals, and wherein the risk measure is based on a comparison of the marker status for the human individual and a relative risk or odds ratio calculated from the frequencies of the allele G in the pluralities of individuals.

26. The method of claim 1, wherein the analyzing of the nucleic acid comprises at least one technique selected from the group consisting of allele-specific probe hybridization and DNA sequencing.

27. The method of claim 1, further comprising physical examination of the human individual identified as having increased genetic susceptibility to arterial disease, for symptoms or evidence of arterial disease.

28. The method of claim 1, wherein the individual has not been diagnosed with arterial disease.

29. The method according to claim 1, that comprises administering a statin to the individual.

30. The method according to claim 1, wherein the individual is Caucasian, as self-reported by the individual.

31. In a medical protocol for arterial disease assessment, prevention, or management for a human individual that includes evaluating the human individual with respect to at least one classical risk factor or non-genetic marker measurement, the improvement that comprises:
analyzing a nucleic acid sample from the human individual for allele G of polymorphic marker rs10757278,
detecting the presence of the allele G of polymorphic marker rs10757278 in the nucleic acid sample,
determining an increased genetic susceptibility to arterial disease for the human individual attributable to the presence of the allele G of polymorphic marker rs10757278,
calculating a combined risk for arterial disease from the genetic susceptibility and the classical risk factor or non-genetic marker measurement, using a multiplicative model, and
administering to the human individual at least one agent selected from statins, beta blockers, calcium channel blockers, antihypertensive agents, diuretics, antiplatelet agents, and anticoagulants.

32. The improvement according to claim 31 that comprises evaluating at least one classical risk factor selected from smoking, hyperlipidemia, hypertension, and diabetes in the human individual.

33. The improvement according to claim 31 that comprises evaluating the individual with respect to at least one classical risk factor selected from weight, bone mineral density (BMD), previous diagnosis, or family history of cardiovascular disease.

34. The improvement according to claim 31 that comprises evaluating the individual with respect to measurement of a non-genetic marker selected from homocysteine, C-reactive protein, B-type natriuretic peptide (BNP), serum amyloid A, and myeloperoxidase (MPO).

35. The improvement according to claim 31 that comprises evaluating the individual with respect to one or more non-genetic or classical risk factors selected from smoking, hyperlipidemia, hypertension, diabetes, age, gender, ethnicity, socioeconomic status, weight, bone mineral density (BMD), previous diagnosis, family history of cardiovascular disease, fibrinogen, PAI-1, homocysteine, asymmetric dimethylarginine, C-reactive protein, B-type natriuretic peptide (BNP), serum amyloid A, interleukin-6, soluble vascular cell adhesion molecules (sVCAM), soluble intervascular adhesion molecules (sICAM), E-selectin, matrix metalloprotease type-1, matrix metalloprotease type-2, matrix metalloprotease type-3, matrix metalloprotease type-9, serum sCD40L, a leukotriene, a leukotriene metabolite, interleukin-6, soluble vascular cell adhesion molecules (sVCAM), soluble intervascular adhesion molecules (sICAM), E-selectin, myeloperoxidase (MPO), and N-tyrosine.

36. The improvement of claim 31, that comprises administering to the individual at least one anticoagulant selected from heparin and low molecular weight heparin.

37. The improvement of claim 31 that comprises administering to the individual at least one antiplatelet agent selected from aspirin and clopidogrel.

38. The improvement of claim 31 that comprises administering to the individual at least one beta blocker selected from metoprolol and carvedilol.

39. The improvement of claim 31 that comprises administering a statin to the individual.

40. A method of using a nucleic acid sample isolated from a human individual to measure a susceptibility to arterial disease, the method comprising:
analyzing the nucleic acid sample for allele G of polymorphic marker rs10757278,
detecting the presence of said allele G of polymorphic marker rs10757278,
measuring an increased genetic susceptibility to arterial disease for the human individual from the presence of the allele G of polymorphic marker rs10757278 in the nucleic acid sample; and
administering to the human individual determined to have the increased genetic susceptibility to arterial disease at least one agent selected from statins, beta blockers, calcium channel blockers, antihypertensive agents, diuretics, antiplatelet agents, and anticoagulants.

41. The method according to claim 40, wherein the human individual has not been diagnosed with arterial disease.

42. The method according to claim 40 comprising detecting the presence of the allele G of polymorphic marker rs10757278 by sequencing or by contacting the nucleic acid with an oligonucleotide probe, wherein the probe comprises a contiguous segment 5-100 nucleotides in length of the nucleotide sequence set forth in SEQ ID NO: 88, or the complement thereof.

43. The method of claim 40, further comprising communicating the measurement of susceptibility to at least one entity selected from the group consisting of the individual, a genetic counselor, a physician, and a healthcare worker.

44. The method of claim 40, further comprising physical examination of the human individual identified as having increased genetic susceptibility to arterial disease, for symptoms or evidence of arterial disease.

45. The method according to claim 40, wherein the arterial disease is at least one of myocardial infarction, coronary artery disease, restenosis, peripheral arterial disease, stroke, abdominal aorta aneurysm and intracranial aneurysm.

46. The method according to claim 45, wherein the individual has not been diagnosed with the arterial disease.

47. The method according to claim 45, wherein the arterial disease is an early onset myocardial infarction before age 50 for males or age 60 for females.

48. The method according to claim 45, wherein the analyzing comprises at least one technique selected from: polymerase chain reaction, allele-specific hybridization, allele-specific primer extension, allele-specific amplification, nucleic acid sequencing, 5'-exonuclease digestion, molecular beacon assay, oligonucleotide ligation assay, size analysis, and single-stranded conformation analysis.

49. The method according to claim 45, wherein the analyzing comprises contacting nucleic acid from the individual with an oligonucleotide probe, wherein the probe comprises a contiguous segment 5-100 nucleotides in length of the nucleotide sequence set forth in SEQ ID NO: 88 or the complement of SEQ ID NO: 88.

50. The method of claim 45, further comprising physical examination of the human individual identified as having increased genetic susceptibility to arterial disease, for symptoms or evidence of arterial disease.

51. The method according to claim 45, that comprises administering a statin to the individual.

52. The method of claim 45, further comprising communicating the susceptibility determination to at least one entity selected from the group consisting of the individual, a genetic counselor, a physician, and a healthcare worker.

53. The method according to claim 40, wherein the step of determining the increased genetic susceptibility includes calculating a risk score for the human individual that includes a relative risk (RR) or odds ratio (OR) of at least 1.2 attributed to the allele G of polymorphic marker rs10757278 being present in the nucleic acid sample from the individual.

54. The method of claim 53, wherein the determining susceptibility is performed using an apparatus for determining a genetic indicator for arterial disease in a human individual, the apparatus comprising:
  a computer readable memory,
  a routine stored on the computer readable memory, and
  a processor specifically programmed to execture the routine: to analyze marker information for a one human individual with respect to the polymorphic marker, and to generate an output based on the marker information, wherein the output comprises a risk measure of the marker as a genetic indicator of arterial disease for the human individual.

55. The method of claim 40, that comprises administering to the individual at least one anticoagulant selected from heparin and low molecular weight heparin.

56. The method of claim 40 that comprises administering to the individual at least one antiplatelet agent selected from aspirin and clopidogrel.

57. The method of claim 40 that comprises administering to the individual at least one beta blocker selected from metoprolol and carvedilol.

\* \* \* \* \*

UNITED STATES PATENT AND TRADEMARK OFFICE
CERTIFICATE OF CORRECTION

PATENT NO. : 9,617,597 B2
APPLICATION NO. : 12/302538
DATED : April 11, 2017
INVENTOR(S) : Anna Helgadottir et al.

Page 1 of 1

It is certified that error appears in the above-identified patent and that said Letters Patent is hereby corrected as shown below:

On the Title Page

At item (57), Lines 3-4, "aneurysm restenosis" should be -- aneurysm, restenosis --.

In the Claims

In Claim 1, Column 451, Line 10, "comprising" should be -- comprising: --.

In Claim 8, Column 451, Lines 44-45, "interleukin-6, tissue necrosis factor-alpha" should be deleted.

In Claim 8, Column 451, Line 50, "tissue necrosis factor" should be -- tumor necrosis factor --.

In Claim 21, Column 452, Lines 45-46, "interleukin-6, tissue necrosis factor-alpha" should be deleted.

In Claim 21, Column 452, Line 51, "tissue necrosis factor" should be -- tumor necrosis factor --.

In Claim 24, Column 453, Line 5, "memory, and" should be -- memory, --.

In Claim 35, Column 454, Lines 20-22, "interleukin-6, soluble vascular cell adhesion molecules (sVCAM), soluble intervascular adhesion molecules (sICAM), E-selectin", should be deleted.

In Claim 40, Column 454, Line 45, "sample;" should be -- sample, --.

In Claim 54, Column 456, Line 15, "execture" should be -- execute --.

Signed and Sealed this
Eighteenth Day of September, 2018

Andrei Iancu
*Director of the United States Patent and Trademark Office*

```
                        SEQUENCE LISTING

<160> NUMBER OF SEQ ID NOS: 201

<210> SEQ ID NO 1
<211> LENGTH: 201
<212> TYPE: DNA
<213> ORGANISM: Homo sapiens

<400> SEQUENCE: 1
tttcgcaatg cttattttca atttcttcag aaatgcctta aagatattaa tggaggtaac      60
aacttaatct caaatagtaa tccatagaca gaatatgtaa magcaatgtt ctctgatctg     120
ttctttggct tctattccct agagaaatag ttctctaaga ccaaacagtc tatagataga     180
attgtagcaa cagtcaatta t                                               201

<210> SEQ ID NO 2
<211> LENGTH: 201
<212> TYPE: DNA
<213> ORGANISM: Homo sapiens

<400> SEQUENCE: 2
gtggagagaa aatgattata ctttgagcta tatggctcca ataaacaaag atagatccct      60
caatttaaat ttgatcctca gaaaactgag ggtcagagaa yccctcaggc atgacgggat     120
aatgtgacag ttaatttggt atgtcaactt ggctaggctg tggtacccag tgtttgagtc     180
aaacaccagt ctaaatattg c                                               201

<210> SEQ ID NO 3
<211> LENGTH: 201
<212> TYPE: DNA
<213> ORGANISM: Homo sapiens

<400> SEQUENCE: 3
agtactatat tacactgttt tttttgtttg ttttgttagt ttttttatt taaagcaaac       60 ctcaaacatt attgggtatc aattaccacc tggttgtatt raaatagtaa cttatcaatg     120
ccatgtaaaa attaattcca ttttcgaagc cacctggcag acaggtttag ctgtttcatc     180
agcagcctaa tatatactgt t                                               201

<210> SEQ ID NO 4
<211> LENGTH: 201
<212> TYPE: DNA
<213> ORGANISM: Homo sapiens
```

<400> SEQUENCE: 4
cattatactg ggtcatgaaa aattatccct tgaaatagat atgaaacatg ttacttcatt        60
tctggtttaa ataacttgtg gaatctttcc taatgacaac ytgatattaa gggaaactaa       120
agaaaatgtt attgtggatc ccacagtact atattacact gttttttttg tttgttttgt       180 tagtttttt tatttaaagc a                                                  201

<210> SEQ ID NO 5
<211> LENGTH: 201
<212> TYPE: DNA
<213> ORGANISM: Homo sapiens

<400> SEQUENCE: 5
tgatacaagt tatgaaactt gtgaagccca agtactgcct ggggatgaat ttaacttgta        60
tgacaggtgc agagctgtcg ctttcagaca tcttaagaaa sacggagtta ttttgaatga       120
ctttctctcg gtcacaaggg agccaccaac gtctccacag tgaaaccaac tggctggctg       180
aaggaacaga aatcctctgc t                                                 201

<210> SEQ ID NO 6
<211> LENGTH: 201
<212> TYPE: DNA
<213> ORGANISM: Homo sapiens

<400> SEQUENCE: 6
aaataaaaat aagatacctg acaaagtggg tttaaatagg taagagtgca aacaaagatt        60
tactgtacaa atatgatgaa actgggatct cagattctta hagtataatt ttttttttgtc      120 ttatgtgtgc caggttgcca ctctcaatct cgaactagtt ttttctctt ttaagggttg        180 tatccataat gcaaaaatgg a                                                 201

<210> SEQ ID NO 7
<211> LENGTH: 201
<212> TYPE: DNA
<213> ORGANISM: Homo sapiens

<400> SEQUENCE: 7
gtccaagaca aatgtgctat tgtattacat gtgaaatgtc atctttgaag tctggtaagg        60
gtgtgctgtg aggtgagcca tctggaaaac acagtgtaga ytgaaaaata attataagcc       120
agtttattac tttttttccag ttaagcctac catgacagct gctaaaaaaa acactatgta      180
gtataaaggg taaaaagact c                                                 201

<210> SEQ ID NO 8
<211> LENGTH: 201
<212> TYPE: DNA
<213> ORGANISM: Homo sapiens

<400> SEQUENCE: 8
ggggtgcagg ttgttggtgt ggccacactt cttcttgcgg caattgacag catagggggtg       60 caggagagca tagcgcttat ggcagatcat cttgtttcag ytgtatttct aggtgagctg       120
gaagagtgaa ggctcaataa tgccacctcg caggtgcagc accaggtgcg gggtgggctg       180
tttctggacg ttgtagtctg a                                                 201

<210> SEQ ID NO 9
<211> LENGTH: 201
<212> TYPE: DNA
<213> ORGANISM: Homo sapiens

```
<400> SEQUENCE: 9
tcttaatttt tacacatttt acttttcatt tcttttaaa ctgttattaa taatttattc      60
atttgaataa ggattaaaat aaggctagga tattgaaatt ygttgaaatt gctacagtct    120
cttgtatctc tctctctctc ttttttttct tataagggac aggtttcatt caccttgtcg    180
accaggctgg agtgcaatac t                                              201

<210> SEQ ID NO 10
<211> LENGTH: 201
<212> TYPE: DNA
<213> ORGANISM: Homo sapiens

<400> SEQUENCE: 10
tgtgattcta gcagccatgg ataattattt catagattat tattttcttg gggatggcaa     60
aatggtgata ttctaatttt actattcctt catttactag stggaatgtc tttttaaatt   120
atttatttat ttatttatta tttgagacag agtcttgcac tgtcacccag gctggagtgc   180
agtggtgtga tcatagctca c                                              201

<210> SEQ ID NO 11
<211> LENGTH: 201
<212> TYPE: DNA
<213> ORGANISM: Homo sapiens

<400> SEQUENCE: 11
tgcgcgcctc ggcctcccaa agtgctggga ttacaggcgt gagccactgc gcctcgccaa     60
cttccttatt ttaaatgcca tttcccacta aaaataaaac magtaattct ttgaaaaaaa   120
gttaatatta tgtataggac tggaagtata taagataaaa ctggaatata ttgtcatacc   180
agaaatcaaa gattttgtca a                                              201

<210> SEQ ID NO 12
<211> LENGTH: 201
<212> TYPE: DNA
<213> ORGANISM: Homo sapiens

<400> SEQUENCE: 12
attactgatg tgacaaggta cacaagccaa tgttgacata atgttttcaa aatgggtgt      60 ctgctgtaac tgaactaaat ataataactt tattcaagaa ygagtttcaa tgataggaca   120
aaacttgata aaatgaataa ataaataatt atatgccaga gttcagtaaa ccctgtgtgt   180
acacctgaaa aagctcaaac t                                              201

<210> SEQ ID NO 13
<211> LENGTH: 201
<212> TYPE: DNA
<213> ORGANISM: Homo sapiens

<400> SEQUENCE: 13
gaacagagca gaagagagtc tggatacaca aatttcacaa ttattggctc ccatcaacat     60
atctaactca agcataaagt tgtttcagca gtagtttaag yttggttact aatgcaacac   120
ctctttgcat gcaatggccc attaaattat cttcaacttt aaaaggttcc tttgttttta   180
aatgcttata atgaacaaat a                                              201

<210> SEQ ID NO 14
<211> LENGTH: 201
<212> TYPE: DNA
```

<213> ORGANISM: Homo sapiens

<400> SEQUENCE: 14

| | |
|---|---|
| tatgtgatgt aaagagcgcc aacatgttta tatcctccta tttcaatcta cttttacttc | 60 |
| atctacattt ttagcaataa tgtgaacatg aaatcttgaa waattagcta tctgtaatat | 120 |
| atttactcat ccactcaaaa tattgagccc ccccaataaa tatcatacac tatattctag | 180 |
| gtacaggtga taaacaattc a | 201 |

<210> SEQ ID NO 15
<211> LENGTH: 201
<212> TYPE: DNA
<213> ORGANISM: Homo sapiens

<400> SEQUENCE: 15

| | |
|---|---|
| ccagtgaaag ttagagagag gggtctagag ctcagggagg agtgtgtatc cctaatttag | 60 |
| actaatttgc attaacagct gtagtaatgc aattttctct rtactgaaat gcagacattt | 120 |
| gagtatagaa aattagcaga catttgaata tagaagaaag atttactttc cttcagaaaa | 180 |
| agaatagtag agtataaaga a | 201 |

<210> SEQ ID NO 16
<211> LENGTH: 201
<212> TYPE: DNA
<213> ORGANISM: Homo sapiens

<400> SEQUENCE: 16

| | |
|---|---|
| tcgtgccact gcactccagc ctgggtgagt tgagagtccg tatcaaaagc aaacctacac | 60 |
| attttttgtgg cctgttttta gctctatcaa gtcagttaca wtcttctgta ttctagcttt | 120 |
| tttatctgta agctcctgca atgctttatt agaattttta gttcctttgc attttgttac | 180 |
| aacatactcc tataactctg c | 201 |

<210> SEQ ID NO 17
<211> LENGTH: 169
<212> TYPE: DNA
<213> ORGANISM: Homo sapiens

<400> SEQUENCE: 17

| | |
|---|---|
| taaaagaaaa aataatccaa atgtcagcaa cctcaaagat tgaaggtaga tgagcccaca | 60 |
| aagataagaa ataatcagca caagaacact gaaaactcaa wacatcacct ctctggcaag | 120 |
| cgttcagtac caggctgagg ctgagatggc tgaaatgata gaagcagaa | 169 |

<210> SEQ ID NO 18
<211> LENGTH: 201
<212> TYPE: DNA
<213> ORGANISM: Homo sapiens

<400> SEQUENCE: 18

| | |
|---|---|
| caagaccact ctgcagatat caagtctgaa aattccccta gggccaaagt ctattatggg | 60 |
| agcaagttga gcctagaggg atcgccatcc ctgtccatgc wctgctgtag acactcctgc | 120 |
| actaaaccct ctgggctcca catcagctgg cttgctgctc taccactttg cttgtctctt | 180 |
| gggggctcca ccccagagag a | 201 |

<210> SEQ ID NO 19
<211> LENGTH: 201
<212> TYPE: DNA
<213> ORGANISM: Homo sapiens

<400> SEQUENCE: 19

```
gtctcttggg ggctccaccc cagagagatg tgggtcagca atcattcagt tcaatcagcc    60
caggatggag agtctgtgct atgggcccaa gccaggggct stctgtctgg tgacgagcag   120
ctgggggtg gggtgggacc tgtgggagat ggactggcct cctctccttg agtcaactgc   180
tgcttattgg aggtgtggat g                                             201
```

<210> SEQ ID NO 20
<211> LENGTH: 201
<212> TYPE: DNA
<213> ORGANISM: Homo sapiens

<400> SEQUENCE: 20

```
ccattgcaga ggtagtggca gagaggcttt cagttgtccg tggcggctct gtccagggag    60
ttgctgagtt gctattggct tgatatctct ggtggggtgt rgctagaggt ccaggcctgg   120
aggacctgct cgttgaagag atgtgggaat gggcacccac ataacagtct gttcactttt   180
ccatagggct gctgtagtat g                                             201
```

<210> SEQ ID NO 21
<211> LENGTH: 201
<212> TYPE: DNA
<213> ORGANISM: Homo sapiens

<400> SEQUENCE: 21

```
ggggagctta agcaggggtg aagggaac cccagcacag aacagctgcc cgacaaaaat    60
gtggccacac tgcttttttt tttttttag caggtcccca rtcccgttcc tcatcactgg   120
gtagagtctc ccatctgggg tccccggcta ccccaactgg tgttctctga ctgagagagg   180
tttcagactt ccatgggacc t                                             201
```

<210> SEQ ID NO 22
<211> LENGTH: 201
<212> TYPE: DNA
<213> ORGANISM: Homo sapiens

<400> SEQUENCE: 22

```
tgggcaaaag tagctgcgac tttggcaaag ctggaggtta gacccccaaa catacccag     60
gaggttagac tccatacat accccagaaa agaggctgaa wccagcgaga tcagcagaga   120
aggtctacag gccccacttc cacagcgcct cacaggataa gacccactgg cttggaattc   180
cagctagcca ccagtagcaa c                                             201
```

<210> SEQ ID NO 23
<211> LENGTH: 201
<212> TYPE: DNA
<213> ORGANISM: Homo sapiens

<400> SEQUENCE: 23

```
aagtggtaag tgaatgcgca actctgggaa tccacactgc tctcacagat ctttgcaaac    60
ctcagatcag gagatcccct tgtgaactca ctccattagg sccttcacac acagccacgt   120
ggagtctcag cagagcagcc actcaggcat gcatggagac ccaagagctt tagctactcc   180
agctttctgg gtgtctgggc a                                             201
```

<210> SEQ ID NO 24
<211> LENGTH: 201
<212> TYPE: DNA

<213> ORGANISM: Homo sapiens

<400> SEQUENCE: 24

| | |
|---|---|
| cttaacagca aagtatcaga ttcatttata aaacaatgtg actgatcttt atgtatggtt | 60 |
| tgtgaaacat ttatgcagtg tcacttcaga aaactctgcc rttatagatt tgaattgatt | 120 |
| aaggatatcc actcctttcc ttggcatgat acaaataaat tactaaagta taattgtaac | 180 |
| aatgataaat ataagtgaca a | 201 |

<210> SEQ ID NO 25
<211> LENGTH: 201
<212> TYPE: DNA
<213> ORGANISM: Homo sapiens

<400> SEQUENCE: 25

| | |
|---|---|
| caccctttgg ggaaggggat caaaatatag tgattttcta attctaagat tcgttctgtg | 60 |
| tatattagct gctattcttc tagaaagaag actttcacca ycgtcccttg gatttttttt | 120 |
| tttaattttt gtatggttta aattgcatca tcattctttt tgatgtccaa attgtcccaa | 180 |
| attaagccag ttagagaaac a | 201 |

<210> SEQ ID NO 26
<211> LENGTH: 201
<212> TYPE: DNA
<213> ORGANISM: Homo sapiens

<400> SEQUENCE: 26

| | |
|---|---|
| taatgggatt cctgatggaa tgtttagtct gaatctaatc acatagagac ttgtctgaca | 60 |
| aatccagatt ttttggatgt tttgcaggac tatttgccac racatttcaa aggattccaa | 120 |
| gagagaatat tggtgtccat gctgtgatga ttcctcagct cctctcatct gatctccgtc | 180 |
| ctggcccccca tgactttctt t | 201 |

<210> SEQ ID NO 27
<211> LENGTH: 201
<212> TYPE: DNA
<213> ORGANISM: Homo sapiens

<400> SEQUENCE: 27

| | |
|---|---|
| ctcttctttt atcacacaga cctgaaagat gatggtttcc caaacagcac ttacagcaat | 60 |
| aggtgtgggc ctcagtggca cataccacac cctaactacc rcaaagaaag tcatgggggc | 120 |
| caggacggag atcagatgag aggagctgag gaatcatcac agcatggaca ccaatattct | 180 |
| ctcttggaat cctttgaaat g | 201 |

<210> SEQ ID NO 28
<211> LENGTH: 201
<212> TYPE: DNA
<213> ORGANISM: Homo sapiens

<400> SEQUENCE: 28

| | |
|---|---|
| caaatctttc cctaagggag atttcagatg aggcccccag ccttggtaga caccttgatt | 60 |
| gcagtcttgt gagagattgt gaagcagagc tattctcaga rttcatgggt gtttttaagct | 120 |
| atgaggtttt ttttgggggg agaatggtca tttgtgattc agctatacat aagtctacaa | 180 |
| aagtcattcc agaagtgatt c | 201 |

<210> SEQ ID NO 29
<211> LENGTH: 201

```
<212> TYPE: DNA
<213> ORGANISM: Homo sapiens

<400> SEQUENCE: 29
tggggctcac aaccacatga ttctacctcc actgaatcac ttctggaatg acttttgtag    60
acttatgtat agctgaatca caaatgacca ttctccccc maaaaaaacc tcatagctta   120
aaacacccat gaattctgag aatagctctg cttcacaatc tctcacaaga ctgcaatcaa   180
ggtgtctacc aaggctgggg g                                            201

<210> SEQ ID NO 30
<211> LENGTH: 201
<212> TYPE: DNA
<213> ORGANISM: Homo sapiens

<400> SEQUENCE: 30
tttttatagt gtgactcatt tacatatgca tgtgtatgtt taggtgctat tattaaattt    60
tgctggcata tagtgaggaa attgtgattc aaattcgtcc rtatgtactc ctcccccacc   120
atctgctctg cccctccatt taccagaagg ctagctttag ctacttgtgc atgtaaaaca   180
gaagcaagca acactgtgaa a                                            201

<210> SEQ ID NO 31
<211> LENGTH: 201
<212> TYPE: DNA
<213> ORGANISM: Homo sapiens

<400> SEQUENCE: 31
gaacatagat actccttcat tcatgtattg tctatgggtg agtctttatt acaacagcag    60
agatgagtag ttgtgacaga aactcgatgg ccctcaaaag ygaaacaagc tactatcagg   120
acctctatag aaaaagtttg ccaacctcta cactgtagta tgccttaagg attttttagaa  180 gattgagtat gataaacact t                                            201

<210> SEQ ID NO 32
<211> LENGTH: 201
<212> TYPE: DNA
<213> ORGANISM: Homo sapiens

<400> SEQUENCE: 32
gaagggatga tcagtccttc cctcctctat tttcttgagc cccgttttc acctttcttt     60 ttctctctcc tttcttatca tgaagaataa agacaaatga kaacagatct accttaggct   120
gatacagggc agggaatcca tttaataata aaacgtgggt caaaattcac ttttctcctt   180
ttgaattgaa attatattgt g                                            201

<210> SEQ ID NO 33
<211> LENGTH: 201
<212> TYPE: DNA
<213> ORGANISM: Homo sapiens

<400> SEQUENCE: 33
atttgatgca acttacacac tgttgttata cctctagaat taaaatgaca atttttaaa     60 taattttggg gggcctagat ttgctatttta acctatcaaa raattgtgtc ttacagtatt  120
attcaaatgt agtgtgtaaa gacttatact attggtccta agcactactg gttgttttag   180 gcttttttctc tttctctgta g                                           201

<210> SEQ ID NO 34
```

```
<211> LENGTH: 201
<212> TYPE: DNA
<213> ORGANISM: Homo sapiens

<400> SEQUENCE: 34
acatttatat aattaagatg ctaacactga ctgacagaaa tgtcagtaag atgaaatcag      60
actgcatggg agttttatgt tacattaatt tgtaaattgt rtatctctgt attcatgtga     120
gtgtggctat catgatgtta gacatccagc tacaaaggag gcattcgtgc acacacacag    180
tctccaatct tctgtttacc t                                               201

<210> SEQ ID NO 35
<211> LENGTH: 201
<212> TYPE: DNA
<213> ORGANISM: Homo sapiens

<400> SEQUENCE: 35
tagacaaagt ttaatgttcc cttttatatg ttttcctggt aaacaaaaat tgtctcaggg      60
ttattatgca tatatgatat tgtcaagaaa ctttctgggt rctgtgggc aaagtcttct     120 ccataaataa gctagggttg attggagttt tcactttgaa aaatatcgca caggaggatc    180
tcaacagcta gacaatttcc a                                               201

<210> SEQ ID NO 36
<211> LENGTH: 201
<212> TYPE: DNA
<213> ORGANISM: Homo sapiens

<400> SEQUENCE: 36
aaattaaatg acatacgtaa agtcctcaat aaataatagc tcttattacc attgctatgg      60
ttactatcac tatttctgta ttttcttttg ccattcctca ygcttgaata tgaatctcat     120
gggtagagtt tcccaaagca tgatatgtgt agtactacta aaggcaagat tttgggtgca    180
tacagacaaa aaaataattt a                                               201

<210> SEQ ID NO 37
<211> LENGTH: 201
<212> TYPE: DNA
<213> ORGANISM: Homo sapiens

<400> SEQUENCE: 37
aaaccagagg agtaaaattc tactttcacc agtaattagc agtgtggagt tgagtaaata      60
aacctctcta agtctcagtt tctacatcta ctaaatctaa rcaaattcaa aacagtgatt     120
atttcattag attagatatt ttgattagtc ttaaatgtct aatatataat aaacactcaa    180
caggtagtag ctattctatg t                                               201

<210> SEQ ID NO 38
<211> LENGTH: 201
<212> TYPE: DNA
<213> ORGANISM: Homo sapiens

<400> SEQUENCE: 38
tcatttcttc ttttaaggtc ttaatttctt gttttcgag tttcatggga gatatccagt      60
caccaatcca atccatatcg gggaaaagta caacaaatga rtgaaatttg taaccaacct    120
tggatgatgg aataagacat ttgggagaac acaggagaag tggggaggtt aaggagggat    180
agctctgtga aaattttgca t                                               201
```

<210> SEQ ID NO 39
<211> LENGTH: 201
<212> TYPE: DNA
<213> ORGANISM: Homo sapiens

<400> SEQUENCE: 39

```
aactaattct ccaaatttgc aatttggcag catcctactg ggactctaga aggctgataa        60
atcatggaga gtaggtattc ataggaac tatgaaagct statgtagta aacactactt        120
aagaaggcct tacatttcat aaaaagttgg agattttgt ggagactcat aaaatgcatc       180
ctttatatca gtgaagtttt t                                                  201
```

<210> SEQ ID NO 40
<211> LENGTH: 201
<212> TYPE: DNA
<213> ORGANISM: Homo sapiens

<400> SEQUENCE: 40

```
actcgtagcc agagctacct tccagatgac ttctttctac cactttcttt cttcccagtg        60
taagagaatg caagtatatg ctgatgtttg gagcaagaac rttcaaaaat tttcttatta       120
acataacttc taatggaaat acagtatact actatggtgc atacaaagaa gaaatagcaa       180
catatatttg ttttagacct g                                                  201
```

<210> SEQ ID NO 41
<211> LENGTH: 201
<212> TYPE: DNA
<213> ORGANISM: Homo sapiens

<400> SEQUENCE: 41

```
ataagcagcc ttaaattaaa aaaaaaaag ttaactcata actaactgtg tgacctggga        60
taagttactg accctcttta gggcttaggg tcctaatctg yaaaacggaa attataataa       120
taaccttagc tagcatttct tgtgcacata ctataagctg gtgataaaca atttatacac       180
actatctcat ttaatcctca c                                                  201
```

<210> SEQ ID NO 42
<211> LENGTH: 201
<212> TYPE: DNA
<213> ORGANISM: Homo sapiens

<400> SEQUENCE: 42

```
tccaatgcaa aagaataata ggagcaaaag cacagtggtg agaaattgga ggggaactgt        60
gaaaattgcc acatagatta gaggcaggaa aataaaggac rgctaagttt atatagtgaa       120
cagtgagccg catggacaca ggtgactgtt ttctcctttt tgaacccctg cttactccag       180
agtcaccacc tctcctggct t                                                  201
```

<210> SEQ ID NO 43
<211> LENGTH: 201
<212> TYPE: DNA
<213> ORGANISM: Homo sapiens

<400> SEQUENCE: 43

```
tattctgagt attaattcct gtttccaaat agattactct tttaaacata gcactactac        60
ttacctaatg aaatttagtt gctattaatg gatgaatttt ktatctaaca ggcttgattt       120
tgattatgca ttttaaatgt cagtcagaca catattaata atgatccatg tttgtagcta       180
ataggcccaa tatatacttt t                                                  201
```

```
<210> SEQ ID NO 44
<211> LENGTH: 201
<212> TYPE: DNA
<213> ORGANISM: Homo sapiens

<400> SEQUENCE: 44
gtaagggctg ggacaaataa acacaagtaa ttttcaaata tattaataat aatattctga      60
gtattaattc ctgttttccaa atagattact cttttaaaca yagcactact acttacctaa    120
tgaaatttag ttgctattaa tggatgaatt ttgtatctaa caggcttgat tttgattatg    180
cattttaaat gtcagtcaga c                                              201

<210> SEQ ID NO 45
<211> LENGTH: 201
<212> TYPE: DNA
<213> ORGANISM: Homo sapiens

<400> SEQUENCE: 45
tggtggtcct aaagtggcat taaggagcca ataaattgtc attcctacct tagctctgtg     60
tcagatgaaa tacacagcat agtgtgggga gaaaatgttg rgcttattgg ggatggggtc   120
tttcacataa aggaagaagg tttcagaagg catagtggta tgaaaagagg agaaaccaaa   180
gggaggaagg tcaataaagg g                                              201

<210> SEQ ID NO 46
<211> LENGTH: 201
<212> TYPE: DNA
<213> ORGANISM: Homo sapiens

<400> SEQUENCE: 46
cagcatagtg tggggagaaa atgttgggct tattggggat ggggtctttc acataaagga     60
agaaggtttc agaaggcata gtggtatgaa aagaggagaa rccaaaggga ggaaggtcaa   120
taaagggtta agaacgaggg gaggcaaatt gactttcttt cagcatatga ggattatagg   180
aatggaaacc ttaattggaa t                                              201

<210> SEQ ID NO 47
<211> LENGTH: 201
<212> TYPE: DNA
<213> ORGANISM: Homo sapiens

<400> SEQUENCE: 47
gaggatttaa tgcaattgtt tgtgggaaag cactttaaca actctaaatt acgatatata     60
tgctaggttt tattgttacc cacacctttg atgtatttct stttgtactc ttcactgtat   120
ctgtaacaca ttccctagga taattagggc taccctttaa caaagccaag attctattta   180
tagtggtaag ctggcacctg g                                              201

<210> SEQ ID NO 48
<211> LENGTH: 201
<212> TYPE: DNA
<213> ORGANISM: Homo sapiens

<400> SEQUENCE: 48
cttctgctat tgaacgaact ttttgttaag gtagctccca agcaggttca gtagctttgt     60
tctattatca cttttctact gacagtgatt ttttccttt saaggcctgg gacatggaga    120
ctgcttttct gcagaaacca catcccttgg agtaatgagc tacacctacc tcaattattc   180
agtgcagtac aacactccag g                                              201
```

<210> SEQ ID NO 49
<211> LENGTH: 201
<212> TYPE: DNA
<213> ORGANISM: Homo sapiens

<400> SEQUENCE: 49

```
acattgtgca catgtaccct agaacttaaa gtataataat aaacaaaaaa aaccactgca    60
caatctctag tattcagatg gagactaagc atgattttc wtataaaaga gcagatcaga   120
atgttgtatc ttttattcag aagactggag ttaatcactg ttatctttag tacttagtgc   180
tgccaaggct gtgtgttcac a                                             201
```

<210> SEQ ID NO 50
<211> LENGTH: 201
<212> TYPE: DNA
<213> ORGANISM: Homo sapiens

<400> SEQUENCE: 50

```
acagagtgct tatttaaaga aaaataaaaa gaacacacac acacacgcac gcacacacac    60
acgcacgcac acacacacac atgtagctac atgtctagga rggatgtgga gagctgaaat   120
atgaaggcaa aataaaacat cttttcaaa gtatacagcc tacagtggtt agcacagagc    180
tggccacata gcaggggttt c                                             201
```

<210> SEQ ID NO 51
<211> LENGTH: 201
<212> TYPE: DNA
<213> ORGANISM: Homo sapiens

<400> SEQUENCE: 51

```
caataatgta gaagcaaaga gcctaaagtg ttttcataaa tcttaagtgg tagctttatg    60
ttccagttca gcaaaacaca aatttgaagg caatctgtac rttagggttc aggtgaagaa   120
ggcaaaggaa tcaatgaaat tgtaaaagct ttccaaattt gccttttctc ttaagattgt   180
ctttctctca ttctcttctc c                                             201
```

<210> SEQ ID NO 52
<211> LENGTH: 201
<212> TYPE: DNA
<213> ORGANISM: Homo sapiens

<400> SEQUENCE: 52

```
tttctgtagc agaagtgtaa gggtgttact cgtaggaggc ctctattgaa ctcttttcca    60
gtgacgtagt gtgtggtctt taagtggctt tgcaatgata rtaagatcag cattgcatta   120
ctgaatgagc tcctttagta aacgtggata tgtgctttct gaatctattt gtttgttttt   180
cccaagtcat aaacagtgaa t                                             201
```

<210> SEQ ID NO 53
<211> LENGTH: 201
<212> TYPE: DNA
<213> ORGANISM: Homo sapiens

<400> SEQUENCE: 53

```
ccatttagag tacttgcctc tgagggaaat aaaaatttgc tagcaatttt ctctaaatga    60
cattatcata ggcacttaat tccttgatag gttcttttag rtaatttttt tataatgaag   120
caattaattt gattcacgaa agtaagtttc tagtttatat aaagaccaga tctggcctat   180
```
ttcttagctt gtctacattt g                                              201

<210> SEQ ID NO 54
<211> LENGTH: 201
<212> TYPE: DNA
<213> ORGANISM: Homo sapiens

<400> SEQUENCE: 54
tgctagcaat tttctctaaa tgacattatc ataggcactt aattccttga taggttcttt    60
tagataattt ttttataatg aagcaattaa tttgattcac saaagtaagt ttctagttta   120
tataaagacc agatctggcc tatttcttag cttgtctaca tttgagtagt tccattgctg   180
gaaaatgacc ctggagcttt t                                             201

<210> SEQ ID NO 55
<211> LENGTH: 201
<212> TYPE: DNA
<213> ORGANISM: Homo sapiens

<400> SEQUENCE: 55
aagttgctct caacatactt aaagttttcc aataactgaa ttaaatatca gtttatcagt    60
ttaatataaa caattagggt aaatgaaaat aaaatttcag ytctttggtt ccattagcca   120
tggttcagga gcagaatagt cacctgaggc tagtgacaac gcttttggat cacaggaaag   180
aagaaaaaaa atcaaaataa t                                             201

<210> SEQ ID NO 56
<211> LENGTH: 201
<212> TYPE: DNA
<213> ORGANISM: Homo sapiens

<400> SEQUENCE: 56
ttataactaa tgaggcaatg tgtcttgagt attttgaatt aactctctag aatcgattct    60
tggggaggtt atttactttg aagtgatgga cagagtgtag kagatttatg agtgaactct   120
tgtctgattt ggaaatatag agttgtttag gctaggtatt accaacccaa agttgacact   180
tgagtcacct aagttcttct c                                             201

<210> SEQ ID NO 57
<211> LENGTH: 201
<212> TYPE: DNA
<213> ORGANISM: Homo sapiens

<400> SEQUENCE: 57
tattagttgt gtaatcttga aaaaatctct gacacttttc cctctgactc agtttcccca    60
tctggcaccc aatctttac agtgttatga aaaataggga raatgtagaa aggaagaaca   120
tggcacccaa tccttaatgg acactcagtg aaagctggct atcatcatca tttttggggt   180
tgttgtgttc tacaaatgta t                                             201

<210> SEQ ID NO 58
<211> LENGTH: 201
<212> TYPE: DNA
<213> ORGANISM: Homo sapiens

<400> SEQUENCE: 58
tccccatctg gcacccaatc ttttacagtg ttatgaaaaa tagggaaaat gtagaaagga    60
agaacatggc acccaatcct taatggacac tcagtgaaag ytggctatca tcatcatttt   120
tggggttgtt gtgttctaca aatgtatttt cccaggagtt ttttttactc tgtctcctct   180

```
ttccttcata taccccagc c                                               201

<210> SEQ ID NO 59
<211> LENGTH: 201
<212> TYPE: DNA
<213> ORGANISM: Homo sapiens

<400> SEQUENCE: 59
tgggaaggat gaattaatgg gatggagtgc aggggatgca gagtgcccac ttatggaatg    60
atttcattca agagagacag gagggtcaga ggtaagaatg ytaccgctgg gacagagagg   120
aaggtacaga tatgagatat ggtaagaagg tatactacaa cagtggctcc caaatctcaa   180
tgagtagcca gttctcatgg a                                             201

<210> SEQ ID NO 60
<211> LENGTH: 201
<212> TYPE: DNA
<213> ORGANISM: Homo sapiens

<400> SEQUENCE: 60
tttgagccca agtctctttc tgactctagg cttagagctt tagggctatt tcacaaaagg    60
gctgttccta ggtcaggcat gacaacttct atattacctt ygtaaagaa gcaatataat   120 ctaccactat taaattttgc aggttaattt tatattatgt ttaaatacag aaaactttat   180
ttaaaactca gttgaatttc t                                             201

<210> SEQ ID NO 61
<211> LENGTH: 201
<212> TYPE: DNA
<213> ORGANISM: Homo sapiens

<400> SEQUENCE: 61
gaaactggat ccctgatgac attgaaccat tgactgaatc taccctggaa ccatcaggaa    60
ataatcctta gttttttaaa gatgctttta gttgtgtttt ytattacaag tacctgaaag   120
catcctaact aatcaatgct aaatgcatct ctcacagttt atgcttattt ttcagaaatg   180
cctagtggaa atttctattg c                                             201

<210> SEQ ID NO 62
<211> LENGTH: 201
<212> TYPE: DNA
<213> ORGANISM: Homo sapiens

<400> SEQUENCE: 62
tccttccact gactgagact atttccttgc cacaatcaga agaactaaaa gaaaggagga    60
tatctgttaa tatatgaatt tatctaaatg tcatgcagtg rcttctaaaa tcatctggtg   120
tgctctgttt ccccttggag gtgacttagg cctggcatcc caaacaatac atactggagt   180
gaagctccag gaaaccctga g                                             201

<210> SEQ ID NO 63
<211> LENGTH: 201
<212> TYPE: DNA
<213> ORGANISM: Homo sapiens

<400> SEQUENCE: 63
atacatactg gagtgaagct ccaggaaacc ctgaggagaa gagaagggct taaagagcaa    60
tcagccttcg attgctggga ttatgaaagg tcgtaagaag ygaatgttgc aatgttttat   120
```

| | |
|---|---|
| tatacttgat attgaagcaa ggacaagtaa taatttatta ttctctccat gtcagtggta | 180 |
| tttacctttt tggaatcatg t | 201 |

<210> SEQ ID NO 64
<211> LENGTH: 201
<212> TYPE: DNA
<213> ORGANISM: Homo sapiens

<400> SEQUENCE: 64

| | |
|---|---|
| ataaaaataa aataaaataa aaaatgaaaa acaaagtcca cttgtaacca catgtcagta | 60 |
| gcatgtttgc tttcagggta catcaaatgc attctatagc rcaggatgtt ccagtcactc | 120 |
| taacaaaaga tgtcctgttt ggaacaccaa ctctgtatca gttacttcag acactttctc | 180 |
| tcattgagtc ccttcagcaa g | 201 |

<210> SEQ ID NO 65
<211> LENGTH: 201
<212> TYPE: DNA
<213> ORGANISM: Homo sapiens

<400> SEQUENCE: 65

| | |
|---|---|
| aaccacatgt cagtagcatg tttgctttca gggtacatca aatgcattct atagcacagg | 60 |
| atgttccagt cactctaaca aaagatgtcc tgtttggaac rccaactctg tatcagttac | 120 |
| ttcagacact ttctctcatt gagtcccttc agcaagccct tttaggttta tgttcttaga | 180 |
| tgaggaaacc aagtcttaga a | 201 |

<210> SEQ ID NO 66
<211> LENGTH: 201
<212> TYPE: DNA
<213> ORGANISM: Homo sapiens

<400> SEQUENCE: 66

| | |
|---|---|
| atattttctt gttttttagat gcacatatac gtactttttt agctggtcat ttctttctga | 60 |
| aattggaatg aatcttacaa tcaatggcat gttataattt mattggcagc attatttgtc | 120 |
| tcttaagggc ccccaaataa tagtgtgtca cataactgat agcatctcaa attagatgaa | 180 |
| atacagtagt ccaggcaaga a | 201 |

<210> SEQ ID NO 67
<211> LENGTH: 201
<212> TYPE: DNA
<213> ORGANISM: Homo sapiens

<400> SEQUENCE: 67

| | |
|---|---|
| gttatgggat aaaggcgata gtattttatt gactatattt tattcttta attattcctc | 60 |
| taatttctta aaacaacttt attgaggtat aacttccacg statatttc acccatttta | 120 |
| agtgcatgaa ttcagtgatt tttagtagag tcattgagta gtgtaaccat tcctacaatg | 180 |
| gttatagcac atttttatca t | 201 |

<210> SEQ ID NO 68
<211> LENGTH: 201
<212> TYPE: DNA
<213> ORGANISM: Homo sapiens

<400> SEQUENCE: 68

| | |
|---|---|
| tgttttcttt tattttcct tctaaaataa tcacacgttt cattgcaacc ctaaccctct | 60 |
| tcaacacaca cacacacaca cacacacaca cacacacaca yggcttctag attctacatg | 120 |

```
tacaagagtg caaatcaaac taccatagaa aaactaagaa gagaggccta gaagcaagag    180
gctgatacac tatctcaggc t                                              201

<210> SEQ ID NO 69
<211> LENGTH: 201
<212> TYPE: DNA
<213> ORGANISM: Homo sapiens

<400> SEQUENCE: 69
aaccaacact taaaatgcag ggaatttaag ataaaaattt gataaaaatg ggaagatttg     60
gccgtattgg gctcatggta actgagatgc atctgaatga yaggcattcc tttgaattgc    120
acatttgctc ttgttttttac tataggccac tctcactttc tgttttttttc cccggctttg   180 aaacgatcag ttttagtact g                                              201

<210> SEQ ID NO 70
<211> LENGTH: 201
<212> TYPE: DNA
<213> ORGANISM: Homo sapiens

<400> SEQUENCE: 70
atgactgggc aattatgtca ttatcaccac tgatatatag ctggaagagt ttagtgttgc     60
cctgctaaga tctggatttt cttttctgga gcttggctat kggggcattg agaagtccag    120
ccaggaggtt ggtcagaggc taacccaaaa agctttgctt aactctgggc tacagctggg    180
ggttgccaga gagaagtgcc t                                              201

<210> SEQ ID NO 71
<211> LENGTH: 201
<212> TYPE: DNA
<213> ORGANISM: Homo sapiens

<400> SEQUENCE: 71
aatttatttg agtagacagc caaccccctg tattgtactc ctttaaaaaa tattttaggc     60
tttttaaatg ctgaggcaag gggacatacc aaacactaac rggcacattg gggttttctg    120
gctattgaaa taaaaatgtc cttacataac actgatgtac tggaatagca ctgcgttcca    180
gtgacggtta ttgcaactca g                                              201

<210> SEQ ID NO 72
<211> LENGTH: 201
<212> TYPE: DNA
<213> ORGANISM: Homo sapiens

<400> SEQUENCE: 72
ggagcatgat gtgctttgat ttcaactatg ggctttatta cttactaact gggttacttt     60
ggttaagttg tttgactctt gttttttgag atggagtcag yctgggagac tccagctctg    120
tcgcccaggc cggagtgcaa tggcacgatc ttggctcact gcaacctctg cctcccggat    180
acaagcgatt ctcatgcctt a                                              201

<210> SEQ ID NO 73
<211> LENGTH: 201
<212> TYPE: DNA
<213> ORGANISM: Homo sapiens

<400> SEQUENCE: 73
ctggcacaaa gtaggcactt catatataaa agctgtgatt attgatgaac cagtagtgag     60
```

```
gtacataact ggggaaggag aaggggccag tttgtgggaa wgcttttta gttattaata      120 gtaaggtggt aaaataataa tagtaataat aaccaaaagt tactgaaaac taaatacagt      180
gctaaactct ttaaaaggag t                                                201

<210> SEQ ID NO 74
<211> LENGTH: 201
<212> TYPE: DNA
<213> ORGANISM: Homo sapiens

<400> SEQUENCE: 74
cttctttagc tgtaaataag taattgtatg aggtgatggt taaggtgatt tactaatttt      60
acaattctat tattttatga atagacccta gttaggatag yttgaaatag atacttaatc      120
cactattatt ctctcttcta agatatagtt actagttgat catacttttc cttaaaggct      180
gaactgaatt ctctgatatc a                                                201

<210> SEQ ID NO 75
<211> LENGTH: 201
<212> TYPE: DNA
<213> ORGANISM: Homo sapiens

<400> SEQUENCE: 75
gaaacatact ggttaatgga attccagaaa ggactgaaca atcaaaccat tttgaaggac      60
agcatagagc tggactctag aacagccaaa acaaggggtt maaccactgc gagggatctc      120
tctccaactc ttgctcaggc ttttctccct ggcttgactt tcttctcttt cactgtagat      180
tggcttctct cacatggcaa g                                                201

<210> SEQ ID NO 76
<211> LENGTH: 201
<212> TYPE: DNA
<213> ORGANISM: Homo sapiens

<400> SEQUENCE: 76
tattatgtgt ggctgactat ataaaaacat ggatattttc ttggaatcac ttggtttgac      60
tgggagaaga ccattctcaa aacaaaggaa gtgcaattta yagaaggtag tagaataggc      120
agataaaaca ataattcttc actatattgc tcaaataatc cccatgacat ttttagtata      180
ttataaagag agttctaaag t                                                201

<210> SEQ ID NO 77
<211> LENGTH: 201
<212> TYPE: DNA
<213> ORGANISM: Homo sapiens

<400> SEQUENCE: 77
gagaaagatg ttaagatgaa attagatgtg caagagattc gccgaggtaa accttgtggg      60
agaaaatgga gaggtacata gaggagcctg ggcagactgt stggctacta tgtaagactc      120
atccccatga aggagaaagg agaggaaggc aaagaagaaa aaccttaaga tttcaattct      180
aagaacgttt tgacaaagct g                                                201

<210> SEQ ID NO 78
<211> LENGTH: 201
<212> TYPE: DNA
<213> ORGANISM: Homo sapiens

<400> SEQUENCE: 78
tgtgcaagag attcgccgag gtaaaccttg tgggagaaaa tggagaggta catagaggag      60
```

```
cctgggcaga ctgtgtggct actatgtaag actcatcccc rtgaaggaga aaggagagga    120
aggcaaagaa gaaaaacctt aagatttcaa ttctaagaac gttttgacaa agctgattag    180
gagtatttaa ggcaaagctg c                                              201
```

<210> SEQ ID NO 79
<211> LENGTH: 201
<212> TYPE: DNA
<213> ORGANISM: Homo sapiens

<400> SEQUENCE: 79

```
aaatacttta actcatggcc cgatgatttt cagttaacca aattctccct tactatcctg     60
gttgcccctt ctgtcttttc cttagaaatg ttattgtagt rtttgcaaga tggcctgaat    120 cctgaaccc ccatcttcaa tgagcaccaa atggtaatta tagattccca gctgtagagc    180
tatgtcagac aaaggaaact t                                              201
```

<210> SEQ ID NO 80
<211> LENGTH: 201
<212> TYPE: DNA
<213> ORGANISM: Homo sapiens

<400> SEQUENCE: 80

```
ctcttccttg gtggcttaaa gttaggctga agaagattta cattatgttg tgcatgacct     60
ctttagtttg gttctactta tactttcaag gagggaagac yggggaaggt gtcccttagt    120
gagcatattt tgtacaaatg aaaacagggt actaacactt atgccaggac gcatgcataa    180
actaggatgg ttctgagaaa a                                              201
```

<210> SEQ ID NO 81
<211> LENGTH: 201
<212> TYPE: DNA
<213> ORGANISM: Homo sapiens

<400> SEQUENCE: 81

```
agaaccttaa tgggagcaca ggtcccaccc accccttgct accccatgta cttgttccca     60
tcttcaccca agagaggaaa cactctggaa ctagggcagc wtaagtgaag cagagtgaaa    120
aggaatgtga agttttgaga agaaagaaaa ggctaaagtg tctatctttc cacattgctt    180
ttttcaggtt tctcttcgga a                                              201
```

<210> SEQ ID NO 82
<211> LENGTH: 201
<212> TYPE: DNA
<213> ORGANISM: Homo sapiens

<400> SEQUENCE: 82

```
gatgaaaaat tcatattcat ctgaatttta taagtgaatc atgagaactc aaagatactt     60
agcccctggg accattttt actcctgttc ggatcccttc rgctaagcat gattatttac    120
tattttcagc tattagttat gtcttgttga aaaagtatga aaagagctgc ccaataaatt    180
agagtgtatg ctcaacattc t                                              201
```

<210> SEQ ID NO 83
<211> LENGTH: 201
<212> TYPE: DNA
<213> ORGANISM: Homo sapiens

<400> SEQUENCE: 83

```
ttcggatccc ttcagctaag catgattatt tactattttc agctattagt tatgtcttgt    60
tgaaaaagta tgaaaagagc tgcccaataa attagagtgt rtgctcaaca ttctcttagc   120
ttctttatct ctttccaaaa ttggatcaaa tgacattgga catgatcaac ttcttactgt   180
tttgacaaac atctgaggat a                                             201
```

<210> SEQ ID NO 84
<211> LENGTH: 201
<212> TYPE: DNA
<213> ORGANISM: Homo sapiens

<400> SEQUENCE: 84

```
ttatttacta ttttcagcta ttagttatgt cttgttgaaa agtatgaaa agagctgccc    60 aataaattag agtgtatgct caacattctc ttagcttctt yatctctttc caaaattgga   120
tcaaatgaca ttggacatga tcaacttctt actgttttga caaacatctg aggatacttt   180
tataattgat aatttggact a                                             201
```

<210> SEQ ID NO 85
<211> LENGTH: 201
<212> TYPE: DNA
<213> ORGANISM: Homo sapiens

<400> SEQUENCE: 85

```
ttttgtgcct cagtttcctc attcaatatg ggtgtaataa ctgtgcctgt cttgtaggat    60
tattgtgagg cccaagtgca ataatatata gtacactgtg yctggcatct agtaagcatt   120
cattaagatg acatgaagat aacacagata tatcttaaca tgtaattatg attttgctta   180
ttcaaggcca agcattccaa t                                             201
```

<210> SEQ ID NO 86
<211> LENGTH: 201
<212> TYPE: DNA
<213> ORGANISM: Homo sapiens

<400> SEQUENCE: 86

```
gaagaagaag acagtcagag agaagtgagg gcttactttt catgtttaaa gtctgttatg    60
tggtaaaggg attagattta tctgtgttgt tccaggggac mgaaatagga caaatggatg   120
caaatagagt gaggaagatt taaaacaaat ggagaagaca ttctaaaatc aactacaatg   180
agcgtaaaca atgacaacgg a                                             201
```

<210> SEQ ID NO 87
<211> LENGTH: 201
<212> TYPE: DNA
<213> ORGANISM: Homo sapiens

<400> SEQUENCE: 87

```
tcatatgcat agacaaatac accaaactga tgaatatttg ccttgtataa tcttttgta    60 gttttttat gaacatatat tactcaaaca atttagaaca wttggcaata tatatatatt   120
tcatttataa aaggttagga agattaatta cactttctga ggtcgcaact aaaagccaag   180
attttaatcc atttctattt g                                             201
```

<210> SEQ ID NO 88
<211> LENGTH: 201
<212> TYPE: DNA
<213> ORGANISM: Homo sapiens

<400> SEQUENCE: 88

```
agtgtcactg gaaagtgaca aagaggacag ttaagttagt tggaactgaa ctgaggccag      60
acagggctgt gggacaagtc agggtgtggt cattccggta rgcagcgatg cagaatcaag     120
acagagtagt ttctccttct ctctctctct ttaattgtaa cgccttttat aacaaacaaa     180
tattatgctt atttctgtct t                                               201

<210> SEQ ID NO 89
<211> LENGTH: 201
<212> TYPE: DNA
<213> ORGANISM: Homo sapiens

<400> SEQUENCE: 89
cagttaagtt agttggaact gaactgaggc cagacagggc tgtgggacaa gtcagggtgt      60
ggtcattccg gtaagcagcg atgcagaatc aagacagagt wgtttctcct tctctctctc     120
tctttaattg taacgccttt tataacaaac aaatattatg cttatttctg tctttaaatt     180
ttttgtagta atttctcatc a                                               201

<210> SEQ ID NO 90
<211> LENGTH: 201
<212> TYPE: DNA
<213> ORGANISM: Homo sapiens

<400> SEQUENCE: 90
ttttctagtt gagctatcat tcatatttat tatgtggaac tagaggtagt cctggctact      60
tgggaacagc gtggagtcta gccatgtcag ggccagaagt sgtctcagct aagttagaat     120
gtgataccat tgtttacaca agtgtggcct gccttcaaga tagggtgagg tgttttatga     180
ccacaggctt tatgagttat a                                               201

<210> SEQ ID NO 91
<211> LENGTH: 201
<212> TYPE: DNA
<213> ORGANISM: Homo sapiens

<400> SEQUENCE: 91
tgactctgaa gatcataccc gaagtagagc tgcaaagata tttggaatat tggtaatatc      60
caataaagaa tgaccttcat gctattttga ggagatgttt maatgtcgaa ttattgaaat     120
atttataaaa tacaaataaa ctaactctgc ttcatattcc aacttgtgta tgacacttct     180
taggctatca tttcattcca a                                               201

<210> SEQ ID NO 92
<211> LENGTH: 201
<212> TYPE: DNA
<213> ORGANISM: Homo sapiens

<400> SEQUENCE: 92
ttccaacttg tgtatgacac ttcttaggct atcatttcat tccaaattta tggtcactac      60
cctactgtca ttcctcatac taaccatatg atcaacagtt saaaagcagc cactcgcaga     120
ggtaagcaag atatatggta aatactgtgt tgacaaaagt atgcagaagc agtcacattt     180
atacagtagt gaaggaaatg t                                               201

<210> SEQ ID NO 93
<211> LENGTH: 201
<212> TYPE: DNA
<213> ORGANISM: Homo sapiens
```

<400> SEQUENCE: 93

```
aattacagta tatctaaaaa aagaataata tataacaact gaaaaaataa aatagttgat      60
ataagcagat attccaagat ctgccagaca tattgttaaa ygaaaatct agatacaaaa     120
ttgtttatag ttctctttca tactatagcc aaagaaaatt cagaaaaaac tacttacagt    180
tgatccttga ataatgcagc a                                               201
```

<210> SEQ ID NO 94
<211> LENGTH: 229836
<212> TYPE: DNA
<213> ORGANISM: Homo sapiens

<400> SEQUENCE: 94

```
gtaaactcaa aattctcttt ttttgggaaa atgaaaccaa gggagctaat cagagccaaa     60
ccccatgtac ccaagtgtta gcaggcatga atgtagctac cagctacctg ggtgtgttgt    120
catccttggt attttgggg gctgtcctca tctcttcttt tgttttgaca tctctacttg     180
tcttaaaacc caaggagcct tctgtgtttg tggccaatca gtttaccaat gcctcctcat    240
taaatggact ggaacttgta ccatagatta tgtaccctg gacatcttta tactccctgg    300
caatctctct cttccagcac caatccatgg gaattctatc ttgcccaggg tgaaaagggc   360
tatccaatta attcccttc ttatgggcct cagcattata gctggtatgg gaacctaaac    420
tgccggaatc tcaaaagcct ccttgaccta tagccaactc tgaaaggaaa tagccagcaa   480
gtttaatatc atggctaaaa cctcaaccat ggccagagca aattaacact ttagcagttg   540
tagtcctcca aaactgtcaa ggactagata tgttaatggc agcacaggga ggaatttgtt    600
tagctttaga tgaaaaatgt tgcttttggg taaatcaatc agtaaaagta caaaacaaca   660
tcagacaact cctaaatcga gcctccagct tacaagaaca agcctctcgt ggttagttag   720
attggtaagg aacctggaaa tgggatcttc cctgggttct tccctttta ggcccacatg    780
ttagcctcta cttttgctcc tttcagtcca tgtcttcaaa aatctaataa cccaatttgt   840
ctcctttctc tcacctttag atgatcaagt tccagatgat cctcagtgag ggataccatc    900
cttcaatat tcaagagtca ccccttctaca gaggactcct agacttccca tcagtgggac   960
atggcagagg tgaaatcctg cccctgtctc ccttagacct ggctggatac tgcttccaac  1020
aacccatgca gccaccctgc cctgacagct agcaagaggc caagacccac agaacaatca  1080
ccatcacacc tctgtcagca ggaagcagtt acagaagact gaccttcatc cagtttccca  1140
aagaattggg tcatggattt ttgcggggga aatgttaga gtaggtaatt aggcagacat   1200
gagtaaggga ggagagaccc cctccaacta ggaatgtcag gtgagcatca gatgatcatc  1260
aggtggttgt taaactctct ctctaaaata ataataggtt gcaactggca gcagggaaag  1320
acaatctccc aatagataga aaagtcctga agctggtgat cagcagcttc ctagtaagat  1380
ctcaggattt gggcaagcag gctcaaacat gggcactaag aggcaaaatc gtggagttta  1440
actggtatac agacttcctc taaaaacaca tgactcatgc acatgtggac agcctgcccc   1500
aaggaaaaat caaagagga gagatgcaaa accccagaag catgccaata tataaaccc   1560
caagtctaag gtcaaacagg gcacttggat ttctcaagtt gcccacttgg ccctcttcta  1620
agtgtacttt atttcctttc attcctgctc taaaacttt taaattcac tcctgctcaa   1680
aaacttgcct cagtctttca ctctgcctta tgcccttgg aagaattatt ccttcaaga   1740
tggcaaaaag caagctgctg cagacccata cagatttgct gctgctaaca ggaggataac  1800
ttgagcccag aaggttaagg ctgcggtgag ccttgattat gccactgctc tccagcctgg  1860
```

```
caacagaatg agactctatt ttttttcctt ttaaaaagac ttttacaaa aggcaaaatg   1920 ataatggaac taaaaatgta cgttgactga cttaactcca actgcttctt ccctcaattg   1980
aaaccacctt tgcaaaaatt ataacagtga gaaaattatg gcagtagggg tgatctgatc   2040
aagccaaacc ccatcttgcc tttagccttc aagctgccca taattattcc tgggcttagg   2100
ccaagctaac tttgggagac acttggtcta tagtttaaat gataatagtc cttccttaaa   2160
attcaaccac ctcagcaaag ctgatgagag gccaccaggc aaggaggata gaggagtcta   2220
aattctgcta aggtgtagat ataaacagtt ccagccatt attctggagg tcacaaaatg   2280
tgcaacttct tcaattactc ctgcagataa catcagtatt ttagaaccta agattggcct   2340
tttgagatgt cttttcaggt ttttttgtgt gtctgactac cgatggctcc acctggaccc   2400
accaaccact cctgtggccc catccagaag caactcagca tgcataagga ctatttccca   2460 caccctatg attgcacccc caaccaatta gcagcaagga cttattgcct aaaacagccc   2520
cattcatccc ccaaaccatc catgaaaaac cctagctttc aaatttccgg ggaagctgat   2580
ttgagcaata ataaaatacg tctcccattt agccaactct acatgtataa aactctttct   2640
ctattgcaat tcccctgcct tgataaatga taaatcagct ctatctgggc agcaggcaag   2700
aagaacccgt tgagtcctta caatatcctt ctttctaccc tcctctgcct aattactctg   2760
aatctactaa ctttttcact cagttatttt tccactttga agacaaaaag ttagaaaaaa   2820
aaatgcctta tgaaattagt ccctcagaat aaaccagctg ggctttcttt agccacctgt   2880 atgcttagt caaaatctaa gctcagaggc aatagtgaaa ggcttcctta tcccaaagga   2940
aaactctcag aaatttgctg aagctatcca cactgagtgt aggtatagaa catgctttgc   3000
cctatttatt catgggcacc atcctgaact cagtaatcta gcttttttct tttgaagctg   3060
gatggggaag acacagatct agctgaatta gttgccaaaa tatgctatct ggcataaaga   3120
ttattttgag agagttattt tgagactctt tgtaagagaa atttatatct acaaaggaag   3180
tctccattta taagcttgtc tctctgcatc aggaagaaaa gaaggactaa atcaccagac   3240
actcttaacc aatggagaag gagtttaagt aacaaacctt acctttgttt aaggtgcttt   3300
ttctggctct ctgccattaa gatctacatt ttccaccctg tctcctctag acctgagggg   3360
ttatctcttt gatatgcaaa tgccagggag attactcacc agaagaagaa gaagaaatag   3420
agctaattgg aaattgagca ataaaaaaaa tcttgttttt tctcccagaa acagtgaaaa   3480
gctttagcca tcctttagat aatcttaact tgttccatct gccagaaaca caatttggat   3540
tcagaaattc tttatgaact gttttgtat tattgtacct ggcacatggc tacagttttc   3600
aaatgaaaac tgtgaaatct gcttctgtct gtattttatg tatgtctgtg tatgcatgta   3660
tgtgtaatat ttttctacct ctagagacta tcctaaaatt aacttataaa gagctgtatt   3720
taattgcctt aaagaaaaag cacttataca aattaagtat ttttttaaact ttcagaaaaa   3780 taagacctag cgcaaatgtt cttcaagttg atattgttaa aagaagaaac ttcagccaaa   3840
ttaaacttaa agaagtttaa ttgagcaatg aatgattcac aaatcaggca gcctccagag   3900
ttacagctga ttcatggaga ctccagggat gcctcatggt cagaacaaat ttatagacaa   3960
aaaaagggaa gtgacataca gaaattagaa gtgaagtaca gaaagagctg gactggttac   4020
aggttggtgt ttgccttatt tgaacacagt ttgaacactc agcagtgtct aagtggttga   4080
agtatggcta ctagaattgg ccaagactcg gctattgtta caggaacgta ctcctaaatt   4140
aggttttcaa tcttgtctac ctgttaagtt aggttacagt tcatccacaa ggactcaaat   4200
```

```
atagaagtac ggagtccttc tcaggctatc ttcagttctc tttaacagta tgatacggga    4260
taatcttcag taaataaaaa tttctttaag tttgttggat taactaaagc aggcatgtct    4320
tcagagttgt caacattaaa tataatacat acatacagtt tttttctacc aggggttact    4380
aggcaaataa gtttgttatt gtaactagat gtttaagatt ataaaactgt cagtttaatc    4440
taagagcaaa agtgaaaatg tggtagctat tttattaagt acagcggtaa agcaagtata    4500
tattaagtat agcagtaaag caaaaaaaca aaaaaaaca agtatttaac ttttttttgg    4560
ttttttttt tgagacggag tctctctctg ttgcccaggc tggaatgcag tggcacaatc     4620
tcagctcact gcaacctcca cctcccgggt tcaagcgatt ctcctacctc agcctcctga    4680
gtagctggga ttacaggcgt gcaccaccat gcccggctaa ttttgtatt tttagtagag     4740
atggtgtttc accatgttgg tcaggctggt ctcgagctcc tgacctcatg atctgctcgc    4800
ctcggcctcc caaagtgctg ggattacagg catgagccac caagcccggc cttaactttt    4860
ttttaggttc ttgcttttgt gatatttggc taacatacat atgctgtaaa aattgttaat    4920
aggaaaatat taataatgag atgttgacta gctttgtctg tctaatgaaa tttcataagt    4980
caattaaaat taagaacaat tgaattatag aatagaattc aattgaattc tattgaatac    5040
acttgctgaa tacaacaatt gaattgtaaa tagaatagaa attataaatg aacttttcaa    5100
tagtaattat tttttaatac gggtacttaa aattgtgtca acttcttaac aaaagaaatg    5160
gaggcaaaat tagtataaac agtttatttg ggccaaattt gagaactgca atgtgggaga    5220
cacgtcttca agttgctatg aatataaact ccaattagca gcagttacaa gcggtttttt    5280
tttttttaaag aagggggcagt tctttagttg catataaact attgattggc tatacatttt   5340
tttttaacca taaattccag gagcatgaac ataatgggtg agggtcacat cccctgggca    5400
tggatttggg gcaggatgtg acaaaaatct catactcatg tctctctggg cctgataaat    5460
tttgcatact ttatatagtt cagactcttc tgagctacgt ttctttctct tccttttggt    5520
tgagtttttt tttcttctga aagtattgat gatcaacatt ttagatgtaa gtttgtccca    5580
tgtcactgga agacttagtt ttagttagtc tcatcccaca ttggaggaag agaggagaga    5640
taaaatggct taagaatgca gtgaagtctc aaggccaagt tgattggcaa cacaaaggga    5700
cagggcaatg gtatttcagg tcatctgctt acaaaggagc tatggcatgt tggatcattt    5760
ctaagcatct agctatcatt attttagtgt ttttgttgat tttggacatc tagaagtgca    5820
aagtataatc aatttgagaa taaaagacat gatgcaaata aagacaatta ctaacaaaag    5880
ccagatctga aaaatgtttt tatttccgaa ggcgaccaaa taaatatgtt ttctacttct    5940
tgtgctgatc taaagatcaa tgtataggag atctccagtg atgagtttgt ccactcaggc    6000
agagctgcct ttttaaaata aaaattatga atgcataagt caatgtattt gaatttaact    6060
ccacaagtat tggttaacaa tacagatatg gtcgcttcca aggtgtttgg agggagtttt    6120
gtatttgatg gcattccaca ttggaggcca tgctatttga tgtcttcatc tcctggaacc    6180
acactgtatt gtttggacat atctatccag acagatgatg ataaattttg catatctcac    6240
atagttcaga ctgctctggg ctactttttct ttctcaatag cttctcattg ttaacttatg   6300
cctgtagagt tttgctaaac taaattagat aatggacatt tattaaatat ttagatcatt    6360
tccaaataac ataaaatgct gaaacattaa ttgcttaaca taagttaatc tacttttggt    6420
ttttattaca aaggaactaa atatatttac atctgttaaa aaacacttta aactgtacta    6480
tgagaaagaa tatacttcta tagaaattat aaaatggtat atttatagat ttaccatttt    6540
atggaatacc ccataaccgt tcacaatttc ttatttccta gttttcacta gaaattgaag    6600
```

```
ttactaagag ttaacaattt taactaatat agagtagtta aaaagactaa aaataataag    6660
ggagataact atatgcaaag aaagtaagac atgttttttgg taaggaaagc cataaggtat   6720
aaggatgtgc ttttttttaa ggaaaaggaa gaataatttg gtctagtttg gaggttattt   6780
aaaggttgtt tcagaatgaa tgaaagataa aatctaaatg gatacaaaaa ggaagagaga   6840
tgacacacac acaaaatgaa tgactcttgt atggacaagt tggctagaac tgaatgtatt   6900
ataaggtttt aaaaatgagt cttgaccaag cactgtggct cacgcctgta atcccagcac   6960
tttgggaggc caaggcgggc agatcatgag gtcaagagat caagaccatg gtgaaactcc   7020
atctctacta aaaatacaaa aattagctgg gcgtggtggt gcgcacctgt agtcccagct   7080
actagggagg ctgaggcagg agaatcgcat gaacccagga ggcagaggtt gcagtgaact   7140
gagatcacac cactgcactc cagcctggcg acacagtgag actccatctc aaaaaaaaaa   7200
agagtcttaa tatcaaaagt aaactgatgc aaaactagaa tttggtcttc tctgtgaaaa   7260
tgacagtttt cttttaaaag agtattgctc cagttttaa aagtgattgt gaaaaatttt    7320
cctttccctt gtaactaatc ggcctacaaa atgaagattt tgtgttttct caaaataatt   7380
ctttgtgctt cgtgttgcct ttttttggtc tttaattact taagaaaatt gaatcttccc   7440
aacaaaagag ctagttttgt ttgttttgtt tttacagtta ttaaactttc tctatttgcc   7500
tttgaaacct cttagttgtt acttttttgtg tcttcacagt gacttttgat atatttaatc   7560
aagtgtttaa acatttgat attttttgcca gacttcctaa aaccaaattc taaactaaat   7620
cttttttta acctcaagct aagtaggatt tccagatgg attcctggaa tatctcaaaa     7680
gactttgttt tctttcctta tagaaagaga ggtcaggcac agtggctcag gcctgtaatt   7740
ctagcacttt gggaggccaa ggtaggcaga tcacttgagc ctgggagttt gagaccagcg   7800
tgagtaacat agggagaccc ttctctacaa aaattagcct ggcagccag cgtggtggct    7860
catgcctgta atcctagcac tttgagaggc taaggtgggc tgattgcctg agctcaggag   7920
tttgagacca gtctgggcag caaggtgaaa ccccatctct actaaaaata caaaaaatta   7980
tctgggcatg gcggcgtgtg cctgtagttc cagttacttg ggaggctgag gcaggaggat   8040
tgcttgaatc cgggaggcag aggttgcagt gagccaagat cacaccactg cactccagcc   8100
tcggcaacag agcgagagtc cttctcaaaa aaaaaaaaaa aaattagcct aacatggtgt   8160
catgcctgta gtcccagcta cttgggaggc tgaggtggga ggatcacctg aacctaagga   8220
ggttcaggct gcagtgagcc atgattatgc tactgtattc cagcctgggc aagaaagtga   8280
gaccttggaa aaaaaagaa agaaagaaag ggaaaaagaa agaaagaaag aaaaaaagag    8340
aattgcatag gaagttgtca ataagggtg atgtttaacc ttcttatgtt ataatattat    8400
tcatgtaagt tttccagatg ttctgtgaac ttctacaact ccgatatgtc ctgatatgtt   8460
atcagtcata atttagtta ccttaaaatg ttgtgtttct cagaaataac aaattacatt    8520
gtcaattgca ttataatgaa cttcatcag atctttaacc atggccattt ttaagtctgt    8580
tgtcatccac aaacagtagt tttactctga tactttcctg aaagttattc caaatgcttt   8640
gtttgcagga agatttatgg aaaatattga aatgtgtggg tttctggtaa ctttaagatc   8700
ataacattgg actgcataag aatttccagg actctattgg aaaaactaaa tttataaaat   8760
tgctaaccca agatcaagta gaagaaaaat taattacatg gtgatatggt ttggctgtgt   8820
ccctactgaa atctcaactt gaattgtatc tcccagaatt cccacatgtt gtgggaggga   8880
cccagggaga ggttattgaa tcatggagtc tggtctttcc catgctattc tcgtgatagt   8940
```

```
gaataggtct catgagatct gatgggttaa tcaggggttt ctgcttttgc ttcttcctca    9000
tttcaccatc aggtaagaag tgcctttcag ctcccgccat aattctgagg cctccccagc    9060
cacgtggaac tgtaagtcca attaaacctc tttttcttcc cagtctctgg tatgtcttta    9120
tcagcagtgt gaaaacggac taatgcacat gggataaaat gtattgataa taatgataat    9180
tttatgactt ttcgtttgaa acattgctgt ttctttaatg tctaattttt cagatttaac    9240 gtaactttt ctttctttcc ttaagctatc tatagcttac agaaatttag cagattatac     9300
ctttatcaac agaaagaag catatacttt ctctcttacc tgatccctcc agaattcaga     9360
aactattagc aagtattatt atttccaagg caatatagtt atatgcataa ctgcaataag    9420
aatatgttct tctgggctgg gcgcagtatc tcatgcctgt aatcccagca ctttgggagg    9480
ccaaggaggg ctgatcactt gaggccaaga gtttgagacc agcatggcca acatggtgaa    9540
accccagctc tatgaaaaaa taataataat aataataata caaaaattaa ctaggtatgg    9600
tggtgcacgc ttgtaatccc agctactcag gtggctgagg cacaagaatt gcttgaacct    9660
gggaggtgga ggctgaagtg atctgagatt gtgccactgc actctagcct gggtgacaga    9720
gtgagactct gtctcaaaaa aaaaagaata tattcttcct ataacaggac acaattagaa    9780
acactggtta tattaccaag gttttaaata gaatatcata cttaaaaata tgtgtaaaat    9840
tttatatgac cagccgggtg tggtggctca cgcctgtaat cccagcactt tgggaggccg    9900
aggcaggtgg atcacctgag gtcgggagtt tgaaaccaag cctggccaac aggacccttta   9960 aggacccta aggagatttt aagaacctaa tgaagaagag aattcaccca aaattatagg     10020
cattgcagat gaagtctgat gacaagtcct tggcttgcct tcctagcttg gaagactttt    10080
ttaaattcta atttgagact ccttattaaa agtcccagca agtatactt tgaaaaagct     10140 tatgtaatga atcactattc ttactatact tatgtaagta atcaggccaa gtgtaacggg    10200
actaggccta ttttgcaaac aaatcagttt tactgtgatt attttttggaa tgggcatgac   10260 tataaagaga aaaactatat attagtagaa aactatagca cacccattgt tagattctag    10320
cctagttcac tgtctttgag gttttgttat ctacttgtaa actgaactgg atcctgaatt    10380
ctaatttcct ccagtatctg gctatgactt ctaccgagct gactacaaat ttgagggttc    10440
ccttgacctc ttcctcatgt tcaataattt actaggacaa ttaacgggaa ctcaggaaaa    10500
cacatatgat tgccagttta taatgaaaaa tacaatttag gaatagccaa gtggaagaga    10560
ttcatggggc aaggtatggg ggctctttct tccatgcctt ctccaggtgc accatcatcc    10620
tagcacctca ttgtgttcac caacccagaa gctctctgaa ccccaaagtt tagaggttag    10680
tatggaggtt ttattacata ggtatgatta gttaaattgc caaccattgg tgcttgaaca    10740
ttatctttac tgccttctct ccccaaccc ccagaagtgg aaagggtgc taaaagttac      10800 aaccctctta tatttgcttt caggtgacaa cttttcaaagt gagttggagc aaagaccaaa   10860
catatatttg catgaaatca tgacatccta tagtaatatt tgattttcaa actctgcatg    10920
tataatagtt acttaaaatt taaattaaat tttaaaatgt accagttatg cagctgaatt    10980
ttggtacttt ttcccttggc tttgtctggt atctgaatcc accatcattt ccctgtacaa    11040
tatctgccat tggagatcca attgggaaaa tacatttaaa gaaaaatct aagaagcatc     11100 tcataggttg tggttcccctt gcatccacac tcattatcat ggtattatct tccccaaggt   11160
gggtaatagt atatccctgg ctaatatcaa gattagcact agctgtctgt agataccatt    11220
tagaaaagtt ttctctacat gtcctctctc accactccta ttcaacatag tattggaagt    11280
taaaaaaaaa gttttctcta cttgaaacta aaatttatgg cagactatat gcttccgaat    11340
```

```
gttctaaaac cttactagaa gacaaacatt gtcaaaggta ggaatgtggc caacatgtca   11400
ggtaacgcct ataacaaatt aaaatctggc gattgctgcc aagatacccca caaaactatc  11460 ggaggcaact gctgctaaaa gaccataaag atgattctgg agacaaaggc ctgtggaagt   11520
caataaaata atggtcaaag tggacaagat ttaaaaaaat taggattcag aaagaagcca   11580
attgtcattt aggaaacaat tatctgataa caaagctcag tgccctctta gggctgacat   11640
tcatgtacat attaaatatt gtagaactga taaggcttgg tggattatat ttgacaaagg   11700
ttatttgtat ttcaaaaagg aatcaacttt tgagacaaag gaatgcttta attcattcaa   11760
caaatatttg ccaagtacct actttaggga tatgatggtg tgtaaaaaaa ttttttgctgc  11820 tatcatggag tttagaatat agaggtaagg ccaatattaa tctagcaaca ttaaatcttg   11880
tgtaattgta aactgaggta gataagtgct caagaaaaaa aggttctgta aagttttata   11940
tcaaaagatc ctgatcaaag aagtattcta ggggaaataa tcattaaact gagagctgaa   12000
ggaagagttg ggttgaatgg cataaatctt aaaatgagac agggtttata cctgagggtt   12060
ggtatattag tttactaggg gtgtataaca aagtatcaca aactgggtag tttaaataac   12120
agaaatgtat tgcctctaag ctctggaggc taaatatctg agatcaaggt gctggtaagg   12180
ctgtttcctt ctgggttgat gagggagatt ctttttcatg actctctcct agattctagt   12240
gatttgctgg aaatctggtg tttcttgact tgtacacctt tgcctttgtt atagactgat   12300
gttgtctccc cctaaaactt atgtgttaaa atcctaaccc ccagtgtgat gggattagga   12360
ggtggctctt ctttggggaa ataattaggt aatgagtgtg caaccctcat caatggaatt   12420 agtacccta gaaaaatgac tccagaaagc tctctcatcc cttctgctat gtggggacac    12480
agtgacaagg gggccatctg taaagcagaa agcaggcct caccagacac taattctgcc    12540
agtgccttga tctgggactt cccagcctcc agaaccatga taaataaatt tctgttgttt   12600
aagccactag cttatggtat ttttgttgtt agtccaaaca gactgagata gccttcatct   12660
ccacatggca ttttttctc tgtgtctttg tgaataaatt tcttcttttt ataaggacac     12720
cactcatatt tgattaggag tctaccctaa tccagtataa gcttatctta atgaattatg   12780
cctgcaatga ctctatttcc aaactaagtc acattttgag gtattgcagt taggacctca   12840
acatatgtat ttttgggga gacacaatac aactcttacc agttgagaaa gagacaatgg    12900
gagcaaagaa gatttgaaat ttacctgctg acttagctag gttaatcatg agagaacaaa   12960
aagctttcat ttgaaaacgc ttcaggaaat tcagtgttct caaggagag ttggattgtg     13020 tttataccaa gaaggggggct gaaactatct gaggaggagg ttcaggctat aaagattata   13080
cagattgatt attgagaaaa gtacaaagga gcacagtgca agtttggga ggtggagaag     13140 tttgagtcaa aaataaggaa gtatagagag cattattggg atgatgggaa ggtaaaataa   13200
actggccagg attaattgct tctattcata tctctgcctg atgaaaatgg gagtgagaag   13260
tgtgatggct ttagtctcaa atgccttctt gagaaaggcc aaagaattta gactgcccag   13320
tccagaacaa tgtcagtccc aataggtata gtctctgttc tcctggccag aactagaatc   13380
aattactggc tccatcattc actagatgtg tgcgtttggg ccagttacag tacctctcta   13440
agaccgagct ttctcattct taaaatgagt ataataataa cacttagttg aggaagcttg   13500
tgtagtacgt ctcagtatca ctattgaagg gctggaggat tctcatgccc tcgataaact   13560
gtgtgatctc tcagatcctc tattttctga ttttaaaact gtcatagtaa tgctttagag   13620
tactgtaata acaacttatg gagatcttat ttataaaaag taatttgaga aatagaaaag   13680
```

```
taacacctag ttactttttt cctagttatt ttgggccagg attgtgttct gtgactgtgt    13740
ctaaatgcac catgagagga cgcccaggga aggcacctcc actccattct atctcattcc    13800
tctttcctag tgtgagttca tcctgtgtgc tgatttattt tccttaatcc acctggtcct    13860
atcaaagggc catttcagtt agttgctcca cttcagttta tgggagataa gtcttgtcca    13920
gattttccta atggccaaaa aagtcaaatc cttatcctct ttgggcttta ctcaaaaatg    13980
cttgttcagt tagggctcta gttttattcc ccagagattc tgcatgtttt atactgatct    14040
tgccagggcc ttcatctttt gggctagtct ctggaaaatc tacctctggt cctgtgcact    14100
tttccccctc tagattctag aaggaaaagc aatgaatagc gtctcccaca aagatatttc    14160
caagacctaa cccccagtac ctgtgaatag tgagagtaaa atgattagtg gctgccagag    14220
gttcaagaga aggagagaaa tattgaatag gtgaaggaca ggggattttt tagagcagtg    14280
aagttattct gtatactgta attgtgtatg catgacatgt ttttcataa cccattggac     14340
tttacaatac aaagaatgaa cttaaggtat gcaaaattta aaaatcactt aggaggggc     14400
agggccaagg tggtagatta gaagcagctc atgtgtgctg ctctcataga gaggaaacaa    14460
aagggctagt gaacattgac cctccaggct gatcatctga aaaaccatgc tgggatccat    14520
caaggcagtg ggtgaacaca gagtacagag atgagcaaag ttgggcacca gcctttcagg    14580
actcagagtg aagccaagag aacctctcca acatgggaaa gggtgagtga gtgagagccc    14640
ccagaggaat tcacactctg cacagggacc cacacaagac ttggaatggg agaatccccc    14700
tggacccccct ggacacctgc caccaccatg ctcctagact gaggcagaga gccaactaga    14760
tgttttgcag gggcaactct tgagtccaag gggacctcta caagccttgg cccttgagt     14820
agaccagcac tggttccaca gccccaaaag aggccacagt tgcagtgcct gggagaagta    14880
agattgcccc gcccctctt gctggacagg gcttgatggc agcttctggc ccagcagtcc     14940
cacttcagcc tgaacttgtc tggccactcc aatcacccct caccactggt atcctggcgg    15000
gcaaccctcg atagagcttc cagcccagta gtcccacttc tgtgtcaact tagcccatgg    15060
acacagcctc ctgttgtccc aggaagcact cagacattag ggcaggagaa tgtacccatc    15120
ctcaccactg atagccaggt ggcccagtgc tcctacttca atggggactc agctggaggg    15180
ctcagcctcc cattgtccca agaaatgcat agacagcagg gtgtgtagcc caaccatcc    15240
ctgccactgg tagacaggcg ggcaatgcct cctagacctt ctggcccaga ggtcctatat    15300
ctgtgggaac tcagccagtg cgcacagcct cctgctgtcc caggaagtat ctggatggta    15360
gggtgggtgt ccccaaacac ccctgctgct ggaagccagg tgagccatgc ctgttagaac    15420
ttctggctca gtggtcctac ttctgccaga atttgctgag ggtcacaacc tcctgctgcc    15480
ctggaaacac ccagagagca gggtgagcaa ctccactcac acctgcctcc catagccaga    15540
cagggcccac ccaatagagc ttccaaccca gcagttctgt tctacctgca ctctgtgaaa    15600
aggcacaagc ccgtgtttct ccaagaagca catggatagt atattagtgc tgacttggca    15660
aggatacagc ttgtctgcca acagcagctc ctgcctgagg aacaccatg gacccgaaaa    15720
cccaacaaaa aacataggca cagagacagt aattggaggg ggctcctcca agacccagga    15780
gtggactaga attgaaacca gtcaaccaaa gccaccttat acaataatga accccccaag    15840
ggcatcaaag aagaaaaaag caaaaaaaaa aaaaaaaat ccactcaaat tacagcaatg     15900
ttaaagactg aaagaacaac agcccataca aatgagaaag atccagcaca agaactctgg    15960
caactcaaaa aaccagagtg ccttctttac tccaagcaac tgcactagtt tcccagcaag    16020
ggtccttaac taggctgaaa tggctaaaat gatggaaata aaactcagaa tacagataag    16080
```

```
aatgaagatc attgagattc agacaatgtt gaaacccaat ccaagtaagc taagaatcac  16140
aataaaatga tacggaaatt gatcgatgaa atagccatca taaaaaagaa cccaactgat  16200
ctgatatagc ttaaaaacac actacaggaa ttgcacaatg taattacaaa tattaacagc  16260
agaacagacc aagctgagga agaacctca gagctcaaag actggctctc tgaaataact  16320
cattcagata aaaaattaaa aaagaataaa caaaacctac aagaaataga agattatgta  16380
aagagaccaa ttataggact cactggcatc tatgaaagag atggggagaa agcaagaaac  16440
ttggaaaaca tattttagga tgtcatacat aaaacttcct caacctcatg agacaggcta  16500
acattcaagt ccaggaaatg cagagaaccc ctgctgacat tacacaaaaa gaccatcccc  16560
aagacccata attatcagat actccaaggt tgaaatttaa aaaaaaaaaa aaaaagacaa  16620
aggcagctag agaaaacggg caagtcgctt gcaaagggaa tcccatcagg cttacaggag  16680
acctttcagc agaaactcta caagccagaa gaggtttgga gcctatattc agcattcttt  16740
ttttatgaga cagagtctcg ctgtttcacc caggctggag tgcagtggtg cgatctcggc  16800
tcactgcaag ctccgcctcc tgggttcaca ccattctcct gcctcagcct cccgagtagc  16860
tgggactaca ggtgcccacc accatgcggg gctaattttt ttttttttt tttttgtatt  16920 tttagtagag acggggtttc accatgttag ccaggatggt cttgatctcc tgacctcgtg  16980
aggaggtcct cctgacccgc ctcggcctcc ccatatattc agcattctta aagaaaaaat  17040
ttacaatcaa gaattttaca tctggccaaa ctaaacttca caagtaaaaa gaaataagat  17100
cattttctta caagcaaatg cttagggaat tcattaccaa cacacctgcc ttataaaaag  17160
tcctgagagg agcactaaat atggaaagac cattcaagc cactacagga acacatttaa  17220
gtacacagac cgatgacact gaaaagcacc cacagaaaaa aaagtctgca taataatcag  17280
ctaaaagcat gattacaaaa tcaaatccac acatattgt actaagctaa tgggctaaat  17340
gatccaatta aaaggcgcag agtggcaagc tgaataaaga agcaaggccc aatggtatgc  17400
tgtcttcaag agaaccatct cacatgcagt gacatctata ggctcaaaat gaaggggcgg  17460
agaaaagtct atgaaacaga agaaatcaga ggttacaatc ttaatttcag acaagatgga  17520
ctttaaacaa acaaacatca aaaatataa agaagggtat tatataatac ccttcaattc  17580
aatggttcaa ttcaacaaga aggtataact ctcctaaata tgacagacat ctaacacaag  17640
agcacccaga ttcacaaaac aagttcttag agacctacaa agggacttag aacccccaca  17700
caataatatt gggagccttc aacatcccac tgacagaatt agacagatca tcaaggcaga  17760
aaattaacaa acatatttaa gacctgaatg caatacttga ccaaagggac ggaatagata  17820
cctatagaac ttgccatcca aaacaacaa aaaatacatt cttctcattg ccacatggca  17880
catactccaa aatcaaacac aaaattggac ataaacaat actcagcaaa ttaaaaaaaa  17940
aacagaaatt ataccaacca caatcttaga ccacagcaca acaaaaatag aaataagttc  18000
taagaacata actcagaacc ataaaattac ataggaatta aacaatctgc tctgaataa  18060 cctttgggta acaacaaaa ttaaggcaga aataaagaaa ttctttgaaa ttaatgagaa  18120
aaagatataa catatccaaa tctctgggaa acagctaagg ccatgttaag agagggaagt  18180
ttatagcact aaatacccac atcaaaaatt tagaaagatc tcaaattaac gacctaacat  18240
cacaaccagg agaactagag aagcaagagc aaagtaagac cccaaagcca ccagaagaca  18300
agaaataacc aaaatcacag ctgaactgaa gaaaactgag acactgaaaa ccatacaaaa  18360
gatcaacaaa tccaggagtt ggttattaga aaatattgat aagatagata gactactggc  18420
```

```
tagactgata aagaaaaaaa gacagaagtt ccaaataaac acaattagaa atgacaaagg   18480
agacgttacc actgaaccca cagatataaa aaaaaacatt gaagactact ataaacactt   18540
ttaagcacac aaactagaaa atttagaagg ctgggtgtgg tcgatcacgc ctataatccc   18600
agcactttgg gaggccaagg agggtggatc acaaggtcag tagatcatga tcatcctggc   18660
caacatggtg aaaccccatc tctactaaaa tataaaaaaa aaaaaaaaaa ttagctgggc   18720
ccagtggcat gtgcctgtag tcccagctac ttgggaggct tgaggcagag gaatcacttg   18780
aacctgggag gcggaggttg ctgtgagctg aggttgagcc actgcactcc agcctggtga   18840
cacagtgaga ctccatctca aaaaaaaaaa aaagaaaga aaaagaaaa gaaaatttag   18900
aagaaatgga taaattccaa gacacataaa ccaggaagaa actgaatccc taaacaaaca   18960
aacaatgagt tccaaagtta aatcagtagt aaaaagccaa ctgtattaat gcattcttat   19020
gttgctataa agaaatacct gagattgggt aactataaag aaaagaggtt taattggtta   19080
acagttctgc aagctgtaca ggaagcatga cagcttctgg gaaggcctca gggaactttt   19140
aatcattgca gaaggcaaag ggaaagcatg tatgtcttac atggccagag caggggggaag   19200
agagagagag gggaggtgct acatactttt aaacaaccag atttgtgaga attctatcac   19260
gagaacagca gtagtgggat ggtgctaaac cattagaaac cacccccatg atctaatcac   19320
ctcccacaag tccccacctc caacactggg gattaaaatt gaacatgaga tttgggttgg   19380
ttcacaggta taaaccatat catctactaa acataaaaag cccaggacta cacagattca   19440
cagccaaatt ctaccagatg tagacagaat agctggtgcc attaataatg aagctattcc   19500
aaaaaattga ggaagaggga ctcctcccca actccttctg tgaggccagc atcatcctga   19560
taacgaaacc tggcagagac aaaacaaaaa aagaaaactt caggccatta tccttgatgc   19620
acatagatgc aaaactcctc aacaaaatac tagcaactga atccagcagc acagtgtaaa   19680
gctaatccac cactatcaag caggctttat ccctgggatg caagattggt ttaacataga   19740
caaaacatat gtttgtgtga ttcattacac aaacagaact aaaaatgaaa accacatgat   19800
aattccaata catgcagaaa aggcttttga taaaattcag catcccttca tgttaaaaac   19860
tctcgataaa ctatgcattg aagaaacata cctgaaaata attagagcca tgtatgacaa   19920
atccacagac aacatcatac tgaatgggca aaagttggaa gcatttccct tgaaaactag   19980
aacagccaga cacgatggct catgcctgta atctcagcac tttgggaagc aaaggcaggc   20040
agaccacttg agcccaggag tttgagacca gcctggtcaa catagggaaa ccctgtcttt   20100
acaaaaaaat aagaaaaatt agccaggcgt gatggcacac acctgtggtc ccagctactc   20160
gggaggctga atgggagga tcacctgagc ctgggagctc aaggctgcag tgagctatga   20220
tcacactact gcactcaagc ctgggtaaga gtgaaaccct gaccaaaaaa aaaaaaaga   20280
aaagataaaa gaaagaggcc aggcgtggtg gctcaggcct gtaattctag cactttggga   20340
ggccgaggca ggcggatcac ctgagattgg gagctcgaga ccagcctgac caacatggag   20400
aaaccctgtc tctactaaaa atacaaaatt agcgggcgtg atggtgcatg cctgtaatcc   20460
cagctgctcg ggaggctgag gcaggagaat cgcttgaatc caggaggcag aggttgcagt   20520
gcgctgagat tgtgccattg cactacagcc tgggcaacaa gagcaaaaaa aaataaaaa   20580
taaaaaataa aaaataaaaa aaaataaag aagaagaaa agaaaactgg cacaaacaag   20640
aatgctctct ctcaccactc ctatttgaca tagtattgga agtcttggct gcagcaatta   20700
ggcaagagaa agaaataaaa ggcatccaaa taggaagaga gggagtcaaa ctatccctgt   20760
ttcaaatgac atgattctat acctagaaaa ccccatagtc tctgccccaa agcacattaa   20820
```

```
tctgattcac atcttcagca aagtttcagc atacaaagtc aacatacaaa agtcagtttc   20880
attcctatac cccgatagct ttcaagctga tagcaaaatc aggaacacta tcccaccaca   20940
attgttataa aaagaacaaa ataccatgaa atacagctag ccagggatgt ggaagatctc   21000
tacaacagga attatataac actgctcaaa gaaatatgag atgatgcaaa caatggaaa   21060 aacattttat tctcatggat aagaaaaatc aatatcatta atatggccat agcgcccaaa   21120
gcaatttaca gatgcattgt tattcctaac aaactaccaa tgccattagt cacaaaacct   21180
aaaaaaataa aaaaactgtt ttaaaatcca tatgaaacca aaaagaccc ttatagccaa    21240 ggcaatctta agcaaaaaga acaaagctgg aggcatcacg ttacccaact tcaaactatg   21300
ctacggggct acagtaacca aaacagcatg gtactggcac aaaaacaggc catggaccca   21360
atggaacaga atagagagcc cagaaataag gccacaacca ctggatattt gacaaagctg   21420
acatcattct accataaaga tacatgcaca caaatgttca ttgcagcact attcacagta   21480
gcaaagatgg gaatcaacct aaatgcccat caaaggtaga ttagataaag gaatgtgat    21540 acatatacac cacataatac tatgcagaca taaaaaggaa tgagatcatg tccttttacag  21600 caacataaat ggagctggag gtcattatgc taagcaaact aacacaggaa cagaaaacca   21660
aaataccaca tgttcttact tataattggg agctaaagga tgagaacaca tggatactag   21720
gaggggtaca acagacactg gtgcctactt gagggcggag ggtgggagga gggagaggat   21780
cagaaaaaat acctgttggg tattatgctt attgcccagt gatgaaattt tctgtacacc   21840 aaaccttct aacacacagt tcatctatat aacaagtctg cacatgtacc cttgaaccta    21900
aaataactat tacaataagt aaatacatat ttttaaaaat catttagaat gtcagaaaat   21960
tccaggattg tattagtctg ttcttgcact gttatgaata aacacctgtg actgggtaaa   22020
tttataaaga aaagaggttt aattggctca cagttccact ggcagtacag aaagcatgac   22080
agcttctggg gaggcctcag gaaactttca atcatggtgg aaggcaaaga gcaagcaggc   22140
atgtcttaca tggccagagc aggaggaaga gagaaggtag acgggctaca cacctacaca   22200
accagatctc gtgtgaactc tatcacaaga atagcactag gaggatggtg ctaaaccatt   22260
agaaaccacc cccatgatcc aatcaccaga cccacaagga cgcacctcca acattgggga   22320
ttatgattga acatgagatt tgtttaggga cacagatcca aactatatca aggatagagt   22380
gtagaatatg acaaaataat ctaactgtat tacaaatgtg tgaaacaacc tcactgcagg   22440
tggtggtaaa agaagtgcag acctaagtaa cttttggaaa ttagtggagt ctgtaatact   22500 aaaatgaaaaa ctgtttataa acgccacact cttgttttc acagggatat gggttaacaa    22560
ttctaatact tctatacgtg tgtattggaa ttgagcagtt aagtaaatta tggtaaattg    22620
tgggtagtga ggctggtttc tctctgctgg agtgagagtt tatgcctaat caagggagg    22680 gagctaaaat aatctctgtg gtaatggatt acagttggat atattaatat taaatcatat   22740
ttggcttaat gtagatacac atggctacat acacgtacac atggctacat atagacacat    22800
atagatatgt gtacatacat gattagtata cacaaacgtt cccttccatt gacaaatgag   22860
aaggcctaga agcaacagta ccccagtagt aacaagcaca tctggcatcc agttcatggt   22920
ttgtaatagc actctgcaat aaaggaaac agggcttctt agaaaaattg gtgtttctag    22980
gactagggca ggaaatatac atgatgagcc tgtaacattt tgtagtgcca gaaaggaaag   23040
aagtgctaac aacaaaaaca agcccacaaa gatgggctg tgtcaaatag atgtactgaa    23100
agagccaata ccaagaactc ctgacgccaa atctggaaca ctttggggaa acaaataaag   23160
```

```
cagtattgaa ttgtaacaca agtataaaa taaatagcca tgagtctaca ctaatataag    23220
taaataagtg aataaataaa taaatggggg caaagaaaca atcttccatg cagaaaaact    23280
ccaaatgatt tatgtagata tgccaaccta aaggagataa agcataactc ctcactgttt    23340
cagttcaggc cacacatagt gactttcttc caaagagtat agtatgaaaa agggaaataa    23400
aagagtaact tgtgatggaa aagcctgaca agcacaaatt acctcagcag agtgatcagg    23460
gtcaacataa acagtaataa atcatatcaa cagtatgttc tcttgatatg atacgatgaa    23520
aatcatctag tcatcctttt ttttttttta gatggagtct tgctcttgtc acccaggctg    23580
gagtgcaatg gagtgatttt ggctcactgc aacatccacc tcctgggttc aagcgattcc    23640
cctgcctcag cctcccgagt agctgggatt acaggcgccc gccaccatgc ccagctaatt    23700
tttgtatttt tagtagagac agggtttcac cactttgacc aggctggtgt cgaactcctg    23760
accttgggtg gtccactctc ctcatccccc caaagtgctg ggattacagg cgtaagccac    23820
cgcgcttggc tgaaaatcgc ccttaacctc tgtagtcttc ttccccaaaa aacattatc    23880 cctgtctaat aatgacaaag acatctaaca aatcccaaaa gatagatatt taaaaaatac    23940
ctgacccatt cttctcaaac tgtcaagatg accaaagcaa ggaacaactg aaaagctgtc    24000
ataaccaaga ggggcctgag aagacatgat gatgaaatgt tatatgatat tctggatggg    24060
ttcttggttt gcaaaaggga atttatgcaa aaactaagga aatttgatta aaacatggac    24120
tttcagttat ggtaatgtct tgatattggt tcattaattg caataaatat accttgctaa    24180
tgtaatatat tcataaaggg gaaactgggt acagagttaa tgagaactcg ctagactata    24240
ttctaatagt tctgtaaatc taaaactatt gtaaaaatca agtttacttt aaaaatatta    24300
ctgactgtct tggttctgtt ttactacttt tttttttttct ttttttttgag tcagggtctc    24360 cctctgtcac ccaggctgga gtgcagtggg gtgatcttgg ctcactgcaa cctctgcctc    24420
ccgggttcaa gcaattctcc cacctcagcc tcagaggttt gaataatact tctttgtttt    24480
aatcattcag ctcagattaa aaacaacgcc taatttctta atgtcaacta ttgccttgcc    24540
ctctgttata tcctaccttc tcccattcgt tatagtcact ctctagtatg gtattgagtt    24600
ggggatgtgc atctgcccaa caaattttta tatttttttgt agagatgggg ttttgtcatg    24660
ttgcccaggc tagtctcaaa ctcctgagct caagcagtcc gcccaccttg gcctcccaaa    24720
gcgctgagat tacaggtatg agccacattg tccagccatt tccatttact tttctttccc    24780
attgagccca attcttaaaa acatccagtg gcagcttagc ttgggtgtct tggctcagct    24840
ctggaggttt gaatgatact tctttgcttt tctttgcttt aatcattcag ctcagattta    24900
aaaatttctt aatgtcaact attggcttgc cccctgttat attctacctt cttccattcg    24960
ctatcctaac tctctagtat ggtattgagt tggggatgtg cacacacagg caaacacaca    25020
cacatacaca tccccataca tatacagtgg tgtgctgaaa ctgtgtcaga ccagctagag    25080
agacccaatt gttaaatatt caagaatgag gcaagccagt tattaagcac atccattatt    25140
aaaaattaaa ggataaagtt acaattaagt aaatcatatt aaaagaaag gttataaata    25200 atatcattac ttctatttat tttactatta tctatacttt ttgaggttaa gtctactgta    25260
tttctataat ggaattacta catactggtg tgctacttct tgattccgta tttggtgatg    25320
tcaccctgat atgacatcat atcattgata tgatatgaaa tagaccatgg gtggagtatt    25380
tgtaccatgg atattgaaaa aacttaaatc agagcttgag ttattgtttt gttgatttc    25440 tactttaaaa agatggatgt gcttaataac cggcccttaaa aagatggggg aaaatgttat    25500
cacggttaat actgtaggtt aagctctaaa atgtttgtag ctgttacatt tgaatagcac    25560
```

```
aaaatattga ggaatattct ttaagtgttt gaaaacagtt ttaaactcag caaagaggtt    25620
aactgatatt gttaacaaga ttcaacttca ttcaattcta ttgttatact ctcatcttac    25680
tcgtcaatat aaatgaaaat gtcaattgat attcatttga gagttactct catttgttaa    25740
ttgcaaccat aggttaacta aagatacaag agtttggcta aatcagtgag aacattgtat    25800
gagaataagt tcattataca gaatagagaa tattatatat tttattatta tttgtaagtt    25860
ttgtattaca tatcctttat gtcagtaaaa tttataataa acatgtacat atttattttt    25920
tgcagtttgt tattaaacag ttactagcaa attgctatgt acacacattc cttatcaaaa    25980
atgtgggaat tatttgcaac ataaatgaga acatatgagg ttatacgtag taggtacaat    26040
cttaaagaga caaaccacaa gtatgattga tacttccact agacatcttg tcaagagaat    26100
tatattccca aataagtatc accaaaaatt ttgttgaaac tagaccttc cacaagctat    26160 gggctcctat aaatacatat ttttaccaga gtttcttcat ctaattaggt ttttaaattg    26220
tggtaagaat aagatacaga taatgaatt agatgcagcc tggccaatat ggtgaaaccc    26280
catctctact aaaaatacaa aaattagctg ggtgtggtgg cagacgcctg taatcccagc    26340
tactcgggag gctgaggcag aagaattgct gggagccggg aggcagaggt tgcagtgagc    26400
tgagattgcg ccactgcact ccagcctggg cgacagagcg agactccaac tcttaaaaaa    26460
aaaaaaaaac aaatcaatta gatgtattaa ttaggaatct gctatgaact gaattgtgtt    26520
cccccaagat ttacatgttg aagcgctaac ctccaatgtg gcaatattta cagatcgggc    26580
ctttaaagag gtaattgagg ctacaagagg ttgtaagggt ggagccctaa tccagtagaa    26640
ctggagtctt tacaagagga agacacacca aaggtgcatg ggcacagaga aaaggccatg    26700
taaggacaca gtgggaaggg gccatctaca agccaatgag agaggcctca ggagaaacca    26760
aatctgtcaa catcaacatc ttgatcttgt acttccagcc tccagactat gaaaaaacaa    26820
ctattgtttg agccgccctg tctgtggtat accatgtacc atggtgtttg tagggaagcc    26880
ctagtaaact aaaacaaaat cttagattgt aagtaataga atcaactgt aggtagatta    26940 tagcagaaag aggacagaaa tgcaggtaaa agttacaact ggaaactgca gtgctatagg    27000
aagcccaaga tgttctcttt ttctgtatct cctctctgct atagcctatc tattttattc    27060
tgaacatctt tattccacac atctttattc cacagctata ctgtccaata tgatagtcac    27120
aaggaacatg cggcttttta aatttaataa aattcagttc ttcagtcaca ttaaagatat    27180
tgcaaatatt aaatagctac atatggctac tgtgttggac actgtagata tagcacacct    27240
ccatcattgt agatagttct tttggacagc actggattat aggattacca gagatcaagg    27300
taaacttccc ttgaagttga aggtaaactt ccatttaacc attaggacac ctcagctgta    27360
tcactccctt ttaaggccta tatttagttt tgaatttata attttttatc attttttctta    27420 gggactgata tcaccagtga cctctaggga aaggattagt agtgaggaga aacattattt    27480
tgtattgttt gaatgtaaat acatccatgt acaaactgca taatatttt taaggtattg    27540 gagttttgta ttgctcatca ttgtatccaa acacccagta tagtaccta acaggtaatg    27600 ttaggaagtc gaagagatgg acatacggtt aatgctaaat cctgtgatgg tgagaagatg    27660
ctctggttat gcctaattct ttctgcttca agcccagcta ggtctgggaa ttgcttgggg    27720
aaactggaag cctgaaccag aggactgtgt gcatgtgtgc atgcgtgcgt gcgtgtgtgt    27780
gtactggtag gtaataaata actactgtgt atctgacact atggtagttt atacttttta    27840
tgtctactct aaacaacaac actacaaagt agtcacccct gtacccattt tataaatgag    27900
```

-continued

```
gaaactaaga ctaactcatt tatcctggtg tgttcttttt tcttttcctg ttagtgcaat    27960
ttgacagtta cacaattgtt actaaataga atgtagccag ttctagagaa acttcattct    28020
accagtgttt attttattat tttattttt attagataat tcatactctt ggatcaaaaa    28080
ctggtagcaa attgtattta gcacgaagta aatcttcctt cacacactac cctcaggcaa    28140
ccgtcaacaa cttcttgtgt gtctttacag aaatatttta tgtgtataca acacatatac    28200
gaatatttct aaaatttaat ttggagtatt ttacatactc caaatctttt ttttcacttg    28260
acaatatatc ttgaaaatca ttatatatta ctagatctgc tgaatttctt ttaatagcta    28320
tatgttattt gttgtaggaa agcctcaaaa tttattcaaa tccctactca tttatgattg    28380
ttgtttcata tcttttgtta ttacaaagct tcagtgacca ttcctataaa taggccattt    28440
tgcacatgtg gaaatatatc tgcagaataa atttctagag gtagagttgc tgagtcaaat    28500
ttaaaggcaa agagtcttta aactcttcat agatattgct aattttatc catagatgtt    28560
atacaaatat acttccctc agcaatgttt atccatacc tttccaatac taagggaacc    28620
cttttcttgta caagagaaaa agaaagaaag aaaaatcaat ctaatttgct tataggcacc    28680
taaagatttt ttttttttg gccttgccca gaagttatgc atttcagtga accctaccct    28740
caccatcccc atttcctgga ataatattaa tactactttc caactgaaac tctgagatca    28800
cattctttct tttctatttt atataatact ggcctacttt atatgact gggatggagg    28860
ttgttcattc tgctcatctg tgtattatgc aaatttgcct ccaagcagat tggcctcttg    28920
caaccctggt gagaggtgac agcatgctgg cagtcctcag agccctcgct tgcacctccc    28980
ctgcctgggc tcccactttg gcggcatttg aggagcccctt cagcccccac ctgcactgtg    29040
ggagcccctt tctgggctgg ccaaggctgg agcccactcc ctcagcttgc agggaggtgt    29100
ggagggagag gcgcgagcgg gaaccggggc tgcgtgcggc gcttgcgggc cagctggagt    29160
tccgggtggg cgtgggcttg gcggccccgc actcagagca gccagccagc ccgctggcc    29220
ccgaggaatg agggacttag cacccgggcc agtggctgcg gagagtgtac tggatccccc    29280
agcagtgccg gcccaccggc gctgtgctcg atttctcgcc gggccttagc tgccttcccg    29340
cggggcaggg cttgggacct gcagcccgcc atgcctgagc ctcccaccca ctccatgggc    29400
tcctgtgctg cccgagcctc cccgacgagc accaccccct gctccacggc gcccagtccc    29460
aacgaccacc caagggctga cgaatgcgag cgcacggcgc aggactggca ggcagctcca    29520
cctgcagccc tggtgcagga tccactaggt gaagccagct gggctcctga gtctggtggg    29580
gacgtggaga acctttgtat ctagttcagg gattgtaaac gcaccaatca gcgccctgac    29640
aaaacaggcc actgggctct accaatcagc aggatgtggg tggggccaga taagagaata    29700
aaagcaggct gccggaggca gcattggcaa cccactcggg tccccttctg caccgtggaa    29760
gttttgttct ttcactcttt gcaataaatc ttgctactgc tcactctttg ggtccacgcc    29820
gcttttatga gctgtaacac tcagtgcgaa gatctgcagc ttcactcctg agcccagcga    29880
gaccacgagc ccatggagag gaacaaacaa ctccagacgc gctgcgttaa gagctgtaac    29940
attcaccgcg aaggtctgca gcttcactcc tgagccagcg agaccaggaa cccaccagaa    30000
agaagaagct ccgaacacat ctgaacatca gaagggagag actccagacg cgtcatctta    30060
agagctgtaa cactcacggc gaaggtctgc agcttcactc ctgagccaac gagaccacga    30120
acccaccaga aggaagaaac tccgaacaca tctgaacatc agaagggaca gactccagac    30180
gcaccacctt aagagctgta acactcaccg cgagggtccg cggcttcatt cttgaagtca    30240
gtgagaccaa gaacccacca attccggaca cactgggtca cttttctgact gcactttctt    30300
```

```
gaagtattcg tctttggtcc tgtggtagta cccagtggac aacctcactt gcctgtaaac  30360
tacttccttg aggtattttc cctaacaacg tgaaatacat tccatttctc tgcttgctct  30420
tttcatgact ctcatttcaa tggtccttag aaaacacttt ttttgattat tattcagctt  30480
tgtaatactt atttcttcag ttccccatcc ataaagtctt tgatttagag gtcaaatctg  30540
ttttgcttta ctattcctat ctaaagcttg aaagtatggt aattaataaa aacattccac  30600
atgttaaatt agctttaatg ttagctttaa agaagatag cagttaatca gtcttgatga  30660
cgtagaggtt gacaggtaga aggatcctaa aatttaattc ctgggctgct aacttcaaat  30720
ctcatctgta tcaacagttt tctcacttaa gtcattaaca tcgaaaatta ttttattaaa  30780
tgatttataa ttgggagagt actatttctc tttctcccca cctccagtta tgagaagata  30840
cttattccca gcttttctg ggtagagcta ttcaatttt ttttttttt ttttttttt  30900
tttttttttt ttttgagat ggagtttcac tcttgttacc taggctggag tgcaatgctg  30960
caaaatctgc tcactgcaac ctccacctcc caggttcaag cgagtctcct gcctcagctt  31020
ctggggtagc tgagattaca ggtaagtgcc cccacgccca gctaattttt gtatttttag  31080
aagagatggg gtttcaccat attagtcagg ctgatctcga actcctgacc tcatgtgatc  31140
cacccgcttc tgccttccaa agtgctggga ttgcaggcgt gaaccaccgc atccagccca  31200
atttgttttt taaatctttt tggcactcta ccaaatcacg aaggctcttc ttagttaggg  31260
gaacagaagg gatttagtct taataaattt ttctccatgc catggggaag actctctcag  31320
aaggtagcat ctagaacaga acattgaaaa gtttataaac aacaccagta cttcatactt  31380
ttgtttatc ttcccttga gatagacgtt tagtccttta ctgttattac ctagcacaat  31440
atctggcaca cagtaggtgg ccactgatta tttcttgaat gaagtaagga atgagaatat  31500
tacctacaga gttagagctc tgcgcattac ttccttccag atttcataca tcttttttta  31560
gtaatgaatg caaacaggct ctggggcagc tacattatcc ttctgaatca agacagggat  31620
ttcgcaatgc ttatttcaa tttcttcaga aatgccttaa agatattaat ggaggtaaca  31680
acttaatctc aaatagtaat ccatagacag aatatgtaac agcaatgttc tctgatctgt  31740
tctttggctt ctattcccta gagaaatagt tctctaagac caaacagtct atagatagaa  31800
ttgtagcaac agtcaattat gatgttagct atttgagaga cggttgagaa ttcagaaaaa  31860
actactgaaa tgttgtaaga caactcactc aaagaacagt tcaaatagtg gaaaagggaa  31920
atgatgatgt atccatttat tttgttctat tttttccaat ttcataggat agcaaatgct  31980
gcccatttat ttatttttt attttcata gttattgggg gtacaggtgg tgtttggtta  32040
catgagtaag ttctttagtg gtgacttgtg agatatgggt tcacccttca cctgagtagg  32100
atacactgaa ccatatttgt agtcttttat ccctcgcccc ctccatctct tccccgtaag  32160
tctccaaagt ccattgtatc attcttatgc ctttgcattc tcatagctta gctcccacat  32220
atcagtgaga acatacaatg cttggttttc cattcctgag gtagttcact tagaatagta  32280
gtctccattc tcatccaggc cactgcaaat gctgttaatt cattccttt catggctgtg  32340
tagtattcca ttatatatat atatatatac cacagtttct ttatacactc attgattgat  32400
gggcttttgg gttagttgca cgattttgct attgtgaatt gtgctgctat aaacatgcgt  32460
atgcaagtat cttttccaaa taatgattcc ttttcctttg ggtagaaacc cagtagtggg  32520
attgctggat caaatggtag ttctactttt agttctttaa ggaatctcca cactgttttc  32580
catagtagct gtacttgttt acattcccac cagtggtgta aaggtgttcc ctgctcacca  32640
```

```
cacccatgcc aacatctact gttttttgat tttttgatta tggccattct tgcaggagta   32700
tagcattgtg gttttgattt gcatttctct gatcattagt gatgttgagc attttttcat   32760
gtttgttggt cagttgtata tcttcttttg agaattgtct tttcatgtcc ttagcccact   32820
ttttgatgaa attgtttgtt ttttttttctt acagatttgt ttgagttcat tgtagattct   32880
ggatatcagt cctttgtcag acgcatagat tgtgaaggtt ttctcccact ctgtgggttg   32940
tctatttact ctgctgactg ttccttttgc tgtggaaaaa ctctttagtt taactgggtc   33000
ccagctacgt acctttgatt ttattgcatt tgcattttgg ttcttggtca tgaaatcctt   33060
gcctagtcaa tgtctagaag ggttttttcca atgttatcgt ctagaatttt tatagtttca   33120
ggtcttaggt ttaagtcctt aatccatctt gagttgattt ttgtataagg tgagagatga   33180
ggatccagtt tcattctcct attatgtggc tagccaatta tcccagcaac atttgtttaa   33240
aagggtgtcc tttccccgtt ttatattttt gttcgctgtg tcaaagatca gttggctgta   33300
agtatttggg tttatttctg agttctctgt tctgttccat cagtctatgt gcctattttt   33360
atactagtac atgctgtttt ggtgactgtg cctttatagt atagtttgaa agcaggtagc   33420
atgatgcctc cacatttgtt cttttttgctt agtcttactt tggctgtgca ggctcttttt   33480
tggtttcata tgaattttag aattgttttt tctaattctg tgaagaatga tggtggtatt   33540
ttgatgggga ttgcattgaa tttgtagatt ttttttggcgg tatggtcatt ttcacaatat   33600
tgattctgct catccatgag catgggatat gttttccattt gtatgttgtc tattatttgt   33660
ttcagcagtg ttttgtagtt tttcttgtag aggtcttttg actccctggt aaggcatatt   33720
cctaagtatt tgatttgatt tgatttttttt tttttttttt ttgccgctac tgtaaaaggg   33780
gttaagttct tgatttgatt ttctgcttgg tcgctgtttg tgtatagaag agctactgat   33840
ttgtatacac taatcttgta tccagaaact ttgctgaatt cttttatcaa ttctagtagc   33900
tttctggagg agtccttagg gttttcaagg taaacgatca tatcatcagc aaacagtgac   33960
agtttgactt cctttttact gatttggata cccttttttat ttttctctct catctgattg   34020
ctctggctag aacttccagt actatgttga agaggagtgg tgagagtggg catccttgtt   34080
ccagttttca gaggaaatgc tttcaacttt tcccattcag tattatgttg ctgtgggtt    34140 ttcatagatg gcttttatta cattaaggta tgtcccttgt atgccaattt tgctgagagt   34200
tttaatcata acaggatgct gaattttgtc aaatgctttt tctgcatcta ttgagatgat   34260
catgtgatgt tttgttttta attctgtttt cgtggtgtat cacatatgtt aaatcatccc   34320
tacattcctg gtatgaaacc cacttgatca tgtcatggtg gattattttt tgatatgttg   34380
ttggattctg ttagctagta ttttgttaag gattttagca tcaatgccca acaaggatat   34440
caatctgtag ttttttaaatg tgcttttctg gaccggcacg gtggctaagg cctgtaatcc   34500
caacactttg ggaggtcgag gagggcggac cacttgaggt caggagttcg agatcagcct   34560
ggccaaaatg gtgaaaatcc gtctctacta aaaaggtgtt gtggcgggcg cctgtaatct   34620
cagctactga ggaggctgag gcaggagaat cgcttgcacc cggaggcgg aggttgcagt   34680 gagccgagat cgcaccactg cactccagcc tgggcgacag agaaagactc cgtctcaaaa   34740
aaaaaaaaaa aaaaaaaaaa gttgtttttct gctatttcct gaactttatt acgtaaatga   34800
gacacgtgag atctggaagg aggtggaggt gaagaccctc ccacctggcc tgcatccaga   34860
gtacttgggg tgtggcactg gcgtgggccc caggaaggat cccagccagt tttggtgctg   34920
gaggcccggc caaggaagg gctgctctcc cgtcccgcgg gctccgaggt cgccgcaccc   34980
gggcgcgcct gggcctcgtc acccgcgctc gtgacgcgtg cttacaaagg aaacttttac   35040
```

| | | | | |
|---|---|---|---|---|
| aggtttcggt | gggcagggcc | ttttattgcc | cttctgctcc | acagccccg tgcttaatcg 35100 |
| gttggttggg | aggtttcttt | cgtccgtggt | tttggaaagt | ccccgcctcc aaaccgcagt 35160 |
| cccgcagtca | gttctgcagc | ctcagggcct | cgaacagcca | tgcttagaat ccgtccttct 35220 |
| ttcctgctcc | atctacccct | cccctctggc | ttctttttt | tcactggaga aagcccaccc 35280 |
| gagtctctca | gcctgcttcg | gaggttactg | cggcctcctc | cacgggtagt tctgggaccc 35340 |
| gggtctagtc | cgcggttccg | gagcaggtcc | ctccctggag | tcgtcaggcc cagtatgcgt 35400 |
| gtgctcagtg | tgctcgggaa | acacgcgtgg | gctttaacag | cagatctcca taaaagggtc 35460 |
| ccggagatag | cctctgcctg | gcccgaggcc | cagtgcctca | aagcggacgc ctttgcgctc 35520 |
| ccggaggtgc | tcacaccaca | gcggagcctg | ctggcgagtg | gagcgtagga ctgcgaacca 35580 |
| gcaatctccc | gagaagcggc | gaggggggagg | ggaatgtctg | tgaatcggtt atccctccca 35640 |
| cccccagcag | aagtcgggga | aatggggggtg | gaaggggggaa | aaagggagag aacaggagtg 35700 |
| gggttgagga | agggtaagga | ggaaggtgag | cttcctacag | ctgcggggga aggtggagaa 35760 |
| aattttcagg | gggacagctg | agtggtagag | ctagcgagct | tcagagaaat gttgacagac 35820 |
| agatgcccag | aaagtgagga | tgccgggcat | gggcactgcg | taccaggcac aggagatata 35880 |
| tggaggcagg | aaattggcac | atcataagca | tttgaccatc | ctgccctaaa acaaaacaaa 35940 |
| ttgaacaaca | acaacaacaa | aagataatag | caaaagtggc | acagtagtga gctcgcaggg 36000 |
| cccattccta | tatagaaaca | cagaaaaata | agcaaaagct | gccagaattg acttcgtggg 36060 |
| aactctggga | aacagtaaga | aagttttaca | gcaaccaagt | gagtgctgaa ccaaggcaaa 36120 |
| ggtaactgaa | acgcaatgat | agagaagagg | ggcagggaag | tgttgggtag acaaaggcgg 36180 |
| gtccctggta | agggccctcc | cctgggcctg | tgcccactgg | acctaggtga ggacaggcac 36240 |
| tccttccttc | acgcccaaat | gttgcatatc | ccaagaccac | cctgtcccgc cacgccccca 36300 |
| tcctttgcct | atgaaaaccc | tgagaccccta | gcaggcagac | acacaagcgg ctctatgtcc 36360 |
| agaggaactc | atcggaggaa | ctggacgtgg | agcggggcac | cccagcggaa gggagcacgc 36420 |
| cagtggaaga | gcacactgac | agaccatagg | agtcagtctg | ttatattatc atagtataat 36480 |
| attataaaat | tattataata | caataaaaat | ataaaaatat | aaataatgta ataaatatgg 36540 |
| ataaaaataa | taattacata | tttatattta | tatgagaaca | ctatgaataa ttttaagcca 36600 |
| aaaaacaact | cgatgttcat | cactggatga | gtagacgagc | aatttccagt atattcatac 36660 |
| aatggaatat | gattcagcca | taaaatgaaa | tgaggtactg | atacatgctg cagcaggaat 36720 |
| gaacccccaa | aacactacac | ttggtgaaag | aagccagaca | cggaaggtca catattgtat 36780 |
| gatcccattt | ataagaaata | ttcagaatag | gtaaatccat | agagacaaaa ggagttttgt 36840 |
| agttgccagt | agttggaggc | aagaagagtt | taacaggtat | gcttaatggg gcctcctatg 36900 |
| cagttgacga | aaatgttttg | ggctagatag | gagtgatggt | tgcataacat tgtactaaat 36960 |
| gccactgaat | tctactcttt | aaaatttta | gttttatgtt | atgtggcgtg taccctaaaa 37020 |
| aaaaaaatag | aggtgcagtg | ctccagcacg | ggatgaggca | gcgtggacag gagcatctcc 37080 |
| caacctcagt | gaagtctgag | ccgcgtgcct | gcaacaatcc | cactgtggca gagaaccgca 37140 |
| gagttccttc | cggtttggca | gcagtcattc | gcaacctcac | agccctctgg aaccccagcc 37200 |
| tgggggtctc | agaacgccga | ggcggggact | gggagccgag | tcggattccg agactatggg 37260 |
| ccagggttgg | ctggattcag | ttacctggct | gaggcctggt | gagcaaaata tcccaaacct 37320 |
| cgcgtgatct | ggaaggggaa | gccggataaa | tacggatctc | cagatgtgcc agtctcgagt 37380 |

```
ctatcgatat gaggtccccc tagagtttct attcatcatt ttaaccgcat tcatcgatc    37440
ttgagacacg gcttttgata ttttatcacc tcaagataaa tagtgttaga tgtctaatag    37500
cagcgttttt ctaagagata catgaaacaa cagtgtcaga aacgatgctg tcttccatgc    37560
gatgaaattg ttgtaatagg tgctcaataa atgttgacaa taaatgagtg aatgaatgaa    37620
aattatttta tttttatttg agctttggtt ctgccatttg ctagcagtgt gactcaagag    37680
aagccagtaa ccccctgag cttccctagt tcacaaaatg cttgtcatga agtcgacagc    37740
ttccggaggc tgcgaggctc gcaagaaatg cccacatgaa tgtgcgctta gggcgtgagt    37800
gctcactcca gaaaactcca acacagtgaa aaggcagaag cggtgttttt cttttttaca    37860
ttttataag aatatataaa aaatgatata aatggacatt tacggtagtg ggggaaggca    37920
tatatctacg ttaaaaggca ggacattttt aaaagctcta ttttctaaat gaaaactacg    37980
aaagcggggt ggggttgtggc gggggcagtt gtggccctgt aggaccttcg gtgactgatg    38040
atctaagttt cccgaggttt ctcagagcct ctctggttct ttcaatcggg gatgtctgca    38100
gagggcagaa agaaaacagg cgttagaaac ctgaggtcaa agatgtgtgg cacatcccgc    38160
cctcctctct tgccgtccct accggcattg aaatacttat ggataaagtt ctcgcaatgg    38220
cttcacgtgc atgtacccgc cgccaccgct ctcccacacc tccctggtcc agcagctagt    38280
ccactgcccg cctggctgct ccaggcgcgc cgaccgctca agcgctccag gtccacccgg    38340
cggagggcag agaaagcgcg accgcgcggc ccgcagggtt gcaagaagaa aacgagtgtt    38400
atataatgag tctcagtggt tgctcacaat gccaggcgcg aaggcgtgaa gatgtggcct    38460
ttcccttccc gcatccccag gcatcttttg cacctggtgc ggagtgagcc agccagcttg    38520
cgataaccaa agggcgcctc aggctctggc gctcctcggc ggaatcccgt agcttcccta    38580
cgcatgcctg cttctacaaa cccacaaatg gtttccgatc atttctgaaa caaaatggat    38640
gctcatttat tcatgtgctc tggcttctgc cttcctctct aatctcgttg cgtatgggct    38700
ccagctcgcc gttcggttct cccgaggcag catttacact tgagagtctc aagattattt    38760
tattcctgag ggagcatttg cacttgaaag tctcttttta cgtttattcc tgaggcagca    38820
tttgcacttg agtttctttc tcccgtagct tgcattagat tctccgacca ctctttagct    38880
tctcctccta ttcacacttc atatttaccc attgcattgg ttttataaac tcgctctctg    38940
aaaatagatt gttatcttcc ttaacgtctg tttcccaggt cgggcaagat agcttgggac    39000
tgtaatccca gtactttagg aggaggaggg gggatgatcg cttgagccca gataacatgg    39060
tgagaccttc gtctctatta aacaaacaaa caaacccagg cgtcgtggcg tgcacctgtg    39120
gtcccagcta gtcgggaggc tcaggtggga gaacccttg agccagggag tttgaggctg    39180
cagtgagctg tgatcgcgcc actgcactcc aggttgggca acagatcgac tctgtctcca    39240
aatgtaaacc ccatgagggc aagactcttg tttggtctca ttcaccttgg cgtgcccacc    39300
acctagaaca gggctgatca cgcagtagaa tctaaccata taattaattg tgcttgaaga    39360
gggggtgttg gggagtaaga gaaggaaggg aggagggaag aaatgaaaga cttgtgtgtt    39420
tggattaaat atattaggtt tggttaagag tcgttcagtt tattcatttg cttgtggccc    39480
aattcagtag ttttactccc tctcccactt ggctcctcag gctttttgct cagccctgga    39540
accgcgctgt aattggcagc tccttctaaa tcgggacccg gatgctagct gtaactggag    39600
ccgaagtctc cttcttcacc tcccgggacc tggatgctag ctgtaactgg agggaattgg    39660
cggggggag gggaggaggg gccgagtaaa gaagaacttc gcgtctttaa cttcgaaggt    39720
gattttgcgt tctgtatttta cagcatctcc aagcagaggg cttagagcta actcttcacc    39780
```

```
ctgtcctccc cagctcccct atggcccaag gagcccaatg ccccgttct gggccaaaat    39840
aagatggatt tcataatctt caaggtcatg ttttacctta aatattcgtg ttaattcccg    39900
tgtactgttt catatatcta ttttgtttca aaaaaaatg ttcctccccc cagaaacaat    39960
tgagtaatgt tggcagtttc agcagacagc tgtgggagta gggaactggg gccatggaat    40020
gggggcggag ggaggatgct ttgagatcac aaaaaggaaa ggcaagggca aggaggacca    40080
taattctacc ttcatcgctc agcgatctct tgcacaagtt taagagggaa aggagccaac    40140
tccggtgcac agactgccag ggtcagcgaa gtcttggtcc tgatgtcccc agaaccccct    40200
ggggcagctc tggaaaactc taccgcataa agcggagggt cagattagct gaggagggtc    40260
agattagttg agttgtgcag aagagccgag atcgagagat ctccagatga tgccacgcac    40320
aattgggttt ggaaatcctg aggttggtcc agccagcttg gtatgcaaat gaggaaacag    40380
acctggtaag tggatgcaac tggccctagt ttggaggaag aggggcact agacctctag    40440
cctcttgagt cttcattgct ccgcagtcta ggccttgaac tagcagaggg taggtgtttg    40500
ggtggtggta tgctttggga agtataatgt acaaaatggg ctttcacgtg cgcaagtcca    40560
tttcgggatt atttcccatt tgccgccctg gcggggcagg gcgatagggga gactcaggcc    40620
gtcccaccga ttggcgcgtg agctgaggca agaccggaga ctggtctccc gggctgaact    40680
ttctgtgctg gaaatgaat gctctgagct ttggaagctc tcagggtaca aattctcaga    40740
tcatcagtcc tcacctgagg gaccttccgc ggcatctatg cgggcatggt tactgcctct    40800
ggtgccccc gcagccgcgc gcaggtaccg tgcgacatcg cgatggccca gctcctcagc    40860
caggtccacg ggcagacggc cccaggcatc gcgcacgtcc agccgcgccc cggcccggtg    40920
cagcaccacc agcgtgtcca ggaagccctc ccgggcagcg tcgtgcacgg gtcgggtgag    40980
agtggcgggg tcggcgcagt tgggctccgc gccgtggagc agcagcagct ccgccactcg    41040
ggcgctgccc atcatcatga cctgccagag agaacagaat ggtcagagcc agggtggggg    41100
ccggcatgac ggaaaggaag cttgtgtaga gcccctcac cgccaagcag accccacac    41160
aagcccagg tgtctaatta ccctacatt tgcttccagt ttccaatttc cttcttgagt    41220
tctctatcca ttcttcagta cacaatgaat tccattatat cctccgaact tctgcggagc    41280
tgtcgtcaca ggcagagagc actgtgaggc acgggcaaaa tagcaaaggg gcagggacag    41340
actgactttt actccaggct aacttcctgt atttccctg agatacaact actgaaattt    41400
cttcctgaaa ttatgttagg cctggagatt ttttttttt ttttgttca ctgctgtata    41460
tccaagcgca gaatgtggta attgttaaaa agagaaaact tgtttgtttg ttaaaacaaa    41520
ttctcacaaa actttaagt tacacttagc ttctgggaat gttgaacttc aatttctttt    41580
tcattatatt agttttaaaa ttatatattg ggatagtaca gttgtatata tttatgtggt    41640
acaatatgaa gttatgatct ttgaacacaa tggggaatta ttaagtcaag ctaagtaacc    41700
tatccatcat ctcaaatatt tgacatttt gtcaaatgag agcatttggg atttactatt    41760
tagctatatt catcatgcta tgaaacacat ctcaaaaaaa acaatcaaac ttattcctcc    41820
catcttaact gaggctttat atcttgatta ccatctcccc attcctccca cccccagct    41880
ctagtaacca ccattctact ctttactgct aagaatgtaa ttgttttata tttcacgat    41940
aagtgagaac atgtgatatt tgtctttctg tgtttggctt atttcattta gcataatgct    42000
ctccaattcc aaaacttcaa tttcttcaag tataaaataa gaaggctagt ttaattaacc    42060
ctaaaattcc ttcctgtggt aggctgaata atgcccccc accccaatg tctatgtcct    42120
```

```
aatcctcaaa aactttaat acattaactt atgtggcaaa agaggctttg cagatgtgat      42180
ttaattaatg gtcttgaggg agattatcca gaattttcag ggtgggccca acataacccc      42240
aagtgttttt attagagggt cacagtcaga gagaagatac aagaatggaa gcacaggcca      42300
cagagaaaat acagagacca tgagccaagg aatttgatgg tcactagaag ctggaaaaga      42360
caaggaaaca gattgcccct tagagtttcc aaaaggaatg aaaccttgtg gacccatttt      42420
tgacttctga tctctagaac tgtaaaataa taattttgtg tttgttttag ctaacacatt      42480
tgtgataatt tgtaacagca gcagtaggaa actaaaacac ttcccaggtt tatgatttga      42540
gagttcatta aacaagagat ggtcacctct ttggttccta aatcatcttg gaaacaaagc      42600
catttccaga gaggaatttt aaaatactgt ctgcagtcat agcaaccta aaatttgagt      42660
gctgcatggt ggaagtagac aatttatttt aggataactg ttatttgtta tattagtttg      42720
aggatggtgg tgttaaagag gagttactta tttttaggta catttcatac taaacacaaa      42780
ttgcataatt tgcctaaatc aaggaattat actaaattat attatggtta ttaaatcctg      42840
tcctgagaaa gtgaaactga ctcagttttc aaagagacaa agagaaagta taagcaaacc      42900
aaattgcagc tacaaaaaga aagacaaaat gttgcagtat atttattgtt ttgtgtattc      42960
aatgaagtcc ttcgtcttgg tcataaaact agccttaaag gtttttctta tatttcatag      43020
tatgaaaaat ctaaaaagta acccatatgt aaatatttaa atcatgatag aaatccaaag      43080
caaaaagaaa atgaatcaat tgaattaaaa tgtgtaggat gcttaaaccc atttgataat      43140
atatccattt gataatatac taatatgaat ttagtacttt aaaatgttat ataaataaat      43200
gttcctatat taaacaccaa tgtagttagg attctaagcc aacatcattt ccccttttct      43260
acatgttctt ctcccgtctc cattaaaaat tgtcaaaact atccactttt cttttccctt      43320
tttgttttta aacaaataag gtctcttcta agatattgta ggactacaaa gccaaactcc      43380
cgggttcaag ctgttggcaa aattttagag atgctaagtt acccatgtat taattacttt      43440
taaatcctcc cctaactccc tcacaaaaca ggagtaggga gaggagaaac acctctgttc      43500
aaaaatgagg aattgaaaac tcttatcaca aataaactat atcaagtaag ctaaagatag      43560
taaaagagca aaaatgttag cagatattcc caaaatggta actacatatt acctctggaa      43620
tgatcacatg aatgtggctc attatttcct aagttcctac agcaaacata tatttatttg      43680
ccctactcag ttaaaaataa acacaatatg tagttgcttc tgaataattt ttctctctct      43740
cttctctct ttcttttcttt cgacaaagtc tcactctgtc acccaggctg gagtgaagtg      43800
gctccatctc gctgttcact acaacctcag cctcccgggt tcaagcgatt ctcctgcctc      43860
aacctcccga gtagctggga ttacaggcgc ctgccaccac ccccggctac ttttttgtatt      43920
tttagtagag gcgaggtttc acctgttggc caggctggtc tcgaactccc gacctcaggt      43980
gattccccc gccttgatct cccaaagtga agggattaca aggcgtgagg caccgcgccc      44040
ggccgcttct gaataatttc gatcaaaatt tatattcgat atttattcca acatacacca      44100
cagatttcca ctgataatcc ctcctagtaa gaaagataag ctccatccag gtatctgtga      44160
attggaggct aagtagtccc agcacatctt acatttcttt aagactccct ttttatccca      44220
aacgttcgta aattttgtat ctgataaaga gcatacttcc atctaataca aatatgttcc      44280
cccccttcaga tcttctcagc attcgagaga tctgtacgcg cgtggctcct cattcctctt      44340
ccttggcttc ccaagccccc agggcgtcgc caggaggagg tctgtgatta caaaccccctt      44400
ctgaaaactc cccaggaagc ctcccctttt tccggagaat cgaagcgcta cctgattcca      44460
attcccctgc aaacttcgtc ctccagagtc gcccgccatc ccctgctccc gctgcagacc      44520
```

```
ctctacccac ctggatcggc ctccgaccgt aactattcgg tgcgttgggc agcgccccg     44580 cctccagcag cgcccgcacc tcctctaccc gaccccgggc cgcggccgtg ccagccagt     44640 cagccgaagg ctccatgctg ctccccgccg ccggctccat gctgctcccc gccgcccgct   44700
gcctgctctc ccctctccg cagccgccga gcgcacgcgg tccgcccac cctctggtga     44760 ccagccagcc cctcctcttt cttcctccgg tgctggcgga agagcccct ccgaccctgt     44820 ccctcaaatc ctctggaggg accgcggtat ctttccaggc aaggggacgc cgtgagcgag   44880
tgctcggagg aggtgctatt aactccgagc acttagcgaa tgtggcaccc ctgaagtcgc   44940
cccaggttgg gtctccccg ggggcaccag ccggaagcag ccctcgccag agccagcgtt    45000
ggcaaggaag gaggactggg ctcctcccca cctgcccccc acaccgccct ccggcctccc   45060
tgctcccagc cgcgctcccc cgcctgccag caaaggcgtg tttgagtgcg ttcactctgt   45120
taaaaagaaa tccgcccccg ccccgtttcc ttcctccgcg atacaacctt cctaactgcc   45180
aaattgaatc ggggtgtttg gtgtcatagg gaaagtatgg cttcttcttt taatcataag   45240
aaaaagcaaa actattcttt cctagttgtg agagcccac cgagaatcga aatcacctgt     45300
acgactagaa agtgtccccc tacccctca acccttgatt ttcaggagcg cggggttcac    45360
taagtcagaa accctagttc aaaggattcc ttttggagag tcggactgct ctctccttcc   45420 cctcccttc ccctcctgcg tgtaaaacgg ctgtctgggg caagggtttc tcagacgtgt    45480
acattgcctg gtataagagc agactctgaa aagatgaggt ttatttaata cggacggggg   45540
agaattctgc ctgtaggcag ataggaaaat ggggagggag tcattggaag gacggactcc   45600
attctcaaag tcataattcc tagaccagaa aaagtgctca gtgttctaga agcagagttg   45660
cacagtgatc caaagaccag cttcaaatac tgtcctgtct ccttcacact tctcacattt   45720
ctctttccta ctgaaaatac cttgcatttt tcgtaattat aaaggggaa gggaatatga    45780 gtgcccctg ctttataggg gttgttgtga gtttaaatga tgtattaata catataagcc    45840
ttaagaacag tgccacacat cctaagctaa tacctgttag ctcttgaatt atccgctttg   45900
aggactggct tgcaatcttg tttttgaggca tagaaagaaa atgctttgga gcaggacgcg   45960
gtggctcaca cctgtaatcc cagcactttg ggaagccgag gcgggcagat cacctgaggt   46020
caggagttcg aggccagctt ggccaaaatg gtgacacccc gtctctacta aaaatacaaa   46080
aattagctgg ccatggtggc gcacgtgtgt aattccagct actcaggagg ctgaggcagg   46140
agaatcgctt gaacccggga ggcagaggtt gcagtaagcc gagatcgcgc caccaccctc   46200
cagcctgggt gacagaatga gactccgact caaaaaaaaa aaaaaaatg ctttggatag    46260 aattatcact attacataaa aggaaagtcc ggatgcggtg gctcacgtct ataatcccag   46320
cattctggga ggccgagaca gcggatcac ctgaggccag gagttcgaga caagcctgac    46380
caacatggcg aaaccctgtc tctactaaaa aatacaaaat tagcggggct tggtggcgca   46440
tgcctgtaat cccagctact cggaggctga tgtaggagaa tcgcttgaac ccaggagaag   46500
gcggaggttg cagtgagccg agatcgcgcc attgcactcc agcctgggag acaagagcga   46560
aacttggtct caagaaaaaa agaaagaaag aaagaaagaa agaccaagaa gaacttactc   46620
cctgaaaaga ttatgggcac cctccaccac cctcacttac aaagaaaagt taaacagcac   46680
taaagagtat aacaagcgca aggaggtaaa agttctaatt tttcctgtga ctactacttt   46740
ttaagcttat caaaaacatg tactacgttt taaaaaatgg attgctcaga cttttgctgat  46800 gccttaagca catgcttaat ctgcctactg gataatccag ctctgtttaa aagttatatt   46860
```

```
tcaatccctg gttgacttaa accttgtaga cccagtatat cttgtacttt tagtgtctgc   46920
ttgattttaa aacatgtagt tttaaaatg aagccaatga aaacaatttg ggatgtcaag    46980
tatgttatta aaatctacaa tgcattactg taccatttat attttcctcg gggtacctct   47040
caattagctg tgtagcaatg atagggaaaa ttcaaactat cgataaataa aattatttta   47100
gtttagttta agatatttta tgatggagga ggaagaaagt ggttgccagg atgggaggga   47160
gggaacacat ttccatcact aatacaatgg ttctttcttt ttgtttgttt gttttgtgtg   47220
tttttttgag atggagtttc gctctgttgc ccaggctgga gtgaaatggc accgcacgat   47280
ctctctcggt tcactgcaac ctccgcctcc cgggttcgag caattctcct gcctcagcct   47340
cccgagtagc tgggattaca ggcacatgct gccataccca gctaattttt gtattattag   47400
tagagacggg gtttcactat gttggctagg cttgtctcga actcctgacc tcaggtgatc   47460
cacccacctt agcctcccaa agtgctggga ttacaggcat gagccatcgt gcccggccta   47520
cagtggttct taatgggggt gggagagtgg gaagagtagg ctccttcaag agtctgttga   47580
aataaatacc ttcttctcaa aaagaaagt aggtaatgat ttttttaaa aaagatgtgt     47640
tcacttgcac atgtatttct agataaaact ttcagtgaat tcagggattt ctctgaaact   47700
ctaccatgga ttcctacatc aagaactctt tcagctcttg tgaaaatat atatagctat    47760
tggtgaagaa gatgggagat gcaaccatat aaaacaaca tttggatgca ttataaacag    47820
gtgtaaaagt tgactgcttt ggaaatacca agaacaagtt ttagatatgt atatctcata   47880
tcttgcagta gagctctgga aggattatgg catccttggg tggggccatt ttgctctaga   47940
aattgaagtc cattatccat tataaatctt atgtaggggg gagggggag ggatagcatt    48000
aggagatata cctaatgcta aatgatgagt tgatgggtgc agcacaccaa catggcacat   48060
gtatacatat gtaacaaacc tgcacattgt gcacatgtac tctaaaactt aaagtataaa   48120
taataataaa attaaaaaaa tattatgtaa ataattaata atagtgggaa actttccta    48180
gttttctgt taaagagccc attatactcc cagtttactc atacatatcg acctgaggtg    48240
caaaatccta gaagaatgaa aatataaagt cctggatctc tgtgctcctt atgccagtct   48300
cagatttcct atgtgcaaaa tgggattata atatatttca tgtggccata aaatatgata   48360
atgtatgtcc aaaagctttt aatgtaaaaa tttactacat ttactaaatt tactaaagtt   48420
tgttggttat tgttattatt attctcacac ttacttttcc tctttcctga aatgccatt    48480
cttttttag atttgcactg cctttgcagt tttgaaaatt ctacacgtga aatttaaacc    48540
tgtcttaatt ctgatcagtc ttataacaaa aaaagactac cacctgttca ttcattcaac   48600
aagctcagaa actaagggca gacatggggt ggggcagag gggagtaggt caaacatagt    48660
atctctacag tcagactgcc agggttcaaa cctcaactgt tccacttatt ggttcttta    48720
cttttatcaa agttactcaa catgtctggg cctctgtttt ctcatttgca tgattaggat   48780
aataactgta cttgcctcaa acagttgttt agggattaaa tgaagcatgt aacgctctta   48840
gaagagcaaa ataaagcaca gaatgataca agaaaatgaa aaggtgacca aactcattct   48900
catttgtctc tagtaggcaa aggcttccgg atgctgagag ctgatcccag tcttgaagaa   48960
tgatgtgaga gtttaaagat ggaaaagaag gagaaagata ttctaggcag aggtaagagg   49020
atgtgcaaag gcatagaagt ttaggaaaac tgaaagtgat tcatttagac ttattcctga   49080
aaaccagcct gtgaaggact cctcagagag ccaaaagaaa aactaggata atgggatggc   49140
aaggaagtgg ggacactgcg ttgactactc tttcatagct tggttgtgat agttcaaggc   49200
cctatgccat gaagtgaggc agatggaagg tggaggagac ctgagcacac atatacctgg   49260
```

```
aagggcaagt gccaagtgaa gagaagggaa agttagaaaa gaataaaaga aaagttaagt    49320
acacaggcaa gataggatat ttttgaggac ttgaggtccc tcaaaaataa tgaagaaata    49380
gaactcaaag tacagcggtg gttatagatt ttgtcacaag agatacatag atttgggagg    49440
gagaaaaggt cagaacgggg aggaagttga ggcacttcct tctatgaatg aggaggttag    49500
cttgtttgca gagtgaaaat aagatggtcg gttaggaagt ttgagaatcg taaaggtttg    49560
gaatacctct tatgagtaga gaggatgggt tgagtaagac tcagacagag aagccttttg    49620
ttttgttctt taaaaccaga ctggagaacc cagctgaggg tggagatcat gacacagtag    49680
ggacacctga ttactttctt taaactaaag aaagccctgc agtggtgcta ctacttcagc    49740
aaccctacaa atcaaagact agtcataata gatgtgaata ttaattcaac atattaccat    49800
aaagagacag aaagatactt gagaaggtag tgttccagag ttgggttctg gttctgatgc    49860
ggcattgtag gattggcaat atgcacgtat ttcatgggat aagcaagatg attttgttag    49920
gaaaataaag ggagttgagg caatagctct acactgagac caagtgacag ttctcatgta    49980
tctaatgaac tattttttga ctgcaaaatc ttttgagatt atttctagat tcattgtcca    50040 taatttttcaa aatgggctct ctcttgttct attgtttacg cttgaggtga gataatacac    50100
acatatttct ttaccagttt caatattaac attattatta aagataattg ttttaaatat    50160
agcttggtgt taaaaacaaa atatacatag aatatctctg gggagataca ggaaaagctg    50220
ttacctgtga ggtaaggaaa tgaagaactg ggatgggcat gtgacttact tttcacattc    50280
catgatttat attgtttgaa ttttgtacta tgtccatggc cttctaatg aattaaataa    50340 acataataaa actagtagac aaataagtta cttttattag aatcatcatt cataacttta    50400
gttgaaaaag agtaactgag tacctaatat atgtcaggca ctcggcttaa agttgtcaat    50460
attaattaag aaagaaggtt tcttagtcaa gagcatgtat tggtaacaac catcaatata    50520
tttgcttctc tgccaggcgc ggtggctcac gcctgtaatc ccagcacttt gggaggccga    50580
ggcgggcgga tcacgaggtc aggagatcta gaccatccta ggtaacacgg tgaaacccca    50640
tctctactaa agatacaaaa aattagccag gcgaggtggc gggcacctgt agtcccagct    50700
actccggagg ctgaggaagg agaatggcgt gaacccgggg ggcggagctt gcagtgagcc    50760
gagatcgcgc cactgcactc cagcctgggc aacagagcga gactccgtct caaaaaaaaa    50820
aaatgtatat atatatatac acgtatatat atatacgtgt atatatatat atacgtgtat    50880
atatatatac gtgtatatat atatatacgt gtatatatat atacgtgtat atatatatat    50940
acgtgtatat atatacgtgt atatatatat atacgtgtat atatatatat acgtgtatat    51000
atatatatac gtgtatatat atatacgt gtatatatat atatacgtgt atatatatat    51060
ttgcttctct ggaggaggaa ggtggtcttg aactgggatg agctcttgag tggagcctac    51120
agtaatcatt tgaggaggga agactggggt gatgcattct gataaatgac acctcacact    51180
tgtgttacca ggaaaaaaag atttcagagt ctggaaaagc tcccataatt aaagagaatt    51240
ccttaggaag tagcttatga gagcgagata tatgccctgt aatggagctc ccaggtacag    51300
ctgtgttaag ccttcataga tgagttctag aataggatgt tgggtgcaat agataaattat    51360 ttgaaggcaa aggcaatgga ggataaattc catgcatccc tttaatttag aaaagcaata    51420
atgtaaggaa attagagtcc ctgtcctagt tctaccacct actttgttac cctgaaaaaa    51480
tgactttttt tttttttttac tagcttcaat gtcttgatct acaaaacggg tataatcaca    51540
aacatgtaaa aacagattgt ggtttagccc cgaagtgcca aagtgctcct gaagctgccc    51600
```

```
cggataaaaa ttctgataat cgagtccaat gtgggtggta agagcatttt aaacgggaaa     51660
gaaacacttt cttaggtaaa taattgcaag gtatttaatt acttatgttc cacaaggaaa     51720
aaagatagct tcagcatgaa agggagacct ctgagaaagt agagcagacc tccaaacaga     51780
tttgctaaga aaaacaatg tgtccctggg agtagatctc tagaagtttc aaaacattgg      51840
atgtttcttt ctcccttta ctattctcta tttaattaaa ttcaatatag cacaattatt      51900
tagtatttgc tataaggaag gtactctttt agaaactctg tgccaacttc cctcattcag     51960
aattactgta aaatttatct tcctactcaa actggatctt agtaaggagt acaaaatgca     52020
aaattctttg atgtgttgta gatttaatgc ataattatag ttaagtcaca attttcaacc    52080 ttagttttcca aaatgttaac tgggtataga attagcagta cctattatca tcttcccaag   52140
aatattttga aggaaactta aaagtatatt acttattata tagcaggtat cttttctaaa    52200
ttatgtgcaa aacaaatgtg attttaaatc tatgtgagaa atttactatt aaaatatctc    52260
tagggtgtac tcttgtgaaa tgagggatct ttgcagctca tggagacaat tattccttaa    52320
cttttttgta aattttttt atgttgataa attacttgtg gcgaattact tatatctatt     52380
tgtagctatt tgatcagctg agaacactaa aagattagca cagtatgtat gtatgtacat    52440
actatatgca catatttggt atatatgtat attatgtaca gcacagatat tgagaattga    52500
cctcatcctg aggaacaaaa taagtaataa acataattag aggagatagg cagaaagaaa    52560
tagagataat aaaaaattca ttaaaagttg ccaagaaaat aatggctatc attttttcaa    52620
cccccagcta tgtgacaagc atcaagcagt tttatatgtg taatttataa ttccacagct    52680
gtcccatggg atagagagta ttattctttc ttcataatgc agacaaaaaa aaaagctcag    52740
agtgcttaag taataaggaa aagaaaagtt caaacttaag gttctcagtt ctgtttgaga    52800
ggtcctcact ctccctacta caatatgttt tcctaatgat aatttatcca gtacattgtg    52860
gacaactcat caatgcttcc ttttctttga ggactctgct ttagagcaag ttgcaaaacc    52920
tgggccaaga ttactgactc tccatttca gaaactactg tgcttctatg attattcttc     52980
agtagtaata catagtgata gaaatttgga actcaaagac acgcaaagtc ccctgaaagt    53040
cacttaattc agtcccctca ttttgaatg atttgctttc ctgattaaag ctcacatatt     53100 taaaataat taaggaatta gctgcacata gaaaatgaaa aactaccca cacaaagcaa      53160 taattattaa catttgaaa tacttcttcc tttttctttg cttaatcttt acattgtgaa     53220
tattatgcaa ttttgaaatg agcttttct aacttattac agcattttcc aaacttctcc     53280
aaaaacactt cataaatgct acttttaaca gctgtaacac atcccactgg aaaaagttat    53340
aatttactta atgatgtccc tgttgtcaga tatttaaggt gtttctaatt gctactaaaa    53400
atagtattgc agttttcaa agggtagaag gctcttgaat atattgtaaa actgcttttt     53460
aaaaagccac cattttgatt tatagataac aaaatggagg agtggtacat attgaggaac   53520
tatgtagcta tggttactca gctaataat gtttgctgta gctgttgaag tcagttcctc     53580
tctccattct ccattctttc tatggccaca gctacttaat tggacttaat gtgggtggcg   53640
ggaaatgcca accatatcct taatcataat tttggaaatg acacatatgc aagtgggaca   53700
agcctagtct ttaaactcag atagaactga cctctcattt accagctctg tgggcttgaa   53760
taagttatgt aaactttctg agcctttatt tcctcacctc acaaagtggg gaaaataaaa   53820
tttaccccat aaggttactg tgaggaataa agaatgtcag atatataaaa atccgggtgc   53880
acggtaggct ctcaataaat ggtgcttttt aattttttga gaatatatat gacatttact    53940
atgaagttat tcatttaggt catcaaaata aatgtccttt tgagtaattt ttcattaatt    54000
```

```
cctgtacatt ctagcaggta tctgtggttt caacaagcaa attctcttct aaaaggtatg    54060
atgctacctc tgaattctaa ccctctgaaa aaacagcttc tttgtaacaa agtttcccat    54120
gttatgacag aagaatttcc aaaaaaaacc cctcattaaa tcatgagaag tgacactgga    54180
gagtgtcact gtgttcagtg tttcctctgc attcattgct acccacctcc actgcttgga    54240
gtgcatttca agtggaaggt acaatggaga aactacagtt aaaactgagg aattgcaaaa    54300
tttactttct ctaaactact tttcctaacc tccctctttt tcattcttga taggacagat    54360
tttcccctct caaatatgct gtcctttta attgctaaca caagcatata taatatctca    54420
tttctgctta tgctgctgat gtacgcatgt gctgttagag ttctgagata atgttgaaag    54480
tcacagataa ataataatgt attcggtttt cactactggg agtggaggtt taatattcat    54540
gtttcactga taggtttaac actggtttag gatactctaa tttcaggggc accatctaca    54600
tggaagcttt tctcatcaaa tggagaatgg ttgtcccect tttgcccctc taaaaaacta    54660
tcctttaaaa gtagcttgct ttcttgggac tctatagtct tactgttatg ttcaattttc    54720
tgtgtccttt cctgaactta ggagagttct gaagccaatc tccctctga tattattaaa    54780 gattgcaaga aaattttctt gtgttagacc attcttcccc aaatcacatt cttcacctga    54840
tatgtgattc aactccactc aagggaatca acttcttgat gaaatataat caactttgat    54900
taaataagta actgcttcct attcatgttt tagcactttt cacatacaga tttaacatttt    54960 ccactcatgt tttcctttga gtctctgggt tgagggtaga gtttatctt ttgtgttgtt    55020 acggttaaga tgataacttc cataattaat ttttcaaaaa ggcaatgata acagaatata    55080
ctgtatgttt actctgtact gatttaaaac ccccaagtca atttagcctt aagaaagcat    55140
actatttagt gtattttgtg ttactctttg atatcctact tctaaataac ttcttcacat    55200
ttgcataaaa ataactgaag gtcaccctcc aaggtaggca ttttgaatgt cgtaaggatg    55260
acagtaatgt ttctgcctat cattcctttc atcacacaga cacacacaca cataattttt    55320
tatactaaag aatttttaga aaattgtttt ggtcaaaact gttgattcag atattcagac    55380
tgtgacaacc attctgaagg aattaaaaat ccagttatct tcagtgattc ctttggaaat    55440
tattattctg ggttattaga tagatagact aataactttt tttccagttt tctaaagcta    55500
ccttgatttc ctgtcttaga aaacaggggt tcacaaacac tgcttaatat ctctttaatg    55560
attatgaata ctagaatagc ttagaggtat accctaaagg ccaccatata gatcttctgt    55620
acagatgtga atttaaaagt atgcaaattt acactgattt tacctaacac cttggaacat    55680
accaggagtc tgaatacata aatatatttt tattatgata tgtatatttt taaagtggag    55740
tttagaaatt tctagctaca ctgaaaaatt ataatgaagt aggtatttac tgtaaaaaac    55800
taatgtgctt tcttaagggc atagtttaat taggcactat aataactgac aaacgtacac    55860
tgtgtaaaag tttacagtga ctcttcacac atactatttt atctacctct tattacggga    55920
ctaccatagg gtctcaggtt tacagatgag aacatgaaag cactgagagt ttctcatact    55980
tcattctggt accatgacag ctaataagca aaagaaatag aatctgctca caggtcatgt    56040
gaatgctaaa gaaagtaatc tttcaactgc acgcttcaag tggttcctgt gctggtgaat    56100
aggtatccca cttattgctt ttaaattaag gtaggaataa gtaatttata tgtacagtca    56160
tatgagaatt tttcactggt tttatttggg tcaaaaaata aattttgaa agatgttaac    56220 ctcctttcaa ccaataaata tttactgtga cttatacggc tgatgcttga gtatagtaga    56280
ggcccaaagg ggttaagcga ctttcaaaat aatagttaac taaagagat ggaactgaaa    56340
```

```
ccatatacat atttatagca ctccatgggc aaccaagttc aactatatat gaattactag    56400
tcaatgactt ttggtaggcc atgcaaccta tctgagcctc agtctccaga tctacaaaat    56460 gaaaaatga aacattgaaa acataaggat attgtgataa ttaaattaga taatggaagt    56520
tgaagtgtcc tattattgtt aagctcctcc taattgtttt tgaagaaaac ataactttta    56580
ccatgtgatt taggaagaaa gtttcaataa gcttttaaaa attaaatgtt aaatataata    56640
tattcaactt caactattca gcatgtaaat tgcatggagt aaaattcaaa gtgtccgatg    56700
ttggacattt aacaattaga tgttcaactg ggggagtcat tgttctctag acagctgctg    56760 tttcttaaa ttgggtgaga gagttataca attgctgagt cagatgatct ggcagcctga     56820
aagagaatga gagcaagaaa atggtggcac tcgagaaaag aaagcaaaac aagcttttc     56880 ctaatacatc agcaaagtca ctggtgtaat attagacaaa ttttagctta aaagcagaaa    56940
aatgatcatt tgaaaggcat gatatttag ttttttcttat aattgttact ttttagctta     57000 cattttcat ctatatttcc ccccccatca ctgtgctttt acagagacat aaagacccat     57060
cattttgtcc ataaatgctt tattctgtta tggctacatt ttcctgcaat cttgccctga    57120
tcttagataa gcataagtta aacctgtgaa acacttgtgc tttgatttt cttttttaca     57180 taattttagg ttgtcatgtt tattacgagc ctggtctgga tcataaaatg aaagaaaccc    57240
cttattacaa cacacacaca cacacacaca cacacacaca cacacagaga gagagagaga    57300
gagagagaga tccattcatc ctgcacgaac agaaagaagt gtatatagtg ttttaaaaag    57360
acaacgtatc ttatatagct tatgtggaaa ttttctgtct ggttctgtaa gctttaaaac    57420
acaaatatat cttgttatat ttttttctct caaactatgt tctgactgta aaaatgtggt    57480
atctacaaga cattcttttc caattcatac aaagggtcac ataataataa agggtctcct    57540
tcatttggtg aaataactcc tccactgatt actcagactc tcctccctgg gatccagtaa    57600
actgactcta aacttaaaat cttacctaaa atcctggacc tcaattcaaa gataaagaag    57660
cagaaataag gtttaaaaag taaaattggt catatttgtc aaattgtgtc ccaatgggcc    57720
acttgtatta gtatctcctt caagtgttta tttaaaatgc agatttctgg gacccacagc    57780
aaatctgaat caaattttct gaacgtgaac cccagaaata tgtattttta aaggcagccc    57840
aggtaataat gctgttgtta accttttgcca tacttttaaa atttctagtt actcacataa    57900
ttcaattaag aaagcagagg cttttttatt tacgttacct tgattgtacg attttattag    57960
tttcaatttg cttaagagat tacatgtctt tgttcatgta attctgaacc tctataaaac    58020
ttttctctct taaaaaaatc ctactgcctt cacaaccatt taaataattt atgatatttt    58080
attttgaagg tgaaagagaa aactgagaaa tagttgaatt aaaaaatcct ttgtgataac    58140
atgtttatat tttcatgaac aaagccaata agtcataaaa attaaaaatc aacatactat    58200
tttttgaaag gacctctgat gctttgggaa tttcaatcct gtagttgatg gctttcactt    58260 tttttccct tttattactt cttttttgatt gtagagttct gcccaaatga aaccatcatt     58320
ccagggctca tgaattaaat gaatgcactg agagacactg acaagcactg agaatttctt    58380
caaccaccct ttttaaaaaa caaatgctaa ttggacataa atatgagaac aatagacatt    58440
ggggactact agatggagga gaaagggaat gagcgagggc tgaaatacta cctactgtgg    58500
gtactgtgct cactacttga gtgacagatt cagtcgtact cgaaacctca gcatggtgca    58560
atataccttt gtaattaacc tgcacatgtg ccctctcctc ctaaataaaa gttgaaaaaa    58620
aatctacgag gcactatatt tttaaaaata ccactatgta caaggcactg tgctatatct    58680
ggaactacaa atattagtta aatagtccaa gattcagtgg gttcagagac tctaagtatt    58740
```

```
tgccattccc tttagatgga aacgttcttt ggtccaccaa gccctatcgt tctgctcttt    58800
ggaaattctc cctcactttc ttcataatgc cgtccttgac taactctcct ctagcaatac    58860
tattggtttt gtatgtgatt taaaatcatt cctgtaattt cttctgttta tatggcttcg    58920
tacaagagat tcacattcaa caaatagaaa aaaaacgcta ttgacatttg gtagcttcga    58980
caattgtaaa cacatgtggg tttgctgaat acacattaaa atagcatgaa ttaggatatg    59040
gtaaatctgt tgcggtccca agttggtggg tttttctagg aagagtcaga ccctttaaaa    59100
ggacctttta tcatctacca aacaaatcct tcatttatta attcccaagg ttttctccat    59160
cggttggctt actgtcatgg aaattgatct tgttttaata gctacttact ttttttttatt    59220 ctaatcaatg atttcatttg aaaagaaaat tttcaaacat ggggaaagct gcaatataag    59280
aagaaaacaa tggagagaca tcgtcactgg aaaaatacta cgggccactc tctataccat    59340 cctgcaccc cagatggaga aactgaggga agtcgtggcc tttcaacact cttgggtctc    59400
catctggctt ggaagggaac gaaatggctg tcaagagtct cagaagcgca ctttccccgt    59460
ggttcctccg ggtaaccctg actcactttt catctaccca tcccctccaa aacaaggcct    59520
agccagttcc aagctggaga ggtgacccag agttgcttc tgtcatgtcc tgcctttcgt    59580
ctcgagtcca ctaaccccac tcagactctg tctgctccca cccccaccgc ggccagtgaa    59640
atcccaatcg tcttccacgt ggaacccag gtccgcagtt atgataacgg atcacatcgc    59700
tcctgcggaa agtgcgcgcg gtggagtgat aattggacct agcgtctaaa ttcttgttgg    59760
aggacctcgt tccagctgcc agttaagcct ctgggatccg cagcgtctct aggaattgag    59820
agagtgggga agttaggatc caggaggagg atggtggggg ctgaggagtg gaggagcagc    59880
gtgcatctca tctcttgtcg ccgggcgggc gctctttcgg gtccagggcc cttgcaccccc   59940 cagcgtggct ccggaggcgg cgagacctgc ctgaaattga ttggagggga ctagagtgtg    60000 cttgtgggt ggggtagtgg gggcggagag aagagatccc aagaagggcg ccaagtgctg    60060
tgaccagagg cctaacacga ggcaccttgg aaacaggtat agctacggat ttatgggttt    60120
taaaatggaa cgtcttggtg aatggacata gcgtgcattt cacagtctga cgtcacagcc    60180
ctcgcaggtt ttcccagacc ttaaagccac gttctcgtgt atgacactta aacaactcag    60240
tttccttgtc tttcctccct ccctacccat ctaagggtag agaagctctt agttcatcca    60300
ctgtgtagga ctgttaccgt gtgtcaaagg ctttggaaat gtatatttta ctgatgatgg    60360
tcatagcact ttggaaaact caaaagtgaa acgaagaaaa taaatatcac caaacttttt    60420 cccaaccct ctcatcctgc ggaaaccatt ataactaatt tggtgagaga gagagagaga    60480
gagagagaga gagagagaga gagaaactgt ttactgtttg gaatcttgct ttaaaaaaac    60540
ctgactttat aatgcaatca tttaacagtc tatgaaatat tcttcagata cctgatgatc    60600
cagaatgtaa ctgtaccata atttaacact ttattgctag aattttatgc agttttttgat    60660 ttcttgctac tacttatcca tctgtattaa tctttgtcag aacctttctt tccttaggat    60720
gatgcctgaa tataaaatag ctgaatgaaa gtggatgggt tcatttttaaa atacaaaatt    60780 gttttttcttg atggtgaagt gtttaagagg tggattaatc tcattgggca acaaatagag    60840
aagatattag tagttaggta tatgagaatc agaattcaga taatttgtct taaaaattca    60900
tattcaatgt aaaaatttta tatttagaaa atgaaactgt acccattgtt tatataactt    60960
aaactgccaa aataaagcac cacaaaaact ttttatcacg ttggttttg tatcaggctg    61020 ggctttgcag cagatggagg agctagggca agcttgtcca acctgtgggc ccgagggtca    61080
```

```
catgcagccc aggatggttt tgaatgctgc ccaacacaaa ttcatacact ttcttaaagt   61140
atcatgagtt tttttttttt tttaagctca tcagctattg ttagtgttag tgtatttaat   61200
gtgtgtccca agacaattct tcttcttcct atgtggccca gggaaggtaa aagattgaac   61260
accctggcc tacagtgttc tactatgaag tttcagtttt agttcggcct agaatgtttt   61320
agtacagaag gcaagtgaga ttttctctgt ttctccaagg acttttgaaa aagtgtaaaa   61380
gcactgggcc cactgttgaa ccttgctata aaaagtatt tttgatacca tttgtatcac    61440
tttagtaata ggagttttc atatgttggg aaaatggttt agcttaactc tatcatggta   61500
gttgatagtg atgaactaac gtggaataat agatctgtaa accatcatag acggtaatag   61560
gctatgttgt tgctacctta ggatcataat ggactttcta aaattcaaga gtactcaaag   61620
aagtaaaatg aatataagtc ttgatttctg aaagggctat ggttcacttg aacacaata    61680
caaactgtga atcatgtaca catggggaat aatggtttat actaactgca cagtgcttac   61740
cttgagagga ctctgtgcta ttaaagaaaa aaataacctg agccttctga agtagctata   61800
aacaaatgaa tatttaactt cataataaaa atatgactat tttgtaaatg caccaaggta   61860
gaagtaacaa atcaactatg gcaatttttc aggtttctgt ggttaagaaa ctggtaacgt   61920
ggaattttag tatatgtatt tccaatcata taaaaataaa aagtcataat aaacatattt   61980
gcagaaactt aaaaaagtt aaaataacat cttatttgca atgatattaa ataattcata    62040
caagtaattt ttagcacttg tgcctctcaa ggaattgtat gaatcctaac ataattagta   62100
tccatatata ttcccaaatc aatatagcca tgggcataaa atatattaat gtgaaatata   62160
taattacata tcattataat taacaccgct agatttata ttatgtatat cattttacat    62220
atgaaattgg aaaattgcat atatttcaag acattctatc caagctgtgt tctatcttga   62280
gaaacttcct gaagattgcg cttttcacat acgtcctgaa aattgattta tacctaaata   62340
acaaaaaatg atctatttca atgaacctat catttaaata tttttgcatt tcatgcatat   62400
acattaacat actataaaat attttctcta acttaaaatc accacaatgt tatgttttat   62460
aggcctaaac taaaaaatac ataattatgg catttatata cattgacatg ttctactttg   62520
ttactacaga ttttcagagg caacttaata atttaaacaa aatgatttta tatagaataa   62580
tattaactag agtaataaat atttttatat agacaataat attaagaact atattcatac   62640
agttaccggt cacagtggct aaactttgc tgatacggat aaaccactgt taaaaaaaac    62700
aacaaccagg gtcttgtcaa tgtttcaaaa tgaattaaaa tcaaatccag caacaggccc   62760
tgaaatcctt tataagctcc tttgactaaa ttaaaaaaat taacttgcat aatatgaaaa   62820
gtaaaaaata aaatgtgcat ttatcctata gattataaat ttttgctaat agaaattgag   62880
acactaaatt aaacactgat agttttaaca ggtttatatt tccatgtcaa agagacaatt   62940
aacattgcag taaaaaaata attcccctc cgctggcctt tgcttttga agctatatat     63000
tcctggcgaa gcataccaca aggacggtca taaaagtgaa gcctcattaa attacttta    63060
gacttattac acaagtttta attagcattg tacatatttt aactgtacat atattctttc   63120
agttttcctg gttataggaa attacactgg ctgtgtcaac atttgtcaat gtgaggacaa   63180
aactaccttg gattctgttt ttcaagaagt aggcctcatt tttaaactgt gctaactgtc   63240
gtctgagatg actaaaatac tatcagttgg gatttctcag gaacagttct acagttctgt   63300
cgtttgctaa acatacgagc attgtcccga gcagtttcaa tcactcaggc cgccggacct   63360
ctacctctaa ctcacaaaga aagcccattt ccctgttggc tgcaaaactc ccccaagaag   63420
caagtgcttg ctcctcgcag cagtaactga tcctacgatc cttgttagca tttcaggaag   63480
```

```
tcgctgcctg cgtgcccgt atctcacggg tcctccactc tcctggaagg tgggagaggg   63540
tgaccccgcc gggaggctgg ggagaaaaaa ggccgcctcc agaaaactta gatggttagc   63600
aataattctc cccaaggaga aagaaagtgt gcttgaaata cacctttcct actgtgtgtg   63660
tgtgtgtgtg tgtgtgtgtg tgtgtgtgtg tgtgtgtgtc ttagtcattc ccacccagga   63720
tattcgggac tcactgactt ctgaggtggg tttagaagct ctgttcgcct cagtttccca   63780
cgattgaggg gctgtgtgaa gggaggtcca ggttcaatgg tactgcgaga accacatgtc   63840
taagtcgttg taacccgaat ggggaagcct ccaccggcgg ttatctcctc ctcctcctag   63900
cctgggctag agacgaatta tctgtttacg aaatcacacc aaacaaaaca agtgccgaat   63960
gcgccccgga cttttcgagg gcctttccta cctggtcttc taggaagcgg ctgctgccct   64020
agacgctggc tcctcagtag catcagcacg agggccacag cggcgggcgc cctggcgct   64080 gcccactccc ccgtgagccg cgggatgtga accacgaaaa ccctcactcg cggcgggccg   64140
cacgcgcgcc gaatccggag ggtcaccaag aacctgcgca ccatgttctc gccgcctcca   64200
gggccgagct cggcagccgc tgcgccgccc tttggcacca gaggtgagca gcgccactcc   64260
tgccccctta actgcagact gggacccacg caccgccccc tgcccatctc cgcccgcag   64320 gcgcgcaccc gccttccctg agcgcgcccg cccccccacct tcaccccccac cccaccccca   64380 cccccactcc cacccggacc tccaagatct cggaacggct ctgagccctg cgcacgcggg   64440
aagggctgcc ggaggcgccc gtaggaggc gcgcgcgcgg gcggctcagg gcccgcgttc   64500 ctctcccctcc cgcctaccgc cactttcccg ccctgtgtgc gccccccaccc ccaccaccat   64560 cttcccaccc tcagcgcggg cgccccgcgg tgacggccca ggggccggac gcctggaacg   64620
caactccagg cagctcgccc cctagctaca tccgtcacct gacacggccc taccaggaac   64680
agccgcgctc ccgcggattc tggtgctgct cgcgtccccg ctcccctatt ccccttattt   64740
tattcctggc tcccctcgtc gaaagtcttc cattcttcaa actagattat ttaaaaatga   64800
aaaaggaaga aaggaaagcg aggtcatctc attgctctat ccgccaatca ggaggctgaa   64860
tgtcagtttt gaactaaaag ccgctccgct cctcttctag atttggaaaa caagcgaaat   64920
taaactaaac cgctgcacgc ctctgacgcg acatctggac acggcgcggc gctggcgctg   64980
ccggagctgt cgaccggcc tggcgccgga ctaggtaggt ggagtcgcac ccgggggtcc   65040
cagctgggtc cgggcgccca ttcccctccc agctgcccgc gtcgccgagg gcgcctggct   65100
gggacaagca ccgagtcctt tgtgtctagc ccatttttat tttcggtttt aaccttcacg   65160 acagccgcg agcatctgag cgcttcttcc tctttcctct tcccccgcgc tcccctcccc   65220
tgctggccgc tcccctcctg tcgccgcgtc ctcgcgtaga atggttgtct tggcgaccgt   65280
tggccgctgc cgcctccacg ctctgccccg cgcccagaca ccccgactcc ccttgatccc   65340
gccgcctgac tcctcggcgt acgttctctc tccggtctcc ccctccatgt cccctcctcc   65400 cctttcttc cacatcaccg atcctttctg gactctctcc cttcctcctt tccagctggg   65460
agacaggaaa agcggtcctg tttgggaaca gtaaaagcag ggcaaggaaa ggaaggagcg   65520
gcagaaagga ggggtgagtc gaggacacag gggcagccgg agaatgcgga ggagccgggt   65580
cctgagcgcg gtctaagcga ggctcggctc tcgtccagga actcggacgc gggctcgccg   65640
gctctccgcg cgcgggaagt cgagcccagg acgccgcctt caggccggcg cgctgacccg   65700 gtgcccgac ccgagcctg cggtctgcct ggatccgtcc taaacctcgc gggctggacc   65760
cgcggcctga gtgggtgggt gtgtgccaga ggattcggga ctaggcccag ctccgggaac   65820
```

```
ctggaaatgt ggcccgcttc tcagtggctt cctgttcatg cgcttgggcc tagtggccta   65880
gttgaagaag tggaaccaca gcgtgagccg acagggcctt acagatcaga cgtcaagccc   65940
cccagacctt acagggagg aaagtgaggc ctgcactggc cgagccaccc acttaaggcg    66000
gtgcggtagc ctagaggagc ggcagacttc tctttcccca tccccgccc catcacttga    66060
cgttgctgcc ggacctcggt acaaacccaa gacaaacgg ggccctttgg aaaaagtgag    66120
atttagcgat cactcttacg tagccactct aaatatctat ctagatattt acaaatgcac   66180
ctccccggta ggtagatttc actcagaatt tacccaacac cgtgctttgt gctggggcca   66240
catgccacct ttctgtctag tatggctgct ctttctccct cttcgcaaat atagctcttt   66300
ttccttcagg tctcttctga agtaagtagc ccttcctcag aaatgcttcc cttttcaggc   66360
accctcatac caccgtgatt tttttcttta tagcacttag gacgaagaga ttattttact   66420
tatgtacttg tttacttgtt tgttgtgtag aatgtcagct ctatgggaac cagatccttt   66480
tatgggtctt cctctgcacc tatgccacgc ccccagcatt ccctcctac caccaccttc     66540
agccggcctc cgcctctgta gggggcatt aggttttctg tcccacagag gaagggcgct    66600
ttagaaaggg ttagttcatc ctggaagaaa aacgatgtcg gatgccagca tagtgtcatt   66660
taaagatact ggaggaatgg agtgggagcg gtgagggttt cttgggccta gacaatgtaa   66720
ctagttgttg caataaagca tggtggggaa aggagaaaag gcacgtatta aacatctttt   66780
gaagtcgcta tctatatcag tcagttctcc agggaaacag aacccattgt gtgtgtgtgc   66840
gtgccagtac cacacatatg tatatgtata tacacaccgt catggggttg cttaacaaca   66900
gggatacatt ctcagacatg tatctttagg cgatttcatt gttgtgcaaa catcatatac   66960
aaacctaggt ggtatagtct attatacatc taggctgtat ggtatgggct attgctccta   67020
ggctgcaaac ctttacaaca tgttactata ctgaatactg tagataattg taacaaaatg   67080
tagtttata tctaaacaca tctaaacata gaaaggtag tatgttgtgc tacaactta      67140
ggacagctat gacatcacta ggggatagga atttttcaca tccattataa tcttatggga   67200
caccaccaat atgtgactgt ggttgactga agcatcgtta tccagcacat gactctgtgt   67260
gtgtatacaa ttttatatat acgtacatta tatgtctaca cacacatatg tgggggagag   67320
aaagagaggg agggagagag agagagagag agagagaaag agaaagagag aaaatactta   67380
ttttaaggaa ttgtctcaga aaatggtggg ggttgacaaa ttggagaccc agggaagagt   67440
tgttgttgca agacttgaat ccaaaggcaa tctggaagca gaatttcttc ttccttgagg   67500
gacctcagtc atttctctta agctcttcaa ctgcttggat gaggaccacc catattattg   67560
aggataatct gcttttcaa gtctactgac ttaaatgtta atcatatcta aaaaatacct    67620
ccacagcaat atttagactg gtgtttgact caaacactgg gtaccacagc ctagccaagt   67680
tgacatacca aattaactgt cacattatcc cgtcatgcct gagggttct ctgaccctca    67740
gttttctgag gatcaaattt aaattgaggg atctatcttt gtttattgga gccatatagc   67800
tcaaagtata atcattttct ctccacagga actagaccta gggataaggg taattgctta   67860
tttcagagga atgccatctg aataaaagga taattatata gtaagctctc tgttcaaaaa   67920
atgtaaatat taagtttga acatctaaat tccatcttgg tttccccac tgccgctgcc    67980
caatacctgt tctctttcag ttgcagtatg caggggaatt ctaagtttaa tattagtctc   68040
agcaaaatac aatggtgaag atgactcttt ctagcataac aatgggtatg tggtattcca   68100
aatactttg gaatgcggag tgactattgg ctatgtgctc ttcaaaaaat taataatgaa    68160
gaactgagca tgtaatttca cttatattac ttattttatc ctcacagtgg cctttcaaaa   68220
```

```
ttgggattat tactcctgtt ttacaggtgg aaagaatgag gcctagaaag gctcaaatct  68280
tgaacacttc atggccagca agagccaggg ctggaatcat caggcaggcc tttgggttac  68340
aagccttgtg ccttttctgt tgtcccaaag gccagggtca atagggagtg agttatctgt  68400
gggtcactta tgcagacaga atcactgaat attggaagtt tttggggttc tcttccactg  68460
gcctaaaaac ctgagttaat tgagtttttt ttaacagggg taaataattt tctgttttag  68520
atcagcaaat tcattccata ggcagggata ggggagaaaa atcttactga atatcccttg  68580
tcttgttctc ctcctcccca aacttaatgt cctatgacac tagctttatc ccttaggtaa  68640
ctcttgatta tccaaatttc atgagaaact ttcctaacat tgcacatgct caaactcaaa  68700
accccaaagt cataagaaaa aagataacat aagcaagaat aaaaaacaat tatttgatca  68760
tatatgtcaa aagattaatt actagactat ataaataaat acataatcca gtaaaacaac  68820
aatccaataa aaaaggcaaa ggatataata gtttatagta gaatatgtgc aaatagtaaa  68880
aaataaaaag ataatcttac tcattaataa atgtaaacag aaacaatggc atataaccac  68940
aagtgtggca aaaagaaaaa agactacttt gacaaagttg tcaggaaaca atcactctta  69000
ctattacaac ttggtgtaat tgttttgaaa ggcagcatta caatatctag tcaaaactgt  69060
atgagaatat aggtacccct tgactcagct attccactat tttaagtatg taaagacaca  69120
cacaaataat gtatggaaat atatatacac atatatacta tatagtatat atagttcata  69180
tgtatgttat atgtttgtgt atatatctat atacttatat acacccttg actcagcaat   69240 tctattccta taactcatgt atgtaacata tataatacat atctttatat acacatatgt  69300
acacacatat ctgtaagtat gggaagatgt atacacatgt acacatatat atacatacat  69360
atgtatatat gtattttatg tatggataca tatgtatata tggatagatt ttacacctac  69420
agacacattt agatatgtaa cttcagctaa agcaattcac tcctatataa attgctacag  69480
ataacttgta taagtatgca gaaatgtttc tttatagcag tgtgtattag caaacaaagt  69540
gcaagaaaga gaaaatgat tgacatgctt gtgaggagac ttttttttgtt gttgttgttg  69600 ttagggctca ttcataaaat aataaaactg tgcatccata aacaataatg aagcacatct  69660
atatgcactg acaatggaag ttgtcaaaga tctattgcta attaaagaaa gcaagtgaca  69720
gaatagtatg atcccattca tgttttccaa atatgcatgc tgggggagag atgtttgcaa  69780
ttatatgtac ttatatttct ggaaggataa ttaaatattt gtaatagtgg ttacctttgg  69840
gtagtaagaa tgagggtggg aaaaatttca gattttgct tactacttt tgctttctgg   69900 actgtttgaa agtttaccat gagcaagaat tattaaataa caaccacagg aatattgggg  69960
ctcaaaccta gagattctaa ttttgtagac ctggagctga tcaacaagtc taaatgttaa  70020
aacatcctca cggatgattc tgacatggag ccaggattga gaaacaattt tctgaaatgg  70080 aagggggtttt aaacttgttg tcctcaaatg actactgagg caaacaccat tcttatagac  70140
ataagacata cttgggagca aatgtataat aaagtggtat gcttccctag aaaggggacg  70200
accttaaatc tttctgttta tggtggtatt taaacatatt aaaaactact aattttggaa  70260
tagtcttact gtgataagtc taactatcaa aggcagtcca gagattagca aataatagag  70320
gatgatcaaa tgttttcag aaaatattat aggtggcact ttggcaggag attctgagaa  70380
tggtgagagg gtgcctctgt gccctaggaa aggtgataga gcttagaaac tcagaactca  70440 gatgaatga ggagccatgc catatacatc tttacaacag tcaccctcta gaagaaaact  70500
ctgtgttgac aataatctgc tgacttgtct gtgggttttt gaacagaata aactgttct   70560
```

```
tcttttatgt ttgtgtatta ttgcttataa atatattcta aaatatataa taacaaacaa    70620
taacagtact tgcagcttaa ttaaagaaaa aatgcaagta tcttatttat actaagagaa    70680
gagagaaacc cgaagaacaa tggattatcc ttacatattt ggtttgggat tacattgaga    70740
gctacctaaa taccagacac tcattcttgg tcctgactcc tactctgtta tccatagctc    70800
agtacctagt atctggcgca gaaagaagtg gaatggaatt atcagggaga cccagttttt    70860
agccaagact aaaaggtttt agccaagggg atggaagaat ttgtgcatag atagacggca    70920
gatgggaatt cgtttaaaat ggaatggaga cccagaggtc acataagaca gggttcagag    70980
gaagtagccc caacaacatc ataatagaga acattgataa tgagaggata gatagattat    71040
gcatttgggg aggaggccaa atatgagaaa taagacatgg tttacttact gtaattggtc    71100
ttaaagtttt gagtggaact ctgttgtaaa atattttctg tgccagagct gactccatat    71160
atctactgga agtctaatgc caggggcttc tgagtgtgaa gtggattaat aggtgtttgg    71220
ggtcctttgt aaacttctag tgtaatgtga atagctgtga ggtagtcagt gtgtcatctt    71280
aatacattgt tcttagttct ttttccagca aactcttttg ttttacattt agttcacacc    71340
acaaattagt aagtcaggct tggtgctttt tgacccatac attaattttc attactgtgc    71400
ttaatataca atccatgcca attacatatt attaattagt ggcactagta ttagttcata    71460
ttttctttta ttatgtaatt aatagggcct atatgtgaaa gttactgtgt ttctgtaaaa    71520
tgaagtattc ttttccctta cgcaaggaat gacattaaaa tcttctgagt agggaattta    71580
agaggcaaga aaggagtaat ttcatttgga tagctgaaat tgagaaacgt tttatagaaa    71640
cttttcaggt atgaaggata gtagtagaga tgttacatga gttagcactc atatattgaa    71700
ttagttaagg aaccaatgtg ggaatctagg tcttctatct tccagtcaag tccttgtttc    71760
acttttcttc attccctctt tctttcctgt cgttataagt agaataggaa aatattgaaa    71820
gtattgaggc tcaactgttg ttgccccttt aagtaatttc taaaattaaa attgtcttat    71880
tttcatatat gtgtgattgt gtatctaggt atctctttgt agcttagtaa ttgaacactg    71940
tgaactacac caacctaagc attattctcc aagttttcat caaataacta gacagtttct    72000
gttaatactg aaaatctagt aaacgtgtca gaatttggtt atgattagtt gctgacataa    72060
aacatgaggg cagacctcac tgtactttag aagatactgg ctttcacatt tgccccagta    72120
ggtagttcac atgagtgctt cttcagataa tgtctctaag ttttgcatat cattagttct    72180
acttgctcca cttttgatag agtggcaatg tattgaacat tgtaaaaatt atgctctatg    72240
atttaaaaaa tccatctctg gtaaagcata aaatgagtat atgtttact gtttaaaata     72300 attgaggggt aattatagaa tcagcaaaaa gaaaaaaaaa ccctactgac tattacatat    72360
caatgcacac agtgtgttaa tattttcaaa aaagggaggg caatctcagt gtaagtgtaa    72420
atgaaattag ttttttgtata tatttgctga agatcagtta cctagcttca tatgataaat    72480
tatttggtgc tggtcacaat attgtgcttg ccatattagg gaaataaaat atcatgaaag    72540
tattcctaag tatacatttt cccagaggcg tttggggttt tatcagtctc gagctctcct    72600
cttgaaactg tttcattcct tagttatgaa attactaatt ttaaccattt aaggcatagg    72660
aaattttaca tagattttgc tttaacagca aaacacccct taaaaaattc atccacttag    72720
gtgaaaaata aaagataaaa atgaagccaa atgaatgtta ttaaatttat aaatttattt    72780
aactttccag atcttcttgg aataaatgtc aggtagtaga atttgtacaa accttggtaa    72840
tgtcttaggt ttagatacga acttaacagg tatatttaat tttctgtatt ccacaatgga    72900
gctagaagca ggactcatga aaatagtaac tatatgtttt gcatgtatcc ttcaaagtga    72960
```

```
aatccttaac aaatttaaca gtatatatta ggctgctgat gaaacagcta aacctgtctg   73020
ccaggtggct tcgaaaatgg aattaatttt tacatggcat tgataagtta ctatttcaat   73080
acaaccaggt ggtaattgat acccaataat gtttgaggtt tgctttaaat aaaaaaaact   73140
aacaaaacaa acaaaaaaaa cagtgtaata tagtactgtg ggatccacaa taacattttc   73200
tttagtttcc cttaatatca ggttgtcatt aggaaagatt ccacaagtta tttaaaccag   73260
aaatgaagta acatgtttca tatctatttc aagggataat ttttcatgac ccagtataat   73320
gcaactagca aatttaaaca tcttggaatt taagatatag aggtcaaatt aagggatttt   73380 ataaccaaa tgggagattt taaagtatca actgacttct tttatataga atgttttcta   73440
ataattgtaa aatactgtaa cttttaaaaat attattcttg tagcctctaa tgattgagtg   73500
cttaagtgat aactagaaat atattttctg tccctgtgct tcagtttgaa aatggaggtt   73560
ccattatctt tgttccaaaa atttgggttt ttataggtgt gttgggggg gttattctcc   73620 atattgttga cattttaaaa tagttttcaa acaaaccgtt tatatttact agaagttaga   73680
gaaagaaaag ccaccttagg agcttacaag ggagatcatt gtgtatttct gctttttttt   73740
aaaaaaagtt atcttcatgt gtatcattca tgattttgga ggacaagctg gtgcaatggg   73800
aagaaaagca agacaaccat aatcagctgt ggaactagat gcacttcttt gtgcatccat   73860
ggaatgaata tcttgtaacc tttggcaagt tacttgatat ttctttgcct cattgtcctc   73920
atctgggaaa caatacctat ctctcaggtt taaatattaa attaacaaat atattttaat   73980
gcatacctgg tacagattat gtgtcaataa acatatcctt tccccaataa catatgctct   74040
gattctcaac taactttccc cagtaatatg ttcattttgg gaataggaat tggtagagaa   74100
gtaaagattt gtgtattcaa ctcaaatgta ctccttctta taagtctcca ctctcaaatg   74160
acttgtttct gttccttttt tctcttttaa atgtgtatct ggtagaatga gcatttagaa   74220
gcataataca tgtatacact ttgtgtttaa ttttctatgg cataagtaag cagttttttat   74280 gaattgctgg tattgcttat gagcaattat tacaaacatt gagagaaggg aaccctgtg   74340 aacctttaac atttctcagg agttagtggt aaacccatga acatgtattt ttaaaccaaa   74400
ttacccacct cttggagttc aatctctgtt aattctttat taaagtagtg aagtatcagt   74460
tgttccaatg atataatgat caagcaaccc tggaaattaa atcccaaagc agtgcacctt   74520
tagtttgttc agtgatagta ggacatccca cgagccatca tatattttca agttttttata   74580 ctcaatctac ttttttcagca atcttttggg aactatccca agataattta ctgcataagt   74640
gcatctatct tctaaaagac atttggaata tttcttagtc tgacctctgc accctgagac   74700
actctataaa ggaaacaatc agaaaaattt aacaagaaa taaataggtt aagaagaaag   74760
caatctaggc gtttgcactg agtttgcaac agtgccattg ctacatttaa gagctgtagt   74820
tcttcctcac atttttaactg agagccacta gttatgttac ttaaaatctc cccattaaat   74880
aagacagttg ctgaacaact aaaaagtaca aaatatcaca aaatcaaaaa gtagcaagtc   74940
ataaggggat ttccgcatcc tagcatgtgt gtgtgtgtgt gtgtgtgtgt gtgtgaaaga   75000
aaacgttaca gttaaccgtt acaattgctc tcactccact ccaccacctc atcctgtgta   75060
gtctgcctgc ggaacccgcg ggaatctctc ctcagtgtag taagagcaaa ggccagcatc   75120
ctgtgcaaag gtgctctgca gcgtcgtgat ccagggattt tagcatctgt cgtcgcttgc   75180
acatcctctc ttacccctct gctatctggt ggagttgggc gagggtctcc agggcttcca   75240
gagagtgtcg tttacgcatg tgacttgcca tgcgctcaaa ctaaagcgcc gccggggact   75300
```

-continued

```
tactgaagcc cacctcggcc ctcctccact ttgtcctcag tcttcaggtt ttcctttctg    75360
ccgctagggc ctaagttgtg ggttcaccat aactcctcag cagacattgg agtgaacgca    75420
tcgactgccg tcacccaagt gctaatcact gccttctccc actcagcgct ggagtgggag    75480
attcatccat cggaagattc gtagccacca ggtccagtca aggatttcat atgcactttc    75540
cctcagaaaa ccctgaaaag caaacgaccc ctggaatgtc acacactcct aaatatccct    75600
ggaaatccgc ttctctgtgt ttcgcttcat ggtgagtgtc gagggccaga taagacaaag    75660
aaaaaaatgt atggaaggtt attcccggtc ggctcctcct tcctgtgagt ctcagacagg    75720
cttgcaggct tacaggcttt ccgccgctcc ccgttggcag ccttcatcga attaggtggg    75780
tgggggtggg aaattgggta agaaaataaa gtcgttgtgg gcggctgggg aacctggcgt    75840
cagtccccccg tggctgtgcg caggtaccct gcaacgtcgc ggtggccccg ctcctcggcc    75900
aagtccacgg gcagacgacc ccaggcatcg cgcacgtcca gccgcgcccc ggcccggtgc    75960
agcaccacca gcgtgtccag gaagccctcc cgggcagcat catgcaccgg tcgggtgaga    76020
gtggcagggt ctgcgcagtt gggctccgcg ccgtggagca gcagcagctc cgccacgcgg    76080
gcgctgccca tcatcatgac ctgccagaga gagcagagtg gtcagagcca gggtgggggc    76140
aggtatggga gatgccggcc ggggcaaggc aggtggagcc atttaaagaa cacctaatt    76200
gcaaagtttt cacccagtgc agaggtgttc aggtctctga tgtctggtgt ttcttcattt    76260
gctgatgcaa tccactttcc cacccccacct tcaggttata ctcagtacaa attaaatgcc    76320
attttattct ctaaacgtgc agagacaaga aagttgatgg taaagtgatg atcatcatta    76380
tggaaaaaca aatcttgatt tccattggaa catgggaatc tattttgtta aatgatttag    76440
gggcagagtt aaatttattc ggcttttaaa gttttaaatt atttgccttg ctgaccccctc    76500
ctccataatc caggtctaca aatatttatt aggtagtcaa ctactgtttg ttagaagttg    76560
ggagtaatgg tttaggggag aaaataaaca actaagtttt tttctttctt tttttttaa    76620
tttatttagt tctcatagca aatcccgtgc ggaaggcttt tgtttgtcat gtgtctgagc    76680
tcataactgg cttgtagtgt gataatttga gccaaagttg gagattagaa gggaaaagta    76740
aattaaatca tgcaaaatct tataaaatta taataaatga ttttccctta acagttcatc    76800
atttttaaatt tagactataa tattttttaat gtaatataaa actaactata tttgtatact    76860
acaggatttt ataatagcta agatttaaaa atgttaaaca gtaaatatttt tgctatataa    76920
aaagagcttg ggccaggccc agtggcttat gcctgtaatc ccagcacttt gggaggccat    76980
agcaggcaga tcacctgagg tcaggagttc gagaccagcc tggccaacat ggtgaaatcc    77040
cgtctctact acaaaaaata aaaaattagc tgggcatggt ggggcgtgcc tgtagtccca    77100
gcaactcagg aggctgaggc aggagaatcg cttgcatcct ggaagaggtt gcagtgagct    77160
gagattgtgc cactgcactc cagcctgtcc gacagagtga ggcctcatct caaaaaaaat    77220
aaaataaata aataaataaa tagagcttgg atgttagcag tcaatcagga tgatgcataa    77280
cttagaaaaa atgatgtttt gcaggagtaa tcctgtagca gccatttgtg tacatgaaca    77340
ttatgaaaac atttgctgtc atatttaaag tcaattataa gacaattttt ggtaactaaa    77400
tgtctaaaat cgagttattt gttatgggtt tatgcactttt aaaatatacc atttaattga    77460
aaggcagtat acttctcatg ttttgttggc ttgtttcatt aatattagaa atgttcattt    77520
catctcttaa aaaccgtgat aagttatatc tactagtgat gtaaggatat tttacataga    77580
aaaaagggg aaaatagctg ctgttagtat ttcagaaaat ggtgaattac atatataact    77640
tgttttttata attattaata aaatttaag ttttttaagat gcacttttaca atattttttgc    77700
```

```
tcctttaaaa atccctcatt tgttatacca ttattctaag aattcaaaag aaatgaacac   77760
ttctttaaaa tctatactat taacaagatc ccttaatatt agcttagttt tagagggtga   77820
tagtgaggtg agtactgaat atgaccacta gccaacggta aagtacaaaa gagttgtccg   77880
agattgtaaa agaaataaaa aatatcagta ctaattaaag caggattcgt acttaaacat   77940
tgaataagtg tattttaaca atgaagataa agatgcatta tttatgaaga tcctttgcca   78000
ttcaaaaagg acctaacagt tgctgcagga atatttttgt aatctgggca ctgagtatga   78060
taattaaaga atgagaaacc tatagaacta tatatttttt ctcttatgca tcactcataa   78120
gacactgcta acataaaagg aactaagtac tgtggttgag gaatcccgtc tcattctcaa   78180
ttaacctcta tgagaaaaca atacaacaga tttcatatag tagcttagaa gtttacattg   78240 atttttttcca tgtactatga ttttgtagaa ttccttaaat ccaatctaga atgcgtaact   78300
tatactttac ttatctttat cgttgaaagc agacagacaa gataatcttc ttccctaaat   78360
aagctttcct tttctccttt tctccccaat tcagtctatt ccttgcatct ctgatcatga   78420
gatggcagaa caaaaccac taaaaaaagc ttaaacagtg ggttttttcaa tgtctctctt   78480 taggattttt gctgggtaaa agcctgtttt acgcgtggaa tgcacacctc cggccaacgg   78540
agactcctgt acaaatctac atcggcgatc taggttccag ccccgatccg ccgaggccgc   78600
gccccgcgtt cgcgcgcccc ctgccggcga ggccctgggg ccccagctac ctggatcgcg   78660
cgcctcccga aacggttgac tccgttggga tccgcgccgg cttccaggag ctgtcgcacc   78720
ttctccacta gtccccgcgc cgcggcgctg gccagaccct catcgctgcc gcccccactg   78780
ggcatgccct tgttctcctc gcgcattccg cagcccccag acgcgcagcg gcccggataa   78840
tccaccgttg gccgtaaact taacgacact cttcccttct ttcccacgct gctccggcgc   78900
actctctcct tcctaggaga cctgggctca gcttcattac cctcccgtcg tccttctgcg   78960
gcttggggcc ccgtgcagtg gccgagcggc cggtcgttag ctccgggctt ttcctggcgc   79020
tcaagaacca gcgggcgcgc ctggattgct tctgggaaaa agcgcctagc gcggacgcag   79080
ccgagctcaa agccgctctg gccgcagggt gcggacgcgt cgcggagtcc tcactgcccc   79140
gcctcgctct ggcagagtgg ggagccagcc ggcaaagaat tccgttttca gctgggccaa   79200
ggggccggcg tctccccacc cccttaggct ccgcccctg tccgctgtga tcgccgggag   79260
gccaggcccg ggccgacgcg tcacgagggc ggggaagcct gcccaaagat gctaggacgc   79320
atgcgccaga gactgggcca gggagccgcc aggaatgctg gctgcactgc tcgctggatg   79380
tccagtaaag ccaaggctaa tattttggga atgttcacca ctgccctcag ctcctaatcc   79440
ccagtaggcg gagcagagga tttctgttcc ttcagccagc cagttggttt cactgtggag   79500
acgttggtgg ctcccttgtg accgagagaa agtcattcaa aataactccg tgtttcttaa   79560
gatgtctgaa agcgacagct ctgcacctgt catacaagtt aaattcatcc ccaggcagta   79620
cttgggcttc acaagtttca taacttgtat caaacttagc aattttctct tggatgtgtc   79680
tttctgtttg aattagtcaa ccataaaaat agagaaaaat cccgagaatc atgttttgcg   79740
tgtgcttttt aattctttcc attttttgcat tatggataca acccctaaaa gagaaaaaaa   79800
ctagttcgag attgagagtg gcaacctggc acacataaga caaaaaaaaa ttatacttta   79860
agaatctgag atcccagttt catcatattt gtacagtaaa tctttgtttg cactcttacc   79920
tatttaaacc cactttgtca ggtatcttat tttattttat catgagtaat aaaggaaatt   79980
tatgcagtaa taatgaaaca tcataagaga ggggtgtggt gctgggcttg tcattaaaca   80040
```

```
ggctgaacct gtcattaaat tctcttctga agatttaaat gccaagtgct ttttttcccc    80100
ttcctaatct tcctaggtga gtttgaatca acatttatta cttaaaatat ttaaaacatt    80160
tcagcggatg ctacattgga taggaagaga accgcaagtt atggatttgt tgcctaaaaa    80220
ctttggtgag gaactgcata agtggacctc tcctaaaagt gaacaatttt tgtttacaga    80280
atcattttgg ttcggagtgc tgaggaagac aaagtcttaa caggagggca attgcttgtg    80340
tattgcaaaa tgagagtctt cacatgtttt tttaggata ccttagctct gactcctcat     80400
cccccaaatc cctgtagaat taaaaaaagc tctttctttt aaaggcagtg gaagtgccac    80460
caccatggaa gtgctggtta gggctgaaaa tctactgaca gagcctcaac agagctgaaa    80520
tccacctgga cagggaaggg aaccgggtag cattaataac aatttctttt tctttcccat    80580
ccaaccccca tttcctagtc ttcagtttct taatttctct accttttact cttatgctct    80640
tgttttgacc tttgagtttc tctgaaactt atcagaaaag ttaggacaag atagtctgac    80700
ccaattcttg agccattttc ttaggtagta aatatgtcag aaaaatgaaa gctgtttgga    80760
gttgataagg aaatggaaga taatgttttt ctttgagggg gacataaaga atggtgatag    80820
ggaaagaacc aatgactaag taaaatgact gagaatcttg cacgaggcag atgtgtgagc    80880
ttcgcgaagc aagttgactg aatgaaaaac aactttgggt agggaaaacg ttgccggggg    80940
cattcgcgct tactagcacc acggacagcg ctttgcttat actcaggcct gggtggtcct    81000
aaccagctcc agacagaatt ctaaagcttc acacttgatc ttccaaagcc ccttttctcc    81060
cgtcaaatag aaaggacatt atggaagctc aatgaatttc tttgaaaaac caacctgctc    81120
aacctggttt tcaaatatga ttggatttta tctaatattc tctgtataaa gaatattata    81180
tagtctatat ttagaagacg agaagagaaa tcaaacttat tgtgtactct gtacgaagtg    81240
ctttacagct gttgtttcat ttaatactca taaaactcct ctgtggcatg tgtccatatt    81300
tcaattttac agacaagcca aaaggatcag agaatttgag tgacttgtat actagctaat    81360
cattgttgga ggtgggtata acttttgcga cttcagagtc tttttaccct ttatactaca    81420
tagtgttttt tttagcagct gtcatggtag gcttaactgg aaaaaagtaa taaactggct    81480
tataattatt tttcagtcta cactgtgttt tccagatggc tcacctcaca gcacacccctt    81540 accagacttc aaagatgaca tttcacatgt aatacaatag cacatttgtc ttggacaata    81600
gagtgagatt atgaaacatt ttacctctcc ttgaaacccca gctgtctcta gggtgaaaca    81660
caatctgttg ttaatgcttt aaacacattt aaaagatgaa gtggatggga acatagtggg    81720
cagctgaaac ttggaattgt cagagccatg tcttttaata aggtggagaa tttataattg    81780
agaagaaaga aagagaaagt taatggtaaa ttggcataga attttggagg tcagtagaag    81840
ggaatgagtg gcatccattc caatgttgca cataactcag atcactagta ataatatttt    81900
tatattctag ttggtgaaat tgtctgtata tgaccttgat atagaagtat gaacagatct    81960
gccatcctct ttttcttcag cgaggcagcc gagctgcaga cacagagatg cagatctttg    82020
tgaagaccct cacgggcaag accatcaccc ttgaggtcga gcccagtgac accattgaga    82080
atgtcagtgc gaaaattcaa gacaaggagg gtatccccc tgacaagcag cgtctgatat    82140
ttgccagcaa acagctggag gatggccgca ctctctcaga ctacaacgtc cagaaacagc    82200
ccaccccgca cctggtgctg cacctgcgag gtggcattat tgagccttca ctcttccagc    82260
tcacctagaa atacagctga aacaagatga tctgccataa gcgctatgct ctcctgcacc    82320
cctatgctgt caattgccgc aagaagaagt gtggccacac caacaacctg cacccccaaga    82380 aggtcaaata aggctcttcc ttcctcggag ggcagcctcc tgcccaggcc ccatggccct    82440
```

```
ggagcctcaa taaagtgtcc ctttcattga ctggaaaaaa aaaaagtatg aatagaactg   82500
gttgactggc aagagaaac agcgacctaa ccttgccctc atttatgcac acttttgcat    82560
atgattagga ctaagatagt gtttataagt gagaagagaa ggaaattcat aatcactttt   82620
ggggcttttt caaattttt atgaacacac cttcccacca agaggtttga ttttctccat    82680
tttatgagtt gggtttattg ctccgtgatc cacagtatat ccacttctat attcccatgt   82740
atttttcaag attaattaaa tggtggactt gttcatcatt ttagtatccg tattagtttg   82800
ctagggctgc cataacagaa taccacagac tgagtagctt aaacaacaaa tatttatttt   82860
ctcagagttt taacttctcc tgaggcttct cttcttgact tgcacatggc catcctactg   82920
ctgcctcttc acatagtcat ccctctgtgc acacgtgccc ctggatctct tgtgtgtgtc   82980
caaatttcct cctcttttga ggacaccagt cagattggat tagggcccac cccaatggcc   83040
ttattttaac ttagtcactt ctttaagggc tctatttcca aatacggtca aattgtgagg   83100
tattgggctt aggactttaa tataaaaatt tagaggtgac agaatttaac ccataacaac   83160
agcatcttaa ttttacaca ttttactttt catttctttt taaactgtta ttaataattt    83220
attcatttga ataaggatta aaataaggct aggatattga aattggttga aattgctaca   83280
gtctcttgta tctctctctc tctcttttt ttcttataag ggacaggttt cattcacctt    83340
gtcgaccagg ctgagtgca atactgtgag caagggtcac tgctgcctcg aattcctggg    83400
cttaagggat gctcctgcct catcctccag agtagatggg actacaggtg ttggccacca   83460
tgactggcta atatttttac ttttttgaag agatgaagtc ttgccatctg cccaggctg    83520 gtcccgaact cctgggctca cacaattctt tcacctcggc cccccaaagt gctggattgc   83580
aagtgtgaac cactgcacct ggcgtcttgt ttcctcttaa tctacagttt cccccttttg   83640
ccttcttttt ttttctttca atttatctat tgcagaaatt ggctttatct gtagttttct   83700
aaagcttgga ttttgctgaa tgcttcttta taatgacact taacatttt ctttgtcatt    83760 tgtatttctc ataacttatt atttaggcct agagtctgta tgtgattcag gtttgatatt   83820
tgggcaaaag tatttaataa gtgggattac gtactttcac caagagacac ataatatggt   83880
tgtctctttc tgtgattcta gcagccatgg ataattattt catagattat tatttcttg    83940 gggatggcaa aatggtgata ttctaatttt actattcctt catttactag ctggaatgtc   84000 ttttaaatt atttatttat ttatttatta tttgagacag agtcttgcac tgtcacccag    84060
gctggagtgc agtggtgtga tcatagctca ctgcaacctg caactccag gctcaagtga    84120 tcctcccacc tcagcttccc caatagctag gactacaggc acacatcacc tggctaattt   84180
ttaaattttt tgtagagatg agggtcttgc ttttttgccc aggctggtct ctaactactg   84240
ggctcagcct cctaagctcc tcctgcttca gcctcccaaa gtgttgggat tacagacata   84300
agccactgtg cctggcctgg aatatttcta tatagaaagt tctcttcatt atctacttca   84360
ttgctttcag gtatatgtaa gaaagacagg ataaaccact agattttgaa atgtatttat   84420
aaattttcaa aataatgagt tgagtcctag aatctttctt ttattattat tattattata   84480
ctttaagttt tagggtacat gtgcacaatg tgcaggttag ttacataggt atacatgtgc   84540
catgctggtg tgctgcaccc attaacttgt catttagcat tagatatata tcctaatgct   84600
atccctcccc cctccccccca ccccacaaca gtccccagag tgtgatgttc cccttcctgt   84660
gtccatgtgt tctcattgtt caattcccat ctatgagtga gaacatggcg gtgtttggtt   84720
ttttgtcctt gtgatagttt actgagaata atgatttcca atttcatcca tgtccctaca   84780
```

```
aaggacatga actcatcatt tttatgactg catagtattc catggtgtat atatgccaca   84840
ttttcttaat ccagtctatc attgttggac atttgggttg gttccaagtc tttgctattg   84900
tgaatagtgc cgcaataaac atacgtgtgc atgtgtcttt atagcagcat gatttataat   84960
cctttgggta tatcccagt aatgggatgg ctgggtcaaa tggtatttct agttctagat    85020
ccctgagaaa tcgccacact gacttccaca atggttgaac tagtttacag tcccaccaac   85080
agtgtaaaag tgttcctatt tctccacatc ctctccagca cctgtttttt cctgactttt   85140
tttttctatt tctagactct ttattaagat tcattttcct atgaaaaagt ccattcttta   85200
gtcagttcta cactgtcttg attaaggtag ctttatagga agtttttaaa tcaggtaatg   85260 taaccccctcc aaattcatcc tccctttcg aaattgtttg gtcattctga atcctttact   85320
ttttaatata aatttaaaaa ttatcttgcc aaataatctt gtttgaattt taattgggat   85380
tgtgtggaat ttatagatca atttggggaa gactgtcatc taaaaatatt gaatcttcaa   85440
ttcattaaca tgaatttatt cccccattta tttttattta tttatttatt tttctttatt   85500
attattatac tttaagtttt agggtacatg tgcacaatgt gcaggttagt tacatatgta   85560
ttcatgtgcc atgctggtgc gctgcaccga ctaactcatc atctaccatt agtttcctga   85620
ctgtttaatg attgccattc taactggtgt gagatggtat ctcattgtgg ttttgatttg   85680
catttctctg atggccagtg atgatgagca ttttttcatg tgtcttttgg ctgcataaat   85740
gtcttctttt gagaagtgtc tgttcatatc cttcgcccat tttttgatgg ggttgtttgt   85800 tttttcttg taaatttgtt tgagttcatt gtagattctg gatattagcc ctttgtcaga   85860
tgagtaggtc gcgaaaattt tctcccattt tgtaggttgc ctgttcactc tgatgatagt   85920
ttcttttgct gtgcagaagc tctttagttt aattagatcc catttgtcaa ttttggcttt   85980
tgttgccatt gcttttggtg ttttagacat gaagtccttg cccatgccta tgtcctgaat   86040
ggtaatgcct aggttttctt ctagggtttt tatggtttta ggtctaatac aagggacgtg   86100
aaggacctct tcaaggagaa ctacaaacca ctgctcaatg aaataaaaga ggatacaaac   86160
aaatggaaga acattccatg cttatggata ggaagaatca atatcgtgaa aatggccata   86220
ctgcccaagg taatttatag attcaatgtc atccccatca agctgccaat gactttcttc   86280
acagaattgg aaaaaactac tttaaagttc atatggaacc aaaaaggagc ccgcattgcc   86340
aagtcaatcc taagccaaaa gaacaaagct ggaggcatca tgcaacctga cttcaaacta   86400
tactacaagg ctacagtaac caaaacagca tggtactggt accaaaacag agatatagat   86460
caatggaaca gaacagagcc ctcagaaata acaccgcata tctacaacta tctgatcttt   86520
gacaaacctg agaaaacaa gcaatgggga aaggattccc tattgaataa atggtgctgg   86580
gaaaactggc tagccatatg tagaaagctg aaactggatc ccttccttac accttataca   86640
aaaattaatt caagatggat taaagagtcg tagcatcttt caaggtgac taatgatttt    86700 aacattatta ctataaacct atagatttaa acataattgc tatgttttaa cccattatag   86760
ttattattcc tgttgatgat caagctctat ctttggccag tgggagcctc tgcaaattga   86820
ttagtgaatc ttttttgacat ggaactatta gtctttgaca aaatctttga tttctggtat   86880
gacaatatat tccagtttta tcttatatac ttccagtcct atacataata ttaacttttt   86940
ttcaaagaat tactggtttt attttttagtg ggaaatggca tttaaaataa ggaagttggc   87000
gaggcgcagt ggctcacgcc tgtaatccca gcactttggg aggccgaggc gcgcagatca   87060
caaggtcagg agttcgagac cagcctggcc aatatggtga aaccccatct ctactaaaaa   87120
caaacaaaat tagccagacg tggtggcaca cacctgtagt cccagctact caggaggctg   87180
```

```
aagcagaaaa aaataaataa aataaggaag tctgcctata tgggttatct acctcttttt    87240
tagggctcaa cctacccgtt tcacacaaac ccaactgaat tcggactcta tatgtgctag    87300
gcaagtttga gcttttttcag gtgtacacac agggtttact gaactctggc atataattat   87360
ttatttattc attttatcaa gttttgtcct atcattgaaa ctcattcttg aataaagtta    87420
ttatatttag ttcagttaca gcagacaccc cattttgaaa acattatgtc aacattggct    87480
tgtgtacctt gtcacatcag taatgtacag ttctcattta ccagaaattt ttatatgaac    87540
aacatattga agttattaag ttaatgaatt ctgccaaggt attggtatat atttgttcat    87600
tataagcatt taaaaacaaa ggaacctttt aaagttgaag ataatttaat gggccattgc    87660
atgcaaagag gtgttgcatt agtaaccaac cttaaactac tgctgaaaca actttatgct    87720
tgagttagat atgttgatgg gagccaataa ttgtgaaatt tgtgtatcca gactctcttc    87780
tgctctgttc ttaatggatc tagtgttaat gttagaatct agtgcatttc acaactgttg    87840
ctattataga tggaatatca ggaggggtag tgaggtattg agatagatga aaacattttc    87900
taaaagtggc tcacgcctgt aatcccagca ctttgggagg ctgaggtggg tggatcacct    87960
gaggtcagga gttcaagacc agcctgacca acatggtgaa accatgtctc tactaaaaat    88020
acaaaaatta gctgggggtg gtgtcaggca cctgtaatcc cagctaccag ggaggctgag    88080
gcaggagaat tgcttgaacc caggaggcag aggttgagtt ttctccacag ctttggatcc    88140
tgatgacttt ttttttttta attgttactt tcaacttcct tgctttgact gaagccatac    88200
ttacatatta ctgataacat atgccatggg ccgcgcatgg tggctcacgc ctgtaatccc    88260
agcactttgg gaggccgagg cgggtggatc acctgaggtc agcagttcag accagcctgg    88320
ccaacatggc gaaaccccgt ctctactaaa aatacaaaaa ttagctgggc ttggtggtgg    88380
gctcctgtaa tcccagctac tcgggaggct gagggaggag aatcgcttga acctgggagg    88440
cagaggttgc ctgtgcactc gggccactgc cgtccagcct gggtgacagc gcaagacttc    88500
atctaaaaac aaacaaagaa aaacataatc catgtatgtg atgtaaagag cgccaacatg    88560
tttatatcct cctatttcaa tctactttta cttcatctac attttttagca ataatgtgaa    88620
catgaaatct tgaataatta gctatctgta atatatttac tcatccactc aaaatattga    88680
gcccccccaa taaatatcat acactatatt ctaggtacag gtgataaaca attcagagag    88740
tattaattc aaaacatggt aagtgcatag tgagagagct gatctggtct ggtggttgag    88800
ggaatcaaga gatatttgag ttgaggtctg cagtattata gaaaattaac taatcaaaag    88860
agaggcagtc attccaagga aggggatgtg agtcagaaga aactgcatgt ggcaagctct    88920
gaggtgggac aaagcaagga catattgaag gaattgtgac tggagcatag ggatggagga    88980
aaacattgta gctagctgag aaataagcat ggaaaaatgt tgtagagctg tataggccat    89040
gttaggactt ttgtctttat cttaaggata agccattgat gtgtttataa agacacatga    89100
tgtgatcaga ttttcagtta aatttaaaaa atacttggaa tgcattttgg agaatggttt    89160
aggggagagg caagagtgga ttctgtgggc cagtagttca gaggataggt tatggtagct    89220
tggactaaag tgcctgagcc aagatggaga gaagtagatt gctttaagac atatttaaag    89280
aataacatca gcacttagca atgaactgga gatggaagat gagggaaggg aaggtgttag    89340
gcaggttttt acaatgagag aggttggtga tcatggtcac caaggtaggg aatgctggat    89400
gaggatgcag tttaaggtga agattatgag ttcaggttca gcaaaactga acttgagaca    89460
tggtgaacta tcaaggtgga gatatccagt gaaagttaga gagagggtc tagagctcag    89520
```

```
ggaggagtgt gtatccctaa tttagactaa tttgcattaa cagctgtagt aatgcaattt    89580
tctctatact gaaatgcaga catttgagta tagaaaatta gcagacattt gaatatagaa    89640
gaaagattta cttttccttca gaaaaagaat agtagagtat aaagaataat atttaatcct    89700
aggaattaat accaaaccct ttaaaaaaaa cttttaagtt caggggtaca tgtgcaggtt    89760
tgttacatag gttaaacttc tgtcatgagg gtttgttgta cagattgttt catcacccag    89820
gtattaagtc tagtacttgt tagttagtta tttttccttta ttttctccct ccacccatct    89880
tccaccttct gataggcccc ggtgtgtgtt gttccctct gtgtgttcat gtgttctcat     89940
catttatctt ccacttataa gtgagaacat gtggtatttg gttttctgtt cctgcattag    90000
tttgctaagc ataatggctt ccagctccat ccatgtccct gcaaaaggac atgctattgt    90060 tctttttta tggctgcata gtattccatg gtgtatatgt accacatttt ctttatccag      90120
tctatcactg atgggcattt atgttgattc aattttttt ggctattgtg aatactattg      90180
caataaacat acacatgcaa gtgtcttcat aatagaatga tttatattcc tttgggtgta    90240
tacccagtaa tgggattgct gggttgaatg gtatttctgt ctttaggtct ttgaggaatc    90300
atcgcacagt cccccacaat ggttgaacca atttacactc ccaccagcag agtctaagtg    90360 ttccttttc tccactacct caacagcatc tgttattttt tttgactttt taataatagc      90420
cattctgact tgtgtgagat agtatctcat tgtggttttg atttgcattt ttctaatgat    90480
cagtgatgtt gagcttttct tcatatgatt gttagccaca tgtatgtctt cttttgaaca    90540
gtgtctgttc atgtcctttg cccattttt aatagggggtg ttttattctt gtaaatttgt     90600
ttaaggtctt tatagatgct ggatattaga cctttgtcag atgcatagtt taaagaaatg    90660
ttctcccatt ctgtaggttg tctgtttact ctgttgatag tttcttttac cgtgcagaag    90720
ctttttagtt taattagatt gcatttgtca atttttctt ttgatgcaat tgctctgtgt     90780
cttcctcatg aaatctttgc ctgtacctat gttctgaatg gtactgccta gactgtcttc    90840 cagggtttttg atagttttgg gttttacatt taagtcttta ctctatcttg agttaagttt    90900
tgtatatggt gtaaggaagg ggtccagatt taatcttctg catatggcta gccagttatc    90960
ccagcaccat ttattgaata gggaatctgt tctccattgc ttgttttttgt caggtttgtt    91020 gaagatcaga tagttggagg tgtgtagtct cattctgggg ttctctgttc tgttccatta    91080
gtctgtgtct gctttttttt atgttcttaa cttttatttta tttatttatt catgtattca    91140 tttatttta ccagtgccat gttgttttgg ttgctgtagc cctgtagtat agtttgaagt     91200
caggtaatgt gatgcctcca gctttgttct ttctgcttag gattggtttg gaaaattagg    91260
gcactttttt ggttccatat gacttttaaa atagttttt ctagttctat gaagagattc     91320
aatggtagtt tcataggtat agcactgaat ctataaattg cttttggccag tatgccatt    91380 ttcacaatac tgattcttcc tatacatgag catagaatgc ttttccattt gtttatgtta    91440
tctctgattt ccttgagcag tagttttgtgg ttctccttgt agagatttt ttttgtatcc     91500 tgagactttg ctgaagttgt ttatcagctt aagaagcttt gggctgaga caatgggtc      91560 ttctagatat aagatcatgt cacctgcaaa gaaagatagt ttgacttcct ctcttcttat    91620
ttggatgcct ttatttcttt ctcttccctg attgcccttg ccagaatatt caatactatg    91680
ttgaatagaa gtgttgaata gaaactaatg ctgcaagcat tagtttcaaa gaacttcttg    91740
atttctgcct taatttgatt gtttacccaa aagtcattca ggagcaggcg tttcactttc    91800
cgtgtaattg tatggtttttg agtgaatttc ttagtattca tctctaatttt aattgtgctg   91860 tggtctggga gacagtttgt tatgatttca gttcttttgc atttgctgag gagtgtttta    91920
```

| | | | | | |
|---|---|---|---|---|---|
| attccaatta | tgtgatcaat | tttagagtat | gtgccatgtg | gtaatgagaa | gaatgtagat | 91980 |
| tctgttgttt | ttcactggag | agttttgtat | atatctatca | ggttcatttg | atccagtgtt | 92040 |
| gagttcaggt | cctgaatatc | ttggttaatt | ttctgtctcg | gtgatctgtc | taatattctc | 92100 |
| actggggtgt | taaagtctcc | cactattatt | gtgtgggagt | cagtctcttt | gaaggtctgt | 92160 |
| aagaacatga | ttatgaatct | gggtgttcct | gtgttgggtg | tatatatatt | taggatagtt | 92220 |
| agattttctc | gttgaattga | acccttacc | attatgtaat | gcgtttcttt | gtcttttttg | 92280 |
| ttcttgttgg | tttaaagtct | gttttgtcag | aaactaggat | tggaaccctg | ctttttttctg | 92340 |
| atttgcattt | ccttgatata | ttttttctcca | tccttttatt | ttgagcctat | ctcattgcat | 92400 |
| gtaagatgga | tctcttgaag | acagcatacc | gatgggtctt | ggctctttac | ttggcttgcc | 92460 |
| gctctgtctt | ctaattggtg | catttagcct | atttacattt | aaggttatga | tcctgtcatc | 92520 |
| ataatgctag | ctggttgctt | tgcagacttg | tttttgtggt | tgctttatag | tgttactaat | 92580 |
| ttgtgtactt | cagtgtgttt | ttatagtgac | tggtaatggt | cttttcctttc | cacaattagt | 92640 |
| gcttccttca | ggagctcttg | taaggcaggt | ctggtggtaa | ctaattcctt | cagcatttgc | 92700 |
| ttgtctgcaa | aggatcttat | ttttccttct | cttatgaaac | ttagtttgac | cagatataaa | 92760 |
| attctgggtt | ggagtttctt | ttctttaaaa | acattgaata | ttggcctcca | atcacttctg | 92820 |
| gcttgtaggg | tttcagctga | gaggtctgtt | gttagtctga | tgggttccc | tttgtaacct | 92880 |
| gggctttctc | tctggctgcc | tttaacattt | gttctttcat | tttgaccta | gagaatatga | 92940 |
| tgattatgtg | tctggggat | gaacttatta | tggggtatct | tactggggtt | ctctgcattt | 93000 |
| cctgaacttg | aatgttggcc | tctctggcta | ggatggggaa | gttctcatgg | atgatatttt | 93060 |
| aaaatatgct | ttccaagttg | gttccactat | cttccatttt | tttcaggtaa | accaatgaat | 93120 |
| tgtagatgtg | gtctctatat | aatcctatat | ttctaggagg | ttttgtttat | tcatttttat | 93180 |
| tcttttttct | ctattcttgt | ctgcttgtct | aattttggaa | aggtagtctt | caagcttgga | 93240 |
| aattctctcc | ttcacttagt | ctattctgtt | attaatactt | gtgattgcat | tatgaaattt | 93300 |
| tgggggttgg | gagtggtggc | tcacacctgt | aattccagca | ctttgggagg | ctgaggtggg | 93360 |
| tggatcattt | gaggtcagga | gtttgagacc | agcctggata | atgtggtgaa | accccacctc | 93420 |
| tactaaaaat | accaaaaaaa | aaaatcatag | ctgggcatgg | gggaacatgc | ttataatctc | 93480 |
| agctactggg | gagactgagg | caggagaatt | gcttgaacct | gggagatgaa | ggttgcagtg | 93540 |
| agctgagatc | gtgccactgc | actccagcct | gggtgagttg | agagtccgta | tcaaaagcaa | 93600 |
| acctacacat | ttttgtggcc | tgtttttagc | tctatcaagt | cagttacatt | cttctgtatt | 93660 |
| ctagcttttt | tatctgtaag | ctcctgcaat | gctttattag | aatttttagt | tcctttgcat | 93720 |
| tttgttacaa | catactccta | taactctgcg | aacttcattc | ctatccatat | tctgaattct | 93780 |
| gcttctatca | tttcagccat | ctcagcctca | gcctggtact | gaacgcttgc | cagagaggtg | 93840 |
| atgtggtcct | ttggaggaaa | gaaggtactc | ttgattattg | agtttcagt | gttcttgtgc | 93900 |
| tgattatttc | ttatctttgt | gggctcatct | accttcaatc | tttgaggttg | ctgacatttg | 93960 |
| gattattttt | tcttttatcc | tatttgatga | ccttgagggt | ttgattgtgt | tataaggtca | 94020 |
| attcaaccaa | ctagctttgt | atctggaaga | ctttaggggg | ccatcgttca | cctcccaact | 94080 |
| cctggactgc | atgttctaac | tctggatgac | ttgtattggg | ccccaacttt | gttctctggt | 94140 |
| tcctcgaggt | ttggagtcta | ctttgttgga | ggaccaaggt | gtggcagctc | cagctgggtg | 94200 |
| ctagcggatt | caggggtgcc | tgcctccctg | caggcattca | ccatgctagt | gaaggcaagg | 94260 |

-continued

```
cattttgtg gggaacagga ggctcctgct atagactgtc tgtgcttttg cactggtgat    94320
ggtgttggtt tggtgagagg cactgaccag tgcagatctg agtgccttct tggtcacctg    94380
caagcaggag ggattgctca gggtgtggga ggatcctctg ttctccatgc agcattacca    94440
caagagtgag gcactggcag ctgcagggct tgctggctgt gtgctgctaa ggttctgtct    94500
gcaatggtgg ttgacagagg tcaaggggca tacttccctc ctgtatgcta gtggggcaac    94560
taaagcaaat tccacctgtg cagacatgtg cctgcaaagt gatgtgggga gttgccatgg    94620
gctcagggga agttgcagta tgggtagcga acacccggct ggtgtgcgca gtaagggctg    94680
tcttgctgga gttctccact ggtcaggcat ggcccactgg tgcagaagct attctgtggg    94740
ccaccacagc acccaagatg gccctagaag aggccagcag accaaggagt gctcaggttg    94800
caccagccct gactgatgta caagaccact ctgcagatat caagtctgaa aattccccta    94860
gggccaaagt ctattatggg agcaagttga gcctagaggg atcgccatcc ctgtccatgc    94920
actgctgtag acactcctgc actaaaccct ctgggctcca catcagctgg cttgctgctc    94980
taccactttg cttgtctctt gggggctcca ccccagagag atgtgggtca gcaatcattc    95040
agttcaatca gcccaggatg gagagtctgt gctatgggcc caagccaggg gctctctgtc    95100
tggtgacgag cagctggggg gtggggtggg acctgtggga gatggactgg cctcctctcc    95160
ttgagtcaac tgctgcttat tggaggtgtg gatgagacac ttagggtctt tgctccttta    95220
ttagtcagag ggtagcaagg acagttccat tgcagaggta gtggcagaga ggcttttcagt    95280 tgtccgtggc ggctctgtcc agggagttgc tgagttgcta ttggcttgat atctctggtg    95340
gggtgtggct agaggtccag gcctggagga cctgctcgtt gaagagatgt gggaatgggc    95400
acccacataa cagtctgttc acttttccat agggctgctg tagtatgctg ggggccagct    95460
ccagtccctg gtcactttag attttccagt acctggaggt gtcaccagtg aaagctgcga    95520
aacagcaaag atggtggcct tccttttctct ctgggagctc catccctggg aaatacaggc    95580
ctgttgctgg cccgaacaca ctggtaggac atggctgaag acgctagttg ggagacctca    95640
cccagccagg aggaatagga tcagggacct gctttcaaaa gtagtcttgc cccatttca    95700 tagaggagtt gtgccatact gggggtatgc tttagcccct gattgcctca gacactctga    95760
agcccaaagg ctggaatggc taagttgttc taacagcaaa tatggtgggc tgctcctctc    95820
cctgggacaa aggtcccatg gaagtctgaa acctctctca gtcagagaac accagttggg    95880
gtagccgggg accccagatg ggagactcta cccagtgatg aggaacggga ttggggacct    95940
gctaaaaaaa aaaaaaaagc agtgtggcca cattttgtc gggcagctgt tctgtgctgg    96000
ggttcccctt ccaccctgc ttaagctccc caaagcctga aggctggaat gggtaagttg    96060
cccaaacagc aaagatggca gcctgcccct ccctctggga gctctgtccc agggagtttt    96120
cagatctctg tcagctggag aacactggca ggtgtggctg gaggcccag ttgggaggtc    96180 ccgcctgtaa ggatgaatgg gatcggggac caacttaaag cagcagtctg gccacatttt    96240
aatagagcaa ctgtgctgtg ctgggggatc tctttggccc ctggttagtt tggactctcc    96300
aaagcccaaa ggccataatg gctaagttgc ccaaacagca gagatggggg cctgcccctc    96360
ctcctgggag ctttgtacca gggaggcaca atgttgctac tggtggctag ctggaattcc    96420
aagccagtgg gtcttatcct gtgaggcgct gtggaagtgg ggcctgtaga ccttctctgc    96480
tgatctcgct ggattcagcc tcttttctgg ggtatgtatg ggagtctaac ctcctggggt    96540
atgtttgggg gtctaacctc cagctttgcc aaagtcgcag ctacttttgc ccagacaccc    96600
agaaagctgg agtagctaaa gctcttgggt ctccatgcat gcctgagtgg ctgctctgct    96660
```

```
gagactccac gtggctgtgt gtgaagggcc taatggagtg agttcacaag gggatctcct    96720
gatctgaggt ttgcaaagat ctgtgagagc agtgtggatt cccagagttg cgcattcact    96780
taccacttcc ctgggaaggg gagtttccct tgactccacg tctttcccaa gtgggctgtc    96840
ttcctgcctt gatttgctct ggtctccgtg ggtcgagttg tttccttgat tacttccaat    96900
gagagtacct taatgtttca gttgaaggtg ctatatttag tcaccccttt ctttccgccc    96960
tgtgagagtc acacacatta actgcttcta gttggccatc ttggccactc ctgccctaaa    97020
cctttctagc aaaaaaaaaa aaaaattaa taacatgttg atctaccgct tctctctctt    97080
taaatttatt taatcattat gaatttttt acatttattt acattgttaa gctgttttat    97140
tttaaaaatt ctaggtccag ctcttcctgg attgctttta tataaggaac atatctcatg    97200
aaataaataa aattcacatt caaatgcaga agaatctatt ggaaaaaact cagaggacag    97260
gataaaagca ctcagaaaaa atgccaggag aaggcgttta tcacataata tcgctgataa    97320
gagtctctcg aaaattttc tctctattca ttcttaccaa atatagaaag tgaacaaaac    97380
aatattagta ttagaaaaaa catccaaaaa taatgacctt tctgaatgaa gactgctttt    97440
ttcatggtta ctcttttgg ggtacagttc tatgttgatt tatccaattt atcaaatagc    97500
cattcagcaa atatttattg agtgtctgtt atgtcacagg cactcttttc ggtcctcaaa    97560
atacatccgt gacaaagagt aaaagattcc tgttcatggc tcttacattc caggagggat    97620
agcaatttct tttgtaaagt taatcacaca acagaaatgt gaataatat tgatgctgta    97680 aggaaaggaa aaataaatga aataaattga aaaagaaatg tgaaggaata attaaaagag    97740
gctatatttt attgaataaa aataaaagag gctatgtttt attgaatatg ctccatgttt    97800
tatactatat cataaaacat acaagatctg gctttaaga aatcaatatc ttcatcaata    97860
tcttcattca gactcatcta gattagatta ctctgaatct aatcacatag agacttgtct    97920
gacaaatcca gatttttgg acgttctgca ggactatttg tcaggatatt tcacaggatt    97980
ccaagaaata atattggtgt ccatgctata atgattcctc agctcctccc atctgataaa    98040
atattgattt cttatacata taaaacatat aaaaatattt aaaatatttt ttgttatatg    98100
agtgaatcaa taataaaacc actatctcaa taatcatcaa ctgattgcaa actgattgtt    98160
catctcagaa aaaccttggc agagttaaaa taaaagtttc aaaatacaga acttagtacc    98220
aaaattaagg cagtgttagg tttctaattt tgctattcac atgttaaatg aattttcaaa    98280
attcagtagc taatactagc tagggttta aacaagacat agttaaaatg aactttaaa    98340 aaaagaatca taaacttcag tatcatcatg atggcagttt taggatttta atgttgacac    98400
cctagtctca aatttgtact taatgtggtt atatagctag gcagtgctgg agtgaaagtt    98460
tcaaaacaaa ttaaatcaa aagttaagaa aaaaatatga aggcaatttt aaggtgttta    98520
atttggcact gtagtttcaa aatagtacct gaaacttaac agcaaagtat cagattcatt    98580
tataaaacaa tgtgactgat ctttatgtat ggtttgtgaa acatttatgc agtgtcactt    98640
cagaaaactc tgccattata gatttgaatt gattaaggat atccactcct ttccttggca    98700
tgatacaaat aaattactaa agtataattg taacaatgat aaatataagt gacaatacca    98760
ccatattact atgaaacaca gattgattat ggtataatac aatttagcat ctccatattt    98820
ttgaaaatga acttgtttct ctaactggct taatttggga caatttggac atcaaaaga    98880 atgatgatgc aatttaaacc atacaaaaat taaaaaaaaa aatccaaggg acggtggtga    98940
aagtcttctt tctagaagaa tagcagctaa tatacacaga acgaatctta gaattagaaa    99000
```

```
atcactatat tttgatcccc ttccccaaag ggtgacaaaa ccattggtag acagtggttg   99060
agaaacagaa tagtctcagg atatcactcc gtagatttat tcattaatta aaaagagaaa   99120
atgtgctttg agagagagaa agctattacc gtctttatca aataggagag cctgatcatg   99180
tgtggtctga agtttatcta atgggattcc tgatggaatg tttagtctga atctaatcac   99240
atagagactt gtctgacaaa tccagatttt ttggatgttt tgcaggacta tttgccacga   99300
catttcaaag gattccaaga gagaatattg gtgtccatgc tgtgatgatt cctcagctcc   99360
tctcatctga tctccgtcct ggcccccatg actttctttg tggtagttag ggtgtggtat   99420
gtgccactga ggcccacacc tattgctgta agtgctgttt gggaaaccat catctttcag   99480
gtctgtgtga taaagaaga gccttgggga aatgttctct tccaaattta atctttacat   99540
tattagaaaa tattttgatg acctgttttc aaatatttc ttataacttt ccattttcat   99600
gtgtttattc tgacagttta ttttatcttg tatttataat cactaagatg ttagtattgt   99660
aatattaata ttcatgatt taaattagga aaaatgtgtt ttctattaca aaatggatag   99720
tggataattt aagtatagaa agtaaatttt tctatatggg actatttcac tctctgtaat   99780
atcctgaatt ctaattccca ctgtagtgag ctataacttt actaatcagt tttcttacaa   99840
tcgattttaa gtctatttg ttagatctaa agacataaag ccaaaagttc ttcttgaaga   99900
gaagcacatt tcagttacgt ttataacttg aaatatctgg ttttactcaa aactcacatg   99960
tcatactgaa aaacagaagg gagatgttgt cttttcttga ggagagactt ctctgcagtt  100020
aaacagctca ccacatgttt agagtacata gacaatacac ttcctctttt gtaatgtaga  100080
tttcagcttt ttgcttgtag aattatcatt ggcgtggagg ttatacaggg gaagtagtga  100140
aaaatgtagc caataccagg aaccttagga agtgtctgaa cttcatcttt tctgtgttcc  100200 tttgcccta gggggtcagt gtaagagttt gggctaggaa gagattgctt cttttactct  100260 attagttg tacttcctat ctgggtattt gacaataaat gactcattct ctttgttgc  100320 cctggtgttg aaaaattttc ccatatgcca gagaaaaaat gttacagtga cacaatgtaa  100380
aattgtaaga ggtggaaaaa gatgaggtat ggacatagtg aatggaagtt cagcccttta  100440
aaactactgg cagagtagat tttactcagg cttcaattaa gtagacctga atgtaaattc  100500
aggtctagct ctgcaactta ctaggtaagt gactttagtc ctctttaaga tttagtttcc  100560
tcattacagg atataataat actattttt ttatgaggta agtattaatt gaaatagtat  100620
atgtacattc tagcatacag tgatcccta ataaatggaa cttatcatta atacattgct  100680
aggaaaagaa aaacacatca gggaacaaaa gatataactg tcttattgat aacagggat  100740 ggattcttgt ggacaaaaaa atttagaatt gaattttcaa ggggtcattt cttttcaccag  100800 gtgtagttag gtttgctctt atggtaacaa tgaatatgtt tgtttagctt cttaaaccgg  100860
catcatggaa cgttaattaa taaacagaat tcaatgtatt tgtggggcat tttattttt  100920 atgcaatcat ttgtatatgt cacctttcaca atgcatgcca cattctcaga ccacctatta  100980
tgttattttc ttaacatttt tcttcaaatt cactcaccct tttaaaaact ttactgaagt  101040
ctcacttaag cacataattt gtaaaatcat gggtttgttg tgcaagtttt gttttctaa  101100 tacactctaa aacaaatacc ttaaaagagt tacacctaca gtccatatac cacccataat  101160
catctcaagt acctccagtg cttgttactg cactttggaa aacactaaca tacattattc  101220
tcattagttt ttataatagt tatatgaggt gaatagagaa ggcataacta tacccatttt  101280
aaagatgaga aaagcaggtt catggataaa atctcatagt aaattgctag aattggtcct  101340
gatactcatg cttctcttag atcaacccag tgctcttact gtaattgata ccaaattctt  101400
```

```
taaggaaact tagagctaaa agtaaaattt tttgtattta gacctgatta ttttgtggta  101460
atttgaatat aggtcaatat gaaaaaaaat aaaagatgaa acaaagaaac tgagagcaga  101520
tcaccaagtt gcggtaggtt agcctaagat agcttttggt tttctcagcc ttctactatt  101580
cacagctttg tgtaatcccc tccacttgag tatcttgctc ataccaatag aatatggtag  101640
tagagtagag gtcacctctc tgataagttt acagaagatt gcgacctccg tcttgccaga  101700
gtacttcctc tcttgctggt tttgatgaag caggctgcca cagaagagag gctcacatgg  101760
cagggacctg agggcagcct ctggccaaca gcaagcagta aacagatgcc ctcagttcaa  101820
tatccctcaa agaaatgaat cttaccaaca gccagttgtg ttagctggga agcaaatctt  101880
tccctaaggg agatttcaga tgaggccccc agccttggta gacaccttga ttgcagtctt  101940
gtgagagatt gtgaagcaga gctattctca gaattcatgg gtgttttaag ctatgaggtt  102000
ttttttgggg ggagaatggt catttgtgat tcagctatac ataagtctac aaaagtcatt  102060
ccagaagtga ttcagtggag gtagaatcat gtggttgtga gccccaggca cttggagttc  102120
tgatagaatt gtgacttcta acactggaca ccttttcttt ttctcttatt ctcccatttt  102180 tctccttttcc ccttttcctc ccttccttcc cttcattcct tctactttttt ccgtacttta  102240 aattaataga gcagttggaa acacaaaagc aatgtctgta tctacaaaat gtcattattt  102300
atactttgta tccacagtgt gctgcctagg gcttcatgcc tgaggtgcat ctgtagaagg  102360
tgctcaacaa aggcttggct gttggtatta ttgaatcact gtggagttta ttcattgttg  102420
tccatgccat tttgagtttt catttttttta tttatgggag tgtctttatt cttttaaaga  102480
gctttgtttg tacactcatt ttctctctct ctcttttctt ccacaggcaa tttatagcac  102540
tgatctgtca tcaataccac ttgctgtctt ggatgtgaag atgattttttc ctgcagggat  102600 tccctctaca aaattaaaaa cactgggcat gtggaaataa tattcatgct ttaaattgtc  102660
ttttctcttc actacaccag gggtccccaa ccccctaggcc acagactgtg gcccagtgt  102720 agtgaataga aaagacaatt taaagcgtga atattatttc ctcatgccca gtgtttttaa  102780
ttttgtactg gtctgtggct tgttagaaac caggctgcac agcagaaggt gggcagcagg  102840
tgagcaagca ttactgcttg agttccgcct cctgtcagat cagcagtggc attagattct  102900
cataggagca caaaccctat tgtgaactgc acacgcaagg gatctaggtt gtgcgccctt  102960
tatgagaatc taactaatgg ctgatgatct gacgtggaac agtttcaacc cagagcaccc  103020
cccacccacc tgcagaagaa ttgacttttta cgaaaccagt ccctggtgcc aaaaaggttg  103080
gggaccaccg ctgcactaca ctacctaaaa gattttcact ttcacagtgt tgcttgcttc  103140
tgttttacat gcacaagtag ctaaagctag ccttctggta aatggagggg cagagcagat  103200
ggtgggggag gagtacatac ggacgaattt gaatcacaat ttcctcacta tatgccagca  103260
aaatttaata atagcaccta aacatacaca tgcatatgta aatgagtcac actataaaaa  103320
cttttaacaa gtactggcaa gtcagatggc agacttaccc tgaaacctgc cactccaata  103380
aaaacctcat aattaaaaac aaggctgtct ataaagcata acatataata acaattattt  103440
gcaactggta caaggctaga ttagaaagtt gaaagttatc tttctcaggt aaaaatgctt  103500
ttcctataca gtatgcagcc agcagattat catccatagt ttgagtagtg agatgccact  103560
tgctccaaca attaacacct gctgatgttg gtccaagaag agactgaggt gatgcagttt  103620 cacctgttttt gtaagaataa cgctggtgtt tgccatctat tgcagagtg cctactacgt  103680 gccagatgct ttgttggcac tgaatgtgct atctcattcc agtttcttta tactcaatga  103740
```

```
aaaaccaact acatttatat tgcattgagg cttaaagtgg tttactgact tgcttaagat    103800
tatacaagta gtaggtggct acagcagggt ttgaacccaa gtatgcttga ttccccaaac    103860
catgctttt  aaaaaatcaa aggtgtaact tcgataaaag acatgaagtt aatgaatata    103920
tgaaagatgg tgaatagata cagatacaat gtggccttag gccagatcat gttgaacatg    103980
tggtgggata gataagagaa ggttcttctt tgttgttacc tggttctcaa ttggttatta    104040
ctttatgtgc tttccatatt aaaattctat tattctggtc tataaattca cccacccaga    104100
cttgcctaaa ctaattaaac cctgaagttt ggcatgtctc ttttttgggg tgcctctatg    104160
ataggtggta gaaatgaaaa tggaattaaa agttttgtga agctatagca ctactttttc    104220
attgtgttcc cccctgactt tctgccttag gtgtttactt tggtgagata tcctgggaga    104280
aattgaggtg aaaagaagcc cgagttagga ttagggaaga gatgaagtag tcaataaaat    104340
tcaaattctt gtattctgaa acgcaactat tctttctcca acttggtttt ggacagaatg    104400
tcttagtgta gctgttaaca aagaaattga tgacaattaa ctcccatttc tcagaatttc    104460
atcattcttt gaaagtgttt atcatactca atcttctaaa aatccttaag gcatactaca    104520
gtgtagaggt tggcaaactt tttctataga ggtcctgata gtagcttgtt tcgcttttga    104580
gggccatcga gtttctgtca caactactca tctctgctgt tgtaataaag actcacccat    104640
agacaataca tgaatgaagg agtatctatg ttccaataag acttttaaaa ataaaattag    104700
gcagcaagac tgatttgaca taagggtcat aatttgctaa cctgtggtat agtgaaagga    104760
gttcaactag agtttgatta tggctgtgcc attctagttg ggtagtttta ggaaagttat    104820
ttaatttaga tttgatgtag ttttctcata tgtaaaatgg ggataataaa acctgcttca    104880
caagactact atgaggagta agctatgtag ctaaatatag caaaatatct ggcatctaat    104940
agatgcctaa taaatggtga ctataatgat tcttatcatt actgtattat tttaaacatt    105000
tatctttttt ttttaggttg ttgtctaact aaggtattta gagaaaataa gtgctgctga    105060
gggcagctgg aactgttttg ctggttcatc actgaaattc tagttcttgt tggtgcttat    105120
ttcataatta tgaaactaat tcttttgaaa agaacttgaa gtagagcaac aagaactaag    105180
atagaactaa taccattctc tctcagttct tattgcttta cttcaagttc ttttgaaaag    105240
aattacatag atatgggtgc atgtgtttgt ttattttcct tgttgggtaa tcgtgaatat    105300
gttgattggc gtcaaacatg ggtctcacct atacccatgg cagtaagctt ctattgattt    105360
gaattcagac tagccctggt ggccctgtga gtgggaaagt ctaggtgtgc ctagcttggt    105420
ctgtggttcc acgaggggtt ggatgcatct gttctacttg tggaatgttg gcaccaatat    105480
attggctgct tctccgagta tttgcctttg tcttctttgt gaaaggtcac tggctggttt    105540
gagctattgg gctgtttatg ccacatcctg tgcatgccac actggctttc tttctgtggt    105600
gtttccagag ataagtttgc ctgatagaag tcagactctg tggcttttta tcattataga    105660
tttttctaga aggagaagag gccatgatca catctgagga tcctgagtca ttgtagacat    105720
gtactgaatt aaagagaatt ttttgactaa aggagaattg catcaatcac ggtgaaggag    105780
atgccacagg acagggcctg aggtgttggc ttagccacag atgtaagggc tacagttaac    105840
agacaacttt cagtttccac tattggaagg gatgatcagt ccttccctcc tctattttct    105900
tgagccccgt ttttcacctt tctttttctc tctcctttct tatcatgaag aataaagaca    105960
aatgagaaca gatctacctt aggctgatac agggcaggga atccatttaa taataaaacg    106020
tgggtcaaaa ttcactttc  tccttttgaa ttgaaattat attgtgcatg ggctaattag    106080
attgaatgct gtaaacatga agataatgct tgcaaagtag ctacagagaa agagaaaaag    106140
```

-continued

```
cctaaaacaa ccagtagtgc ttaggaccaa tagtataagt ctttacacac tacatttgaa 106200
taatactgta agacacaatt ctttgatagg ttaaatagca aatctaggcc ccccaaaatt 106260
atttaaaaaa ttgtcatttt aattctagag gtataacaac agtgtgtaag ttgcatcaaa 106320
taacaaagtt agtctacagc ctaaattgtt tcgtcctgct tttttcactt ctatgcatat 106380
ttttatactt ccatgctaga gctacctcat tcttttaaaa ttgtgagata ttctataatt 106440
tatttgtatt cccctattaa tatattttta gcttattagt ttacttaaaa agattttatgt 106500 ttgccttcta atgtcaaagt taggagtcat ctgtccattt aacaggtggt gttttcttgt 106560
gtaactcctc tgccttcatg caaacctttg agaacaatct cttgaaacaa ggctaaaatg 106620
cctttggaga ggtattatag atgatcatat ctactttgtg cctctttcca ttacttagct 106680
gcattagagg cccagctgtg taggtgtaac tcaaaatcca ccaaaactaa tactgtggtt 106740
agattctggt caaacaagtt gccattaatc cagatgtaga atgggattga aggtggctc 106800 ttccacaccc tgacatcaat gtaccagttt ggctctgtgc attctttctc cccttctccc 106860
tttaccaccc tcatataatt gtttgtgtac atgtctggtt tcgtcactac gctgatggca 106920
aggatcatgc atgccttatt catatttgtg ttattcaagg attctactct gggttctatt 106980
atggggcctg gcctaaagtg gttgttcaag aaatgtgtgt tagagaaatc atacataaac 107040
tagcaattct catttggatt cctgtatctg aacaactaac tttcagcttc ttcagtggga 107100
taaagaagaa aaatgggggtt taaagtacat actattcagt attaatgtag aatttaacag 107160
ctgccatcca agtgcagaat cctctgtagt ttcccagtgt taacctcact tctatctcta 107220
gccatgtctc agtgctgggt gactctctcc tggcatgttc tggcaagact ctacctggtt 107280
tgcgtaatct acatcggctt ctagtttcca caagaattgt ttatatgcat ttaattttag 107340
ctcttgggct ataacatgtc attgttcttt ttacttatct cctcttactt ctggaaacag 107400
ggcaggcatc ttcaatactt gctgttcctg tttggtgtgc tcttagatta atttttaactt 107460 tcctcttcag ctttcatgac acttcaagac attttccagt catatttcct gtataagaaa 107520
atacagacta tgtcaccaca aagggtagtg gagattgggg ggcataattt aattcattca 107580
gggaactcat attttggtgt gaatggaaat taaagcaagg tatttggatt aatttacctc 107640
atttggttct atattccatt tagaggataa cacattaagc ttttattcaa ttttatctgt 107700
tatggtcaca gtgaatctgg aaaaaaatat atatgggggct tagttttcat atttagggga 107760
aaatgaatat cctagagaat aataataaaa gttagggaaa ataatgtttt cctaagagta 107820
ggcaatgaaa atctgaaggt actcaaagca gtccttgcaca agtgctttga aaagcctctt 107880
gcacaatttt atttctttat agtacttaca caatcatatt tcataatgac ttgctataaa 107940
caatgttctt gacaagaagc ttaaagatac aaaactgaag gaagcacttt tgggagaaaa 108000
tacttttata tttgcttact tctacactac aacagacata aaattatgga ttttttttc 108060 agtgcaattt tcatatgtca gttctaggag acaggaaatg tgaaacactg taggaggtat 108120
gagtttgcca cctagaggag agaggtgaaa ttcaacttttt ctccaatttc tttagtataa 108180
ttcattaatt tatttaatta tttactcgtt taattattca aaaataatta tctaccaagc 108240
ttaactattt tgccagcgca gatttgataa atctgttcaa gatttatgag ctcaagaaa 108300 ccacaaagtg catcttactt taattgctca gctgcctctt ttaaaaatct tttacttta 108360 agagagtata gcacaaatat ctgaacaact ctaaatatcc atactgggga tggatattac 108420
tttgagctct tgcactataa taaaactttta ttcttttgta ctaattcagt cctttactt 108480
```

```
tttctttttt aataytttaag aaacaagttg gatatggaca agatgtaatt tcttctgtca 108540
aggaacccac aggataatag gttaatgata gagaccaaca atgctgatgc attttaatg 108600 acggagataa tgtctagaaa aaatccatt atttggtaaa gacaaagtat gcatatgtat 108660
tcctttgttt caattatttt taaagttaaa aaacaactgc ttatctcctt ttgtactaca 108720
agcaatatct ggtatagtgt atgcatagta agtattctag aaatagtaat ttcattgttg 108780
acttgattat attggagtgg aacttactct ggaagagatc ctaactttca tttatctgag 108840
aaaatttcca gttaggacat ggaaattttt tccttgtcaa tatttattct taatgtgttt 108900
agaattttag aaaatgggtt tagggattta gaaatttctt tactaaataa ctctagggaa 108960
cagtacctta aaaatattca aaatgacaaa aacttaaaat gacatctaat tttttaaggc 109020
caagaatcat taaaagggga tccaaatctt tagactttgt tgctcggtgg aactagaatc 109080
attaatatct cagtcagggg aagccatgtc aacttactgg tttaatttcc tgtgagcttc 109140
ccatgttctc tccctgcaag gaccacctca aatccctcag tagtcctgtc tttatgaaac 109200
cagtataatt tttcttttcg ctcttgtcct tcaccttcct gtggcaacaa gagtcaattc 109260
tccatatata aatactcggc ccctgtttta gctgtgtctt aattgcgcaa catctgttta 109320
ctctgtgttt taacatctgt gtggatagca ttgttgttgt aatattttga ctgtaagctt 109380
ctaggaggta gaggccagca ttattttctc cattttggaa atgagaaaat acagattacc 109440
acaatcaaag tagaatggca gcttatagta gttatttgga taatttatat agtctcttaa 109500
aaaaacagat tatagtaaga agtggctgag caattagcta tggcacactg cacggttttt 109560
ctgacctctc agctcctaaa taaactttgc caaatcttca ggccctcaaa atttttcat 109620 tccatttgtt atgggctgaa ttgtgttccc ccgaaatgac tatgctgaag tcctaactcc 109680
tagtgcttca gaatgtgacc ttatttggaa acagggtcat tgcaaatata attagttaag 109740
atgcgatctt actgacatag gagaagctcc taatcatggt gtccttataa aaggagaat 109800 tttggccata gagacatgca ctgggagaat gctctctgaa gactggagtt atgctgctaa 109860
aagtcacaaa attaacagaa gctacggaag agaccttgaa taaattcttc cctgtagcct 109920
tgagggagag gatggcccag ccaactgcta atctcagacg tctagcttcc agagctgtga 109980
gacaatttct cttttaggc cactcagttt gtggcacttt gtacagcagt cctagccgac 110040
taacacacca ctctaactgt tgatcaaggc aagagcctgt gatcatgtat tatcttgctt 110100
attccttatc agcattctat ggtgtagata ttagtgccat ctatatacaa attaggaaat 110160
ggagcctcat agaaattaaa tgacaagttc aaggtgtcat ggctatttca ttatagtgcc 110220
agtgtttgaa cacaaatcaa tttgactcca aaacatcatt actctactca attctagttc 110280
aatccagatg ttcacaaaca accagactat agtggagatg tgggtggtgg gttgagaagg 110340
agatcataac caacatcaga ctgtcagtga agcagactgg gagaagtttt atgaagccaa 110400
gcagctgtgc aaggtacagt agagatggtc agattgttca tgtgtatgga ttccatcttc 110460
tgaggaatga actccttgat attcctgagt tagtccagtt taggcaggag taaacagaag 110520
gtaaacagaa gattggagac tgtgtgtgtg cacgaatgcc tcctttgtag ctggatgtct 110580
aacatcatga tagccacact cacatgaata cagagataca caatttacaa attaatgtaa 110640
cataaaactc ccatgcagtc tgatttcatc ttactgacat ttctgtcagt cagtgttagc 110700
atcttaatta tataaatgtg gaaactgaaa tactcaagag gttccctgac ttcccaggcc 110760
acacagtaag ctttggtgcc agaatgtatc tctaggcttt ctcatctcaa cccagcattc 110820
attatactat tgctcactgc gtgtagaatc agatttgatt tctctgactt tcttagtca 110880
```

```
cttctgtggt tttgtaccac tccctctctc actaaataac tgcctgcaaa agtaaaaatt    110940
tccatgaaaa cagaaaacaa atgtaccaga aatgttgatg gtgtaagaga taaaactggg    111000
ataaagagaa aatgtgttgg aaagtggtgt cctttaatgc aacagaaaag tatattggga    111060 gaaaagaaa  agagagaaaa atagacaatc tgaagtgatg agaagagcaa atgctacaga    111120
tgtacctgaa cctcttcagt aggtgtgatc ctgaagagtt gtgtataaca acaatgaaca    111180
aaaataaaat gtactgtgga aattgtctag ctgttgagat cctcctgtgc gatattttc     111240 aaagtgaaaa ctccaatcaa ccctagctta tttatggaga agactttgcc ccacagtacc    111300
cagaaagttt cttgacaata tcatatatgc ataataaccc tgagacaatt tttgtttacc    111360
aggaaaacat ataaaaggga acattaaact ttgtctagtt ctactgcata aacatgtgat    111420
aatgtgcatg gtgaccttct gttgtaaatg gaaagagtta agctctctga atctactgct    111480
gaaaggtgaa aacactttct tagggctttg aacttcattt gaaatcttac tgaaaaaaca    111540
ctacagactc tattttcttt atatttgaag atactttaca taaaaatcta aagcattttg    111600
acttatgttt tcatctactt gagaaggaaa ctcacagact ccaaagcaac tgttgtctgt    111660
tttgaaaaaa atttcagaaa tcaccagaag caatagggag tggccttgat tcctgttctt    111720
gtatttatgg gtagctaaag ttcatatttc tcaacatacc ataatctctg tgtaattggc    111780
caaattccat ggtggataat tagatctagc ttaccagggc agatttggat ggtgagagca    111840
gtcacactgt tctgggaata tgttagccaa gtttactatg ttttacatga gttgacagac    111900
tcacctcact tgctgaagga ctagcccagc aggttctacg ggtgagatca ctgctagctc    111960
attcactgct gggcctggta ggcacaagag gccaagaaat aaataatgtg aatttgggct    112020
tcagaagttc tctttcctat tttctttcct aaacccttc  ttctaccagc tgtctagggg    112080
ctaaaacatt tgttcatacg tttattaact aattcaacaa atatttacca accatgtttc    112140
aggcactgga cactagaaat ataatagtga actagacatt ttctgccttc aagggtctat    112200
gaacaattat aatattctga aaatattac  aattcacaga gctcagtaat ccaaatcctt    112260
attatttctg tctttaaaaa gcagaaagtg aaaaatgctc ttaaaagagg atggcataga    112320
aatgtattta tgcattgcaa cagataaaat taaggaatgc atgaagactg gttcatctgt    112380
gtggttgtga gtcaagaata aatcccaccc tccctgaagt actcagactc taccttgccc    112440
catggccacc actgtggccc aatggaagca ccagtccagg gggtctccat tcatgctgtc    112500
tttggatgtc ttcagaatgt tgtttcacaa gtactcagac ccaacagtaa gattttaaaa    112560
attgtccata atattaacct tggcattatt atgttaaaga aagcaaaaca gatatcactg    112620
agtttacttc tcaaaaaaac cttgcgttcc tgcaaaagtt tcttgaattc tgactcttgt    112680
cacacaatca cacaagaatg gctatactta aacccttcta atcaattata tccttaatat    112740
gtatgactga gtgatgtgtt ttcatgacta tgaaatgtat acatgtttgg aaaatctatt    112800
cacaatagag ttttatgata ttcctgttaa caggctgtca ttgtaacact gtttatgcag    112860
gaattgtaat tctatctgtt tttatttta  gcgtcttttc tctccatccc ccaaatttta    112920
aggagctatc aggtctgtat tttatttggt tttgaagttt taggttattt gtagttataa    112980
tagccatatc aattattcat ttagcaaaca tgtattgagt gctactatgt gcttagattt    113040
ttccaatgtt gtgaaggata attggctaaa acttttccac ttttattagt aatttgagag    113100
tttttttctc catggatttt agtcactggt aaaggctgtt tcatattcat agatttttt     113160 ctacggtaag aaacatatga tgttgaataa ggtatgaatt acaaattaag gcttttccac    113220
```

```
attcgctgcc tttataagat ttttttttct tcatcaaaat ctattcacac acacacagac   113280
acacatgcgc tgttttgatt ttcttcaaat atatccagtg ttcagttctt gggcacatat   113340
taatatactt gcctagatga agactatgtg tcctcaggaa tttataatct agcaggtgaa   113400
agatttgctt ctttcaaaat gtgactctac ttccccactc cttaggttgt gaaagcagtt   113460
gtttacgctt tatttcattg ttttccaaac tttagttatt tatgtgccat cttcatgatt   113520
atgctattca cataccacct atactattat gcttctgaaa atatactatg attttcaact   113580
taattaaatt tgtttagtaa taacagtagc tgttacatca ctaggttgat gtgctagtta   113640 aaaatttta aatatacttt aatataaata tgttactact aaattatttt tttgtctgta    113700
tgcacccaaa atcttgcctt tagtagtact acacatatca tgctttggga aactctaccc   113760
atgagattca tattcaagca tgaggaatgg caaaagaaaa tacagaaata gtgatagtaa   113820
ccatagcaat ggtaataaga gctattattt attgaggact ttacgtatgt catttaattt   113880
tattttatcc tcacaacaaa ttttagccat gagtatcaga taaatatgag gcaaagggc    113940 aggaaagaag gaacagtgga agtcaagctt ttttttcgcct aggtcagcta taactaacac  114000
gacaagatgt tttagtattt gtactttatt tttagtcagc tcagatttca cacctgacta   114060
ttttacaaaa atttggatgt gatggtggca gattaacata attactttta gcaattatta   114120
tgggacaaat tagttaaagg ttgtaaaatg cctagaaaca gagtagaata tcctagtagg   114180
atatcctaga atatcctata attaagttat caaacaatta ctctgattat ttttcacagt   114240
agttcaatca aagtgtaact ttgggtctgt tagtatacat gagtgtgaat actctggaga   114300
tttgatcttt ggctttcctg tgtaagttca tatatatttt tgttattatc ctgtaaataa   114360
ctgaattata gtacagtgat tctgtaaaaa acactttagt tattaatatt ctttggtgtg   114420
aagttcacat taaaaattgt tatatttcca gaacctggtt tttacctgtg aaagtcaatg    114480
catccttctt ttaatcctct gcattggttt tgcatagctt gatgaaatat gacttgcttc    114540
tcctccctcc ccctccttcc tgtgcctgta tccccatcat ttttttttct attcctcttg    114600
gtatctggac ttcttttttct gccaaatgag tcagtaagag aggaaatgtt taacccacat   114660
ttgtcatctt ggctgggaaa gaagtttgaa ggcaaaaggt gcctgaatat gtttcactag    114720
gatgctgaca caacctttt gactctctcc taagaatact actctatatt caagttataa    114780
agtgctaaat gatctatttc caccatgtat acatttcata tgatcaatac ttattttgta   114840
acttttttct ttgaggagaa gtattttttct tttggaaaaa tattatttat ttgtgtgtgt  114900
gtgtgtgtgt gtgtgtgtgt gtgtatttat ttctcttttaa tatgtggtct ccctatgcaa  114960
aggatttgat tttataaaca gaagcaatag gattaagagg ataaaggaaa aataggagaa   115020
ggggaaatat gagtatcatg ataaggtaaa aatgaattgc ttgtattcta acatagaata   115080
gctactacct gttgagtgtt tattatatat tagacattta agactaatca aaatatctaa   115140
tctaatgaaa taatcactgt tttgaattttg cttagattta gtagatgtag aaactgagac   115200
ttagagaggt ttatttactc aactccacac tgctaattac tggtgaaagt agaattttac   115260
tcctctggtt ttctcatcca gcacatcatc actataaccc ttatagtttg cttttggcac   115320
aagtattcat tattaatgga aatgcatagt attatctcag caaatgtaca aatagtttag   115380
cttcactaaa ctagtcaatt ttttttttct aaacatcaat gcttaggaag caaaacaggc   115440
tgggggaaca gtagttgtac tggtggcagc tgtggtgctg atggaggaag tggtggaatg   115500
cataggctgc tcatgctttt tgccacaatg aaggtcaaaa agtagatcac ttaaagtcta   115560
aagttaacct tgggggtcat attcttcacc aaaaaactatg tttatacata tagacttagc   115620
```

```
agtatgctat aaaagtgaag atatagcact ataaaattcc accataaagt aaattgttca    115680
agattgtggt ccaagctctt caaaatgctc ataaatcaga aggtgtattt attaaacaat    115740
attttatatg tacctataat aatacaatac tatactacac aaattggacc taaaatgaat    115800
tctcttgcta tattaaatat taaacattaa ataggcagaa attttgtttg cactggactt    115860
agaatataag aagaaaattt gggacaacct gaatagttga ggtctcttga gaaacccttc    115920
agcttctttt cctccaaata aatttctctg tagcaaatgg aagccatcca aatgattccc    115980
tagctacctc aaagtactgt aatttgtcta cttcacaaag tggaggacta tatctagcaa    116040
taattcaaga aaaatgcagt gactcccatt atatcttagg cactatgcta ggaagtttat    116100
gcatatcatt ttgtttgatt ttaatagcaa cttcatgaaa taaatcatca taataaatca    116160
ctatttcaga tattgagaaa ccacagaaag agagaagtta ataattttc ctgtcaaaga    116220 ccacatcaat gatgaagcca gaatttgagc tcatgtactt aaccactgga ctacctgcct    116280
gccctgtcga ggaacagcta aggttgtcat agagtcttga ctgtgtatag atagttgttt    116340
gaagagagaa aaaaggcagg aggatctggg gcatatgttt aaatcaggca ttggcatctg    116400
tactagaatt gaaaggtgga actattattg tgttctattt attgagtata ggtataccat    116460
attcaatgta tttctctgct tcatacacta tccaaggtga taaaagtgtt tatgaagagg    116520
gattaggaaa tatctgctgt gtttaggtca tagtccaacc aaaggattaa ttaacatttg    116580 cctcttttt ctcctacatc cagtgtccct tttgatgaga agaataagcc tcattctgat    116640
tcaacagcag agatcaaaga aaagacttct gttttctggc caccagatat atgttatctg    116700
tgcttaaaga attgaaaaac acacatcaaa ggagaatttt cttggaaaga gaggtaatga    116760
gatacagtga aagagaatgg agattcttta aatcacagag acctaggatc aaatcctgtg    116820
attagcactt tttagtaatg tagcctactt catttctttg agccctcgtt tattttctg    116880 aaaatgaggg tgatctaaat tacgtctgga gtagtaataa agattaaatc catgtgatac    116940
aggtaaactc atgacaataa tagacatgaa acaaatagtc tttcatctcc ctcctttgct    117000
caagcattgc tctgctcttc tcacctcctt tcccttcctt tttctttct cctctttatt    117060 ttgtctgtac ccaatagctt ttcccaagcc ttaaaactat gtataggtat attgttgcag    117120
caaaatgcat aaaggagaca ctcattattt gcatccattt atatgctgat ataaatattt    117180
catcctcaca agtttcagag ggaaagacca catgctggtg atttggtgag aaagaagcaa    117240
ctatttctgt gatttaattt caacctgagc attaagagg caccctttca ctactagtgg    117300
taactccatg cttccaagaa ctaatgagct gaagaactta gcacttgtga tgaattagtc    117360
aagcaaaaat tatgaagcga gtaatctata acattatagt acattacaaa tgctgaaata    117420
tattagttat tatttattat gattcttata gctcatttat actgtacaaa attcttctgt    117480
cattttatga agatgttaca catatacata acaaaactta gctaattaga tacaaagact    117540
atagaaccaa ataactcttt tctaaatatt ttccctttaa ggaggttttg caatccagct    117600
ttgctgtggt tagacactgt tgatgagaaa acttttttt tctttctttt ttttttag    117660 acagggaatc attctgttgc ccaggctgta atgcagtggc acaatcatgg ttcattgcag    117720
cctcaacctc ttgggctata gtcgtcctcc tgcctcagtc ttctgagtag ctgggactat    117780
ttgatgtgca ctcccatgtg cggctaattt ttgtattttt ttttttttgt agagatgggt    117840
tttcaacatg ttgcctaggc tggtctcgag ctcctaggct caaggtatcc acctgcctca    117900
gcctctcaaa gtgctgggat tacaggcgtg agtcagtgcg cctgacctgg atgagaaaat    117960
```

-continued

```
attgagttgg aaacccaaaa tatgacataa ataattggta tattttagag ctggatttca 118020
acaactttc aacactgtca tcctgtaaat gtctttccgt cctaatccca ttgcccatgc 118080
actcagcaga agtgtgtgcc tctaaggtgg atgctggtat gaaatatctc agctggggca 118140
ggctctgaaa gggagagatc tggttaaagt gctcatacca aacaaagctc ctcatgatgc 118200
tggcctaact ctcccaatcc tgcatttctc aacaaaactt tttgctcttc tctttcacat 118260
aactcccgtg gaataatttc cattgaattg catggaagag gctgttcatg gggttagtct 118320
ggcagataag aggtctccac tggattttt cattttgcaa tcagtttcat acatatacgt 118380
acatactttt cttggagtca tagttcattc tcaggtcttt tagagttaaa tatctttcat 118440
ttcttctttt aaggtcttaa tttcttgttt ttcgagtttc atgggagata tccagtcacc 118500
aatccaatcc atatcgggga aaagtacaac aaatgagtga aatttgtaac caaccttgga 118560
tgatggaata agacatttgg gagaacacag gagaagtggg gaggttaagg agggatagct 118620
ctgtgaaaat tttgcattac tcttgcctga ggtctactct tccttgtcat gttggtggct 118680
gttttgacaa tgagaaatat ttaatggcaa acttagtctt ctaatttgaa aatggaaatc 118740
ataacagttc ttgcctctta gggatagtgt gagacaagtg aaataatcca tgtaagaggt 118800
atagtactat gcttgccatt cttaagagc tcaacaaata ttcactttt acctattagt 118860
atcaatctta attctaaaat tctattattt aatattttcc agtggtgttt ctaaataata 118920
tctaatgact aggctaatac actatgtggt tcttctaggg ttcaagcatc actgttaggt 118980
gtgctggaat cctttcccga gtcagtactg ctttctagaa gaaaccggg gagatctatt 119040
tggaatgtat ctaactccaa agaaaccatc agaggtaaca ggtaggagat atgaaacgac 119100
ctttagata tgaaccctaa ttgaataaaa gttgccaaac aactgttccc aaacatctaa 119160
agaagagttt tagtctaagt ggaatggctg gagagtatgg gaagagttct ttcctactct 119220
gtccaaacac aagcctctgt gacatttatc aaagaaatgc agcccttaa atctgggtat 119280
aagtccgaaa ggtgctttcc ttgtgaagct tcttttgtcc tctgctttta ggactctctg 119340
cacactgcat cctctatgtc accctccagt acatctgctc ttacacaagg ggcccacag 119400
ggactggccc acacaccagc cagggcacat gggccaactt ttaacagcaa aaggaaatgc 119460
taaatcctag agtagggcag atgagaaaaa tggcattctt cagagagctg ggatgactca 119520
cattaagatc aagggccctg aagtaagaca gacctgagtc tgaatctcaa ttccaacaat 119580
aaatttgttt atacacttaa ggcatcatgt atagtattgt taaatagata ctttacaaga 119640
ttgtaactaa gaggaagcaa aataatatct gtaaagcgtt tcatagattg gccagcatat 119700
agtaaacatt taataattag tagctattat tattttcct taaatatttt ttttctggct 119760
tcctagcaat cataaaattt agtcttgtat agactccatg gctaggactt gcagaattaa 119820
aaatggtctg aacaatttag acattgcctt tttgtcctca aaccaagggg tgaattttta 119880
ttctaaaata tccagattgt ccatatcact taaccagttg attgctaagt ctgtatttct 119940
cttttatgca attgggaaac attaaaaagt tgaatgtata tactgtacac atacatgcac 120000
acacatagac ttaagtacat aaatgtgtat gtaccttcca tagcacttag ctcatctgtt 120060
cttcctatg acctttcta taatcctgtg aagtaggttt tatattatcc tatttatgaa 120120
ttaaggaga agggaagaca gaaaagcagc ctggcttggc cagaggcctt gcaattgatt 120180
acgtatagag ccagggagtc ctgacccctt ttcagttttt cttcctctgt actgctgtga 120240
tgactgtgga agtgaagtac ttctttggct gccaaggaag tcccagctga aaggtaacca 120300
aaggaaagga gtatttggga gcagcatggc tgaaatccag ttaacagtta aatcccgtt 120360
```

```
gggcaatttc tcgttaattg acaacaggaa ttgctgtcac tgtcctgtct agccactttc  120420
aaacggtggg gatgttagca agagctccca gtgaatgctt cctaggagag cagtgattgc  120480
tttggctagc ttcttctgta gcagttttct ggcggtgaaa agtctgtact aagacaattg  120540
gaggtggtaa tcattttcta ataaccacct caggcttttg gcacctaatt cgctggcact  120600
gtctagggaa gctccttatg ctaactcatg cttcttgcca tgtcaatctg cttatctaat  120660
tttgctggga aatctgatat cacccttcaa atagttcacc tcagtgggat ccagtgtgtg  120720
acctgcaaag tgctcaagga agagtctgat cagctctgac aagcaaacag cagaaagaag  120780
ttttgaaaaa acggctaccg tttttgcagc tttttcactg tggttccatg gtgtttgaaa  120840
tcagaatgta atattgagtt aatgacacaa ggaaacactt ggatgttcat attgtctact  120900
tggttttcat gaacctcaca tggactggct tcatcctgtt tcagagtcca ttcaactgta  120960
atttccactc tacttcctgt gcaggccttc ctctggtttg tgggctgtac atttcagcct  121020
gctcctttaa ggggccccct gagctgaaaa tgaaagagac attttgttgc ttctgctacc  121080
tgcttatcgt ccaatcccaa tctcagattt cttttttcta ttttttaaac ccgagtagca  121140
cttttccaac tagtgtgtag ttttttcttc aattctctgc tcttcacagt aattaaacaa  121200
gagctagcct ccttttccaa atcttgtttt tgtaatacct ttattcccaa agagttatgc  121260
ttataagagt aacataaatg tgttaaactt ggtattgatt tgatgatttc ataaccccca  121320
gactccttga aattctgcag gttttgtga aaggacttgc ttaaaatctt tgctaatcta  121380
cctgaatttt cttccaaagg cagttatata caatgtttct taaaactaat tctccaaatt  121440
tgcaatttgg cagcatccta ctgggactct agaaggctga taaatcatgg agagtaggta  121500
ttcatatagg aactatgaaa gctgtatgta gtaaacacta cttaagaagg ccttacattt  121560
cataaaaagt tggagatttt tgtggagact cataaaatgc atcctttata tcagtgaagt  121620
ttttgcttct aggtatatta tactcacatc gaaacactcc agggattttg ttttcagcct  121680
gcatatacca cgtatattta ttatctggat agataaatta gacgtataca tttaaaggag  121740
tttgcatcag ctgctgctag gaagttttc ttgtgttagt taagatcctg tgaaacaacc  121800
cttgacattt cactagctgc acagtttgta ataaaatcca ttttagcctg aggttaaatc  121860
atgactgtgg tcctcacatc atggtggggg atcctggtgg ccagattaaa ggaaactcca  121920
cattctcatt tctgacttcc ctacaacctt gtattaagac cttaattgaa aaacttattg  121980
cctctctcac caaaatattt caaatttttaa tagtttcccc caatgaaatt acaagtacta  122040
ttttactttt ttcagtgccc ttggaatttc gaggctggat gggggggcttc aatgtctgac  122100 tcattaagtg ttctatatac aaagccctac atggtcccta gagcatagca ggcattcagt  122160
gaatgaaatg aatgaatgaa aagctagagt cacattttag tgacctaact gtatattttc  122220
agagtaatgt agtgcttaaa aaaggacaat gataacacgt ttctacaaag agatgcatga  122280
cagataacac ttctcaagaa gaaggaattt agcttctgtc atttgatcta ggttttcaat  122340
tacagaagca ttgagaattt cctgtggctg gataagggcg aatctttaag gcaagttgaa  122400
gacccaggct gcccatgtgg acatcaatac tcccacagag cactcttcat gaagaaaagt  122460
gtgggcttgc tgtctttttca tcaaaactcg tagaatttgg ctgactgcct ggtttatccc  122520
aggacattag tcagcccaca aatcccgcat ttgtttattc agtccagagc aagtgaatac  122580
tgccattttc tcatctcctt tgttggcaac actttgttaa cctgaattgg gttctcaaca  122640
taaaatgaag tgactaatct tttggggggt tccccctccc aggttcttgt atgagcaact  122700
```

```
aaatctacac accacaaagc cccatgctgt catttttct catcctgccc ctttatttg    122760
atgattccac attgtagttc atgaaaccaa taccttctag agtgtggctg aactggcgcc   122820
agcattaaga aaaggagttt ccaaacttt tagttttgtg agaaaatgtt agaggaagag   122880
ggaggttagg ttgactattt atacttatgt aatcttctgt gaatttgcag tagttatcac   122940
cttgtactct caaaagtttt ctagctctga gtatgtgaat ctgaaagtgc aggaagtagg   123000
aatcttagca caaacaacc agtttggatt atcacacaat taatatggga cggagctgga    123060
ggatggacct gaacagaatg tatattcttt atcactaggt tatttatcta tctacagatg   123120
tctagaaaga cctgggcttt tttagcaaac gtttgagaat ctaggtttct aagtttccat   123180
tgaccatgaa agagtgatta gttttagaag acagttgggg gcaacattgt gcaagtcaga   123240
agagggatg aagaaaatca taaagctaaa catgtttgcc ataggcccag gctgtttttc    123300
agcatgtttc acctagcagc ttggcagata attcccagtg atcattaggt ctgtggaaat   123360
tctgtttggt ttataaagtt ttggcccta ctatgtgtac cactgataac ttgttttct    123420
ctctcttccc ttttcctcca actcgtagcc agagctacct tccagatgac ttcttctac    123480
cactttcttt cttcccagtg taagagaatg caagtatatg ctgatgtttg gagcaagaac   123540
attcaaaaat tttcttatta acataacttc taatggaaat acagtatact actatggtgc   123600
atacaaagaa gaaatagcaa catatatttg ttttagacct gattgctgta ttttattcct   123660
taggtcctcc ttgatgtctt gtagaccgtc actagctaat tgttacagcc atcgaaggaa   123720
aaaataagga tttttactta ggacatacgt aacagaaaaa gagatggttt agcaaaaaag   123780
cacaggcttt gcaataagca gccttaaatt aaaaaaaaaa aagttaactc ataactaact   123840
gtgtgacctg ggataagtta ctgaccctct ttagggctta gggtcctaat ctgcaaaacg   123900
gaaattataa taataacctt agctagcatt tcttgtgcac atactataag ctggtgataa   123960
acaatttata cacactatct catttaatcc tcacaacaat cctgtgagat aggtactatt   124020
atcatttcta ttttacagat gaagaatcca gacataagaa gtgaagttaa gtaactttct   124080
caaggtcgca cagctaccat atgatggagc tggaatgtga atctctgcag tttgacgcca   124140
gagtgcatgc tcttagtcac tacatttgtc tacaaatcta aaacacgtaa gacacatagg   124200
aggtgctcag ttagtggtat ctattattaa atcagactat aaataatcac caggcaatac   124260
ttgaaaggcc acaaacaatt tcttaggatt tgtgacaata ctaataatta taactgatta   124320
tgagcatacc ttgtgtcagg cacttctttt catagtattt cagtcattat ttaagagatt   124380
tattcttatt tttattttc tagtgagaaa actgaggctc aaaaaagccg acaaatttgt    124440
ttaggattac aaaaatatca aatgatagga ttgaaaatca aatccatatc ctttctatgt   124500
gaaaacctgt gttctttcag cttttttat ttttattttt ttatttttta tttatttttt    124560
taaattttta tttatttat tttttatt tataagcctt tttatttta tttatttac    124620
tttatttgtt gttgctggtg ttttttctt gagacagagt ctcactctgt ctcagctcac   124680
tgtaacttct gcctcccggg ttcaagcaat tctcctgcct ctgcctccca aggagctggg   124740
attacaggca cctgccacca tgcctggctc acttttgtat ttttagtaga tatgggttt    124800
caccatgttg gccaggctgg tctcgaactc ctgacctcaa gtgatctgcc tgccttggcc   124860
tcccaaagtg ctgggattta caggcatgag ccaccacgcc cagcctgcct gatttttaaa   124920
attattaaat tcatatttgt tatttatcag atgcctctgc cactttattt ttaaaaatt    124980
tatttttatt aaggtatagt taacaaataa aaattctata tatttattgt gtacagtgga   125040
atgttttgat atatgtatac attgtgaaat ggttaaatca aactaagata tctgtcatct   125100
```

```
catatgcatg ccatattttt gtggtgagaa catttatgat ctactctctt agcaattttt   125160
aatattctgc tgtttgactt ttaaaccaag gcttggatta ggacagtctt tgtagcttag   125220
ttttaggttc agggataaca aaagttgttt tatcctttgg gcttttgcaa cttgccattt   125280
tcttaatgaa gatctgggag aaaaattagt ttaagtggtt tttaaaatag ccattagctc   125340
aggacatact cagccaaggc aggataagta gttttgccag cattcttctg taggtaggtt   125400
ggttgttttt tgttttttg ccacagtctt tttaaaaat ataactttaa aaaaccttg    125460 gttttctgtg attgatcttt ttcactattt tttatagagg gccaggaata tgagtaaata   125520
attcttgggc ttgggtgcag atgatccacg tgctggcaga cagaaatcta aagggacaaa   125580
agaggctgtc ctttgaagat acttttcctg gcttgggttt tatattttg gatttgattt    125640 agtgaaaatt tttattgagg acctactgca taccagacac tcggctacat tatgagaggt   125700 ttgggggggcc tatattggca tatagggagg atgaataaag aatacaaaca attatagtac   125760
aaatcagaat aaaatttggc atgcaacggg ctatcagata gtatggagga agaaagcata   125820
ttttattagt ggagctagga aatacgttac aaagttgata gcattcttga tgggtcttga   125880
aggttacata gattttttt tcttttttt tttttgagac ggagtcttgc agtgtcgtct     125940
gggctggagt gcagtggtgc aatctcacct cccgggttca agtgactctc ctgcctcagc   126000
ctcctgagta gctcggatta gaggctcctg ccaccacatc cagctaattt atatatgtgt   126060
gtgtgtatat atatatatat atatatattt ttttttttt ccagtagaga cggggtttca    126120
ccatgttggc cagactggtc ttgaactctc gacctcgtga ttcgcccgcc tcggcctccc   126180
aaagtgctgg gattacaggt gtgagacacc acacccggcg gatagagaga attttgacag    126240
gtgaggaggt attccaatgc aaagaataa taggagcaaa agcacagtgg tgagaaattg     126300
gaggggaact gtgaaaattg ccacatagat tagaggcagg aaaataaagg acggctaagt   126360
ttatatagtg aacagtgagc cgcatggaca caggtgactg ttttctcctt tttgaacccc   126420
tgcttactcc agagtcacca cctctcctgg cttctgcca atcttcttgg ccacagtttc    126480
tcggtcttct tttctggctt ctcttccttg gcctgaatgc tacatgttaa gtgatgtcag   126540
cttcagtttt cttaacctct cttctcttaa gttgctatca tttaaatatc tttaaatatc   126600
atctacatcc aagtgacctc taaaccagta atttaccca tgacccatct cctcaactcc     126660
ggattgtata taaaactgtc tactcaacat cttcactttt gatgtctaaa tctctatgtc   126720
caatttagaa ttcttgattc tttgcttcc ctccctcctg gaaatcctgc tcttaccagt    126780
cttccccatc ttaattaatg aacctgacat tcacctagta gcttagtcct caaaactagg   126840
gattaatcta gatttagtca ttttcttac tcttgccata taataacata ttattctgag    126900 tttacccttta cccgacccca aataggtaac tgctgttttt gttataagat agtaatattt   126960
gcctctgagt gtatgtgaat tatttgata aaaataaata ttatttttaa aatattaatt    127020
ttacagggat tgtctcttga tttctttcca aaagttaact cataagttgt tcagcagagc   127080
tatgtattct tcagtatgtt ataatttcgt tccatcttcc aaaaggcctt cacattctct   127140
tggcttacag actcagatgc tatggattag atacacaagt acatgttcct gtatatctat   127200
tatatagtga acataacaat tatgattgtg atcttccaaa gctcgtattt ttaatcaaaa   127260
ttaattaaat attttaagcc aaagaataaa ggtagatgca gcatctagtc aaaaggatat   127320
ttctgctggc cacactcagg aagacataaa gatatagttg tagaaagtga tatagtattg   127380
gccaggtgtg gtggctcaca cctgtaatcc cagcactttg ggaggccaag gtgggctgat   127440
```

-continued

```
tgcttgagct caggagttcg aggccagctt gggcaacatg gtgtaaaccc catctctaca   127500
aaatacaaaa attagccagg tgtggtggtg ggcacctgga gtctcagcta ctcaggaggc   127560
agaggtggag gattgcttga gcctgcgagg tggaggttgc agtgagctga ggtagtgcca   127620
ctgcactcca gcctgggcga tagagtgaga ccctgtcttg agaaaaaaaa aagcaaccca   127680
gtgataggct gggcaaggtg gctcatgcct atatttctag cagtttgaga ggccaaggcg   127740
ggtggatcac ctgaggtcag gagttttgcaa ccagccttgc caacatggtg aaaccctgtc   127800
tctactaaaa atataaaaaa ttagccaggt gtggtggtgg gcacctgtaa tcccagctac   127860
tggggaggct gaggcaggag atttgcttga aaaaaaatta gccaggtgtg gtggtgggca   127920
cctgtaatcc cagctactgg ggaggctgag gcaggagatt tgcttgaatc cgagaggcag   127980
aggctacagt gagccgagat tgcgccattg cacttcagcc tgggcagcaa gagcgaaact   128040
ccatctcaaa aatgaaacaa acaaacccag tgaaaccag tattgaaaat agattgcctc    128100
tcccttgctt catggtctgt tcttacgtaa ttttcaagat aagttcattt tggcgggtac   128160
tgacaaattt ccatttattt actttttttcc cttacattca tttcttctca gtctctccaa   128220
tgaacgcctt cactgatatc caaagcatga aggacacacc agggaaaaac atagacctaa   128280
cacaggacaa atggaattat tagaaacatt ttctagcaga agaacactat tctgttgcca   128340
tttgaatctt tgcttctttc taggtttgac aatgagccta tcatataagc ccaaatgtaa   128400
acagaaagag gttgaatcag tcacgataag cccaattatg ctgtggtaac aaacaacctc   128460
aaaatctcat tggcttaaaa tatacagaat tattcttact catggcacat atccatctat   128520
catctgcagg ggatctgctc actgaagtca cttaggaact tggactgatg gaacggccac   128580
ttttttggtca ctatatgtat taatctgttt taatcctgct gataaagacc caaaattggg    128640
aacaaaaaga agtttaacta gacttacagt tccgcatggc tgaggaggcc tcagaatcat   128700
ggtgggaggc gaaaggcact tcttacatgg tggcagcaag agaaaaatga ggaagaagca   128760
aaagcggaaa cctctgataa acccatcaga tcttatgaga cttattccac tatcaagaga   128820
atagcatggg aaagactggc tcccataatt tacctccctc tgggtccctc cctcaacatg    128880
tgggaattct gggagaaaca attcaaggtg agatttggtg gggatgcagc caaaccacgt   128940
aatttcaccc ctggccccctc caaatctcat gtcctcacat ttccaaacca accatgcctt   129000
cccaatagtc acccaaagtc ttaactcatt tcagcattaa tccaaaagtc cacagtccaa   129060
attctcatct gagacaaggg tagtcccttc tgcctatgag cctgtaaaat caaagcaagc   129120
tagttacttc ctagatacaa tggtggtacc agtattgagt aaatacagct gttccaaatg   129180
ggagaaattg gccgaagcaa aagggttaca gggcccatgc aagtccaaaa tccagcgagg   129240
cagtcaaact ttgaagctcc aaaatgatct cctgtgactc caggtctcat atccaggtta   129300
tgctgatgca ggaggtgggt tgccatggtc ttgggcagct ccgtccctgt ggctttgcag   129360
ggtacagcct ccctccaatc tgcttttcacc ggctggtgtt gagtgtctgt gcttttcca    129420
gatgaatagt gtaagctatt ggtagatcta ccactctggg gtctgaagga cgatggccct   129480
cttctcacag ctccactagg cagtgcctag ggactgtgtg tgggggctct aaccccacat   129540
ttctcttctg cactgcccta gcagaggttc tccatgagag ccccgcccca gcagcaaact   129600
tttgcctggg cattcaggca tttccataca tcttctgaaa tctaagtgga ggtttccaaa    129660
cctcaattct tgacttctgg gcacccacag ggtcaacacc acgtggaagc tgccaaggct   129720
tggggcttcc accctctgaa gccacagcct gagctatata ttggcctctt tcagccacag   129780
ctggagcagc tgggacacag ggcactaaat ccctaggctg cccatggcgc agggaccctg   129840
```

```
ggtccagtcc atgaaaccac ttttcctct tgggcctctg ggcctgtgat gggaggggct    129900
gccatgaagg tctctgacaa ggcttggaga cattttcccc atggtctcgg ggattaacat    129960
taggccccat gctacttatg caaatttcta cagctagctt gaatttcttc ccagaaaatg    130020
ggttttctt ttctattgca tagtcaggct gcaaattttc tgaactctgt ttccctttta    130080
aaactgaatg cctttaacag tacccaagtc acatcttgaa tgctttgctg cttagaaatt    130140
tcttccgcca aataccctaa atcatctctc tcaagttcaa agttcacaa atctctaggg    130200
cagaggcaaa atgccaccag tctctttgct aaaacctaac aagagtcaca tttgctccag    130260
ttcccaacaa attcctcatc tccatctgag accacctcag cctggatttt attgtccata    130320
tcgctgttgg cattttggac aaagccatta acaaatctc taggaaattc taagcattcc    130380
cacattttcc tttcttcttc tgagcctttc aaactgttcc agtccctgcc tgttacccag    130440
ttccaaagtc acttccacat ttttgggtat ctattcagca aagccccact ctactggtac    130500
caatttactg tattagtctg ttttcatgct gctgataaag acatacctga aactaggaac    130560
aaaaagaggt ttcattggac ttacagttag ttccacatgg ctggagaggc cttagaatca    130620
tggcaggagg tgaaaggcac ttctcatgtg gcagtggcaa gagtaaaatg aggaggaagc    130680
aaaagtggaa accctgata aacccatcag atctcgtgag acttacttca ctatcaggag    130740
aatagcacga gaaagatcgg ccctcgggat tcagttacct cacctgggat acctcccaca    130800
aaatgtggga attctgggag atacaattca agttgagatt tggtagggac acaggcaaac    130860
catatcacta taccacaagt ttttttaaaa aaacaaactt ttgagaatct tgtactgata    130920
attaatatct ggtctggaag tgaagcacat ttctttttct tgcaactgat tggccagaac    130980
cagctagatg gccccaccaa gccaacattg ggggagaact gaaatatttg gcaaacagca    131040
accatgacca tcacagctgg aagttctcag tctggaactc cttccccagg cctcccattt    131100
ctggaactct gagaacaaca atccaggaat ctgatgacat cttttccttt actagccaaa    131160
atctgatgac atttttttcct ttactagcca aaagggagaa caataagcaa ataaattcaa    131220
ttttctccca tttatacttt taaatctgag aacgaattgt gtgtttataa gaaagtgagg    131280
gttgagcatc atgaagaaaa atataaagat ctttaaaaag tatatattgg gcctattagc    131340
tacaaacatg gatcattatt aatatgtgtc tgactgacat ttaaaatgca taatcaaaat    131400
caagcctgtt agatacaaaa ttcatccatt aatagcaact aaatttcatt aggtaagtag    131460
tagtgctatg tttaaaagag taatctattt ggaaacagga attaatactc agaatattat    131520
tattaatata tttgaaaatt acttgtgttt atttgtccca gcccttacaa ggtgtgtggt    131580
aatggttaag gtatttctcc tctatatgcc tgagttttct tctttacaaa agggggagg    131640
gaataatagc acctgatttt actttgttg tgaagattaa atttgtacat atataaatct    131700
atatatctat atatacactt atatatgtat gtaaaatatg taggcttgtg cctgacatta    131760
aatactaaaa aatactagct attatttta tcctcatatt atcagatatg acacattcat    131820
aatttaaaca gaagcctacg aagaactcat aaattaaaag aagataatct tttcacaagg    131880
taacaaattt tggaacaatt ttttagagtc tctagacatc tgttactgac gttgtgagtg    131940
aaatgggtct gtgaagggaa gatacaggtg gaactgggcc agtgtttgca gaggaccatg    132000
atatttctat atctctgctg gctccctatc agttctagag ctagttcaag tgaagcctcc    132060
ataacctctg gacaataaaa atgcaccatg ctattgttag catgatgaat gaatttattt    132120
ttgtttagct tacagaaagt tagtagtttt caaaagggtc tttatgtata caattgaaga    132180
```

```
tactacattc ttgaaaagga aatctttaca gcatacaggt ccctggcact aatacctcat   132240
ttctgggcac agcttgatat ggaggtatag tttgtgtttt atctgaggaa aatttaggtt   132300
ggtgttatgt tttgggctag ctctgctgaa acattattct cttttctttt agagccaggg   132360
ctgtgggctg tgtcacttgt gacttggcag cccttaatgg ggctacatga ggaagacatt   132420
tccttacatg attccaagag tctttctctg gggttctgag gtagtctctg tgtttcttgg   132480
agatatcgtt ggctctaaaa tttcccctaa gtgaggtgat attctgtcat ctcatgcatg   132540
ggttttggag gctgaggggt gtctgggttg gctccaccac ctaccagttg ggtaatattg   132600
tgtagttttt tttttaaacc tttctcagct ttagtttcct tatttgaaca gggttaaaaa   132660
ttgggcttga gagaaggatt agagataata ttagtagata ttgttgatga attgggcgaa   132720
gcagagggag ggggcaaagt tgactacctt tgtttctgtc tcaaacaagt aggtggtgat   132780
gcctttgagg agataagaaa agtgacttgt gtgtgtgtgt gaaagacaga cacacacaca   132840
tatatatata tagagagaga gagagagaga gagagactta taaattttgg atatatggtt   132900
tcaaggcact tttctggatg cataagtgta aatgttcagt tgaagtttta atggtgctta   132960
ggagagagat gtgaacgata atagagattc caaaggcctt tacatcaaga ggataactga   133020
agctatagga gcagatgagg cacacctgta aagatgagac aagaagaaag cctagggtag   133080
ctctgagaac tttgctattt agtgtcctca tagaggggat ggaggattct tcacaaaaag   133140
ttcagttttg tgcaccaca ttcccctgat tttactctta cctcttgaga caccaatttt   133200
ttaatgaaga agaaaattat gttgcctgct taaagtaagg aaagcaggtg ttggtgggat   133260
tccttaatag aaatatagag gtttaaaata cctacaagag taggagatag aattgatcaa   133320
gtaaaaaaat tgaagagatt aattgaggac ttaacatcag agaccatatg tttgttgtga   133380
caataatcca aattattgta ataatgtgtt taggagtatt tagccttgta ggtaccaaga   133440
ttgcattgat cctgtgttag gagtttgcca ggtgtgtgca atagtgagaa agacatgaag   133500
ggatttgagg ttgctgatga gtgaccagtt tagatgacaa ctactgtttc ttcaactctt   133560
tcttcaactt caactgtctg ttttgggaaa ggctagtggc ctgtgaggaa acgaagaccc   133620
cggagctgga ggactcaaag agtttggaga gcagacgtgt gcaagtgagg gttttgtgag   133680
cactggagga caggcagctg gggaagagag tgtgttattt gcagttatga tattgggtgt   133740
ggagctattt ttggtggcag caaagctcag gatgtatttt tttattattc ccataggtga   133800
tggaggcttt ttattttgcc acaaaaccac tggtgacgtt gcctgtggcc accttggaga   133860
agacactgga ggtacacagg atgtatccct ggaagtggca ggggtataa gtttagtagg    133920 agatttgtta ctgagtattt aaggtctagg aacagattga gggtgttggg tggattgccc   133980
actaagacac tgggttttct agcatgatga cagaaattgg agtttggggg gagaagagtt   134040
ctattgtgtc ttgaagaatg tgatcaggag gtatttctaa tgacacaaac atagaagtat   134100
acacactggt atagtcagat ggcatgagta ccaaggtgga agtgtggtgg tcctaaagtg   134160
gcattaagga gccaataaat tgtcattcct accttagctc tgtgtcagat gaaatacaca   134220
gcatagtgtg gggagaaaat gttgggctta ttggggatgg ggtctttcac ataaaggaag   134280
aaggtttcag aaggcatagt ggtatgaaaa gaggagaaac caagggagg aaggtcaata    134340 aagggttaag aacgagggga ggcaaattga cttcctttca gcatatgagg attataggaa   134400
tggaaacctt aattggaatt aattgaccac aaatattcca aagatggagt gaatcagttc   134460
gagacagaga tatctgaggg tctgagggtc tgaagtagga tttgtcccag tcgtgtgtgg   134520
gtgggttcac tgtgtggagc ctggggtctt gaggatctga acatgggctg cctcctgtgt   134580
```

```
gcacggtgga ggcatctggc ctgttctccc tggggtggac tcatgatgag ctgagtggcc    134640
aaacacacaa tggttttcat ttaacatctc atttctagcc taacgacaaa cctaaaaggt    134700
gggcataaca ataatgttaa taaaacatct gcatttctcc catccttgga gttgtgagga    134760
tttaatgcaa ttgtttgtgg gaaagcactt taacaactct aaattacgat atatatgcta    134820
ggttttattg ttacccacac ctttgatgta tttctctttg tactcttcac tgtatctgta    134880
acacattccc taggataatt agggctaccc tttaacaaag ccaagattct atttatagtg    134940
gtaagctggc acctgggctg attctctcta gtgattatgt agttttgatg tggactggca    135000
ttcttccctg gagtttgagt acctccgtca gcacttctcc cgtccagaag ttccatctct    135060
gtgttttcct attacaaagc ccagacaccc atctaggcca cccaccaggt tcctcttttcc   135120 agtcttaagg acatctttag ctcctggctc atttgtgaga tggagtggac tgacatgccc    135180
taagcaaaga ttgccagcct ggtctagttt tccaggtctc ccttgactcg acaataaagt    135240
aaccactaga ctttgagaat tgcagtttta cattgtctag agtcttctag actttcatga    135300
agataggcaa atatgattct aaccaagatg tattaatacc tcctacttcc tttgaaatgt    135360
aactgagact gtacttgaga cgttacaatt tcttggaagg ggaaaggaag cttctgctat    135420
tgaacgaact ttttgttaag gtagctccca agcaggttca gtagctttgt tctattatca    135480
cttttctact gacagtgatt ttttttcctt gaaggcctgg gacatggaga ctgctttct    135540 gcagaaacca catcccttgg agtaatgagc tacacctacc tcaattattc agtgcagtac    135600
aacactccag gtcagctatt aagaggtgca cacattattt ttagaaaatg tgagtcagtc    135660
ttggggaaaa caaatctatg ctatatgttc tttttactca cttgatttac aacatactgt    135720
gatgtattct ttttctattc agcatctttt tgtacccgta gctctttgtt ctgagcataa    135780
atgtgacctt ttggcttcag gtagaaactc tgtctcatga gcactccctg gacacggaag    135840
ttctttgaaa tagcattgat tttgtttaag ccttcatgtt cccctggaag gctgattaac    135900
cttagtgcct tctttctgta atagctcata ttgaattatc tccctctgtc tgattatatc    135960
catttgaatc acctgcaagt ttcttttaca tgtctagagt gaggacaatg tgggtgatga    136020
agagctgaaa tcttctaggt aaacattaga ttttaaaaaa ttctattttt ttttttttat    136080
ttttaagaca gggtctcact ctgtcaccca ggctggagtg tattggcatg attacagctc    136140
actgcaacct tgaactccca ggctcaaacc tgagcagctg ggactacaga tgcaccacca    136200
tgcatggtta gttttttaat ttttttttgt agatagaggt tctcactatg ttgcccaggc    136260
tcatctcaaa ttcatggcct ccagagatcc acctgcctca gccttccaaa gtgctgggat    136320
tacagacatg agccactgca ctaagccaaa aactcttgtt caaattacat tttctgcctt    136380
agtaatgctg ctttcctagc ttctgagaat ttctaagacc caatggtaac tctatgctaa    136440
aattaaaata cgaatgtcct tttcaaaact gcacaatatc tttgctattg tcaataatgt    136500
ctcaataaac ataaaatagc aaagagattg tgcagtttta aaaagaacat tcgtattta     136560 attttagcat agagttacca tcgggtctta gaaattctca gaagctggaa aagcagcgtt    136620
actaaggcag aaaatgtatt cacaatagca aagacttgga accaacccaa atgtccatca    136680
atgatagact ggattaagaa aatgtggcat atatacacca tggaatacta tgcagccata    136740
aaaagggatg agttcttgtc ctttgtaggg acatggatga agctggaaac catcattctg    136800
agcaaactat cgcaaggaca gaaaaccaaa cactgatgtt ctcactcata ggtgggagtt    136860
gaacaatgag aacacttgga cacagggtgg ggaacatcac acaccagggc ctgttgtggg    136920
```

-continued

```
gtggggagag gagggaggga tagcattagg agaaatacct aatgtaaatg acgagttaat 136980
gggtgcagca caccaacata gcacatgtat acatatgtaa taaacctgca cattgtgcac 137040
atgtacccta gaacttaaag tataataata aacaaaaaaa accactgcac aatctctagt 137100
attcagatgg agactaagca tgattttttct tataaaagag cagatcagaa tgttgtatct 137160
tttattcaga agactggagt taatcactgt tatctttagt acttagtgct gccaaggctg 137220
tgtgttcaca atgaggatag gatgtcaaat aaatgaagct tcatagaaca agagcaggat 137280
tgagtcatgt aggcaactgt ttcagcttcc tcacctaact tagcaccaaa atgtgttatt 137340
gtcattacag agtgcttatt taagaaaaaa taaaaagaac acacacacac acgcacgcac 137400
acacacacgc acgcacacac acacacatgt agctacatgt ctaggaagga tgtggagagc 137460
tgaaatatga aggcaaaata aaacatcttt ttcaaagtat acagcctaca gtggttagca 137520
cagagctggc cacatagcag gggtttcata aatgcttgtt gattaaactc tttttttttga 137580
aaacaataat gtagaagcaa agagcctaaa gtgttttcat aaatcttaag tggtagcttt 137640
atgttccagt tcagcaaaac acaaatttga aggcaatctg tacgttaggg ttcaggtgaa 137700
gaaggcaaag gaatcaatga aattgtaaaa gctttccaaa tttgcctttt ctcttaagat 137760
tgtctttctc tcattctctt ctccctattt caggaatgca aatatcctgt ttcatcaatc 137820
ttttgttttc tgactcaaga taacaacaat aatttattga gcacaaacca tgacttttgg 137880
gtctgtgtag ccccgaagct tcatagttca atatctgaca cataagaggg gcttactcta 137940
cacttaaatg ttagttttgt cctcactttt ttctctttct cagagatctc ccttttcccc 138000
tacttgtata agcatgaaga aatctttctt ttcattctct ccaagtttaa tcagacaact 138060
ccacatacat acatctttgt tcacaactat gaacaagaca gaaaagttgc tggacctcaa 138120
ggactttaca atcaatctgg gaaggcaaac attgaacata taatgtccag tctgataagt 138180
gttagggaag gaaagctcag aatgcaaggg aatataatct aatctaggag atcgtgggaa 138240
atatcactgg ggaatttgga actgaaagaa aaataagatt tgattagggg aaattgaagg 138300
atcagggagt caggcggaga agaatgtccc ggcagatgag acactatgta ccaagcccga 138360
gtttgacaga gagcgtggtt tacagaagga atctaaaagg tgtagtttct gtagcagaag 138420
tgtaagggtg ttactcgtag gaggcctcta ttgaactctt ttccagtgac gtagtgtgtg 138480
gtctttaagt ggctttgcaa tgatagtaag atcagcattg cattactgaa tgagctcctt 138540
tagtaaacgt ggatatgtgc tttctgaatc tatttgtttg ttttttcccaa gtcataaaca 138600
gtgaatcaag caaatgaaac ataatcaagc ttggatagta tcttccacta atttccttgg 138660
tcttaagtaa gactgacagt aaactgatgg tcaacctgtt caatgggctt taacaagtag 138720
tagccacatc caagtcaaca aacagtacag gcaatcaggg cccctggcct acagtgaatc 138780
atgggaatta ccccagggac ctatgctttg gggactcgtc cttcctggca gctatagatg 138840
ccatcagaaa ctcatttgca cactcttata accaagataa gggcaatggt tagtcccctg 138900
tcattgcatg ttagctttct ttcccttttc taggcttttt cagatgcctc ttttacatta 138960
ttacttttcc tgtgtgaaaa taatgcgtgg gaaatgggta ggtcatacag agcgataatt 139020
tcattcctgg gcccctgtct tgcagctccc taagtaaagt tttgcgcctg cactcctct 139080
ggcatagtaa cctctgacaa acccttgggt aatagaggag tagcaaaacc catgggtaat 139140
ggaggagtag caggaatatt atgattagct aacaaattca caagtacat agaaattttt 139200
ttctcgaata accactatag ctgaggaata tagattagta acaaaattgt gcactcaacc 139260
aactctatta aaagtatttc attattcccg tgaaaaaact cctaggaaaa tgattcactg 139320
```

```
agagatatac gattgtataa gtattgagaa acagtctttc ttttttgctt tttatttatt   139380
tatttaatag acattatagt tacacataat tatgggatac aatttgatgg ttcgatacat   139440
ttttatgttg tataataatc caatcaaggt atatttagtg tactcatcac ttcatgcatt   139500
tattattcct ttttgatgag aacattcaaa agcctctctt ctagctcttt cgtaatatca   139560
ataccttact gttaatcata gtcactctac tgtgcaatag aatgctagaa tttattcctc   139620
ctattgaatt gtaactttgt acctgtcgac cagcctctcc ccatcttctt cccctttctt   139680
cttgcttccc cagtctctgg taaccactgt tctattcctt tttttgtttt ttcttttttgc  139740 agagttcgct ctgccgccca gactggagtg cagtgcacaa tcttggctca ctgctacctc   139800
cgcctcccag gttcaagtga ttctttctat tttttgggaa tgtgcgttat ctaatactta   139860
ggtgcctcag atttaatggt ggtaaatctc actcatttta tgaaaaccaa atgaacacta   139920
tcctcacaat ggttagaaag caagatcagc tcaactttat gaaaatatga ctataaaacc   139980
atttattatt gccaagtggt tggagtggag ttgacagaaa gatgcattat tttaaattgt   140040
gttttagatg acagaacagg agtcagtaat gttccagttt ggaggaatta gagttaattg   140100
gttaattgat tgattcgatt cagtcaaatt tattgaatga ctgctgtttc agacactgta   140160
tttggtcctg ggaaaacaca gataaataat atataattgt attataaatt aataaaatag   140220
ttttttccct ccaaatgtca gtagtccttg gaaaggacat gtaaacaatg aatataaagt   140280
gacacatagt ccagtcaaga taggtaggaa ggtctaagta caattgagtg gtcaatttca   140340
cttcagggaa gggcaatgat cagggaagat ttcccaggga aagtgatgct tgggcaaata   140400
agtaagcatt ttacaaagag acaaggaagg atagggcgtc ctgggcagag gaaggagtgt   140460
gtacaaaggc caagtgacat atgacaacat tgtacatgaa ggaaactacc atcaggcaga   140520
gctgaaatgt tggcacatgg tgaagtgcta gttaccggtc ccagccatga cagtagtgta   140580
acaaatgcct gcctctggtg cacagcaaga tattaagatt cctcaaaaca gttcatatat   140640
tttataaatt aagatagaca ttaacagaag ctcatagaat caattaatgc aaatgtaagt   140700
gacctaagag gcattttgtt cagcatagtt attgattttg cctgacccag aggatttgaa   140760
tttaggaaga tgtaagccta gagtagctgt cagttatctt gtgatacatg ggccttggaa   140820
gcaaggtaca gggacacagt ggaccaatgg gggaagatta ggtcctggtg atgtgattca   140880
agccactgga ttaagccaca tctgaaacgt ctatttctgt actcttcagt tacaagagat   140940
gttagtttga attatttgct taagtcagtt ttttaaaaat tcaattgcaa cttaggagat   141000
acatctggcc tcttcatttt acaacttagg agactaatat ctagtatgac aaagtgactt   141060
gccaccaaat ggctggttaa aaactgatac caggacccag atctaatgac tcagaggcca   141120
ggcttagaaa tatctagctt tttttttttt ttttttttt tttttttta gacacggagt    141180 cttgctctgt tgaccaggct ggagtgcagt gcgcgatct tggctcacag caaattttta   141240
aagcatctac atgtgagggc ctaagtatac gagtacctag aaatctattt tgcagcaact   141300
atatatttga tagagtgatt gagtttagtt taaagatgac atttctaagt ggtagtgctg   141360
tcaaaagagc attgcattga atcaagaatc tggcattctg tgttcatagt tcactttgc    141420 cactaattat ttttgtgacc ctgggtattt cttctcggga ctgtattcat tggatatgag   141480
tatctctaaa tcttcttcaa cttctatgat tctaaatgga agtacactca attttcaagt   141540
atccattgtg gattttatat actgctatgt atcctgagaa aatcttcctt ttgaattatt   141600
tttcgtatta atgagttcaa cttcacaaat atttactgaa caccaactat gagctaggtg   141660
```

```
atgtaaaagt gaatagttac ttctagtcag tattacttac ttacttttgt attccacagt 141720
gcagtttgat attgtttgta gttccaaagc attaaacaat gccttttaat ctaggacatg 141780
tggaatcttc aaataagagc agaattacaa agagttttag actgccactt tgcatcattc 141840
tgagaggcaa taccataagt gttcagcagt cagaagaagg gacaggggaa agtcctgagc 141900
agtgcaggtg gattaagaac taaatatgcc tacaaaagca cattcatgcc taaatgtcat 141960
tgcatttgga tcacaggcct tgagaagatc tgtaccatca ctgtgggtaa cttgggccca 142020
tttagagtac ttgcctctga gggaaataaa aatttgctag caattttctc taaatgacat 142080
tatcataggc acttaattcc ttgataggtt cttttagata atttttttat aatgaagcaa 142140
ttaatttgat tcacgaaagt aagtttctag tttatataaa gaccagatct ggcctatttc 142200
ttagcttgtc tacatttgag tagttccatt gctggaaaat gaccctggag cttttcaatc 142260
tcatttgaag agtccagggg acagacagag acactagtta tgcagtttac tagagccagg 142320
ttccatttca tctctaataa tttttgcctg tgtgcgcctg cacatgtagc ttaagctatc 142380
taagccttag ttagttttgt catcagtcaa aggggaatag tgatatctcc ctctaagggt 142440
tgtacaacat ggtggttatt tatagcacag cttgaataaa tgttattaga tgatatagtc 142500
tcagtcaggt tttccttgga ccatgtttta gtgacatatt agactccaaa gaagcaaaat 142560
gctaggagca caaggcagcc taacttgtga gttgatgtac agtgtgaaga tgcaccacag 142620
atttagaatt tcagttgact agaagaataa gtggtagaat ttgtccctgg ttgactactg 142680
tcttaacttt gtgtctttgg ggaaatattt aagctctcca gacttctatt tcttcatgtt 142740
taaatcggga ataatattcc tttctcattt cgtagaaatt gaaaggagat aagtatgaaa 142800
gcgtttatga gagtagaaat catgagtgtg aaagttcatg ctattatggc acaattgatg 142860
ttgaaagtta atattacaga ccattccttt tttgcacagt gaaaattgtt ttatatccat 142920
attggcccct gtcacatatt aaaatattat tttctcttat taatttctat gagaataata 142980
ctgccttcat acttttataa agggacctag gaaaccaata tttgtctaat gtttcaggct 143040
aaagagtaaa aaggaatagg tatactcttg aaaatagatg gctattgtca atattttttcc 143100 taccaagaaa ataattcctt ctctataaag aactgttact gtttagagca atattttcac 143160
gattcaaaaa gattatctga gcatgtgtcc aaccataact gacccctgca aaatatttct 143220
aaaagcactg tgcatctagg ctgggaagta tgcaaaatta gcaaaaatcc cctagcattt 143280
tcacaccaag ccatgtgtat ttaatataca ccacctcaaa gaggaacatt accaccctag 143340
cactatgagt gaggtgagac agagagattt ctaagaatat atgggtgtaa ttttctgtta 143400
actgagagtg attgacagtt cgtggaaatc tgccctccaa aataacctgt tttgcagcac 143460
ccttagtttt atttgatatg aagaaactgc ctgctgtttt gacccattta gctactagga 143520
actctattta ctaccctaac tgcctaaatc cctatggata aattaggcag tatctgttta 143580
ttttagttta gatttatttt taaaaccagt gttcctttga ctgttcttac tatttctatt 143640
tgagagttgg ttgaaataag atcatgtaaa taaaaataca atgtagtcta gatctaaagt 143700
cactgtacat acctagataa tttttttttt ttttgagaca ggatcttgct ctgtctccca 143760
ggctggagag cagtgttatg atcacagctt actgcaacct ctggctccca gattcaggtg 143820
attctcccac ctcagcctcc ctagtagttt ggactacagg tgtgtgccac cacacctggc 143880
taatttttgt attttttgtag agatggggtt ttgccatgtt gcccaggctg gtctcgaact 143940
cctaggctca agtgatctgc tcatcttggc ctcccaaatg agaaggatta caggtgtgaa 144000
ccactgtgct tggcacctag aggatttcaa taaaatttga ggtcctataa ttttaagatc 144060
```

```
acatttccaa aggaaggagt tttgcttctt ttcaaatgca tggacaatga gcaactatat  144120
tgttttggta aaactagtag tcccaaataa gaaagaggtc ctactagtcc ctagtagtct  144180
agtcccttga ctagaagaaa aagtcaagcc caatttattt tatctgcagg acttggttta  144240
agggggatta taaaactatc accacataaa gtctttgatg aagaggacat aggggggatgt 144300 agggagtact tcagagatgc atctggtcac tctcgaatac ataacacatt tacataaata  144360
tatatatcca agtaaacttc agacttcaca tatttgtttc cttttgtttc cttgttgaaa  144420
atctttatcc aagctgacaa tcacagtaca ctgctcatgt agattccact gctgagagct  144480
ggaagctgag agtagagtgg gctggggagc gactttcttg ggactattat gcttttcttg  144540
cactttacta ggttcctgtt cttccccacc cactacctct cctgggcact gattccaggc  144600
aagtgagatg catatctgtg gactatggtt aagtgaaagc ctttgttctg gaaagctcta  144660
tctggtttct cttaagccag acagaccagc ttgccatgaa ggctttcata ggctctggtc  144720
cacactttag acttccaact ggtctgctac tgacattcta ggctattgtt tctccaagta  144780
atgaatgagt ataccattgg tggtggaaga gagaatttta gatggtacat agacaaatgt  144840
ttttattgtg attgttatgt attttttaatt catatgagaa aaatgttttc cattcatggt 144900
agcaatatac agtttcttct ttaaatacat ttacttaaaa atgtgagttg atttaaagag  144960
aaatattaat aagacttctg gggaaactca ggcatgacaa aatacatgaa ggtgacatgt  145020
gagtagttga ggtttagaaa gcactgcaat gttatagact ctaggctagc tccctgccta  145080
tccccaggcc agttaactag ttgaattctc tcaagagtca ggatgtcttt gcctgttggc  145140 cttcaccttta agaaagtcag gcaatgatga ggaatcacac ctgaggagat tgtaggagac 145200
cttaacttaa aagagtggtg atgaatatga aagaaagagt catagtatat gatcaaagca  145260
gagaggactt tgagactcag cgattgggat gtaggaaggt ttcctgtaaa aataaagtct  145320
taactgggct tcaaaggatg aacaggaatt atcctgtgga gaaaagtagg agaagaatga  145380
catatgccaa gtttgtttct taaaaccaca acccccaaat tgtgagctct gggtcttaat  145440
ttggtgggga tgggaagcgc caatctatct gtgacttctt tcctgacatg ggctttcaag  145500
tgcatgtaac ttgacattta tgatttcctc tgcaaaagaa gaaaggaaca gggtgatggt  145560
gcctctgtga tcagttgcat ttatgggtgc aacagcaaag gaggtgggac acctaaggga  145620
caaccgttca cgtgaaatga agcagggatg agaagaaatg cccgtttgta tttaatacat  145680
cccagaaatg aaccccttta ttttctggga ctgttagagc agggaaacta tatatttcta  145740
agaatggggg ctctgctcaa atctttgtat tacagtacaa agaagggtga ggacaggaag  145800
cagtggtgat cttgctcttt ttggaagagt ttgtgtctgt ccttttaaag tcaggtatga  145860
ttgataggaa agtcaagtac tggcatcctc agattggaga ggttttattt tattttattt  145920
tttttaatgg agtcttgctc ttgtcatcca ggctggagtg caatgccacg atttcagctc  145980
actccaacct ctgcctcttg ggttcaagca attctcctgt ctcaacctcc caagtagttg  146040
gattacaggc acctgccacc atgcctatct taattttttgt attttttagta gagacagggt  146100 ttcaccatgt tggcccggct ggtcttgaac tcctgacctc aggtgatcca cccgcctggg  146160
cctcccaaag tgtgggatta caggtgtgag ccaccacacc tggcctgagt ttaacataaa  146220
caaagaaata aaataatat aatctctcaa aatagcaaag aacagggttg tctaatcaaa  146280
atatataact atttattttt aatagccaca ttacaaaagt aaaagaaaac aggtaaaatt  146340
aatttaattt aattttaaaa atatattta aggtatacaa cacggtgcta tgggtaaaat  146400
```

```
ggttattaca atgaaacaaa ttaacatctc catcatctca catagttacc tgcttccctt   146460
cccactccaa acccctcatt gcaagagcag ctatagttta ctcatttagc aaaaatcctg   146520
aacgcaatac accattttta ttatttttta aatttatttt tttgagacaa ggtctcactc   146580
tgtcacccag gctggagtgc agtggcgcaa tcttggctca ctgcaacctc cacctcccag   146640
gctcaagcaa tcctctcacc tgagccttgc gagtagctgg gactacaggc acgggccacc   146700
acatttggct aattttgta gagacagggt ttcaccatgt tgctcaggct ggtctcgaac   146760
tccttgggct taagtgatct gcccacctca gcctcccaaa gtgctgggat tacaggcatg   146820
agccatcatg cctggcctac aatgcactaa tattaactat agttggcagg ttgggcatta   146880
gatcttcaga cttgttcatc ctacatattt gctactttgt atcctttgag gtacatctac   146940
ccatttcctc cacccaccct acctctggta atcactattt tattctctat ttctgtatat   147000
ttgactttta aaaaattct acatatatgt aaaataatgc aatagttttc tttttgtatc   147060
tggcatattt tacttaatat aatttaaata atatacttca tttaactcaa tatatttaaa   147120
gtattttaac atacaatgaa tgtaaaaata ttgaaatgtt ttgcactttt ttcatgtaaa   147180
tatttaaaat ttggggtata tgttatagta catgccattt aggacattaa attgccaatg   147240
gaaataatat tcagattta taacatttgc agttgaaaaa gtagatacat gtatccaagt   147300
tgctctcaac atacttaaag ttttccaata actgaattaa atatcagttt atcagtttaa   147360
tataaacaat tagggtaaat gaaaataaaa tttcagctct ttggttccat tagccatggt   147420
tcaggagcag aatagtcacc tgaggctagt gacaacgctt ttggatcaca ggaaagaaga   147480
aaaaaaatca aaataatttt tcttggtcac atttagctcc ttttcttcca ggatgattac   147540
ggagctagga atttcctacg aagctgggtg ataaaggac attggacaaa acacagata   147600 gcttcattct ataccaggat ccatcactga ttagctgtat tatatttgtc tctactgtaa   147660
tttgaggaga atgatacctg cttctctatc ttgttgggtt ttacagatga tgtattgaaa   147720
gttcaataaa atctataaac aatagatctc tgtggcttga atggtcctca gatatcttga   147780
ccaatgattc tcaaatgctt accatagacc ataattttc cccacatgac actgcttcat   147840 attttaagt ttttttcac caaatatttt gttttactat ctccaagccc tgaaacttt   147900 tttctccctc aaacatgact tcaactttac tatcctggtc cctttctatt gaatgtgttt   147960
tgtttgtgtc tatatttctt atagtgtctt gaactgattg tacttacgat atgacttgac   148020
tagcataaga tagaataggg cagtcatctt ctttgatcta gactagatgc tatccttcta   148080
ttaatgcagt tgctagtttt gtatttgctt gctttcaatt ttttttttc agattttggt   148140 aaccactgtt acttgactcg tatcaaactt atcagtagct aaaaccccca ttttccctct   148200
tcctgtgctt atttgactag ttttgttgcg cttttctgaaa tgtttctcac ttgttttttga   148260 ccaaaaaaat aaaaataaca aatgccattg attctgtgtc tatactattt gaggcagtta   148320
ggcctttact tacttcttcc aacattttaa gcagtgttgc attcaatttg aacaagagga   148380
ataaaaaggc ttgagaaatc ttagggaagt gtgtctcaag ctttagcaaa caaacaacag   148440
atctgcagga gatcttgtta aaatgctaaa ttctgattca gcaggtctgg agtagggtcc   148500
aagattttac atttctagta agtttctatg gattatgttt tgagcaacaa attcttagag   148560
tgtctgaaag gttttaaaa taactgattt cccttcaaaa tcttcttcat taggagtaaa   148620
atatacatct tctcactctg taaatcagct ctgagatctt ctataatctt agctgaggtt   148680
tgggtatgca gagttttgaa actcttattt gcttaagaga ggagccatgt atgatcttct   148740
tttgggtttc cccattgtct ggtaaaatga ggagcattac taaacggcac tcactttac   148800
```

```
tgagtttgtt tggatcccac agagaactga aaaagtcacc attatggaag ccttatcaga 148860
gagatgggga caagtcgccc caaagcagtt gtcaatatct ggaagatatt tttctagttg 148920
gccttatatt tcatttctat tttcctcagt tctaattcag tttatcacaa ttaaaaagaa 148980
accaatgaaa aacataaata ttggagatca tttgatttca ttggaggctg gaaggatag 149040
aaaggctgaa aagtggccgg gtgcagtggc tcacgcctgt aatcccagca ctttgggaag 149100
ccgaggcggg aggatcacct gaggtcagga gttcgagacc agcctggcca acatggtgaa 149160
aacccatctc tactaaaaat aaatacaaaa attagttggg cgtggtggca cgtgcctgta 149220
gttccggcta ctcgggaggc tgaggcagga gacttgcttg aatgcaggaa gtggaggtta 149280
cagtaagccg agactgtgcc tctgtactcc agcttgggtg acagagcaag acagagtgtg 149340
acagagcaaa acaccatcta aaaaaaaaa aaaagggaa agaaaaaaaa gaaaagctga 149400
agggtgtgct gggtcctgtc ctgggtgagg gaacaacttg tggaaaagtg aattgaggct 149460
tatcggaatg tttggggctc ctcaataatg ttggcactct gagatacaga ccaaaagtga 149520
ggtaaaaagc gagtgtttcc ttttttttcag ataggactt tactccagat tttcttactc 149580
ttctcttgat tccttcacca tccttgatcg acattcacct cagatgccca tgtcccttct 149640
ccaccggcat agcttgtttt cttcttaatc ttcttgtgtt catctagcct cacattgcat 149700
ttgtcacact tcgttgaaaa cctactgttt gtcaaagtgt cttttctagta atccagatat 149760
ctcttccccc atgcctttgg tgtggtttcg gtagagtcat acagagcagc aatgccttat 149820
gaaaacgaat tttacagaat ctgcctgttc atcaaaggag gccagacagg aggtgagaaa 149880
aaccaggtgt gtcccacacc agtctcaatg aagccttttg gggtgtcttg tgctcttgac 149940
taaatctcag atggtactga atgaataatc accaaaggcg tgagctgtta aggaatccca 150000
gtttggctgg ctctgtgcag tcagatgtag ccagccctgt ttatgtgtga aaggattggg 150060
tttttcccca gctgtttggt aatgttgcaa gaacagactt tcccctccct ggctccctgg 150120
agtaaaatgg ctgccaaagt attttggaac agaaacttag aaatgtaccg accactagaa 150180
gagagtaaca agggtccttt gatattttcc gtgttcacta tgatcaagct ggcatcgttt 150240
ccttctgagc taaagattct gagctatcat tggctgatgt gagcttgtga cctagctact 150300
tctgttcaca atacactgtg gagggcagc gggggcagcc ctatttgggt tgagagtctt 150360
taaggagagc tttacagatg agttctagtg aagcccatca gggagaagaa aatcaaacac 150420
aatgggaaat gtttaacaat taaaaccagg cttttgcctgt gtggtcctgt gttttaccac 150480
atcactctat ggaaatgggc tgttggaagg aagactgtat ttctgacagt ttgcagagcc 150540
aaaaacctgt tgaaggcttt ttgtaaggta gtggagaaaa tggcaaaacc tttaaaactt 150600
aagggaaatt acttgatagt tctgatgacc acaggccacc agactgctgg gtcatggaat 150660
tatagctaca tgacaaagaa aataggaggg tgggctgagc cagactcaga aactattcca 150720
aaagtactat gacttttag gaagctagtt ctttttattt gaatatttt gtgtttttt 150780
gcatgagaat tagcctatgc ttcttaaaaa tatcataaaa tgtcagctag tagaaaaata 150840
aagagtttaa tctccactcc gactacctag agtcaaccct tgttcatact gcagtacatt 150900
tttttctttt agttctgttc tatgctttaa ataaaaatac aattaggtcc atatggcaat 150960
ataattttga ctccttttaa aactgtagct tatatcataa gtctatttga tgttgttttg 151020
aagttgtcat gtacattttg tcatacaagt ttttaatgac tgtttttatg gggttgtgcc 151080
ccaagttact tattcattcc catgttatca gatattttgt tctttagctt tttttttttt 151140
```

-continued

```
tttttttaca ttataactaa tgaggcaatg tgtcttgagt attttgaatt aactctctag 151200
aatcgattct tggggaggtt atttactttg aagtgatgga cagagtgtag gagatttatg 151260
agtgaactct tgtctgattt ggaaatatag agttgtttag gctaggtatt accaacccaa 151320
agttgacact tgagtcacct aagttcttct ctactccaga gacttggccc tgcctggcct 151380
gatcccagga aaagagattt tagggattac agaaatggga acaagttgtg ggtctgagca 151440
cagcatgcaa attaattcaa cacagcccct gggacaggcc catgatcagt gagctgaaac 151500
tcccccttca agtgctttca tgattagact ccagcctagg aagcttgtct attagttgtg 151560
taatcttgaa aaaatctctg acacttttcc ctctgactca gtttcccat ctggcaccca 151620
atcttttaca gtgttatgaa aaatagggaa aatgtagaaa ggaagaacat ggcacccaat 151680
ccttaatgga cactcagtga aagctggcta tcatcatcat ttttggggtt gttgtgttct 151740
acaaatgtat tttcccagga gttttttta ctctgtctcc tctttccttc atataccccc 151800
agcctgtggc tggggtcttg cttcaaccac catgcacctt tctgaaaccc aagttttact 151860
ccctgataaa ggtattgacc tcttgttggt ctcatcctcc agacctacct atacttaaga 151920
aaatgacatc tctttaaact ggtccccagt tcacttgttt tccctaacat tttaattcac 151980
aagattaatc acttcccta caggccagtc ttactgcaga gttgatttt ataatttggg 152040
gcctgttggt ctggttgtac ttttctcttt ctgctggtct gctagttata gcgggtcttg 152100
aaagcagtga tatgttatga cattgtcatc accctcatta ttgctcttta tataacagta 152160
gcagcataac tgtgttttga tttcttgtac aaggcataaa gtgtgctagt ggctcactat 152220
tcacatcaat ctcatcagaa aatgttattt cctccttttg ttgatcatga tatagaggcc 152280
cagtgacatt aggtaacttg ctcaagatca cacatgtgga aagctacaga gccagacttg 152340
gaactgagtc cattatatct taatcccact gcactccaaa atttgttgaa tgaaggaata 152400
gataaacgta tcatgatttt gatgttctga ctaattcgta gccagtactt tattgctatc 152460
ggagcttaag ctttaagtac tggctaggaa atagtcagaa cttatttttt aaggaggagc 152520
atataattat gtatatttta tacctgtagt aaattgggaa ctatagaaaa catgtagagg 152580
attgtgttta ccaacttcat gtagagtgag gataccgac tctagcttgc tggtagttag 152640
gtaagtcaga catgggcagg ggataaacca aattagacta tttccatttg actaagccat 152700
ataatcaggt gtaagccacg gaaagaaatc tggaaagaca ggtgcaatat tagaagatgg 152760
ctcatgatag tgatcattag aggttcaggc ttgagaaagc caattggaat caagaaggcc 152820
taatcctggg gttctgtcac agaaaagaag gctggtagca ggaagaggac atgtaacatg 152880
aattacatga ttagatttgt gtcataataa caaaaacaat aatgataata acactaatag 152940
cttgttatat gccatgccct gtactaagaa ctatacgtat gttatcccat ctaaatcaca 153000
tttaatagat tcccattttt ctcatgagaa aattgcatca tacagagatg aactaacttg 153060
ctcaaggcta tagacctggt aattagcaaa gcagggattt gaatttagat gtatttttct 153120
ctgaaggctg ggtttagata aatggatctg gaagcactgg gaaggatgaa ttaatgggat 153180
ggagtgcagg ggatgcagag tgcccactta tggaatgatt tcattcaaga gagacaggag 153240
ggtcagaggt aagaatgcta ccgctgggac agagaggaag gtacagatat gagatatggt 153300
aagaaggtat actacaacag tggctcccaa atctcaatga gtagccagtt ctcatggagg 153360
ttttgttttt attttgaat gaagattccc atggcatacc ttgaatattc tgaatcagaa 153420
tctctggaat acaacttggt attccttataa agcaccctag gtgatgctga agctctgcca 153480
ggttcaagaa ccacagctcg atcagcctat atttagatgt ttggggtgga gaatgagaga 153540
```

```
aagaaaagat tttagggtgg catccaggtt tctgaatttt gtgactcagt gaagtttttg   153600
gagggtaggt aagatgctga gttcagtttt ggatgtgttg agatggactg gtcctgtgga   153660
tttagttgga tattagagtc taacgcttag aacagaggtc aaggctgtag atttagatat   153720
ggaggacact ggtgtttggg tggtgatggc gctatatatt acatggaatt ttcaaaatac   153780
tcaaaacttc agttttccct caataattaa tcactttaca tctttgtgat cttaaatctc   153840
tttctgacca ttgattgaaa cttttgcttt taaaatttac attacctttc ttaacagttc   153900
cttaagattc atgcattgtt gtaagtagtt acttgcacca tttcattgga ttcacaccaa   153960
caattgttaa agtaaaattt attttcctg tgttttagat gaagagattt aggcaggtta    154020
tgtaacacac ccaaggtaat atagtcaaat aattgagcca gaatttgagc ccaagtctct   154080
ttctgactct aggcttagag ctttagggct atttcacaaa agggctgttc ctaggtcagg   154140
catgacaact tctatattac cttcgtaaaa gaagcaatat aatctaccac tattaaattt   154200
tgcaggttaa ttttatatta tgtttaaata cagaaaactt tatttaaaac tcagttgaat   154260
ttctcttgag aaattggcca tgtagtaaat tatatttaat agaagagttt gtgtacttcc   154320
cagggagcag agtattggcc tgatcaaagc acctttcagc ctttgtctaa cagcatgtgg   154380
gtaggctaca ttttttttac tctcagagaa aggggggtggg caggggtgtg atatgggttt   154440
ttgtctctgg gagttctgtt gcatgatttg acctcccaaa ttgttttgtg gggcatatcc   154500
aactttgggt tgaaactaaa atgggttctt ggtaatccca gattgaaaat atgtctcagc   154560
agtaacattg tttatctttta ggtttaggta aatacagaca tttgccatgt cttcttggta   154620
gcactgtaag aatgagtagg gctgtgaaaa atgcacaggg cattcattat gaagactggc   154680
tggttaaaac tgatacacta aagaaattgc attcttttcc acaagctgag tcatacagct   154740
gaaattgtgg aatcatctga gccagcagct gtaatatgat acttaatctc cataagtgac   154800
agatatctaa gataacacga acacccagac gacaactcag gcaacccag cacagtgttt     154860 tggtatgaga acaggagaaa tgttagtaga gtgaacattt ttccacagag aactcaaata   154920
tggtaacatt tcatagcttt tgataatccc caataaactg tggttactaa aatgcatgac   154980
aaaaagaact tctatctata aagaacttct ttatacattt ccaatacttg ggttatgatc   155040
aaggagaaaa aagtttatca gttaattaag agttaggtag ctagtttgcc cacagattaa   155100
tttgtatgag gtaaaggaaa tctccacctaa ctgggaaaaa gcaagcttac cctcaaggta   155160
tgcttatccc aaccccaccc tgccaagtgc attccttatt cctcaggtgt gcctgtttat    155220
cccaaggacc tagccacacc tacatcttgt tctggcccca caccaaggaa catataaaag    155280
ttccctctct ggccgggcgc ggtggctcac gcctgtaatt cccagcactt gggaggctg    155340 aggcgggcgg atcacgaggt caggagatca agaccaccct ggctaacacg gtgaaacccc   155400
gtctctacta aaaatacaa aaaattagcc aggtgtggtg gcgggcccct gtagtcccag    155460
gtactcggga agctgaggca ggagaatggc gtgaacctg gaggaggagc ttgcagtgag    155520
ccgagatcgt gccactgcac tccagcgagg gcaacagagc gagactccgt ctcaaaaaa    155580 aaaaaaaaaa aaagtccctc tctttatatc tcagggtatc ttggagtcac tactgatcct   155640 tgacctcccct cctttctctg accatgtcta gacaagtgtc caggtctcct gtgccaaatg   155700
tctatttgtt gcctggatta ggttttgact tgtttttcta tttctttgca tctcgtagcc   155760
catttctttg attcaatttc acaatctctt gattttgtcc ttaagtattt ggcaacacaa   155820
accctcgaga ggcaggatag ttcaacagaa agaagatgaa ccttgggggt cagagattc    155880
```

```
aaacttccag aatttaaatc ttcattctgc tattactaga tttataaact ttatcaaatc   155940
actctcctac tctatcccct aattcaacat atttaaaatt ggaataaaaa tctcaatgtg   156000
gtagagttat tattgagatg aaaatcagaa tagatacaaa gaacttgata gccccaagga   156060
gcttgatcag tgtttgttta atggcccttc ctctcttctc atatctcagt tcagatccta   156120
ctcagccatt tatttattc tgctccttt ggagtagaga ataaagccaa gaattatgct   156180
taaaaagtag cataattaaa agtatttaaa acacaagtaa cttgagaaag gtgagttgga   156240
agtttatatc taacctcagt ttttttggga gagaaattta cccgtcaggg ccagattaaa   156300
acatttacaa gtcccaagca cacgtgagat gaagatgccc ctcacttatc tcacatgtaa   156360
gttgaaagtt aaaaagtgaa aatgtctact agagttcaat aatattcttt ttttcccatg   156420
acttctctga agcttttaga aaatatgaaa ttcttaaaaa caataacagt aacccacatt   156480
tttattgccc tggtttgccc tatcttatct ttctcctgct cacagggtct gaggcagctg   156540
ggatagggga gaatgattac cagccaatca atattttttg aaccccagag attatttatt   156600
tatctatcca tttatttatt ttgagatctt atttatctg gaatcttaat aaacgattag   156660
tttccaaact gtatctactg tgtgtatttt atccatatgg cccagatttg tattacttat   156720
ttgtgattct gaataatatt ttttccaaca ttaattatca gcctctctgt gcccctccag   156780
aattgttaca acctatgtta atgcacacta tggcaagcca tgtgaattgc ctacgcaggg   156840
aagttttctt catacttcct tgccaagaga accccattat tggtcagtta ctagtcacat   156900
gatcttcttt agcccctcct tagcccctgt agtgaatcag gagtagccta aggccatggt   156960
ggtaactccc cttttcttg gaaatgtttg atttagatat ggagaagagg tgcaactttg   157020
cttatgaaat gggagggcaa atatgggaaa cttaaggta agttttcttt cccttgaag   157080 gggaccaaaa agttgtggtt tatactttct tgactctggt cactgttggg tgaagagttg   157140
gtgctatgga agccatcttc agaccatgag gggacaagtc tgaggataca attacatgct   157200
accggtggca gaggacagta tagcaagaaa ctggatccct gatgcattg aaccattgac   157260 tgaatctacc ctggaaccat caggaaataa tccttagttt tttaaagatg cttttagttg   157320
tgttttttat tacaagtacc tgaaagcatc ctaactaatc aatgctaaat gcatctctca   157380
cagtttatgc ttatttttca gaaatgccta gtggaaattt ctattgctga ttataatatt   157440
tgtcctaaat aaattgaata gactgtcaat cttttgaaaa taaaagcatg acttgattag   157500
caattgttta gtctgatgtt ttcctaattt ctgtcatttg cataccactt ctttgatttt   157560
gtcatatcct tgtatcatct gcactaatag aaatatttt ccttaagttg tctctccttt   157620
aaaaaattat atccatttat tttgaagaga aacttttca ctaactataa attgaaaacc   157680
gatatcattt gccttaaata gaagattgtc ataaaaagaa atgccatgag tgaaataatg   157740
ttattaaata tttgccagat atagtttcct atgaagactc tgagcttgtg gcttgctgtc   157800
tctgttgaaa ggagagacta gggagtgtta tagaagtggt aaaataatcc ttccactgac   157860
tgagactatt tccttgccac aatcagaaga actaaaagaa aggaggatat ctgttaatat   157920
atgaatttat ctaaatgtca tgcagtgact tctaaaatca tctggtgtgc tctgtttccc   157980
cttggaggtg acttaggcct ggcatcccaa acaatacata ctggagtgaa gctccaggaa   158040
accctgagga gaagagaagg gcttaaagag caatcagcct tcgattgctg ggattatgaa   158100
aggtcgtaag aagcgaatgt tgcaatgttt tattatactt gatattgaag caaggacaag   158160
taataattta ttattctctc catgtcagtg gtatttacct ttttggaatc atgtgcccca   158220
ttgagaattt ctggaaaacc atggttcttc tactcaggag aatgcacaat tgcacacata   158280
```

```
cacaaatgtg caagcacaca cacacacaca cacacacaca gaattgccac agaaggtcag    158340
taggttcaca ggccctaggc taagaaccag cattctgtat attttacatg tgttctctta    158400
caagttaccg tgtgattcag ttcactccaa actgcggtta agtgcaaaac atggttttga    158460
atatttctat caattagtaa gagtggtatg ttaatttaaa tacaccaaag tggagaatta    158520
ctgtcctctc aatagctact ttaaatagac ataagttaca gtgatattgc cttccaggag    158580
gcttcaagaa atgagatcag gctctataaa agaaaatcac ccaaccctat aaagtcatct    158640
ttatgaactt tgaaacacca ctgtatgtac ctagtaaaaa ttattcctgg gtaagcagac    158700
tcccaggcct gggtggagtt cacatgagtc cctttgctaa aataaacaga agtgactggg    158760
aactttggat tgcctttgtc tgaacttgag tgtctggatg gatcagcatc agcagcatac    158820
cacacacctg cttgtccagc caagagaaa cccaaagact tggcatttgt tttttacatt    158880
gtcaactgtg caaaaatatc acgattctaa tttatgaggg tccatgagtt ttaaaaacac    158940
cccctgacat ttttctagcc aaataatttt tcctttaaaa ggcacaggat gagcaacaag    159000
attaggtaga tcacttcaat ctctaatttc aaaagataat agttaaaaat tcaactgtag    159060
gactaacaca ttaactatgt aataagaccc agaatagtct ttggagcaaa tttcagtgga    159120
tacttgatca aaataatgtt gaagacaaaa tcttgaattg atgatattta tctgatacaa    159180
ttatttacat aacaaatgtt aaaagaatta gaaaatttc ataggtaaga tgttcattat    159240
cttcaagtga agttacttgc tttatattaa gaaccacaaa aacttactaa acttttttt    159300 ttaaaagggt ctcactctgt cacccaggct ggaccggagt ggctcaatca cagctcactg    159360
cagccttgat ctacccagat tcaagtgatc ttcccacctc tgcctcccaa gtaactggga    159420
ctataggcac atgccaccat gcctggctaa tatctctctt ttcttttttt ttcccccttat    159480 tttgtaggga caagttttct ccatgttgct gaggctggtc ttgaactcct gggctcaagt    159540
gatcctccta cctcagcctc ccaaagtgct ggagttatag gcatgagcta ctttgccccc    159600
tagcagacgt cttactttttt tttttaattt ggtattagat tgagccaatg actaatttca    159660
aacatttata aattactaaa ttcttttttt taattatact ttacgtttta gggtacatgt    159720
gcacaacgtg caggtttgtt acctatgtat acatgtgcca tgttggtgtg ctgcacccag    159780
taactcgtca tttaatatta ggtatatctc ctaatgctat ccctcccccc tcccccacc    159840 ccacaacagg ccccggtgtg tgatgttccc cttcctgtgt ccatttgttc tcattgttca    159900
attcccacct atgagtgaga acatgcagtg tttggttttt tgtccttgtg ataatttgct    159960
gagaatgatg gtttccagct tcatccatgt ccccacaaag gacatgaact catccttttt    160020
tatggctgca tagtattcca tggtgtatat gtgccacatt ttcttaatcc actctatcat    160080
tgttggacat ttgggttggt tccaagtctt tgctattgtc aatagtgcca caataaacat    160140
acgtgtgcat gtgtctttat agcagcatga tttataatcc tttgggtata gacccagtaa    160200
tgggatggct gggtcaaatg gtatttctag ttctagatcc ctgaggaatc gacacactga    160260
cttccacaac ggttgaacta gtttacagtc ccaccagcag tgtaaaagtg ttcctatttc    160320
tccacatcct ctccagcacc tgttgttct tgacttttta atgatcgcca ttctgactgg    160380
tgtcagatgg tatctcattg tggttttgat ttgcatttct ctgatgccca gtgatgatga    160440 gcaattttc atgtgtcttt tggctgcata aatgtcttct tttgagaagt gtctgttcat    160500
atccttcacc cactttttga tggggctgtt ttttttcctt gtaaatttgt ttgagttcat    160560
tgtagattct ggatattagc cctttgttgg atgagtagat tgcaaatatt ttctcccatt    160620
```

```
ctgtaggttg gctgttcact ctgatggtag tttcttttgc tgtgcagaag ttctttagtt 160680
taattagatc ccatttgtca attttggctt ttgttgccat tgcttttggt gtttagaca  160740
tgaagtcctt gcccatgcct atgtcctgaa tggtattgcc taggttttct tctagggttt 160800
ttatggtttt aggtctaaca tttaagtctt aatccatct  tgaactaatt tttgtataag 160860
gtataaggaa aggatccagt ttcagctttc tacatatggc tagccagttt tcccagcacc 160920
atctattaaa tagggaatcc tttccccatt gcttgttttt atcaggtttg tcaaagatca 160980
gattgttgta gatatgtggc attatttctg agcgctttgt tctgttccat tggtctatat 161040
ctctgttttg gtaccagtac catgctgttt tggttactgt agtcttgtag tatagtttga 161100
agtcaggtag cgtgatgcct ccagctttgt tcttttggct taggattgac ttggcaatgc 161160
aggctctttt ttggttccat atgaacttta aagtagtttt ttccagttct gtgaagaaag 161220
tcattggtag cttgatgggg attgcattga atctataaat tactttgggc agtatggcca 161280
ttttcatgtt attgattctt cctacccatg agcatggaat gttcttccat tgtttgtat  161340
cctctttat  ttcattgagc agtggtttgt agttctcctt gaagaggtcc ttcacatccc 161400
ttgcaagttg gattcctagg tattttattc tctttgaagg aattgtgaat gggagttcac 161460
tcatgatttg gctctctgtc tgttattggt gtataagaat gcttgtgatt ttcgcacatt 161520
gatttttat  cctgagactt tgctgaagtt gcttatcagc ttgaggagat tttggctgag 161580
acgatggggt tttctagata tacaatcatg tcatctgcaa acaggacaa  tttgacttcc 161640
tcttttccta attgaatact atttatttcc ttctcctgcc tgattgccgt ggccagaact 161700
tccaacacta tgttgaatag gagtggtgag agagggcatc cctgtcttgt gccagttttc 161760
aaagggaatg cttccaggtt ttgcccattc agtatgatat tggctgtggt tttgttatag 161820
atagctctta ttattttgag atacatccca tcaatacctcaatttattgag agtttttagc 161880
atgaaggttg ttgaatttg  tcaaaggcct tttctgcatc cgttgagatt atcatatggt 161940
ttttgtcgtt ggtctgtttt atatgctgga ttatgtttat tgatttgcgt atgttgaaca 162000
agccttgcat cccagggatg aagcccactt gatcatggtg gataagcctt ttggtgtgct 162060
actggattca gtttgccagt attttattga agattttttgc atcgatgttc gtcagggata 162120
ttggtctaaa attctctttt ttttgttgtg tctctgccag gctttggtat caggatgatt 162180
ctggcctcat aaaatgagtt ggggagaatt ccctcttttt ctattgaatg gaatagtttc 162240
agaaggaatg gtaccagctc ctctttgtac ctctggtaga attcggctgt gaatccatct 162300
ggtcctggac ttttttttggt tggtaagcta ttaattattg cctcaatttt agagcctgtt 162360
attgctttat tcagagattc aacttcttca tggtttagtc ttgagaggat gtatgtgtcg 162420
aggaatttat ccatttcttc tagattttct agtttatttg catagaggtg tttatagtat 162480
tctctgatgg tagtttgtat ttctgtggga ttggtggtga tatccccttt taattttta  162540
ttgtgtctat ttgattcttc tctcttttct tctttattaa tcttgctagt ggtctatcaa 162600
ttttgttgat cttttcaaaa aaccagctcc tggattcatt gatttttttg gagggttttt 162660
tgtgtctcta tttccttcag ttctgctctg atcttagttg tttcttgcct tctgctagct 162720
tttgaatctg tttgctcttg cttctatagt tcttttaatt gtgatgttag ggtgtcaatt 162780
ttagatcttt gctcctttct cttgtgggca tttagtgcta taaatttccc tctacacact 162840
gctttgaatg tgtcccagag attctggtat gttgtgtctt tgttgtcttt ggtttcaaag 162900
aacatctttt tttctgcctt catttgttta tgtacccagt agtcattcag gagtgggtag 162960
ttcagttttcc atgtaggtga gcggttttga gtgagtttct taatcttgag ttctagtttg 163020
```

```
cactgtggtc tgagagacag tttgttataa tttctgttct tttacatttg ctgaggagtg   163080
ctttacttcc aactatgtgg tcaattttgg aataagtgca gtgtggttct gagaagaatg   163140
tatattctgt tgatttgggg tggagagttc tgtagatgtc tattaggtcc gcttggtgca   163200
gagctgactt caattcctgg atatccttgt taactttctg tctcgttgat ctgtctaatg   163260
ttgacagtgg ggtgttaaag tgtcctatta ttattgtgtg ggagtctaag tctccttgta   163320
ggtttctaag gacttgcttt atgaatcttg gtgctcctgt attgggtgca tacagattta   163380
ggatagttag ctcttcttgt tgaattgatc ccttaccatt atgtaatggc cttctttgtc   163440
tcttttgatt ttgttggttt aaagtctgtt ttatcagaga ctaggattgc aaccccctgcc  163500
tttttttgtt ttccatttgc ttggtagatc ttcctccatc cctttatttt gagcctatgt   163560
gtgtttctgc acatgagatg ggattcctga atacagcaca ctgatgggtc ttgactcttt   163620
atccaatttg ccagtctgtg tcttttaatt ggagcattta gcccatttac atttaaggtt   163680
aatatgttat gtgtgaattt gatcctgtca ttatgatgtt agctggttat tttgctcatt   163740
agttgatgaa gtttcttcct agccttgatg gtctttacaa tttggcatgt ttttgcagtg   163800
gctggtagtg gttgttcctt tccatgttta gtgcttctt caggaactct tttagggcag    163860
gcctggtggt gacaaaatct cttagcattt gcttttctgt aaagtatttt atttctcctt   163920
cacttatgaa gcttagtttg gctggatatg aaattctggg ttgaaaattc ttttctttaa   163980
gaatgttgaa tattggcccc cactctcttc tggcttgtag agtttctacc gagagatcag   164040
ctgttagtct gatgggcttc cctttgtggg taacccgacc tttctctctg gctgcccta    164100
acatttttc cttcatttca actttggcaa atccgacaat tatgtgtctt ggagttgctc    164160
ttcttgagga gtatctttgt ggcattctct gtatttcctg aatttgaatg ttggcctgcc   164220
ttgctagatt ggggaagttc tcctggataa tatcctgcag agtgttttcc aacttggttc    164280
cattctgccc gtcactttca ggtactccaa tcagaagtag atttggtctt ttcacatagt   164340
cccatatttc ttggaggctt tgtttgtttc tttttattct ttttcctcta aacttcttgc   164400
ttcttttcat tcatttgatc ttccatcact gataccctt cttccagttg atcgaatcgg    164460
ctactgaggc ttgtgcattc gtcatgtagt tctcgtgcct tggttttcag ctccgtcagg   164520
tcctttaaag acttctctgc gttggttatt ctagttagcc atttgtctaa tttttttca    164580
aggtttttaa cttctttgcc atgggttcga acttcctcct ttagcttgga gtagtttgat   164640
catctgaaga cttcttctct caactcgtca aagtcattct ccatccagct ttgttccatt   164700
gctggtgagg agctgcattc ctttggagga ggagaggcac tctgattttt agagtttcca   164760
gttttttctgc tctgtttttt cccatctttg tggttttatc tacctttggt gtttgatgat   164820
ggtgacgtac agatggggtt ttggtgtgga tgtccttct gtttgttagt tttccttcta    164880
acagtcagga ccctcagctg caggtctgtt ggagtttgct ggaggtccac tccagacgct   164940
gtttgcctgg gtatcagcag cggaggctgc agaacggcga atgttgctga acagcaaatg   165000
ttcctgcctg attgttcctc tggaagcttc gtctcagagg ggtacccagc cgtgtgaggt   165060
gtcagtctgc ccctactggg gggtgcctca cagttaggct actcgggggt cagggaccca   165120
cctgaggagg cagtctgtcc attctcagat ctcaaactgg tttcaaagaa catctttatt   165180
tctgccttca ttttgttatg tacccagtag tcattcagga gtgggtagtt cagtttccat   165240
gtaggtgagc ggttttgagt gagtttctta atccttgagtt ctagtttgca ctgtggtctg   165300
agagacagtt tgttataatt tctgttcttt tacatttgct gaggagtgct ttacttccaa    165360
```

```
ctatgtggtc aattttggaa taagtgcagt gtggttctga gaagaatgta tattctgttg 165420
ttttggggtg gagagttctg tagatgtcta ttaggtccgc ttggtgcaga gctgacttca 165480
attcctggat atccttgtta actttctgtc tcgttgatct gtctaatgtt gacagtgggg 165540
tgttaaagtg tcctattatt attgtgtggg agtctaagtc tccttgtagg tttctaagga 165600
cttgctttat gaatcttggt gctcctgtat tgggtgcata cagatttagg atagttagct 165660
cttcttgttg aattgatccc ttaccattat gtaatggcct tctttgtctc ttttgatttt 165720
gttggtttaa agtctgtttt atcagagact aggattgcaa cccctgcctt tttttgtttt 165780
ccatttgctt ggtagatctt cctccatccc tttattttga gcctatgtgt gtttctgcac 165840
atggtgatgg gaggtactgg tattacaaaa agcttctccc ccgtgggtca aatctaagct 165900
gagtgttgag acataattga aattcactag atagatagga gatagggta gggaattcta 165960
atcagaggga atagcacatg taaggcaaac aatacagtgc atctgggaaa gctatacaat 166020
tttattgtta taggacaaat gttggggaat gttgagagat ggaactggag agtgaggcag 166080
aagttagcat ttattcattt attcagcaga cctttatcta ttacctacat tgcactaagt 166140
actgtgtgag cattagagag aaaaagatga atgagattgg acaccattcg ttcattcctg 166200
actatgaact tggcattgtt ctaggtacca gagatataat aatgagaaac agacatgctc 166260
cctcccctca ttgaggttac agcttagtgt ggagacacac agatgcctaa cgcactatgg 166320
tatgaaggt gctatggaca cagtgctcaa atccatgatc tacataggta tgagagtgac 166380
ttttctacaa cttaaatctg atcttgttat tccctgctta aaatcctgca gtagctccca 166440
gtagtgcctt ctggttaaaa tacaagatat atagtatgac ctctcaagga cctttgttat 166500
ttgtctctgg ccacctctcc aattttcac catgaccctg gcctgtccc actggcattc 166560
catctccaat cacacggaac tatgtggagt tattaaaatg ccctatgtta tttcaagact 166620
cagagattta gtgcctcagc ctgttttgtt ccctctcccc tcctccacct ggccttctcc 166680
agctcactca tcaatctatt agactcaggc atcatctgct tgccttcgta accctcccca 166740
ccccgctcac cttgctggat tctgtgcctt tgcttgctgg ttcccagaga tccctgccct 166800
tatttttctt tgcctgctgg atttgcagtg ttgtgtccta tatggtgtag aaaaccagct 166860
caggctccca cttctctggg cttatgtggt cagatgcaga cctgtcttcc atccatacca 166920
aaggccatca gggagtttct tttgtcctct tcaccagccc attcttaatc tttctgataa 166980
attttctgca ctgtgtgcgc gtgacaaatt gggtcaaggt gatggtaatt tacagcatga 167040
gatggtgaac ttgctgcctg tgctgatgag cccattggat ttcccctaac tagtctgttt 167100
ccctacccag gtggagaact tcagtagagg aagtggcagg aatttgggaa tgaggagcac 167160
agtgattaaa ctggggccat tcatatgaga gtttaagaac tcagaccagt gacttaggtg 167220
agtaaaaata tcagaaaaag ggaagagga taagagcaac ttgggccata attaaacttg 167280
tcaatgaaat gaaggtctgt tattctaatg cctacatttt gccaaacctt tgtgcttata 167340
acttcatcat ttgctgtgat taacaaagtt gaaagaataa taactactta caaggcccac 167400
atcacctcct tataccacta gcttttgctt tccgtacaga catagcttta aaaagtgcaa 167460
atcctattct gtacctgagc cacaacccta aagggaact tgtttacaat tctaagaata 167520
atattgtcct ttaaaggtga aggctcgctg gaaaacatgc cattcatgtg ataaaaagca 167580
ggtagcaggt agtgctaaag acttactaga ctgcatgttt gtgctttctg ctgcattcct 167640
ctaatctcaa ggcagtataa ggagataaca tcttcacagc cctttcagcc ctgttgcaat 167700
ttctttgacc ctggcctgat ataaaaggca aacttggttt ttcactgttc tagtcatgca 167760
```

```
gtttctttgt ggttcccttt agaaagactt gaggctatga gtcaaagctt ttacgtcttg  167820
ctgatagttc agagttgtga tgtgaagcaa taaataaaat ccctccttcc acatacttgt  167880
ctccttgatt agaatcattc tgggcaaatt tagaggctca taaagtccat ttagatattt  167940
agtgaaaaaa caccagcact cagaacagaa tgttgataat gtagatggaa tatctttctc  168000
tctctgtctc tgtgtgtgtg tgtgtgtgtg tgtgtgtgta tttatatatg tgtgtattta  168060
tattatatat gtgtatattt atatatgtgt gtgtatacat ttatatgtgt atatgtattt  168120
atagtaaata tatcacatgt atttatatat agtaaaaaag aggggactat aatatatctt  168180
tatatgttag catttatttt aaaaagaaaa cacaggaata tctaaaagaa actattactt  168240 atagggggtta tgggaaatgc catgggcaag aatttttttt tttttatca ccatgctttc  168300 tgaaacaaca cgatatgtat cacctttata aaaataaaat aaaataaaaa atgaaaaaca  168360
aagtccactt gtaaccacat gtcagtagca tgtttgcttt cagggtacat caaatgcatt  168420
ctatagcaca ggatgttcca gtcactctaa caaaagatgt cctgtttgga acaccaactc  168480
tgtatcagtt acttcagaca ctttctctca ttgagtccct tcagcaagcc cttttaggtt  168540
tatgttctta gatgaggaaa ccaagtctta gaaacattaa ctggccaaac taagatcaga  168600
gagttagaaa tgtcagagcc cagaactggc atcttctgac ttcagatccc atgtactttc  168660
ccctacactg tgctgaccac acctccatta ctacagatgt gttgattaca tctaggggcc  168720
aaagtacaca ttcatccaat aaatgcttac tgaatgctta ccgtgttcag ggcactgtgg  168780
caatcttttg taatgcaaga aaaataagag tagtgaagac agtcaaggaa acaaagaagc  168840
ctaatactag gcaagaagtg cttttgatgg aattaagcac aatgagggtg ttagtacaga  168900
aaggacattt aattgaactg ggaaagttca tggcagtttt cccagagatg agtcttgaag  168960
gacaaatggt atttagccag gaggaaaggg ggtcaagtgt attccaggga gagggaacaa  169020
catgtacaaa agcacagttt tgaaagaaca ctccattttt gaggaatagc caatagctgg  169080
gcacgtctag agcataggggt agtagagaga aaggaggccg gaaatgggaa gagacttgaa  169140
tgccacattc agttatgtgg acttcatctt gtagcaatgg gagcctacaa aattttaagt  169200
agaggaataa aaagattcca tctaaaactt agaaaaatta ctttggcagg ataagagaca  169260
atgaattgac ggggagctgg gtttgatagc aagaaactgt ttgggagact gttctaatta  169320
catattttct tgtttttaga tgcacatata cgtacttttt tagctggtca tttctttctg  169380
aaattggaat gaatcttaca atcaatggca tgttataatt tcattggcag cattatttgt  169440
ctcttaaggg cccccaaata atagtgtgtc acataactga tagcatctca aattagatga  169500
aatacagtag tccaggcaag aaatactgag atggtggggt ggtaaagagg gaaaagattt  169560
gagccacatt tagatcctga tgtggtatta attattaagt aaaaaaaagg aatgtgcagt  169620
acatattcag tatgccacaa gttgtggaaa aaaggtgtgc atggatagat gcacatgtat  169680
gtattcataa agttaatgtg gatgcataaa gcgtctctag aatgatacac aagaaacaaa  169740
taacacccgt ggcttttagt gggggggcatt gggtggctga gggagaacag cggtaggaaa  169800 attttttcatt gtgttctatt ttgtacattt gatagtttga actagtcgta ttatgcactt  169860
caaatatgta aaaagataaa aagtaagaga tatttagaaa ggagcattga cacatttgtt  169920
gacagattgg ttatgggata aaggcgatag tattttattg actatatttt attcttttaa  169980
ttattcctct aatttcttaa aacaacttta ttgaggtata acttccacgg tataatttca  170040 cccatttta a gtgcatgaat tcagtgattt ttagtagagt cattgagtag tgtaaccatt  170100
```

```
cctacaatgg ttatagcaca tttttatcat cctaatgaga tccttcatgc tcatttattt   170160
aatctccatt cccatctcca tccccaggca accataatct tccatgtttt taaaatagct   170220
ttgcctattt ttggatgttt catacaaatg gaatcataca aaaggtggtg ttctgtgtct   170280
agcttctttc ccttaggata atgttttctg gtttataaat gttgcaaatg tcagtatgat   170340
acttcattcc tttttatttg tgtctacaaa atactctatt ttatgtatat accaccttttt  170400
gttttttctgt tcatcagttg aagaacattg cagccgtttt tgcttttttga cttttatgaa  170460
taatgctgtt ataaacgttt atgtttaagt ctttgtgtgg aagtatttttt tcatttcctt  170520
gggtagacac ctagaagtag gatgttgtat ggaaaattaa tgtttgactt tttaagaaac   170580
tgttttccaa agtggctgta acagtttaca cttctactaa caatgtatgg aggttcccac   170640
ttctccacat ctttgcttac acttattatt gcctgtcttt ttggcagact taagcctagt   170700
ggttgtgaag tggtacttca ttgtgggttt gacttccatt cccctaatga ccaatgattt   170760
cggacatctt tcaagtgctt attaaccatt cacgtgtctt ctgtgatgaa atgtctattt   170820
gaatattttg cccaatttaa aactggggttg tttacctccc tattcttgac ttgttaggat  170880
tctttgtatt tttaacttta atttgactga ggataatgat ccaccagtaa agagatgcat   170940
ttatttctgt atttatgaaa atcttttaaaa ttcctctacc tttcagagac acccttcaac  171000
agactgcgct tcttatttttc agagtatgta tttccatgat aacacaagta tcaattataa  171060
atattaatta caactttccc tcctcactgc agactcaacc aagagttata aatctgtgta   171120
ttactttcaa tgctcataac aatcttctta accaccataa gcagactgaa aaagtcaatc   171180
tagttgaatt gttttacttt ataatgcttt tataagatac tcagtctgaa actgaaagat   171240
aggtagctct agaaatgtga taaatggcca cagaagtaac aacttttaat aaattaaatt   171300
atggatgtta tgtcaatttt aagtaatgtc tcagttttat atcttgttac ctgacctaaa   171360
tatcattccc tttagtaaaa tatctattaa agctttgtgg caaaataaga acagaaaaat   171420
ggttttttgat tttcagcttt ctctggtgaa taatttgttt tctttttattt ttccttctaa  171480
aataatcaca cgtttcattg caaccctaac cctcttcaac acacacacac acacacacac   171540
acacacacac acacatggct tctagattct acatgtacaa gagtgcaaat caaactacca   171600
tagaaaaact aagaagagag gcctagaagc aagaggctga tacactatct caggcttcaa   171660
caaaatattt atctctgact ataccaagga tgggcagagc ttgcatgtaa gtggcttggg   171720
ctagcagact gggttttgaa ggaggacaac atggccatgt tcttggttcg gtcatgaact   171780
gtctatggca cataccttaa atactgttgg aaggatccgt tagctccaga gactgcaacc   171840
aactgcctat ggtcataact cagctctcag acacattttg ttgtgcccac agagtgctgt   171900
ttgcctgttt ggttttttaaa ccaacactta aaatgcaggg aatttaagat aaaaatttga   171960
taaaaatggg aagatttggc cgtattgggc tcatggtaac tgagatgcat ctgaatgaca   172020
ggcattcctt tgaattgcac atttgctctt gttttttacta taggccactc tcactttctg   172080
ttttttttccc cggctttgaa acgatcagtt ttagtactga aaaattatct aggatactaa   172140
aaccagaatt tctctgctag atggcttgct cattacatta cctacatgat tctgtgtaag   172200
ggattgtgta agttttctat ggttgccata actatcacaa acttgatggc tttataacaa   172260
cagaaatgta tttacagttt ggaggcagaa ggtctaaaat caagacttct gatttttagtc  172320
tgtccaagag cctctgctgg tagggccatg ctctcggcag aggctcttgg ggagaatctg   172380
ttccttgcct cttccacctt ctggtggctt caggtgtttt gtggcttgtg gctgtatcac   172440
tccaatttct gcctctgttt tcgtatggcc ttctactctg ctcctttagt ctctccttta   172500
```

```
ggctgtttct tataagacac tcacctaaaa cccaaaaaca atctaaaaga tttttgcaaat  172560
atgaacattc taattacctt agagttaaga ttttcttttc tgctaagtga gggcatggtg  172620
cagagagcag gaaagatgtg aaactagata gcatacaaaa ataggtgttc atagatctgg  172680
gcctaacaag ggtgtggcca gcaactctgc cctgctttat cagcattaga aagccagtcc  172740
tctcagaaag tgcccagtta gctaaattca tgagattata gactattaag gtggaatgga  172800
cctcagagat ggtccttgct ctcatctgag gcttcagttg ggccagtcag aaatgtggga  172860
aaattgaggc aggtcaaata accaggagta caaacaaaca caatctatcc agaaaactag  172920
aaatcttact agtgactatt cacaggttac tttctgcatt ctggggtttt cattctagaa  172980
cagatgtgtg tgtgtgtgtg tgtgtgtgtg tgtgtgtgtg tgtgtgtgtg tggtgcgtga  173040
agagagggga ggggtgccca gaaaaccata cccactttcc cacatatccc aactatgact  173100
gggcaattat gtcattatca ccactgatat atagctggaa gagtttagtg ttgccctgct  173160
aagatctgga ttttcttttc tggagcttgg ctattgggc attgagaagt ccagccagga  173220
ggttggtcag aggctaaccc aaaaagcttt gcttaactct gggctacagc tgggggttgc  173280
cagagagaag tgcctggcat tcctgcatgc tgacatcaag cttcgaagtt gctgccctct  173340
ggtgagtcag cagcaaaggc ccacatcgtt cgagaatgct gcccaatcag aagatgtgat  173400
gccacacctc agaaatcttt ctaaacctca gcattctgta gacttcaaac aactcctcct  173460
gagaaagaat gtagaaataa ttaaatttat aagattaaag ttataaaaag catagagcct  173520
ataataataa cagcaataag ataaactcca catttgcttt taaaacaatt tatttgagta  173580
gacagccaac cccctgtatt gtactccttt aaaaaatatt ttaggctttt taaatgctga  173640
ggcaagggga cataccaaac actaacaggc acattggggt tttctggcta ttgaaataaa  173700
aatgtcctta cataacactg atgtactgga atagcactgc gttccagtga cggttattgc  173760
aactcagcca gcatatctgt agcttgtgag ctttcttat cagaattta tctataaata  173820
tacatatacg taaattctat tgtgaaataa aaataaaatg tagaatcttc tcatctttct  173880
tattagtcaa tattgtgcta ctctttaata atttctctca atttttcat taagcagata  173940
ttactaggga aatatacatg aggcagaagg caaattattt gcttagtgca atgcaaactt  174000
gcttaacagg taagagcaga gtcccttcca tagcattgcc accatatggc attgccatat  174060
cgtggaggcc ataagagga atgacattgt aaagattaac tggattttac ttggcaaggt  174120
caggcaccta gatggcatgc tataaaatgg ttagaagtgc aaaggaaacc tgtagctaga  174180
ggccatgtga gattatggaa gtgacttttc ttacaatcct gccatctggt ttggattgtc  174240
aggatcaaaa catttcactt gcccaagtga ggatgctctc tacatggttt tggggatgag  174300
ggagactcag aaataatgtt tgtggtactg tagcaccact aggaaaagag aaaaattgga  174360
cctgacatga agaaaagcat gcagccagcc actaagacta cttcccacag gactggaaat  174420
ctctaccacc gtacctctcc tacatgctgg gtataagaag ttaaagggaa gccagattat  174480
atttacctac tctttcattc attcattcac tcattcattt attcatccat ttaccatttg  174540
tttgttttt gttcatttac ttatttaata aaaattgtgt tttgcatatt ctaggtgcca  174600
ggcattgaag aaccactgtt attgttctca atgactgac agtttagagg agaaaatgga  174660
agaataaata gacacttgtg atgcaatata atagtgctct aataagagca acatatattg  174720
aataccactg aatattaaat accagggact ttgctaggag ctataaatta atctccacag  174780
tacatctaag atagaagttt tataattact ctctttagga ggaaataggg gtctatagag  174840
```

```
gttaagtctc acagcctgga aggagtcaac aaaaaaatac tcagccttag gtattctgac  174900
tagaagcttg ggtccttaac cacctactca ccaatttgaa gaaagatgat tgaaactgca  174960
acagctacac tgactcttga aagcaaagta actcgttaaa tgagggtatg tgtatactgg  175020
ctgggatatt gtgggctcat gatgacttgt aggccgaggc agctgcacat atgaagacta  175080
tggagggtat atcatcagcg gaaatgaaag tgattagtgt tggaggtttc agtgcatatt  175140
ctggttttct attactgcat aacaaatcac cctaaaattt agtgacttaa ataaacatga  175200
tcatttattt agctcatgaa tttgcaagtt gtgcagcact tgggtgggat agctcacctt  175260
tcttccatgc agtgtctgct gggactgcat gattgcatga agcggggctg ggcagctaga  175320
gctcttcatg aatctctatt tttgcatgat attttcacaa ggtctctcaa gcatgggagc  175380
ttcaggtagc agaacttctg acagggcagc ttagtccttt gaaagtgtat gtctgaaaag  175440
agagactcag gcagatgcta tattgccttt tgtgaccaag ccttggaaat cactagtctc  175500
tcttgtgttg aggtggttat aagagcctgt ccaggttcag tagggagcat aaatttcacc  175560
tctgaatgga gaagtgccaa tgtcctgaaa aagcatgtgg gcccagaaat actgttgtgg  175620
caattttttg aaaatcaagt gtgataaaga cagcatagtg tagtcataaa aaacagatta  175680
ggagcatgat gtgctttgat ttcaactatg ggctttatta cttactaact gggttacttt  175740
ggttaagttg tttgactctt gttttttgag atggagtcag tctgggagac tccagctctg  175800
tcgcccaggc cggagtgcaa tggcacgatc ttggctcact gcaacctctg cctcccggat  175860
acaagcgatt ctcatgcctt agcctcccga gtagctggga ttacaggcac ctgccaccac  175920
atctggataa ttttttgtact ttttttcttt ttcgagaccg tgtctcactc tgtcacccag  175980
gctggagtgc agtggcatga actcggctca ctgcaacttc cacctcctgg gttcaagcca  176040
ttctcctgcc tcagcctcct gagtagctgg gagtacaggc acacgccacc atgccaggtt  176100
aattttgta ttcttagtaa agataggggtt tcagcatgtt ggccaggttg gtctcaaact  176160
cttgacctca tgatccgccc gcctcagcct ctcaaagtgc tgggattaca ggcatgagcc  176220
actgtgcccg gcctaatttt tgtatttta gtagagacag gattacacca tgttgaccag  176280
gctggtctgg aactcctgac ctcaggtgat ctgcccacct tggcttccca aagtgctcgg  176340
attataggca tgcgctaccg tgcccagccc aagttgtctg actcttaatt ctcagctttc  176400
ttatttgtaa aatgaaggta ctagtactaa tttggagagt tgttaaagat taaataatat  176460
atgtaaatgc cttggcataa gggactggca caaagtaggc acttcatata taaaagctgt  176520
gattattgat gaaccagtag tgaggtacat aactggggaa ggagaagggg ccagtttgtg  176580
ggaatgcttt tttagttatt aatagtaagg tggtaaaata ataatagtaa taataaccaa  176640
aagttactga aaactaaata cagtgctaaa ctctttaaaa ggagtatcta attggatctt  176700
aacaacaaag ctatgaagca ggactaatgt tatctcattt tataaatgag gaaatgtaag  176760
atcaaacagg ttaagaaact ttcccaagtt gatcagtagc aaagacagga ttcgaaccaa  176820
ggtaattgtc ctatcagaaa ctgtactagg atagtctgca tttcatggta aagactatca  176880
gatgccacta aaacttttta aaagggaag tcttgtggtc aaatttgctc tttagaaggc  176940
agtatggagt gcagatcaga tgctggcagc agggagatca gttagaagat ggttgctcta  177000
attcagttga gaaatactga gacatctgaa atattgaaga catcagtagt gtgggtgatg  177060
tgaaagtggt tctaagaaac tagcggcaat catccttcat tactgattgg gcgtggagag  177120
aaagagaggt agcattggta gccgttagtc aactctgagt gcaggcactg gcatgtgcat  177180
tattacccag ggctctaagt ggagaaagaa acaaccccca gggtgtcttc aaacctaaag  177240
```

```
catatttcct aagcctttgc actctcagtc tagactaaaa acaaacaaag cagcctcctc 177300
tgaaatgctg gaaactttcc ccacttgaaa ctctcagatc tcttaccttg caattctagc 177360
tttcaaattc caagctgagc ttcctttccc acaccccgag tccttgtact ggggattaca 177420
atgatcattt gtatgtacta ggtgattgtt ccttccacat caggggcctt ggagcggatg 177480
acctaaagct gctttctcct gtcctgactt tctccaccca gcactgcaac catacataca 177540
attttctggt cttgtagaga atgactgact ggtcattata gtcttccaaa aggataagag 177600
attagtgtca tgatgtggcc ttcaggcagc caggggaat ctccatatga ggtacttgtt 177660
gactgtatta cttagttta ggtgaacttc ctgtggaggg acaatatgtg cttagaagga 177720
cagagaagga atgtattagg taaggcattc tacatctcag ataaagaact tcaatgaatt 177780
gttgggtcaa ggtctaagaa acaaaccagc cgtcaatggg aaagttaact aaaatgaaga 177840
acccaacata caaccccaaa tcctagtttt tctgactatg ttttcttaaa ctgaaataat 177900
ttctgagatt aaaaagaagt tgctgtgact ttgtctgata gatgtatttt tttgttatat 177960
attagtttgg gccttctatc tctcctactt tgttttcttt ataatagaat taatctctga 178020
aaagtaactt tactgtattc tgatgctcca ttttgaataa gtcagttctt ctccgaatgg 178080
gctctggaga ttggcatttg attgaacagc ttttgtgtat tgattgtttt aggtagactg 178140
ggtactccat ttaacttagt atttctgaca ataaatcagt cgagaaggga gtattactct 178200
aacggtttga acacttgtct atgcacattg cttggtcatt caataagtag ttattggtga 178260
gatcgggcac gttcagggtg gtatggccat agacaataaa tggttacgac tctgccttca 178320
gctgtaccag tatttaagtt ataaggtagt taagttacac cagtgcaaaa tcatacagtt 178380
tggtcacagt cctacttgag gatctcaaac ctagctcccc ttaacaaaca tggaggctta 178440
atcttggctt tgcacactga attattcctt tagaaaaata cttggtgtac aactcatcct 178500
tttcatttac aaagaaacaa atttgagcag tttcacaatt taaaaagtct cccaaatgga 178560
ttatatttaa ttgtccattt ccaatgaaac tcactaaatt ggtaaatagc agtgagtgaa 178620
taactgatga ggtcatactt tcttgttttg gactactaca aacaccacgg agcaacaaca 178680
gattagaata taaaggttaa gcaagggttt agttttgtt caaaagccgt tttgcttgtt 178740
acaaaggcta ccaaacccttt gaacatcaga ccaaaccaaa aacaaaacaa aacaaaataa 178800
aaaaaacccc aaaactgaaa gatgaaaaca tagtttgata atctaagctg ctcttccttt 178860 atttaaccctt gaatttatga gattattttt ttccccagaa gaaaaattct cttagggaca 178920
ctttcagcaa tttaacattt tctaagcatt acagcaaata agaggcgatc atcattcttc 178980
agtcataaag ataagccaag gaatgaaagt gttttgcagg tcatgtcacc tgacagaaac 179040
tttggactgg tcctttcctg gttcaagagt tcagccataa tacctacttt ccctatcagc 179100
tggctcaagc tgataaggtc ctgaagcaag caaagcttct ttatgagctt ttatttaatt 179160
gtccttgcca cataagggtt gaggggattc gtctgtacag agttacttct tgttggtcta 179220
ttttttcttt ggaataaatc gctgtctccc ctgactggat agagtaaata gagtttgttt 179280
aaacactttt catcaaattc ctagtgccta gtacagagct tttaacccta atacgttccc 179340
tgcgtgtact tattgaagga ataatgacaa actctgcctt agattggtga ctggctaggg 179400
agaaacatgg ttcaagagct gaataagtaa gagcaagtat tttattgtat gcccatcaaa 179460
tgtattcgat gctggtgatg gaggtaagag tgtgatagag gctgagttct ctgaaattac 179520
atatgagatg tcatctgcca tttagtatta gctgtgtctg tcttttttcc aggaatttgg 179580
```

```
ccttaaaaga gatcattcaa aagtattacc caaatagtga tttatcaggc tttattgtgg   179640
ggaacctaaa gtggattgca actgctatgg tcccttttgaa gggagctggt gcaagatttt  179700
ccatgcctaa tcacactcat tttcccttgc tctcccaatg acctcccatc tttccttcta   179760
tttggtctga taaacaccaa caataggatc ctttctgcag cttccatcct aacttgtatt   179820
ctagccttaa cactgcaaca aactcactgt tacctagaag tcaattgact tccctgaatg   179880
ttagcttctt tagctgtaaa taagtaattg tatgaggtga tggttaaggt gatttactaa   179940
ttttacaatt ctattatttt atgaatagac cctagttagg atagtttgaa atagatactt   180000
aatccactat tattctctct tctaagatat agttactagt tgatcatact tttccttaaa   180060
ggctgaactg aattctctga tatcagcaac taaacatctc atatttgtca gtatgaacat   180120
ccactgggtg cctgttattt aaccaggtag aattcttagc tgtgattgaa aatctaggta   180180
tctcttctgg tactatcact tggatgagta aagtttgaaa accattaagt tgacatttct   180240
aataggactg tggatttaac atagattccc agaagtcttg gaatacaaca gtgtacacag   180300
atgaagatac agtacttttt ggtattttct ttttgcaagt gttacaaata tctgcatgtc   180360
ataacatcat cactatggat cccatctttt aatgagagct tagtatatgc tacacactgt   180420
cactaaacat gtaggatctt gtttagtttt ctcaaaatgt tgtagttact atgattattt   180480
tttgtgtctt gcaatcattg tgtataagtg cgtaaaccat gtatctagag tttatagaag   180540
aattaaaatt caaaaaccct atactcatct ctcattttta aaaaatacca ttttacctgt   180600
ctttagatgc cctgtatttc ctccccaatc tcatcccgct cctactcttg aaagtgatca   180660
ctatccaaat tttgtgccaa acattaactt gttttcttta gctttgccat ctatgtatgt   180720
atccctaggt aatacatggc ttagttacac ttgtttttaa atttgatgta aatgtaatcc   180780
tatagtatga attttctaag acttgattaa tctatgaaca ttttattttg agattcatca   180840
atattgatgt gtgtagctat agtttattca ttgctgttgc tgaaaaatat tctattggat   180900
gactttgcta caatttattc taccattgtt ggatatttga gttgttccca tttatttat   180960
ttattttatt tttttgctgt tatgaacaat gtggctttga acattcttat actacctggc   181020
gtgtatatgt atgtatctgt ctgtctgttc atcttaagat gcactacaaa actgaggcct   181080
agagtcacca agcaacttgt ttaatgtcag agtgagttgg tggtgaggcc aaagtctgaa   181140
ttcagcagtc tgttaccata gttttcatcc ttaaccacaa tactctatga atccttattt   181200
taaaaaggaa ggtctggaga atttaaaata acttcctaaa gagcagggat tcaacaaagc   181260
tcagtctgac taatgccttc cattttaaa aaatcaccca aagcacatat tatgattcta   181320
tttgtgaagt attagctaat tacaagagaa tgagttcata cttggcacta ctatctcttt   181380
cttacaagtg atcagatgtc aaaatgtgaa aactatacat ttcacattat ccatatatat   181440
gtgacatttt tcctttagga atatgagtag aaatagaaag acaggttttt acagtgaaat   181500
agatttttt tctctctctt tagcctacca aatctctttc gcaataccta acacttataa   181560
atgcatttaa tttcagtgcc aattaaagaa attcgaaagt agataataag tgagacaagc   181620
acccagtaaa tgtttatgat gtgacactga caaattatgg gctgctataa tcaagatagc   181680
attaaaaatt ttaaagtgtt tgtatgaaca aaccattttg gaaggagtgt ttggtgtggc   181740
agtgagcaaa acaacccagt aactatggca gttagtgtta aagctctgat tttgacatga   181800
aaggaataaa aatggaagtc cagctaaatc acaagtgtcc tggagaaact tggatgagtt   181860
tcttggctag aggttttttcc caccacagta agtattttca aaggaaaaca aagtaaaatt   181920
tttctcttgt atgagtcaca tctctgttgg ttgtaagtgg ctgaaactca tcttgaacta   181980
```

```
ccaaggtaag agaagaaaca tactggttaa tggaattcca gaaaggactg aacaatcaaa   182040
ccattttgaa ggacagcata gagctggact ctagaacagc caaaacaagg ggttaaacca   182100
ctgcgaggga tctctctcca actcttgctc aggcttttct ccctggcttg actttcttct   182160 cttttcactgt agattggctt ctctcacatg gcaagaaaca ttgctgctag cacttcccga   182220
gttctacgtt ctacaacatc caccactggt gagagattaa cttatggttt ttctgttgaa   182280
aagtcaaaaa ttacctggga aaagtctgat tgtctcagat tggagatgtt gcccatctct   182340
ggaccaatac actattatgt gtggctgact atataaaaac atggatattt tcttggaatc   182400
acttggtttg actgggagaa gaccattctc aaaacaaagg aagtgcaatt tatagaaggt   182460
agtagaatag gcagataaaa caataattct tcactatatt gctcaaataa tccccatgac   182520 attttagta tattataaag agagttctaa agtgtttcca aactattata gcaaaattta    182580
atcttataat aatttcttct tgaactatgt ataatttacc tgaaatattt tccaaaaagc   182640
aatcaatgtg agaaaatgag agccctgtct tcttaaaaaa atgagtaaaa gtccacaagt   182700
tcagaacaaa agaaaatgag gtaaggccta aaataaattg tgctaagaaa gctaaaattc   182760
tagacaaagt cacatcggca aaactagaag gttggtactg tgcttcagtt tactgcttgc   182820
tgtttggtta agaggagggg tgatgtgata aaaatagtga cgaagtgaga aaactgacgt   182880
attagttttc tattgcatta taacaagtca ccacaaactt agaggtttga aataacgccc   182940
atgtattatc tcgcagttcc tgtgtgtcag acctccaggc actgcgtggc tcggctgggt   183000
tctctgctta gaatctcaca ggtcaaaatc aaagtatcaa tgggagctgc agttctccca   183060
agctggagcc tgtgtccctt ttaaactctc aggctgctgg cataatttat ttccttatca   183120
agccatccat atgatcccct ccatcttcag gccagcaatg gcctgtcaaa tccttctcat   183180
tctttgaaaa tctctgactt cccttttctgt cacagctctg taacttcttt tctcttctgc   183240
caccagcaga agaggctttt aagagtttat gggattagat tacatccgtc tggataatct   183300
tttacttaaa ggtcaactat gctatataac atagccaatc acattcgcac attgcagaga   183360
ctagggtata aaatcttcgg ggtcattcct agaaattctg cctgctgcag cctggtttct   183420
tgcttggact ctagtatata tttgctaaat ctcccaagcc tcagtctcac tatttgcaaa   183480
agtgagtttt aatgctcttt gccctgcttg cctcacagga tcttaacata gacgtaagat   183540
caaatgcaat agcatgtcaa acaatgtgta actccagtta tacaaacatt actgtatctc   183600
attggggata cgaagctcta cacacttgaa gatggtgaag gaatataaaa atgtaagtat   183660
tgcttttata ataaatgtgt tcctattggc tgaaaatttc aatatctgat acaaatagtc   183720
aactttctat tttactttt ctaattatgc aagaccttgt aatcacaaat gtaaaaattg    183780
caagccacat gccctaagg ccaaataaaa atttgtaaaa ttctcttaaa aagactctat    183840
agagtccaaa tgaaaatacg tcgagtcctt ttaaaaggat ccaaccacat atatcaactg   183900
atatacatgg taccaaaaac aatgaatctc tttcagattc tctaattggc ctttggaact   183960
tatgtagcat caggtatgca aatgaacaac ttcagacctt gattactcca acctcctctc   184020
ccactgtcac agccacttct gtcatgacct agttgttctc agaaagttcc ctcttatacc   184080
tggtcaaact tctcttacaa tcacctgtga ctttccctct tggtcttgga tcaaatcatc   184140
ctaaatacat taaaagtcct gattcttcct gtcccttaaa tatatctcta cttgaatcac   184200
tgtgttagtt caggtcctct gagagaaaga tgttaagatg aaattagatg tgcaagagat   184260
tcgccgaggt aaaccttgtg gggagaaaatg gagaggtaca tagaggagcc tgggcagact   184320
```

```
gtgtggctac tatgtaagac tcatccccat gaaggagaaa ggagaggaag gcaaagaaga    184380
aaaaccttaa gatttcaatt ctaagaacgt tttgacaaag ctgattagga gtatttaagg    184440
caaagctgcc caccagaaga gtactgcatc tttcaggaac ggacttgctt tagtacatct    184500
gctgtgctta gtaattggct gggagcagcc atagaaagca tggactcagt acaaacttgg    184560
tgatgaattt cagaggcagc ggctaagacc atcagtctat tattttcctt gcaatagctg    184620
tcataattac tatcagagca aacaattttt tgtgtgtgaa ttcatgagat aatggtcttt    184680
tctttcctgc tttcaagagc catgtcattg aaagagctaa tcattcaaat ttatgctgca    184740
ttactgacta aatactttca tttatcatac tttattttaa aatactttaa ctcatggccc    184800
gatgattttc agttaaccaa attctccctt actatcctgg ttgccccttc tgtcttttcc    184860
ttagaaatgt tattgtagta tttgcaagat ggcctgaatc ctgaaccccc catcttcaat    184920
gagcaccaaa tggtaattat agattcccag ctgtagagct atgtcagaca aaggaaactt    184980
cattagtatg taccaatgtt tggactccaa atgcttttgt gtctgagtca caaggactcc    185040
tcttccttgg tggcttaaag ttaggctgaa gaagatttac attatgttgt gcatgacctc    185100
tttagtttgg ttctacttat actttcaagg agggaagact ggggaaggtg tcccttagtg    185160
agcatatttt gtacaaatga aaacagggta ctaacactta tgccaggacg catgcataaa    185220
ctaggatggt tctgagaaaa ctgcgatata tgatcactcc agggtctccc ctctcagaag    185280
cgagggagac ttaaaccttt tacatcacca agtacatgga aagaaagaca gcagggaagt    185340
gattccgaag agaaacctga aaaaagcaat gtggaaagat agacacttta gccttttctt    185400
tcttctcaaa acttcacatt ccttttcact ctgcttcact taagctgccc tagttccaga    185460
gtgtttcctc tcttgggtga agatgggaac aagtacatgg ggtagcaagg ggtgggtggg    185520
acctgtgctc ccattaaggt tcttccagaa tcatttctat gtgattatca gcttggatca    185580
catggacttg gggattattg gtggttttct agggtaaaca gggcatattg tgctggagga    185640
catattttat atgtaacaat ttggggaaat tttcttttat attaaataaa actgagatat    185700
gtaatgaatt aggatgaaaa attcatattc atctgaattt tataagtgaa tcatgagaac    185760
tcaaagatac ttagcccttg ggaccatttt ttactcctgt tcggatccct tcagctaagc    185820
atgattattt actattttca gctattagtt atgtcttgtt gaaaaagtat gaaaagagct    185880
gcccaataaa ttagagtgta tgctcaacat tctcttagct tctttatctc tttccaaaat    185940
tggatcaaat gacattggac atgatcaact tcttactgtt ttgacaaaca tctgaggata    186000 ctttttataat tgataatttg gactagatta tgcaatgtgt gatgagacac aaggtagtct    186060
gtactcccca tgatatgtat atctgtttga tatactcaaa cggtgtatat caaacggata    186120
taagtttgag taggtatgga gatgagccag ggtttatttc ttcaactagt atttactgaa    186180
tggtcttatg tgccacaact gttctggaaa ctgtgataca ttaattaaca gataaagcct    186240
ttccctcaca atgcataaca gacccaacag agtatgaatg tacatacaaa ctagtaaata    186300
agaaaacaaa taaagtatt cagatagtgc tataactact gggatgaaaa tcgagcagga    186360
aggaaaatat agcctgcttg atgtggaaga cagggatagc ctctctgagg aggtgacatt    186420
tgacccaaga cctaaatgag gagaaggaga cagtgagatg aaaatgaggg aaacagcaat    186480
ggcaaataca gagaacttga gacaacttgg cccattggag ggacagagac aaagccaatg    186540
tgggaccaca ggggatgaaa gggaggctga ttggagaaat aggcagtgct gaggccataa    186600
aaggtcctat aggtcatgga aagacatttg gttaccattc taatgacagt gagatgttac    186660
tggggagttt taaactggag aatgtcataa ctgtccagat gtaaccaaat agtaaaacca    186720
```

```
ttcttcctga ataacttggc taaaaggaat attatgacta cagatgtaca tgaagattaa  186780
gcagaacatg gaagaaaggc ctcaagtaaa cttgacctca cataaatatg ggaggaagat  186840
caaatggaag ctgggagtgt tgaaagaatg taaggggaat gacttctaat aatgaacaaa  186900
aagctgttat tttattatga agaaaaatgt tatgcatctt atgcatgcag aagaaattcc  186960
cattcaaaag acttggaaaa tgtcttgggt gtttactata ataaaccttt taagatatag  187020
aaaattcaca tatttagagc ttaatttcta aagagctcag acttctcagt ttattatatg  187080
ctatgaaatt ttgtttattt ttaatttaac ctacttgtgt gcaaaatcaa taaggaagct  187140
taaggaatat aaacaactat ttaacatggc catttaaata gattcaaagt aaagaatatc  187200
agcatagtgt ttctttgata tgacaacccc tcctcccagg gcacttaaat gaagggttgg  187260
gggggaatct taacctgaaa ttgaaaaccc tgaaatcatg tttccaagga aggagaagga  187320
aaataggaaa aacaaaaaca aaaagcagca actcatttgg aagctcgtgg gagaggagag  187380
gaggattcat acatctcgga ctggtttgcc ttagcaagtg aatcatttaa ataggaaaaa  187440
acaggggggct gactcagctt gagcaaactc ttgctatccc ctgctgaggt ccgcacttgc  187500
tgtggcccct gccgctctcc tcggaccttg ctgccctcct cctttgtcac tgtggagaaa  187560
caggaaggaa tgtttattag caagactgac tggggtcaca cccaaggcaa tatcaggttt  187620
ttacctctcc caggcctggg aagaggttca aggatcaagg acaagctccc ggttagagtg  187680
agaggcaagt tcaaaccttt gaaaaataaa ctcacaacca gcatttggca caggcctctg  187740
gagtttacag aatgtatctg cctgtgtgtg atttcattag ttcctcctgc caatctaatg  187800
agattttacg tcctgtaaca gtgaggcaat tggagtctca gcagggaaag gaacttgcct  187860
aaaactgcag gatgggtagc gcttggatcc tgactttctg actcctagga ctgtgctgtc  187920
ttcagatgat cacatgcctt cttggcagat gttttctaaca aggagagag ttgcccaggg  187980
tggggctctg ctagctcccct tgtcatgagc cattctctcc acattgcctt ttagttgcac  188040
cacatagtca ccttcaatta gctgtgcgaa taggctcact cttatgctaa catgtactaa  188100
aagtgaaaat ggggagagag agagagagag agaaagagag acacacagag agagagactc  188160
atattatggt atgttccctg ccccaccccca ctccactccc tctcaacagg gagaaagtac  188220
ctgaagaaaa tcattgctat gaagggcata gccagctaaa tgggtgtcac ttagtctgaa  188280
aaatctcaaa gatgtcaata agccactcga gacaacaagg aacctgtttt cctgtcatca  188340
ttccttctca gtccttggct ttgggaaggg taactttatg gagagagaag aacctctgtg  188400
gagttaaaag gtttatgaac ttttttccct gcaacaaatc agtgacagct gttccacagg  188460
ctgatggttt tccctttacc tttcgttttt taacagctat gtctcacagt ccagacttgg  188520
agtacaagta ataagaagaa taaaacttaa tcccttaagt agattcacca taagttagct  188580
cagagcaatt ccagtgcaag tatggtctgt gatccagtag gtgagtgact ctgctgctga  188640
aattcacatg tatgtgaatt tcacagtggc ctttgctttg tagcatgctg taatcctttt  188700
gtccattttc atcacacgaa ctgctgaata taggattgtt aaatggatgg ggagatatca  188760
tgaaaatgat taaagaagaa agttcttatt taggggtgca tacctgccta tctgaccatt  188820
gtacttaggc aatcgggatc ttgctttaag aaaaggtagg cattggagtc aggctgctgg  188880
agtatgaatc actatgctat catttttcat ttgttttttgc tctgttacat taggaaagtt  188940
atgtagaatt ttgtgcctca gtttcctcat tcaatatggg tgtaataact gtgcctgtct  189000
tgtaggatta ttgtgaggcc caagtgcaat aatatatagt acactgtgtc tggcatctag  189060
```

```
taagcattca ttaagatgac atgaagataa cacagatata tcttaacatg taattatgat   189120
tttgcttatt caaggccaag cattccaatt taatggagtt aggcaaacac agtaaattca   189180
ttgctctttc cttttatgc tacttccttt gaagaggcag tcaagttcca tttgactgat   189240
tcggaacttt ttagcaatgt atattatgct gacttcactc ttatgcgctc ttggggctat   189300
aattcatcaa gttaggcgag caaagaagtg tgttggtgaa agagaaatga ggaagaacaa   189360
ggaagaaaaa aagggtcatg agcttattca ctgccaatat ttattatatg gaacaatgac   189420
catccttcag aagtgtttgt tctctattat actgtaggtg tggaagaatt atcattgctc   189480
aatagctgtc tcagtcacta cctgatagac ttgggaggtc tggctatttc agggcgcatt   189540
tgacatacag tgacattttt ggattaaagc tttcatgatg agtgccagtc tgggtccaaa   189600
agggttgaaa gctgtcgcca tctataggct agttgtttgt agtaaaatac tttccctcac   189660
tgcattaggt tcttggtacc atttatctag cagagttctt cagtgggctt gaggcttagc   189720
agtcaagtta aaacaataac caacatccca aacccagtgg ctgtcaaatt tcagtgaggt   189780
ggcatagaac tttagcatga acttgagctt gggttcagct agactttcat ataaatcctt   189840
gtttgaagtt agtagctgtg tgatcttggg cactgatatt aaacctttat gagaaagtta   189900
tgtctgaaat atgggaaata aaccttccac ttaggttgtt gtgaagattc aatgagttgt   189960
aacgattgta tacactataa tgatctatat tacagttgtt tcataaatat gattgccttc   190020
attttattct ttccttgtct cgttcttccc agtatcttac agacagcaag ttgaacattg   190080
tgggatgcat gagctattga ggcctttgca gctttctgct acatggaggc tagggccaga   190140
gtcaagattt atgctttgca gcacactggt cagctgtttt tgcaaatcag attaaatgat   190200 tttaaatga ggctgagagc atgggagata ctaatgtgtg tttccttgtg agctactgca   190260
taagtaagtg ctttgtaaaa tgtcaggggc tccaggatta tatggtatta ctgtcactat   190320
tgtaagcact tctacctttt ttttctcctt ttacaggtta ggaaattgaa atacagaaag   190380
atgaaaagtg atttgcccaa gcatatagat caaagctgtg gcagaaccag gactggaacc   190440
tatatctctc tactaatggt tttttttaaa aaataacctt gtttcaaaaa tattaaaaag   190500
tcacaagaaa ggtaaacatg tggataaaca aaatgaagaa aataaaaatt atccagtaat   190560
aacatattgg catatgtctt tctggtatat tttcctgtgt tgtcatcatt atcatctcca   190620
tcatcattat atccatcatt atcatcatca tcatcatcat catcatcatt atcatcacca   190680
tagtgaacat gtaatgctta cctagtgcca gatgctgtct aggcatttta catgtgttac   190740
tggtaactca tgtaatcctc ataacaacct tataaggtgg ttgctattat ccccatgtta   190800
catatgaaga gacagaagca taagaagtt gcaccgctgg taattggctg ggatttgaac   190860
ttaagcagtc taaccttaga gtaatgattt taacaactat gctatataca tacaaattta   190920
caaaataaaa ctgggctcag acaataaaaa cagctctctt ttcatgttat aatacttttt   190980
caccccataa cacataatca ctaatgtttt aaagatcaaa acaatgcaca taaaatgtac   191040
tggttttaaa aaaagagga aatagccact tacctcaacc aaactaactt ggagatagat   191100
tagattgata atggcaaggg tgatgggtag atgggtagag gttgctcaaa aagaaacaca   191160
aaatatatcc tcttttaagg atcctgatgc tttgctcaaa gtaatttta ttcttttaaa   191220 actaaaaaaa aactgtacaa aattcatagg gtacatagtg gcgctttgat atatataatg   191280
tatagtgatc agatcagggt aattcgcata cccagtcatc ctatagtggg tatagaacac   191340
cagaacttat tctttctatg tagctataat tttgtatcct ttaacaattc tctccctatc   191400
cctcccttcc ccctactttt cctagcttct agtatcctct gttctacttt ttacttctat   191460
```

```
gaaatcaact ttttcagctt ctgtatgtga gtgagaacat gcggtgttta gtaggaaatt    191520
tctgttcctg gcttatttca cttaacacag tgtcctccaa gagcatccat ccaggatttt    191580 attgctttt  atggcttaat agtatttcat tgtgtatata taccatattt tctttgtcca    191640
ttcctttgtt tttggatgcc tggattgatt ctataacttg gctattgtga atagtactgc    191700
aataaacatg gtctgtagat gtctctttga tataatgatt ttctttcctt tggataaatt    191760
gctagtaatg ggattgctca atcataccat agtactattc gtagttttt  gaggaacctc    191820 cattctgtcc tccatagtgg ttgtactagt ttacgttccc accaacagtg tataagaatt    191880
cccttttctc caaatccctg ccagcatttg ttattttttt ttttttgtct ctttgacaat    191940
agtcatccta actggggtga gatgatacct cattgcagct tcaattcaca tctccctgat    192000
gattagggat gttgagcatt ttttcatata tttattggcc atttgtatgt gttcttttga    192060
gaaacgtctg ttcagatcat tttcctactc tttaattaga ttgttttac  tgttgagatg    192120 tttgagtccc ttatatattc tagatattaa tctcttgtca gatgagtagt ttgcaaatat    192180
tttcttccat tctgtagttt gtatattcac tctgttgatt acttcctttg ctgtacaaaa    192240
gctatttgga ttgatataat cccatttgtg tattttgttt gtgttaccta tgttttaag   192300 gtattattca gaaaatttt  gcccagacca aggtcctgaa gcatttcttc tatgttttct    192360
tctagtaatt ctattttca  tgtcttacat ttaggtttt  gatccatttt gcaatgatat    192420
ttatataggg tgagagacgg gaatctagtt taattcttct gcatatagat atccagtttt    192480
cccagcacca ttcgttgagg agactgtcct ttacccactg agtgttcttg atatctttgt    192540
taaaaatcag gtggttgtag atatgtggat taatttctgg gttctctatt ctgttctatt    192600
gatctatgtg tctgttttta taccagtacc atgctatttt gtttactata gctttgtagt    192660
atactttgat gtctggtagt gtgataactc cagctttgtt cttttgctt  aggattgctt    192720 tggctgtttg gggtcttttg tggttccata taaattttag aattttttt  tctatttctg    192780 tgaagaacgt cattagtatt ttgataggga ttgcattgaa tctataggtt gctttgggca    192840
gcagatatct ttccatttgt ttatgtcctt ttccatttct ttcatcagta ttttgtagtt    192900
ttagttgcag aggtctttca cctccttggt tacatttatt ccttggtatt ttattgtttt    192960
cgtagctatt gtaaatggga ttgccttctt gattgctttt tcagctagtt cattgttcat    193020
gtatagaaat actactgatt tttgtatatt gatatcgtat tctgcaactt tacagaatt    193080 gttattagct ctgagttttt tggtagagtc attagatttt tctgtatata aaatcatgtc    193140
atctgcaaac aggaacaatt tgacttcctc ctttccaatt tggatgtcct ttatttcttt    193200
gtcttgccta gttgcttggg ctaggacttc cattactgtg ttgaataaga atgttaagag    193260
tgggcatcct tgtcttgttt cagttcttag aggaaatgct agtgtagctg aggagagaaa    193320
tgaaaacaga ataaaaactt cagtagaagt tggggagaaa tgtgtttgca ccaaaagagg    193380
tgagggatgg aactgaggga ggtctcgagg ggtaagagag gccaaagagc tggcaggtgc    193440
tgctattagg atggccaatg atccagaagt aatgatgaat gagaagatgg attaaaaaaa    193500
ccctgacatt gtttaactag aagaagaaga cagtcagaga gaagtgaggg cttactttc    193560 atgtttaaag tctgttatgt ggtaaaggga ttagattat  ctgtgttgtt ccaggggaca    193620
gaaataggac aaatggatgc aaatagagtg aggaagattt aaaacaaatg gagaagacat    193680
tctaaaatca actacaatga gcgtaaacaa tgacaacgga aaggactatt tttgcaatta    193740
tgtagctctt gttctctata gatagatgtg taagcagacg ctgaataacc atttactgaa    193800
```

```
aatataaata aaaacaaagc aaattgcagg caataaatat tgtattagtt ctcattttgt   193860
aaaacttata caggtatcat atgcatagac aaatacacca aactgatgaa tatttgcctt   193920
gtataatctt tttgtagttt ttttatgaac atatattact caaacaattt agaacatttg   193980
gcaatatata tatatttcat ttataaaagg ttaggaagat taattacact ttctgaggtc   194040
gcaactaaaa gccaagattt taatccattt ctatttgatg taaagtctgg tctttttttca  194100 gcaaaccaca atcccacatt ttaagggcat taagaaaggg atgggtagac aaaatgtaga   194160
ggtagtaggt acagaataca aagtttcaag aaattaaaag cttctaaact aacaaacagc   194220
caatttgtgg agtgtcactg gaaagtgaca aagaggacag ttaagttagt tggaactgaa   194280
ctgaggccag acagggctgt gggacaagtc agggtgtggt cattccggta agcagcgatg   194340
cagaatcaag acagagtagt ttctccttct ctctctctct ttaattgtaa cgccttttat   194400
aacaaacaaa tattatgctt atttctgtct ttaaatttttt tgtagtaatt tctcatcact   194460
taacctctat tttttaaaaa actaactttt ctcttgtttt tctagttgag ctatcattca   194520
tatttattat gtggaactag aggtagtcct ggctacttgg gaacagcgtg gagtctagcc   194580
atgtcagggc cagaagtcgt ctcagctaag ttagaatgtg ataccattgt ttacacaagt   194640
gtggcctgcc ttcaagatag ggtgaggtgt tttatgacca caggctttat gagttatagc   194700
tataaaacaa tcaatctttt aaagcaaaca caccacaatg tctacacgca aatgagaatt   194760
gtccttcagg gctgtgacct tgggaaactc ttcacacata ctagcataaa acatatttaa   194820
actcttcact gaaaatatta ttcagaccta gtttctctct cagtctctct ctatgtttct   194880
ctctcacatg tacgtgcatg cacgcacacg tgtgcacaca cacatatgct cacatcattt   194940
taagatacat ctcattttta accaaaacca ttttatcttg cttgataacc aatttttattt  195000 gttagatgac ttggctataa atgccttttgg ctatcaggaa aatcaaatca aaattaaaag   195060
acactgttac tactgaagaa gtaaaaaaag aatgggctgc tgactctgaa gatcataccc   195120
gaagtagagc tgcaaagata tttggaatat tggtaatatc caataaagaa tgaccttcat   195180
gctattttga ggagatgttt aaatgtcgaa ttattgaaat atttataaaa tacaaataaa   195240
ctaactctgc ttcatattcc aacttgtgta tgacacttct taggctatca tttcattcca   195300
aatttatggt cactacccta ctgtcattcc tcatactaac catatgatca acagttgaaa   195360
agcagccact cgcagaggta agcaagatat atggtaaata ctgtgttgac aaaagtatgc   195420
agaagcagtc acatttatac agtagtgaag gaaatgtaaa ttggacaaac ttttttggaag  195480 ataagttgag aatgtcaaaa atcaaaacac actttctgtt ttattcagca attatgagcc   195540
cttgttttta cagctatgct cacaaatata tacaaacatg tatgcacaat tatgttcact   195600
gtggtattgc gctagaaaaa tactaaaaac aaaccaaatg ttcatcaata gggaaattgt   195660
tcaacaaatt acagtatatc taaaaaaaga ataatatata acaactgaaa aaataaaata   195720
gttgatataa gcagatattc caagatctgc cagacatatt gttaaacgaa aaatctagat   195780
acaaaattgt ttatagttct cttttcatact atagccaaag aaaattcaga aaaaactact   195840
tacagttgat ccttgaataa tgcagcaggt aggggcacca gcttcctgcg cagtcaagaa   195900
ttgcatataa cttttgactc ccccaaaact ttgctaatag cctactgttg actgaaagcc   195960
ttatcaacaa catcaacagt tgattaacac tggaaaagga ggggttggtc ttactgtctc   196020
aagggtggca aaggcggaag aaaagccacc tataagtgaa cccttgaagt tccaacctat   196080 gttttttccag gcaatcata catccatgtc catattcatg atgaatatgt gaaagggtac   196140
ataagaaaat gtgatagtcg tttcctctgg agaataaaat gagaggtcta tcataggtga   196200
```

```
gaaaataatt ttttattata tattcttttg taggtttatt tttttgtcat gtgtatgtat    196260
tcttttcaaa ataataaaaa caataacaac gattaaaata tacaagggga aatgcattgg    196320
ccaaggttta gttgagagca aagtttgctt atctttcgaa agaggtgaac taagcttttc    196380 cttttctct ttgggtatac ttgaatgggg atggagtaag tggattcttt tttttttttt    196440 tttttttga dacggagtct cgctcgccca ggccgactgc agtggcgcta tctcggctca    196500
ctgcaaactc cgcctccgga gttcacgcca ttctcctgcc tcagcctccc gagtagctgg    196560
gactacaggc gcccgccact gcacccggct aattttttgt attttttagta gacgggggt    196620 ttcaccatgt tagccaggat ggcctggatc tcctgacctc gtgatcagcc cgcctcggcc    196680
tcccaaagtg ctgggattac aggcgtgaga agtgagtgaa ttctaaggag tatcgagaac    196740
agtgattaaa acagaaggtg gggaggtgtc ataagcttat ttgtaggtga agtattaaga    196800
ctagaagaat gacattatgc atcaaatctt ttacattgtt tgatctcttt tacctaaaaa    196860
caaaacaaga tactttttg ttgtttgaca tatgaccaat tagcagccag ttggagctaa    196920
atgttttctt ttttctttttt cttttctttt tttagatgta gtgtcactct gtcgcccagg    196980
ctggagtgca gtggcgtgat ctcggctcac tgcaacctct gctacccagg ttcaagcgat    197040
tctcctgcct cagcctccca aggagctggg attgcaggca cctgccacca cgcccagcta    197100 attttttgtag ttttggtaga gatggtgttt caccattttg gccaggctgg tcttaaactc    197160
ctgaccttgt gatccacctg ccttcgcctc ccaaagtgct ggtattacag gcatgagcca    197220
ctgtgcccag cctaaatgtt ttcttttaaaa gcaaggtaag tatgcctaga tgcactgcct    197280
cttagtaatt tttgaggatg gattattcat taaattgctt cccttctca cagctggtga    197340 attagaacga tagtgagctt acaagagctt taacgaggaa aagatggtca ttgtttaaca    197400
gagaaggatg gtttgggtga gcatttttgt gttttttggag gggaactttg agggcaatga    197460
gtgttgcacc tgtgtccact gaggatctct gggcggggta aaaggaaggc agggatgaga    197520
gtgaggaagg gagacaggag ggtcccaaat acgaactttg acttaacgag gatgattact    197580
agaagggaaa gattgtggat tcattgatga gatgttgaac catgaaaact ctaattgtag    197640
aactcacttc agactgaatt gacttggctt tcagtagcag aagccctttg tctacttctc    197700
tagtattgaa gtgaatgcaa atttctcaat gtaagaaaag tagagtggtg aaataagagt    197760
gtgggttcca gggtcagaca actgggtgca taaaagggt aaggatgcta caactggtaa    197820
gccctgtgag aattatttaa tccttccatg tctcattccg ctcatctgga aatgatgat    197880 catactaact tatgagatgt gtgtacagac tagatataat attaaaacat ttctgatacc    197940
tatgcattat attggatcaa tatatatttg caataaatga tcaactttt attaatgaag    198000 ttagtactta tttcataacg agattgttta cttctaattt actagtattg tcattattac    198060
tgttgctgtt atactgctac tgctgttgct actaactctt tatgaagtac ctaatatgct    198120
ctaagccttg ctctaggtgt tgtatatgaa gtatttctaa acctgaaaac tatctaagat    198180
ggctcagtct agcccatttt atagacgaag actgaagcca agagagttga aataatgagt    198240
aaagttgaga tttgactttg tcttccaaac aactagaagc ataaagcaat ggaccaggtt    198300
ccaaagtgac agggaggggc attagtttgg cccataggct gcagagcctg tgaccacaga    198360
gccctatata ttccagtggt gaattatgtt tgggaatgtg gcagaccata tggctatggc    198420
atcgttagac atgaggtgga gagaggcaga tgtgtggtta ctcgattgag ttgagagatg    198480
ccatggaaag gaggaagaag agcctgagag agcaacttca ctcatgggga gagaagctta    198540
```

```
tgtggagata agcttcactt cactaatggg gagataagct tcacttatgg ggagacaagt    198600
aaggaagcag ggatctccag aggatgtgga gtatgcctgg tactttcatt gttcttttc     198660 cttattcttc tttattcttt tcattatttt acctaggtta gatgttaaac acttcctgtt    198720
gtttagtcag gcttcctttt ctaattataa gactaaacac taagatttca tttgtagata    198780
taattattag agaattttga taaaatttcc aagcagtgtt ccctctgttt atcatcgtgt    198840
tccctgctgt tattagttca cagtttggtc tggaattact ccagttaatc ttggggtttc    198900
aggagagaaa ttgtgctcag ggtacatgag aagagaaagt ttagaaagcg aagggcttcc    198960
ctgtctagtt tctagctcag aaaagcaaag atattctact ttcatatgta tgataattgg    199020
agctgagctg actttaaaaa cagataattt ttcttttta tccctaataa ataatggtgc     199080
ttacagcaat gagtgttgct ggtaacagat tccaccaatg ggtgtggtgt gaagtttagc    199140
atttgtggat tttgcagctt ctgctattgt ctacagcatt tcctctcttg tctcggaggt    199200
tcatactttc tcaggcaagg acacttttaa ctccagataa atgtctgggt tttctcactc    199260
caaggataag aaggtggggg tgatggagtg gtggtggtag ttgtggagtt gtcttcctgg    199320
cagggatttc attgtggggg aaagtctgtc tttagaaaag aaatgtaaac tgggcaagta    199380
gtctcatcag ttaaatgatt tccttgttga cataaggtga ggaaaagaag aacaacttt     199440 gggaaaagta actgtgagaa tacaagggaa gaagaaaaat aagggttga acattgagga     199500 agacttatga gacagataaa gtaaaaggc aggtaatttg ttctttcaat ttggcatggg     199560
gacagtaaaa attttttctt actaaacaaa taaagcccat gtatttcttc tgctctggga    199620
gcaccaatta tattgagcct ctaaataaag aaagtcaaca tccacaagtg ttctaaattc    199680
catctcgtag tgagagtcct gaaaattgca atagctagag tcaatacttg gagtatatgc    199740
ataagacgtg gtgtctcaaa taggattaag gcctactctt ggcatcttct gttattggtg    199800
ttgtttctct gtattgattg gtataacgtt agacaaaact gcaggtcatc tttgagaaaa    199860
actcagtata aacaatgaaa aaaatgtgta gctgcacatg taatttgcat gtaacaaaac    199920
caaaggatgc tttagatagt aacagcagcc tgtactttac tccaacccat tagttttatg    199980
ataaatgtgg tctggggaag tgctcgatct aggttgttca ctttgtgttt ttgtttcttt    200040
ctatcattcg ggtgttgagt cacctgtttg tctgtgtcag tgtcagagca ctgggtcaca    200100
tcctgcattg tccaggtttt attggtccct ttcttaaatt aaagctgatt ttccacttaa    200160
agagaattct gtctccttct gcaattgttc aaagtctagc atctcaagtg cagactctaa    200220
actgtatgta tatgtattgt gcaggctatc tatcttctta gctttgaatt ctctagaaat    200280
attccagagg tgtgattcct ctgttattca agagtgattt ccaaattgcc tcagccaatg    200340
tgcctgcaca agttgtttgt aactcagggt gtaatgggaa atgctttaga gccacatttg    200400
tggcttttga tgggaaaaaa aaaaaatcag tgtcctccta agacttatac agtccttgaa    200460
gccttttagg ctattcctgc atctcatgtt gcatccatac ggactattta gccatattca    200520
acaccatcct cttgctattt tgttaagatt tgactgttgt tgttgttgtt tttaaatata    200580
aatgtgtgat cacatgcaca tacacagaca atgatgtgta actcataaac atgaaaagta    200640
aaaatttgaa ttttaactga agaaaaatca gcattattca taaaaagctg gtaagatatt    200700
ctaaaagtgg aaattcatgc agaaaattga ttcttaagca cttactaaat gccaggaata    200760
ttttaccagc atattatcat ttaattttta aacaagtttg agagatagag atgtcttatt    200820
ttatagaaga ggcaactggg gttctgaaat gtgaaataac ttgcaaaggc tatggttaag    200880
ggcagggcca gccacgtgtc tagtgtctct gacacctgag atcacacact gtatgctggg    200940
```

```
cttcaattaa tttgcagcta cttgttgcat taaattcaca atccttgctt tcatcataat   201000
aaaaacaata ataatcatac aacacaacta ttttcagtga gctctggcta aggccatttg   201060
attcagagtc aaaaccttct atttgtatag tattttatat tgtcaaaatc taataaggat   201120
agttttcata tctgacgtaa accaaactga tctgtctcca tttgatatag tgacatatca   201180
aattgttact ttcatatatc ttagtcaacc tctatgttta tcattctcta tgttttagaa   201240
agtaaagaat ttaaaattac ttcagaaaga tttcttcttc ataaacataa aatgattaga   201300 tgtcccttt aaaggcaaca gcttcttctt tttctttttt cttttctttt tttttttttt    201360 ttttttgag aaggagtctg gctctgccgc ccaggctgga gtgcagtggc gccatctcga    201420
ctcactgcaa gctccacctc ccgggtttaa gccattctcc tgcctcagcc tcccgagtag   201480
ctgggactgc aggcgcctgc cactacgcct ggctaatttt tcgtattttt agtagagacg   201540
gcgtttcacc gtgttagcca ggatggtctg gatctcctga cctcgtgatc cgcccgcctt   201600
ggcctcccaa agtgctggga taacaggcgt gagccaccgc gcccggccaa ggcaacagtt   201660
tcttaatgag agagtagaaa tgagaattca cattcataac aaagagttta ttgtctttcc   201720
tagtatactg tactatctag tagctaatct gtctaaagac atgtttctta tctattaata   201780
gtcctattaa taatgtaaag tagctttaga tatgccaagc tgttactggc tggggaacta   201840
aaaaagcttc cagagttata tctagaaagt cttgggggtt tcttaatgtt atgtgattag   201900
caactaaaac tgtgacagga aggaagtcca catgaattga gcatctacta gtttcaagat   201960
ttatcattat gcacattact tataataact ttgtgaagct gatattaact ttacaatgga   202020 taaaagata gatgaattag taatttacct ccagtggtgc agacagcagg atttgaattt     202080
agtctgtcca acaccaaagc ctccgtactt ttcattaccc tgcatccatc tagtttaaaa   202140
aataaatgta ctaggcatag tggcttgcac ctgcaatccc agctgcttgg gaggttgagg   202200
ccagaggatc acttgagccc agaagttcaa ggctgcagtg agttatgagc acacaactgc   202260
actccagcct gggtgataga cagaccccat ctcaaaaaaa aaaaaaaaa aaaaaaaga     202320 gagagagaaa ataaaagaaa aatcgaatgt attgcatttc atgtctggac cacctgtatg   202380
agaaaattgg gcactttctc tctgaagtaa ctcatactaa aaacaaacac cttcttcctc   202440
ccaggagctt cccaaggttg aagagaggaa ccctgaagct ctaatatgcc taagatgctc   202500
tctggtgtta tctaaaatca aaatatatca cctagagcac ttatttattt atttatttat   202560
ttttgagatg gagtctagct ctatcaccca ggctggagtg caatggcatg atctcggctc   202620
actgcaacct ccgcctccca ggttcaagcc attctcctgc ctcagcctct gggattatag   202680
gtgcacgcca ccatggccgg ctaattttg tattttagt agagatgggg tttcaccatg      202740
ttggtcaggc tggtctcgaa ctcctgacct cgtgatccgc ccaccttggc ctcctgaagt   202800
gctgggatta caggcgtgag ccaccacgcc cggccagagc acttttttt cttaattttt     202860 tatgatggaa aatttcaagc atacattaag tagagaaaat agtataatga acaactgaat   202920
acttaaatct ggcttcaata atttctaatt ttatgttctg tctaatgttg acataaagta   202980
tagtttgtat gtatttggtg gtgagtacat aatgggccac atgattttta ccttttaggc   203040
tgtagttcta catcagtata agatggttgt ttttttcttc caatacaaaa tctaaagcgt   203100
tgtcggcagt gacatttta aaacacaat atgagacgca acaataaatc agttattaaa      203160
ataagataaa gtaggtatat aaatatttca ccttggaaat aaagcaaagt cagtggaaga   203220
gtgtgaagac tgtgaagatt aggagcatga aaataaacga ctattgggag ccattctatt   203280
```

```
cccatgagtg aatgtgtatt ggttccattc aatgtaggga agagcagtaa aagggaataa 203340
ccataaggat aagaccactg gattatctga gagccacagt tgtcctttgc cacatggagc 203400
atctgcccta ggtattacag ctctgtgaga aacagaggtt caaggaaaga aatttgttat 203460
ttttcaatta tctgcataaa ttctttggaa cagggggcatg gattataaaa gatgtaagat 203520
aataaaaagc atttgtattt gactttggaa tgtattgtac ttacatttgt ctagaggtgt 203580
gtctattctg gctattctct ttaaaggagc cattctatcg tgaacagatc ctgttggagc 203640
tgttttcttg ttctaccaac cttcagccac ctctctgtct ttcatattac ttattggcag 203700
ggtttcaaaa ggttttagtc cttacttaat ataaacaaaa atgtacaata ttgacaaagt 203760
ttcagttaag cagatgaaat tctaagagtt aagctgggat tttccaaaat aatcctgtta 203820
acagacttga aagcacttat cagttctgtc taatgaagac attagaacac cataaccttt 203880
ccggcccatt ttctttgtca ataagcgttc ttgccctgtc agcagctcac ctccagcttt 203940
agttttctca tgacagtaag tctattaccc tcctgatctg tcttctggct cctcctaccc 204000
aggatgggga aggtttttga ctttactgat attctcagaa caaattttgg gaagtaaata 204060
taaggttttc cagtcgggtg cagtggctca cgcctatgat cccagcgctt gggaaaccca 204120
aggtgggtgg atcacctgag gtcaggagtt tgagaccagc ttggccaata aggtgaaacc 204180
ccatctctac aaaaattagt tgggcgtggt ggcggcacct gtaaatccag ctactcagga 204240
ggctgaggca agaggattgc ttgaatctgg gagccggagg ttgaagtgaa ctgagattgg 204300
gccactgcat tctagcctgg gcgacaagag tgaagctcca tctcaaaaaa aaaaaaaaag 204360
atgaggtttt ccttaagagc actaacctag tatactgcac aggtgcctgt attcatgcat 204420
cccacacaga aagagaaaat acttgtctga acttgtccat aaattcagaa tcctgcccct 204480
taacttgtat gccaggtttc tggcatactc ttatctgaaa actcactcta ttagaaaagc 204540
aaagcacagt gattttccca tcctgattac ctggcactgt ttttattc agtgcttctg 204600
tttctttgcc atgtaaatgc ctgtgatttg ccaggtcatt tgtcctgatt ttagttgaaa 204660
cagtgcagtc atcatacttg cagaatgata caaaataata taaaatatat tgcctttgta 204720
ctaaacagaa gtgcctctct gttggtgaaa taatacatat aaacaaaaat aataattagt 204780
gatacttatt gtgtgttcac tatctactag cactgtattg agtgctttac ctgcattgct 204840
tcattttctc ctcacaatat ccctattagg taaattcagt tataattccc atttacaga 204900
tgggggcatt gaggcttgat gaggttagtt aacctgcttc atggtagtaa aagcagagct 204960
tggatttgag cacagcatga atgactccag aacttacaca cacacaccca ctcacacaca 205020
tgcaaagaga gagagagaga gagagagaca actgctgaac atagacccaa ggcaaaatat 205080
ccttgagtag aggaacagtg tgagagtgaa gctgtagtgc tggttggggt taatcaggat 205140
gggctcactg ggcaagacca ggttgtgggg ggcaaaggag atggaaaatt gtgtgaagag 205200
aagaagggtg gactaggtag ataaaggtag tggactaggt aaataaaggt ggtaattcag 205260
acatccactt taggcttcaa atcactttag gagaagtggt ggtctattgc tttgcccttt 205320
agtagcaaca tgcttattat acaatttaat aagattctat ccaatacact gttttaaggg 205380
ctcccatctc ccggattaga gctgagttct aacttccttt tccaatgata atgatctgag 205440
aaatttcctt catgttgcac ttttttttc tgaagacttg acattgatgg aaagaagtga 205500
aacccaccta tgcttttgat tttggtgact aatattaatt gtcatgtatt actaatagtg 205560
aatctgcatt tttaaagtct tgttggaaag cacattaggt gtgtatataa aggtattaac 205620
cttgaaagta tgaacgtgtt ttctataatt agtcctatga taatttaaaa tttaacatgt 205680
```

```
gcttgacaca tttgataaag gctttgtcta ctatggtttt atttatggtt gttaattaag  205740
taggagcagc agcatactac ttgaaagtat gaaggtgtcc tctatagtta gtcctatgat  205800
aatttaaaat ttaacaggta cttgacacat ttgataaagg ctttgtctac tatggtttta  205860
ttggaataga caacttatct tttcttaaag tatattttac cttggtacca ggaaacttga  205920
gaccaaggta aaatgtaata ctttaaaaaa tgcctaaata ggaactgtca tatatagtta  205980
tatttagggt tgattcatat tttgaaatat attctagaat ataaaaacta ctatatttta  206040
caattacttt accaagctct ctaataatac ctgtttacct ttaaaatctt ggtctttccc  206100
acagaggaca agtattata ttttaattg ttaagccttc tgatcatatg aattcttttc  206160
atatttcatt gaattatat aaaacatttt acttcaaagg aaaaatgtta tgaatttata  206220
atgcttttag aatttaaaaa tctgtttcct attttgttga ttaagacaga gaagcattgc  206280
ttgtgaataa atagcatgct atgttgaaaa gaaaattaag gatcctgatg tttctctgcc  206340
agataggaca aaaactaagg acgccacagg aattttttcaa cattttttaac ctcttgacaa  206400 tatgtgggtc gtataaagga caaatgaatg tttggatgga ctgagaatgc caattttaac  206460
agattgtcca atcactgtag ataaatattt gtgttcctgg ggattatctg attattatca  206520
agcaaattga attggaaaca tagcatgtat taagtcatta ctacttattg tctagttctt  206580
tttctcatag aagtgtctat gtactagaag agcactaagt catcagttag acatgatctt  206640
tatcatatcc agacaaaaat aaaaaccttt taagaagcta ctttacaaga caactgcata  206700
gctttcttca caggaacttg ttaaataaat aatgattatt aaagcaattg ggtcagtctc  206760
ttacactaat ttaacaagag cagttccaag atgtctagcc cattccacat tccgtgtgac  206820
taaccatggt atccagagct tggaaaatat ccaggcaacc cacagtagct tttcttaaat  206880
gcattatgga cactggaatg taaggaaagt gatagaacta ggtgaacaag aagagagtct  206940
ttaaggcata cccattgtca gtgtcgtaaa tggcctcaat tgtatgttga acattgttca  207000
aaagtaccca tggctgaaac agtgtagatt tagctcctat ctgtattgaa gttgataaat  207060
gcataaatct taatcattga catggaggtt tattgtattc aatgagacag atatacttgg  207120
agttttccac aaaccaccaa taagagtcta ttgtgaattg gaatgattag cttttaaaga  207180
tgtatacatg ttaaccaccc ttttatatta agttggtgca caagtaattg tgctttcaac  207240
ggcaaaaacc acaattactt gtgcaccaac ctaatactta cagttatgcc aagataggg  207300 tagaagcaga aggaaaattt agagtgagaa gatagagaca agagataggg aggacaggaa  207360
ttgagtcaaa caaagattct ggaaagtctg tgattaattc tgtggttgtt aattaagtag  207420
gagcagcaga tattataaaa ctcaatatac aagtggtcaa gttcaggaag agccaaggag  207480
gagaccagtt gatattctag gtccatgttt cttgtaagca agtttggaa accagaactt  207540 tggatctgtt tcaagagccc aaggtaagag gctttagaat aaagtctaac ccaggccaag  207600
aatctgggta acagaaccag ggatctccta gggcactagc actaactggt ggccaaggca  207660
agtacttcta catttcctgc tttgagtcca aacttgtgaa aattttttaga aggcctgagc  207720 ccacagattt attttttcat caattcatat ttattaggca cctatatgtg ccaggcactg  207780
tattaggagc atggactatt ggtgatctca atggacatat tatccgtttt tataaaggag  207840
atgtatcgtg gaccagtaaa taagaagtg aacaaatagc actagaagga aataaaagg  207900 gcaataaatc agataatcta ggggagggtg ttttagatag aatgatcagg gaaagcctat  207960
ccaaagaagt gatgtttgag aatgagaatt aagtttgaga atgagcagat acatgaggag  208020
```

```
ctggaaggag gacactccaa agtctaggcc aagtggaaag gcttggaggg gagaaaggcc   208080
ttggcatgtt caaggcttgg aaggaagtgg atttagacgc tagcaagcag aaaagagagg   208140
gtgtgacttg gggcatagag aaattggtaa gagccagatc aagcagtggg aggggaaaag   208200
ccacttagct agagtaaggg atggaccaag tactctgtag aacagatatg aaattattca   208260
gtgtttttat agctgtaaac tggaaaatag attacaggga cttaaaattc tccctaagta   208320
ctccatgcat tgtgaagggt ttactaatga aatcttctta gagatggaaa catgaggcag   208380
accattagtg ctagatcatg gtggtcatat tagttctggg gagtccaggg ttaaaaaaag   208440
tagcttcagg gcaaagcatt gcagttcaag agagtggtgg taatagccag agagttttgc   208500
ctttggatga tgaaactggt tggcaaatga cagtggagca gggtagtgag gcacccaggg   208560
tgggctggtt tgaaacagag cataatgtga gtgaacctgg gatgcacatg aataataaga   208620
tggaagaaac ataaagcatc atccttctta ggatttcctt tcttccacag agtcagctaa   208680
gttataggtg ccctgaggag gtcttccaaa tggttaacag tatattatgc tcttcctttg   208740 aattttagt ttgaaaattt gttaatagcc aaacaatagt aatgatatcc ttaccactct   208800
ttggattgaa tgatgtcccc caccaaacca aaacatcagt taagtcctaa tccccagtag   208860
ctcagaatgt ggtcttattt ggaaacagag tcattgcaga tgacattagt taaatgaaga   208920
tgaggtcata ctggaatagc atgggccatt tatccaacac gactggtgtc tttacaagaa   208980
gaggaaattt gaacacagtg ggaagatggc tgtataaaga tacaaagatg gctgcagtga   209040
gtcatggtca tgctactgca ctccagactg gacgacagag tgagaatttg tctcaaagga   209100
aaagaaaaag aaaaaaaagc taggcatagt ggttcatgcc tgtaacccta gcactttggg   209160
aggttaaagt tggaggatca cttgagctta ggagtttgag acaagcatgg gcaacatagc   209220 aagacccgt cttcgcaaaa aataaaacta gccaggtgtt gtggtgcatg cctgtagtcc   209280
cagctactga ggtggctgag gtgggaggat tgcctaagcc cagcaggtca aggttgcagt   209340
gaccagtgat ctcaccactg caatccagcc tgggcaaaag agcaagaccc tgtcaaaaaa   209400
agaaagaaag tagaaagaaa gaaagagaaa aagaaaacaa aagaaaaaa gacagataca   209460 gagctgcaga aggagaatat tatgtgaaga aggagacaaa gattgaagtg atatatctat   209520
tatcaaggaa atgctagggc atgatgcctg tcatcacaag ctgggagatg gcatggaaca   209580
gattcttcct tagggccttc caaaggaacc accactgcca caccttgacc tcagaatttt   209640
agcctccaga actgtgatat aataaatttc tgtttaaagc cacccagtgt gtggtactca   209700
ttagggcagc cgtagaaaag gaaaactacc ccttcccatt cctcttgtcg tattcttttc   209760
caccgttttg tctcacacac tacaatcgat gaaaaccaaa ttgcttttt taccacttgt   209820 actctttcaa cccagaatag cctcctcttt tttttttttt ttttttttg tctccaggga   209880 cctattttaa aataagaaaa aagttttaa gcatagtacc tgatagtttt ttaatcttca   209940
cccacaccca ccccttcccc ataacttttt tgattgatta tgaaatattt caagcaaaca   210000
cagaaaataa tatgacagta ttcttctaaa atctacattc atcagattac aacttttgc    210060 catatttgct tcaaatcact ccttttcacc ctaaaaagaa aatattactg agagagagaa   210120
agtctcctct cttcatactt tctttcactt cactgttcgc atccttaatt tttatttatt   210180
tatttttaat ttttttttta gagacagggt ctcttttgt tgtccaggct agagtgcagt   210240
ggcacaatca tagctcactg cagcctcaaa ctccttggct caagcaatcc tcatgtctca   210300
gcctcctgag tagctgggac tacaggtaca tgccaccatg ccccactcca attcttattt   210360 attttttaaag tggcatcact tgttagtaa agccttccca ttatcactca gatttactta   210420
```

```
actctatcac ctattcccac aatattttat acacaaatta tattacagga atgatcatat 210480
tgtattttaa ttgtagtcac tttttctcta taagaaaaaa atgacttggt catttttaat 210540
catctagtgc ctatgcaata tctaactctg ggttaaactg aattttaata taatagtgtt 210600
tacatcgaac cgtttgacct tcaaaagagc cctaagagtc aggactagaa ttgtcattct 210660
ttattccaga aatggcaact ttatgaattt tacgtgttta atgtggtcga ttattgtttg 210720
tcactgttgg tgaagtttac ttccttgccc tcctgatgtt gggcttggcc gtgtggtttg 210780
cttaggccag tggaaggcag gtggaagtga caacatgtca gttccaaact gaggctgtaa 210840
gaagttcaca tatttctgct ttcttctttg tgcttctgac attcaccgtg aaaacattcc 210900
ctgagtagct gttggtccca gaatgaagag acagatggag ccaacctgaa cccaacttga 210960
aggctgaatg ccaacaaaca tagcaggatc acagcaaacc tgaagtgaat gctcgctgat 211020
gtcagttacc aagatttggg gtggtggtta cccagcatta gcatagttga aacctcacta 211080
atacacctag atggttgata ataaaggcag aactagaata cacgttatct gattagcaat 211140
atagtgtctt tttactaaat tattctgtta ttcatctgca cattcaacaa gtatttaatc 211200
atatatttac tgtagaaaac agcacatcat taaacagaca gactgtggtc tctgccccca 211260
aggagaatat gtttctagtg agggaaagag atacaaattc ataaatctaa actatagaaa 211320
atggcaaact ctatagcaca aatgtctttt gagagagaat aatgggtgag gggaaggaaa 211380
ggagatgaat acctttaagg tggcaggggt agagctcttt gagagactgc aaagcagaga 211440
agatgcttca agaaaaagaa gtacacattt ctctccctgg aatggtctca gtggtctcag 211500
ataatggttt cagttttcca tattccttta tttatgtagt gtcaggccaa cagtgtactt 211560
tagctccagg ctaaccagtt gtccttggtt tgcatcccgt gtattcagaa agctattgga 211620
ttgttttgta agttcttaaa gaaggactga aaaaggcttc attttccctt tttccaaagg 211680
gagcaattac atactgtcac tggaataata aacttaagtc ctaggctgcg aatgaaattt 211740
gatttctctc aggtgagagg tattttgtat atggaaagct aaggaaagaa atgcaatgtt 211800
tttttttttt tttttttttt ttagcaatcc agtagggaac tgtggccagc attgagctga 211860
taaagacctt tgttttccat gttttgattg gcccagtgag aagcctcgag cagtttgcac 211920
acccatctgt gtccatactg gtggggcaga aaagtgctga cacaggattg cagattagcc 211980
cctgcagctt gccagggtaa acttgtgtaa tgcactgtac accactccta acaacagtgg 212040
tccttttgtc acttaaacag aggttattaa gaatatgagt cattaaaaag agctttagaa 212100
aagcaggcaa cattttccaa tacagtggct ttaggggatc tttggaaagt atcagaagtt 212160
ccggaagaag taaagcatct cattaataac taacaataga cacagaatca aaatctgaat 212220
tgatgaaaaa aagtaatatt taaaatgtaa tttttgaatg ttgaaaagag cccatttttg 212280
tagagaattg gatgaggatt aacttagata ttttcttgaa tgtgtataaa tattacatat 212340
aagaatactt tcaagtctta aattggcccg gggatctcca gcttgctgat aaaaacaaat 212400
caaagaaact acctttagga cttctttttc ttatttttga aacattaaaa agttgcaagt 212460
gccggaataa tggggaaaaa gtctttattc tattatccag acaaaaagct ggtcaacatt 212520
ttaatgctgt ttctgctggc atttttctct acaaatactt tctatgtagt taagatcata 212580
tggtatatgt aatcttgttt cattcatttt ctttcacttt tgttattcct tattcagtga 212640
ttggaaaact atggtttata ggccaaatct ggactactgc tacacgtgga acacagccac 212700
atgcattcat ttacatattg tgtatgactg ctgtctctgt accataatag aattgagggc 212760
```

-continued

```
ggctacagag cttaagtgac tcacaaagcc tgaaatattt gctctctgga cctttataga 212820
aacagttttc cagtttgtga gatagattat tagagtcata tgaacacaat agaattttac 212880
aaaaatatac caaaagttta tacagccatt gatactttaa ctagcattgt ctgatgaaac 212940
tgttttattg cctataacaa tatatatggt aaatatatat ggttatgcat atataaccat 213000
atatatgtaa tagccagcta tatatatata tgtataattt tatatgtata cagttttgga 213060
ttttaataga catagaatgt tagtgtatct cttttttgct ttaatattta tttctttgag 213120
tagcagttag acaaaatgat tttccatttt tttagttctt taattttctt tatcttcaac 213180
tgccttctta tgacgtttgc ccctttttaa atagagggtt tttttaaaaa taaatttgta 213240
agggctctat atagatgcgg aataccaact cttattgttt ttactttgac tatattttct 213300
cagtttttta atcctttaat ttgagagatt ttttgaaac ttgaaagttg tttaatcagt 213360
gtaaaatttc ctctgtgatt cctttccaag ctccaatata tcatgctgag gaagtatctt 213420
atcattttta attttttaaa aatttataag gattgatatt ttatgaaagg cctcttgagt 213480
gtctattttt aaaacatac tttgttctta gaatagtttt ggacttacag aaaaattgag 213540
aagatagtac aaagggttct cataaactcc acagtgattt ttccctgtca ttaacatcat 213600
tcattagcat tttgtcatta gtatctttca ttagtattgt atgttcgtta caatcaatta 213660
actaagattg atgcattgtc attacctaaa gtccatattt tattagaatt gtttaagttt 213720
ttacctaata tactttttgt tctggtatct tgtcctagat accaccattc aaccattcat 213780
ttagttgtta tgtctcctta tgttttttctt ggcttgttat attttctcat agttttttgg 213840
tttttgatga ccttgacaat tttaaggagt attgactagg cattttgtaa aactcctttc 213900
tattagaatt ggtcactgtg agcagtccac attttaggaa taggaagttt tatttcccca 213960
tcttgagggt gaagttgttg cataaacttt tggggattct tctgcatggg agattttttc 214020
tacttctcct tttatttatt tattcagtca tttagtatga gctcatagat attaatttta 214080
tactttgggt tataatctaa tacttttta ttattttgtt gcttacatac ttctagattt 214140
ggccactggg agctctttca gttgacttcc gtatttcttt gacataccttt ggcaaatgta 214200 ggatttgtgt gtgtgtgtgt ttattagcac atttttcatt tctggcacta caagatcctc 214260
caggctcatc ttgtttatt cctgtgccag tcctaggatt agtcatttct acaatgtgcc 214320
ctgattcctt tagtcagttt ccttttatta ggaaccaata tctggacact ggttatgctt 214380
atttgtacaa gcatgtagtt acttctgggc cctctcagct tacagagcaa ggaaccatac 214440
tatgctatgt gtgtgtatgc taagctgtgt atacacacac agaaaaaat atatatatat 214500 atatgcacac acatatattt ctatacatag ccatctgtat caattttgag ctaaacatga 214560
gtgttcatac tggtgtctcc aactctaatc cagtatcaca tgtatcattt tagccttatc 214620
cccttgttta tctgtacact cccatcccaa cagtgataat cctggctcct gccatctgtc 214680
aattccagta tacaggtatt ggaatatcag aattttaac ttgtactcta gttattttaa 214740
ccaagaaata actttgttaa ctagagtaca atgcttatgt actgtcaaac gagattccac 214800
tcgtttccaa agttatttag gttcctctcc tgatttttaa ctcttatttc actgcatttt 214860
aatccggatt tatttattgt tcctggttgt cagtcctgaa actaaagtgg taataaagga 214920
aacaggtggt atacgtgaga ggctttcaaa ttccttgagg tcataaaata tatatgtatg 214980
tgcatatatt taaaataaag ccttgaacag gcagaaaaac tgatattgca ttgtagataa 215040
caaatggcat aaaacactta tgtagaatta gtcccatcaa aatatgtaaa gaagtaaggt 215100
tcgataaaag ttgtgggcat tataataaaa tatttctctc cctttatatt cactccttac 215160
```

```
ctgttctcag taaaataagt tcaactctgt acaattaatt ttctgccatg tctactgctt 215220
gtacttggga acaaatgcta tattataata taaagatatg tgtggaactt ggtttcaaaa 215280
gtcaggtaat gcaaatatca aaaaacaggt gatctctcaa acaccttatg ataagtcagt 215340
cagataaagt gctctgcaga actccagcca acaaacaggt tgattatcag tgaagtatct 215400
catattttca ggtagtcctc acactaagaa agctaatgaa aaagagtttg agctcacata 215460
atcatgagaa agtacatttc aaaccacctt cccaaatttc ctgctgcagt ttcttctctt 215520
tttactcatt attttctttt ttacctcagt ttactttctg gttttcttgg ctgagtgcct 215580
ttttaactgc tttgaagtaa gatgctatct tctttatcag gtttgcaaac tatttattga 215640
atttagcaat taaaattgtc gctgtggttg aactggaaaa tgtccttttg gtacttgaat 215700
ttactgaata taatgactga aaaagcattt caaacaaaca aatcaacaaa caaaaaatct 215760
caattagttt gttgcataga cacaatagta actcacagca ctggcatatt attttgatt 215820
cacaaaacac atatagagcc tggcatctat tagacatgga agccacttat taagtattta 215880
tttaatcaat gaatgcatca aaggattagt aatatcaact tcaacacaat cctgtagtat 215940
atgtaatatt cttcctcttc cctacctta acaatgagga atttgagctc agaaggatta 216000
agtgaattac ttgaagttat attattaatt aaactactga agccagaaca cgaatctaga 216060
acttaatcat cagaagggca actactacct ccacctacgt tactcatgat agtattaaca 216120
tggtagcaca gtggtacata gtagttgctc attgaatatt atttagtaaa agaaatgaaa 216180
agagtggtgc tagatacttg gaagaataag aattctaaga aggagaataa aggtgtatat 216240
acatattcat ttgataagta ttcaaataat agttaaagag atgcatagga tactgcagag 216300
ctctttcaga attgagaagc tgaaattaaa agatgtatta gacttgtttc catcttaaat 216360
catcatcata tcaagtgata gacattggta cctgcagtat ttcagtggca tttgattttt 216420
ttcctgcaga gttctattaa tacagtattt taaaatttta ttgtatgtca tttaaaaaat 216480
acttttaaaa agcaagaaca ccacattttt ctgggcataa gagacaaggt tgcttttgc 216540
atgcatgtat gcaattctaa cctttaaatt tcctatgtct ttattttttc ccctgacttt 216600
agagcctaat attgactaac agctcatttt gaaagataaa aatccacaaa ataataattt 216660
agaaagtgaa aatgaaaaat tacattaatt tctcctctac cattgttttt cgttcaaaac 216720
cacagttaac atgagttgat ttattttttt taaatgaatc tactgtgacc ggccttatga 216780
tccacccatt cgcctaagtt tgaaaccaca ttgattcagt caacaaactc tataccacct 216840
actaattgat aggtaatgac tagttttgtt aatacttggt tacagcgata gctttgagca 216900
aattttcaaa gtgaagcttt tctcaacttt ttcttgttga ttcggtatct gaaatagctt 216960
attaattcat tccttccttg tttccactga cactgccaat cagttgtagg tgaaaactct 217020
aaactggtct cctgtacttt actatcccat tttctgcctt aattcatctt ctccagtgtc 217080
tcaagtgtaa tcttgctaaa atacaaacct aattatgtta ctcctctgtt tacagtcttt 217140
aaatgtttta ccaaattaaa tccaaactcc ttgagaagtt catacaaggt tgtatcagag 217200
cctctgaaac gctaacccac atcttcacag cttcatctct tgattccagc ctggatgcaa 217260
tgggcattct ggatttgact catattacaa caacaaaata atctcaagtg aataccatgc 217320
acttttact tttttttccac tgggcttctt cagtgccaca cctgggaatg gggttttact 217380
tgttaagctt acctatggag ctccaaaatg caaggaagtt taacttttga gagcaatgtc 217440
caaccaatga gggatggaaa cataggaaaa catgctttcc caagttattc ttctaacaaa 217500
```

```
cagctctaag gtacgttctg tatgcttatt cccectagat gtcagggttg agttccagtg   217560
tcccaaagct atataataaa aatgcacctt ggtatagact ttcccgcctt cccttactct   217620
ctttagtctc cttttgtact ccataggatt atctcattga ctgggctttg ctttctagta   217680
gaacctaagc tatgacatat agtactagac tctctcacca ggagtgattt aggacgagga   217740
ggcgttgaaa actgaagctt tggacatctc agatagttaa agcactcgca atttctggca   217800
tttatgtgct cataatgtag tggtgaatgg caattgcggc aaccatggcc tgacaagagc   217860
aaggtcatca agagcttaga ttgtttggag ctgaaggtct gagtcacccc attaggctaa   217920
aaacctagaa aagtagaagt gctgatggag ggtgaggaaa atctaatatg gattgtggag   217980
gaaggagacg atacatataa aacatgactg caggacctgc agttgtagca gtgagggctg   218040
taacttattc cattaatatt tgtgtgttaa gtcacatgta gagattgtgg ctaactacca   218100
ccttgaagac ttagaggttg ctggaactta ttctagggcg taggtgtatc tgtgtggtac   218160
aaaggataga ctgtatgggt tgttttggc tttctgactc atatcctctt ggcttcatct   218220
ctgattacag tgtagatgca gtgggtagtt tggcttacgt caggctgaca tctttcctca   218280
agcactggat gttttgcact tttgcccttg gttttttcca atgccacaat tgccattggg   218340
aagccctctg ttcaagcagg catgctcagt cgagaagcca acaggggttt acatcccaa    218400
agcaaacctt aactaatgga ggatacaagt tgatggataa aaatagtcaa accttaagta   218460
cataattcca aaaggtattc taaacactcc ttagaagatt ccaggcaggg ctgagcacaa   218520
gttgcctaca atggtgatat taataatgca tctatatata tgccttttca cattccctcc   218580
ctcttctgtc tctcactcct gctccctgtt cataaatttt tgcagcaggc tctgcttttg   218640
ggaaaactca agctaaaaca aaagtcctta aattccagta tgcctctgtc ctccactttc   218700
tacccaattt tgtgttgttt cttttggttg tttccctgat atatgccaag aaaataaatg   218760
gagaaataga agggtgggac tatcaacaaa tactttaata gaatttccag aaggacttaa   218820
gctgtcagat tgaaaggatc cactaagtag cccagaaaat agtttaaaag ttggttgttt   218880
tgaagttttt ttctcccctgg tttgttttaa tctctacatc tggtgtacag ctgtcctcat   218940
gagatgcctt gttactatta ttctcttgtg ccaaaacttc tatttcttat ccctgtaatg   219000
ttttctttct tggagcacct cctaaatagt cttagaaagg atgcatggga ggtaactttt   219060
ttgaggcctc aaacatctaa tgaagtctct atttatttc ctttgacctg attgaatgat    219120
tatggattta taggttagaa actatttctt tcaaatacat gaagggagtg tcttattttc   219180
tgtgttgcta ttaaaaagtc ctaatgcaac tcttttatc attctgtgta cagtgtatgt    219240
gatttttttt cttctctgga agcatgtgga gtcttcttta gtccctgtg ttctgaaatt    219300
tcaacagaaa tacccttatt aaggtctgct gcttggtttc tattctccat gttaaaactt   219360
tccacacatg tttggtaatc cttggaagtg tttaaatttt cagttatctt ttaagtaagt   219420
taagagaaga aaaaacttta aaaggcagt ttttatgttt actcatgtat ttcccatttc     219480
tgttgctctt cattctttcc tgtaattctt agttcccatt taatgtcatt ttcttcacct   219540
gaataacttc ttttactgca tattttctgc ttataaattc tctcagtttc catttatccc   219600
ataaagtcta ttttacccttt attttcaaag gatcttttca ctggatatag atttatggtt   219660
gacagtattt tgttgttgtt gttgttgtta atttacttca gtacttacat atattctagt   219720
ttcttctgtc tccactgttt ctgatgagaa gtcattattg gtatcagtgt tcctttgtat   219780
ataatatgtt cttttccctc cagctacttt caagagtttc cccttgtctt tgttttttca   219840
gtttgattgt gatgtacttc gttttcttta tgtttatcct gcttcaggtt ccctgaaatt   219900
```

```
cttggatatg taggttgatg ttttaaataa attttttaaac attagaccat tatttcttca 219960
aatattttct tcttctcttc atctaagact tcaatgatat acatggagac tccttgatat 220020
tgttccattg tcacaaagcc tttattaatt tctttcaata gttttttctt tttgcagctt 220080
gaacttaaaa ttcactgcac tctgcacctc ctttccccc cgtgaagtct ccaatccatt 220140
gttaagctca ttcaggattt ctccacttca gatattatac gctgtagttc taaaatttcc 220200 attttctgc tgctatccca tatgcattca ctgattatga ccataatttc tatacatttt 220260
tgagcatatt tataataagt gctttaaagt ccttttctac taattataca tctggggcat 220320
ttcagagttc agtttctcct gactactttg tctcttgagt atgcttttc ttccagtgtc 220380 taataatttt taaattatac acaaagcatt aaagataatt tgttggccag gagcggtggt 220440
tcacgcctgt aatcccagca ctttgggagg ccaaggcgga cagatcatga agtcaggaga 220500
ttgagatcat cctggctatc actgtgaaac cctgtctcta ctaaaaatac aaaaaaaaga 220560
aaaaattagc tgggcatggt ggcgggcgcc tgtagtccca gctacttggg aggctgaggc 220620
aggagaatgg cgtgaacctg ggaggcggag cttgtagtga gccgagatcg cgccactaca 220680
ctccagcctg ggtgacagag cgagactgtc tcaaaaaaaa taataacttt gtagagattt 220740
tggagtctgt tacctttctc tgaagaatgt tgattttgt tgtagcagca gggcatcagt 220800
gaaatctctg ctcggtttac aagtctttt ttcttttctt ttcttttttt ttgagatgga 220860
gtttcgctct tgttgtcttg ttgtccaggc tggagtgcaa tggcgtgatc ttggctcacc 220920
gcgacctcca cctcccgggt tcaagagagt ctcttgcctc agcctcctga gtagttggga 220980
ttacaggcag gcgccaccac acctggctaa ttttgtattt ttagtagaga cgtggtttct 221040
ccatgttggt caggctggtc tcgaactcct gaccttaggt gatcctccca tctcagcctc 221100
ccaaactgct gggattacag gcgtgagcca cggcgcccgg cctagtcttt taactattgc 221160
tatctgctgg gcttttggga gtctctacca tgcatgcata gtccagtagt tagtcaagga 221220
tttgaaggga gttgatacac agattttgtg gcttcctcct ctgtgcgtct ctcctttcag 221280 caattttct gtttaaattc agtcaccctg gaatccctga gctcactctc tgactccaca 221340
actcagaaag acaatgactt tctttatgaa ttttagctac cctgcatcac ttgggctgca 221400
agatgctctc cagagaaaat ctacattaaa acatgtcact caatgcagtt accttctttc 221460
aaaggttgaa tcaccttctt tttgaatccc tgttggttgt tattttgtac cttaaataat 221520
tatttttaat actggtccag agtttataat tgttatctat gaggagtgtt agtctaacac 221580
aagatatttt gtcatttcta gaacaagact actccactct tatgtagctg tgacattgtc 221640
atgcatttct ttaaaacatt ttagtggttc tttattgttt atcaaataga aaatattcct 221700
taaactgcat gtactctatt ttttcattgt ttcccataac aaagaaatat tatttcattg 221760
aaatattgaa atattgagca tgccttcaaa tattatgttt caccatgttc ttttgctcat 221820
accgttttcc atccagaata cattttcccc cctacatttg aatgcccaaa tcctgcctat 221880
tctttaagat ctagctaaaa tgtcacctcc tccacgaaag ctattcttct ccctccagtt 221940
tcagttttga ctaaattatc tgtttctatt tcattgcttt acttatgttt tataaggaca 222000
ataagagatt agtgcccta taaaagagac cccacaaagc ttccttgccc cttctactat 222060
gtgaggacac agcaagaaga cagccaacta tgagcctgga agcagggcct catcaaacct 222120
tgagcatgct ggtacactga tcttggactt tccagtctcc aaaactgtaa gaataaaatt 222180
tctgttgttg atggctgggc gtggtggctc acgcctgtat tcccagcact tgggaggccg 222240
```

```
aggtgggcga atcacgaggt caggagatcg agaccatcct ggctaacatg gtgaaaccct   222300
gtctctacta aaaatacaaa aaattagctg ggtgtggtgg caggtgcctg cagtcccagc   222360
tactcgggag gctgaggcag gagaatggcg tgaacctgaa aggtggagct tgcagtgagc   222420
caagatctca ccagtgcact ccagcctggg tgacagagcg agactccgtc tcaaaaaaaa   222480
gaaagaaatt tctgtttttt ataagccacc cagtctatgg tactttgtta tagctgcctg   222540
aatggactaa gacacaatgt gaaagtacat tatcttcttt ttgattctca agttaccacc   222600
ttttctcaaa cgaccaccaa ctctctctgg acttctgaaa tattcttgta actggtctct   222660
ctgcttccat tcttgtacct ttaaacctta gtattccaca gtagcctaag aggtcttagg   222720
gtatataaac aaaatgacgt taatttcctg catctaatca ttcaatagct tcccattgca   222780
ctaaagtgga acccttcctt tagagtcctt gccatgatca ataaggtctc ctctcctaca   222840
aggtatgggc actgcctact actctgacct catttattac actcttccct gccttaacat   222900
atgccaaaag tattcgacct tccccccaat tctcaaacac tgcaaaaaac cctcaaagg    222960
cctactactt tacagttgct ctatcttctt cctcgaatgc cctccttatc tttatagatg   223020
gctccttctt ttaagttctt agtaaaaata tcatctcctt agagggacct tcacccctc    223080
agtcacaacc ttgttttaaa ttcctcagac cctcatgatt atctgaaatt atcttattat   223140
atttctttct ttgttgttta atgtttctct ctgtcacaaa gcaatacatt ttttttaaa    223200
gcaggaatgg gctatatatt cttcattttg ttgacctcta ggagctgcat cagttggggt   223260
cccctgcctc tgccctccag ttgagttcag ttaagtaaag accagaggat aagaaagaag   223320
gctactgtgt gtttctactg aggggttatag ctcctttcag gcagtcctct tctacagctt  223380
ttgggttcca taactatttc ttctccttga tgatctccgg taattcaact tggctccttg   223440
ttttctcttt ctgtcctcct cactgttgct agccttaggg tgcttcagtt tcccttaacg   223500
cagttcacat cttttaaaaa cagactcttc attaaattct ctttaatgat tgtttcaag    223560
tatgacaaat ctgtctttct gggaccttga atttttattct tcaaaatatt accagcccct  223620
agcacagaac ctgttacatg gtgacgttca acacatattt gttgaatgaa tggatgaatt   223680
aataggctct tttgctcttc attcagaatc tattaagcta tacactccct cagtatttta   223740
aacccaaaat tcagtttta aaaactaaac ttcttgagag catagtctat ctatatctct    223800
ttaaaattta ggcctaagac aggacactgc cccacattga gtcccacaca acaacctgtg   223860
agtctggctc cccaggaggg ccccccagaca gctcccaggc acttcatagg caaagcctgt  223920
cccccccact caggattccc aaggtctggg gtcccgctca ccccgctttc ctctcatgcc   223980
cagcctgacc ccaggtttca gctgggagag gccacttccc ttagccaagg aaaacgagaa   224040
cccccagggt acaggaggaa gctgggacag gtccccttgg gtgtcactcc ctcacccct    224100
gcccaggccc actcccactg gtgctggagt acgcactggt ggggggaccc tgctcagccc   224160
agcctggagg gccccagtgt caccacaacc agggggcacgg caacatcatt gatgggttct  224220
gcagcccagg gccccgatg cggggtcaga gtgtgtgggg cacagggccc ccgatgcggg    224280
gtcagtgtgt gggggtgcag ggccccgat gtggggtcag tggggtggg gcgcagggtc    224340
cccgatgcgg ggtcagagtg tgtggggcac agggcccccg atgcgggtc agtgtgtggg   224400
ggtgcagggc cccgatgcg gggtcagtgg gggtggggcg caggtcccc gatgcgggt     224460
cagagtgtgt ggggcgcagg gccccgatg cgggtcagt ggggtgggg cgcagggtcc     224520
ccgatgcggg gtcagagtgt gtgggggcgca gggcccccga tgcggggtca gattgtgtgg  224580
agcgcagggc cccctcgtgt ccagggcact ttggtacact gtcccacaag gcacctgtct   224640
```

```
cagaggaggg gtcctggcag gcagtgtggc aactcccttc cagagcccag ctccatgcta   224700
acctgcccac agcaacccca cagagccaca tcccctgctg cacctggcct gcaggagtgt   224760
cccaggacag gcccaagtca gcccagcatg cagctgccct cctaccctga agaagggagt   224820
gggctttcca ggggacataa ggatgccagg cctggacctc ctgggcagga aagggagcag   224880
gtcctgaggg cctgtgcccc acagcccag caccaggtgg actgcagcgc agtgggtggg    224940
ccagtggcag ctggggagaa gccccccgtc agcaggctgg ggtctgccca ccagggcctc   225000
cccacgtctg cctttgaggg tgcctgccat gccctggggg atcctggtat ctttactgga   225060
ctggaagcag gagacagaac agtgtctgtc ccggggtgac ttcatcagga daccgcccac   225120
atagagctgg accccgcagc tgaagcggaa atgtgagaca ggctggcacc tccggaaaaa   225180
ctgccttca gccttggtgt tccgtgcaag gtgaaaaaaa ataggtcctc caagtttaca   225240
gcttgaaatc aggctactgt gtggccctgg agaccacgag gggagaattt aaagtggccc   225300
cggctggcag gtctaggtg gctggcagag gcacatgcag accctacctg gagcccgccc    225360
tagggacgct gggcaggtca gtctccgtgc aggatgtgag cagcgtccct gggctctatc   225420
cgcgaggtgc cagtagcgtg tgcaggtaca tacacatgcg tgcacactgt tatgacaccc   225480
agaaatgtct caggacgtcg aaatgtgtcc ttgggagcag aagtgtcccc ggttgagaat   225540
ctgtcccaga ggaacacgac cacgacaggc ctcaggattt tgtgttgatc aagttccaag   225600
gaaaaggaac atctcggcca ggcgtggtgg ctcacgcctg aatcccagc acttgaggcc    225660
aggagttcga ccagcctg gcaacgcag tgagagaccc ccatctctac aaaaaaaaaa     225720
aagaaaaaa aagaaagaa agaaagaaaa gaaaatgaga tctccaggtt taaaaattca    225780
taaacaccac aaggaaacaa tacactatga gatccagcag aagcaacaga ttgactctgt   225840
agacccagat actggaatta tcagagagaa tataaagtaa cagtgtttta tatatctaaa   225900
gaaataaaag agatttctgg aaaaaaaaat ttaggcctaa gaattagtga aaatcccaac   225960
attaaggaag ggattatatg ttcagttttt gaaaggataa tgtgtcattt ttaatatttg   226020
ctatttcctg gaatcttagt tctaggatac accataaatg tctgctttta taggtgaaga   226080
aactgagggt gagaactgaa gagggattta tctgaagacg ttatggtagt ggaaccaatt   226140
tttactttaa tgttgttgct ctcttgatga tattagatgg tttcatcaat tactaagtaa   226200
attcccaaga tttacctcga agtcacatta ccctattaac ttattctcca gttgtaccaa   226260
tttgccattt cattctggta acaaagctct cttactacaa ttcagaaaat atttgggagg   226320
cagctgccac tgagcccaga ctttgacaaa atatcctccc acagaggccc agttaaacta   226380
tggattgcac tgagcattct gtccttaggt gctctggcct cccagtagat agcggatgct   226440
gtggtaattt atcacaaccc tctacccctc cgattacctg ccaggtgact cttcactcct   226500
ggcttctgca gcctctgctc tccccaagat ccagctctct cagcccccca tctaaggttg   226560
cacagtttag gtacatgctg aaatcaccaa tacagaatcg ttttaaaatt cgaattaatt   226620
ggctgagtgt tttgttaaga cctgattgtg ggcaagaact atttgttaaa tactctaaat   226680
tcttagaacc cagcccagta cttgctagtc atcatttaaa tacattgaat gatagagaaa   226740
attcttctga tcacaaacct tataccagcg ttgtcaaaat tataatgata aagtagctca   226800
ttttaagcgc gtcctgggtt gggaaactta acaattttaa aacttggaat aaattcaata   226860
aaatgacata gtatggttac aatgtctgtc tacagagtca gggcaagaac aaagaaaatt   226920
gaaagaagat tgttttagtg tagtaaaatt actggataat tttcatttcc tttgctcttt   226980
```

```
aaagaattat ttgtaaaggg tatttgaaat gaaaacaaga ttggagaaaa acaacttgga   227040
agaaaatcat aggcaaataa caataatgat tgaagagttg tgaataagga gagttaggaa   227100
tcaagtggtt ccaggcttgc agaatctgaa aggagcctag agtgaggagg ttgatctgtg   227160
aaggatgatg atgatctcca ttaaggacca gacaggaggc aataggctta agctgcagta   227220
tgagggattt agataagaga aaaggaaaaa ttttcagaca gtgaggttca tagatactgg   227280
aatgtgtaac tgaggaagct tgtggaattt ccttctctag aagtctttta aaaatagggc   227340
agtgtctcat ctgcctgaag gatggactct atttgacctc tcaaattgtc tactgaactc   227400
agaaggtgaa ccacacctta gataagaaag agagcctgaa tgatcctggg tagcttgagt   227460
aataaaagta gggtgaacaa gtcatattta ttttgattta tatatgtcat atatgtaaat   227520
tatgtctgct ataattcctt tttttctttc aattgaatgt tttcatttt aaggcctaga    227580 gattagagtt caagtaaaga tattatagga aagcaaggaa gaactctttt atcttactgt   227640
agaacaaatt tttagaggaa taaaggaga aaaggatata ttggacatat ttgattttga    227700
tttcactccc tattctaaat aaaaaaaat acactgccct ttctgttagc tttagtattt     227760
taagggtaaa tttcaaaaag ttaatttagt gtaagtgttt ctcacggtgt ttttggcaga   227820
accggtatcc caaactggaa gaggttctct gtatttaatt tcctctcagg aagtttaccg   227880
tcagaagtcc aaatgtgagg tcaagttttg ggttgccgga aatggtaatg tcctttactg   227940
tctgaacacc cagacaacac ttaatgaaac attctacttt gtggacattg aaagaaatta   228000
aaatgctttg tttcctcctt tttatgattg gtgatttctg tattcagtct tctaaaactc    228060
agaaacaaga ctatgtgtaa gtaagagcat ctgcattctc aggatcaagt tataactgca   228120
gattttcagt tacaggtgat atccatcttt tttttcccttc ctaaaaataa aaatgtactt   228180
acttcaggcc aaaggagagg caagctttag aactcattag ccttcaagaa aaacaattcc   228240
agagcattct aaacctgatt tctttctaac tctgtttgag ttgacctgag gacttttaca   228300
ggttaaagca gtgagtcatt atatctcaca ttcatacagc tctacatatt tgtcaaagtg   228360
cttactcatc taatatctaa tatgatctta ataagaacct tgtgaatgtc attatcttat   228420
agatgaaaaa atgatatctt cataagatac agtttgctca agatcacaaa actagaaaat   228480
gtagtttgaa cacttctgat ttcaaagcca gagtcttctc cactgcccca tgctgtactg   228540
tttttgagaa tttgtgattt cctggtgttg tattatttt accattgatg agattttgc     228600 ctgtgattta tcctgaatca aaatagatac tgtgatatga tactaaagta attgttacca   228660
aacaaaaagt tgtgctagca ttcttatgaa gtacagcact aaagattttc aaaacatttt   228720 gttatttta cataattggt catgtaaatt tctggtagga cactccttat gagattacaa     228780
cccattctaa tttatgctag ctatttattg ttaagcagta tgttgttttt attacaaaac   228840
ctcctttaat cattgcatca gtctctggca gaatattaaa aacaactccc ataatccctg   228900
gcactctgtc ctgggtgtct ttgggggtac agtggcttta tttccttccc taatagttcg    228960
gaagtttgtt taatactgac tcagaggaag cattctagct gagtcctcac atggtcttgt   229020
ttacagctcc ggagtgtaca taatagataa gctactgact tccacaagac ccccacgctt   229080
cctgggtgtg tgggtgtgtg tgcttgtgct tgtgaattaa ggttgtgcaa tctccctgct   229140
agctgcatca ggttgcaaag tcatttactt ctctaaaata ttcctctagc cagcctgact   229200
tgataaacca aaatcattgt attccatggt ggacatgctg gtaactcatg ataaacacta   229260
aaaatcctac gggtttataa caagataaaa cctgatattg gggcagggtg tagagaaatt   229320
tgcccaagga aatattgtga aataaagttg caaatggcta tagatgaatg cttttctatc   229380
```

```
tataggattt cttttcttga ttgtaattat aaattctttt actggttgta aatataatta  229440
tgattcttat gttacccagt ctgtaccaag aactttgtta ggccaacaac atcttacttg  229500
attgtagtag taaccttaaa agataaatat aggtataatg cttttcaga agaaaaactg   229560 gagaattcaa acatgttctg cattgcacag atggtaaatg agtgatgaat agggtccttt  229620
gactccaaag atcaactagg ttcttttccac atatctctct ttggttccct tttttgatat 229680
gactgtatga aatataattg tatttacata aagtgcagta gagttcatta gaaaaactat  229740
ttctgaatct tagggttcag actaaaggtg tttggaggct gatgatagtg ggctgcaaag  229800
agcttcatgg tgggctgcga atagcttcat caaacc                            229836
```

<210> SEQ ID NO 95
<211> LENGTH: 23
<212> TYPE: DNA
<213> ORGANISM: Artificial Sequence
<220> FEATURE:
<223> OTHER INFORMATION: Synthetic primer

<400> SEQUENCE: 95
ttggtgtcca tgctgtgatg att                                          23

<210> SEQ ID NO 96
<211> LENGTH: 24
<212> TYPE: DNA
<213> ORGANISM: Artificial Sequence
<220> FEATURE:
<223> OTHER INFORMATION: Synthetic primer

<400> SEQUENCE: 96
ggttcaagca tcactgttag gtgt                                         24

<210> SEQ ID NO 97
<211> LENGTH: 23
<212> TYPE: DNA
<213> ORGANISM: Artificial Sequence
<220> FEATURE:
<223> OTHER INFORMATION: Synthetic primer

<400> SEQUENCE: 97
gctcagagca attccagtgc aag                                          23

<210> SEQ ID NO 98
<211> LENGTH: 23
<212> TYPE: DNA
<213> ORGANISM: Artificial Sequence
<220> FEATURE:
<223> OTHER INFORMATION: Synthetic primer

<400> SEQUENCE: 98
tctcattggg gatacgaagc tct                                          23

<210> SEQ ID NO 99
<211> LENGTH: 23
<212> TYPE: DNA
<213> ORGANISM: Artificial Sequence
<220> FEATURE:
<223> OTHER INFORMATION: Synthetic primer

<400> SEQUENCE: 99
aactccaaag aaaccatcag agg                                          23

<210> SEQ ID NO 100

```
<211> LENGTH: 25
<212> TYPE: DNA
<213> ORGANISM: Artificial Sequence
<220> FEATURE:
<223> OTHER INFORMATION: Synthetic primer

<400> SEQUENCE: 100
ctttcccgag tcagtactgc tttct                                25

<210> SEQ ID NO 101
<211> LENGTH: 24
<212> TYPE: DNA
<213> ORGANISM: Artificial Sequence
<220> FEATURE:
<223> OTHER INFORMATION: Synthetic primer

<400> SEQUENCE: 101
ttccagtgca agtatggtct gtga                                 24

<210> SEQ ID NO 102
<211> LENGTH: 24
<212> TYPE: DNA
<213> ORGANISM: Artificial Sequence
<220> FEATURE:
<223> OTHER INFORMATION: Synthetic primer

<400> SEQUENCE: 102
tcattgggga tacgaagctc taca                                 24

<210> SEQ ID NO 103
<211> LENGTH: 20
<212> TYPE: DNA
<213> ORGANISM: Artificial Sequence
<220> FEATURE:
<223> OTHER INFORMATION: Synthetic primer

<400> SEQUENCE: 103
ggttggggac ccctggtgta                                      20

<210> SEQ ID NO 104
<211> LENGTH: 18
<212> TYPE: DNA
<213> ORGANISM: Artificial Sequence
<220> FEATURE:
<223> OTHER INFORMATION: Synthetic primer

<400> SEQUENCE: 104
gaggcgggcg aatcacga                                        18

<210> SEQ ID NO 105
<211> LENGTH: 20
<212> TYPE: DNA
<213> ORGANISM: Artificial Sequence
<220> FEATURE:
<223> OTHER INFORMATION: Synthetic primer

<400> SEQUENCE: 105
ggttccagtc ctggttctgc                                      20

<210> SEQ ID NO 106
<211> LENGTH: 20
<212> TYPE: DNA
<213> ORGANISM: Artificial Sequence
<220> FEATURE:
<223> OTHER INFORMATION: Synthetic primer

<400> SEQUENCE: 106
```
tctggcccta gcctccatgt                                               20

<210> SEQ ID NO 107
<211> LENGTH: 20
<212> TYPE: DNA
<213> ORGANISM: Artificial Sequence
<220> FEATURE:
<223> OTHER INFORMATION: Synthetic primer

<400> SEQUENCE: 107
tggggacccc tggtgtagtg                                               20

<210> SEQ ID NO 108
<211> LENGTH: 18
<212> TYPE: DNA
<213> ORGANISM: Artificial Sequence
<220> FEATURE:
<223> OTHER INFORMATION: Synthetic primer

<400> SEQUENCE: 108
cgggcgaatc acgaggtc                                                 18

<210> SEQ ID NO 109
<211> LENGTH: 20
<212> TYPE: DNA
<213> ORGANISM: Artificial Sequence
<220> FEATURE:
<223> OTHER INFORMATION: Synthetic primer

<400> SEQUENCE: 109
ccagtcctgg ttctgccaca                                               20

<210> SEQ ID NO 110
<211> LENGTH: 21
<212> TYPE: DNA
<213> ORGANISM: Artificial Sequence
<220> FEATURE:
<223> OTHER INFORMATION: Synthetic primer

<400> SEQUENCE: 110
cagaaagctg caaaggcctc a                                             21

<210> SEQ ID NO 111
<211> LENGTH: 20
<212> TYPE: DNA
<213> ORGANISM: Artificial Sequence
<220> FEATURE:
<223> OTHER INFORMATION: Synthetic primer

<400> SEQUENCE: 111
aaagaagcca gacacggaag                                               20

<210> SEQ ID NO 112
<211> LENGTH: 18
<212> TYPE: DNA
<213> ORGANISM: Artificial Sequence
<220> FEATURE:
<223> OTHER INFORMATION: Synthetic primer

<400> SEQUENCE: 112
ggatgaggca gcgtggac                                                 18

<210> SEQ ID NO 113
<211> LENGTH: 18
<212> TYPE: DNA

```
<213> ORGANISM: Artificial Sequence
<220> FEATURE:
<223> OTHER INFORMATION: Synthetic primer

<400> SEQUENCE: 113
tccggtttgg cagcagtc                                                 18

<210> SEQ ID NO 114
<211> LENGTH: 21
<212> TYPE: DNA
<213> ORGANISM: Artificial Sequence
<220> FEATURE:
<223> OTHER INFORMATION: Synthetic primer

<400> SEQUENCE: 114
caacagtgtc agaaacgatg c                                             21

<210> SEQ ID NO 115
<211> LENGTH: 21
<212> TYPE: DNA
<213> ORGANISM: Artificial Sequence
<220> FEATURE:
<223> OTHER INFORMATION: Synthetic primer

<400> SEQUENCE: 115
cttgatctcc caaagtgaag g                                             21

<210> SEQ ID NO 116
<211> LENGTH: 18
<212> TYPE: DNA
<213> ORGANISM: Artificial Sequence
<220> FEATURE:
<223> OTHER INFORMATION: Synthetic primer

<400> SEQUENCE: 116
agatctcgga acggctct                                                 18

<210> SEQ ID NO 117
<211> LENGTH: 20
<212> TYPE: DNA
<213> ORGANISM: Artificial Sequence
<220> FEATURE:
<223> OTHER INFORMATION: Synthetic primer

<400> SEQUENCE: 117
ggaagaaagg aaagcgaggt                                               20

<210> SEQ ID NO 118
<211> LENGTH: 20
<212> TYPE: DNA
<213> ORGANISM: Artificial Sequence
<220> FEATURE:
<223> OTHER INFORMATION: Synthetic primer

<400> SEQUENCE: 118
tcctcgcgta gaatggttgt                                               20

<210> SEQ ID NO 119
<211> LENGTH: 18
<212> TYPE: DNA
<213> ORGANISM: Artificial Sequence
<220> FEATURE:
<223> OTHER INFORMATION: Synthetic primer

<400> SEQUENCE: 119
cctgagcgcg gtctaagc                                                 18
```

```
<210> SEQ ID NO 120
<211> LENGTH: 20
<212> TYPE: DNA
<213> ORGANISM: Artificial Sequence
<220> FEATURE:
<223> OTHER INFORMATION: Synthetic primer

<400> SEQUENCE: 120
ccccttcaga tcttctcagc                                                 20

<210> SEQ ID NO 121
<211> LENGTH: 18
<212> TYPE: DNA
<213> ORGANISM: Artificial Sequence
<220> FEATURE:
<223> OTHER INFORMATION: Synthetic primer

<400> SEQUENCE: 121
cccgcacctc ctctaccc                                                   18

<210> SEQ ID NO 122
<211> LENGTH: 20
<212> TYPE: DNA
<213> ORGANISM: Artificial Sequence
<220> FEATURE:
<223> OTHER INFORMATION: Synthetic primer

<400> SEQUENCE: 122
ttggcaagga aggaggactg                                                 20

<210> SEQ ID NO 123
<211> LENGTH: 25
<212> TYPE: DNA
<213> ORGANISM: Artificial Sequence
<220> FEATURE:
<223> OTHER INFORMATION: Synthetic primer

<400> SEQUENCE: 123
ggttcactaa gtcagaaacc ctagt                                           25

<210> SEQ ID NO 124
<211> LENGTH: 20
<212> TYPE: DNA
<213> ORGANISM: Artificial Sequence
<220> FEATURE:
<223> OTHER INFORMATION: Synthetic primer

<400> SEQUENCE: 124
agtcttcatt gctccgcagt                                                 20

<210> SEQ ID NO 125
<211> LENGTH: 20
<212> TYPE: DNA
<213> ORGANISM: Artificial Sequence
<220> FEATURE:
<223> OTHER INFORMATION: Synthetic primer

<400> SEQUENCE: 125
atctatgcgg gcatggttac                                                 20

<210> SEQ ID NO 126
<211> LENGTH: 22
<212> TYPE: DNA
<213> ORGANISM: Artificial Sequence
<220> FEATURE:
```

<223> OTHER INFORMATION: Synthetic primer

<400> SEQUENCE: 126
caaaatgctt gtcatgaagt cg                                          22

<210> SEQ ID NO 127
<211> LENGTH: 20
<212> TYPE: DNA
<213> ORGANISM: Artificial Sequence
<220> FEATURE:
<223> OTHER INFORMATION: Synthetic primer

<400> SEQUENCE: 127
tttcaatcgg ggatgtctgc                                             20

<210> SEQ ID NO 128
<211> LENGTH: 20
<212> TYPE: DNA
<213> ORGANISM: Artificial Sequence
<220> FEATURE:
<223> OTHER INFORMATION: Synthetic primer

<400> SEQUENCE: 128
attcccaccc aggatattcg                                             20

<210> SEQ ID NO 129
<211> LENGTH: 18
<212> TYPE: DNA
<213> ORGANISM: Artificial Sequence
<220> FEATURE:
<223> OTHER INFORMATION: Synthetic primer

<400> SEQUENCE: 129
ctgcgcacca tgttctcg                                               18

<210> SEQ ID NO 130
<211> LENGTH: 26
<212> TYPE: DNA
<213> ORGANISM: Artificial Sequence
<220> FEATURE:
<223> OTHER INFORMATION: Synthetic primer

<400> SEQUENCE: 130
ccctactgac tattacatat caatgc                                      26

<210> SEQ ID NO 131
<211> LENGTH: 23
<212> TYPE: DNA
<213> ORGANISM: Artificial Sequence
<220> FEATURE:
<223> OTHER INFORMATION: Synthetic primer

<400> SEQUENCE: 131
ttttaaccat ttaaggcata gga                                         23

<210> SEQ ID NO 132
<211> LENGTH: 22
<212> TYPE: DNA
<213> ORGANISM: Artificial Sequence
<220> FEATURE:
<223> OTHER INFORMATION: Synthetic primer

<400> SEQUENCE: 132
ctgctgatga aacagctaaa cc                                          22

```
<210> SEQ ID NO 133
<211> LENGTH: 27
<212> TYPE: DNA
<213> ORGANISM: Artificial Sequence
<220> FEATURE:
<223> OTHER INFORMATION: Synthetic primer

<400> SEQUENCE: 133
tcttggaatt taagatatag aggtcaa                                           27

<210> SEQ ID NO 134
<211> LENGTH: 25
<212> TYPE: DNA
<213> ORGANISM: Artificial Sequence
<220> FEATURE:
<223> OTHER INFORMATION: Synthetic primer

<400> SEQUENCE: 134
gttagagaaa gaaaagccac cttag                                             25

<210> SEQ ID NO 135
<211> LENGTH: 26
<212> TYPE: DNA
<213> ORGANISM: Artificial Sequence
<220> FEATURE:
<223> OTHER INFORMATION: Synthetic primer

<400> SEQUENCE: 135
aacatatgct ctgattctca actaac                                            26

<210> SEQ ID NO 136
<211> LENGTH: 22
<212> TYPE: DNA
<213> ORGANISM: Artificial Sequence
<220> FEATURE:
<223> OTHER INFORMATION: Synthetic primer

<400> SEQUENCE: 136
caaacattga gagaagggaa cc                                                22

<210> SEQ ID NO 137
<211> LENGTH: 21
<212> TYPE: DNA
<213> ORGANISM: Artificial Sequence
<220> FEATURE:
<223> OTHER INFORMATION: Synthetic primer

<400> SEQUENCE: 137
tctgcaccct gagacactct a                                                 21

<210> SEQ ID NO 138
<211> LENGTH: 21
<212> TYPE: DNA
<213> ORGANISM: Artificial Sequence
<220> FEATURE:
<223> OTHER INFORMATION: Synthetic primer

<400> SEQUENCE: 138
taagagcaaa ggccagcatc c                                                 21

<210> SEQ ID NO 139
<211> LENGTH: 22
<212> TYPE: DNA
<213> ORGANISM: Artificial Sequence
<220> FEATURE:
<223> OTHER INFORMATION: Synthetic primer
```

```
<400> SEQUENCE: 139
taatcactgc cttctcccac tc                                              22

<210> SEQ ID NO 140
<211> LENGTH: 18
<212> TYPE: DNA
<213> ORGANISM: Artificial Sequence
<220> FEATURE:
<223> OTHER INFORMATION: Synthetic primer

<400> SEQUENCE: 140
gggtgggaaa ttgggtaa                                                   18

<210> SEQ ID NO 141
<211> LENGTH: 18
<212> TYPE: DNA
<213> ORGANISM: Artificial Sequence
<220> FEATURE:
<223> OTHER INFORMATION: Synthetic primer

<400> SEQUENCE: 141
ggcaggtatg ggagatgc                                                   18

<210> SEQ ID NO 142
<211> LENGTH: 31
<212> TYPE: DNA
<213> ORGANISM: Artificial Sequence
<220> FEATURE:
<223> OTHER INFORMATION: Synthetic primer

<400> SEQUENCE: 142
acaatacaac agatttcata tagtagctta g                                    31

<210> SEQ ID NO 143
<211> LENGTH: 19
<212> TYPE: DNA
<213> ORGANISM: Artificial Sequence
<220> FEATURE:
<223> OTHER INFORMATION: Synthetic primer

<400> SEQUENCE: 143
taggttccag ccccgatcc                                                  19

<210> SEQ ID NO 144
<211> LENGTH: 19
<212> TYPE: DNA
<213> ORGANISM: Artificial Sequence
<220> FEATURE:
<223> OTHER INFORMATION: Synthetic primer

<400> SEQUENCE: 144
ttcctggcgc tcaagaacc                                                  19

<210> SEQ ID NO 145
<211> LENGTH: 18
<212> TYPE: DNA
<213> ORGANISM: Artificial Sequence
<220> FEATURE:
<223> OTHER INFORMATION: Synthetic primer

<400> SEQUENCE: 145
cactgccctc agctccta                                                   18

<210> SEQ ID NO 146
<211> LENGTH: 22
```

```
<212> TYPE: DNA
<213> ORGANISM: Artificial Sequence
<220> FEATURE:
<223> OTHER INFORMATION: Synthetic primer

<400> SEQUENCE: 146
tgcattatgg atacaaccct ta                                       22

<210> SEQ ID NO 147
<211> LENGTH: 20
<212> TYPE: DNA
<213> ORGANISM: Artificial Sequence
<220> FEATURE:
<223> OTHER INFORMATION: Synthetic primer

<400> SEQUENCE: 147
cggatgctac attggatagg                                          20

<210> SEQ ID NO 148
<211> LENGTH: 18
<212> TYPE: DNA
<213> ORGANISM: Artificial Sequence
<220> FEATURE:
<223> OTHER INFORMATION: Synthetic primer

<400> SEQUENCE: 148
gaagggaacc gggtagca                                            18

<210> SEQ ID NO 149
<211> LENGTH: 20
<212> TYPE: DNA
<213> ORGANISM: Artificial Sequence
<220> FEATURE:
<223> OTHER INFORMATION: Synthetic primer

<400> SEQUENCE: 149
gtaactgaat ccagccaacc                                          20

<210> SEQ ID NO 150
<211> LENGTH: 19
<212> TYPE: DNA
<213> ORGANISM: Artificial Sequence
<220> FEATURE:
<223> OTHER INFORMATION: Synthetic primer

<400> SEQUENCE: 150
aagccgtgtc tcaagatcg                                           19

<210> SEQ ID NO 151
<211> LENGTH: 19
<212> TYPE: DNA
<213> ORGANISM: Artificial Sequence
<220> FEATURE:
<223> OTHER INFORMATION: Synthetic primer

<400> SEQUENCE: 151
ctagcaaatg gcagaacca                                           19

<210> SEQ ID NO 152
<211> LENGTH: 20
<212> TYPE: DNA
<213> ORGANISM: Artificial Sequence
<220> FEATURE:
<223> OTHER INFORMATION: Synthetic primer

<400> SEQUENCE: 152
```
atcagtcacc gaaggtccta                                              20

<210> SEQ ID NO 153
<211> LENGTH: 20
<212> TYPE: DNA
<213> ORGANISM: Artificial Sequence
<220> FEATURE:
<223> OTHER INFORMATION: Synthetic primer

<400> SEQUENCE: 153
cgactctgga ggacgaagtt                                              20

<210> SEQ ID NO 154
<211> LENGTH: 18
<212> TYPE: DNA
<213> ORGANISM: Artificial Sequence
<220> FEATURE:
<223> OTHER INFORMATION: Synthetic primer

<400> SEQUENCE: 154
gaggcgtgca gcggttta                                                18

<210> SEQ ID NO 155
<211> LENGTH: 18
<212> TYPE: DNA
<213> ORGANISM: Artificial Sequence
<220> FEATURE:
<223> OTHER INFORMATION: Synthetic primer

<400> SEQUENCE: 155
cgggatcaag gggagtcg                                                18

<210> SEQ ID NO 156
<211> LENGTH: 19
<212> TYPE: DNA
<213> ORGANISM: Artificial Sequence
<220> FEATURE:
<223> OTHER INFORMATION: Synthetic primer

<400> SEQUENCE: 156
agcccgcgag gtttaggac                                               19

<210> SEQ ID NO 157
<211> LENGTH: 22
<212> TYPE: DNA
<213> ORGANISM: Artificial Sequence
<220> FEATURE:
<223> OTHER INFORMATION: Synthetic primer

<400> SEQUENCE: 157
cgttttgtct tgggtttgta cc                                           22

<210> SEQ ID NO 158
<211> LENGTH: 20
<212> TYPE: DNA
<213> ORGANISM: Artificial Sequence
<220> FEATURE:
<223> OTHER INFORMATION: Synthetic primer

<400> SEQUENCE: 158
agcaccggag gaagaaagag                                              20

<210> SEQ ID NO 159
<211> LENGTH: 20
<212> TYPE: DNA
<213> ORGANISM: Artificial Sequence
<220> FEATURE:
<223> OTHER INFORMATION: Synthetic primer

<400> SEQUENCE: 159
agtgaacgca ctcaaacacg                                               20

<210> SEQ ID NO 160
<211> LENGTH: 20
<212> TYPE: DNA
<213> ORGANISM: Artificial Sequence
<220> FEATURE:
<223> OTHER INFORMATION: Synthetic primer

<400> SEQUENCE: 160
taccaggcaa tgtacacgtc                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic primer

<400> SEQUENCE: 161
agcttaggat gtgtggcact                                               20

<210> SEQ ID NO 162
<211> LENGTH: 18
<212> TYPE: DNA
<213> ORGANISM: Artificial Sequence
<220> FEATURE:
<223> OTHER INFORMATION: Synthetic primer

<400> SEQUENCE: 162
gacacgctgg tggtgctg                                                 18

<210> SEQ ID NO 163
<211> LENGTH: 21
<212> TYPE: DNA
<213> ORGANISM: Artificial Sequence
<220> FEATURE:
<223> OTHER INFORMATION: Synthetic primer

<400> SEQUENCE: 163
acagtgctct ctgcctgtga c                                             21

<210> SEQ ID NO 164
<211> LENGTH: 18
<212> TYPE: DNA
<213> ORGANISM: Artificial Sequence
<220> FEATURE:
<223> OTHER INFORMATION: Synthetic primer

<400> SEQUENCE: 164
gtgaagccat tgcgagaa                                                 18

<210> SEQ ID NO 165
<211> LENGTH: 29
<212> TYPE: DNA
<213> ORGANISM: Artificial Sequence
<220> FEATURE:
<223> OTHER INFORMATION: Synthetic primer

<400> SEQUENCE: 165
ccactgagac tcattatata acactcgtt                                     29

<210> SEQ ID NO 166
<211> LENGTH: 20
<212> TYPE: DNA
<213> ORGANISM: Artificial Sequence
<220> FEATURE:
<223> OTHER INFORMATION: Synthetic primer

<400> SEQUENCE: 166
ggtcccagtc tgcagttaag                                              20

<210> SEQ ID NO 167
<211> LENGTH: 18
<212> TYPE: DNA
<213> ORGANISM: Artificial Sequence
<220> FEATURE:
<223> OTHER INFORMATION: Synthetic primer

<400> SEQUENCE: 167
cgagcagcac cagaatcc                                                18

<210> SEQ ID NO 168
<211> LENGTH: 29
<212> TYPE: DNA
<213> ORGANISM: Artificial Sequence
<220> FEATURE:
<223> OTHER INFORMATION: Synthetic primer

<400> SEQUENCE: 168
cagaaaatta aatatacctg ttaagttcg                                    29

<210> SEQ ID NO 169
<211> LENGTH: 21
<212> TYPE: DNA
<213> ORGANISM: Artificial Sequence
<220> FEATURE:
<223> OTHER INFORMATION: Synthetic primer

<400> SEQUENCE: 169
gcaaacctca aacattattg g                                            21

<210> SEQ ID NO 170
<211> LENGTH: 23
<212> TYPE: DNA
<213> ORGANISM: Artificial Sequence
<220> FEATURE:
<223> OTHER INFORMATION: Synthetic primer

<400> SEQUENCE: 170
gcactcaatc attagaggct aca                                          23

<210> SEQ ID NO 171
<211> LENGTH: 22
<212> TYPE: DNA
<213> ORGANISM: Artificial Sequence
<220> FEATURE:
<223> OTHER INFORMATION: Synthetic primer

<400> SEQUENCE: 171
tgcacaaaga agtgcatcta gt                                           22

<210> SEQ ID NO 172
<211> LENGTH: 23
<212> TYPE: DNA
<213> ORGANISM: Artificial Sequence
<220> FEATURE:
<223> OTHER INFORMATION: Synthetic primer -continued

<400> SEQUENCE: 172
acaagtcatt tgagagtgga gac                                          23

<210> SEQ ID NO 173
<211> LENGTH: 21
<212> TYPE: DNA
<213> ORGANISM: Artificial Sequence
<220> FEATURE:
<223> OTHER INFORMATION: Synthetic primer

<400> SEQUENCE: 173
gggatttaat ttccagggtt g                                            21

<210> SEQ ID NO 174
<211> LENGTH: 27
<212> TYPE: DNA
<213> ORGANISM: Artificial Sequence
<220> FEATURE:
<223> OTHER INFORMATION: Synthetic primer

<400> SEQUENCE: 174
ggaagaacta cagctcttaa atgtagc                                      27

<210> SEQ ID NO 175
<211> LENGTH: 18
<212> TYPE: DNA
<213> ORGANISM: Artificial Sequence
<220> FEATURE:
<223> OTHER INFORMATION: Synthetic primer

<400> SEQUENCE: 175
ggagaccctc gcccaact                                                18

<210> SEQ ID NO 176
<211> LENGTH: 20
<212> TYPE: DNA
<213> ORGANISM: Artificial Sequence
<220> FEATURE:
<223> OTHER INFORMATION: Synthetic primer

<400> SEQUENCE: 176
cactcaccat gaagcgaaac                                              20

<210> SEQ ID NO 177
<211> LENGTH: 18
<212> TYPE: DNA
<213> ORGANISM: Artificial Sequence
<220> FEATURE:
<223> OTHER INFORMATION: Synthetic primer

<400> SEQUENCE: 177
ggagggcttc ctggacac                                                18

<210> SEQ ID NO 178
<211> LENGTH: 20
<212> TYPE: DNA
<213> ORGANISM: Artificial Sequence
<220> FEATURE:
<223> OTHER INFORMATION: Synthetic primer

<400> SEQUENCE: 178
ggaaagtgga ttgcatcagc                                              20

<210> SEQ ID NO 179

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 179
tctcccctaa accattactc c                                              21

<210> SEQ ID NO 180
<211> LENGTH: 20
<212> TYPE: DNA
<213> ORGANISM: Artificial Sequence
<220> FEATURE:
<223> OTHER INFORMATION: Synthetic primer

<400> SEQUENCE: 180
tagtggagaa ggtgcgacag                                                20

<210> SEQ ID NO 181
<211> LENGTH: 18
<212> TYPE: DNA
<213> ORGANISM: Artificial Sequence
<220> FEATURE:
<223> OTHER INFORMATION: Synthetic primer

<400> SEQUENCE: 181
ggctggctcc ccactctg                                                  18

<210> SEQ ID NO 182
<211> LENGTH: 18
<212> TYPE: DNA
<213> ORGANISM: Artificial Sequence
<220> FEATURE:
<223> OTHER INFORMATION: Synthetic primer

<400> SEQUENCE: 182
cacaagggag ccaccaac                                                  18

<210> SEQ ID NO 183
<211> LENGTH: 25
<212> TYPE: DNA
<213> ORGANISM: Artificial Sequence
<220> FEATURE:
<223> OTHER INFORMATION: Synthetic primer

<400> SEQUENCE: 183
cctgacaaag tgggtttaaa taggt                                          25

<210> SEQ ID NO 184
<211> LENGTH: 20
<212> TYPE: DNA
<213> ORGANISM: Artificial Sequence
<220> FEATURE:
<223> OTHER INFORMATION: Synthetic primer

<400> SEQUENCE: 184
tcttcctcag cactccgaac                                                20

<210> SEQ ID NO 185
<211> LENGTH: 18
<212> TYPE: DNA
<213> ORGANISM: Artificial Sequence
<220> FEATURE:
<223> OTHER INFORMATION: Synthetic primer

<400> SEQUENCE: 185
```
ggctcaagaa ttgggtca                                                    18

<210> SEQ ID NO 186
<211> LENGTH: 24
<212> TYPE: DNA
<213> ORGANISM: Artificial Sequence
<220> FEATURE:
<223> OTHER INFORMATION: Synthetic primer

<400> SEQUENCE: 186
ccataatgtc ctttctattt gacg                                             24

<210> SEQ ID NO 187
<211> LENGTH: 21
<212> TYPE: DNA
<213> ORGANISM: Artificial Sequence
<220> FEATURE:
<223> OTHER INFORMATION: Synthetic primer

<400> SEQUENCE: 187
ttattacgag cctggtctgg a                                                21

<210> SEQ ID NO 188
<211> LENGTH: 21
<212> TYPE: DNA
<213> ORGANISM: Artificial Sequence
<220> FEATURE:
<223> OTHER INFORMATION: Synthetic primer

<400> SEQUENCE: 188
cccatctaag ggtagagaag c                                                21

<210> SEQ ID NO 189
<211> LENGTH: 20
<212> TYPE: DNA
<213> ORGANISM: Artificial Sequence
<220> FEATURE:
<223> OTHER INFORMATION: Synthetic primer

<400> SEQUENCE: 189
agcaatctag gcgtttgcac                                                  20

<210> SEQ ID NO 190
<211> LENGTH: 24
<212> TYPE: DNA
<213> ORGANISM: Artificial Sequence
<220> FEATURE:
<223> OTHER INFORMATION: Synthetic primer

<400> SEQUENCE: 190
tgctaaatga tctatttcca ccat                                             24

<210> SEQ ID NO 191
<211> LENGTH: 20
<212> TYPE: DNA
<213> ORGANISM: Artificial Sequence
<220> FEATURE:
<223> OTHER INFORMATION: Synthetic primer

<400> SEQUENCE: 191
cttcgattgc tgggattatg                                                  20

<210> SEQ ID NO 192
<211> LENGTH: 17
<212> TYPE: DNA

```
<213> ORGANISM: Artificial Sequence
<220> FEATURE:
<223> OTHER INFORMATION: Synthetic primer

<400> SEQUENCE: 192
tgggtatggt tttctgg                                                    17

<210> SEQ ID NO 193
<211> LENGTH: 20
<212> TYPE: DNA
<213> ORGANISM: Artificial Sequence
<220> FEATURE:
<223> OTHER INFORMATION: Synthetic primer

<400> SEQUENCE: 193
ctgttcgtgc aggatgaatg                                                 20

<210> SEQ ID NO 194
<211> LENGTH: 24
<212> TYPE: DNA
<213> ORGANISM: Artificial Sequence
<220> FEATURE:
<223> OTHER INFORMATION: Synthetic primer

<400> SEQUENCE: 194
aagcaagatt ccaaacagta aaca                                            24

<210> SEQ ID NO 195
<211> LENGTH: 20
<212> TYPE: DNA
<213> ORGANISM: Artificial Sequence
<220> FEATURE:
<223> OTHER INFORMATION: Synthetic primer

<400> SEQUENCE: 195
tgctggcctt tgctcttact                                                 20

<210> SEQ ID NO 196
<211> LENGTH: 20
<212> TYPE: DNA
<213> ORGANISM: Artificial Sequence
<220> FEATURE:
<223> OTHER INFORMATION: Synthetic primer

<400> SEQUENCE: 196
cctttgcata gggagaccac                                                 20

<210> SEQ ID NO 197
<211> LENGTH: 20
<212> TYPE: DNA
<213> ORGANISM: Artificial Sequence
<220> FEATURE:
<223> OTHER INFORMATION: Synthetic primer

<400> SEQUENCE: 197
gggcctgtga acctactgac                                                 20

<210> SEQ ID NO 198
<211> LENGTH: 18
<212> TYPE: DNA
<213> ORGANISM: Artificial Sequence
<220> FEATURE:
<223> OTHER INFORMATION: Synthetic primer

<400> SEQUENCE: 198
ttgaggcagg tcaaataa                                                   18
```

```
<210> SEQ ID NO 199
<211> LENGTH: 414
<212> TYPE: DNA
<213> ORGANISM: Homo sapiens

<400> SEQUENCE: 199
ggaagcagcc ctcgccagag ccagcgttgg caaggaagga ggactgggct cctccccacc      60 tgcccccac accgccctcc ggcctccctg ctcccagccg cgctccccg cctgccagca      120 aaggcgtgtt tgagtgcgtt cactctgtta aaagaaatc cgccccgcc ccgtttcctt      180 cctccgcgat acaaccttcc waactgccaa attgaatcgg ggtgtttggt gtcatagga      240 aagtatggct tcttctttta atcataagaa aaagcaaaac tattctttcc tagttgtgag      300
agccccaccg agaatcgaaa tcacctgtac gactagaaag tgtcccccta cccctcaac      360 ccttgatttt caggagcgcg gggttcacta agtcagaaac cctagttcaa agga           414

<210> SEQ ID NO 200
<211> LENGTH: 425
<212> TYPE: DNA
<213> ORGANISM: Homo sapiens

<400> SEQUENCE: 200
attggaagga cggactccat tctcaaagtc ataattccta gaccagaaaa agtgctcagt      60
gttctagaag cagagttgma cagtgatcca agaccagct tcaaatactg tcctgtctcc      120
ttcacacttc tcacatttct cttcctact gaaaatacct tgcatttttc gtaattataa      180 aggggaagg gaatatgagt gcccctgct ttatagggt tgttgtgagt ttaaatgatg      240
tattaataca tataagcctt aagaacagtg ccacacatcc taagctaata cctgttagct      300
cttgaattat ccgctttgag gactggcttg caatcttgtt ttgaggcata gaaagaaaat      360
gctttggagc aggacgcggt ggctcacacc tgtaatccca gcactttggg aagccgaggc      420
gggca                                                                 425

<210> SEQ ID NO 201
<211> LENGTH: 824
<212> TYPE: DNA
<213> ORGANISM: Homo sapiens

<400> SEQUENCE: 201
tgaatcaaca tttattactt aaaatattta aaacatttca gcggatgcta cattggatag      60
gaagagaacc gcaagttatg gatttgttgc ctaaaaactt tggtgaggaa ctgcataagt      120
ggacctctcc taaaagtgaa caattttttgt ttacagaatc attttggttc ggagtgctga      180
ggaagacaaa gtcttaacag gagggcaatt gcttgtgtat tgcaaaatga gagtcttcac      240
atgttttttt taggatacct tagctctgac tcctcatccc ccaaatccct gtagaattaa      300
aaaaagctct ttctttttaaa ggcagtggaa gtgccaccac catggaagtg ctggttaggg      360
ctgaaaatct actgacagag cctcaacaga gctgaaatcc acctggacag graagggaac      420
cgggtagcat taataacaat ttctttttct ttcccatcca accccatttt cctagtcttc      480
agtttcttaa tttctctacc ttttactctt atgctcttgt tttgaccttt gagtttctct      540
gaaacttatc agaaaagtta ggacaagata gtctgaccca attcttgagc cattttctta      600
ggtagtaaat atgtcagaaa aatgaaagct gtttggagtt gataaggaaa tggaagataa      660 tgttttttctt tgaggggggac ataaagaatg gtgatagga aagaaccaat gactaagtaa      720
```

```
-continued aatgactgag aatcttgcac gaggcagatg tgtgagcttc gcgaagcaag ttgactgaat    780
gaaaaacaac tttgggtagg gaaaacgttg ccggggcat tcgc                      824
```